(12) United States Patent
Fischl et al.

(10) Patent No.: US 11,091,428 B2
(45) Date of Patent: Aug. 17, 2021

(54) ANTIVIRAL COMPOUNDS

(71) Applicant: HAPLOGEN GMBH, Vienna (AT)

(72) Inventors: Wolfgang Fischl, Vienna (AT); Mark Whittaker, Abingdon (GB); Christopher John Yarnold, Abingdon (GB); Jean-Francois Pons, Shrivenham (GB); Mark Anthony Kerry, Abingdon (GB); Patricia Leonie Amouzegh, Abingdon (GB); Inaki Morao, Abingdon (GB); Peter Neville Ingram, Abingdon (GB); Ewa Iwona Chudyk, Abingdon (GB)

(73) Assignee: HAPLOGEN GMBH, Vienna (AT)

( * ) Notice: Subject to any disclaimer, the term of this patent is extended or adjusted under 35 U.S.C. 154(b) by 0 days.

(21) Appl. No.: 16/333,159

(22) PCT Filed: Sep. 12, 2017

(86) PCT No.: PCT/EP2017/072880
§ 371 (c)(1),
(2) Date: Mar. 13, 2019

(87) PCT Pub. No.: WO2018/050631
PCT Pub. Date: Mar. 22, 2018

(65) Prior Publication Data
US 2019/0225575 A1   Jul. 25, 2019

(30) Foreign Application Priority Data
Sep. 13, 2016   (EP) .................................... 16188559

(51) Int. Cl.
| C07D 207/27 | (2006.01) |
| --- | --- |
| C07D 207/26 | (2006.01) |
| C07D 261/18 | (2006.01) |
| C07D 211/26 | (2006.01) |
| C07D 405/06 | (2006.01) |
| C07D 309/04 | (2006.01) |
| C07D 309/14 | (2006.01) |
| C07D 403/06 | (2006.01) |
| C07D 403/12 | (2006.01) |
| C07D 307/14 | (2006.01) |
| C07D 215/14 | (2006.01) |

(Continued)

(52) U.S. Cl.
CPC ............ *C07C 235/74* (2013.01); *A61P 31/14* (2018.01); *C07C 237/22* (2013.01); *C07C 271/24* (2013.01); *C07C 311/03* (2013.01); *C07C 311/06* (2013.01); *C07C 311/10* (2013.01); *C07C 311/13* (2013.01); *C07C 311/19* (2013.01); *C07C 311/29* (2013.01); *C07D 205/04* (2013.01); *C07D 207/26* (2013.01); *C07D 207/27* (2013.01); *C07D 211/26* (2013.01); *C07D 215/14* (2013.01); *C07D 233/64* (2013.01); *C07D 241/12* (2013.01); *C07D 261/18* (2013.01); *C07D 307/14* (2013.01); *C07D 309/04* (2013.01); *C07D 309/14* (2013.01); *C07D 401/12* (2013.01); *C07D 403/06* (2013.01); *C07D 403/12* (2013.01); *C07D 405/06* (2013.01); *C07D 417/12* (2013.01); *C07C 2601/02* (2017.05); *C07C 2601/04* (2017.05); *C07C 2601/08* (2017.05); *C07C 2601/14* (2017.05)

(58) Field of Classification Search
CPC .. C07D 207/27; C07D 207/26; C07D 261/18; C07D 211/26; C07D 405/06; C07D 309/04; C07D 309/14; C07D 403/06; C07D 403/12; C07D 307/14; C07D 215/14; C07D 233/64; C07D 401/12; C07D 417/12; C07D 205/04; C07D 241/12; A61P 31/14; C07C 311/29; C07C 311/10; C07C 311/06; C07C 311/13; C07C 311/14; C07C 311/03; C07C 237/22; C07C 235/74; C07C 271/24
See application file for complete search history.

(56) References Cited

U.S. PATENT DOCUMENTS

| 2011/0183895 A1 | 7/2011 | Zhan |
| 2014/0256698 A1 | 9/2014 | Booth et al. |

FOREIGN PATENT DOCUMENTS

| WO | 9825883 A1 | 6/1998 |
| WO | 0110894 A2 | 2/2001 |

(Continued)

OTHER PUBLICATIONS

Titov, 1959, caplus an 1959:65928.*

(Continued)

*Primary Examiner* — Sun Jae Yoo
(74) *Attorney, Agent, or Firm* — Loza & Loza, LLP; Michael F. Fedrick

(57) ABSTRACT

The present invention relates to novel compounds of general formula (I) wherein the groups X, and $R^1$ to $R^4$ have the meanings given in the description and claims, process for preparing these compounds and their use as for treating, preventing or ameliorating viral infections and their use for treating, preventing or ameliorating diseases which are associated with PLA2G16.

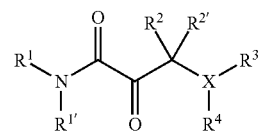

3 Claims, No Drawings

(51) Int. Cl.

| | |
|---|---|
| C07D 233/64 | (2006.01) |
| C07D 401/12 | (2006.01) |
| C07D 417/12 | (2006.01) |
| C07D 205/04 | (2006.01) |
| C07D 241/12 | (2006.01) |
| C07C 311/10 | (2006.01) |
| C07C 311/13 | (2006.01) |
| C07C 311/14 | (2006.01) |
| C07C 311/06 | (2006.01) |
| C07C 311/03 | (2006.01) |
| C07C 237/22 | (2006.01) |
| C07C 235/74 | (2006.01) |
| C07C 271/24 | (2006.01) |
| C07C 311/19 | (2006.01) |
| C07C 311/29 | (2006.01) |
| A61P 31/14 | (2006.01) |

(56) References Cited

FOREIGN PATENT DOCUMENTS

| | | |
|---|---|---|
| WO | 2011160043 A2 | 12/2011 |
| WO | 2013049382 A2 | 4/2013 |
| WO | 2014154829 A1 | 10/2014 |
| WO | 2015154039 A2 | 10/2015 |

OTHER PUBLICATIONS

RN1415464-65-1, registry database compound, entry date Dec. 26, 2012.*

Basso, A. et al. "Solid-phase synthesis of modified oligopeptides via Passerini multicomponent reaction", Tetrahedron Letters, vol. 44, No. 11, pp. 2367-2370 (2003).

Catalano, John et al. "Design of small molecule ketomide-based inhibitors of cathepsin K", Bioorganic & Medicinal Chemistry Letters, vol. 14, No. 3, pp. 719-722 (2004).

Chatterjee, S. et al. "P2-achiral, P'-extended alpha-ketoamide inhibitors of calpain I", Bioorganic & Medicinal Chemistry Letters, vol. 9, No. 16, pp. 2371-2374 (1999).

Chicheng, M.A. et al. "Photochemical Cleavage and Release of Para-Substituted Phenols from α-Keto Amides", The J. of Organic Chemistry, vol. 71, No. 11, pp. 4206-4215 (2006).

Jaworski, K. et al. "AdPLA ablation increases lipolysis and prevents obesity induced by high fat feeding or leptin deficiency", Nat. Med., vol. 15, No. 2, pp. 159-168 (2009).

Kabbe, Hans-Joachim "Umsetzungen von 2.3-Bis-alkylimino-oxetanen", Chem. Ber., vol. 102, pp. 159-168 (1969).

Li, L. et al. "PLA2G16 promotes osteosarcoma metastasis and drug resistance via the MAPK pathway", Oncotarget, vol. 7, No. 14, pp. 18021-18035 (2016).

Li, Z. et al. "Novel Peptidyl α-Keto Amide Inhibitors of Calpains and Other Cysteine Proteases", Journal of medicinal Chemistry, vol. 39, pp. 4089-4098 (1996).

Malkoch M. "Orthogonal Approaches to the Simultaneous and Cascade Functionalization of Macromolecules Using Click Chemistry", Journal of the American Chemical Society, vol. 127, No. 42, pp. 14942-14949 (2005).

Moffatt, B.A. et al. "Use of Bacteriophage T7 RNA Polymerase to Direct Selective High-Level Expression of Cloned Genes", J. Mol. Biol., vol. 189, pp. 113-130 (1986).

Ocain, T.D. et al. "α-Keto Amide Inhibitors of Aminopeptidases", J of Medicinal Chemistry, vol. 35, No. 3, pp. 451-456 (1992).

Ota, Eisuke et al. "Photo-induced Formation of cyclopropanols from a-ketomides via γ-C—H bond activation", Tetrahedron Letters, vol. 56, No. 44, pp. 5991-599 (2015).

Rosenberg, A.H. et al. "Vectors for selective expression of cloned DNAs by T7 RNA polymerase", Gene, vol. 56, pp. 125-135 (1987).

Tsuda, Makoto et al. "Poststatin, a New Inhibitor of Prolyl Endopeptidase" . . . ???, The Journal of Antibiotics, vol. 49, No. 10, pp. 1022-1030 (1996).

Weik, Steffen et al. "A Phosphorane as Supported Acylanion Equivalent: Linker Reagents for Smooth and Versatile C—C CouplingReactions", Angewandte Chemie International Edition, vol. 42, No. 22, pp. 2491-2494 (2003).

Xiong, S. et al. "Pla2g16 phospholipase mediates gain-of-function activities of mutant p53", Proc Natl Acad Sci U S A., vol. 111, No. 30, pp. 11145-11150 (2014).

International Patent Application No. PCT/EP2017/072880, International Search Report (dated Dec. 4, 2017).

International Patent Application No. PCT/EP2017/072880, Written Opinion (dated Dec. 4, 2017).

European Patent Appln. No. 16188559.5, Extended European Search Report dated Feb. 14, 2017.

International Patent Application No. PCT/EP2017/072880, International Preliminary Report of Patentability (dated Sep. 12, 2017).

* cited by examiner

ANTIVIRAL COMPOUNDS

CROSS-REFERENCE TO RELATED APPLICATIONS

This application is the U.S. national stage of International Patent Application No. PCT/EP2017/072880, filed on Sep. 12, 2017 and entitled ANTIVIRAL COMPOUNDS, which claims the benefit of priority under 35 U.S.C. § 119 from European Patent Application No. 16188559.5, filed Sep. 13, 2016. The disclosures of the foregoing applications are incorporated herein by reference in their entirety.

FIELD OF THE INVENTION

The present invention relates to novel compounds of general formula I

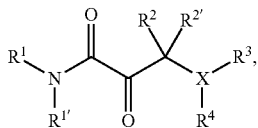

wherein the groups X, and $R^1$ to $R^4$ have the meanings given in the description and claims, process for preparing these compounds and their use as medicaments.

BACKGROUND ART

Viruses are major causes of disease and death throughout the world. Although vaccines and public health measures have greatly reduced the incidence of certain viral infections, such approaches have been less successful in tackling many viruses of significant medical and/or veterinary importance.

For example, chronic infection with hepatitis C virus (HCV) is a major health problem that affects more than 170 million people worldwide and is a causative agent of liver cirrhosis, hepatocellular carcinoma, and liver failure. Flaviviruses such as West Nile virus (WNV), Japanese Encephalitis virus (JEV), and the Dengue viruses (DENV) are significant human pathogens that cause millions of infections each year. Rhinoviruses are the most common viral infectious agents in humans and are the predominant cause of the common cold.

Pathogenic viruses can be classified into two general types with respect to the viral structure: enveloped viruses and non-enveloped viruses. Some well-known enveloped viruses include herpes virus, influenza virus, paramyxovirus, respiratory syncytial virus, corona virus, HIV, hepatitis B virus, hepatitis C virus and SARS-CoV virus. Non-enveloped viruses, sometimes referred to as "naked" viruses, include the families Picornaviridae, Reoviridae, Caliciviridae, Adenoviridae and Parvoviridae. Members of these families include rhinovirus, poliovirus, adenovirus, hepatitis A virus, norovirus, papillomavirus, and rotavirus.

The phospholipase A2, group XVI (PLA2G16) was identified as a new molecular target for antiviral drugs (WO2011160043).

PLA2G16 encodes an A2 group XVI phospholipase which is also reported to play roles in tumor metastasis (Xiong S. et al., Proc Natl Acad Sci USA. 2014 Jul. 29; 111(30), 11145-11150; Li L. et al., Oncotarget. 7(14), 18021-18035, 2016).

PLA2G16 has also been reported to play a crucial role in the development of obesity in mouse models (Jaworski K. et al., Nat. Med. 15 (2): 159-68, 2009).

Catalano John et al. disclose α-ketoamide-based small molecules as inhibitors of cathepsin K bearing a tert-butoxycarbonyl protecting group. The inhibitory compounds act as antiresorptive agent by attenuating type I collagen hydrolysis in bone (Bioorganic & Medicinal Chemistry Letters 2004, 14(3):719-722). Steffen Weik et al. describe phosphorane supported C—C coupling reaction for synthesis of α-ketocarbonyl products (Angewandte Chemie International Edition 2003, 42(22):2491-2494). Basso A et al. disclose solid-phase synthesis of modified oligopeptides via Passerini multicomponent reaction (Tetrahedron Letters 2003, 44(11):2367-2370). Li Z et al. describe novel peptityl α-keto amide inhibitors of capains and other cysteine proteases (Journal of Medicinal Chemistry 1996, 39:4089-4098). Makoto Tsuda et al., disclose endopeptidase inhibitory activity of non-peptidyl poststatin analogues wherein the pyrrolidine moiety does not bear an oxo substituent. (The Journal of Antibiotics 1996). Chatterjee S et al., disclose α-ketoamide inhibitors of calpain I (Bioorganic & Medicinal Chemistry Letters 1999, 9(16):2371-2374). WO98/25883 A1 describe ketobenzamides as calpain inhibitors. Ota Eisuke et al., describe photo-induced formation of cyclopropanols from α-ketoamides via γ-C—H bond activation (Tetrahedron Letters 2015, 56(44):5991-599). Antipicornaviral compounds are disclosed in WO01/10894. WO2013/049382 discloses antiviral agents bearing a pyrrolidin-2-one residue.

However, there are still relatively few viral diseases for which effective drugs are available. Thus, there is still a need for new antiviral compounds and for new approaches to identifying such compounds. It is a further aim of the present invention to provide for new compounds which have an inhibitory effect on the enzyme PLA2G16 in vitro and in vivo and have suitable pharmacological and/or pharmacokinetic properties to enable them to be used as medicaments.

SUMMARY OF INVENTION

It has surprisingly been found, that compounds of general formula I, wherein the groups X, and $R^1$ to $R^4$ have the meanings below, act as specific inhibitors against PLA2G16. The compounds according to the invention are specifically useful as antiviral compounds. Thus, the compounds according to the invention may be used for example for treating, preventing, and/or ameliorating viral infections.

Various objects, features, aspects, and advantages of the present invention will become more apparent from the following detailed description of embodiments of the invention.

DESCRIPTION OF EMBODIMENTS

The present invention relates to compounds of general formula I

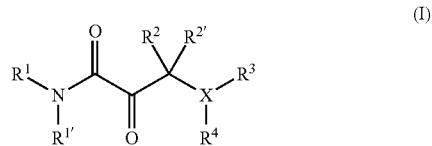

wherein
R¹ denotes H, —C(O)R$^a$, —(CH$_2$)$_n$C(O)OR$^a$ or a group, optionally substituted by one or more, identical or different R$^a$ and/or R$^b$, selected independently from one another among C$_{1-8}$alkyl, C$_{2-6}$alkenyl, C$_{2-6}$alkynyl, C$_{3-10}$cycloalkyl, C$_{6-10}$aryl, 3-8 membered heterocycloalkyl, and 5-12 membered heteroaryl, and R$^{1'}$ denotes H or C$_{1-4}$alkyl, or R$^1$ and R$^{1'}$ together with the adjacent nitrogen atom form a 4- to 10-membered heterocyclic group, which optionally may be substituted by one or more, identical or different R$^a$ and/or R$^b$;

X denotes —(CH$_2$)$_n$—N— or O;

R² denotes H, —C(O)R$^a$ or a group, optionally substituted by one or more, identical or different R$^a$ and/or R$^b$, selected independently from one another among C$_{1-6}$alkyl, C$_{2-6}$alkenyl, C$_{2-6}$alkynyl, C$_{3-10}$cycloalkyl, C$_{4-16}$cycloalkylalkyl, C$_{6-10}$aryl, C$_{7-16}$arylalkyl, 3-8 membered heterocycloalkyl, 5-12 membered heteroaryl and 6-18 membered heteroarylalkyl;

or R² forms together with R³ a 5-7 membered heterocycloalkyl ring when X denotes N, wherein said heterocycloalkyl ring bears an oxo group, and is optionally substituted by one or more, identical or different R$^a$ and/or R$^b$;

R$^{2'}$ denotes H or C$_{1-6}$alkyl;

R³ denotes H, —C(O)R$^c$, or —SO$_2$R$^a$; and

R⁴ denotes H, or a group, optionally substituted by one or more, identical or different R$^a$ and/or R$^b$, selected independently from one another among C$_{1-6}$alkyl, C$_{2-6}$alkenyl, C$_{2-6}$alkynyl, C$_{3-10}$cycloalkyl, C$_{4-16}$cycloalkyl, C$_{6-10}$aryl, C$_{7-16}$arylalkyl, 3-8 membered heterocycloalkyl, 4-14 membered heterocycloalkylalkyl, 5-12 membered heteroaryl, and 6-18 membered heteroarylalkyl;

or R⁴ form together with R³ a 4-6-membered heterocycloalkyl ring when X denotes —N—, wherein said heterocycloalkyl ring bears an oxo group, and is optionally substituted by one or more, identical or different R$^a$ and/or R$^b$; and n denotes 0, 1, 2 or 3;

each R$^a$ independently of one another denotes hydrogen or a group, optionally substituted by one or more, identical or different R$^b$ and/or R$^c$, selected from among C$_{1-6}$alkyl, C$_{2-6}$alkenyl, C$_{2-6}$alkynyl, C$_{3-10}$cycloalkyl, C$_{4-16}$cycloalkylalkyl, C$_{6-10}$aryl, C$_{7-16}$arylalkyl, 3-8 membered heterocycloalkyl, 4-14 membered heterocycloalkylalkyl, 5-12 membered heteroaryl and 6-18 membered heteroarylalkyl; each R$^b$ is a suitable substituent and is selected in each case independently of one another from among =O, —OR$^c$, C$_{1-3}$haloalkyloxy, —OCF$_3$, =S, —SR$^c$, =NR$^c$, =NOR$^c$, =NNR$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —O(CH$_2$)$_p$(CH$_2$)$_p$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^g$NR$^c$R$^c$, —N(R$^g$)N(R$^g$)C(O)NR$^c$R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$ and —N(R$^g$)C(NR$^g$)NR$^c$R$^c$;

each R$^c$ independently of one another denotes hydrogen or a group, optionally substituted by one or more, identical or different R$^d$ and/or R$^e$, selected from among C$_{1-6}$alkyl, C$_{2-6}$alkenyl, C$_{2-6}$alkynyl, C$_{3-10}$cycloalkyl, C$_{4-16}$cycloalkylalkyl, C$_{6-10}$aryl, C$_{7-16}$arylalkyl, 3-8 membered heterocycloalkyl, 4-14 membered heterocycloalkylalkyl, 5-12 membered heteroaryl and 6-18 membered heteroarylalkyl;

each R$^d$ denotes a suitable substituent and is selected in each case independently of one another from among =O, —OR$^e$, C$_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(OR$^e$)R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$; and each R$^e$ independently of one another denotes hydrogen or a group selected from among C$_{1-6}$alkyl, C$_{2-6}$alkenyl, C$_{2-6}$alkynyl, C$_{3-8}$cycloalkyl, C$_{6-10}$aryl, 3-8 membered heterocycloalkyl, and 5-12 membered heteroaryl; and each R$^g$ independently of one another denotes hydrogen, C$_{1-6}$alkyl, C$_{2-6}$alkenyl, C$_{2-6}$alkynyl, C$_{3-8}$cycloalkyl, C$_{6-10}$aryl, 3-8 membered heterocycloalkyl, or 5-12 membered heteroaryl; and p denotes independently from one another 1, 2, 3, or 4; and provided that when X denotes O R³ is absent and provided that when X denotes N— and R¹ and R$^{1'}$ denote hydrogen R³ and R⁴ are other than hydrogen; and provided that R² is not benzyl, and optionally in the form of the tautomers, the racemates, the enantiomers, the diastereomers, hydrates, isotopes, and mixtures thereof, and optionally the pharmacologically acceptable salts thereof.

One embodiment of the invention relates to compounds as described herein, wherein X is N.

One embodiment of the invention relates to compounds as described herein, wherein the 4- to 10-membered heterocyclic group formed by R¹ and R$^{1'}$ together with the adjacent nitrogen atom does not contain any additional heteroatom.

One embodiment of the invention relates to compounds as described herein, wherein R³ is —C(O)R$^c$.

One embodiment of the invention relates to compounds as described herein, wherein X is O.

One embodiment of the invention relates to compounds as described herein, wherein R⁴ is selected from optionally substituted C$_{1-6}$alkyl, C$_{3-6}$cycloalkyl, C$_6$aryl, 3-8 membered heterocycloalkyl, and 5-6 membered heteroaryl.

One embodiment of the invention relates to compounds as described herein, wherein $R^4$ is $C_{1-6}$alkyl.

One embodiment of the invention relates to compounds as described herein, wherein $R^2$ forms together with $R^3$ an oxo bearing pyrrolidinyl group.

One embodiment of the invention relates to compounds as described herein, wherein $R^{1'}$ is H.

One embodiment of the invention relates to compounds as described herein, wherein $R^1$ is optionally substituted $C_{1-6}$alkyl, $C_{3-6}$cycloalkyl, or $C_{4-16}$cycloalkylalkyl.

One embodiment of the invention relates to compounds as described herein, wherein $R^2$ is H.

One embodiment of the invention relates to compounds as described herein, wherein $R^2$ is optionally substituted $C_{1-6}$alkyl.

One embodiment of the invention relates to compounds of general formula II,

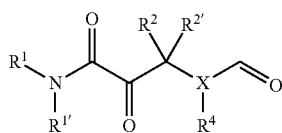

(II)

wherein

X denotes —(CH$_2$)$_n$—N—;

$R^1$ denotes H, —C(O)$R^a$, —(CH$_2$)$_n$C(O)O$R^a$, or a group, optionally substituted by one or more, identical or different $R^a$ and/or $R^b$, selected independently from one another among $C_{1-8}$alkyl, $C_{2-6}$alkenyl, $C_{2-6}$alkynyl, $C_{3-10}$cycloalkyl, $C_{6-10}$aryl, 3-8 membered heterocycloalkyl, and 5-12 membered heteroaryl;

$R^{1'}$ denotes H or $C_{1-4}$alkyl;

or $R^1$ and $R^{1'}$ together with the adjacent nitrogen atom form a 4- to 10-membered heterocyclic group, which optionally may be substituted by one or more, identical or different $R^a$ and/or $R^b$;

$R^2$ denotes H, —C(O)$R^a$, or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;

$R^{2'}$ denotes H or $C_{1-6}$alkyl;

$R^4$ denotes H, —C(O)$R^a$, or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{6-10}$aryl, 3-8 membered heterocycloalkyl, and 5-12 membered heteroaryl;

each $R^a$ independently of one another denotes hydrogen or a group, optionally substituted by one or more, identical or different $R^b$ and/or $R^c$, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;

each $R^b$ is a suitable substituent and is selected in each case independently of one another from among =O, —O$R^c$, $C_{1-3}$haloalkyloxy, —OCF$_3$, =S, —S$R^c$, =N$R^c$, =NO$R^c$, =NNR$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^g$NR$^c$R$^c$, —N(R$^g$)N(R$^g$)C(O)NR$^c$R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$ and —N(R$^g$)C(NR$^g$)NR$^c$R$^c$;

each $R^c$ independently of one another denotes hydrogen or a group, optionally substituted by one or more, identical or different $R^d$ and/or $R^e$, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;

each $R^d$ denotes a suitable substituent and is selected in each case independently of one another from among =O, —O$R^e$, $C_{1-3}$haloalkyloxy, —OCF$_3$, =S, —S$R^e$, =N$R^e$, =NO$R^e$, =NNR$^e$R$^e$, =NN(R$^g$)C(O)NR$^e$R$^e$, —NR$^e$R$^e$, —ONR$^e$R$^e$, —N(OR$^e$)R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$;

each $R^e$ independently of one another denotes hydrogen or a group selected from among $C_{1-6}$alkyl, $C_{2-6}$alkenyl, $C_{2-6}$alkynyl, $C_{3-8}$cycloalkyl, $C_{6-10}$aryl, 3-8 membered heterocycloalkyl, and 5-12 membered heteroaryl;

each $R^g$ independently of one another denotes hydrogen, $C_{1-6}$alkyl, $C_{2-6}$alkenyl, $C_{2-6}$alkynyl, $C_{3-8}$cycloalkyl, $C_{6-10}$aryl, 3-8 membered heterocycloalkyl, or 5-12 membered heteroaryl;

n denotes 0, 1, 2 or 3;

optionally in the form of the tautomers, the racemates, the enantiomers, the diastereomers, hydrates, isotopes, and the mixtures thereof, and optionally the pharmacologically acceptable salts thereof.

One embodiment of the invention relates to compounds of general formula II as described herein, wherein X is N.

One embodiment of the invention relates to compounds of general formula II as described herein, wherein $R^4$ is selected from optionally substituted $C_{1-6}$alkyl, $C_{3-6}$cycloalkyl, phenyl, 3-8 membered heterocycloalkyl, and 5-6 membered heteroaryl.

One embodiment of the invention relates to compounds of general formula II as described herein, wherein $R^{1'}$ is H.

One embodiment of the invention relates to compounds of general formula II as described herein, wherein $R_1$ is optionally substituted $C_{1-6}$alkyl or $C_{3-6}$cycloalkyl.

One embodiment of the invention relates to compounds of general formula II as described herein, wherein $R^{2'}$ is H.

One embodiment of the invention relates to compounds of general formula II as described herein, wherein $R^2$ is optionally substituted $C_{1-6}$alkyl.

One embodiment of the invention relates to compounds of general formula III,

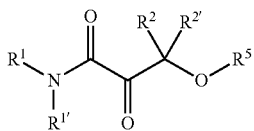

(III)

wherein $R^1$ denotes H, —C(O)$R^a$, —(CH$_2$)$_n$C(O)OR$^a$, or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{6-10}$aryl, 3-8 membered heterocycloalkyl, and 5-12 membered heteroaryl;

$R^{1'}$ denotes H or $C_{1-4}$alkyl;

or $R^1$ and $R^{1'}$ together with the adjacent nitrogen atom form a 4- to 10-membered heterocyclic group, which optionally may be substituted by one or more, identical or different $R^a$ and/or $R^b$;

$R^2$ denotes H, —C(O)$R^a$, or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;

$R^{2'}$ denotes H or $C_{1-6}$alkyl;

$R^5$ denotes a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{6-10}$aryl, 3-8 membered heterocycloalkyl, and 5-12 membered heteroaryl;

each $R^a$ independently of one another denotes hydrogen or a group, optionally substituted by one or more, identical or different $R^b$ and/or $R^c$, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;

each $R^b$ is a suitable substituent and is selected in each case independently of one another from among =O, —OR$^c$, $C_{1-3}$haloalkyloxy, —OCF$_3$, =S, —SR$^c$, =NR$^c$, =NOR$^c$, =NNR$^c$R$^c$, =NN(R$^g$)C(O)NR$^c$R$^c$, —NR$^c$R$^c$, —ONR$^c$R$^c$, —N(OR$^c$)R$^c$, —N(R$^g$)NR$^c$R$^c$, halogen, —CF$_3$, —CN, —NC, —OCN, —SCN, —NO, —NO$_2$, =N$_2$, —N$_3$, —S(O)R$^c$, —S(O)OR$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)NR$^c$R$^c$, —OS(O)$_2$NR$^c$R$^c$, —C(O)R$^c$, —C(O)OR$^c$, —C(O)SR$^c$, —C(O)NR$^c$R$^c$, —C(O)N(R$^g$)NR$^c$R$^c$, —C(O)N(R$^g$)OR$^c$, —C(NR$^g$)NR$^c$R$^c$, —C(NOH)R$^c$, —C(NOH)NR$^c$R$^c$, —OC(O)R$^c$, —OC(O)OR$^c$, —OC(O)SR$^c$, —OC(O)NR$^c$R$^c$, —OC(NR$^g$)NR$^c$R$^c$, —SC(O)R$^c$, —SC(O)OR$^c$, —SC(O)NR$^c$R$^c$, —SC(NR$^g$)NR$^c$R$^c$, —N(R$^g$)C(O)R$^c$, —N[C(O)R$^c$]$_2$, —N(OR$^g$)C(O)R$^c$, —N(R$^g$)C(NR$^g$)R$^c$, —N(R$^g$)N(R$^g$)C(O)R$^c$, —N[C(O)R$^c$]NR$^c$R$^c$, —N(R$^g$)C(S)R$^c$, —N(R$^g$)S(O)R$^c$, —N(R$^g$)S(O)OR$^c$, —N(R$^g$)S(O)$_2$R$^c$, —N[S(O)$_2$R$^c$]$_2$, —N(R$^g$)S(O)$_2$OR$^c$, —N(R$^g$)S(O)$_2$NR$^c$R$^c$, —N(R$^g$)[S(O)$_2$]$_2$R$^c$, —N(R$^g$)C(O)OR$^c$, —N(R$^g$)C(O)SR$^c$, —N(R$^g$)C(O)NR$^c$R$^c$, —N(R$^g$)C(O)NR$^g$NR$^c$R$^c$, —N(R$^g$)N(R$^g$)C(O)NR$^c$R$^c$, —N(R$^g$)C(S)NR$^c$R$^c$, —[N(R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$ and —N(R$^g$)C(NR$^g$)NR$^c$R$^c$;

each $R^c$ independently of one another denotes hydrogen or a group, optionally substituted by one or more, identical or different $R^d$ and/or $R^e$, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;

each $R^d$ denotes a suitable substituent and is selected in each case independently of one another from among =O, —OR$^e$, $C_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(OR$^e$)R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$;

each $R^e$ independently of one another denotes hydrogen or a group selected from among $C_{1-6}$alkyl, $C_{2-6}$alkenyl, $C_{2-6}$alkynyl, $C_{3-8}$cycloalkyl, $C_{6-10}$aryl, 3-8 membered heterocycloalkyl, and 5-12 membered heteroaryl; and each $R^c$ independently of one another denotes hydrogen, $C_{1-6}$alkyl, $C_{2-6}$alkenyl, $C_{2-6}$alkynyl, $C_{3-8}$cycloalkyl, $C_{6-10}$aryl, 3-8 membered heterocycloalkyl, or 5-12 membered heteroaryl;

n denotes 0, 1, 2, or 3;

optionally in the form of the tautomers, the racemates, the enantiomers, the diastereomers, hydrates, isotopes, and the mixtures thereof, and optionally the pharmacologically acceptable salts thereof.

One embodiment of the invention relates to compounds of general formula III as described herein, wherein $R^{1'}$ is H.

One embodiment of the invention relates to compounds of general formula III as described herein, wherein $R^1$ is optionally substituted $C_{1-6}$alkyl or $C_{3-6}$cycloalkyl.

One embodiment of the invention relates to compounds of general formula III as described herein, wherein $R^{2'}$ is H.

One embodiment of the invention relates to compounds of general formula III as described herein, wherein $R^2$ is optionally substituted $C_{1-6}$alkyl.

One embodiment of the invention relates to compounds of general formula IV,

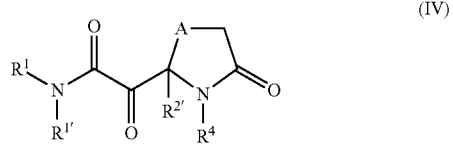

(IV)

wherein

A denotes N, O, S, or —$(CH_2)_m$— and is optionally substituted by $R^e$;

$R^1$ denotes H, —C(O)$R^a$, —$(CH_2)_n$C(O)O$R^a$, or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{6-10}$aryl, 3-8 membered heterocycloalkyl, and 5-12 membered heteroaryl;

$R^{1'}$ denotes H or $C_{1-4}$alkyl;

or $R^1$ and $R^{1'}$ together with the adjacent nitrogen atom form a 4- to 10-membered heterocyclic group, which optionally may be substituted by one or more, identical or different $R^a$ and/or $R^b$;

$R^2$ denotes H or $C_{1-6}$alkyl;

$R^4$ denotes H, —C(O)$R^a$, or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{6-10}$aryl, 3-8 membered heterocycloalkyl, and 5-12 membered heteroaryl;

each $R^a$ independently of one another denotes hydrogen or a group, optionally substituted by one or more, identical or different $R^b$ and/or $R^c$, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;

each $R^b$ is a suitable substituent and is selected in each case independently of one another from among =O, —O$R^e$, $C_{1-3}$haloalkyloxy, —OCF$_3$, =S, —S$R^e$, =N$R^e$, =NO$R^e$, =NN$R^e R^e$, =NN($R^g$)C(O)N$R^e R^e$, —N$R^e R^e$, —ON$R^e R^e$, —N(O$R^e$)$R^e$, —N($R^g$)N$R^e R^e$, halogen, —CF$_3$, —CN, —NC, —OCN, —SCN, —NO, —NO$_2$, =N$_2$, —N$_3$, —S(O)$R^e$, —S(O)O$R^e$, —S(O)$_2 R^e$, —S(O)$_2$O$R^e$, —S(O)N$R^e R^e$, —S(O)$_2$N$R^e R^e$, —OS(O)$R^e$, —OS(O)$_2 R^e$, —OS(O)$_2$O$R^e$, —OS(O)N$R^e R^e$, —OS(O)$_2$N$R^e R^e$, —C(O)$R^e$, —C(O)O$R^e$, —C(O)S$R^e$, —C(O)N$R^e R^e$, —C(O)N($R^g$)N$R^e R^e$, —C(O)N($R^g$)O$R^e$, —C(N$R^g$)N$R^e R^e$, —C(NOH)$R^e$, —C(NOH)N$R^e R^e$, —OC(O)$R^e$, —OC(O)O$R^e$, —OC(O)S$R^e$, —OC(O)N$R^e R^e$, —OC(N$R^g$)N$R^e R^e$, —SC(O)$R^e$, —SC(O)O$R^e$, —SC(O)N$R^e R^e$, —SC(N$R^g$)N$R^e R^e$, —N($R^g$)C(O)$R^e$, —N[C(O)$R^e$]$_2$, —N(O$R^g$)C(O)$R^e$, —N($R^g$)C(N$R^g$)$R^e$, —N($R^g$)N($R^g$)C(O)$R^e$, —N[C(O)$R^e$]N$R^e R^e$, —N($R^g$)C(S)$R^e$, —N($R^g$)S(O)$R^e$, —N($R^g$)S(O)O$R^e$, —N($R^g$)S(O)$_2 R^e$, —N[S(O)$_2 R^e$]$_2$, —N($R^g$)S(O)$_2$O$R^e$, —N($R^g$)S(O)$_2$N$R^e R^e$, —N($R^g$)[S(O)$_2$]$_2 R^e$, —N($R^g$)C(O)O$R^e$, —N($R^g$)C(O)S$R^e$, —N($R^g$)C(O)N$R^e R^e$, —N($R^g$)C(O) N$R^g$N$R^e R^e$, —N($R^g$)N($R^g$)C(O)N$R^e R^e$, —N($R^g$)C(S) N$R^e R^e$, —[N($R^g$)C(O)]$_2 R^e$, —N($R^g$)[C(O)]$_2 R^e$, —N{[C (O)]$_2 R^e$}$_2$, —N($R^g$)[C(O)]$_2$O$R^e$, —N($R^g$)[C(O)]$_2$N$R^e R^e$, —N{[C(O)]$_2$O$R^e$}$_2$, —N{[C(O)]$_2$N$R^e R^e$}$_2$, —[N($R^g$) C(O)]$_2$O$R^e$, —N($R^g$)C(N$R^g$)O$R^e$, —N($R^g$)C(NOH)$R^e$, —N($R^g$)C(N$R^g$)S$R^e$ and —N($R^g$)C(N$R^g$)N$R^e R^e$;

each $R^c$ independently of one another denotes hydrogen or a group, optionally substituted by one or more, identical or different $R^d$ and/or $R^e$, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;

each $R^d$ denotes a suitable substituent and is selected in each case independently of one another from among =O, —O$R^e$, $C_{1-3}$haloalkyloxy, —OCF$_3$, =S, —S$R^e$, =N$R^e$, =NO$R^e$, =NN$R^e R^e$, =NN($R^g$)C(O)N$R^e R^e$, —N$R^e R^e$, —ON$R^e R^e$, —N(O$R^e$)$R^e$, —N($R^g$)N$R^e R^e$, halogen, —CF$_3$, —CN, —NC, —OCN, —SCN, —NO, —NO$_2$, =N$_2$, —N$_3$, —S(O)$R^e$, —S(O)O$R^e$, —S(O)$_2 R^e$, —S(O)$_2$O$R^e$, —S(O) N$R^e R^e$, —S(O)$_2$N$R^e R^e$, —OS(O)$R^e$, —OS(O)$_2 R^e$, —OS (O)$_2$O$R^e$, —OS(O)N$R^e R^e$, —OS(O)$_2$N$R^e R^e$, —C(O)$R^e$, —C(O)O$R^e$, —C(O)S$R^e$, —C(O)N$R^e R^e$, —C(O)N($R^g$) N$R^e R^e$, —C(O)N($R^g$)O$R^e$, —C(N$R^g$)N$R^e R^e$, —C(NOH)$R^e$, —C(NOH)N$R^e R^e$, —OC(O)$R^e$, —OC(O)O$R^e$, —OC(O) S$R^e$, —OC(O)N$R^e R^e$, —OC(N$R^g$)N$R^e R^e$, —SC(O)$R^e$, —SC(O)O$R^e$, —SC(O)N$R^e R^e$, —SC(N$R^g$)N$R^e R^e$, —N($R^g$) C(O)$R^e$, —N[C(O)$R^e$]$_2$, —N(O$R^g$)C(O)$R^e$, —N($R^g$)C (N$R^g$)$R^e$, —N($R^g$)N($R^g$)C(O)$R^e$, —N[C(O)$R^e$]N$R^e R^e$, —N($R^g$)C(S)$R^e$, —N($R^g$)S(O)$R^e$, —N($R^g$)S(O)O$R^e$, —N($R^g$)S(O)$_2 R^e$, —N[S(O)$_2 R^e$]$_2$, —N($R^g$)S(O)$_2$O$R^e$, —N($R^g$)S(O)$_2$N$R^e R^e$, —N($R^g$)[S(O)$_2$]$_2 R^e$, —N($R^g$)C(O) O$R^e$, —N($R^g$)C(O)S$R^e$, —N($R^g$)C(O)N$R^e R^e$, —N($R^g$)C(O) N$R^g$N$R^e R^e$, —N($R^g$)N($R^g$)C(O)N$R^e R^e$, —N($R^g$)C(S) N$R^e R^e$, —[N($R^g$)C(O)]$_2 R^e$, —N($R^g$)[C(O)]$_2 R^e$, —N{[C (O)]$_2 R^e$}$_2$, —N($R^g$)[C(O)]$_2$O$R^e$, —N($R^g$)[C(O)]$_2$N$R^e R^e$, —N{[C(O)]$_2$O$R^e$}$_2$, —N{[C(O)]$_2$N$R^e R^e$}$_2$, —[N($R^g$) C(O)]$_2$O$R^e$, —N($R^g$)C(N$R^g$)O$R^e$, —N($R^g$)C(NOH)$R^e$, —N($R^g$)C(N$R^g$)S$R^e$ and —N($R^g$)C(N$R^g$)N$R^e R^e$;

each $R^e$ independently of one another denotes hydrogen or a group selected from among $C_{1-6}$alkyl, $C_{2-6}$alkenyl, $C_{2-6}$alkynyl, $C_{3-8}$acycloalkyl, $C_{6-10}$aryl, 3-8 membered heterocycloalkyl, and 5-12 membered heteroaryl;

each $R^g$ independently of one another denotes hydrogen, $C_{1-6}$alkyl, $C_{2-6}$alkenyl, $C_{2-6}$alkynyl, $C_{3-8}$cycloalkyl, $C_{6-10}$aryl, 3-8 membered heterocycloalkyl, or 5-12 membered heteroaryl;

m denotes 1, 2 or 3;

n denotes 0, 1, 2, or 3;

optionally in the form of the tautomers, the racemates, the enantiomers, the diastereomers, hydrates, isotopes, and the mixtures thereof, and optionally the pharmacologically acceptable salts thereof.

One embodiment of the invention relates to compounds of general formula IV as described herein, wherein A is —(CH$_2$)—.

One embodiment of the invention relates to compounds of general formula IV as described herein, wherein $R^1$ is optionally substituted $C_{1-6}$alkyl or $C_{3-6}$cycloalkyl.

One embodiment of the invention relates to compounds of general formula IV as described herein, wherein $R^4$ is selected from optionally substituted $C_{1-6}$alkyl, $C_{3-6}$cycloalkyl, $C_6$aryl, 3-8 membered heterocycloalkyl, and 5-6 membered heteroaryl.

One embodiment of the invention relates to compounds of general formula V

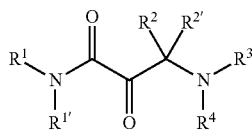

wherein
R¹ denotes H, —C(O)Rᵃ, —(CH₂)ₙC(O)ORᵃ, or a group, optionally substituted by one or more, Rᵃ and/or Rᵇ, selected independently from one another among $C_{1-8}$alkyl, $C_{2-6}$alkenyl, $C_{2-6}$alkynyl, $C_{3-10}$cycloalkyl, $C_{6-10}$aryl, 3-8 membered heterocycloalkyl, and 5-12 membered heteroaryl;
R¹' denotes H or $C_{1-4}$alkyl;
or R¹ and R¹' together with the adjacent nitrogen atom form a 4- to 10-membered heterocyclic group; which optionally may be substituted by one or more, identical or different Rᵃ and/or Rᵇ;
R² denotes H, —C(O)Rᵃ, or a group, optionally substituted by one or more, identical or different Rᵃ and/or Rᵇ, selected independently from one another among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;
or R² forms together with R³ and the adjacent nitrogen a 5-7 membered heterocycloalkyl ring, wherein said heterocycloalkyl ring bears an oxo group, and optionally is substituted by one or more, identical or different Rᵃ and/or Rᵇ;
R²' denotes H or $C_{1-6}$alkyl;
R³ denotes H, —C(O)Rᶜ, —C(O)ORᵃ, —SO₂Rᵃ or a group, optionally substituted by one or more, identical or different Rᵃ and/or Rᵇ, selected independently from one another among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 4-14 membered heterocycloalkylalkyl, 5-12 membered heteroaryl and 6-18 membered heteroarylalkyl;
R⁴ denotes H, —C(O)Rᵃ, or a group, optionally substituted by one or more, identical or different Rᵃ and/or Rᵇ, selected independently from one another among $C_{1-6}$alkyl, $C_{2-6}$alkenyl, $C_{2-6}$alkynyl, $C_{3-10}$cycloalkyl, $C_{6-10}$aryl, 3-8 membered heterocycloalkyl, and 5-12 membered heteroaryl;
or R⁴ and R³ form together with the adjacent nitrogen atom a 4- to 6-membered heterocycloalkyl ring, wherein said heterocycloalkyl ring bears an oxo group, and
optionally is substituted by one or more, identical or different Rᵃ and/or Rᵇ; each Rᵃ independently of one another denotes hydrogen or a group, optionally substituted by one or more, identical or different Rᵇ and/or Rᶜ, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;
each Rᵇ is a suitable substituent and is selected in each case independently of one another from among =O, —ORᶜ, $C_{1-3}$haloalkyloxy, —OCF₃, =S, —SRᶜ, =NRᶜ, =NORᶜ, =NNRᶜRᶜ, =NN(Rᵍ)C(O)NRᶜRᶜ, —NRᶜRᶜ, —ONRᶜRᶜ, —N(ORᶜ)Rᶜ, —N(Rᵍ)NRᶜRᶜ, halogen, —CF₃, —CN, —NC, —OCN, —SCN, —NO, —NO₂, =N₂, —N₃, —S(O)Rᶜ, —S(O)ORᶜ, —S(O)₂Rᶜ, —S(O)₂ORᶜ, —S(O)NRᶜRᶜ, —S(O)₂NRᶜRᶜ, —OS(O)Rᶜ, —OS(O)₂Rᶜ, —OS(O)₂ORᶜ, —OS(O)NRᶜRᶜ, —OS(O)₂NRᶜRᶜ, —C(O)Rᶜ, —C(O)ORᶜ, —C(O)SRᶜ, —C(O)NRᶜRᶜ, —C(O)N(Rᵍ)NRᶜRᶜ, —C(O)N(Rᵍ)ORᶜ, —C(NRᵍ)NRᶜRᶜ, —C(NOH)Rᶜ, —C(NOH)NRᶜRᶜ, —OC(O)Rᶜ, —OC(O)ORᶜ, —OC(O)SRᶜ, —OC(O)NRᶜRᶜ, —OC(NRᵍ)NRᶜRᶜ, —SC(O)Rᶜ, —SC(O)ORᶜ, —SC(O)NRᶜRᶜ, —SC(NRᵍ)NRᶜRᶜ, —N(Rᵍ)C(O)Rᶜ, —N[C(O)Rᶜ]₂, —N(ORᵍ)C(O)Rᶜ, —N(Rᵍ)C(NRᵍ)Rᶜ, —N(Rᵍ)N(Rᵍ)C(O)Rᶜ, —N[C(O)Rᶜ]NRᶜRᶜ, —N(Rᵍ)C(S)Rᶜ, —N(Rᵍ)S(O)Rᶜ, —N(Rᵍ)S(O)ORᶜ, —N(Rᵍ)S(O)₂Rᶜ, —N[S(O)₂Rᶜ]₂, —N(Rᵍ)S(O)₂ORᶜ, —N(Rᵍ)S(O)₂NRᶜRᶜ, —N(Rᵍ)[S(O)₂]₂Rᶜ, —N(Rᵍ)C(O)ORᶜ, —N(Rᵍ)C(O)SRᶜ, —N(Rᵍ)C(O)NRᶜRᶜ, —N(Rᵍ)C(O)NRᵍNRᶜRᶜ, —N(Rᵍ)N(Rᵍ)C(O)NRᶜRᶜ, —N(Rᵍ)C(S)NRᶜRᶜ, —[N(Rᵍ)C(O)]₂Rᶜ, —N(Rᵍ)[C(O)]₂Rᶜ, —N{[C(O)]₂Rᶜ}₂, —N(Rᵍ)[C(O)]₂ORᶜ, —N(Rᵍ)[C(O)]₂NRᶜRᶜ, —N{[C(O)]₂ORᶜ}₂, —N{[C(O)]₂NRᶜRᶜ}₂, —[N(Rᵍ)C(O)]₂ORᶜ, —N(Rᵍ)C(NRᵍ)ORᶜ, —N(Rᵍ)C(NOH)Rᶜ, —N(Rᵍ)C(NRᵍ)SRᶜ and —N(Rᵍ)C(NRᵍ)NRᶜRᶜ;
each Rᶜ independently of one another denotes hydrogen or a group, optionally substituted by one or more, identical or different Rᵈ and/or Rᵉ, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl; each Rᵈ denotes a suitable substituent and is selected in each case independently of one another from among =O, —ORᵉ, $C_{1-3}$haloalkyloxy, —OCF₃, =S, —SRᵉ, =NRᵉ, =NORᵉ, =NNRᵉRᵉ, =NN(Rᵍ)C(O)NRᵉRᵉ, —NRᵉRᵉ, —ONRᵉRᵉ, —N(ORᵉ)Rᵉ, —N(Rᵍ)NRᵉRᵉ, halogen, —CF₃, —CN, —NC, —OCN, —SCN, —NO, —NO₂, =N₂, —N₃, —S(O)Rᵉ, —S(O)ORᵉ, —S(O)₂Rᵉ, —S(O)₂ORᵉ, —S(O)NRᵉRᵉ, —S(O)₂NRᵉRᵉ, —OS(O)Rᵉ, —OS(O)₂Rᵉ, —OS(O)₂ORᵉ, —OS(O)NRᵉRᵉ, —OS(O)₂NRᵉRᵉ, —C(O)Rᵉ, —C(O)ORᵉ, —C(O)SRᵉ, —C(O)NRᵉRᵉ, —C(O)N(Rᵍ)NRᵉRᵉ, —C(O)N(Rᵍ)ORᵉ, —C(NRᵍ)NRᵉRᵉ, —C(NOH)Rᵉ, —C(NOH)NRᵉRᵉ, —OC(O)Rᵉ, —OC(O)ORᵉ, —OC(O)SRᵉ, —OC(O)NRᵉRᵉ, —OC(NRᵍ)NRᵉRᵉ, —SC(O)Rᵉ, —SC(O)ORᵉ, —SC(O)NRᵉRᵉ, —SC(NRᵍ)NRᵉRᵉ, —N(Rᵍ)C(O)Rᵉ, —N[C(O)Rᵉ]₂, —N(ORᵍ)C(O)Rᵉ, —N(Rᵍ)C(NRᵍ)Rᵉ, —N(Rᵍ)N(Rᵍ)C(O)Rᵉ, —N[C(O)Rᵉ]NRᵉRᵉ, —N(Rᵍ)C(S)Rᵉ, —N(Rᵍ)S(O)Rᵉ, —N(Rᵍ)S(O)ORᵉ, —N(Rᵍ)S(O)₂Rᵉ, —N[S(O)₂Rᵉ]₂, —N(Rᵍ)S(O)₂ORᵉ, —N(Rᵍ)S(O)₂NRᵉRᵉ, —N(Rᵍ)[S(O)₂]₂Rᵉ, —N(Rᵍ)C(O)ORᵉ, —N(Rᵍ)C(O)SRᵉ, —N(Rᵍ)C(O)NRᵉRᵉ, —N(Rᵍ)C(O)NRᵍNRᵉRᵉ, —N(Rᵍ)N(Rᵍ)C(O)NRᵉRᵉ, —N(Rᵍ)C(S)NRᵉRᵉ, —[N(Rᵍ)C(O)]₂Rᵉ, —N(Rᵍ)[C(O)]₂Rᵉ, —N{[C(O)]₂Rᵉ}₂, —N(Rᵍ)[C(O)]₂ORᵉ, —N(Rᵍ)[C(O)]₂NRᵉRᵉ, —N{[C(O)]₂ORᵉ}₂, —N{[C(O)]₂NRᵉRᵉ}₂, —[N(Rᵍ)C(O)]₂ORᵉ, —N(Rᵍ)C(NRᵍ)ORᵉ, —N(Rᵍ)C(NOH)Rᵉ, —N(Rᵍ)C(NRᵍ)SRᵉ and —N(Rᵍ)C(NRᵍ)NRᵉRᵉ;
each Rᵉ independently of one another denotes hydrogen or a group selected from among $C_{1-6}$alkyl, $C_{2-6}$alkenyl, $C_{2-6}$alkynyl, $C_{3-8}$cycloalkyl, $C_{6-10}$aryl, 3-8 membered heterocycloalkyl, and 5-12 membered heteroaryl;
each Rᵍ independently of one another denotes hydrogen, $C_{1-6}$alkyl, $C_{2-6}$alkenyl, $C_{2-6}$alkynyl, $C_{3-8}$cycloalkyl, $C_{6-10}$aryl, 3-8 membered heterocycloalkyl, or 5-12 membered heteroaryl;
n denotes 0, 1, 2 or 3;
optionally in the form of the tautomers, the racemates, the enantiomers, the diastereomers, hydrates, isotopes, and the mixtures thereof, and optionally the pharmacologically acceptable salts thereof.

One embodiment of the invention relates to compounds of general formula V as described herein, wherein R¹ is optionally substituted $C_{1-6}$alkyl or $C_{3-6}$cycloalkyl.

One embodiment of the invention relates to compounds of general formula V as described herein, wherein $R^3$ is —C(O)$R^c$, or —SO$_2$$R^a$.

One embodiment of the invention relates to compounds of general formula V as described herein, wherein $R^4$ is H or optionally substituted $C_{1-6}$alkyl, $C_{3-6}$cycloalkyl, or phenyl.

One embodiment of the invention relates to compounds as described herein, wherein the compounds are selected from Table 2.

One embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use as medicament.

The invention contemplates treatment of a wide variety of viral infections in human and/or animal subjects, e.g., infection due to any virus. In some embodiments, the virus is a picornavirus, e.g., a cardiovirus, enterovirus (e.g. a coxsackievirus, a rhinovirus, a poliovirus or echovirus), or hepatovirus. In some embodiments, the virus clusters phylogenetically within the enterovirus genus. In some embodiments, the picornavirus is classified with a species selected from the group consisting of: human enterovirus A, human enterovirus B, human enterovirus C, human enterovirus D, simian enterovirus A, bovine enterovirus, porcine enterovirus B, human rhinovirus A, human rhinovirus B and human rhinovirus C. In some embodiments, the picornavirus is classified with a species selected from the group consisting of: human enterovirus A, human enterovirus B, human enterovirus C, human enterovirus D, human rhinovirus A, human rhinovirus B and human rhinovirus C.

The invention provides use of the compounds for treating diseases and medical conditions resulting from viral infection, e.g., by a picornavirus. Exemplary diseases and conditions include, e.g., asthma exacerbation, bronchiolitis, colitis, common cold, COPD exacerbation, encephalitis, encephalomyelitis, enterocolitis, foot-and-mouth disease, hand-foot-and-mouth disease, gastroenteritis, herpangina, hepatitis, meningitis, meningoencephalitis, myocarditis, pancreatitis, poliomyelitis, and pneumonia. In some aspects, the invention contemplates ex vivo uses of the PLA2G16 inhibitors.

Thus, one embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use as antiviral agents.

A further embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use in the treatment or prevention of infectious diseases, cancer or obesity.

One embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use in treating, preventing, and/or ameliorating viral infections.

One embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use in treating, preventing, and/or ameliorating viral infections caused by a picornavirus, e.g. by a rhinovirus.

One embodiment of the invention relates to pharmaceutical preparations containing as active substance one or more compounds of general formula I as described herein, optionally in the form of the tautomers, the racemates, the enantiomers, the diastereomers, hydrates, isotopes, and mixtures thereof, or the pharmacologically acceptable salt thereof, or the pharmacologically acceptable salts thereof, optionally in combination with conventional excipients and/or carriers.

One embodiment of the invention relates to pharmaceutical preparations comprising a compound of general formula I as described herein, wherein the compounds are optionally present in the form of the tautomers, racemates, enantiomers, diastereomers, hydrates, isotopes, and mixtures thereof, or also as the respective pharmacologically acceptable salts of all the above mentioned forms, and at least one further active substance different from formula I.

Definition

As used herein, the following definitions apply, unless stated otherwise:

Unless specified otherwise, the term "alkyl", when used alone or in combination with other groups or atoms, refers to a saturated straight or branched chain consisting solely of 1 to 6 hydrogen-substituted carbon atoms, and includes methyl, ethyl, propyl, isopropyl, n-butyl, 1-methylpropyl, isobutyl, tert-butyl, 2,2-dimethylbutyl, 2,2-dimethylpropyl, n-pentyl, 2-methylpentyl, 3-methylpentyl, 4-methylpentyl, n-hexyl and the like.

Unless specified otherwise, the term "alkenyl" refers to a partially unsaturated straight or branched chain consisting solely of 2 to 6 hydrogen-substituted carbon atoms that contains at least one double bond, and includes vinyl, allyl, 2-methylprop-1-enyl, but-1-enyl, but-2-enyl, but-3-enyl, buta-1,3-dienyl, penta-1,3-dienyl, penta-2,4-dienyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

Unless specified otherwise, the term "alkynyl" refers to a partially unsaturated straight or branched chain consisting solely of 2 to 6 hydrogen-substituted carbon atoms that contains at least one triple bond, and includes ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl, 4-methylpent-2-ynyl, 1-hexynyl, and the like.

Unless specified otherwise, the term "cycloalkyl", when used alone or in combination with other groups or atoms, refers to monocyclic hydrocarbon rings, bicyclic hydrocarbon rings or spirohydrocarbon rings, which each may be either saturated or unsaturated (cycloalkenyl). The term unsaturated means that in the ring system in question there is at least one double bond, but no aromatic system is formed. In bicyclic hydrocarbon rings two rings are linked such that they have at least two carbon atoms in common. In spirohydrocarbon rings one carbon atom (spiroatom) is shared by two rings. If a cycloalkyl is substituted, the substitution may be mono- or polysubstitution in each case, at all the hydrogen-carrying carbon atoms, independently of one another. Cycloalkyl itself may be linked to the molecule as substituent via any suitable position of the ring system.

Typical examples of individual sub-groups are listed below.

Monocyclic saturated hydrocarbon rings: cyclopropyl; cyclobutyl; cyclopentyl; cyclohexyl; cycloheptyl; etc.

Monocyclic unsaturated hydrocarbon rings: cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl, etc. Saturated and unsaturated bicyclic hydrocarbon rings: bicyclo[1.1.1]pentyl, bicyclo[2.2.0]hexyl; bicyclo[3.2.0]heptyl; bicyclo[3.2.1]octyl; bicyclo[2.2.2]octyl; bicyclo[4.3.0]nonyl (octahydroindenyl); bicyclo[4.4.0]decyl (decahydronaphthalene); bicyclo[2,2,1]heptyl (norbornyl); (bicyclo[2.2.1]hepta-2,5-dienyl (norborna-2,5-dienyl); bicyclo[2,2,1]hept-2-enyl (norbornenyl); bicyclo[4.1.0]heptyl (norcaranyl); bicyclo-[3.1.1]heptyl (pinanyl), etc.
Saturated and unsaturated spirohydrocarbon rings: spiro[2.5]octyl, spiro[3.3]heptyl, spiro[4.5]dec-2-ene, etc.

"Cycloalkylalkyl" denotes the combination of the above-defined groups alkyl, alkenyl, alkynyl, and cycloalkyl, in each case in their broadest sense. The alkyl group as substituent is directly linked to the molecule and is in turn substituted by a cycloalkyl group. The alkyl and cycloalkyl may be linked in both groups via any carbon atoms suitable for this purpose. The respective sub-groups of alkyl and cycloalkyl are also included in the combination of the two groups.

Unless specified otherwise, the term "aryl" refers to an aromatic mono- or bicyclic group containing from 6 to 14 carbon atoms, preferably 6 to 10 carbon atoms, that may be optionally fused with a fully or partially saturated or unsaturated carbocyclic ring and may optionally be substituted with one or more, identical or different substituents, suitably one to three substituents. Examples of aryl groups include phenyl, naphthyl, indanyl, and the like.

"Arylalkyl" denotes the combination of the groups alkyl, alkenyl, alkynyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. Typical examples include benzyl, 1-phenylethyl, 2-phenylethyl, phenylvinyl, phenylallyl, etc.

Unless specified otherwise, the term "heteroaryl" refers to an aromatic mono- or bicyclic group containing from 5 to 14 carbon atoms, preferably 5 to 12 carbon atoms, of which one to five is replaced with a heteroatom selected from N, S and O, that may optionally be reduced to a non-aromatic heterocycle and may optionally be substituted with one or more, identical or different substituents. Examples of heteroaryl groups include pyrrolyl, dihydropyrrolyl, pyrrolidinyl, oxopyrrolidinyl, indolyl, isoindolyl, indolizinyl, imidazolyl, pyrazolyl, benzimidazolyl, imidazo(1,2-a)pyridinyl, indazolyl, purinyl, pyrrolo(2,3-c)pyridinyl, pyrrolo(3,2-c)pyridinyl, pyrrolo(2,3-b)pyridinyl, pyrazolo(1,5-a)pyridinyl, 1,2,3-triazolyl, 1,2,4-triazolyl, tetrazolyl, oxazolyl, 1,2 oxazolyl, isoxazolyl, 1,3,4-oxadiazolyl, 1,2,5-oxadiazolyl, 1,2,4-oxadiazolyl, 1,2,3-oxadiazolyl, thiazolyl, isothiazolyl, 1,3,4-thiadiazolyl, 1,2,5-thiadiazolyl, 1,2,4-thiadiazolyl, 1,2,3-thiadiazolyl, furanyl, dihydrofuranyl, tetrahydrofuranyl, benzofuranyl, isobenzofuranyl, thiophenyl, dihydrothiophenyl, tetrahydrothiophenyl, benzothiophenyl, benzoisothiophenyl, pyridyl, piperidinyl, quinolinyl, isoquinolinyl, tetrahydroisoqinolinyl, quinolizinyl, pyrazinyl, pyridazinyl, pyrimidinyl, pyranyl, tetrahydropyranyl, 1,2,3-triazinyl, 1,2, 4-triazinyl, 1,3,5-triazinyl, chromenyl, morpholinyl, diazepinyl, benzodiazepinyl, and the like.

"Heteroarylalkyl" denotes the combination of the alkyl, alkenyl, alkynyl, and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose.

By the term "heterocycloalkyl" are meant groups which are derived from cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —SO$_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

The term "heterocyclic group" as used herein refers to a heterocycloalkyl group which optionally may be fused to an aromatic aryl or heteroaryl group.

Typical examples of individual sub-groups are listed below: Monocyclic heterorings (saturated and unsaturated): oxolane, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S, S-dioxide, 1,3-dioxolanyl, oxane, tetrahydrothiopyranyl, 1,4-oxazepanyl, tetrahydrothienyl, homothiomorpholinyl-S, S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, etc; Bicyclic heterorings (saturated and unsaturated): 8-azabicyclo[3.2.1]octyl, 8-azabicyclo[5.1.0]octyl, 2-oxa-5-azabicyclo[2.2.1]heptyl, 8-oxa-3-azabicyclo[3.2.1]octyl, 3,8-diaza-bicyclo[3.2.1]octyl, 2,5-diaza-bicyclo[2.2.1]heptyl, 1-azabicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, hexahydro-furo[3,2-b]furyl, etc; Spiro-heterorings (saturated and unsaturated): 1,4-dioxa-spiro[4.5]decyl; 1-oxa-3,8-diaza-spiro[4.5]decyl; 2-oxaspiro[3.3]

heptyl, 5-azaspiro[2.4]heptyl, 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl, etc.

"Heterocycloalkylalkyl" denotes the combination of the alkyl, alkenyl, alkynyl, and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose.

By the term "suitable substituent" is meant a substituent that on the one hand is fitting on account of its valency and on the other hand leads to a system with chemical stability.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base.

It is also to be understood that compounds (e.g., dihydro bases described herein) that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively).

A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "hydrate" refers to a compound which is associated with water. Typically, the number of the water molecules contained in a hydrate of a compound is in a definite ratio to the number of the compound molecules in the hydrate.

Any formula or structure given herein, including Formula I compounds, is also intended to represent unlabeled forms as well as isotopically-labeled forms of the compounds. Isotopically-labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125J.

The term "pharmacologically acceptable" means compatible with the treatment of animals, in particular, humans. The term pharmacologically acceptable salt includes both pharmacologically acceptable acid addition salts and pharmacologically acceptable basic addition salts.

The term "pharmacologically acceptable acid addition salt" as used herein means any non-toxic organic or inorganic salt of any base compound of the disclosure, or any of its intermediates. Basic compounds of the disclosure that may form an acid addition salt include, for example, compounds that contain a basic nitrogen atom. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono-, di- or the triacid salts can be formed, and such salts may exist in either a hydrated, solvated or substantially anhydrous form. In general, the acid addition salts of the compounds of the disclosure are more soluble in water and various hydrophilic organic solvents, and generally demonstrate higher melting points in comparison to their free base forms. The selection of the appropriate salt will be known to one skilled in the art. Other non-pharmacologically acceptable acid addition salts, e.g. oxalates, may be used, for example, in the isolation of the compounds of the disclosure, for laboratory use, or for subsequent conversion to a pharmacologically acceptable acid addition salt.

The term "pharmacologically acceptable basic salt" as used herein means any non-toxic organic or inorganic basic addition salt of any acid compound of the invention, or any of its intermediates, which are suitable for or compatible with the treatment of animals, in particular humans. Acidic compounds of the invention that may form a basic addition salt include, for example compounds that contain carboxylic acid, sulfonic acid, sulfinic acid, sulfonamide, N-unsubstituted tetrazole, phosphoric acid ester, or sulfuric acid ester. Illustrative inorganic bases which form suitable salts include lithium, sodium, potassium, calcium, magnesium, or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmacologically acceptable basic addition salts, may be used, for example, in the isolation of the compounds of the invention, for laboratory use, or for subsequent conversion to a pharmacologically acceptable basic addition salt. The formation of a desired compound salt is achieved using standard techniques. For example, the neutral compound is treated with a base in a suitable solvent and the formed salt is isolated by filtration, extraction or any other suitable method.

The term "therapeutically effective amount", "effective amount" or "sufficient amount" of a compound of the present invention is a quantity sufficient to, when administered to the subject, including a mammal, for example a human, effect beneficial or desired results, including clinical results, and, as such, an effective amount or synonym thereof depends upon the context in which it is being applied.

ABBREVIATIONS

AcOH acetic acid
atm atmosphere
Boc tert-butyloxycarbonyl
$CHCl_3$ chloroform
$CO_2$ carbon dioxide
conc concentrated
CV column volume
1,2-DCE 1,2-dichloroethane
DABCO 1,4-diazabicyclo[2.2.2]octane
DBU 1,8-diazabicyclo[5.4.0]undec-7-ene
DCM dichloromethane
DIPEA N,N-diisopropyl-N-ethylamine
DMF N,N-dimethylformamide
DMP Dess-Martin periodinane (1,1,1-triacetoxy-1,1-dihydro-1,2-benziodoxol-3(1H)-one)
DMSO dimethylsulfoxide
ee enantiomeric excess
ESI electron-spray ionisation
$Et_2O$ diethyl ether
EtOAc ethyl acetate
EtOH ethanol
g gram
h hour
$H_2O$ water
$H_2SO_4$ sulfuric acid
HATU 1-[bis(dimethylamino)methylene]-1H-1,2,3-triazolo[4,5-b]pyridinium 3-oxid hexafluorophosphate
HBr hydrogen bromide
HCl hydrochloric acid
HPLC high-performance liquid chromatography
I intermediate
IBX 2-iodoxybenzoic acid
IPA isopropanol
$K_2CO_3$ potassium carbonate
KI potassium iodide
LC liquid chromatography
LiOH lithium hydroxide
m-CPBA meta-chloroperoxybenzoic acid
MeCN acetonitrile
MeOH methanol
$MgSO_4$ magnesium sulfate
mHz mega Hertz
min minute
mL milliliter
$NaBH_4$ sodium borohydride
$NaCNBH_3$ sodium cyanoborohydride
NaH sodium hydride
$NaHCO_3$ sodium bicarbonate
NaOEt sodium ethoxide
NaOH sodium hydroxide
$Na_2S_2O_3$ sodium thiosulfate
$Na_2SO_4$ sodium sulfate
$NH_4Cl$ ammonium chloride
NMR nuclear magnetic resonance
Pc/C palladium on carbon
ppm parts per million
RT room temperature
Rt retention time
sec second
SFC supercritical fluid chromatography
STAB sodium triacetoxyborohydride
T3P propylphosphonic anhydride
TBME tert-butyl methyl ether
TEA N,N,N-triethylamine
TFA trifluoroacetic acid
THF tetrahydrofuran
UV ultraviolet

EXAMPLES

The Examples which follow are set forth to aid in the understanding of the invention but are not intended to, and should not be construed to limit the scope of the invention in any way. The Examples do not include detailed descriptions of conventional methods. Such methods are well known to those of ordinary skill in the art.

General Experimental Details

Commercially available reagents and solvents (HPLC grade) were used without further purification. $^1$H NMR spectra were recorded on a Bruker DRX 500 MHz spectrometer or a Bruker DPX 250 MHz spectrometer in deuterated solvents. Chemical shifts (δ) are in parts per million.

Compounds were purified by flash column chromatography on normal phase silica on Biotage Isolera systems using the appropriate SNAP cartridge and gradient. Alternatively, compounds were purified on reverse phase silica using Biotage Isolera systems with the appropriate SNAP C18 cartridges and reverse phase eluent or by preparative LC (if stated otherwise).

Reverse Phase Chromatography Using Acidic pH, Standard Elution Method

Purifications by flash column chromatography on reverse phase silica (acidic pH, standard elution method) were performed on Biotage Isolera systems using the appropriate SNAP C18 cartridge and a gradient of 10% B (A=0.1% formic acid in water; B=0.1% formic acid in acetonitrile) over 1.7 CV then 10-100% B over 19.5 CV and 100% B for 2 CV.

Reverse Phase Chromatography Using Basic pH, Standard Elution Method

Purifications by flash column chromatography on reverse phase silica (basic pH, standard elution method) were performed on Biotage Isolera systems using the appropriate SNAP C18 cartridge and a gradient of 10% B (A=0.1% ammonia hydroxide in water; B=0.1 ammonia hydroxide in acetonitrile) over 2 CV then 10-100% B over 19.5 CV and 100% B for 2 CV.

Preparative LC Using Acidic pH, Standard Elution Method

Purifications by preparative LC (acidic pH, standard elution method) were performed on a Gilson LC system using a Waters Sunfire C18 column (30 mm×10 mm, 10 μM; temperature: RT) and a gradient of 30-95% B (A=0.1% formic acid in water; B=0.1% formic acid in acetonitrile) over 11.00 min then 95% B for 2.10 min, with an injection volume of 1500 μL and a flow rate of 40 mU/min. UV spectra were recorded at 215 nm using a Gilson detector.

Preparative LC Using Acidic pH, Early Elution Method

Purifications by preparative LC (acidic pH, early elution method) were performed on a Gilson LC system using a Waters Sunfire C18 column (30 mm×100 mm, 10 μM; temperature: RT) and a gradient of 10-95% B (A=0.1% formic acid in water; B=0.1% formic acid in acetonitrile) over 14.44 min then 95% B for 2.11 min, with an injection volume of 1500 μL and a flow rate of 40 mU/min. UV spectra were recorded at 215 nm using a Gilson detector.

Preparative LC Using Basic pH, Standard Elution Method

Purifications by preparative LC (basic pH, standard elution method) were performed on a Gilson LC system using Waters Xbridge C18 columns (30 mm×100 mm, 10 μM; temperature: RT) and a gradient of 30-95% (A=0.2% ammonium hydroxide in water; B=0.2% ammonium hydroxide in acetonitrile) over 11.00 min then 100% B for 2.10 min, with an injection volume of 1500 μL and a flow rate of 40 mU/min. UV spectra were recorded at 215 nm using a Gilson detector.

Preparative LC Using Basic pH, Early Elution Method

Purifications by preparative LC (basic pH, early elution method) were performed on a Gilson LC system using a Waters Xbridge C18 column (30 mm×100 mm, 10 μM; temperature: RT) and a gradient of 10-95% (A=0.2% ammonium hydroxide in water; B=0.2% ammonium hydroxide in acetonitrile) over 14.44 min then 100% B for 2.11 min, with an injection volume of 1500 μL and a flow rate of 40 mU/min. UV spectra were recorded at 215 nm using a Gilson detector.

Preparative LC Using Neutral pH, Standard Elution Method

Purifications by preparative LC (acidic pH, standard elution method) were performed on a Gilson LC system using Waters Sunfire C18 columns (30 mm×10 mm, 10 μM; temperature: RT) and a gradient of 10-100% B (A=water; B=acetonitrile) over 14.5 min then 100% B for 1.0 min, with an injection volume of 1500 μL and a flow rate of 40 mU/min. UV spectra were recorded at 215 nm using a Gilson detector.

Method METCR0990

Analytical METCR0990 HPLC-MS were performed on a Agilent G1312A system with Waters PDA and ELS detectors using a Phenomenex Gemini-NX C18 column (2.0 mm×50 mm, 3 μM; temperature: 40° C.) and a gradient of 1-100% (A=2 mM ammonium bicarbonate, buffered to pH 10 with ammonium hydroxide solution; B=acetonitrile) over 1.8 min then 100% B for 0.3 min, with an injection volume of 3 μL and a flow rate of 1.0 mU/min. UV spectra were recorded at 215 nm using a Waters 2996 photo diode array detector. Mass spectra were obtained over the range m/z 150 to 850 at a sampling rate of 5 scans per sec using a Waters ZQ. Data were integrated and reported using Waters MassLynx and OpenLynx software.

Method METCR1278

Analytical METCR1278 HPLC-MS were performed on Waters HPLC system systems using reverse phase Water Atlantis dC18 columns (2.1 mm×50 mm, 3 μm; temperature: 40° C.) and a gradient of 5-100% B (A=0.1% formic acid in water; B=0.1% formic acid in acetonitrile) over 2.5 min then 100% B for 0.2 min, with an injection volume of 3 μL and a flow rate of 1.0 mU/min. UV spectra were recorded at 215 nm using a Waters UV detector. Mass spectra were obtained over the range m/z 150 to 850 at a sampling rate of 2 scans per sec using a Waters ZQ. Data were integrated and reported using Waters MassLynx and OpenLynx software.

Method METCR1410

Analytical METCR1410 HPLC-MS were performed on Shimadzu LCMS-2010EV systems using reverse phase Kinetex Core shell C18 columns (2.1 mm×50 mm, 5 μm; temperature: 40° C.) and a gradient of 5-100% B (A=0.1% formic acid in water; B=0.1% formic acid in acetonitrile) over 1.2 min then 100% B for 0.1 min, with an injection volume of 3 μL and a flow rate of 1.2 mL/min. UV spectra were recorded at 215 nm using a SPD-M20A photo diode array detector. Mass spectra were obtained over the range m/z 150 to 850 at a sampling rate of 2 scans per sec using a LCMS2010EV. Data were integrated and reported using Shimadzu LCMS-Solutions and PsiPort software.

Method METCR1416

Analytical METCR1416 HPLC-MS were performed on Shimadzu LCMS-2010EV systems using reverse phase Water Atlantis dC18 columns (2.1 mm×50 mm, 3 μm; temperature: 40° C.) and a gradient of 5-100% B (A=0.1% formic acid in water; B=0.1% formic acid in acetonitrile) over 5.0 min then 100% B for 0.4 min, with an injection volume of 3 μL and a flow rate of 0.6 mL/min. UV spectra were recorded at 215 nm using a SPD-M20A photo diode array detector. Mass spectra were obtained over the range m/z 150 to 850 at a sampling rate of 2 scans per sec using a LCMS2010EV. Data were integrated and reported using Shimadzu LCMS-Solutions and PsiPort software.

Method METCR1600

Analytical METCR16001 HPLC-MS were performed on a Agilent G1312A system with Waters PDA and ELS detectors using a Phenomenex Gemini-NX C18 column (2.0 mm×100 mm, 3 μM; temperature: 50° C.) and a gradient of 5-100% (A=2 mM ammonium bicarbonate, buffered to pH 10 with ammonium hydroxide solution; B=acetonitrile) over 5.5 min then 100% B for 0.4 min, with an injection volume of 3 μL and a flow rate of 0.5 mL/min. UV spectra were recorded at 215 nm using a Waters 2996 photo diode array detector. Mass spectra were obtained over the range m/z 100 to 1000 at a sampling rate of 5 scans per sec using a Waters ZQ. Data were integrated and reported using Waters MassLynx and OpenLynxsoftware.

Method METCR1602

Analytical METCR1602 HPLC-MS were performed on a Waters Acquity UPLC system with Waters Acquity PDA detector using a Waters BEH C18 column (30×2 mm, 1.7 μm column; temperature: 40° C.) and a gradient of 5-100% (A=2 mM ammonium bicarbonate, buffered to pH 10; B=acetonitrile) over 0.75 min then 100% B for 0.1 min, with an injection volume of 2 μL and a flow rate of 1.0 mL/min. UV spectra were recorded at 215 nm using a Waters Acquity photo diode array detector. Mass spectra were obtained over the range m/z 100 to 1000 at a sampling rate of 5 scans per sec using a Water QDa mass detector. Data were integrated and reported using Waters MassLynx and OpenLynx software.

Method METCR1603

Analytical METCR1603 HPLC-MS were performed on a Agilent G1312A system with Waters 2996 PDA detector and Waters 2420 ELS detector using a Phenomenex Gemini-NX C18 column (2.0×100 mm, 3m column; temperature: 40° C.) and a gradient of 5-100% (A=2 mM ammonium bicarbonate, buffered to pH 10; B=acetonitrile) over 5.5 min then 100% B for 0.4 min, with an injection volume of 3 μL and a flow rate of 0.6 mL/min. UV spectra were recorded at 215 nm using a Waters Acquity photo diode array detector. Mass spectra were obtained over the range m/z 150 to 850 at a sampling rate of 5 scans per sec using a Waters ZQ mass detector. Data were integrated and reported using Waters MassLynx and OpenLynx software.

Method METCR1673

Analytical METCR1673 HPLC-MS were performed on a Waters 2795 system with Waters PDA and ELS detectors using a Supelco Ascentis Express column (2.1×30 mm, 2.7 μm; temperature: 40° C.) and a gradient of 5-100% (A=water+0.1% formic acid; B=acetonitrile+0.1% formic acid) over 1.5 min then 100% B for 0.1 min, with an injection volume of 3 μL and a flow rate of 1.0 mL/min. UV spectra were recorded at 215 nm using a Waters 2996 photo diode array detector. Mass spectra were obtained over the range m/z 100 to 1000 at a sampling rate of 5 scans per sec using a Shimadzu LCMS2010EV. Data were integrated and reported using the PsiPort data browser.

Method MET-uHPLC-AB-101

Analytical MET-uHPLC-AB-101 HPLC-MS were performed on a Waters Acquity uPLC system with Waters PDA and ELS detectors using a Phenomenex Kinetex-XB C18 column (2.1 mm×100 mm, 1.7 µM; temperature: 40° C.) and a gradient of 5-100% B (A=0.1% formic acid in water; B=0.1% formic acid in acetonitrile) over 5.3 min then 100% B for 0.5 min, with an injection solution of 3 µL and a flow rate of 0.6 mL/min. UV spectra were recorded at 215 nm using a Waters Acquity photo diode array detector. Mass spectra were obtained over the range m/z 150 to 850 at a sampling rate of 5 scans per sec using a Waters SQD. Data were integrated and reported using Waters MassLynx and OpenLynx software.

Method MET-uHPLC-AB-102

Analytical MET-uHPLC-AB-102 HPLC-MS were performed on a Waters Acquity uPLC system with Waters PDA and ELS detectors using a Waters uPLC CSH C18 column (2.1 mm×100 mm, 1.7 µM; temperature: 40° C.) and a gradient of 5-100% (A=2 mM ammonium bicarbonate, buffered to pH 10 with ammonium hydroxide solution; B=acetonitrile) over 5.3 min then 100% B for 0.5 min a flow rate of 0.6 mL/min. UV spectra were recorded at 215 nm using a Waters Acquity photo diode array detector. Mass spectra were obtained over the range m/z 150 to 850 at a sampling rate of 5 scans per sec using a Waters Quatro Premier XE. Data were integrated and reported using Waters MassLynx and OpenLynx software.

Method Achiral SFC

Analytical Achiral SFC HPLC-MS were performed on Waters SFC system using Waters Viridis 2-EP columns (4.6 mm×250 mm, 5 µm; temperature: 40° C.) and an isocratic eluent of 1:4 ACN/CO$_2$ over 10 min, with an injection volume of 10 µL and a flow rate of 4.0 mL/min. UV spectra were recorded at 215 nm using a Waters 2998 photo diode array detector. Mass spectra were obtained over the range m/z 150 to 850 at a sampling rate of 5 scans per sec using a Waters 3100. Data were integrated and reported using Waters MassLynx and OpenLynx software.

Method CAM-A1

Analytical CAM-A1 chiral HPLC were performed on Waters LC system using Chiralcel OJ-H columns (4.6 mm×250 mm, 5 µm; temperature: RT) and an isocratic eluent of 7/3 heptane/IPA over 15 min, with an injection volume of 20 µL and a flow rate of 0.5 mL/min. UV spectra were recorded at 215 nm using a Waters 2996 photo diode array detector. Data were integrated and reported using Waters MassLynx and OpenLynx software.

Method CAM-A2

Analytical CAM-A2 chiral HPLC were performed on Waters LC system using Chiralcel OJ-H columns (4.6 mm×250 mm, 5 µm; temperature: RT) and an isocratic eluent of 9/1 heptane/IPA over 10 min, with an injection volume of 20 µL and a flow rate of 1 mL/min. UV spectra were recorded at 215 nm using a Waters 2996 photo diode array detector. Data were integrated and reported using Waters MassLynx and OpenLynx software.

Method CAM-F1

Analytical CAM-F1 chiral HPLC were performed on Waters SFC system using Chiralpak AD-H columns (4.6 mm×250 mm, 5 µm; temperature: 40° C.) and an isocratic eluent of 1:4 MeOH/CO$_2$ over 10 min, with an injection volume of 10 µL and a flow rate of 4.0 mU/min. UV spectra were recorded at 215 nm using a Waters 2998 photo diode array detector. Data were integrated and reported using Waters MassLynx and OpenLynx software.

Method CAM-F2

Analytical CAM-F2 chiral HPLC were performed on Waters LC system using Chiralpak AS-H columns (4.6 mm×250 mm, 5 µm; temperature: RT) and an isocratic eluent of 85/15 heptane/EtOH over 40 min, with an injection volume of 20 µL and a flow rate of 0.5 mU/min. UV spectra were recorded at 254 nm using a Waters 2996 photo diode array detector. Data were integrated and reported using Waters MassLynx and OpenLynx software.

Method CAM-F3

Analytical CAM-F3 chiral LC were performed on Waters LC system using Chiralpak AS-H columns (4.6 mm×250 mm, 5 µm; temperature: RT) and an isocratic eluent of ⅔ heptane/EtOH over 30 min, with an injection volume of 20 µL and a flow rate of 1 mU/min. UV spectra were recorded at 254 nm using a Waters 2996 photo diode array detector. Data were integrated and reported using Waters MassLynx and OpenLynx software.

Method CAM-F4

Analytical CAM-F4 chiral LC were performed on Waters LC system using Chiralpak AS-H columns (4.6 mm×250 mm, 5 µm; temperature: RT) and an isocratic eluent of 7/3 heptane/EtOH over 60 min, with an injection volume of 20 µL and a flow rate of 1 mU/min. UV spectra were recorded at 254 nm using a Waters 2996 photo diode array detector. Data were integrated and reported using Waters MassLynx and OpenLynx software.

All compounds displayed a purity >95% as determined by these methods unless otherwise stated.

Compound names were generated using ChemAxon software: Instant JChem Excel IUPAC Name function.

Epoxide Route: Synthesis of Intermediates I-1-I-26

GENERAL SCHEME 1:

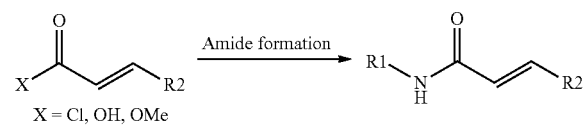

X = Cl, OH, OMe

Method A: Amide Formation Using Acid Chloride (2E)-N-[(3-Chlorophenyl)methyl]but-2-enamide
(I-1)

To a stirred solution of (3-chlorophenyl)methanamine (2.34 mL, 19.13 mmol) and DIPEA (10 mL, 57.41 mmol) in DCM (50 mL) at 0° C. was added (2E)-but-2-enoyl chloride (1.83 mL, 19.13 mmol) dropwise, and the resulting mixture stirred at RT, under nitrogen for 2 h. The solution was washed with saturated K$_2$CO$_3$ (20 mL) followed by 1N HCl (20 mL). The organic layer was separated, dried over sodium sulfate, filtered and concentrated in vacuo. The residue was suspended in Et$_2$O (30 mL), the precipitate was filtered and washed with Et$_2$O (2×15 mL) to afford 2 g of the title compound (50%) as an off-white solid. The filtrate was concentrated and suspended in Et$_2$O (20 mL) to afford, after filtration, 0.65 g of the required amide (16%). The two crops were combined to give 2.65 g of (2E)-N-[(3-chlorophenyl)methyl]but-2-enamide as an off-white solid (99% purity, 76%) which was used in the next step without further purification.

$^1$H NMR (250 MHz, Chloroform-d) δ 1.87 (dd, J=6.9, 1.7 Hz, 3H), 4.48 (d, J=5.9 Hz, 2H), 5.82 (dq, J=15.2, 1.6 Hz, 2H), 6.79-7.01 (m, 1H), 7.11-7.33 (m, 4H).

LC-MS (METCR1410): 99% (UV), Rt=1.02 min, m/z (ESI$^+$)=210.1/212.1 [M+H]$^+$

N-[(3-Chlorophenyl)methyl]-3-methylbut-2-enamide (I-2)

The title compound was synthesized in a similar manner to method A, general scheme 1, as a yellow viscous oil (5.1 g, 100% purity, quantitative) which was used in the next step without further purification.

$^1$H NMR (500 MHz, Chloroform-d) δ 1.85 (d, J=1.3 Hz, 3H), 2.18 (d, J=1.2 Hz, 3H), 4.43 (d, J=6.0 Hz, 2H), 5.58-5.61 (m, 1H), 5.85 (s, 1H), 7.14-7.18 (m, 1H), 7.21-7.25 (m, 2H), 7.25-7.27 (m, 1H).

LC-MS (METCR1278): 100% (UV), Rt=1.95 min, m/z (ESI$^+$)=223.9/225.9 [M+H]$^+$

(2E)-N-[(3-Chlorophenyl)methyl]-3-phenylprop-2-enamide (I-3)

The title compound was synthesized in a similar manner to method A, general scheme 1 as a yellow solid (6 g, 94% purity, quantitative) and was used in the next step without further purification.

$^1$H NMR (250 MHz, Chloroform-d) δ 4.55 (d, J=5.9 Hz, 2H), 5.90-6.12 (m, 1H), 6.37-6.58 (m, 1H), 7.18-7.28 (m, 3H), 7.29-7.33 (m, 1H), 7.33-7.45 (m, 3H), 7.46-7.61 (m, 2H), 7.63-7.90 (m, 1H).

LC-MS (METCR1278): 94% (UV), Rt=2.10 min, m/z (ESI$^+$)=271.9/273.9 [M+H]$^+$

(2E)-N-(Cyclopropylmethyl)but-2-enamide (I-4)

The title compound was synthesized in a similar manner to method A, general scheme 1 as a white crystalline solid (4.86 g, 90% purity by 1H NMR, 69%) after purification by flash column chromatography on normal phase silica (100 g SNAP HP-SIL cartridge, 10-100% EtOAc in heptane gradient).

$^1$H NMR (500 MHz, Chloroform-d) δ 0.15-0.26 (m, 2H), 0.41-0.54 (m, 2H), 0.88-1.04 (m, 1H), 1.82-1.88 (m, 3H), 3.16 (dd, J=5.6, 7.1 Hz, 2H), 5.56-5.73 (m, 1H), 5.77-5.85 (m, 1H), 6.76-6.92 (m, 1H).

LC-MS (METCR1410): 89% (UV), Rt=0.82 min, m/z (ESI$^+$)=140.1 [M+H]$^+$

(2E)-N-Cyclopropylbut-2-enamide (I-5)

The title compound was synthesized in a similar manner to method A, general scheme 1 as a yellow crystalline solid (3.91 g, 93% purity by $^1$H NMR, 83%) used in the next step without further purification.

$^1$H NMR (250 MHz, Chloroform-d) δ 0.39-0.56 (m, 2H), 0.76 (q, J=7.0 Hz, 2H), 1.81 (dd, J=1.5, 6.9 Hz, 3H), 2.75 (tq, J=3.6, 7.1 Hz, 1H), 5.67-6.00 (m, 2H), 6.81 (dq, J=6.9, 13.7 Hz, 1H).

LC-MS (METCR1410): 97% (UV), Rt=0.59 min, m/z (ESI$^+$)=126.0 [M+H]$^+$

(2E)-N-(2-methylpropyl)but-2-enamide (I-6)

The title compound was synthesized in a similar manner to method A, general scheme 1 as a colourless powder (6.08 g, 100% purity, 90%) following purification by recrystallization from hot heptane.

$^1$H NMR (250 MHz, Chloroform-d) δ 0.91 (d, J=6.7 Hz, 6H), 1.80-1.72 (m, 1H), 1.84 (dd, J=6.9, 1.7 Hz, 3H), 3.13 (t, 2H), 5.54 (s, 1H), 5.80 (dd, J=15.2, 1.7 Hz, 1H), 6.82 (dq, J=15.0, 6.9 Hz, 1H).

LC-MS (METCR1410): 100% (UV), Rt=0.94 min, m/z (ESI$^+$)=141.9 [M+H]$^+$

N-[(3-Chlorophenyl)methyl]prop-2-enamide (I-7)

The title compound was synthesized in a similar manner to method A, general scheme 1 as an off-white solid (3.8 g, 80% purity by 1H NMR, 81%) used in the next step without further purification.

$^1$H NMR (250 MHz, Chloroform-d) δ 4.47 (d, J=6.0 Hz, 2H), 5.67 (dd, J=1.6, 10.1 Hz, 1H), 6.04-6.24 (m, 2H), 6.32 (dd, J=1.6, 17.0 Hz, 1H), 7.11-7.31 (m, 4H).

LC-MS (METCR1410): 84% (UV), Rt=0.98 min, m/z (ESI$^+$)=196.0/198.0 [M+H]$^+$

(2E)-N-(Cyclohexylmethyl)but-2-enamide (I-8)

The title compound was synthesized in a similar manner to method A, general scheme 1 as an off-white solid (1.56 g, 100% purity, 97%) after purification by flash column chromatography on normal phase silica (100 g SNAP KP-SIL cartridge, 0-100% TBME in heptane gradient).

$^1$H NMR (250 MHz, Chloroform-d) δ 0.81-1.03 (m, 2H), 1.10-1.33 (m, 3H), 1.39-1.52 (m, 1H), 1.62-1.78 (m, 5H), 1.85 (dd, J=1.7, 6.9 Hz, 3H), 3.16 (t, J=6.5 Hz, 2H), 5.41 (s, 1H), 5.67-5.86 (m, 1H), 6.74-6.94 (m, 1H).

LC-MS (METCR1410): 100% (UV), Rt=1.03 min, m/z (ESI$^+$)=182.4 [M+H]$^+$

(2E)-N-[2-(Cyclohexyloxy)ethyl]but-2-enamide (I-9)

The title compound was synthesized in a similar manner to method A, general scheme 1 as an off-white solid (905 mg, 99% purity, 61%) after purification by flash column chromatography on normal phase silica (25 g SNAP KP-SIL cartridge, 0-100% TBME in heptane gradient).

$^1$H NMR (250 MHz, Chloroform-d) δ 1.13-1.36 (m, 6H), 1.48-1.59 (m, 1H), 1.68-1.79 (m, 1H), 1.81-1.94 (m, 5H), 3.13-3.38 (m, 1H), 3.38-3.65 (m, 4H), 5.62-6.07 (m, 2H), 6.70-6.97 (m, 1H).

LC-MS (METCR1410): 99% (UV), Rt=1.08 min, m/z (ESI$^+$)=212.1 [M+H]$^+$

Methyl 2-[(2E)-but-2-enamido]acetate (I-10)

The title compound was synthesized in a similar manner to method A, general scheme 1 as a yellow free-flowing oil (2.4 g, 95% purity by $^1$H NMR, 76%) used in the next step without further purification.

$^1$H NMR (500 MHz, Chloroform-d) δ 1.86 (dd, J=1.7, 6.9 Hz, 3H), 3.77 (s, 3H), 4.11 (d, J=5.2 Hz, 2H), 5.87 (dq, J=1.6, 15.2 Hz, 1H), 5.96 (br. s, 1H), 6.88 (dq, J=6.9, 15.0 Hz, 1H).

LC-MS (METCR0990): 100% (UV), Rt=1 min, m/z (ESI$^+$)=158.2 [M+H]$^+$

(2E)-N-[2-(3-Chlorophenyl)propan-2-yl]but-2-enamide (I-11)

The title compound was synthesized in a similar manner to method A, general scheme 1 as an off-white solid (1.9 g, 97% purity, 66%) after purification by flash column chromatography on normal phase silica (100 g SNAP KP-SIL cartridge, 0-100% EtOAc in heptane gradient).

$^1$H NMR (500 MHz, DMSO-d6) δ 1.55 (s, 6H), 1.78 (dd, J=6.9, 1.5 Hz, 3H), 6.04 (dd, J=15.3, 1.7 Hz, 1H), 6.40-6.58 (m, 1H), 7.17-7.35 (m, 4H), 8.13 (s, 1H).

LC-MS (METCR1410): 97% (UV), Rt=1.13 min, m/z (ESI$^+$)=238.1/240.0 [M+H]$^+$ (2E)-N-tert-Butylbut-2-enamide (I-12)

The title compound was synthesized in a similar manner to method A, general scheme 1 as a colourless powder (597 mg, 100% purity, 65%) after purification by recrystallization from EtOAc.

$^1$H NMR (250 MHz, Chloroform-d) δ 1.37 (s, 9H), 1.82 (dd, J=1.5, 6.9 Hz, 3H), 5.23 (s, 1H), 5.71 (dd, J=1.7, 15.1 Hz, 1H), 6.66-6.89 (m, 1H).

LC-MS (METCR1278): 100% (UV), Rt=1.41 min, m/z (ESI$^+$)=142.0 [M+H]$^+$ (2E)-N-(Propan-2-yl)but-2-enamide (I-13)

The title compound was synthesized in a similar manner to method A, general scheme 1 as an off-white solid (11 g, 98% purity by $^1$H NMR, 63%) after purification by flash column chromatography on normal phase silica (100 g SNAP KP-SIL cartridge, 0-100% EtOAc in heptane gradient).

$^1$H NMR (500 MHz, DMSO-d6) δ 1.06 (d, J=6.6 Hz, 6H), 1.77 (dd, J=6.9, 1.7 Hz, 3H), 3.93-3.80 (m, 1H), 5.86 (dq, J=15.2, 1.6 Hz, 1H), 6.58 (dq, J=15.2, 6.9 Hz, 1H), 7.71 (d, J=6.9 Hz, 1H).

LC-MS (METCR1410): 100% (UV), Rt=0.75 min, m/z (ESI$^+$)=128.0 [M+H]$^+$ (2E)-1-(7-Chloro-1,2,3,4-tetrahydroisoquinolin-2-yl) but-2-en-1-one (I-14)

The title compound was synthesized in a similar manner to method A, general scheme 1 as a yellow oil (614 mg, 90% purity by $^1$H NMR, 83%) used in the next step without further purification.

$^1$H NMR (250 MHz, Chloroform-d) δ 1.91 (dd, J=1.7, 6.8 Hz, 3H), 2.85 (s, 2H), 3.77 (s, 2H), 4.72 (s, 2H), 6.32 (dq, J=1.6, 15.0 Hz, 1H), 6.83-7.03 (m, 1H), 7.03-7.21 (m, 3H).

LC-MS (METCR1278): 89% (UV), Rt=1.96 min, m/z (ESI$^+$)=236.0/238.0 [M+H]$^+$

Method B: Amide Formation Using Carboxylic Acid (2E)-N-(Cyclopropylmethyl)pent-2-enamide (I-15)

To a stirred solution of (2E)-pent-2-enoic acid (5.1 mL, 49.94 mmol) and DIPEA (13.1 mL, 74.91 mmol) in dry DMF (40 mL) at 0° C. was added HATU (20.9 g, 54.94 mmol). The reaction mixture was stirred under nitrogen at 0° C. for 15 min and 1-cyclopropylmethanamine (4.3 mL, 49.94 mmol) was added dropwise. The mixture was stirred at 0° C. for 15 min, then RT for 3 h. The reaction mixture was diluted with water (100 mL) and the aqueous layer extracted with EtOAc (3×150 mL). The organic layers were combined, washed with saturated K$_2$CO$_3$ (100 mL), 1N HCl (100 mL), dried over sodium sulfate, filtered and concentrated in vacuo. The crude material was purified by flash column chromatography on normal phase silica in 2 batches (100 g SNAP Ultra cartridge, 0-80% EtOAc in heptane gradient) to give 6.48 g of (2E)-N-(cyclopropyl-methyl) pent-2-enamide as a yellow oil (90% purity by $^1$HNMR, 76%).

$^1$H NMR (500 MHz, DMSO-d6) δ 0.08-0.20 (m, 2H), 0.34-0.46 (m, 2H), 0.83-0.95 (m, 1H), 0.99 (t, J=7.4 Hz, 3H), 2.09-2.18 (m, 2H), 2.95-3.02 (m, 2H), 5.89 (dt, J=1.7, 15.4 Hz, 1H), 6.65 (dt, J=6.4, 15.4 Hz, 1H), 7.94 (s, 1H).

LC-MS (METCR1410): 95% (UV), Rt=0.94 min, m/z (ESI$^+$)=154.1 [M+H]$^+$ (2E)-N-[(3-Chlorophenyl)methyl]pent-2-enamide (I-16)

The title compound was synthesized in a similar manner to method B, general scheme 1 as an off-white solid (5.43 g, 98% purity, 80%) after purification by recrystallization from 1:4 EtOAc/heptane.

$^1$H NMR (500 MHz, Chloroform-d) δ 1.06 (t, J=7.4 Hz, 3H), 2.18-2.26 (m, 2H), 4.49 (d, J=6.0 Hz, 2H), 5.73-5.88 (m, 2H), 6.94 (dt, J=6.4, 15.3 Hz, 1H), 7.15-7.19 (m, 1H), 7.22-7.26 (m, 2H), 7.27-7.29 (m, 1H).

LC-MS (METCR1410): 98% (UV), Rt=1.06 min, m/z (ESI$^+$)=224.1/226.1 [M+H]$^+$

N-(Cyclopropylmethyl)-4-methylpent-2-enamide (I-17)

The title compound was synthesized in a similar manner to method B, general scheme 1 as a yellow free-flowing oil (7.27 g, 91% purity, 90%) after purification by flash column chromatography on normal phase silica (100 g SNAP Ultra cartridge, 0-50% EtOAc in heptane gradient).

$^1$H NMR (250 MHz, Chloroform-d) δ 0.17-0.25 (m, 2H), 0.46-0.55 (m, 2H), 0.92-1.00 (m, 1H), 1.05 (d, J=6.8 Hz, 6H), 2.43 (dqd, J=1.4, 6.7, 13.5 Hz, 1H), 3.18 (dd, J=5.5, 7.1 Hz, 2H), 5.60 (s, 1H), 5.72 (dd, J=1.4, 15.4 Hz, 1H), 6.81 (dd, J=6.6, 15.4 Hz, 1H).

LC-MS (METCR1410): 91% (UV), Rt=0.99 min, m/z (ESI$^+$)=168.4 [M+H]$^+$ (2E)-N-(Cyclopropylmethyl)hex-2-enamide (I-18)

The title compound was synthesized in a similar manner to method B, general scheme 1 as a yellow oil (6.78 g, 90% purity by $^1$H NMR, 83%) after purification by flash column chromatography on normal phase silica in 2 batches (100 g SNAP Ultra cartridge, 0-50% EtOAc in heptane gradient).

$^1$H NMR (500 MHz, DMSO-d6) δ 0.09-0.20 (m, 2H), 0.33-0.46 (m, 2H), 0.82-0.95 (m, 4H), 1.41 (h, J=7.3 Hz, 2H), 2.10 (qd, J=1.5, 7.2 Hz, 2H), 2.93-3.02 (m, 2H), 5.89 (dt, J=1.5, 15.4 Hz, 1H), 6.59 (dt, J=7.0, 15.3 Hz, 1H), 7.94 (s, 1H)

LC-MS (METCR1410): 96% (UV), Rt=1.02 min, m/z (ESI$^+$)=168.1 [M+H]$^+$ (2E)-N-(Cyclohexylmethyl)pent-2-enamide (I-19)

The title compound was synthesized in a similar manner to method B, general scheme 1 as an off-white solid (6 g, 99% purity, 89%) after purification by flash column chromatography on normal phase silica (100 g SNAP KP-SIL cartridge, 0-100% EtOAc in heptane gradient).

$^1$H NMR (500 MHz, Chloroform-d) δ 0.89-0.98 (m, 2H), 1.05 (t, J=7.4 Hz, 3H), 1.12-1.27 (m, 3H), 1.43-1.53 (m, 1H), 1.63-1.68 (m, 1H), 1.72 (d, J=11.3 Hz, 4H), 2.20 (pd, J=1.6, 7.5 Hz, 2H), 3.16 (t, J=6.5 Hz, 2H), 5.50 (s, 1H), 5.75 (dt, J=1.6, 15.3 Hz, 1H), 6.87 (dt, J=6.4, 15.3 Hz, 1H).

LC-MS (METCR1410): 99% (UV), Rt=1.08 min, m/z (ESI⁺)=196.4 [M+H]⁺

N-[(3-Chlorophenyl)methyl]-4-methylpent-2-enamide (I-20)

The title compound was synthesized in a similar manner to method B, general scheme 1 as an off-white solid in 2 batches (1.8 g, 95% purity, 41% and 1.7 g, 98% purity, 40%) after purification by flash column chromatography on normal phase silica (25 g SNAP Ultra and 100 g SNAP KP-SIL cartridges, 10-100% EtOAc in heptane gradient).

$^1$H NMR (500 MHz, Chloroform-d) δ 1.06 (d, J=6.8 Hz, 6H), 2.38-2.52 (m, 1H), 4.49 (d, J=5.9 Hz, 2H), 5.68-5.81 (m, 2H), 6.88 (dd, J=6.6, 15.4 Hz, 1H), 7.10-7.22 (m, 1H), 7.22-7.33 (m, 3H).

LC-MS (METCR1410): 95% (UV), Rt=1.18 min, m/z (ESI⁺)=238.4/240.4 [M+H]⁺

LC-MS (METCR1410): 98% (UV), Rt=1.15 min, m/z (ESI⁺)=238.4/240.4 [M+H]⁺

Method C: Amide Formation Using Methyl Ester (2E)-N-(Cyclopropylmethyl)-5-methylhex-2-enamide (I-21)

To a stirred solution of methyl (2E)-5-methylhex-2-enoate (10.0 g, 70.33 mmol) in 2:2:1 THF/H₂O/MeOH (75 mL) was added lithium hydroxide hydrate (1:1:1) (2.95 g, 70.33 mmol) and the reaction stirred at RT for 2 h. The mixture was concentrated in vacuo and the resulting solid was dried in a high-vac oven for 18 h to afford 9.86 g of (2E)-5-methylhex-2-enoic acid lithium salt as an off-white solid (89% purity by $^1$H NMR, 93%) used in the next step without further purification.

$^1$H NMR (500 MHz, DMSO-d₆) δ 0.86 (d, J=6.7 Hz, 6H), 1.61 (dt, J=6.7, 13.3 Hz, 1H), 1.87-1.94 (m, 2H), 5.57-5.64 (m, 1H), 6.26 (dt, J=7.4, 15.1 Hz, 1H).

LC-MS (METCR1410): 98% (UV), Rt=1.03 min, no mass ion detected

To a stirred solution of (2E)-5-methylhex-2-enoic acid lithium salt (89%, 4.5 g, 29.87 mmol) and DIPEA (10.4 mL, 59.73 mmol) in DMF (90 mL) at RT was added HATU (12.5 g, 32.85 mmol) portion wise over 20 min. The mixture was stirred at RT for 30 min, cooled to 0° C. and 1-cyclopropylmethanamine (2.9 mL, 32.85 mmol) added. The reaction was stirred at 0° C. for 20 min then at RT for 1 h. HATU (2.3 g, 5.97 mmol) was added and the reaction stirred at RT for 60 h. The mixture was diluted with DCM (100 mL) and 1M HCl (100 mL) added. The biphasic layers were separated and the aqueous phase extracted with DCM (20 mL). The organic phases were combined, washed with saturated NaHCO₃ (2×100 mL), dried over sodium sulfate, filtered and concentrated in vacuo. The crude residue was purified by flash column chromatography on normal phase silica (100 g SNAP KP-SIL cartridge, 10-80% TBME in heptane gradient) to afford 2.93 g of (2E)-N-(cyclopropyl-methyl)-5-methylhex-2-enamide as a brown oil (93% purity, 50%).

$^1$H NMR (500 MHz, Chloroform-d) δ 0.22 (q, J=4.8 Hz, 2H), 0.49-0.54 (m, 2H), 0.89-1.03 (m, 7H), 1.75 (dt, J=6.7, 13.3 Hz, 1H), 2.03-2.09 (m, 2H), 3.16-3.21 (m, 2H), 5.56 (s, 1H), 5.76 (d, J=15.2 Hz, 1H), 6.82 (dt, J=7.5, 15.1 Hz, 1H).

LC-MS (METCR1410): 93% (UV), Rt=1.08 min, m/z (ESI⁺)=182.1 [M+H]⁺

(2E)-N-[(3-Chlorophenyl)methyl]-5-methylhex-2-enamide (I-22)

The title compound was synthesized in a similar manner to method C, general scheme 1 as an off-white solid (3 g, 95% purity by 1H NMR, 32%) after purification by flash column chromatography on normal phase silica (100 g SNAP KP-SIL cartridge, 0-100% EtOAc in heptane gradient).

$^1$H NMR (500 MHz, DMSO-d6) δ 0.89 (d, J=6.7 Hz, 6H), 1.69 (tp, J=6.7, 13.3 Hz, 1H), 1.98-2.09 (m, 2H), 4.34 (d, J=6.0 Hz, 2H), 5.95 (dt, J=1.3, 15.3 Hz, 1H), 6.65 (dt, J=7.4, 15.1 Hz, 1H), 7.22 (d, J=7.5 Hz, 1H), 7.27-7.39 (m, 3H), 8.46 (t, J=5.9 Hz, 1H).

LC-MS (METCR1410): 91% (UV), Rt=1.24 min, m/z (ESI⁺)=252.0/254.0 [M+H]⁺

GENERAL SCHEME 2:

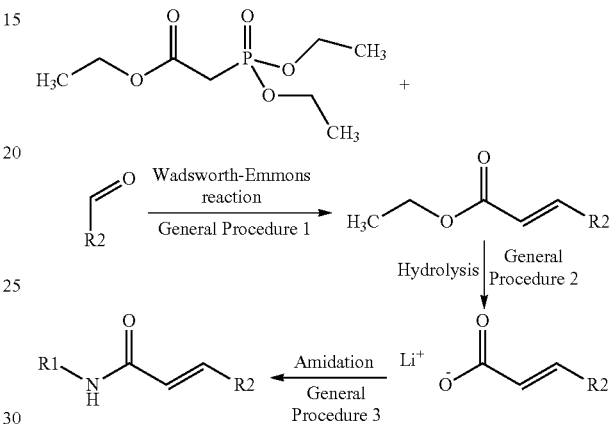

General Procedure 1 (General Scheme 2): Wadsworth-Emmons Reaction

Ethyl (2E)-3-cyclopropylprop-2-enoate (I-23a)

To an ice-cold stirred solution of triethyl phosphonoacetate (9.0 mL, 45.16 mmol) in anhydrous THF (70 mL) was added NaH (60% in mineral oil, 1.90 g, 47.50 mmol) portion wise over 10 min. The reaction mixture was stirred at RT under nitrogen for 1 h. Cyclopropanecarbaldehyde (3 mL, 40.15 mmol) was added dropwise and the resulting mixture was stirred at RT for 1 h. The reaction mixture was diluted with EtOAc (50 mL) and washed with saturated NaHCO₃ (80 mL). The organic layer was separated, dried over sodium sulfate, filtered and concentrated in vacuo to give a pale yellow liquid which was purified by flash column chromatography on normal phase silica (100 g SNAP KP-SIL cartridge, 0-60% EtOAc in heptane gradient) to afford 4.2 g of ethyl (2E)-3-cyclopropylprop-2-enoate as a colourless liquid (95% purity by $^1$H NMR, 71%).

$^1$H NMR (250 MHz, Chloroform-d) δ 0.58-0.66 (m, 2H), 0.88-0.98 (m, 2H), 1.27 (t, J=7.1 Hz, 3H), 1.48-1.64 (m, 1H), 4.16 (q, J=7.1 Hz, 2H), 5.87 (d, J=15.4 Hz, 1H), 6.41 (dd, J=10.0, 15.4 Hz, 1H).

LC-MS (METCR1410): 77% (UV), Rt=1.17 min, m/z (ESI⁺)=140.9 [M+H]⁺

General Procedure 2 (General Scheme 2): Hydrolysis (2E)-3-Cyclopropylprop-2-enoic acid lithium salt (I-23b)

To a stirred solution of ethyl (2E)-3-cyclopropylprop-2-enoate (I-23a, 95% purity by 1H NMR, 4.2 g, 28.46 mmol)

in 1:1 THF/H₂O (60 mL) was added lithium hydroxide hydrate (1.2 g, 28.60 mmol). The mixture was stirred at 50° C. for 1 h and at RT for 3 days. Lithium hydroxide hydrate (200 mg, 4.77 mmol) was added and the reaction heated at 50° C. for 5 h. The reaction was concentrated in vacuo to give a yellow solid which was triturated via sonication in 9:1 heptane/EtOAc (30 mL) and filtered. The solid was dried in vacuo to afford 3.67 g of (2E)-3-cyclopropylprop-2-enoic acid lithium salt as a yellow solid (100% purity, quantitative).

¹H NMR (250 MHz, Deuterium Oxide) δ 0.56-0.64 (m, 2H), 0.86-0.96 (m, 2H), 1.52-1.68 (m, 1H), 5.92 (d, J=15.5 Hz, 1H), 6.16 (dd, J=9.7, 15.5 Hz, 1H).

LC-MS (METCR1410): 100% (UV), Rt=0.76 min, m/z (ESI⁺)=113.6 [M+H]⁺

General Procedure 3 (General Scheme 2): Amide Formation (2E)-3-Cyclopropyl-N-(cyclopropylmethyl)prop-2-enamide (I-23c)

To a stirred suspension of (2E)-3-cyclopropylprop-2-enoic acid lithium salt (I-23b) (1.8 g, 15.25 mmol) and DIPEA (5.3 mL, 30.43 mmol) in dry DMF (70 mL) was added HATU (6.3 g, 16.57 mmol) portion wise and the reaction stirred at RT for 15 min. Cyclopropylmethylamine (1.7 mL, 19.60 mmol) was added and the mixture stirred at RT under nitrogen for 1 h. The reaction mixture was diluted with water (200 mL) and extracted with EtOAc (3×60 mL). The combined organic extracts were washed with water (2×100 mL) and brine (50 mL), dried over sodium sulfate and concentrated in vacuo to give a brown solid which was purified by flash column chromatography on normal phase silica (50 g SNAP KP-SIL cartridge, 0-50% EtOAc in heptane gradient) to afford 1.67 g of (2E)-3-cyclopropyl-N-(cyclopropylmethyl)prop-2-enamide as a yellow solid (97% purity, 67%).

¹H NMR (500 MHz, Chloroform-d) δ 0.21 (q, J=4.7 Hz, 2H), 0.47-0.53 (m, 2H), 0.57-0.63 (m, 2H), 0.84-0.91 (m, 2H), 0.92-1.02 (m, 1H), 1.46-1.58 (m, 1H), 3.17 (dd, J=5.6, 7.1 Hz, 2H), 5.47 (s, 1H), 5.85 (d, J=15.0 Hz, 1H), 6.32 (dd, J=10.0, 15.0 Hz, 1H).

LC-MS (METCR1410): 97% (UV), Rt=0.88 min, m/z (ESI⁺)=166.4 [M+H]⁺

GENERAL SCHEME 3:

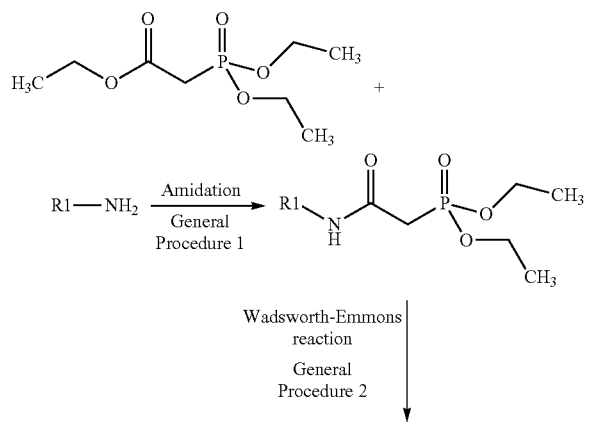

General Procedure 1 (General Scheme 3): Amide Formation

Diethyl {[(cyclopropylmethyl)carbamoyl]methyl}phosphonate (I-24a)

To a solution of cyclopropylmethylamine (7.5 mL, 86.47 mmol) in ethanol (40 mL) was added triethyl phosphonoacetate (6 mL, 30.11 mmol) dropwise and the mixture was stirred at 60° C. for 50 h. The reaction was stood at RT for 64 h and solvent and excess amine were removed in vacuo to give 8.2 g of diethyl{[(cyclo-propylmethyl)carbamoyl]methyl}phosphonate as a yellow oil (90% purity, 98%). The crude material was used in the next step without further purification.

¹H NMR (500 MHz, Chloroform-d) δ 0.13-0.35 (m, 2H), 0.41-0.57 (m, 2H), 0.86-1.19 (m, 1H), 1.24-1.36 (m, 6H), 2.64-2.97 (m, 3H), 3.04-3.14 (m, 1H), 3.87-4.22 (m, 4H), 6.77-7.60 (m, 1H).

LC-MS (METCR1410): 90% (UV), Rt=0.80 min, m/z (ESI⁺)=250.5 [M+H]⁺

General Procedure 2 (General Scheme 3): Wadsworth-Emmons Reaction

Method A: Preparation of Aldehyde In Situ (2E)-N-(Cyclopropylmethyl)-5-methoxypent-2-enamide (I-24b)

To a cold stirred solution of 1,1,3-trimethoxypropane (0.72 mL, 5.05 mmol) in THF (8 mL) was added 6M HCl (0.6 mL) and the mixture stirred at RT for 1 h. The reaction mixture was dried over sodium sulfate, filtered and the filtrate (filtrate A) containing 3-methoxypropanal used in the next step. To a cold stirred solution of diethyl{[(cyclopropylmethyl)carbamoyl]methyl}phosphonate (I-24a, 91% purity, 1.0 g, 3.65 mmol) in dry THF (15 mL) was added NaH (60% in mineral oil, 315 mg, 7.88 mmol) portion wise over 5 min under nitrogen. The mixture was stirred at RT for 15 min and filtrate A added dropwise over 5 min. The mixture was stirred at RT for 1 h, NaH (60% in mineral oil, 100 mg, 2.50 mmol) added and the reaction stirred at RT for 1 h. Water (20 mL) was added and the mixture acidified to pH 5 with 2N HCl. The crude product was extracted into EtOAc (2×20 mL) and the combined organic layers dried over sodium sulfate, filtered and concentrated in vacuo to give a yellow oil which was purified by flash column chromatography on normal phase silica (10 g SNAP KP-SIL cartridge, 0-80% EtOAc in heptane gradient) to afford 158 mg of (2E)-N-(cyclopropyl-methyl)-5-methoxypent-2-enamide as a colourless oil (96% purity, 23%).

¹H NMR (500 MHz, Chloroform-d) δ 0.18-0.23 (m, 2H), 0.48-0.54 (m, 2H), 0.91-1.01 (m, 1H), 2.45 (qd, J=1.5, 6.6 Hz, 2H), 3.17 (dd, J=5.5, 7.1 Hz, 2H), 3.34 (s, 3H), 3.49 (t, J=6.5 Hz, 2H), 5.56 (s, 1H), 5.86 (dt, J=1.5, 15.3 Hz, 1H), 6.81 (dt, J=6.9, 15.3 Hz, 1H).

LC-MS (METCR1410): 96% (UV), Rt=0.79 min, m/z (ESI⁺)=184.4 [M+H]⁺

Method B: Use of Commercially Available Aldehyde (2E) N-(Cyclopropylmethyl)-3-(oxan-4-yl)prop-2-enamide (I-25)

To a cold, stirred solution of diethyl{[(cyclopropylmethyl)carbamoyl]methyl}-phosphonate (I-24a, 91% purity, 700 mg, 2.56 mmol) in dry THF (15 mL) under nitrogen was

GENERAL SCHEME 4:

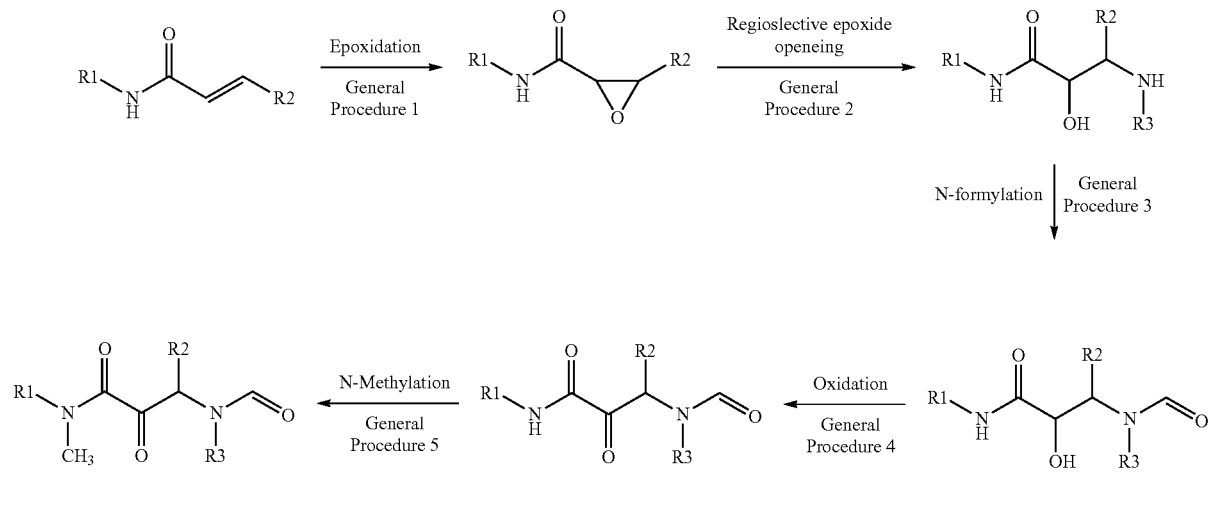

added NaH (60% in mineral oil, 210 mg, 5.25 mmol) over 5 min. The mixture was stirred at RT under nitrogen for 15 min and a solution of oxane-4-carbaldehyde (320 mg, 2.80 mmol) in THF (2 mL) added. The mixture was stirred at RT for 45 min, quenched with water (20 mL) and acidified to pH 5 with 2N HCl and the aqueous layer was extracted with EtOAc (2×20 mL). The combined organic layers were dried over sodium sulfate, filtered and concentrated in vacuo to give a yellow solid which was purified by flash column chromatography on normal phase silica (10 g SNAP KP-SIL cartridge, 0-80% EtOAc in heptane gradient) to afford 238 mg of (2E) N-(cyclopropylmethyl)-3-(oxan-4-yl)prop-2-enamide as an off-white solid (93% purity, 41%).

¹H NMR (500 MHz, Chloroform-d) δ 0.18-0.24 (m, 2H), 0.49-0.55 (m, 2H), 0.90-1.02 (m, 1H), 1.49-1.57 (m, 2H), 1.62-1.70 (m, 2H), 2.31-2.41 (m, 1H), 3.18 (dd, J=5.6, 7.1 Hz, 2H), 3.43 (td, J=2.1, 11.7 Hz, 2H), 3.96-4.01 (m, 2H), 5.54-5.60 (m, 1H), 5.75 (dd, J=1.3, 15.4 Hz, 1H), 6.80 (dd, J=6.5, 15.4 Hz, 1H).

LC-MS (METCR1410): 93% (UV), Rt=0.84 min, m/z (ESI⁺)=210.3 [M+H]⁺

(2E)-N-(Cyclopropylmethyl)-5-phenylpent-2-enamide (I-26)

The title compound was synthesized in a similar manner to method B, general procedure 2 (general scheme 3) as a yellow viscous oil (974 mg, 97% purity, 57%) following purification by flash column chromatography on normal phase silica (25 g SNAP KP-SIL cartridge, 0-40% EtOAc in heptane gradient).

¹H NMR (500 MHz, Chloroform-d) δ 0.15-0.23 (m, 2H), 0.46-0.54 (m, 2H), 0.92-1.00 (m, 1H), 2.46-2.54 (m, 2H), 2.74-2.81 (m, 2H), 3.17 (dd, J=5.5, 7.1 Hz, 2H), 5.53 (s, 1H), 5.75-5.82 (m, 1H), 6.88 (dt, J=6.9, 15.2 Hz, 1H), 7.17-7.21 (m, 3H), 7.26-7.32 (m, 2H).

LC-MS (METCR1410): 97% (UV), Rt=1.08 min, m/z (ESI⁺)=230.3 [M+H]⁺

Epoxide Route: Synthesis of Final Compounds (FP 1-82)

General Procedure 1 (General Scheme 4): Epoxidation

N-[(3-Chlorophenyl)methyl]-3-methyloxirane-2-carboxamide (I-27)

To a stirred solution of (2E)-N-[(3-chlorophenyl)methyl]but-2-enamide (I-1, 2.13 g, 9.85 mmol) in DCM (40 mL) at RT was added m-CPBA (70%, 12.15 g, 49.27 mmol). The resulting mixture was stirred at RT for 3 days. The solution was washed with 20% Na₂S₂O₃ (30 mL), saturated NaHCO₃ (30 mL) and water (10 mL). The organic layer was separated, dried over sodium sulfate, filtered and concentrated in vacuo. The residue was purified by flash column chromatography on normal phase silica (25 g SNAP KP-SIL cartridge, 0-80% EtOAc in heptane gradient) to afford a colourless solid which was suspended in EtOAc (20 mL) and washed with 1N NaOH (20 mL). The organic layer was separated, dried over sodium sulfate and concentrated in vacuo to afford 276 mg of N-[(3-chlorophenyl)-methyl]-3-methyloxirane-2-carboxamide as a colourless oil (85% purity, 11%).

¹H NMR (500 MHz, Chloroform-d) δ 1.41 (d, J=5.1 Hz, 3H), 3.05 (qd, J=5.1, 2.1 Hz, 1H), 3.26 (d, J=2.1 Hz, 1H), 4.39 (d, J=6.2 Hz, 2H), 6.45 (s, 1H), 7.10-7.14 (m, 1H), 7.21-7.24 (m, 1H), 7.25-7.27 (m, 2H).

LC-MS (METCR1278): 85% (UV), Rt=1.75 min, m/z (ESI⁺)=225.9/227.9 [M+H]⁺

N-[(3-Chlorophenyl)methyl]-3,3-dimethyloxirane-2-carboxamide (I-28)

The title compound was synthesized from N-[(3-chlorophenyl)methyl]-3-methylbut-2-enamide (I-2) in a similar manner to general procedure 1 (general scheme 4) as an off-white solid (1.17 g, 90% purity by $^1$H NMR, 63%) after purification by flash column chromatography on normal phase silica (25 g SNAP KP-SIL cartridge, 0-75% EtOAc in heptane gradient).

$^1$H NMR (500 MHz, Chloroform-d) δ 1.30 (s, 3H), 1.42 (s, 3H), 3.36 (s, 1H), 4.43 (d, J=6.2 Hz, 2H), 6.51 (s, 1H), 7.13-7.17 (m, 1H), 7.23-7.28 (m, 3H).

LC-MS (METCR1278): 100% (UV), Rt=1.82 min, m/z (ESI$^+$)=239.9/241.9 [M+H]$^+$

N-[(3-Chlorophenyl)methyl]-3-phenyloxirane-2-carboxamide (I-29)

The title compound was synthesized from (2E)-N-[(3-chlorophenyl)methyl]-3-phenylprop-2-enamide (I-3) in a similar manner general procedure 1 (general scheme 4) as an off-white solid (1.26 g, 100% purity, 67%) after purification by recrystallization from 1:3 EtOAc/heptane.

$^1$H NMR (500 MHz, Chloroform-d) δ 3.59 (d, J=2.0 Hz, 1H), 3.91 (d, J=2.0 Hz, 1H), 4.43 (dd, J=14.9, 6.0 Hz, 1H), 4.50 (dd, J=14.9, 6.3 Hz, 1H), 6.50-6.64 (m, 1H), 7.16-7.20 (m, 1H), 7.26-7.30 (m, 5H), 7.33-7.40 (m, 3H).

LC-MS (MET-µHPLC-AB-101): 100% (UV), Rt=3.26 min, m/z (ESI$^+$)=288.0/290.0 [M+H]$^+$

N-(Cyclopropylmethyl)-3-methyloxirane-2-carboxamide (I-30)

The title compound was synthesized from (2E)-N-(cyclopropylmethyl)but-2-enamide (I-4) in a similar manner to general procedure 1 (general scheme 4) as a light yellow solid (8.94 g, 84% purity by $^1$H NMR, 53%) after trituration in EtOAc to remove the 3-chlorobenzoic acid by-product.

$^1$H NMR (500 MHz, Chloroform-d) δ 0.17 (q, J=4.7 Hz, 2H), 0.42-0.55 (m, 2H), 0.84-0.97 (m, 1H), 1.39 (d, J=5.2 Hz, 3H), 2.99-3.14 (m, 3H), 3.18 (d, J=2.1 Hz, 1H), 6.22 (s, 1H).

LC-MS (METCR1410): 63% (UV), Rt=0.70 min, m/z (ESI$^+$)=156.5 [M+H]$^+$

N-Cyclopropyl-3-methyloxirane-2-carboxamide (I-31)

The title compound was synthesized from (2E)-N-cyclopropylbut-2-enamide (I-5) in a similar manner to general procedure 1 (general scheme 4) as a colourless free-flowing oil (1.98 g, 89% purity by 1H NMR, 40%) after purification by flash column chromatography on normal phase silica (25 g SNAP Ultra cartridge, 10-100% EtOAc in heptane gradient).

$^1$H NMR (250 MHz, Chloroform-d) δ 0.37-0.60 (m, 2H), 0.76 (qd, J=1.5, 6.4 Hz, 2H), 1.36 (d, J=5.1 Hz, 3H), 2.66 (tq, J=3.7, 7.3 Hz, 1H), 2.96 (qd, J=2.1, 5.1 Hz, 1H), 3.15 (d, J=2.1 Hz, 1H), 6.02-6.39 (m, 1H).

LC-MS (METCR1410): 80% (UV), Rt=0.42 min, m/z (ESI$^+$)=142.0 [M+H]$^+$

3-Methyl-N-(2-methylpropyl)oxirane-2-carboxamide (I-32)

The title compound was synthesized from (2E)-N-(2-methylpropyl)but-2-enamide (I-6) in a similar manner to general procedure 1 (general scheme 4) as a yellow free-flowing oil (5.3 g, 100% purity by $^1$H NMR, 78%) after purification by flash column chromatography on normal phase silica (100 g SNAP KP-SIL cartridge, 0-100% TBME in heptane gradient).

$^1$H NMR (250 MHz, Chloroform-d) δ 0.91 (d, J=6.7 Hz, 6H), 1.42 (d, J=5.1 Hz, 3H), 1.82-1.71 (m, 1H), 3.11-2.99 (m, 3H), 3.22 (d, J=2.1 Hz, 1H), 6.20 (s, 1H).

LC-MS (METCR1278): 86% (UV), Rt=1.19-1.28 min (two peaks), m/z (ESI$^+$)=158.0 [M+H]$^+$

N-[(3-Chlorophenyl)methyl]oxirane-2-carboxamide (I-33)

The title compound was synthesized from N-[(3-chlorophenyl)methyl]prop-2-enamide (I-7) in a similar manner to general procedure 1 (general scheme 4) at 55° C. in 1,2-DCE and was obtained as a colourless viscous oil (1.4 g, 80% purity by $^1$H NMR, 46%) after purification by flash column chromatography on normal phase silica (100 g SNAP KP-SIL cartridge, 5-100% EtOAc in heptane gradient).

$^1$H NMR (500 MHz, Chloroform-d) δ 2.78 (dd, J=2.6, 5.5 Hz, 1H), 3.01 (dd, J=4.8, 5.4 Hz, 1H), 3.50 (dd, J=2.6, 4.6 Hz, 1H), 4.40 (qd, J=6.2, 15.0 Hz, 2H), 6.34-6.61 (m, 1H), 7.05-7.16 (m, 1H), 7.20-7.30 (m, 3H).

LC-MS (METCR1410): 95% (UV), Rt=0.96 min, m/z (ESI$^+$)=212.0/214.0 [M+H]$^+$

N-(Cyclohexylmethyl)-3-methyloxirane-2-carboxamide (I-34)

The title compound was synthesized from (2E)-N-(cyclohexylmethyl)but-2-enamide (I-8) in a similar manner to general procedure 1 (general scheme 4) as a yellow viscous oil (1.23 g, 87% purity, 62%) used in the next step without further purification.

$^1$H NMR (250 MHz, Chloroform-d) δ 0.78-1.02 (m, 2H), 1.08-1.30 (m, 3H), 1.35-1.50 (m, 4H), 1.60-1.79 (m, 6H), 2.95-3.11 (m, 3H), 3.19 (d, J=2.1 Hz, 1H).

LC-MS (METCR1410): 87% (UV), Rt=0.99 min, m/z (ESI$^+$)=198.5 [M+H]$^+$

N-[2-(Cyclohexyloxy)ethyl]-3-methyloxirane-2-carboxamide (I-35)

The title compound was synthesized from (2E)-N-[2-(cyclohexyloxy)ethyl]-but-2-enamide (I-9) in a similar manner to general procedure 1 (general scheme 4) as a yellow viscous oil (275 mg, 93% purity, 59%) after purification by flash column chromatography on normal phase silica (50 g SNAP KP-SIL cartridge, 0-100% EtOAc in heptane gradient).

$^1$H NMR (250 MHz, Chloroform-d) δ 1.10-1.34 (m, 5H), 1.40 (d, J=5.13 Hz, 3H), 1.48-1.56 (m, 1H), 1.64-1.78 (m, 2H), 1.78-1.93 (m, 2H), 2.95-3.07 (m, 1H), 3.14-3.29 (m, 2H), 3.34-3.56 (m, 4H), 6.49 (s, 1H).

LC-MS (METCR1410): 93% (UV), Rt=1 min, m/z (ESI$^+$)=228.2 [M+H]$^+$

Methyl 2-[(3-methyloxiran-2-yl)formamido]acetate (I-36)

The title compound was synthesized from methyl 2-[(2E)-but-2-enamido]-acetate (I-10) in a similar manner to general procedure 1 (general scheme 4) as a colourless viscous oil (629 mg, 100% purity, 50%) after purification by flash column chromatography on normal phase silica (100 g SNAP KP-SIL cartridge, 0-100% TBME in heptane gradient).

$^1$H NMR (500 MHz, Chloroform-d) δ 1.41 (d, J=5.1 Hz, 3H), 3.11 (qd, J=2.1, 5.1 Hz, 1H), 3.24 (d, J=2.1 Hz, 1H), 3.76 (s, 3H), 3.96 (dd, J=5.2, 18.3 Hz, 1H), 4.09 (dd, J=6.1, 18.3 Hz, 1H), 6.57 (br. s, 1H).

LC-MS (METCR0990): 100% (UV), Rt=0.90-1.10 min, m/z (ESI$^+$)=174.2 [M+H]$^+$

N-[2-(3-Chlorophenyl)propan-2-yl]-3-methyloxirane-2-carboxamide (I-37)

The title compound was synthesized from (2E)-N-[2-(3-chlorophenyl)-propan-2-yl]but-2-enamide (I-11) in a similar manner to general procedure 1 (general scheme 4) as a yellow viscous oil (1.05 g, 94% purity, 50%) after purification by flash column chromatography on normal phase silica (100 g SNAP KP-SIL cartridge, 0-100% EtOAc in heptane gradient).

$^1$H NMR (500 MHz, DMSO-d6) δ 1.29 (d, J=5.1 Hz, 3H), 1.53-1.59 (m, 6H), 3.09 (qd, J=2.0, 5.1 Hz, 1H), 3.19 (d, J=2.0 Hz, 1H), 7.19-7.38 (m, 4H), 8.13 (s, 1H).

LC-MS (METCR1410): 94% (UV), Rt=1.11 min, m/z (ESI$^+$)=254.0 [M+H]$^+$

N-tert-Butyl-3-methyloxirane-2-carboxamide (I-38)

The title compound was synthesized from (2E)-N-tert-butylbut-2-enamide (I-12) in a similar manner to general procedure 1 (general scheme 4) as an off-white crystalline solid (659 mg, 80% purity by $^1$H NMR, 79%) after purification by flash column chromatography on normal phase silica (25 g SNAP KP-SIL cartridge, 0-50% EtOAc in heptane gradient).

$^1$H NMR (250 MHz, Chloroform-d) δ 1.33 (s, 9H), 1.38 (d, J=5.2 Hz, 3H), 2.97 (qd, J=5.1, 2.1 Hz, 1H), 3.09 (d, J=2.1 Hz, 1H), 5.94 (s, 1H).

3-Methyl-N-(propan-2-yl)oxirane-2-carboxamide (I-39)

The title compound was synthesized from (2E)-N-(propan-2-yl)but-2-enamide (I-13) in a similar manner to general procedure 1 (general scheme 4) as an off-white crystalline solid (4 g, 95% purity by $^1$H NMR, 32%) after purification by flash column chromatography on normal phase silica (100 g SNAP KP-SIL cartridge, 0-80% EtOAc in heptane gradient).

$^1$H NMR (500 MHz, DMSO-d6) δ 1.05 (t, J=6.6 Hz, 6H), 1.28 (d, J=5.1 Hz, 3H), 3.05 (qd, J=5.1, 2.0 Hz, 1H), 3.09 (d, J=2.0 Hz, 1H), 3.77-3.93 (m, 1H), 7.82 (d, J=7.3 Hz, 1H).

7-Chloro-2-(3-methyloxirane-2-carbonyl)-1,2,3,4-tetrahydroisoquinoline (I-40)

The title compound was synthesized from (2E)-1-(7-chloro-1,2,3,4-tetrahydroisoquinolin-2-yl)but-2-en-1-one (I-14) in a similar manner to general procedure 1 (general scheme 4) as a colourless crystalline solid (292 mg, 100% purity by 1H NMR, 45%) after purification by flash column chromatography on normal phase silica (25 g SNAP KP-SIL cartridge, 0-50% EtOAc in heptane gradient).

$^1$H NMR (250 MHz, Chloroform-d) δ 1.44 (d, J=5.2 Hz, 3H), 2.81-3.01 (m, 2H), 3.21-3.31 (m, 1H), 3.40 (d, J=2.1 Hz, 1H), 3.64-3.83 (m, 1H), 3.88-4.00 (m, 1H), 4.60-4.81 (m, 2H), 7.02-7.23 (m, 3H).

N-(Cyclopropylmethyl)-3-ethyloxirane-2-carboxamide (I-41)

The title compound was synthesized from (2E)-N-(cyclopropylmethyl)pent-2-enamide (I-15) in a similar manner to general procedure 1 (general scheme 4) as a colourless free-flowing oil (4.02 g, 91% purity by $^1$H NMR, 54%) after trituration in EtOAc to remove the 3-chlorobenzoic acid by-product.

$^1$H NMR (500 MHz, Chloroform-d) δ 0.17 (q, J=4.8 Hz, 2H), 0.45-0.52 (m, 2H), 0.85-0.95 (m, 1H), 1.00 (t, J=7.5 Hz, 3H), 1.60 (dp, J=7.4, 14.5 Hz, 1H), 1.72 (dqd, J=4.7, 7.6, 15.0 Hz, 1H), 2.91-2.96 (m, 1H), 3.08 (tp, J=6.5, 13.7 Hz, 2H), 3.23 (d, J=2.0 Hz, 1H), 6.23 (s, 1H).

LC-MS (METCR1410): 48% (UV), Rt=0.82 min, m/z (ESI$^+$)=170.4 [M+H]$^+$

N-[(3-Chlorophenyl)methyl]-3-ethyloxirane-2-carboxamide (I-42)

The title compound was synthesized from (2E)-N-[(3-chlorophenyl)methyl]-pent-2-enamide (I-16) in a similar manner to general procedure 1 (general scheme 4) as a yellow solid (4.12 g, 100% purity, 72%) after purification by flash column chromatography on normal phase silica (100 g SNAP KP-SIL cartridge, 0-80% EtOAc in heptane gradient).

$^1$H NMR (250 MHz, Chloroform-d) δ 1.01 (t, J=7.5 Hz, 3H), 1.55-1.77 (m, 2H), 2.96 (ddd, J=2.2, 4.7, 5.9 Hz, 1H), 3.30 (d, J=2.1 Hz, 1H), 4.39 (d, J=6.1 Hz, 2H), 6.48 (s, 1H), 7.08-7.16 (m, 1H), 7.20-7.31 (m, 3H).

LC-MS (METCR1278): 100% (UV), Rt=1.82 min, m/z (ESI$^+$)=240.0/241.9 [M+H]$^+$

N-(Cyclopropylmethyl)-3-(propan-2-yl)oxirane-2-carboxamide (I-43)

The title compound was synthesized from N-(cyclopropylmethyl)-4-methylpent-2-enamide (I-17) in a similar manner to general procedure 1 (general scheme 4) in 1,2-DCE at RT then at 60° C. and was obtained as an off-white crystalline solid (6.83 g, 90% purity by $^1$H NMR, 77%) after purification by flash column chromatography on normal phase silica (100 g SNAP KP-SIL cartridge, 0-100% TBME in heptane gradient).

$^1$H NMR (250 MHz, Chloroform-d) δ 0.12-0.23 (m, 2H), 0.44-0.55 (m, 2H), 0.87-0.94 (m, 1H), 1.01 (t, J=6.3 Hz, 6H), 1.60-1.73 (m, 1H), 2.77 (dd, J=2.1, 6.4 Hz, 1H), 3.00-3.18 (m, 2H), 3.27 (d, J=2.1 Hz, 1H), 6.22 (s, 1H).

N-(Cyclopropylmethyl)-3-propyloxirane-2-carboxamide (I-44)

The title compound was synthesized from (2E)-N-(cyclopropylmethyl)hex-2-enamide (I-18) in a similar manner to general procedure 1 (general scheme 4) as a yellow crystalline solid (4.54 g, 89% purity by 1H NMR, 57%) after trituration in EtOAc to remove the 3-chlorobenzoic acid by-product.

$^1$H NMR (500 MHz, Chloroform-d) δ 0.18 (q, J=4.8 Hz, 2H), 0.46-0.52 (m, 2H), 0.86-0.94 (m, 1H), 0.97 (t, J=7.3 Hz, 3H), 1.42-1.58 (m, 3H), 1.60-1.71 (m, 1H), 2.91-2.97 (m, 1H), 3.01-3.15 (m, 2H), 3.21 (d, J=2.1 Hz, 1H), 6.22 (s, 1H).

LC-MS (METCR1410): 74% (UV), Rt=0.92 min, m/z (ESI$^+$)=184.4 [M+H]$^+$

N-(Cyclohexylmethyl)-3-ethyloxirane-2-carboxamide (I-45)

The title compound was synthesized from (2E)-N-(cyclohexylmethyl)pent-2-enamide (I-19) in a similar manner to general procedure 1 (general scheme 4) as an off-white viscous oil (4.6 g, 94% purity by $^1$H NMR, 67%) used in the next step without further purification.

$^1$H NMR (500 MHz, Chloroform-d) δ 0.87-0.96 (m, 2H), 1.02 (t, J=7.5 Hz, 3H), 1.11-1.27 (m, 3H), 1.44 (dddq, J=3.4, 6.8, 10.3, 14.4 Hz, 1H), 1.57-1.65 (m, 1H), 1.65-1.78 (m, 6H), 2.93 (ddd, J=2.2, 4.7, 6.6 Hz, 1H), 3.08 (t, J=6.6 Hz, 2H), 3.25 (d, J=2.1 Hz, 1H), 6.19 (s, 1H).

LC-MS (METCR1410): 53% (UV), Rt=1.09 min, m/z (ESI$^+$)=212.0 [M+H]$^+$

N-[(3-Chlorophenyl)methyl]-3-(propan-2-yl)oxirane-2-carboxamide (I-46)

The title compound was synthesized from N-[(3-chlorophenyl)methyl]-4-methylpent-2-enamide (I-20) in a similar manner to general procedure 1 (general scheme 4) as an off-white crystalline solid (1.4 g, 90% purity by $^1$H NMR, 66%) after purification by flash column chromatography on normal phase silica (100 g SNAP KP-SIL cartridge, 5-100% EtOAc in heptane gradient).

$^1$H NMR (500 MHz, Chloroform-d) δ 1.01 (t, J=7.0 Hz, 6H), 1.68 (dq, J=6.7, 13.5 Hz, 1H), 2.78 (dd, J=2.2, 6.3 Hz, 1H), 3.33 (d, J=2.2 Hz, 1H), 4.39 (qd, J=6.1, 15.0 Hz, 2H), 6.39-6.55 (m, 1H), 7.08-7.17 (m, 1H), 7.20-7.30 (m, 3H).

LC-MS (METCR1410): 81% (UV), Rt=1.15 min, m/z (ESI$^+$)=254.1/256.0 [M+H]$^+$

N-(Cyclopropylmethyl)-3-(2-methylpropyl)oxirane-2-carboxamide (I-47)

The title compound was synthesized from (2E)-N-(cyclopropylmethyl)-5-methylhex-2-enamide (I-21) in a similar manner to general procedure 1 (general scheme 4) as a yellow oil (975 mg, 100% purity by $^1$H NMR, 20%) after purification by flash column chromatography on normal phase silica (100 g SNAP KP-SIL cartridge, 0-100% TBME in heptane gradient).

$^1$H NMR (500 MHz, Chloroform-d) δ 0.16-0.23 (m, 2H), 0.47-0.54 (m, 2H), 0.88-0.96 (m, 1H), 0.99 (dd, J=6.7, 1.1 Hz, 6H), 1.40-1.48 (m, 1H), 1.55 (ddd, J=14.1, 7.4, 4.8 Hz, 1H), 1.85 (dp, J=13.4, 6.7 Hz, 1H), 2.95 (ddd, J=6.9, 4.8, 2.2 Hz, 1H), 3.02-3.10 (m, 1H), 3.14 (ddd, J=13.1, 7.1, 5.8 Hz, 1H), 3.19 (d, J=2.2 Hz, 1H), 6.21 (s, 1H)

LC-MS (METCR1410): 60% (UV), Rt=1.02-1.05 min (two peaks), m/z (ESI$^+$)=198.4 [M+H]$^+$

N-[(3-Chlorophenyl)methyl]-3-(2-methylpropyl)oxirane-2-carboxamide (I-48)

The title compound was synthesized from (2E)-N-[(3-chlorophenyl)methyl]-5-methylhex-2-enamide (I-22) in a similar manner to general procedure 1 (general scheme 4) as an off-white viscous oil (1 g, 70% purity by $^1$H NMR, 27%) after purification by flash column chromatography on normal phase silica (25 g SNAP KP-SIL cartridge, 0-80% EtOAc in heptane gradient).

$^1$H NMR (500 MHz, DMSO-d6) δ 8.57 (t, J=6.0 Hz, 1H), 7.41-7.27 (m, 3H), 7.21 (d, J=7.5 Hz, 1H), 4.32-4.19 (m, 2H), 3.23 (d, J=2.0 Hz, 1H), 3.04 (td, J=5.9, 2.0 Hz, 1H), 1.79 (dp, J=13.5, 6.7 Hz, 1H), 1.46-1.41 (m, 2H), 0.94 (d, J=6.7 Hz, 6H).

LC-MS (METCR1673): 50% (UV), Rt=1.21 min, m/z (ESI$^+$)=268.0/270.0 [M+H]$^+$

3-Cyclopropyl-N-(cyclopropylmethyl)oxirane-2-carboxamide (I-49)

The title compound was synthesized from (2E)-3-cyclopropyl-N-(cyclopropyl-methyl)prop-2-enamide (I-23c) in a similar manner to general procedure 1 (general scheme 4) as an off-white solid (587 mg, 95% purity, 37%) after purification by flash column chromatography on normal phase silica (25 g SNAP KP-SIL cartridge, 0-60% EtOAc in heptane gradient).

$^1$H NMR (500 MHz, Chloroform-d) δ 0.14-0.20 (m, 2H), 0.38-0.45 (m, 2H), 0.46-0.51 (m, 2H), 0.53-0.65 (m, 2H), 0.84-0.99 (m, 2H), 2.76 (dd, J=2.1, 5.6 Hz, 1H), 3.01-3.14 (m, 2H), 3.28 (d, J=2.1 Hz, 1H), 6.19 (s, 1H).

LC-MS (METCR1410): 95% (UV), Rt=0.86 min, m/z (ESI$^+$)=182.4 [M+H]$^+$

N-(Cyclopropylmethyl)-3-(2-methoxyethyl)oxirane-2-carboxamide (I-50)

The title compound was synthesized from (2E)-N-(cyclopropylmethyl)-5-methoxypent-2-enamide (I-24b) in a similar manner to general procedure 1 (general scheme 4) as a colourless viscous oil (116 mg, 97% purity, 68%) after purification by flash column chromatography on normal phase silica (10 g SNAP KP-SIL cartridge, 0-80% EtOAc in heptane gradient).

$^1$H NMR (500 MHz, Chloroform-d) δ 0.18 (q, J=4.8 Hz, 2H), 0.45-0.52 (m, 2H), 0.84-0.95 (m, 1H), 1.68-1.76 (m, 1H), 1.97-2.06 (m, 1H), 3.01-3.16 (m, 3H), 3.26 (d, J=2.2 Hz, 1H), 3.36 (s, 3H), 3.47-3.57 (m, 2H), 6.22 (s, 1H).

LC-MS (METCR1410): 97% (UV), Rt=1.08 min, m/z (ESI$^+$)=200.0 [M+H]$^+$

N-(Cyclopropylmethyl)-3-(oxan-4-yl)oxirane-2-carboxamide (I-51)

The title compound was synthesized from (2E)-N-(cyclopropylmethyl)-3-(oxan-4-yl)prop-2-enamide (I-25) in a similar manner to general procedure 1 (general scheme 4) as a colourless viscous oil (165 mg, 59% purity, 41%) after purification by flash column chromatography on normal phase silica (10 g SNAP KP-SIL cartridge, 0-100% EtOAc in heptane gradient).

LC-MS (METCR1410): 59% (UV), Rt=0.81 min, m/z (ESI$^+$)=226.2 [M+H]$^+$

N-(Cyclopropylmethyl)-3-(2-phenylethyl)oxirane-2-carboxamide (I-52)

The title compound was synthesized from (2E)-N-(cyclopropylmethyl)-5-phenylpent-2-enamide (I-26) in a similar manner to procedure 1 (general scheme 4) as a colourless free-flowing oil (435 mg, 87% purity, 37%) after purification by flash column chromatography on normal phase silica (25 g SNAP KP-SIL cartridge, 0-70% EtOAc in heptane gradient).

$^1$H NMR (500 MHz, Chloroform-d) δ 0.14-0.22 (m, 2H), 0.44-0.54 (m, 2H), 0.87-0.95 (m, 1H), 1.82-1.93 (m, 1H), 1.99-2.09 (m, 1H), 2.73-2.86 (m, 2H), 2.99 (ddd, J=2.2, 4.5, 6.6 Hz, 1H), 3.01-3.09 (m, 1H), 3.10-3.17 (m, 1H), 3.26 (d, J=2.2 Hz, 1H), 6.18 (s, 1H), 7.18-7.24 (m, 3H), 7.28-7.33 (m, 2H).

LC-MS (METCR1410): 87% (UV), Rt=1.07 min, m/z (ESI+)=246.5 [M+H]+

3-Methyloxirane-2-carboxamide (I-53)

The title compound was synthesized from (2E)-but-2-enamide in a similar manner to general procedure 1 (general scheme 4) as an off-white solid (316 mg, 60% purity by 1H NMR, 16%) used in the next step without further purification.

$^1$H NMR (500 MHz, DMSO-d6) δ 1.27 (d, J=4.7 Hz, 3H), 2.98-3.13 (m, 2H), 7.11-7.37 (m, 2H).

General Procedure 2 (General Scheme 4): Regioselective Epoxide Opening

Method A: Epoxide Opening in the Presence of Titanium(IV) Isopropoxide at RT

N-[(3-chlorophenyl)methyl]-2-hydroxy-3-[(2-methoxyphenyl) amino]butanamide (I-54)

To a stirred solution of N-[(3-chlorophenyl)methyl]-3-methyloxirane-2-carboxamide (I-27, 200 mg, 0.89 mmol) and 2-methoxyaniline (0.8 mL, 7.09 mmol) was added at RT titanium(IV) isopropoxide (378 mg, 1.33 mmol). The mixture was stirred at RT for 16 h. The reaction was quenched with 10% tartaric acid (10 mL) and the aqueous layer extracted with EtOAc (3×15 mL). The organic layers were combined, washed with water (10 mL), dried over sodium sulfate, filtered and concentrated in vacuo. The residue was purified by flash column chromatography on normal phase silica (25 g SNAP KP-SIL cartridge, 5-100% EtOAc in heptane gradient) to afford 200 mg of N-[(3-chlorophenyl) methyl]-2-hydroxy-3-[(2-methoxyphenyl) amino]butanamide as a viscous yellow oil (85% purity by $^1$H NMR, 55%). 130 mg of 1-54 were further purified by flash column chromatography on normal phase silica (25 g SNAP-HP-SIL cartridge, 10-100% EtOAc in heptane gradient) to afford 65 mg of N-[(3-chlorophenyl)methyl]-2-hydroxy-3-[(2-methoxyphenyl) amino]butanamide as a viscous yellow oil (95% purity, 20%).

$^1$H NMR (500 MHz, Chloroform-d) δ 1.21 (d, J=6.62 Hz, 3H), 3.05-3.15 (m, 1H), 3.85 (s, 3H), 3.97-4.04 (m, 1H), 4.37-4.52 (m, 3H), 6.78-6.84 (m, 2H), 6.85-6.93 (m, 2H), 7.12-7.18 (m, 1H), 7.18-7.23 (m, 1H), 7.23-7.26 (m, 3H)

LC-MS (METCR1416): 96% (UV), Rt=3.88 min, m/z (ESI+)=349.2/351.2 [M+H]+

N-[(3-Chlorophenyl)methyl]-3-(cyclohexylamino)-2-hydroxybutanamide (I-55)

The title compound was synthesized from N-[(3-chlorophenyl)methyl]-3-methyl-oxirane-2-carboxamide (I-27) in a similar manner to method A, general procedure 2 (general scheme 4) as an off-white solid (110 mg, 97% purity, 32%) after purification by flash column chromatography on normal phase silica (10 g SNAP KP-SIL cartridge, 0-100% EtOAc in heptane gradient followed by 0-10% MeOH in EtOAc gradient and 10% 7N methanolic ammonia solution in EtOAc flush).

$^1$H NMR (500 MHz, Chloroform-d) δ 1.01-1.05 (m, 1H), 1.07 (d, J=6.5 Hz, 3H), 1.09-1.20 (m, 2H), 1.20-1.28 (m, 2H), 1.55-1.65 (m, 1H), 1.65-1.78 (m, 2H), 1.80-1.90 (m, 1H), 1.92-2.01 (m, 1H), 2.51-2.63 (m, 1H), 3.27-3.39 (m, 1H), 4.09 (d, J=4.9 Hz, 1H), 4.37-4.49 (m, 2H), 7.14-7.18 (m, 1H), 7.21-7.26 (m, 2H), 7.27-7.28 (m, 1H), 7.68-7.78 (m, 1H)

LC-MS (METCR1410): 97% (UV), Rt=0.99 min, m/z (ESI+)=325.0/327.0 [M+H]+

N-[(3-Chlorophenyl)methyl]-2-hydroxy-3-[(3-methoxyphenyl)-amino]butanamide (I-56)

The title compound was synthesized from N-[(3-chlorophenyl)methyl]-3-methyl-oxirane-2-carboxamide (I-27) in a similar manner to method A, general procedure 2 (general scheme 4) as an off-white solid (258 mg, 100% purity, 46%) after purification by flash column chromatography on normal phase silica (50 g SNAP KP-SIL cartridge, 0-50% EtOAc in heptane gradient) followed by recrystallization from 1:1 EtOAc/heptane.

$^1$H NMR (500 MHz, Chloroform-d) δ 1.17 (d, J=6.6 Hz, 3H), 3.00 (s, 1H), 3.76 (s, 3H), 3.97-4.03 (m, 1H), 4.38-4.50 (m, 3H), 6.29 (t, J=2.2 Hz, 1H), 6.33-6.38 (m, 2H), 7.08-7.13 (m, 2H), 7.13-7.16 (m, 1H), 7.24-7.26 (m, 3H).

LC-MS (METCR1278): 100% (UV), Rt=1.93 min, m/z (ESI+)=348.9/350.9 [M+H]+

N-[(3-Chlorophenyl)methyl]-2-hydroxy-3-[(4-methoxyphenyl)amino]butanamide (I-57)

The title compound was synthesized from N-[(3-chlorophenyl)methyl]-3-methyl-oxirane-2-carboxamide (I-27) in a similar manner to method A, general procedure 2 (general scheme 4) as a brown solid (371 mg, 100% purity, 64%) after purification by flash column chromatography on normal phase silica (25 g SNAP KP-SIL cartridge, 0-50% EtOAc in heptane gradient).

$^1$H NMR (500 MHz, Chloroform-d) δ 1.16 (d, J=6.6 Hz, 3H), 3.75 (s, 3H), 3.82-3.92 (m, 1H), 4.33 (d, J=4.2 Hz, 1H), 4.39-4.50 (m, 2H), 6.69-6.74 (m, 2H), 6.77-6.82 (m, 2H), 7.13-7.17 (m, 1H), 7.21-7.26 (m, 4H).

LC-MS (METCR1278): 100% (UV), Rt=1.59 min, m/z (ESI+)=349.0/351.0 [M+H]+

N-[(3-Chlorophenyl)methyl]-2-hydroxy-3-(phenylamino)butanamide (I-58)

The title compound was synthesized from N-[(3-chlorophenyl)methyl]-3-methyl-oxirane-2-carboxamide (I-27) in a similar manner to method A, general procedure 2 (general scheme 4) as an off-white solid (500 mg, 97% purity, 85%) after purification by recrystallization from 1:1 EtOAc/heptane.

$^1$H NMR (500 MHz, Chloroform-d) δ 1.17 (d, J=6.6 Hz, 3H), 3.97-4.05 (m, 1H), 4.37-4.50 (m, 3H), 6.77 (d, J=7.9 Hz, 2H), 6.82 (t, J=7.3 Hz, 1H), 7.11-7.18 (m, 2H), 7.11-7.17 (m, 2H), 7.18-7.24 (m, 3H).

LC-MS (METCR1278): 97% (UV), Rt=1.86 min, m/z (ESI+)=318.9/321.0 [M+H]+

3-(Benzylamino)-N-[(3-chlorophenyl)methyl]-2-hydroxybutanamide (I-59)

The title compound was synthesized from N-[(3-chlorophenyl)methyl]-3-methyl-oxirane-2-carboxamide (I-27) in a similar manner to method A, general procedure 2 (general scheme 4) as an off-white solid (394 mg, 90% purity by $^1$H NMR, 93%) after purification by flash column chromatography on reverse phase silica (60 g SNAP KP-C18-HS cartridge, acidic pH, standard elution method).

¹H NMR (500 MHz, DMSO-d6) δ 0.95 (d, J=6.5 Hz, 3H), 3.08-3.18 (m, 1H), 3.89 (s, 2H), 4.20-4.25 (m, 1H), 4.24-4.34 (m, 2H), 7.22 (d, J=7.5 Hz, 1H), 7.25-7.31 (m, 2H), 7.30-7.37 (m, 4H), 7.40 (d, J=7.4 Hz, 2H), 8.16 (s, 1H), 8.54 (t, J=6.0 Hz, 1H).

LC-MS (METCR1410): 97% (UV), Rt=0.81 min, m/z (ESI$^+$)=333.4/335.0 [M+H]$^+$

N-[(3-Chlorophenyl)methyl]-2-hydroxy-3-[(propan-2-yl)amino]butanamide (I-60)

The title compound was synthesized from N-[(3-chlorophenyl)methyl]-3-methyl-oxirane-2-carboxamide (I-27) in a similar manner to method A, general procedure 2 (general scheme 4) as a yellow oil (212 mg, 93% purity by ¹H NMR, 60%) after purification by flash column chromatography on reverse phase silica (30 g SNAP KP-SIL-HS cartridge, acidic pH, standard elution method).

¹H NMR (500 MHz, Chloroform-d) δ 1.19 (d, J=6.6 Hz, 3H), 1.34 (d, J=6.4 Hz, 3H), 1.39 (d, J=6.4 Hz, 3H), 3.37 (p, J=6.3 Hz, 1H), 3.72-3.85 (m, 1H), 4.29-4.50 (m, 2H), 4.69 (s, 1H), 7.10-7.17 (m, 1H), 7.20-7.26 (m, 3H), 7.76 (s, 1H), 8.38 (s, 1H).

LC-MS (METCR1410): 99% (UV), Rt=0.74 min, m/z (ESI$^+$)=285.0/287.0 [M+H]$^+$

N-[(3-chlorophenyl)methyl]-2-hydroxy-3-[(oxan-4-yl)amino]butanamide (I-61)

The title compound was synthesized from N-[(3-chlorophenyl)methyl]-3-methyl-oxirane-2-carboxamide (I-27) in a similar manner to method A, general procedure 2 (general scheme 4) as an off-white solid (180 mg, 65% purity, 27%) used in the next step without further purification.

LC-MS (METCR1410): 65% (UV), Rt=0.78 min, m/z (ESI$^+$)=327.0/329.0 [M+H]$^+$

N-[(3-Chlorophenyl)methyl]-2-hydroxy-3-[(2-methoxyphenyl)amino]-3-methylbutanamide (I-62)

The title compound was synthesized from N-[(3-chlorophenyl)methyl]-3,3-dimethyloxirane-2-carboxamide (I-28) in a similar manner to method A, general procedure 2 (general scheme 4) as a brown viscous oil (203 mg, 71% purity, 24%) after purification by flash column chromatography on normal phase silica (25 g SNAP KP-SIL cartridge, 0-50% EtOAc in heptane gradient) followed by recrystallization from heptane.

¹H NMR (500 MHz, Chloroform-d) δ 1.29-1.31 (m, 6H), 3.84 (s, 3H), 4.29-4.41 (m, 1H), 4.43-4.48 (m, 3H), 6.85-6.90 (m, 2H), 6.95-7.06 (m, 2H), 7.15-7.20 (m, 1H), 7.24-7.27 (m, 2H), 7.27-7.30 (m, 1H), 7.68-7.76 (m, 1H).

LC-MS (METCR1278): 71% (UV), Rt=1.63 min, m/z (ESI$^+$)=363.0/365.0 [M+H]$^+$

N-[(3-Chlorophenyl)methyl]-2-hydroxy-3-[(2-methoxyphenyl)amino]-3-phenylpropanamide (I-63)

The title compound was synthesized from N-[(3-chlorophenyl)methyl]-3-phenyloxirane-2-carboxamide (I-29) in a similar manner to method A, general procedure 2 (general scheme 4) as a brown solid (680 mg, 100% purity, 95%) after purification by flash column chromatography on normal phase silica (25 g SNAP KP-SIL cartridge, 0-50% EtOAc in heptane gradient) followed by recrystallization from heptane.

¹H NMR (500 MHz, Chloroform-d) δ 3.17 (s, 1H), 3.87 (s, 3H), 4.18 (dd, J=15.0, 5.3 Hz, 1H), 4.38 (dd, J=15.0, 6.6 Hz, 1H), 4.67 (s, 1H), 4.96 (d, J=4.1 Hz, 1H), 6.57-6.63 (m, 1H), 6.63-6.67 (m, 1H), 6.71-6.83 (m, 4H), 6.97-7.00 (m, 1H), 7.15 (t, J=7.8 Hz, 1H), 7.18-7.22 (m, 1H), 7.28-7.33 (m, 3H), 7.36-7.40 (m, 2H).

LC-MS (METCR1278): 100% (UV), Rt=2.2 min, m/z (ESI$^+$)=411.0/413.0 [M+H]$^+$

N-[(3-Chlorophenyl)methyl]-2-hydroxy-3-[(2-methoxyphenyl)amino]-5-methylhexanamide (I-64)

The title compound was synthesized from N-[(3-chlorophenyl)methyl]-3-(2-methylpropyl)oxirane-2-carboxamide (I-48) in a similar manner to method A, general procedure 2 (general scheme 4) as an off-white solid (250 mg, 80% purity by ¹H NMR, 46%) after purification by flash column chromatography on normal phase silica (10 g SNAP KP-SIL cartridge, 0-100% EtOAc in heptane gradient).

¹H NMR (500 MHz, DMSO-d6) δ 0.69 (d, J=6.5 Hz, 3H), 0.80-0.83 (m, 3H), 1.24-1.28 (m, 1H), 1.43-1.51 (m, 1H), 1.54-1.65 (m, 1H), 3.78 (s, 3H), 4.05-4.08 (m, 1H), 4.18 (dd, J=5.6, 14.9 Hz, 1H), 4.33-4.47 (m, 2H), 5.73-5.79 (m, 1H), 6.56 (td, J=1.3, 7.8 Hz, 1H), 6.62-6.67 (m, 1H), 6.76-6.84 (m, 2H), 7.22-7.26 (m, 1H), 7.27-7.35 (m, 3H), 8.51 (t, J=6.4 Hz, 1H).

LC-MS (METCR1410): 85% (UV), Rt=1.26 min, m/z (ESI$^+$)=391.1/393.1 [M+H]$^+$

Method B: Epoxide Opening in Presence of Titanium(IV) Isopropoxide at 50-75° C.

N-[(3-Chlorophenyl)methyl]-3-[(5-fluoro-2-methoxyphenyl)amino]-2-hydroxybutanamide (I-65)

To a stirred solution of N-[(3-chlorophenyl)methyl]-3-methyloxirane-2-carboxamide (I-27, 86% purity, 340 mg, 1.30 mmol) and 5-fluoro-2-methoxyaniline (1.3 mL, 10.69 mmol) was added titanium(IV) isopropoxide (0.6 mL, 2.03 mmol) at RT. The mixture was stirred at RT for 4 h, heated at 50° C. for 18 h, cooled, diluted with EtOAc (30 mL) and washed with 10% citric acid (30 mL). The aqueous layer was extracted with EtOAc (20 mL). The combined organic extracts were washed with brine (20 mL), dried over sodium sulfate and concentrated in vacuo to give a brown oil which was triturated in 1:5 EtOAc/heptane (25 mL). The resulting precipitate was collected by filtration, dissolved in hot EtOAc (10 mL), diluted with heptane (25 mL) and sonicated in a cold water bath for 5 min. The resulting precipitate was collected by filtration and dried in vacuo to afford 207 mg of N-[(3-chlorophenyl)methyl]-3-[(5-fluoro-2-methoxy-phenyl)amino]-2-hydroxybutanamide as an off-white solid (100% purity, 44%).

¹H NMR (500 MHz, Chloroform-d) δ 1.19 (d, J=6.6 Hz, 3H), 2.66-3.19 (m, 1H), 3.82 (s, 3H), 3.92-3.98 (m, 1H), 4.39-4.51 (m, 3H), 6.40 (td, J=2.9, 8.5 Hz, 1H), 6.56 (dd, J=2.8, 10.3 Hz, 1H), 6.67 (dd, J=5.0, 8.8 Hz, 1H), 7.07-7.13 (m, 1H), 7.13-7.18 (m, 1H), 7.24-7.26 (m, 3H).

LC-MS (METCR1410): 100% (UV), Rt=1.17 min, m/z (ESI$^+$)=367.1/369.1 [M+H]$^+$

N-[(3-Chlorophenyl)methyl]-3-[(4-fluoro-2-methoxyphenyl)amino]-2-hydroxybutanamide (I-66)

The title compound was synthesized from N-[(3-chlorophenyl)methyl]-3-methyl-oxirane-2-carboxamide (I-27) in a similar manner to method B, general procedure 2 (general scheme 4) as a light brown solid (377 mg, 95% purity, 75%) after purification by flash column chromatography on normal phase silica (50 g SNAP KP-SIL silica cartridge, 0-100% EtOAc in heptane gradient) followed by recrystallization from heptane.

$^1$H NMR (250 MHz, DMSO-d6) δ 0.96 (d, J=6.5 Hz, 3H), 3.67 (s, 3H), 3.74-3.87 (m, 1H), 4.08 (dd, J=2.8, 5.2 Hz, 1H), 4.25-4.39 (m, 3H), 5.83 (d, J=5.3 Hz, 1H), 6.59-6.68 (m, 1H), 6.70-6.82 (m, 2H), 7.18-7.38 (m, 4H), 8.50 (t, J=6.2 Hz, 1H).

LC-MS (METCR1410): 95% (UV), Rt=1.28 min, m/z (ESI$^+$)=367.0/369.0 [M+H]$^+$

N-[(3-Chlorophenyl)methyl]-3-[(cyclohexylmethyl)amino]-2-hydroxybutanamide (I-67)

The title compound was synthesized from N-[(3-chlorophenyl)methyl]-3-methyl-oxirane-2-carboxamide (I-27) in a similar manner to method B, general procedure 2 (general scheme 4) as an off-white solid (633 mg, 99% purity, 121%) after purification by trituration in 1:1 EtOAc/heptane.

$^1$H NMR (500 MHz, DMSO-d6) δ 0.81-1.28 (m, 5H), 1.32-1.43 (m, 1H), 1.57-1.68 (m, 6H), 1.69-1.76 (m, 3H), 2.42-2.47 (m, 2H), 4.09 (s, 1H), 4.28 (qd, J=6.4, 15.2 Hz, 2H), 7.21-7.24 (m, 1H), 7.26-7.29 (m, 1H), 7.29-7.36 (m, 2H), 8.42-8.53 (m, 1H).

LC-MS (METCR1410): 99% (UV), Rt=0.89 min, m/z (ESI$^+$)=339.0/341.1 [M+H]$^+$

N-[(3-Chlorophenyl)methyl]-3-[(2,2-dimethylpropyl)amino]-2-hydroxybutanamide (I-68)

The title compound was synthesized from N-[(3-chlorophenyl)methyl]-3-methyl-oxirane-2-carboxamide (I-27) in a similar manner to method B, general procedure 2 (general scheme 4) as a yellow solid (267 mg, 98% purity, 73%) after purification by ion-exchange flash chromatography (5 g Isolute SCX-2 cartridge, 0-20% MeOH in EtOAc gradient then 0-10% 7N methanolic ammonia in EtOAc gradient).

$^1$H NMR (500 MHz, DMSO-d6) δ 0.81-0.86 (m, 12H), 1.21-1.44 (m, 1H), 2.19-2.31 (m, 2H), 2.76-2.84 (m, 1H), 3.97-4.03 (m, 1H), 4.20-4.34 (m, 2H), 5.47 (d, J=4.3 Hz, 1H), 7.20-7.24 (m, 1H), 7.26-7.29 (m, 1H), 7.29-7.35 (m, 2H), 8.42 (t, J=6.3 Hz, 1H).

LC-MS (METCR1410): 98% (UV), Rt=0.85 min, m/z (ESI$^+$)=313.1/315.1 [M+H]$^+$

N-[(3-Chlorophenyl)methyl]-2-hydroxy-3-{[(oxan-4-yl)methyl]amino}butanamide (I-69)

The title compound was synthesized from N-[(3-chlorophenyl)methyl]-3-methyl-oxirane-2-carboxamide (I-27) in a similar manner to method B, general procedure 2 (general scheme 4) as an off-white solid (505 mg, 100% purity, 78%) after purification by trituration in 1:2 EtOAc/heptane.

$^1$H NMR (500 MHz, DMSO-d6) δ 0.83 (d, J=6.5 Hz, 3H), 1.05-1.19 (m, 2H), 1.33-1.62 (m, 4H), 2.32-2.44 (m, 2H), 2.78-2.88 (m, 1H), 3.21-3.28 (m, 2H), 3.81 (dd, J=3.5, 11.1 Hz, 2H), 3.96-4.04 (m, 1H), 4.27 (qd, J=6.4, 15.2 Hz, 2H), 5.46 (d, J=4.2 Hz, 1H), 7.20-7.25 (m, 1H), 7.25-7.29 (m, 1H), 7.30-7.35 (m, 2H), 8.41 (t, J=6.3 Hz, 1H).

LC-MS (METCR1278): 100% (UV), Rt=1.32 min, m/z (ESI$^+$)=341.1/343.1 [M+H]$^+$

N-[(3-Chlorophenyl)methyl]-2-hydroxy-3-[(2-methoxyphenyl)amino]propanamide (I-70)

The title compound was synthesized from N-[(3-chlorophenyl)methyl]-oxirane-2-carboxamide (I-33) in a similar manner to method B, general procedure 2 (general scheme 4) as a colourless viscous oil (1.66 g, 90% purity by $^1$H NMR, 67%) after purification by flash column chromatography on normal phase silica (100 g SNAP HP-SIL cartridge, 20-100% EtOAc in heptane gradient).

$^1$H NMR (250 MHz, Chloroform-d) δ 3.46 (dd, J=6.8, 13.6 Hz, 2H), 3.65 (dd, J=4.8, 13.6 Hz, 1H), 3.84 (s, 3H), 4.37 (dd, J=4.9, 6.7 Hz, 1H), 4.45 (d, J=6.1 Hz, 2H), 6.67-6.96 (m, 4H), 7.08-7.33 (m, 5H).

LC-MS (METCR1410): 88% (UV), Rt=1.11 min, m/z (ESI$^+$)=335.1/337.1 [M+H]$^+$

N-(Cyclohexylmethyl)-2-hydroxy-3-[(2-methoxyphenyl)amino]butanamide (I-71)

The title compound was synthesized from N-(cyclohexylmethyl)-3-methyl-oxirane-2-carboxamide (I-34) in a similar manner to method B, general procedure 2 (general scheme 4) as an off-white solid (479 mg, 100% purity, 57%) after purification by flash column chromatography on normal phase silica (100 g SNAP Ultra cartridge, 0-40% EtOAc in heptane gradient) followed by recrystallization from 1:1 EtOAc/heptane.

$^1$H NMR (250 MHz, Chloroform-d) δ 0.82-1.02 (m, 2H), 1.07-1.32 (m, 6H), 1.39-1.58 (m, 1H), 1.63-1.80 (m, 5H), 3.01 (s, 1H), 3.05-3.24 (m, 2H), 3.86 (s, 3H), 3.90-4.04 (m, 1H), 4.32 (d, J=3.8 Hz, 1H), 6.71-6.95 (m, 5H).

LC-MS (METCR1410): 100% (UV), Rt=1.16 min, m/z (ESI$^+$)=321.1 [M+H]$^+$

N-[2-(3-Chlorophenyl)propan-2-yl]-2-hydroxy-3-[(2-methoxyphenyl)amino]butanamide (I-72)

The title compound was synthesized from N-[2-(3-chlorophenyl)propan-2-yl]-3-methyloxirane-2-carboxamide (I-37) in a similar manner to method B, general procedure 2 (general scheme 4) as a brown viscous oil (360 mg, 88% purity, 76%) after purification by flash column chromatography on normal phase silica (10 g SNAP KP-SIL cartridge, 0-100% EtOAc in heptane gradient).

$^1$H NMR (500 MHz, DMSO-d6) δ 0.99 (d, J=6.5 Hz, 3H), 1.59 (d, J=5.7 Hz, 6H), 3.78 (s, 3H), 3.99-4.03 (m, 1H), 4.57 (d, J=10.1 Hz, 1H), 5.79 (d, J=5.8 Hz, 1H), 6.53-6.60 (m, 2H), 6.74-6.80 (m, 1H), 6.80-6.85 (m, 1H), 7.24 (dt, J=2.0, 6.8 Hz, 1H), 7.27-7.32 (m, 2H), 7.35-7.37 (m, 1H), 7.77 (s, 1H).

LC-MS (METCR1410): 88% (UV), Rt=1.19 min, m/z (ESI$^+$)=377.1/379.1 [M+H]$^+$

N-[2-(3-Chlorophenyl)propan-2-yl]-2-hydroxy-3-[(propan-2-yl)amino]butanamide (I-73)

The title compound was synthesized from N-[2-(3-chlorophenyl)propan-2-yl]-3-methyloxirane-2-carboxamide (I-37) in a similar manner to method B, general procedure 2 (general scheme 4) as a colourless crystalline solid (110 mg, 95% purity, 45%) after purification by ion-exchange flash chromatography (5 g Isolute SCX-2 cartridge, 0-10% 7N methanolic ammonia in EtOAc gradient).

$^1$H NMR (500 MHz, DMSO-d6) δ 0.88 (d, J=6.5 Hz, 3H), 0.95-1.03 (m, 6H), 1.58 (s, 6H), 2.98 (d, J=39.7 Hz, 2H), 3.91 (s, 1H), 7.23-7.27 (m, 1H), 7.31-7.33 (m, 2H), 7.35-7.37 (m, 1H), 7.87 (s, 1H).

LC-MS (METCR1410): 100% (UV), Rt=0.79 min, m/z (ESI$^+$)=313.4/315.0 [M+H]$^+$

N-[2-(3-Chlorophenyl)propan-2-yl]-3-(cyclohexylamino)-2-hydroxybutanamide (I-74)

The title compound was synthesized from N-[2-(3-chlorophenyl)propan-2-yl]-3-methyloxirane-2-carboxamide (I-37) in a similar manner to method B, general procedure 2 (general scheme 4) as an off-white crystalline solid (160 mg, 80% purity by $^1$H NMR, 39%) after purification by flash column chromatography on normal phase silica (25 g SNAP KP-SIL cartridge, 0-70% EtOAc in heptane gradient).

$^1$H NMR (500 MHz, DMSO-d6) δ 1.09 (d, J=6.7 Hz, 3H), 1.17-1.21 (m, 1H), 1.21-1.41 (m, 4H), 1.55 (s, 1H), 1.57-1.62 (m, 6H), 1.70-1.79 (m, 2H), 1.95-2.12 (m, 2H), 3.04-3.17 (m, 1H), 3.52-3.69 (m, 1H), 4.37 (s, 1H), 6.47 (s, 1H), 7.24-7.27 (m, 1H), 7.30-7.34 (m, 2H), 7.38 (s, 1H), 8.05 (s, 1H).

LC-MS (METCR1410): 72% (UV), Rt=0.94 min, m/z (ESI$^+$)=353.6/355.2 [M+H]$^+$

N-tert-butyl-2-hydroxy-3-[(2-methoxyphenyl)amino]butanamide (I-75)

The title compound was synthesized from N-tertbutyl-3-methyloxirane-2-carboxamide (I-38) in a similar manner to method B, general procedure 2 (general scheme 4) as an orange crystalline solid (186 mg, 90% purity by $^1$H NMR, 57%) after purification by flash column chromatography on normal phase silica (25 g SNAP KP-SIL cartridge, 0-50% EtOAc in heptane gradient).

$^1$H NMR (250 MHz, Chloroform-d) δ 1.17 (d, J=6.6 Hz, 3H), 1.36 (s, 9H), 2.88 (d, J=3.3 Hz, 1H), 3.85 (s, 3H), 3.89-3.98 (m, 1H), 4.20 (t, J=3.3 Hz, 1H), 6.62 (s, 1H), 6.68-6.91 (m, 4H).

2-Hydroxy-3-[(2-methoxyphenyl)amino]-N-(propan-2-yl)butanamide (I-76)

The title compound was synthesized from 3-methyl-N-(propan-2-yl)oxirane-2-carboxamide (I-39) in a similar manner to method B, general procedure 2 (general scheme 4) as an off-white solid (214 mg, 100% purity, 29%) after purification by flash column chromatography on normal phase silica (25 g SNAP KP-SIL cartridge, 0-50% EtOAc in heptane gradient) followed by recrystallization from 1:1 EtOAc/heptane.

$^1$H NMR (500 MHz, Chloroform-d) δ 1.13 (d, J=6.6 Hz, 3H), 1.15-1.19 (m, 6H), 2.95 (s, 1H), 3.85 (s, 3H), 3.96 (qd, J=3.9, 6.6 Hz, 1H), 4.10 (dt, J=6.6, 8.0 Hz, 1H), 4.29 (d, J=3.5 Hz, 1H), 6.60 (d, J=7.5 Hz, 1H), 6.74 (td, J=1.5, 7.7 Hz, 1H), 6.78-6.82 (m, 2H), 6.88 (td, J=1.4, 7.8 Hz, 1H)

LC-MS (METCR1278): 100% (UV), Rt=1.45 min, m/z (ESI$^+$)=267.0 [M+H]$^+$

3-[(2,2-Dimethylpropyl)amino]-2-hydroxy-N-(propan-2-yl)butanamide (I-77)

The title compound was synthesized from 3-methyl-N-(propan-2-yl)oxirane-2-carboxamide (I-39) in a similar manner to method B, general procedure 2 (general scheme 4) as a yellow solid (196 mg, 85% purity by $^1$H NMR, 26%) after purification by ion exchange flash chromatography (10 g Isolute SCX-2 cartridge, 0-20% MeOH in EtOAc gradient then 0-10% 7N methanolic ammonia in EtOAc gradient).

$^1$H NMR (500 MHz, Chloroform-d) δ 0.90-0.93 (m, 9H), 1.02 (d, J=6.5 Hz, 3H), 1.14-1.18 (m, 6H), 2.29 (d, J=11.3 Hz, 1H), 2.51 (d, J=11.3 Hz, 1H), 3.00-3.07 (m, 1H), 3.96 (d, J=5.1 Hz, 1H), 4.06-4.16 (m, 1H), 6.96-7.18 (m, 1H).

LC-MS (METCR1410): 74% (UV), Rt=0.76 min, m/z (ESI$^+$)=231.1 [M+H]$^+$

1-(7-Chloro-1,2,3,4-tetrahydroisoquinolin-2-yl)-2-hydroxy-3-[(2-methoxyphenyl)amino]-butan-1-one (I-78)

The title compound was synthesized from 7-chloro-2-(3-methyloxirane-2-carbonyl)-1,2,3,4-tetrahydroisoquinoline (I-40) in a similar manner to method B, general procedure 2 (general scheme 4) at 50° C. then 75° C. and was obtained as a yellow viscous oil (85 mg, 60% purity by 1H NMR, 25%) after purification by flash column chromatography on normal phase silica (25 g SNAP KP-SIL cartridge, 0-50% EtOAc in heptane gradient).

$^1$H NMR (250 MHz, Chloroform-d) δ 1.08-1.22 (m, 3H), 2.76-2.96 (m, 1H), 3.53-3.96 (m, 7H), 4.39-4.91 (m, 4H), 6.54-6.72 (m, 2H), 6.75-7.20 (m, 5H).

N-[(3-Chlorophenyl)methyl]-2-hydroxy-3-[(2-methoxyphenyl)amino]pentanamide (I-79)

The title compound was synthesized from N-[(3-chlorophenyl)methyl]-3-ethyloxirane-2-carboxamide (I-42) in a similar manner to method B, general procedure 2 (general scheme 4) as a brown solid (427 mg, 100% purity, 63%) after purification by flash column chromatography on normal phase silica (25 g SNAP KP-SIL cartridge, 0-60% EtOAc in heptane gradient) then recrystallization from 1:1 EtOAc/heptane.

$^1$H NMR (500 MHz, Chloroform-d) δ 0.98 (t, J=7.4 Hz, 3H), 1.53-1.62 (m, 1H), 1.65-1.72 (m, 1H), 3.04 (s, 1H), 3.74 (dt, J=4.0, 8.7 Hz, 1H), 3.85 (s, 3H), 4.30-4.34 (m, 1H), 4.42 (qd, J=6.0, 14.9 Hz, 2H), 6.74 (td, J=1.5, 7.7 Hz, 1H), 6.79 (ddd, J=1.3, 8.0, 9.4 Hz, 2H), 6.87 (td, J=1.4, 7.7 Hz, 1H), 7.09-7.14 (m, 1H), 7.14-7.19 (m, 1H), 7.19-7.22 (m, 1H), 7.22-7.26 (m, 2H).

LC-MS (METCR1410): 100% (UV), Rt=1.17 min, m/z (ESI$^+$)=363.0/365.0 [M+H]$^+$

N-(Cyclopropylmethyl)-2-hydroxy-4-methyl-3-[(2-methylpropyl)amino]pentanamide (I-80)

The title compound was synthesized from N-(cyclopropylmethyl)-3-(propan-2-yl)oxirane-2-carboxamide (I-43) in a similar manner to method B, general procedure 2 (general scheme 4) as a yellow solid (135 mg, 100% purity by $^1$H NMR, 32%) after purification by recrystallization from hot heptane.

$^1$H NMR (500 MHz, Chloroform-d) δ 0.16-0.25 (m, 2H), 0.44-0.54 (m, 2H), 0.86-1.00 (m, 13H), 1.67-1.76 (m, 1H), 2.06-2.17 (m, 1H), 2.38-2.55 (m, 2H), 2.66-2.72 (m, 1H), 3.06-3.23 (m, 2H), 4.00 (d, J=6.6 Hz, 1H), 7.52 (s, 1H).

N-(Cyclopropylmethyl)-3-[(2,2-dimethylpropyl)amino]-2-hydroxy-4-methylpentanamide (I-81)

The title compound was synthesized from N-(cyclopropylmethyl)-3-(propan-2-yl)oxirane-2-carboxamide (I-43) in a similar manner to method B, general procedure 2 (general scheme 4) as a colourless powder (183 mg, 85% purity by $^1$H NMR, 35%) after purification by recrystallization from heptane followed by trituration in cooled heptane.

$^1$H NMR (250 MHz, Chloroform-d) δ 0.21 (q, J=4.8 Hz, 2H), 0.44-0.56 (m, 2H), 0.92-1.02 (m, 16H), 2.07-2.19 (m, 1H), 2.33-2.51 (m, 2H), 2.69 (dd, J=3.9, 6.3 Hz, 1H), 3.03-3.29 (m, 2H), 4.04 (d, J=6.3 Hz, 1H), 7.41-7.50 (m, 1H).

N-[(3-Chlorophenyl)methyl]-2-hydroxy-3-[(2-methoxyphenyl)amino]-4-methylpentanamide (I-82)

The title compound was synthesized from N-[(3-chlorophenyl)methyl]-3-(propan-2-yl)oxirane-2-carboxamide (I-46) in a similar manner to method B, general procedure 2 (general scheme 4) as a brown-beige solid (468 mg, 90% purity by $^1$H NMR, 56%) after purification by flash column chromatography on normal phase silica (50 g SNAP Ultra cartridge, 7-60% EtOAc in heptane gradient).

$^1$H NMR (500 MHz, Chloroform-d) δ 0.84 (d, J=6.9 Hz, 3H), 0.92-0.98 (m, 3H), 2.18-2.30 (m, 1H), 3.42-3.50 (m, 1H), 3.64 (s, 1H), 3.79 (s, 3H), 4.08-4.14 (m, 1H), 4.16 (dd, J=5.4, 14.8 Hz, 1H), 4.33-4.40 (m, 1H), 6.64-6.81 (m, 4H), 6.94 (d, J=7.3 Hz, 1H), 7.03 (s, 1H), 7.04-7.10 (m, 1H), 7.09-7.18 (m, 2H).

LC-MS (METCR1410): 94% (UV), Rt=1.22 min, m/z (ESI$^+$)=377.1/379.1 [M+H]$^+$

2-Hydroxy-3-[(2-methoxyphenyl)amino]butanamide (I-83)

The title compound was synthesized from 3-methyloxirane-2-carboxamide (I-53) in a similar manner to method B, general procedure 2 (general scheme 4) as a brown oil (56 mg, 90% purity, 10%) after purification by flash column chromatography on normal phase silica (10 g SNAP KP-SIL cartridge, 0-80% EtOAc in heptane gradient).

LC-MS (METCR1410): 90% (UV), Rt=0.63 min, m/z (ESI$^+$)=225.2 [M+H]$^+$

Method C: Epoxide Opening without Titanium(IV) Isopropoxide

3-(Cyclohexylamino)-2-hydroxy-N-(propan-2-yl)butanamide (I-84)

To a stirred solution of 3-methyl-N-(propan-2-yl)oxirane-2-carboxamide (I-39) (400 mg, 2.79 mmol) in EtOH (10 mL) was added cyclohexylamine (2.5 mL, 21.9 mmol) at RT. The reaction mixture was stirred at RT for 18 h, heated and stirred at 50° C. for 24 h then concentrated in vacuo. The solid residue was dissolved in hot EtOAc (25 mL), the solution diluted with heptane (25 mL) and cooled by sonication in a cold water bath for 10 min. The precipitate was collected by filtration and dried in vacuo to afford 320 mg of 3-(cyclohexylamino)-2-hydroxy-N-(propan-2-yl)butanamide as an off-white solid (100% purity, 47%).

$^1$H NMR (500 MHz, Chloroform-d) δ 1.01 (d, J=6.5 Hz, 3H), 1.02-1.10 (m, 2H), 1.10-1.19 (m, 7H), 1.19-1.32 (m, 2H), 1.62 (dt, J=3.5, 12.6 Hz, 1H), 1.67-1.79 (m, 2H), 1.83-1.92 (m, 1H), 1.92-2.01 (m, 1H), 2.44-2.58 (m, 1H), 3.26 (p, J=6.4 Hz, 1H), 3.91 (d, J=5.1 Hz, 1H), 4.01-4.18 (m, 1H), 6.99-7.17 (m, 1H).

LC-MS (METCR1410): 100% (UV), Rt=0.70 min, m/z (ESI$^+$)=243.2 [M+H]$^+$

N-(Cyclopropylmethyl)-2-hydroxy-4-methyl-3-{[(oxan-4-yl)methyl]amino}pentanamide (I-85)

The title compound was synthesized from N-(cyclopropylmethyl)-3-(propan-2-yl)oxirane-2-carboxamide (I-43) in a similar manner to method C, general procedure 2 (general scheme 4) at 70° C. and was obtained as an off-white solid (203 mg, 92% purity, 42%) after purification by recrystallization from 1:1 EtOAc/heptane followed by ion-exchange flash chromatography (10 g Isolute SCX cartridge, 0-10% 7N methanolic ammonia in EtOAc gradient).

$^1$H NMR (500 MHz, Chloroform-d) δ 0.16-0.26 (m, 2H), 0.46-0.54 (m, 2H), 0.91-1.02 (m, 7H), 1.24-1.38 (m, 3H), 1.59-1.70 (m, 4H), 2.06-2.14 (m, 1H), 2.50 (dd, J=6.7, 11.7 Hz, 1H), 2.59-2.63 (m, 1H), 2.72 (dd, J=3.6, 6.2 Hz, 1H), 3.05-3.14 (m, 1H), 3.17-3.24 (m, 1H), 3.35-3.43 (m, 2H), 3.96-4.00 (m, 2H), 4.04 (d, J=6.2 Hz, 1H), 7.32-7.40 (m, 1H).

LC-MS (METCR0990): 92% (UV), Rt=1.48 min, m/z (ESI$^+$)=299.3 [M+H]$^+$

3-(Benzylamino)-N-(cyclopropylmethyl)-2-hydroxybutanamide (I-86)

The title compound was synthesized from N-(cyclopropylmethyl)-3-methyl-oxirane-2-carboxamide (I-30) in a similar manner to method C, general procedure 2 (general scheme 4) as an off-white solid (365.5 mg, 96% purity, 61%) after purification by recrystallization from 1:2 EtOAc/heptane.

$^1$H NMR (500 MHz, Chloroform-d) δ 0.01 (q, J=4.7 Hz, 2H), 0.26-0.32 (m, 2H), 0.74 (dtt, J=4.8, 7.5, 15.2 Hz, 1H), 0.85 (d, J=6.5 Hz, 3H), 2.86-2.97 (m, 2H), 2.98-3.05 (m, 1H), 3.57-3.65 (m, 2H), 3.87 (d, J=4.7 Hz, 1H), 7.00-7.15 (m, 6H).

LC-MS (METCR1410): 96% (UV), Rt=0.75 min, m/z (ESI$^+$)=263.1 [M+H]$^+$

3-[(Cyclohexylmethyl)amino]-N-(cyclopropylmethyl)-2-hydroxybutanamide (I-87)

The title compound was synthesized from N-(cyclopropylmethyl)-3-methyl-oxirane-2-carboxamide (I-30) in a similar manner to method C, general procedure 2 (general scheme 4) as an off-white solid (282 mg, 100% purity, 47%) after purification by recrystallization from EtOAc/heptane.

$^1$H NMR (500 MHz, Chloroform-d) δ 0.21 (q, J=4.8 Hz, 2H), 0.47-0.54 (m, 2H), 0.94 (ttd, J=4.1, 8.3, 9.2, 17.0 Hz, 3H), 1.00 (d, J=6.5 Hz, 3H), 1.10-1.29 (m, 3H), 1.40 (dtt, J=3.4, 7.1, 14.5 Hz, 1H), 1.63-1.83 (m, 5H), 2.39 (dd, J=7.1, 11.6 Hz, 1H), 2.56 (dd, J=6.1, 11.6 Hz, 1H), 3.00-3.08 (m, 1H), 3.08-3.22 (m, 2H), 3.98 (d, J=5.1 Hz, 1H), 7.35 (s, 1H).

LC-MS (METCR1410): 100% (UV), Rt=0.82 min, m/z (ESI$^+$)=269.1 [M+H]$^+$ tert-Butyl 4-[({1-[(cyclopropylmethyl)carbamoyl]-1-hydroxypropan-2-yl}amino)methyl]-piperidine-1-carboxylate (I-88)

The title compound was synthesized from N-(cyclopropylmethyl)-3-methyl-oxirane-2-carboxamide (I-30) in a similar manner to method C, general procedure 2 (general scheme 4) as a yellow solid (959 mg, 90% purity by $^1$H NMR, 48%) after purification by trituration in 95:5 heptane/EtOAc then in 90:10 heptane/EtOAc.

$^1$H NMR (500 MHz, Chloroform-d) δ 0.21 (q, J=4.7 Hz, 2H), 0.47-0.54 (m, 2H), 0.90-0.99 (m, 1H), 1.03 (d, J=6.5 Hz, 3H), 1.07-1.21 (m, 2H), 1.45 (s, 9H), 1.54-1.63 (m, 1H), 1.63-1.78 (m, 2H), 1.82-2.38 (m, 2H), 2.47 (dd, J=7.2, 11.9 Hz, 1H), 2.62-2.75 (m, 3H), 3.08-3.21 (m, 3H), 4.05 (d, J=4.7 Hz, 1H), 4.11 (s, 2H), 7.15-7.25 (m, 1H).

LC-MS (METCR0990): 77% (UV), Rt=1.6 min, m/z (ESI⁺)=370.3 [M+H]⁺

3-(Cyclohexylamino)-N-(cyclopropylmethyl)-2-hydroxybutanamide (I-89)

The title compound was synthesized from N-(cyclopropylmethyl)-3-methyl-oxirane-2-carboxamide (I-30) in a similar manner to method C, general procedure 2 (general scheme 4) at 60° C. and was obtained as an off-white solid (435 mg, 95% purity by 1H NMR, 73%) after purification by trituration in Et₂O and heptane.

¹H NMR (500 MHz, Chloroform-d) δ 0.14-0.28 (m, 2H), 0.45-0.58 (m, 2H), 0.90-1.01 (m, 1H), 1.09 (d, J=6.5 Hz, 3H), 1.11-1.36 (m, 5H), 1.57-2.06 (m, 7H), 2.62 (t, J=9.4 Hz, 1H), 3.14 (h, J=6.8 Hz, 2H), 3.33 (p, J=6.0 Hz, 1H), 3.99-4.09 (m, 1H), 7.34-7.45 (m, 1H).

LC-MS (METCR1410): 88% (UV), Rt=0.76 min, m/z (ESI⁴)=255.6 [M+H]⁺

N-(Cyclopropylmethyl)-3-[(2,2-dimethylpropyl)amino]-2-hydroxybutanamide (I-90)

The title compound was synthesized from N-(cyclopropylmethyl)-3-methyl-oxirane-2-carboxamide (I-30) in a similar manner to method C, general procedure 2 (general scheme 4) at 60° C. and was obtained as an off-white solid (418 mg, 95% purity, 74%) after purification by trituration in Et₂O and heptane.

1H NMR (500 MHz, Chloroform-d) δ 0.14-0.26 (m, 2H), 0.43-0.57 (m, 2H), 0.87-1.01 (m, 11H), 1.10 (d, J=6.4 Hz, 3H), 1.84 (br.s, 1H), 2.34 (d, J=11.4 Hz, 1H), 2.58 (d, J=11.4 Hz, 1H), 3.02-3.23 (m, 3H), 4.09 (d, J=4.0 Hz, 1H), 7.39 (s, 1H).

LC-MS (METCR1410): 100% (UV), Rt=0.74 min, m/z (ESI⁺)=243.2 [M+H]⁺

3-(Cyclohexylamino)-N-cyclopropyl-2-hydroxybutanamide (I-91)

The title compound was synthesized from N-cyclopropyl-3-methyloxirane-2-carboxamide (I-31) in a similar manner to method C, general procedure 2 (general scheme 4) at 60° C. and was obtained as an off-white solid (355 mg, 100% purity by ¹H NMR, 78%) after purification by recrystallization from 1:2.5 EtOAc/heptane.

¹H NMR (500 MHz, Chloroform-d) δ 0.47-0.55 (m, 2H), 0.74-0.82 (m, 2H), 1.02 (d, J=6.5 Hz, 3H), 1.04-1.32 (m, 5H), 1.58-1.65 (m, 1H), 1.69-1.76 (m, 2H), 1.84-1.90 (m, 1H), 1.94-2.00 (m, 1H), 2.49-2.57 (m, 1H), 2.69-2.79 (m, 1H), 3.22-3.28 (m, 1H), 3.92 (d, J=5.3 Hz, 1H), 7.35 (s, 1H).

LC-MS (METCR1410): No UV integration, Rt=0.59 min, m/z (ESI⁺)=241.1 [M+H]⁺

3-[(Cyclohexylmethyl)amino]-N-cyclopropyl-2-hydroxybutanamide (I-92)

The title compound was synthesized from N-cyclopropyl-3-methyloxirane-2-carboxamide (I-31) in a similar manner to method C, general procedure 2 (general scheme 4) at 60° C. and was obtained as a white solid (344 mg, 100% purity, 72%) after purification by recrystallization from 1:2.5 EtOAc/heptane.

¹H NMR (500 MHz, Chloroform-d) δ 0.44-0.56 (m, 2H), 0.74-0.81 (m, 2H), 0.87-0.97 (m, 2H), 1.00 (d, J=6.5 Hz, 3H), 1.13-1.29 (m, 3H), 1.35-1.44 (m, 1H), 1.65-1.80 (m, 5H), 2.37 (dd, J=7.1, 11.7 Hz, 1H), 2.53-2.59 (m, 1H), 2.71-2.77 (m, 1H), 3.00-3.06 (m, 1H), 3.95 (d, J=5.3 Hz, 1H), 7.33 (s, 1H).

LC-MS (METCR1410): 100% (UV), Rt=0.72 min, m/z (ESI⁺)=255.1 [M+H]⁺

3-(Benzylamino)-N-cyclopropyl-2-hydroxybutanamide (I-93)

The title compound was synthesized from N-cyclopropyl-3-methyloxirane-2-carboxamide (I-31) in a similar manner to method C, general procedure 2 (general scheme 4) at 60° C. and was obtained as an off-white solid (360 mg, 96% purity, 63%) after purification by trituration in 1:4 EtOAc/heptane.

¹H NMR (500 MHz, Chloroform-d) δ 0.43-0.54 (m, 2H), 0.72-0.82 (m, 2H), 1.04 (d, J=6.5 Hz, 3H), 2.70-2.78 (m, 1H), 3.17-3.24 (m, 1H), 3.75-3.86 (m, 2H), 4.03 (d, J=4.8 Hz, 1H), 7.22 (s, 1H), 7.27-7.36 (m, 5H).

LC-MS (METCR0990): 96% (UV), Rt=1.36 min, m/z (ESI⁺)=249.3 [M+H]⁺

3-(Cyclohexylamino)-2-hydroxy-N-(2-methylpropyl)butanamide (I-94)

The title compound was synthesized from 3-methyl-N-(2-methylpropyl)-oxirane-2-carboxamide (I-32) in a similar manner to method C, general procedure 2 (general scheme 4) as a white solid (310 mg, 90% purity by ¹H NMR, 43%) after purification by recrystallization from 1:1 EtOAc/heptane.

¹H NMR (500 MHz, Chloroform-d) δ 0.95 (d, J=6.7 Hz, 6H), 1.15 (d, J=6.6 Hz, 3H), 1.18-1.35 (m, 5H), 1.61-1.68 (m, 1H), 1.74-1.88 (m, 3H), 1.94-2.02 (m, 1H), 2.05-2.13 (m, 1H), 2.66-2.77 (m, 1H), 3.02-3.09 (m, 1H), 3.15-3.23 (m, 1H), 3.40-3.49 (m, 1H), 4.20 (d, J=4.7 Hz, 1H), 7.31 (m, 1H).

LC-MS (METCR1410): 73% (UV), Rt=0.81 min, m/z (ESI⁺)=257.2 [M+H]⁺

3-[(Cyclopropylmethyl)amino]-2-hydroxy-N-(2-methylpropyl)butanamide (I-95)

The title compound was synthesized from 3-methyl-N-(2-methylpropyl)-oxirane-2-carboxamide (I-32) in a similar manner to method C, general procedure 2 (general scheme 4) as an off-white solid (320 mg, 80% purity by ¹H NMR, 44%) after purification by recrystallization from 1:1 EtOAc/heptane followed by recrystallization from EtOAc and trituration in heptane.

¹H NMR (500 MHz, Chloroform-d) δ −0.06-0.05 (m, 2H), 0.30-0.42 (m, 2H), 0.81 (d, J=6.7 Hz, 6H), 0.90 (d, J=6.5 Hz, 3H), 1.11 (dd, J=26.2, 6.4 Hz, 1H), 1.59-1.75 (m, 1H), 2.29 (dd, J=12.1, 7.4 Hz, 1H), 2.45 (dd, J=12.1, 6.4 Hz, 1H), 2.90-3.12 (m, 3H), 3.87 (d, J=5.0 Hz, 1H), 7.24 (s, 1H).

3-[(2,2-Dimethylpropyl)amino]-2-hydroxy-N-(2-methylpropyl)butanamide (I-96)

The title compound was synthesized from 3-methyl-N-(2-methylpropyl)-oxirane-2-carboxamide (I-32) in a similar manner to method C, general procedure 2 (general scheme 4) as an off-white solid (242 mg, 100% purity, 28%) after purification by recrystallization from 1:1 EtOAc/heptane.

¹H NMR (250 MHz, Chloroform-d) δ 0.87-1.01 (m, 15H), 1.11 (d, J=6.5 Hz, 3H), 1.81 (dt, J=13.4, 6.7 Hz, 1H), 2.36

(d, J=11.4 Hz, 1H), 2.60 (d, J=11.4 Hz, 1H), 2.96-3.26 (m, 4H), 4.12 (d, J=5.3 Hz, 1H), 7.35 (s, 1H).
LC-MS (METCR1410): 100% (UV), Rt=0.76 min, m/z (ESI⁺)=245.6 [M+H]⁺

2-Hydroxy-N-(2-methylpropyl)-3-[(2,2,2-trifluoroethyl)amino]butanamide (I-97)

The title compound was synthesized from 3-methyl-N-(2-methylpropyl)-oxirane-2-carboxamide (I-32) in a similar manner to method C, general procedure 2 (general scheme 4) at 70° C. and was obtained as a white solid (382 mg, 100% purity, 68%) after purification by recrystallization from 1:3 EtOAc/heptane.
¹H NMR (500 MHz, Chloroform-d) δ 0.92 (d, J=6.7 Hz, 6H), 1.08 (d, J=6.5 Hz, 3H), 1.79 (dp, J=6.7, 13.5 Hz, 1H), 3.01-3.09 (m, 1H), 3.10-3.23 (m, 3H), 3.36 (dq, J=9.0, 14.4 Hz, 1H), 3.43-3.58 (m, 1H), 4.00 (d, J=4.7 Hz, 1H), 6.98-7.12 (m, 1H).
LC-MS (METCR1410): 100% (UV), Rt=0.71 min, m/z (ESI⁺)=257.1 [M+H]⁺

3-(Benzylamino)-2-hydroxy-N-(2-methylpropyl) butanamide (I-98)

The title compound was synthesized from 3-methyl-N-(2-methylpropyl)-oxirane-2-carboxamide (I-32) in a similar manner to method C, general procedure 2 (general scheme 4) at 60° C. and was obtained as an off-white solid (301 mg, 98% purity, 50%) after purification by trituration in 1:4 EtOAc/heptane.
¹H NMR (500 MHz, Chloroform-d) δ 0.92 (d, J=6.7 Hz, 6H), 1.05 (d, J=6.5 Hz, 3H), 1.73-1.83 (m, 1H), 2.99-3.07 (m, 1H), 3.14-3.20 (m, 1H), 3.20-3.27 (m, 1H), 3.78-3.86 (m, 2H), 4.09 (d, J=4.7 Hz, 1H), 7.12-7.22 (m, 1H), 7.26-7.37 (m, 5H).
LC-MS (METCR1410): 98% (UV), Rt=0.75 min, m/z (ESI⁺)=265.5 [M+H]⁺

N-(Cyclohexylmethyl)-2-hydroxy-3-[(propan-2-yl) amino]butanamide (I-99)

The title compound was synthesized from N-(cyclohexylmethyl)-3-methyl-oxirane-2-carboxamide (I-34) in a similar manner to method C, general procedure 2 (general scheme 4) as an off-white solid (420 mg, 100% purity, 95%) after purification by recrystallization from EtOAc.
¹H NMR (250 MHz, DMSO-d6) δ 0.81 (d, J=6.5 Hz, 3H), 0.87 (s, 1H), 0.92-0.98 (m, 6H), 1.06-1.22 (m, 3H), 1.29-1.55 (m, 2H), 1.64 (d, J=10.8 Hz, 5H), 2.79-3.06 (m, 4H), 3.90 (s, 1H), 5.34 (s, 1H), 7.69 (t, J=5.9 Hz, 1H).
LC-MS (METCR1410): 100% (UV), Rt=0.79 min, m/z (ESI⁺)=257.1 [M+H]⁺

N-(Cyclohexylmethyl)-2-hydroxy-3-{[(oxan-4-yl) methyl]amino}butanamide (I-100)

The title compound was synthesized from N-(cyclohexylmethyl)-3-methyl-oxirane-2-carboxamide (I-34) in a similar manner to method C, general procedure 2 (general scheme 4) at 60° C. as an off-white solid (500 mg, 88% purity by ¹H NMR, 81%) after purification by recrystallization from 1:1 EtOAc/heptane.
¹H NMR (500 MHz, Chloroform-d) δ 0.89-0.98 (m, 2H), 1.03 (d, J=6.5 Hz, 3H), 1.10-1.37 (m, 7H), 1.42-1.52 (m, 1H), 1.69-1.76 (m, 7H), 2.47 (dd, J=7.0, 11.9 Hz, 1H), 2.67 (dd, J=5.9, 11.9 Hz, 1H), 3.05-3.20 (m, 2H), 3.33-3.43 (m, 2H), 3.94-4.01 (m, 2H), 4.04 (d, J=4.9 Hz, 1H), 7.12-7.23 (m, 1H).
LC-MS (METCR1416): 100% (UV), Rt=2.66 min, m/z (ESI⁺)=313.5 [M+H]⁺

N-(Cyclohexylmethyl)-2-hydroxy-3-[(2,2,2-trifluoroethyl)amino]butanamide (I-101)

The title compound was synthesized from N-(cyclohexylmethyl)-3-methyl-oxirane-2-carboxamide (I-34) in a similar manner to method C, general procedure 2 (general scheme 4) at 60° C. and was obtained as an off-white powder (300 mg, 10% purity, 8%) used in the next step without further purification.

N-(Cyclohexylmethyl)-3-[(cyclopropylmethyl) amino]-2-hydroxybutanamide (I-102)

The title compound was synthesized from N-(cyclohexylmethyl)-3-methyl-oxirane-2-carboxamide (I-34) in a similar manner to method C, general procedure 2 (general scheme 4) at 60° C. and was obtained as an off-white solid (337 mg, 100% purity, 71%) after purification by recrystallization from 1:2 EtOAc/heptane.
¹H NMR (500 MHz, Chloroform-d) δ 0.07-0.19 (m, 2H), 0.45-0.54 (m, 2H), 0.85-0.99 (m, 3H), 1.01 (d, J=6.5 Hz, 3H), 1.10-1.28 (m, 3H), 1.41-1.52 (m, 1H), 1.62-1.69 (m, 1H), 1.69-1.76 (m, 4H), 2.41 (dd, J=7.4, 12.1 Hz, 1H), 2.56 (dd, J=6.4, 12.1 Hz, 1H), 3.04-3.12 (m, 2H), 3.12-3.20 (m, 1H), 3.99 (d, J=5.0 Hz, 1H), 7.33 (s, 1H).
LC-MS (METCR1410): 100% (UV), Rt=0.81 min, m/z (ESI⁺)=269.2 [M+H]⁺

3-(Cyclohexylamino)-N-(cyclohexylmethyl)-2-hydroxybutanamide (I-103)

The title compound was synthesized from N-(cyclohexylmethyl)-3-methyl-oxirane-2-carboxamide (I-34) in a similar manner to method C, general procedure 2 (general scheme 4) as an off-white powder (441 mg, 100% purity, 69%) after purification by recrystallization from 1:2 EtOAc/heptane.
¹H NMR (500 MHz, Chloroform-d) δ 0.90-1.05 (m, 7H), 1.10-1.30 (m, 6H), 1.41-1.52 (m, 1H), 1.59-1.67 (m, 2H), 1.68-1.76 (m, 6H), 1.81-1.89 (m, 1H), 1.91-1.99 (m, 1H), 2.49 (tt, J=3.7, 10.5 Hz, 1H), 3.03-3.10 (m, 1H), 3.14-3.21 (m, 1H), 3.21-3.27 (m, 1H), 3.91 (d, J=5.2 Hz, 1H), 7.27-7.35 (m, 1H).
LC-MS (METCR1410): 100% (UV), Rt=0.87 min, m/z (ESI⁺)=297.2 [M+H]⁺ tert-Butyl 4-[({1-[(cyclohexylmethyl)carbamoyl]-1-hydroxypropan-2-yl}amino)methyl]-piperidine-1-carboxylate (I-104)

The title compound was synthesized from N-(cyclohexylmethyl)-3-methyl-oxirane-2-carboxamide (I-34) in a similar manner to method C, general procedure 2 (general scheme 4) at 60° C. and was obtained as an off-white solid (410 mg, 85% purity by ¹H NMR, 66%) after purification by recrystallization from heptane.
¹H NMR (500 MHz, Chloroform-d) δ 0.84-1.00 (m, 2H), 1.08 (d, J=6.5 Hz, 3H), 1.10-1.28 (m, 6H), 1.39-1.51 (m, 11H), 1.59-1.79 (m, 6H), 2.50 (dd, J=7.0, 11.9 Hz, 1H), 2.65-2.77 (m, 3H), 3.04-3.19 (m, 3H), 3.98-4.23 (m, 3H), 7.10-7.21 (m, 1H).

tert-Butyl N-[(1s,4s)-4-({1-[(cyclohexylmethyl)carbamoyl]-1-hydroxy-propan-2-yl}amino)cyclohexyl]carbamate (I-105)

The title compound was synthesized from N-(cyclohexylmethyl)-3-methyl-oxirane-2-carboxamide (I-34) in a similar manner to method C, general procedure 2 (general scheme 4) at 60° C. then 70° C. and was obtained as an off-white powder (552 mg, 93% purity by 1H NMR, 82%) after purification by flash column chromatography on normal phase silica (50 g SNAP KP-SIL cartridge, 0-100% TBME in heptane gradient then 0-20% MeOH in TBME gradient).

$^1$H NMR (250 MHz, Chloroform-d) δ 0.83-1.07 (m, 5H), 1.07-1.41 (m, 7H), 1.41-1.50 (m, 10H), 1.53-1.82 (m, 9H), 2.59-2.76 (m, 1H), 2.97-3.31 (m, 3H), 3.55-3.71 (m, 1H), 3.95 (d, J=4.7 Hz, 1H), 4.40-4.70 (m, 1H), 7.12 (t, J=5.7 Hz, 1H).

LC-MS (METCR1410): 100% (UV), Rt=0.93 min, m/z (ESI$^+$)=412.6 [M+H]$^+$

3-(Cyclohexylamino)-N-[2-(cyclohexyloxy)ethyl]-2-hydroxybutanamide (I-106)

The title compound was synthesized from N-[2-(cyclohexyloxy)ethyl]-3-methyl-oxirane-2-carboxamide (I-35) in a similar manner to method C, general procedure 2 (general scheme 4) at 50-70° C. and was obtained as an off-white powder (247 mg, 100% purity, 63%) after purification by triturated in Et$_2$O.

$^1$H NMR (250 MHz, Chloroform-d) δ 0.91-1.02 (m, 4H), 1.03-1.38 (m, 10H), 1.41-2.03 (m, 9H), 2.40-2.59 (m, 1H), 3.16-3.34 (m, 2H), 3.34-3.59 (m, 4H), 3.94 (d, J=5.1 Hz, 1H), 7.54 (s, 1H).

LC-MS (METCR1410): 100% (UV), Rt=0.89 min, m/z (ESI$^+$)=327.6 [M+H]$^+$

Methyl 2-[3-(benzylamino)-2-hydroxybutanamido]acetate (I-107)

The title compound was synthesized from methyl 2-[(3-methyloxiran-2-yl) formamido]acetate (I-36) in a similar manner to method C, general procedure 2 (general scheme 4) at 70° C. and was obtained as a yellow viscous oil (594 mg, 77% purity, 63%) after 2 purifications by flash column chromatography on normal phase silica (10 g SNAP KP-SIL cartridge, 0-20% MeOH in DCM gradient then 10 g SNAP KP-SIL cartridge, 2-12% MeOH in DCM gradient).

LC-MS (METCR0990): 77% (UV), Rt=1.32 min, m/z (ESI$^+$)=281.2 [M+H]$^+$

3-(Benzylamino)-2-hydroxy-N-(propan-2-yl)butanamide (I-108)

The title compound was synthesized from 3-methyl-N-(propan-2-yl)oxirane-2-carboxamide (I-39) in a similar manner to method C, general procedure 2 (general scheme 4) at 50-60° C. and was obtained as an off-white solid (148 mg, 96% purity, 33%) after purification by trituration in 1:5 EtOAc/heptane.

$^1$H NMR (500 MHz, Chloroform-d) δ 1.03 (d, J=6.5 Hz, 3H), 1.13-1.19 (m, 6H), 3.18-3.25 (m, 1H), 3.76-3.86 (m, 2H), 4.04 (d, J=4.7 Hz, 1H), 4.06-4.15 (m, 1H), 6.89-7.00 (m, 1H), 7.26-7.37 (m, 5H).

LC-MS (METCR1410): 96% (UV), Rt=0.65 min, m/z (ESI$^+$)=251.1 [M+H]$^+$

N-(Cyclopropylmethyl)-2-hydroxy-3-{[(oxan-4-yl)methyl]amino}hexanamide (I-109)

The title compound was synthesized from N-(cyclopropylmethyl)-3-propyloxirane-2-carboxamide (I-44) in a similar manner to method C, general procedure 2 (general scheme 4) at 60° C. and was obtained as an off-white solid (360 mg, 90% purity by $^1$H NMR, 57%) after purification by trituration in 1:5 EtOAc/heptane.

$^1$H NMR (500 MHz, Chloroform-d) δ 0.16-0.27 (m, 2H), 0.45-0.56 (m, 2H), 0.87-1.00 (m, 4H), 1.22-1.55 (m, 6H), 1.56-1.76 (m, 3H), 2.48-2.55 (m, 1H), 2.64 (dd, J=5.9, 12.1 Hz, 1H), 2.93-3.01 (m, 1H), 3.04-3.23 (m, 2H), 3.34-3.42 (m, 2H), 3.93-4.02 (m, 2H), 4.11 (d, J=4.7 Hz, 1H), 7.11-7.25 (m, 1H).

LC-MS (METCR1410): 52% (UV), Rt=0.72 min, m/z (ESI$^+$)=299.1 [M+H]$^+$ tert-Butyl 4-[({1-[(cyclohexylmethyl)carbamoyl]-1-hydroxybutan-2-yl}amino)methyl]-piperidine-1-carboxylate (I-110)

The title compound was synthesized from N-(cyclohexylmethyl)-3-ethyloxirane-2-carboxamide (I-45) in a similar manner to method C, general procedure 2 (general scheme 4) at 70° C. and was obtained as an off-white crystalline solid (600 mg, 96% purity, 61%) after purification by flash column chromatography on normal phase silica (25 g SNAP Ultra cartridge, 0-100% EtOAc in heptane gradient).

$^1$H NMR (500 MHz, Chloroform-d) δ 0.87-0.99 (m, 5H), 1.05-1.28 (m, 5H), 1.30-1.40 (m, 1H), 1.44 (s, 9H), 1.46-1.61 (m, 4H), 1.61-1.67 (m, 2H), 1.67-1.76 (m, 4H), 2.44 (dd, J=7.2, 11.9 Hz, 1H), 2.60 (dd, J=6.0, 11.8 Hz, 1H), 2.63-2.75 (m, 2H), 2.79-2.85 (m, 1H), 3.04-3.16 (m, 2H), 4.01 (d, J=5.1 Hz, 1H), 4.03-4.19 (m, 2H), 7.23 (t, J=5.6 Hz, 1H).

LC-MS (METCR1410): 96% (UV), Rt=0.9 min, m/z (ESI$^+$)=426.8 [M+H]$^+$

3-(Cyclohexylamino)-N-(cyclohexylmethyl)-2-hydroxypentanamide (I-111)

The title compound was synthesized from N-(cyclohexylmethyl)-3-ethyloxirane-2-carboxamide (I-45) in a similar manner to method C, general procedure 2 (general scheme 4) at 70° C. and was obtained as an off-white powder (400 mg, 76% purity by 1H NMR, 72%) after purification by flash column chromatography on normal phase silica (10 g SNAP Ultra cartridge, 0-100% EtOAc in heptane gradient).

$^1$H NMR (500 MHz, Chloroform-d) δ 0.88-0.96 (m, 3H), 0.96-1.09 (m, 3H), 1.09-1.36 (m, 7H), 1.42-1.52 (m, 2H), 1.54-1.76 (m, 8H), 1.78-1.88 (m, 2H), 1.93-1.99 (m, 1H), 2.47 (tt, J=3.7, 10.4 Hz, 1H), 3.00-3.18 (m, 3H), 3.97 (d, J=5.2 Hz, 1H), 7.21-7.31 (m, 1H).

LC-MS (METCR1410): 51% (UV), Rt=0.85 min, m/z (ESI$^+$)=311.7 [M+H]$^+$ tert-Butyl 3-[({1-[(cyclohexylmethyl)carbamoyl]-1-hydroxybutan-2-yl}amino)methyl]-azetidine-1-carboxylate (I-112)

The title compound was synthesized from N-(cyclohexylmethyl)-3-ethyloxirane-2-carboxamide (I-45) in a similar manner to method C, general procedure 2 (general scheme 4) at 60° C. then 70° C. and was obtained as a colourless gum (630 mg, 85% purity by $^1$H NMR, 50%) after purification by flash column chromatography on normal phase silica (50 g SNAP KP-SIL cartridge, 0-20% MeOH in heptane gradient).

$^1$H NMR (250 MHz, Chloroform-d) δ 0.71-1.02 (m, 6H), 1.09-1.21 (m, 2H), 1.29-1.55 (m, 11H), 1.57-1.81 (m, 6H), 2.46-3.22 (m, 5H), 3.46-3.79 (m, 3H), 3.90-4.06 (m, 2H), 4.25-4.41 (m, 1H), 6.53-7.21 (m, 1H).

LC-MS (METCR1410): 47% (UV), Rt=0.88 min, m/z (ESI$^+$)=398.8 [M+H]$^+$

N-(Cyclopropylmethyl)-3-[(cyclopropylmethyl)amino]-2-hydroxy-5-methylhexanamide (I-113)

The title compound was synthesized from N-(cyclopropylmethyl)-3-(2-methyl-propyl)oxirane-2-carboxamide (I-47) in a similar manner to method C, general procedure 2 (general scheme 4) at 60° C. and was obtained as an off-white powder (240 mg, 98% purity by 1H NMR, 58%) after purification by recrystallization from 1:1 EtOAc/heptane.

H NMR (500 MHz, Chloroform-d) δ 0.11-0.28 (m, 4H), 0.46-0.58 (m, 4H), 0.86-1.04 (m, 8H), 1.20-1.39 (m, 2H), 1.59-1.71 (m, 1H), 2.47 (dd, J=7.4, 12.3 Hz, 1H), 2.67 (dd, J=6.6, 12.3 Hz, 1H), 3.07-3.22 (m, 3H), 4.17 (d, J=4.1 Hz, 1H), 7.07-7.19 (m, 1H).

LC-MS (METCR1410): 100% (UV), Rt=0.81 min, m/z (ESI$^+$)=269.2 [M+H]$^+$

N-(Cyclopropylmethyl)-2-hydroxy-5-methyl-3-{[(oxan-4-yl)methyl]amino} hexanamide (I-114)

The title compound was synthesized from N-(cyclopropylmethyl)-3-(2-methyl-propyl)oxirane-2-carboxamide (I-47) in a similar manner to method C, general procedure 2 (general scheme 4) as an off-white solid (400 mg, 55% purity by 1H NMR, 53%) after concentration of the filtrate obtained from trituration in EtOAc/heptane.

$^1$H NMR (500 MHz, Chloroform-d) δ 0.16-0.27 (m, 2H), 0.44-0.57 (m, 2H), 0.88 (d, J=6.5 Hz, 3H), 0.92 (d, J=6.6 Hz, 3H), 0.93-1.00 (m, 1H), 1.12-1.39 (m, 3H), 1.49-1.72 (m, 4H), 2.46-2.52 (m, 1H), 2.56-2.63 (m, 3H), 2.97-3.04 (m, 1H), 3.08-3.22 (m, 2H), 3.31-3.43 (m, 2H), 3.93-4.04 (m, 2H), 4.10 (d, J=4.3 Hz, 1H), 6.95-7.05 (m, 1H).

LC-MS (METCR1410): 77% (UV), Rt=0.82 min, m/z (ESI$^+$)=313.3 [M+H]$^+$

N-(Cyclopropylmethyl)-2-hydroxy-5-methyl-3-({[(3S)-oxolan-3-yl]methyl} amino)hexanamide (I-115)

The title compound was synthesized from N-(cyclopropylmethyl)-3-(2-methyl-propyl)oxirane-2-carboxamide (I-47) in a similar manner to method C, general procedure 2 (general scheme 4) at 60° C. then 70° C. and was obtained as an off-white powder (333 mg, 85% purity by 1H NMR, 79%) after purification by flash column chromatography on normal phase silica (25 g SNAP KP-SIL cartridge, 0-100% TBME in heptane gradient then 0-30% MeOH in TBME gradient).

$^1$H NMR (250 MHz, Chloroform-d) δ 0.04-0.33 (m, 2H), 0.40-0.62 (m, 2H), 0.84-0.98 (m, 7H), 1.12-1.26 (m, 2H), 1.48-1.71 (m, 3H), 1.92-2.18 (m, 1H), 2.22-2.47 (m, 1H), 2.57-2.79 (m, 1H), 2.95-3.08 (m, 1H), 3.10-3.23 (m, 2H), 3.42-3.59 (m, 1H), 3.66-3.85 (m, 1H), 3.85-3.96 (m, 2H), 4.11 (d, J=4.2 Hz, 1H), 6.98 (s, 1H).

LC-MS (METCR1278): 78% (UV), Rt=1.44 min, m/z (ESI$^+$)=299.1 [M+H]$^+$

N-(Cyclopropylmethyl)-2-hydroxy-5-methyl-3-({[(3R)-oxolan-3-yl]methyl}amino)hexanamide (I-116)

The title compound was synthesized from N-(cyclopropylmethyl)-3-(2-methyl-propyl)oxirane-2-carboxamide (I-47) in a similar manner to method C, general procedure 2 (general scheme 4) at 60° C. then 70° C. and was obtained as an off-white powder (304 mg, 93% purity, 79%) after purification by flash column chromatography on normal phase silica (25 g SNAP KP-SIL cartridge, 0-100% TBME in heptane gradient then 0-30% MeOH in TBME gradient).

$^1$H NMR (250 MHz, Chloroform-d) δ 0.16-0.26 (m, 2H), 0.44-0.60 (m, 2H), 0.82-0.98 (m, 8H), 1.10-1.27 (m, 2H), 1.51-1.68 (m, 3H), 1.96-2.13 (m, 1H), 2.26-2.45 (m, 1H), 2.58-2.78 (m, 2H), 2.93-3.06 (m, 1H), 3.11-3.21 (m, 2H), 3.42-3.59 (m, 1H), 3.65-3.82 (m, 1H), 3.82-3.96 (m, 2H), 4.11 (d, J=4.2 Hz, 1H), 6.98 (s, 1H).

LC-MS (METCR1278): 93% (UV), Rt=1.44 min, m/z (ESI$^+$)=299.1 [M+H]$^+$

N-(Cyclopropylmethyl)-2-hydroxy-3-[(3-methoxypropyl)amino]-5-methylhexanamide (I-117)

The title compound was synthesized from N-(cyclopropylmethyl)-3-(2-methyl-propyl)oxirane-2-carboxamide (I-47) in a similar manner to method C, general procedure 2 (general scheme 4) at 70° C. and was obtained as an off-white powder (225 mg, 100% purity by $^1$H NMR, 54%) after purification by trituration in heptane.

$^1$H NMR (500 MHz, Chloroform-d) δ 0.19-0.24 (m, 2H), 0.48-0.53 (m, 2H), 0.87-0.94 (m, 7H), 0.94-1.03 (m, 1H), 1.19 (ddd, J=3.5, 9.7, 13.9 Hz, 1H), 1.32 (ddd, J=4.8, 9.8, 14.4 Hz, 1H), 1.53-1.65 (m, 1H), 1.71-1.94 (m, 3H), 2.66-2.80 (m, 1H), 2.88-2.97 (m, 1H), 3.08-3.21 (m, 3H), 3.31-3.36 (m, 3H), 3.39-3.57 (m, 2H), 4.20 (d, J=3.8 Hz, 1H), 7.08 (br. m, 1H).

LC-MS (METCR1410): 87% (UV), Rt=0.80 min, m/z (ESI$^+$)=287.3 [M+H]$^+$

N-(Cyclopropylmethyl)-2-hydroxy-5-methyl-3-{[(oxolan-3-yl)methyl]amino}hexanamide (I-118)

The title compound was synthesized from N-(cyclopropylmethyl)-3-(2-methyl-propyl)oxirane-2-carboxamide (I-47) in a similar manner to method C, general procedure 2 (general scheme 4) at 70° C. and was obtained as an off-white powder (219 mg, 97% purity, 59%) after purification twice by ion exchange flash chromatography (5 g Isolute SCX-2 cartridge, 1-5% 7N methanolic ammonia in DCM gradient) followed by trituration in heptane.

$^1$H NMR (500 MHz, Chloroform-d) δ 0.17-0.27 (m, 2H), 0.45-0.56 (m, 2H), 0.89 (d, J=6.6 Hz, 3H), 0.92 (d, J=6.6 Hz, 3H), 0.94-1.01 (m, 1H), 1.14-1.29 (m, 3H), 1.52-1.64 (m, 3H), 2.01-2.11 (m, 1H), 2.30-2.43 (m, 1H), 2.59-2.66 (m, 1H), 2.68-2.75 (m, 1H), 2.99-3.06 (m, 1H), 3.08-3.23 (m, 2H), 3.44-3.53 (m, 1H), 3.74 (q, J=7.5 Hz, 1H), 3.82-3.92 (m, 2H), 4.11 (d, J=4.1 Hz, 1H), 6.90-7.06 (m, 1H).

LC-MS (METCR0990): 97% (UV), Rt=1.48 min, m/z (ESI$^+$)=299.3 [M+H]$^+$

N-(Cyclopropylmethyl)-2-hydroxy-5-methyl-3-{[(oxolan-2-yl)methyl]amino}hexanamide (I-119)

The title compound was synthesized from N-(cyclopropylmethyl)-3-(2-methyl-propyl)oxirane-2-carboxamide (I-47) in a similar manner to method C, general procedure 2 (general scheme 4) at 70° C. and was obtained as a yellow powder (175 mg, 98% purity, 48%) after purification by ion exchange flash chromatography (5 g Isolute SCX-2 cartridge, 1-5% 7N methanolic ammonia in DCM gradient) followed by trituration in heptane.

$^1$H NMR (500 MHz, Chloroform-d) δ 0.15-0.28 (m, 2H), 0.44-0.56 (m, 2H), 0.75-1.02 (m, 8H), 1.13-1.23 (m, 1H), 1.27-1.31 (m, 1H), 1.46-1.67 (m, 3H), 1.85-2.05 (m, 3H), 2.57-2.69 (m, 1H), 2.71-2.87 (m, 1H), 2.98-3.23 (m, 3H), 3.71-3.80 (m, 1H), 3.82-3.89 (m, 1H), 3.92-4.03 (m, 1H), 4.11 (t, J=3.9 Hz, 1H), 6.99-7.18 (m, 1H).

LC-MS (METCR0990): 98% (UV), Rt=1.54 min, m/z (ESI$^+$)=299.3 [M+H]$^+$

3-Cyclopropyl-N-(cyclopropylmethyl)-2-hydroxy-3-{[(oxan-4-yl)methyl]amino}propanamide (I-120)

The title compound was synthesized from 3-cyclopropyl-N-(cyclopropyl-methyl)oxirane-2-carboxamide (I-49) in a similar manner to method C, general procedure 2 (general scheme 4) as an off-white solid (390 mg, 100% purity, 88%) after purification by trituration in heptane.

$^1$H NMR (500 MHz, Chloroform-d) δ 0.05-0.12 (m, 1H), 0.22 (q, J=5.0 Hz, 2H), 0.40-0.48 (m, 3H), 0.49-0.55 (m, 2H), 0.79-0.86 (m, 1H), 0.92-1.02 (m, 1H), 1.27-1.34 (m, 2H), 1.56-1.62 (m, 1H), 1.63-1.72 (m, 2H), 2.20 (dd, J=3.7, 9.8 Hz, 1H), 2.45 (dd, J=7.2, 12.0 Hz, 1H), 2.59 (dd, J=5.6, 12.0 Hz, 1H), 3.07-3.14 (m, 1H), 3.18-3.24 (m, 1H), 3.35-3.42 (m, 2H), 3.98 (dt, J=2.2, 11.4 Hz, 2H), 4.13 (d, J=3.7 Hz, 1H), 6.93-7.02 (m, 1H).

LC-MS (METCR1410): 100% (UV), Rt=0.71 min, m/z (ESI$^+$)=297.1 [M+H]$^+$ 3-(Benzylamino)-3-cyclopropyl-N-(cyclopropylmethyl)-2-hydroxypropanamide (I-121)

The title compound was synthesized from 3-cyclopropyl-N-(cyclopropyl-methyl)oxirane-2-carboxamide (I-49) in a similar manner to method C, general procedure 2 (general scheme 4) as an off-white solid (278 mg, 97% purity, 63%) after purification by trituration in heptane.

$^1$H NMR (500 MHz, Chloroform-d) δ 0.00-0.09 (m, 1H), 0.22 (q, J=5.0 Hz, 2H), 0.37-0.47 (m, 3H), 0.47-0.53 (m, 2H), 0.83-0.92 (m, 1H), 0.93-1.03 (m, 1H), 2.31 (dd, J=3.6, 9.8 Hz, 1H), 3.06-3.15 (m, 1H), 3.17-3.25 (m, 1H), 3.72-3.86 (m, 2H), 4.21 (d, J=3.6 Hz, 1H), 6.95-7.04 (m, 1H), 7.26-7.37 (m, 5H).

LC-MS (METCR1410): 97% (UV), Rt=0.8 min, m/z (ESI$^+$)=289.5 [M+H]$^+$ 3-(Benzylamino)-N-(cyclopropylmethyl)-2-hydroxy-5-methoxypentanamide (I-122)

The title compound was synthesized from N-(cyclopropylmethyl)-3-(2-methoxy-ethyl)oxirane-2-carboxamide (I-50) in a similar manner to method C, general procedure 2 (general scheme 4) as a yellow viscous oil (155 mg, 90% purity, 81%). The crude material was suspended in heptane and used in the next step without further purification.

$^1$H NMR (500 MHz, Chloroform-d) δ 0.16-0.24 (m, 2H), 0.45-0.53 (m, 2H), 0.90-0.98 (m, 1H), 1.67-1.72 (m, 2H), 3.02-3.19 (m, 3H), 3.28-3.38 (m, 3H), 3.41-3.56 (m, 2H), 3.78-3.88 (m, 2H), 4.12 (d, J=5.2 Hz, 1H), 7.28-7.36 (m, 6H).

LC-MS (METCR1410): 90% (UV), Rt=0.75-0.90 min (two peaks), m/z (ESI$^+$)=307.5 [M+H]$^+$ 3-(Benzylamino)-N-(cyclopropylmethyl)-2-hydroxy-3-(oxan-4-yl)propanamide (I-123)

The title compound was synthesized from N-(cyclopropylmethyl)-3-(oxan-4-yl)oxirane-2-carboxamide (I-51) in a similar manner to method C, general procedure 2 (general scheme 4) at 70° C. and was obtained as a yellow viscous oil (134 mg, 56% purity, 52%). The crude material was suspended in heptane and used in the next step without further purification.

LC-MS (METCR1410): 56% (UV), Rt=0.8 min, m/z (ESI$^+$)=333.3 [M+H]$^+$

N-(Cyclopropylmethyl)-2-hydroxy-3-{[(oxan-4-yl)methyl]amino}-5-phenylpentanamide (I-124)

The title compound was synthesized from N-(cyclopropylmethyl)-3-(2-phenyl-ethyl)oxirane-2-carboxamide (I-52) in a similar manner to method C, general procedure 2 (general scheme 4) at 70° C. and was obtained as an off-white solid (590 mg, 90% purity, 97%) after purification by trituration in heptane.

$^1$H NMR (500 MHz, Chloroform-d) δ 0.17-0.23 (m, 2H), 0.45-0.51 (m, 2H), 0.89-0.98 (m, 1H), 1.20-1.30 (m, 2H), 1.47-1.63 (m, 3H), 1.63-1.71 (m, 1H), 1.77-1.90 (m, 1H), 2.38-2.46 (m, 1H), 2.48-2.55 (m, 1H), 2.62-2.75 (m, 2H), 2.92-2.99 (m, 1H), 3.09-3.21 (m, 2H), 3.35 (tdd, J=2.2, 4.7, 11.8 Hz, 2H), 3.92-3.97 (m, 2H), 4.07 (d, J=5.0 Hz, 1H), 7.16-7.21 (m, 4H), 7.26-7.30 (m, 2H).

LC-MS (METCR1410): 90% (UV), Rt=0.89 min, m/z (ESI$^+$)=361.6 [M+H]$^+$

Method D: Epoxide opening with methylamine in methanol

N-[(3-Chlorophenyl)methyl]-2-hydroxy-3-(methylamino)butanamide (I-125)

A solution of N-[(3-chlorophenyl)methyl]-3-methyloxirane-2-carboxamide (I-27) (86% purity, 300 mg, 1.14 mmol) in 33% methylamine in ethanol (3 mL, 24.1 mmol) was stirred in a sealed tube at RT for 42 h. 33% methylamine in ethanol (1 mL) was added and the reaction mixture stood at RT for 24 h. The reaction mixture was concentrated in vacuo to give a solid which was dissolved in hot EtOAc (5 mL). The solution was diluted with heptane (15 mL) and cooled in a sonic bath over 5 min. The resulting precipitate was collected via filtration and dried in vacuo at 40° C. for 1 h to afford 265 mg of N-[(3-chlorophenyl)methyl]-2-hydroxy-3-(methylamino)-butanamide as an off-white solid (100% purity, 81%).

$^1$H NMR (500 MHz, Chloroform-d) δ 1.01 (d, J=6.5 Hz, 3H), 2.43 (s, 3H), 2.95-3.06 (m, 1H), 4.10 (d, J=4.9 Hz, 1H), 4.40-4.51 (m, 2H), 7.15-7.19 (m, 1H), 7.22-7.26 (m, 2H), 7.27-7.29 (m, 1H), 7.55-7.65 (m, 1H).

LC-MS (METCR1410): 100% (UV), Rt=0.72 min, m/z (ESI$^+$)=257.0/259.0 [M+H]$^+$

General Procedure 3 (General Scheme 4): N-Formylation

Method A: Direct Addition of Acetic Anhydride

N-[(3-Chlorophenyl)methyl]-2-hydroxy-3-[N-(2-methoxyphenyl)formamido]butanamide (I-126)

To a stirred suspension of N-[(3-chlorophenyl)methyl]-2-hydroxy-3-[(2-methoxy phenyl)amino]butanamide (I-54, 85% purity, 120 mg, 0.29 mmol) and formic acid (75 µL, 1.91 mmol) was added dropwise acetic anhydride (0.5 mL). The reaction was stirred at RT in a sealed vial for 1 h. The reaction mixture was quenched with ice/water (1 mL) and the solution partitioned between saturated NaHCO$_3$ (5 mL) and EtOAc (2×5 mL). The organic layers were combined, dried over sodium sulfate, filtered and concentrated in vacuo. The crude material was purified twice by preparative LC (acidic pH, standard elution method) to afford 8 mg of N-[(3-chlorophenyl)methyl]-2-hydroxy-3-[N-(2-methoxyphenyl)formamido]butanamide as a brown oil (100% purity, 7%).

$^1$H NMR (500 MHz, Chloroform-d) δ 1.34 (d, J=7.2 Hz, 3H), 3.88 (s, 3H), 4.11-4.21 (m, 1H), 4.40 (dd, J=6.1, 15.1 Hz, 1H), 4.48 (dd, J=6.3, 15.1 Hz, 1H), 4.73 (s, 1H), 6.30-6.42 (m, 1H), 6.93-7.02 (m, 2H), 7.12-7.19 (m, 2H), 7.21-7.29 (m, 3H), 7.32-7.39 (m, 1H), 7.41-7.53 (m, 1H), 8.08 (s, 1H).

LC-MS (METCR1416): 100% (UV), Rt=3.88 min, m/z (ESI$^+$)=377.1/379.1 [M+H]$^+$

N-[(3-Chlorophenyl)methyl]-2-hydroxy-3-[N-(3-methoxyphenyl)formamido]butanamide (I-127)

The title compound was synthesized from N-[(3-chlorophenyl)methyl]-2-hydroxy-3-[(3-methoxyphenyl)amino]butanamide (I-56) in a similar manner to method A, general procedure 3 (general scheme 4) as a yellow viscous oil (273 mg, 91% purity, 94%) used in the next step without further purification.

$^1$H NMR (500 MHz, Chloroform-d) δ 1.36 (d, J=7.2 Hz, 3H), 3.83 (s, 3H), 4.42-4.51 (m, 3H), 4.62 (s, 1H), 6.16 (s, 1H), 6.76 (t, J=2.2 Hz, 1H), 6.79-6.84 (m, 1H), 6.86-6.91 (m, 1H), 7.14-7.20 (m, 1H), 7.22-7.28 (m, 3H), 7.32 (t, J=8.1 Hz, 1H), 7.39-7.47 (m, 1H), 8.28 (s, 1H).

LC-MS (METCR1278): 91% (UV), Rt=1.93 min, m/z (ESI$^+$)=377.0/379.0 [M+H]$^+$

N-[(3-Chlorophenyl)methyl]-2-hydroxy-3-[N-(4-methoxyphenyl)formamido]butanamide (I-128)

The title compound was synthesized from N-[(3-chlorophenyl)methyl]-2-hydroxy-3-[(4-methoxyphenyl)amino]butanamide (I-57) in a similar manner to method A, general procedure 3 (general scheme 4) as a brown solid (273 mg, 90% purity by 1H NMR, 89%) used in the next step without further purification.

$^1$H NMR (500 MHz, Chloroform-d) δ 1.33 (d, J=7.2 Hz, 3H), 3.82 (s, 3H), 4.33-4.39 (m, 1H), 4.40-4.50 (m, 2H), 4.59-4.64 (m, 1H), 6.18 (s, 1H), 6.89-6.93 (m, 2H), 7.13-7.17 (m, 3H), 7.23-7.26 (m, 2H), 7.26-7.28 (m, 1H), 7.39-7.46 (m, 1H), 8.20 (s, 1H).

N-[(3-Chlorophenyl)methyl]-2-hydroxy-3-(N-phenylformamido)butanamide (I-129)

The title compound was synthesized from N-[(3-chlorophenyl)methyl]-2-hydroxy-3-(phenylamino)butanamide (I-58) in a similar manner to method A, general procedure 3 (general scheme 4) as a brown solid (273 mg, 81% purity, 84%) used in the next step without further purification.

$^1$H NMR (500 MHz, Chloroform-d) δ 1.36 (d, J=7.2 Hz, 3H), 4.43-4.50 (m, 3H), 4.64 (s, 1H), 6.18 (s, 1H), 7.14-7.19 (m, 2H), 7.22-7.25 (m, 3H), 7.26-7.28 (m, 1H), 7.30-7.37 (m, 2H), 7.41-7.45 (m, 2H), 8.28 (s, 1H).

LC-MS (METCR1278): 81% (UV), Rt=1.9 min, m/z (ESI$^+$)=346.9/348.9 [M+H]$^+$

N-[(3-Chlorophenyl)methyl]-3-[N-(5-fluoro-2-methoxyphenyl)formamido]-2-hydroxy-butanamide (I-130)

The title compound was synthesized from N-[(3-chlorophenyl)methyl]-3-[(5-fluoro-2-methoxyphenyl)amino]-2-hydroxybutanamide (I-65) in a similar manner to method A, general procedure 3 (general scheme 4) as a brown viscous oil (217 mg, 98% purity, 96%) used in the next step without further purification.

$^1$H NMR (500 MHz, Chloroform-d) δ 1.33 (d, J=7.2 Hz, 3H), 3.86 (s, 3H), 4.15-4.21 (m, 1H), 4.37-4.51 (m, 2H), 4.70 (s, 1H), 6.16 (s, 1H), 6.91-6.95 (m, 2H), 7.05-7.09 (m, 1H), 7.14-7.18 (m, 1H), 7.24-7.26 (m, 2H), 7.26-7.28 (m, 1H), 7.39-7.46 (m, 1H), 8.08 (s, 1H).

LC-MS (METCR1278): 98% (UV), Rt=2.05 min, m/z (ESI$^+$)=394.9/396.9 [M+H]$^+$

N-[(3-Chlorophenyl)methyl]-3-[N-(4-fluoro-2-methoxyphenyl)formamido]-2-hydroxy-butanamide (I-131)

The title compound was synthesized from N-[(3-chlorophenyl)methyl]-3-[(4-fluoro-2-methoxyphenyl)amino]-2-hydroxybutanamide (I-66) in a similar manner to method A, general procedure 3 (general scheme 4) as a yellow viscous oil (340 mg, 96% purity, 85%) after purification by flash column chromatography on normal phase silica (25 g SNAP KP-SIL cartridge, 0-100% EtOAc in heptane gradient).

$^1$H NMR (500 MHz, DMSO-d6) δ 0.86-1.22 (m, 3H), 3.76-3.82 (m, 3H), 3.97-4.12 (m, 1H), 4.24-4.72 (m, 3H), 6.00-6.24 (m, 1H), 6.76-6.84 (m, 1H), 6.89-6.99 (m, 1H), 7.18-7.58 (m, 5H), 8.00-8.39 (m, 1H), 8.45-8.66 (m, 1H).

LC-MS (METCR1410): 96% (UV), Rt=1.04-1.20 min (two peaks), m/z (ESI$^+$)=395.1/397.1 [M+H]$^+$ N-[(3-Chlorophenyl)methyl]-2-hydroxy-3-[N-(2-methoxyphenyl)formamido]-3-methylbutanamide (I-132)

The title compound was synthesized from N-[(3-chlorophenyl)methyl]-2-hydroxy-3-[(2-methoxyphenyl)amino]-3-methylbutanamide (I-62) in a similar manner to method A, general procedure 3 (general scheme 4) as a brown free-flowing oil (242 mg, 96% purity, quantitative) used in the next step without further purification. LC-MS (METCR1410): 98% (UV), Rt=1.20-1.30 min (multiple peaks), m/z (ESI$^+$)=391.0/393.0 [M+H]$^+$ N-[(3-Chlorophenyl)methyl]-2-hydroxy-3-[N-(2-methoxyphenyl)formamido]-3-phenylpropanamide (I-133)

The title compound was synthesized from N-[(3-chlorophenyl)methyl]-2-hydroxy-3-[(2-methoxyphenyl)amino]-3-phenylpropanamide (I-63) in a similar manner to method A, general procedure 3 (general scheme 4) as a brown viscous oil (255 mg, 100% purity, quantitative) used in the next step without further purification.

$^1$H NMR (500 MHz, Chloroform-d) δ 3.86 (s, 3H), 4.21 (dd, J=15.1, 5.5 Hz, 1H), 4.50 (dd, J=15.1, 7.0 Hz, 1H), 5.01-5.05 (m, 1H), 5.29 (s, 1H), 6.61-6.67 (m, 1H), 6.83 (td, J=7.6, 1.1 Hz, 1H), 6.91-6.95 (m, 2H), 6.97 (dd, J=8.3, 0.9

Hz, 1H), 7.09-7.11 (m, 1H), 7.14-7.21 (m, 3H), 7.21-7.26 (m, 4H), 7.26-7.32 (m, 2H), 8.26 (s, 1H).

LC-MS (METCR1278): 100% (UV), Rt=2.13 min, m/z (ESI$^+$)=439.0/441.0 [M+H]$^+$

N-[2-(3-Chlorophenyl)propan-2-yl]-2-hydroxy-3-[N-(2-methoxyphenyl)formamido]-butanamide (I-134)

The title compound was synthesized from A[2-(3-chlorophenyl)propan-2-yl]-2-hydroxy-3-[(2-methoxyphenyl)amino]butanamide (I-72) in a similar manner to method A, general procedure 3 (general scheme 4) as a yellow viscous oil (250 mg, 83% purity, 62%) after purification by flash column chromatography on normal phase silica (25 g SNAP KP-SIL cartridge, 0-100% EtOAc in heptane gradient).

LC-MS (METCR1410): 83% (UV), Rt=1.07-1.30 min (multiple peaks), m/z (ESI$^+$)=405.1/407.0 [M+H]$^+$

N-[(3-Chlorophenyl)methyl]-2-hydroxy-3-[N-(2-methoxyphenyl)formamido]pentanamide (I-135)

The title compound was synthesized from N-[(3-chlorophenyl)methyl]-2-hydroxy-3-[(2-methoxyphenyl)amino]pentanamide (I-79) in a similar manner to method A, general procedure 3 (general scheme 4) as a yellow viscous oil (150 mg, 85% purity by $^1$H NMR, 62%) after purification by flash column chromatography on normal phase silica (10 g SNAP KP-SIL cartridge, 0-100% EtOAc in heptane gradient).

$^1$H NMR (250 MHz, DMSO-d6) δ 0.67-1.08 (m, 4H), 1.38-1.58 (m, 1H), 3.58-3.73 (m, 1H), 3.74-3.81 (m, 3H), 4.15-4.45 (m, 3H), 5.81-6.34 (m, 1H), 6.89-7.04 (m, 1H), 7.08-7.52 (m, 7H), 7.98-8.36 (m, 1H), 8.41-8.69 (m, 1H).

LC-MS (METCR1410): 99% (UV), Rt=1.05-1.25 min (multiple peaks), m/z (ESI$^+$)=391.0/393.0 [M+H]$^+$

N-[(3-Chlorophenyl)methyl]-2-hydroxy-3-[N-(2-methoxyphenyl)formamido]-5-methylhexanamide (I-136)

The title compound was synthesized from N-[(3-chlorophenyl)methyl]-2-hydroxy-3-[(2-methoxyphenyl)amino]-5-methylhexanamide (I-64) in a similar manner to method A, general procedure 3 (general scheme 4) as a yellow viscous oil (140 mg, 87% purity, 48%) used in the next step without further purification.

LC-MS (METCR1410): 87% (UV), Rt=1.08-1.30 min (multiple peaks), m/z (ESI$^+$)=419.1/421.1 [M+H]$^+$

2-Hydroxy-3-[N-(2-methoxyphenyl)formamido]butanamide (I-137)

The title compound was synthesized from 2-hydroxy-3-[(2-methoxyphenyl) amino]butanamide (I-83) in a similar manner to method A, general procedure 3 (general scheme 4) as an orange oil (18 mg, 91% purity, 26%) after purification by flash column chromatography on normal phase silica (10 g SNAP KP-SIL cartridge, 0-100% EtOAc in heptane gradient).

$^1$H NMR (500 MHz, Chloroform-d) δ 1.37 (d, J=7.2 Hz, 3H), 3.87 (s, 3H), 4.14 (q, J=7.0 Hz, 1H), 4.69 (s, 1H), 5.45-5.63 (m, 1H), 6.95-7.05 (m, 3H), 7.14-7.18 (m, 1H), 7.32-7.38 (m, 1H), 8.08 (s, 1H).

LC-MS (METCR1410): 91% (UV), Rt=0.60-0.85 min (broad peak), m/z (ESI$^+$)=253.0 [M+H]$^+$ Method B: Direct Addition of Acetic Anhydride Followed by Hydrolysis

3-(N-Cyclohexylformamido)-2-hydroxy-N-(2-methylpropyl)butanamide (I-138)

To a stirred suspension of 3-(cyclohexylamino)-2-hydroxy-N-(2-methylpropyl)-butanamide (I-94, 287 μL, 1.09 mmol) in formic acid (292 μL, 7.58 mmol) was added acetic anhydride (3 mL) dropwise and the reaction stirred at RT for 18 h. The mixture was quenched with saturated NaHCO$_3$ (4 mL) and the aqueous layer extracted with EtOAc (2×5 mL). The combined organic layers were dried over sodium sulfate, filtered and concentrated in vacuo to give a crude material which was purified by flash column chromatography on normal phase silica (10 g SNAP KP-SIL cartridge, 0-100% EtOAc in heptane gradient). The yellow oil obtained was dissolved in 1:1 MeOH/THF (4 mL) and 2M NaOH (2 mL) added. The reaction was stirred at RT for 2 h, THF and MeOH were removed in vacuo and the aqueous layer was extracted with EtOAc (3×5 ml). The combined organics were dried over sodium sulfate, filtered and concentrated in vacuo to afford 332 mg of 3-(N-cyclohexylformamido)-2-hydroxy-N-(2-methylpropyl)-butanamide as a clear oil (89% purity, 95%).

$^1$H NMR (500 MHz, Chloroform-d) δ 0.90-0.95 (m, 6H), 1.21-1.28 (m, 3H), 1.28-1.36 (m, 5H), 1.61-1.69 (m, 1H), 1.72-1.92 (m, 3H), 2.07-2.30 (m, 2H), 3.01-3.20 (m, 2H), 3.30-3.40 (m, 1H), 4.02 (q, J=7.2 Hz, 1H), 4.22 (s, 1H), 6.56 (s, 1H), 7.05-7.17 (m, 1H), 8.08 (s, 1H).

LC-MS (METCR1410): 89% (UV), Rt=0.95-1.15 (two peaks), m/z (ESI$^+$)=285.2 [M+H]$^+$

3-[N-(Cyclopropylmethyl)formamido]-2-hydroxy-N-(2-methylpropyl)butanamide (I-139)

The title compound was synthesized from 3-[(cyclopropylmethyl)amino]-2-hydroxy-N-(2-methylpropyl)butanamide (I-95) in a similar manner to method B, general procedure 3 (general scheme 4) as a clear oil (300 mg, 80% purity by $^1$H NMR, 74%) used in the next step without further purification.

$^1$H NMR (500 MHz, Chloroform-d) δ 0.23-0.32 (m, 2H), 0.60-0.70 (m, 2H), 0.93 (d, J=6.7 Hz, 6H), 1.04-1.14 (m, 1H), 1.29 (d, J=7.2 Hz, 3H), 1.75-1.86 (m, 1H), 3.03-3.09 (m, 1H), 3.11-3.21 (m, 3H), 3.97-4.06 (m, 1H), 4.38 (s, 1H), 7.12 (s, 1H), 8.00 (s, 1H).

LC-MS (METCR1410): 96% (UV), Rt=0.90-1.01 min, m/z (ESI$^+$)=257.2 [M+H]$^+$

N-[(3-Chlorophenyl)methyl]-3-(N-cyclohexylformamido)-2-hydroxybutanamide (I-140)

The title compound was synthesized from N-[(3-chlorophenyl)methyl]-3-(cyclohexylamino)-2-hydroxybutanamide (I-55) in a similar manner to method B, general procedure 3 (general scheme 4) as a colourless solid (97 mg, 75% purity, 63%) used in the next step without further purification.

LC-MS (METCR1410): 75% (UV), Rt=1.14-1.36 min (multiple peaks), m/z (ESI$^+$)=353.0/355.0 [M+H]$^+$

N-[(3-Chlorophenyl)methyl]-3-[AN-(cyclohexylmethyl)formamido]-2-hydroxybutanamide (I-141)

To ice cooled acetic anhydride (0.18 mL, 1.91 mmol) in a sealed tube was added at 0° C. formic acid (0.1 mL, 2.54 mmol). The reaction was stirred at 50° C. for 1 h and dry THF (2.5 mL) added at RT. The mixture was cooled in an ice bath and a solution of N-[(3-chlorophenyl)methyl]-3-[(cyclohexylmethyl)amino]-2-hydroxybutanamide (I-67, 250 mg, 0.73 mmol) in dry THF (2.5 mL) added. The reaction was stirred at RT for 2 h, heated at 35° C. for 4 h and stirred at RT for 18 h. The mixture was partitioned between saturated NaHCO$_3$(15 mL) and EtOAc (2×10 mL). The combined organic layers were dried over sodium sulfate, filtered and concentrated in vacuo to afford a colourless oil which was dissolved in 1:1 MeOH/THF (6 mL). 2N NaOH (2 mL) was added and the reaction was stirred at RT for 1 h. The mixture was partitioned between EtOAc (15 mL) and water (15 mL). The aqueous layer was extracted with EtOAc (2×10 mL) and the combined organic layers were dried over sodium sulfate, filtered and concentrated in vacuo to afford N-[(3-chlorophenyl)methyl]-3-[N-(cyclo-hexylmethyl)formamido]-2-hydroxybutanamide as a colourless oil (133 mg, 80% purity by $^1$H NMR, 40%).

$^1$H NMR (500 MHz, Chloroform-d) δ 0.80-1.01 (m, 2H), 1.10-1.34 (m, 6H), 1.63-1.80 (m, 6H), 3.01-3.18 (m, 2H), 3.86 (q, J=7.0 Hz, 1H), 4.36 (s, 1H), 4.38-4.51 (m, 2H), 6.57 (s, 1H), 7.14-7.19 (m, 1H), 7.22-7.28 (m, 3H), 7.40-7.48 (m, 1H), 7.87-8.25 (m, 1H).

LC-MS (METCR1278): 95% (UV), Rt=1.90-2.25 min (multiple peaks), m/z (ESI$^+$)=367.4/369.4 [M+H]$^+$ N-[(3-Chlorophenyl)methyl]-2-hydroxy-3-[N-(2-methoxyphenyl)formamido]propanamide (I-142)

The title compound was synthesized from N-[(3-chlorophenyl)methyl]-2-hydroxy-3-[(2-methoxyphenyl)amino]propanamide (I-70) in a similar manner to method B, general procedure 3 (general scheme 4) as a light yellow oil (239 mg, 80% purity by $^1$H NMR, 57%) used in the next step without further purification.

$^1$H NMR (500 MHz, Chloroform-d) δ 3.78 (s, 3H), 3.95 (dd, J=2.4, 14.6 Hz, 1H), 4.09 (dd, J=7.9, 14.6 Hz, 1H), 4.28-4.32 (m, 1H), 4.32-4.37 (m, 2H), 4.37-4.41 (m, 1H), 5.29 (d, J=3.6 Hz, 1H), 6.88-6.94 (m, 2H), 7.04-7.07 (m, 1H), 7.07-7.11 (m, 1H), 7.15-7.23 (m, 2H), 7.25-7.31 (m, 1H), 7.34-7.43 (m, 1H), 8.06-8.22 (m, 1H).

LC-MS (METCR1410): 80% (UV), Rt=1.03 min, m/z (ESI$^+$)=363.0/365.0 [M+H]$^+$

Method C: Pre-Formation of Mixed Anhydride 3-(N-Benzylformamido)-N-[(3-chlorophenyl)methyl]-2-hydroxybutanamide (I-143)

To ice-cold acetic anhydride (129 μL, 1.37 mmol) was added dropwise at 0° C. formic acid (67 μL, 1.69 mmol). The mixture was heated at 50-60° C. for 2 h and cooled to RT. The solution was diluted with dry THF (4 mL) and cooled to 0° C. A solution of 3-(benzylamino)-N-[(3-chlorophenyl)methyl]-2-hydroxybutanamide (I-59, 90% purity, 195 mg, 0.53 mmol) in dry THF (4 mL) was added and the reaction stirred at RT for 18 h. The mixture was concentrated in vacuo to afford 205 mg of 3-(N-benzylformamido)-N-[(3-chlorophenyl)methyl]-2-hydroxybutanamide as a yellow viscous oil (83% purity, 89%) used in the next step without further purification.

$^1$H NMR (500 MHz, Chloroform-d) δ 1.09 (d, J=7.1 Hz, 3H), 3.93 (q, J=7.1 Hz, 1H), 4.30 (s, 1H), 4.33-4.43 (m, 1H), 4.42-4.51 (m, 2H), 6.32 (s, 1H), 7.09-7.14 (m, 1H), 7.20-7.25 (m, 3H), 7.27-7.32 (m, 2H), 7.32-7.42 (m, 4H), 8.27 (s, 1H)

LC-MS (MET-μHPLC-AB-101): 83% (UV), Rt=2.87 min, m/z (ESI$^+$)=361.1/363.1 [M+H]$^+$ N-[(3-Chlorophenyl)methyl]-2-hydroxy-3-[N-(propan-2-yl)formamido]butanamide (I-144)

The title compound was synthesized from N-[(3-chlorophenyl)methyl]-2-hydroxy-3-[(propan-2-yl)amino]butanamide (I-60) in a similar manner to method C, general procedure 3 (general scheme 4) as a pink viscous oil (213 mg, 80% purity by $^1$H NMR, 87%) used in the next step without further purification.

$^1$H NMR (500 MHz, Chloroform-d) δ 1.26 (d, J=7.1 Hz, 3H), 1.30 (d, J=6.8 Hz, 3H), 1.35 (d, J=6.8 Hz, 3H), 3.87 (hept, J=6.7 Hz, 1H), 4.03 (q, J=7.1 Hz, 1H), 4.29 (s, 1H), 4.39-4.50 (m, 2H), 6.60 (s, 1H), 7.14-7.18 (m, 1H), 7.23-7.28 (m, 3H), 7.39-7.51 (m, 1H), 8.08-8.11 (m, 1H).

LC-MS (METCR1410): 92% (UV), Rt=0.95-1.10 min (multiple peaks), m/z (ESI$^+$)=313.0/315.0 [M+H]$^+$ N-[(3-Chlorophenyl)methyl]-2-hydroxy-3-[N-(oxan-4-yl)formamido]butanamide (I-145)

The title compound was synthesized from N-[(3-chlorophenyl)methyl]-2-hydroxy-3-[(oxan-4-yl)amino]butanamide (I-61) in a similar manner to method C, general procedure 3 (general scheme 4) as a yellow viscous oil (180 mg, 62% purity, 88%) used in the next step without further purification.

LC-MS (METCR1410): 62% (UV), Rt=1.03 min, m/z (ESI$^+$)=355.0/357.0 [M+H]$^+$

N-[(3-Chlorophenyl)methyl]-3-[N-(2,2-dimethylpropyl)formamido]-2-hydroxybutanamide (I-146)

The title compound was synthesized from N-[(3-chlorophenyl)methyl]-3-[(2,2-dimethylpropyl)amino]-2-hydroxybutanamide (I-68) in a similar manner to method C, general procedure 3 (general scheme 4) as a yellow solid (220 mg, 85% purity by 1H NMR, 67%) used in the next step without further purification.

$^1$H NMR (500 MHz, DMSO-d6) δ 0.82-0.90 (m, 9H), 1.12-1.27 (m, 3H), 2.53-2.57 (m, 1H), 3.48-3.57 (m, 1H), 3.64 (qd, J=3.0, 7.2 Hz, 1H), 4.03-4.12 (m, 1H), 4.21-4.36 (m, 2H), 6.17-6.29 (m, 1H), 7.20-7.24 (m, 1H), 7.27-7.37 (m, 3H), 7.88-8.33 (m, 1H), 8.46-8.67 (m, 1H).

LC-MS (METCR1410): 98% (UV), Rt=1.04-1.02 min (multiple peaks), m/z (ESI$^+$)=341.0/343.0 [M+H]$^+$ N-[(3-Chlorophenyl)methyl]-2-hydroxy-3-{N-[(oxan-4-yl)methyl]formamido}butanamide (I-147)

The title compound was synthesized from N-[(3-chlorophenyl)methyl]-2-hydroxy-3-{[(oxan-4-yl)methyl]amino}butanamide (I-69) in a similar manner to method C, general procedure 3 (general scheme 4) as a colourless viscous oil (188 mg, 90% purity by 1H NMR, 88%) used in the next step without further purification.

$^1$H NMR (500 MHz, Chloroform-d) δ 1.22-1.28 (m, 4H), 1.51-1.70 (m, 3H), 1.93 (dq, J=3.7, 11.3 Hz, 1H), 3.16 (qd, J=7.2, 14.2 Hz, 2H), 3.40 (td, J=2.1, 11.9 Hz, 2H), 3.89 (q, J=7.1 Hz, 1H), 4.00 (dd, J=3.2, 11.5 Hz, 2H), 4.35 (s, 1H), 4.38-4.51 (m, 2H), 6.40-6.68 (m, 1H), 7.12-7.18 (m, 1H), 7.23-7.30 (m, 3H), 7.36-7.53 (m, 1H), 7.92-8.12 (m, 1H).

LC-MS (METCR1410): 98% (UV), Rt=0.92-1.00 min (two peaks), m/z (ESI$^+$)=369.0/371.0 [M+H]$^+$

N-(Cyclohexylmethyl)-2-hydroxy-3-[N-(2-methoxyphenyl)formamido]butanamide (I-148)

The title compound was synthesized from N-(cyclohexylmethyl)-2-hydroxy-3-[(2-methoxyphenyl)amino]butanamide (I-71) in a similar manner to method C, general procedure 3 (general scheme 4) as a colourless viscous oil (325 mg, 99% purity, 62%) used in the next step without further purification.

$^1$H NMR (250 MHz, Chloroform-d) δ 0.83-1.03 (m, 2H), 1.14-1.29 (m, 4H), 1.32 (d, J=7.2 Hz, 3H), 1.38-1.54 (m, 1H), 1.55-1.63 (m, 2H), 1.74 (s, 2H), 3.12 (dh, J=6.4, 19.6 Hz, 2H), 3.84-3.94 (m, 3H), 4.04-4.24 (m, 1H), 4.63-4.70 (m, 1H), 6.28 (s, 1H), 6.94-7.02 (m, 2H), 7.08-7.20 (m, 2H), 7.29-7.41 (m, 1H), 8.07 (s, 1H).

LC-MS (METCR1410): 99% (UV), Rt=1.04-1.20 min (multiple peaks), m/z (ESI$^+$)=349.1 [M+H]$^+$

N-[2-(3-Chlorophenyl)propan-2-yl]-2-hydroxy-3-[N-(propan-2-yl)formamido]butanamide (I-149)

The title compound was synthesized from N-[2-(3-chlorophenyl)propan-2-yl]-2-hydroxy-3-[(propan-2-yl)amino]butanamide (I-73) in a similar manner to method C, general procedure 3 (general scheme 4) as a colourless viscous oil (110 mg, 85% purity by $^1$H NMR, 78%) used in the next step without further purification.

$^1$H NMR (500 MHz, Chloroform-d) δ 1.22-1.31 (m, 9H), 1.66-1.73 (m, 6H), 3.78-3.88 (m, 1H), 3.93 (q, J=7.1 Hz, 1H), 4.15-4.16 (m, 1H), 6.53-6.74 (m, 1H), 7.18-7.22 (m, 1H), 7.23-7.27 (m, 2H), 7.30-7.36 (m, 1H), 7.39-7.47 (m, 1H), 8.06-8.20 (m, 1H).

LC-MS (METCR1410): 89% (UV), Rt=1.04-1.20 min (multiple peaks), m/z (ESI$^+$)=341.0/343.0 [M+H]$^+$

N-[2-(3-Chlorophenyl)propan-2-yl]-3-(N-cyclohexylformamido)-2-hydroxybutanamide (I-150)

The title compound was synthesized from N-[2-(3-chlorophenyl)propan-2-yl]-3-(cyclohexylamino)-2-hydroxybutanamide (I-74) in a similar manner to method C, general procedure 3 (general scheme 4) as a colourless viscous oil (150 mg, 70% purity by $^1$H NMR, 61%) used in the next step without further purification.

$^1$H NMR (500 MHz, Chloroform-d) δ 1.23-1.28 (m, 3H), 1.58-1.64 (m, 2H), 1.65-1.74 (m, 10H), 1.74-1.88 (m, 5H), 3.33 (tt, J=4.0, 11.9 Hz, 1H), 3.93-3.98 (m, 1H), 4.14-4.16 (m, 1H), 6.74 (s, 1H), 7.16-7.21 (m, 1H), 7.23-7.25 (m, 1H), 7.33-7.37 (m, 1H), 7.41-7.47 (m, 1H), 8.06-8.24 (m, 1H).

LC-MS (METCR1410): 71% (UV), Rt=0.94 min (broad peak), m/z (ESI$^+$)=381.2/383.2 [M+H]$^+$

N-tert-Butyl-2-hydroxy-3-[N-(2-methoxyphenyl)formamido]butanamide (I-151)

The title compound was synthesized from N-tert-butyl-2-hydroxy-3-[(2-methoxyphenyl)amino]butanamide (I-75) in a similar manner to method C, general procedure 3 (general scheme 4) as a beige crystalline solid (117 mg, 98% purity by $^1$H NMR, 58%) after purification by flash column chromatography on normal phase silica (10 g SNAP KP-SIL cartridge, 0-50% EtOAc in heptane gradient).

$^1$H NMR (250 MHz, Chloroform-d) δ 1.32 (d, J=7.2 Hz, 3H), 1.36 (s, 9H), 3.84-3.93 (m, 3H), 4.04-4.19 (m, 1H), 4.48-4.61 (m, 1H), 6.21-6.36 (m, 1H), 6.89-7.01 (m, 3H), 7.13-7.20 (m, 1H), 7.28-7.38 (m, 1H), 8.03-8.46 (m, 1H).

2-Hydroxy-3-[N-(2-methoxyphenyl)formamido]-N-(propan-2-yl)butanamide (I-152)

The title compound was synthesized from 2-hydroxy-3-[(2-methoxyphenyl)-amino]-N-(propan-2-yl)butanamide (I-76) in a similar manner to method C, general procedure 3 (general scheme 4) as a colourless viscous oil (217 mg, 88% purity, 82%) used in the next step without further purification.

$^1$H NMR (500 MHz, Chloroform-d) δ 1.12-1.21 (m, 6H), 1.31 (d, J=7.2 Hz, 3H), 3.86-3.90 (m, 3H), 4.01-4.10 (m, 1H), 4.10-4.15 (m, 1H), 4.62 (s, 1H), 6.26 (s, 1H), 6.86-6.94 (m, 1H), 6.94-7.00 (m, 2H), 7.15 (dd, J=1.6, 7.6 Hz, 1H), 7.31-7.38 (m, 1H), 8.03-9.12 (m, 1H).

LC-MS (METCR1278): 88% (UV), Rt=1.40-1.75 min (multiple peaks), m/z (ESI$^+$)=295.0 [M+H]$^+$

3-[N-(2,2-Dimethylpropyl)formamido]-2-hydroxy-N-(propan-2-yl)butanamide (I-153)

The title compound was synthesized from 3-[(2,2-dimethylpropyl)amino]-2-hydroxy-N-(propan-2-yl)butanamide (I-77) in a similar manner to method C, general procedure 3 (general scheme 4) as an off-white solid (217 mg, 79% purity, 93%) used in the next step without further purification.

$^1$H NMR (500 MHz, Chloroform-d) δ 0.89-1.01 (m, 9H), 1.15-1.18 (m, 6H), 1.19-1.29 (m, 3H), 2.98 (d, J=14.5 Hz, 1H), 3.20 (d, J=14.6 Hz, 1H), 3.89 (m, 1H), 4.02-4.11 (m, 1H), 4.21-4.39 (m, 1H), 6.59 (s, 1H), 6.79-6.94 (m, 1H), 7.92-8.34 (m, 1H).

LC-MS (METCR1278): 79% (UV), Rt=1.50-1.80 min (multiple peaks), m/z (ESI$^+$)=259.1 [M+H]$^+$

N-[4-(7-Chloro-1,2,3,4-tetrahydroisoquinolin-2-yl)-3-hydroxy-4-oxobutan-2-yl]-N-(2-methoxyphenyl)formamide (I-154)

The title compound was synthesized from 1-(7-chloro-1,2,3,4-tetra-hydroiso-quinolin-2-yl)-2-hydroxy-3-[(2-methoxyphenyl)amino]butan-1-one (I-78) in a similar manner to method C, general procedure 3 (general scheme 4) as a red viscous oil (50 mg, 70% purity by 1H NMR, 38%) after purification by flash column chromatography on normal phase silica (10 g SNAP KP-SIL cartridge, 0-50% EtOAc in heptane gradient).

$^1$H NMR (250 MHz, Chloroform-d) δ 0.80-0.88 (m, 3H), 2.81-2.96 (m, 1H), 3.01 (q, J=5.5 Hz, 1H), 3.81 (d, J=2.9 Hz, 3H), 3.83-4.33 (m, 4H), 4.75 (d, J=4.4 Hz, 1H), 4.89-5.32 (m, 2H), 6.88-7.02 (m, 2H), 7.05-7.23 (m, 3H), 7.30-7.39 (m, 1H), 7.60 (d, J=7.6 Hz, 1H), 8.01-8.13 (m, 1H).

LC-MS (METCR1278): 92% (UV), Rt=1.90-2.10 min (multiple peaks), m/z (ESI$^+$)=403.0/405.0 [M+H]$^+$

N-(Cyclopropylmethyl)-2-hydroxy-4-methyl-3-[N-(2-methylpropyl)-formamido]pentanamide (I-155)

The title compound was synthesized from N-(cyclopropylmethyl)-2-hydroxy-4-methyl-3-[(2-methylpropyl)amino]pentanamide (I-80) in a similar manner to method C, general procedure 3 (general scheme 4) as a colourless glass (95 mg, 80% purity by 1H NMR, 42%) after purification by flash column chromatography on normal phase silica (10 g SNAP KP-SIL cartridge, 0-100% TBME in heptane gradient).

$^1$H NMR (500 MHz, Chloroform-d) δ 0.15-0.24 (m, 2H), 0.44-0.53 (m, 2H), 0.84-0.98 (m, 13H), 1.94-2.15 (m, 1H), 2.25-2.63 (m, 1H), 3.02-3.30 (m, 4H), 3.57 (d, J=10.9 Hz, 1H), 4.21-4.25 (m, 1H), 6.02-6.27 (m, 1H), 6.59-7.13 (m, 1H), 7.96-8.35 (m, 1H).

LC-MS (METCR1410): 88% (UV), Rt=1.18 min, m/z (ESI$^+$)=285.1 [M+H]$^+$

N-(Cyclopropylmethyl)-3-[N-(2,2-dimethylpropyl)formamido]-2-hydroxy-4-methylpentanamide (I-156)

The title compound was synthesized from N-(cyclopropylmethyl)-3-[(2,2-dimethylpropyl)amino]-2-hydroxy-4-methylpentanamide (I-81) in a similar manner to method C, general procedure 3 (general scheme 4) as a colourless viscous oil (95 mg, 75% purity by $^1$H NMR, 42%) after purification by flash column chromatography on normal phase silica (10 g SNAP KP-SIL cartridge, 0-100% TBME in heptane gradient).

$^1$H NMR (500 MHz, Chloroform-d) δ 0.17-0.20 (m, 2H), 0.46-0.50 (m, 2H), 0.86-0.94 (m, 6H), 0.97-0.98 (m, 10H), 2.46-2.55 (m, 1H), 2.94 (d, J=14.5 Hz, 1H), 3.01-3.08 (m, 1H), 3.13-3.20 (m, 1H), 3.30-3.34 (m, 1H), 3.63-3.67 (m, 1H), 4.42-4.46 (m, 1H), 6.41 (s, 1H), 7.04-7.17 (m, 1H), 8.00-8.42 (m, 1H).

LC-MS (METCR1410): 88% (UV), Rt=1.24 min, m/z (ESI$^+$)=299.0 [M+H]$^+$

N-(Cyclopropylmethyl)-2-hydroxy-4-methyl-3-{N-[(oxan-4-yl)methyl]formamido}pentanamide (I-157)

The title compound was synthesized from N-(cyclopropylmethyl)-2-hydroxy-4-methyl-3-{[(oxan-4-yl)methyl]amino}pentanamide (I-85) in a similar manner to method C, general procedure 3 (general scheme 4) as a colourless viscous oil (108 mg, 81% purity by $^1$H NMR, 38%) after purification by flash column chromatography on normal phase silica (10 g SNAP KP-SIL cartridge, 0-100% TBME in heptane gradient).

$^1$H NMR (500 MHz, Chloroform-d) δ 0.15-0.25 (m, 2H), 0.43-0.55 (m, 2H), 0.84-0.98 (m, 7H), 1.13-1.42 (m, 2H), 1.51-1.69 (m, 1H), 1.81-2.09 (m, 2H), 2.22-2.62 (m, 1H), 3.00-3.27 (m, 3H), 3.28-3.45 (m, 3H), 3.56 (t, J=10.5 Hz, 1H), 3.88-4.01 (m, 2H), 4.15-4.21 (m, 1H), 5.94-6.44 (m, 1H), 7.02-7.27 (m, 1H), 7.95-8.31 (m, 1H).

LC-MS (METCR1410): 26% (UV), Rt=1.00 min, m/z (ESI$^+$)=327.1 [M+H]$^+$

N-[(3-Chlorophenyl)methyl]-2-hydroxy-3-[N-(2-methoxyphenyl)formamido]-4-methylpentanamide (I-158)

The title compound was synthesized from N-[(3-chlorophenyl)methyl]-2-hydroxy-3-[(2-methoxyphenyl)amino]-4-methylpentanamide (I-82) in a similar manner to method C, general procedure 3 (general scheme 4) as a brown free-flowing oil (276 mg, 90% purity by 1H NMR, 53%) after purification by flash column chromatography on normal phase silica (50 g SNAP Ultra cartridge, 10-73% EtOAc in heptane gradient).

$^1$H NMR (500 MHz, Chloroform-d) δ 0.84 (d, J=6.7 Hz, 3H), 0.98 (d, J=6.7 Hz, 3H), 2.64-2.76 (m, 1H), 3.86 (s, 3H), 3.97 (d, J=10.5 Hz, 1H), 4.37-4.50 (m, 2H), 4.84 (s, 1H), 5.95 (s, 1H), 6.94-7.02 (m, 2H), 7.15-7.21 (m, 1H), 7.21-7.33 (m, 5H), 7.38 (t, J=4.8 Hz, 1H), 8.20 (s, 1H).

LC-MS (METCR1410): 99% (UV), Rt=1.08-1.28 min (multiple peaks), m/z (ESI$^+$)=405.1/407.1 [M+H]$^+$

3-(N-Cyclohexylformamido)-2-hydroxy-N-(propan-2-yl)butanamide (I-159)

The title compound was synthesized from 3-(cyclohexylamino)-2-hydroxy-N-(propan-2-yl)butanamide (I-84) in a similar manner to method C, general procedure 3 (general scheme 4) as a brown free-flowing oil (303 mg, 85% purity by $^1$H NMR, 73%) used in the next step without further purification.

$^1$H NMR (500 MHz, Chloroform-d) δ 1.16-1.19 (m, 6H), 1.22 (d, J=7.2 Hz, 3H), 1.27-1.36 (m, 2H), 1.50-1.63 (m, 2H), 1.63-1.69 (m, 1H), 1.70-1.78 (m, 2H), 1.79-1.89 (m, 3H), 3.31-3.40 (m, 1H), 3.97-4.08 (m, 2H), 4.15-4.19 (m, 1H), 6.55 (s, 1H), 6.80-6.91 (m, 1H), 8.08 (s, 1H).

LC-MS (METCR1278): 100% (UV), Rt=1.55-1.80 min (multiple peaks), m/z (ESI$^+$)=271.1 [M+H]$^+$

3-(N-Benzylformamido)-N-(cyclopropylmethyl)-2-hydroxybutanamide (I-160)

The title compound was synthesized from 3-(benzylamino)-N-(cyclopropyl-methyl)-2-hydroxybutanamide (I-86) in a similar manner to method C, general procedure 3 (general scheme 4) as an off-white solid (355 mg, 88% purity, 77%) used in the next step without further purification.

$^1$H NMR (500 MHz, Chloroform-d) δ 0.13-0.24 (m, 2H), 0.43-0.55 (m, 2H), 0.88-0.97 (m, 1H), 1.08 (d, J=7.1 Hz, 3H), 3.02-3.15 (m, 2H), 3.90 (q, J=7.1 Hz, 1H), 4.25 (s, 1H), 4.40-4.52 (m, 2H), 6.25 (s, 1H), 7.01-7.14 (m, 1H), 7.27-7.41 (m, 5H), 8.27 (s, 1H).

LC-MS (METCR1410): 88% (UV), Rt=0.88-1.00 min (two peaks), m/z (ESI$^+$)=291.1 [M+H]$^+$

3-[N-(Cyclohexylmethyl)formamido]-N-(cyclopropylmethyl)-2-hydroxybutanamide (I-161)

The title compound was synthesized from 3-[(cyclohexylmethyl)amino]-N-(cyclopropylmethyl)-2-hydroxybutanamide (I-87) in a similar manner to method C, general procedure 3 (general scheme 4) as an off-white solid (298 mg, 92% purity, 88%) used in the next step without further purification.

$^1$H NMR (500 MHz, Chloroform-d) δ 0.15-0.28 (m, 2H), 0.45-0.58 (m, 2H), 0.80-0.92 (m, 2H), 0.92-1.01 (m, 1H), 1.10-1.32 (m, 6H), 1.60-1.78 (m, 6H), 3.01-3.20 (m, 4H), 3.84 (q, J=7.1 Hz, 1H), 4.30 (s, 1H), 6.51 (s, 1H), 7.07-7.22 (m, 1H), 7.92 (s, 1H).

LC-MS (METCR1410): 92% (UV), Rt=0.96-1.12 min (multiple peaks), m/z (ESI$^+$)=297.1 [M+H]$^+$ tert-Butyl 4-[(N-{1-[(cyclopropylmethyl)carbamoyl]-1-hydroxypropan-2-yl}formamido)-methyl]piperidine-1-carboxylate (I-162)

The title compound was synthesized from tert-butyl 4-[({1-[(cyclopropyl-methyl)carbamoyl]-1-hydroxypropan-2-yl}amino)methyl]piperidine-1-carboxylate (I-88) in a similar manner to method C, general procedure 3 (general scheme 4) as a yellow viscous oil (1.02 g, 86% purity, 95%) used in the next step without further purification.

$^1$H NMR (500 MHz, Chloroform-d) δ 0.15-0.24 (m, 2H), 0.47-0.55 (m, 2H), 0.88-1.00 (m, 1H), 1.01-1.16 (m, 2H), 1.22-1.25 (m, 3H), 1.41-1.47 (m, 9H), 1.54-1.73 (m, 2H), 1.79-1.89 (m, 1H), 2.61-2.76 (m, 2H), 3.06-3.21 (m, 4H), 3.86 (q, J=7.1 Hz, 1H), 4.00-4.21 (m, 2H), 4.28 (s, 1H), 6.24-6.41 (m, 1H), 6.98-7.20 (m, 1H), 7.90-7.95 (m, 1H).

LC-MS (METCR1410): 86% (UV), Rt=0.98-1.08 min (multiple peaks), m/z (ESI⁺)=420.2 [M+Na]⁺

3-(N-Cyclohexylformamido)-N-(cyclopropylmethyl)-2-hydroxybutanamide (I-163)

The title compound was synthesized from 3-(cyclohexylamino)-N-(cyclo-propylmethyl)-2-hydroxybutanamide (I-89) in a similar manner to method C, general procedure 3 (general scheme 4) as a brown free-flowing oil (262 mg, 80% purity by $^1$H NMR, 99%) used in the next step without further purification.
$^1$H NMR (500 MHz, Chloroform-d) δ 0.15-0.27 (m, 2H), 0.44-0.58 (m, 2H), 0.88-1.03 (m, 1H), 1.08-1.45 (m, 6H), 1.49-1.92 (m, 6H), 3.05-3.42 (m, 3H), 3.71-3.87 (m, 1H), 3.97-4.17 (m, 1H), 4.19-4.71 (m, 1H), 6.25-6.71 (m, 1H), 7.01-7.24 (m, 1H), 8.00-8.15 (m, 1H).
LC-MS (METCR1410): 96% (UV), Rt=0.96-1.08 min (multiple peaks), m/z (ESI⁺)=283.2 [M+H]⁺

N-(Cyclopropylmethyl)-3-[N-(2,2-dimethylpropyl)formamido]-2-hydroxybutanamide (I-164)

The title compound was synthesized from N-(cyclopropylmethyl)-3-[(2,2-dimethylpropyl)amino]-2-hydroxybutanamide (I-90) in a similar manner to method C, general procedure 3 (general scheme 4) as a brown free-flowing oil (203 mg, 95% purity by 1H NMR, 91%) used in the next step without further purification.
$^1$H NMR (500 MHz, Chloroform-d) δ 0.14-0.28 (m, 2H), 0.43-0.59 (m, 2H), 0.89-1.05 (m, 10H), 1.23 (d, J=7.1 Hz, 3H), 2.99 (d, J=14.5 Hz, 1H), 3.11-3.16 (m, 2H), 3.20 (d, J=14.6 Hz, 1H), 3.91 (q, J=7.1 Hz, 1H), 4.42 (s, 1H), 6.47-6.70 (m, 1H), 7.07-7.22 (m, 1H), 7.96 (s, 1H).
LC-MS (METCR1410): 92% (UV), Rt=0.92-1.08 min (two peaks), m/z (ESI⁺)=271.2 [M+H]⁺

3-(N-Cyclohexylformamido)-N-cyclopropyl-2-hydroxybutanamide (I-165)

The title compound was synthesized from 3-(cyclohexylamino)-N-cyclopropyl-2-hydroxybutanamide (I-91) in a similar manner to method C, general procedure 3 (general scheme 4) as a colourless viscous oil (178 mg, 85% purity by $^1$H NMR, 81%) used in the next step without further purification.
$^1$H NMR (500 MHz, Chloroform-d) δ 0.48-0.58 (m, 2H), 0.74-0.83 (m, 2H), 1.11-1.19 (m, 1H), 1.21 (d, J=7.1 Hz, 3H), 1.28-1.36 (m, 2H), 1.51-1.57 (m, 1H), 1.63-1.70 (m, 1H), 1.72-1.78 (m, 2H), 1.79-1.89 (m, 3H), 2.69-2.77 (m, 1H), 3.30-3.40 (m, 1H), 4.02 (q, J=7.3 Hz, 1H), 4.18 (s, 1H), 6.50 (s, 1H), 7.03 (br. s, 1H), 8.07 (s, 1H).
LC-MS (METCR1410): 81% (UV), Rt=0.84-1.00 min (two peaks), m/z (ESI⁺)=269.1 [M+H]⁺

3-[N-(Cyclohexylmethyl)formamido]-N-cyclopropyl-2-hydroxybutanamide (I-166)

The title compound was synthesized from 3-[(cyclohexylmethyl)amino]-N-cyclopropyl-2-hydroxybutanamide (I-92) in a similar manner to method C, general procedure 3 (general scheme 4) as a colourless viscous oil (195 mg, 90% purity by $^1$H NMR, 89%) used in the next step without further purification.
$^1$H NMR (500 MHz, Chloroform-d) δ 0.48-0.57 (m, 2H), 0.76-0.81 (m, 2H), 0.83-0.93 (m, 2H), 1.13-1.31 (m, 7H), 1.63-1.78 (m, 5H), 2.70-2.77 (m, 1H), 3.01-3.07 (m, 1H), 3.09-3.14 (m, 1H), 3.83 (q, J=7.1 Hz, 1H), 4.26 (s, 1H), 6.46 (s, 1H), 7.04 (br. s, 1H), 7.91 (s, 1H).
LC-MS (METCR1410): 60% (UV), Rt=0.92-1.04 min (two peaks), m/z (ESI⁺)=283.1 [M+H]⁺

3-(N-Benzylformamido)-N-cyclopropyl-2-hydroxybutanamide (I-167)

The title compound was synthesized from 3-(benzylamino)-N-cyclopropyl-2-hydroxybutanamide (I-93) in a similar manner to method C, general procedure 3 (general scheme 4) as a colourless viscous oil (192 mg, 93% purity, 93%) used in the next step without further purification.
$^1$H NMR (500 MHz, Chloroform-d) δ 0.40-0.56 (m, 2H), 0.68-0.81 (m, 2H), 0.99-1.47 (m, 4H), 2.61-2.74 (m, 1H), 3.84-4.51 (m, 4H), 6.78-7.07 (m, 1H), 7.21-7.41 (m, 5H), 8.23-8.39 (m, 1H).
LC-MS (METCR1410): 93% (UV), Rt=0.80-0.96 min (multiple peaks), m/z (ESI⁺)=277.1 [M+H]⁺

3-[N-(2,2-Dimethylpropyl)formamido]-2-hydroxy-N-(2-methylpropyl) butanamide (I-168)

The title compound was synthesized from 3-[(2,2-dimethylpropyl)amino]-2-hydroxy-N-(2-methylpropyl)butanamide (I-96) in a similar manner to method C, general procedure 3 (general scheme 4) as a yellow oil (242 mg, 35% purity by 1H NMR, 43%) used in the next step without further purification.
$^1$H NMR (500 MHz, Chloroform-d) δ 0.87-0.93 (m, 6H), 0.99 (s, 9H), 1.22 (d, J=7.1 Hz, 3H), 1.72-1.83 (m, 1H), 2.95-3.24 (m, 4H), 3.90 (q, J=7.1 Hz, 1H), 4.43 (s, 1H), 6.57 (s, 1H), 7.12-7.21 (m, 1H), 7.96 (s, 1H).

2-Hydroxy-N-(2-methylpropyl)-3-[N-(2,2,2-trifluoroethyl)formamido]butanamide (I-169)

The title compound was synthesized from 2-hydroxy-N-(2-methylpropyl)-3-[(2,2,2-trifluoroethyl)amino]butanamide (I-97) in a similar manner to method C, general procedure 3 (general scheme 4) as a colourless solid (197 mg, 100% purity, 99%) used in the next step without further purification.
$^1$H NMR (500 MHz, Chloroform-d) δ 0.89-0.96 (m, 6H), 1.28-1.37 (m, 3H), 1.74-1.84 (m, 1H), 3.03-3.11 (m, 1H), 3.12-3.22 (m, 1H), 3.72-3.94 (m, 2H), 4.00-4.09 (m, 1H), 4.35 (s, 1H), 5.62 (d, J=1.1 Hz, 1H), 6.80-7.07 (m, 1H), 8.08-8.46 (m, 1H).
LC-MS (METCR1410): 100% (UV), Rt=0.93 min, m/z (ESI⁺)=285.0 [M+H]⁺

3-(N-Benzylformamido)-2-hydroxy-N-(2-methylpropyl)butanamide (I-170)

The title compound was synthesized from 3-(benzylamino)-2-hydroxy-N-(2-methylpropyl)butanamide (I-98) in a similar manner to method C, general procedure 3 (general scheme 4) as a colourless viscous oil (159 mg, 90% purity by 1H NMR, 98%) used in the next step without further purification.
$^1$H NMR (500 MHz, Chloroform-d) δ 0.85-0.93 (m, 6H), 1.05-1.22 (m, 3H), 1.69-1.79 (m, 1H), 2.94-3.03 (m, 1H), 3.07-3.17 (m, 1H), 3.86-4.52 (m, 4H), 5.83-6.39 (m, 1H), 6.80-7.11 (m, 1H), 7.27-7.30 (m, 2H), 7.31-7.41 (m, 3H), 8.24-8.42 (m, 1H).

N-(Cyclohexylmethyl)-2-hydroxy-3-[N-(propan-2-yl)formamido]butanamide (I-171)

The title compound was synthesized from N-(cyclohexylmethyl)-2-hydroxy-3-[(propan-2-yl)amino]butanamide (I-99) in a similar manner to method C, general procedure 3 (general scheme 4) as a colourless viscous oil (400 mg, 50% purity by $^1$H NMR, 43%) used in the next step without further purification.

$^1$H NMR (250 MHz, Chloroform-d) δ 0.79-1.02 (m, 2H), 1.03-1.57 (m, 14H), 1.58-1.79 (m, 4H), 2.92-3.23 (m, 3H), 3.64-4.05 (m, 2H), 4.21 (s, 1H), 6.92-7.23 (m, 1H), 8.04-8.13 (m, 1H).

LC-MS (METCR1410): 100% (UV), Rt=0.96-1.12 min (multiple peaks), m/z (ESI$^+$)=285.2 [M+H]$^+$

N-(Cyclohexylmethyl)-2-hydroxy-3-{N-[(oxan-4-yl)methyl]formamido}butanamide (I-172)

The title compound was synthesized from N-(cyclohexylmethyl)-2-hydroxy-3-{[(oxan-4-yl)methyl]amino}butanamide (I-100) in a similar manner to method C, general procedure 3 (general scheme 4) as a colourless viscous oil (400 mg, 87% purity, 64%) used in the next step without further purification.

$^1$H NMR (500 MHz, Chloroform-d) δ 0.79-1.03 (m, 2H), 1.07-1.35 (m, 9H), 1.37-1.54 (m, 1H), 1.55-1.78 (m, 7H), 1.86-2.01 (m, 1H), 3.03-3.24 (m, 4H), 3.39 (td, J=2.0, 11.8 Hz, 2H), 3.87 (q, J=7.1 Hz, 1H), 3.99 (dd, J=4.2, 11.5 Hz, 2H), 4.28 (s, 1H), 6.98-7.16 (m, 1H), 7.80-8.01 (m, 1H).

LC-MS (METCR1410): 87% (UV), Rt=0.96-1.08 min (multiple peaks), m/z (ESI$^+$)=341.2 [M+H]$^+$

N-(Cyclohexylmethyl)-2-hydroxy-3-[N-(2,2,2-trifluoroethyl)formamido]butanamide (I-173)

The title compound was synthesized from N-(cyclohexylmethyl)-2-hydroxy-3-[(2,2,2-trifluoroethyl)amino]butanamide (I-101) in a similar manner to method C, general procedure 3 (general scheme 4) as a colourless viscous oil (250 mg, 67% purity, 68%) used in the next step without further purification.

LC-MS (METCR1410): 67% (UV), Rt=1.02 min, m/z (ESI$^+$)=325.4 [M+H]$^+$

N-(Cyclohexylmethyl)-3-[N-(cyclopropylmethyl)formamido]-2-hydroxybutanamide (I-174)

The title compound was synthesized from N-(cyclohexylmethyl)-3-[(cyclopropylmethyl)amino]-2-hydroxybutanamide (I-102) in a similar manner to method C, general procedure 3 (general scheme 4) as a colourless viscous oil (194 mg, 100% purity, 98%) used in the next step without further purification.

$^1$H NMR (250 MHz, Chloroform-d) δ 0.20-0.35 (m, 2H), 0.57-0.72 (m, 2H), 0.84-1.02 (m, 2H), 1.02-1.23 (m, 4H), 1.28 (d, J=7.2 Hz, 3H), 1.38-1.55 (m, 1H), 1.65-1.79 (m, 5H), 3.04-3.23 (m, 4H), 4.01 (q, J=7.2 Hz, 1H), 4.37 (s, 1H), 6.43 (s, 1H), 7.01-7.18 (m, 1H), 8.00 (s, 1H).

LC-MS (METCR1410): 100% (UV), Rt=1.00-1.12 min (multiple peaks), m/z (ESI$^+$)=297.1 [M+H]$^+$

3-(N-Cyclohexylformamido)-N-(cyclohexylmethyl)-2-hydroxybutanamide (I-175)

The title compound was synthesized from 3-(cyclohexylamino)-N-(cyclohexyl-methyl)-2-hydroxybutanamide (I-103) in a similar manner to method C, general procedure 3 (general scheme 4) as a colourless viscous oil (194 mg, 82% purity by $^1$H NMR, 82%) used in the next step without further purification.

$^1$H NMR (250 MHz, Chloroform-d) δ 0.81-1.03 (m, 2H), 1.08-1.43 (m, 9H), 1.44-1.95 (m, 13H), 2.98-3.23 (m, 2H), 3.27-3.43 (m, 1H), 4.02 (q, J=7.1 Hz, 1H), 4.21 (s, 1H), 6.55 (s, 1H), 6.95-7.18 (m, 1H), 8.04-8.25 (m, 1H).

LC-MS (METCR1410): 100% (UV), Rt=1.04-1.24 min (multiple peaks), m/z (ESI$^+$)=325.2 [M+H]$^+$ tert-Butyl 4-[(N-{1-[(cyclohexylmethyl)carbamoyl]-1-hydroxypropan-2-yl}formamido)-methyl]piperidine-1-carboxylate (I-176)

The title compound was synthesized from tert-butyl 4-[({1-[(cyclohexyl-methyl)-carbamoyl]-1-hydroxypropan-2-yl}amino)methyl]piperidine-1-carboxylate (I-104) in a similar manner to method C, general procedure 3 (general scheme 4) as a colourless viscous oil (250 mg, 90% purity by 1H NMR, 35%) used in the next step without further purification.

$^1$H NMR (500 MHz, Chloroform-d) δ 0.79-0.92 (m, 2H), 0.95-1.11 (m, 3H), 1.12-1.20 (m, 5H), 1.34-1.44 (m, 11H), 1.56-1.68 (m, 7H), 1.73-1.82 (m, 1H), 2.62 (q, J=11.6, 12.2 Hz, 2H), 2.96-3.16 (m, 4H), 4.00-4.12 (m, 3H), 7.00-7.05 (m, 1H), 7.84-7.88 (m, 1H).

LC-MS (METCR1410): 84% (UV), Rt=1.10-1.24 min, m/z (ESI$^+$)=384.6 [M+H-$^t$Bu]$^+$ tert-Butyl N-[(1S,4S)-4-(N-{1-[(cyclohexylmethyl)carbamoyl]-1-hydroxypropan-2-yl}formamido)cyclohexyl]carbamate (I-177)

The title compound was synthesized from tert-butyl N-[(1S,4S)-4-({1-[(cyclo-hexylmethyl)carbamoyl]-1-hydroxypropan-2-yl}amino)cyclohexyl]carbamate (I-105) in a similar manner to method C, general procedure 3 (general scheme 4) as an orange oil (593 mg, 79% purity by $^1$H NMR, 80%) used in the next step without further purification.

$^1$H NMR (250 MHz, Chloroform-d) δ 0.85-1.02 (m, 2H), 1.14-1.29 (m, 5H), 1.45 (s, 9H), 1.56-1.80 (m, 11H), 1.83-2.01 (m, 5H), 3.06-3.18 (m, 2H), 3.29-3.46 (m, 1H), 3.73-3.93 (m, 1H), 3.93-4.07 (m, 1H), 4.21 (s, 1H), 4.93-5.12 (m, 1H), 6.53 (s, 1H), 7.06-7.22 (m, 1H).

LC-MS (METCR1410): 95% (UV), Rt=1.14-1.28 min (multiple peaks), m/z (ESI$^+$)=384.3 [M+H-$^t$Bu]$^+$

3-(N-Cyclohexylformamido)-N-[2-(cyclohexyloxy)ethyl]-2-hydroxybutanamide (I-178)

The title compound was synthesized from 3-(cyclohexylamino)-N-[2-(cyclo-hexyloxy)ethyl]-2-hydroxybutanamide (I-106) in a similar manner to method C, general procedure 3 (general scheme 4) as a colourless gum (240 mg, 90% purity by $^1$H NMR, 81%) used in the next step without further purification.

$^1$H NMR (250 MHz, Chloroform-d) δ 0.99-1.47 (m, 12H), 1.50-1.94 (m, 13H), 3.14-3.32 (m, 1H), 3.32-3.60 (m, 5H), 3.93-4.18 (m, 1H), 7.32-7.42 (m, 1H), 8.02-8.30 (m, 1H).

LC-MS (METCR0990): 98% (UV), Rt=1.56-1.80 min (multiple peaks), m/z (ESI$^+$)=355.3 [M+H]$^+$

Methyl 2-[3-(N-benzylformamido)-2-hydroxybutanamido]acetate (I-179)

The title compound was synthesized from methyl 2-[3-(benzylamino)-2-hydroxybutanamido]acetate (I-107) in a similar manner to method C, general procedure 3 (general scheme 4) as a colourless viscous oil (417 mg, 77% purity, 85%) used in the next step without further purification.

LC-MS (METCR1410): 77% (UV), Rt=0.85-0.89 min, m/z (ESI$^+$)=309.1 [M+H]$^+$

3-(N-Benzylformamido)-2-hydroxy-N-(propan-2-yl)butanamide (I-180)

The title compound was synthesized from 3-(benzylamino)-2-hydroxy-N-(propan-2-yl)butanamide (I-108) in a similar manner to method C, general procedure 3 (general scheme 4) as an off-white solid (125 mg, 99% purity, 81%) used in the next step without further purification.

$^1$H NMR (250 MHz, Chloroform-d) δ 1.06 (d, J=7.1 Hz, 3H), 1.09-1.17 (m, 6H), 3.83-4.09 (m, 2H), 4.20 (s, 1H), 4.36-4.54 (m, 2H), 6.23 (s, 1H), 6.72-6.88 (m, 1H), 7.27-7.43 (m, 5H), 8.24-8.43 (m, 1H).

LC-MS (METCR1410): 99% (UV), Rt=0.88-1.00 min (multiple peaks), m/z (ESI$^+$)=279.1 [M+H]$^+$

N-(Cyclopropylmethyl)-2-hydroxy-3-{N-[(oxan-4-yl)methyl]formamido}hexanamide (I-181)

The title compound was synthesized from N-(cyclopropylmethyl)-2-hydroxy-3-{[(oxan-4-yl)methyl]amino}hexanamide (I-109) in a similar manner to method C, general procedure 3 (general scheme 4) as a colourless viscous oil (400 mg, 87% purity by 1H NMR, 92%) used in the next step without further purification.

$^1$H NMR (500 MHz, Chloroform-d) δ 0.18-0.26 (m, 2H), 0.48-0.55 (m, 2H), 0.88-1.00 (m, 4H), 1.16-1.39 (m, 4H), 1.41-1.65 (m, 4H), 1.74-1.90 (m, 1H), 1.91-2.01 (m, 1H), 2.84-3.24 (m, 4H), 3.28-3.51 (m, 3H), 3.69-3.82 (m, 1H), 3.92-4.01 (m, 2H), 7.13 (s, 1H), 7.93-8.26 (m, 1H).

LC-MS (METCR1410): 86% (UV), Rt=0.84-1.00 min (multiple peaks), m/z (ESI$^+$)=327.2 [M+H]$^+$ tert-Butyl 4-[(N-{1-[(cyclohexylmethyl)carbamoyl]-1-hydroxybutan-2-yl}formamido)-methyl]piperidine-1-carboxylate (I-182)

The title compound was synthesized from tert-butyl 4-[({1-[(cyclohexylmethyl) carbamoyl]-1-hydroxybutan-2-yl}amino)methyl]piperidine-1-carboxylate (I-110) in a similar manner to method C, general procedure 3 (general scheme 4) as a yellow viscous oil (580 mg, 97% purity, 88%) used in the next step without further purification.

$^1$H NMR (500 MHz, Chloroform-d) δ 0.82-1.28 (m, 10H), 1.37-1.50 (m, 10H), 1.51-1.80 (m, 8H), 1.79-1.96 (m, 1H), 1.94-2.08 (m, 1H), 2.52-2.94 (m, 2H), 3.01-3.26 (m, 4H), 3.41-3.78 (m, 1H), 3.99-4.21 (m, 2H), 4.19-4.28 (m, 1H), 6.11-7.14 (m, 1H), 7.85-8.25 (m, 1H).

LC-MS (METCR1410): 97% (UV), Rt=1.20-1.29 min (multiple peaks), m/z (ESI$^+$)=398.2 [M+H-$^t$Bu]$^+$

3-(N-cyclohexylformamido)-N-(cyclohexylmethyl)-2-hydroxypentanamide (I-183)

The title compound was synthesized from 3-(cyclohexylamino)-N-(cyclohexyl-methyl)-2-hydroxypentanamide (I-111) in a similar manner to method C, general procedure 3 (general scheme 4) as a yellow viscous oil (460 mg, 88% purity, 98%) used in the next step without further purification.

$^1$H NMR (500 MHz, Chloroform-d) δ 0.75-1.03 (m, 4H), 1.06-1.55 (m, 11H), 1.54-1.99 (m, 13H), 3.01-3.35 (m, 2H), 3.71-3.92 (m, 1H), 4.18-4.33 (m, 1H), 6.12-7.13 (m, 1H), 8.05-8.26 (m, 1H).

LC-MS (METCR1410): 88% (UV), Rt=1.13-1.24 min (multiple peaks), m/z (ESI$^+$)=339.2 [M+H]$^+$ tert-Butyl 3-[(N-{1-[(cyclohexylmethyl)carbamoyl]-1-hydroxybutan-2-yl}formamido)-methyl]azetidine-1-carboxylate (I-184)

The title compound was synthesized from tert-butyl 3-[({1-[(cyclohexylmethyl)-carbamoyl]-1-hydroxybutan-2-yl}amino)methyl]azetidine-1-carboxylate (I-112) in a similar manner to method C, general procedure 3 (general scheme 4) as an orange gum (475 mg, 60% purity, 53%) used in the next step without further purification.

$^1$H NMR (250 MHz, Chloroform-d) δ 0.75-1.07 (m, 6H), 1.05-1.35 (m, 5H), 1.43 (d, J=2.8 Hz, 11H), 1.61-1.81 (m, 6H), 2.91-3.21 (m, 1H), 3.30-3.81 (m, 4H), 3.78-4.42 (m, 4H), 6.47-7.09 (m, 1H), 8.00-8.29 (m, 1H).

LC-MS (METCR1410): 60% (UV), Rt=1.11 min, m/z (ESI$^+$)=426.3 [M+H]$^+$

N-(Cyclopropylmethyl)-3-[N-(cyclopropylmethyl)formamido]-2-hydroxy-5-methylhexanamide (I-185)

The title compound was synthesized from N-(cyclopropylmethyl)-3-[(cyclo-propylmethyl)amino]-2-hydroxy-5-methylhexanamide (I-113) in a similar manner to method C, general procedure 3 (general scheme 4) as a colourless viscous oil (252 mg, 96% purity, 91%) used in the next step without further purification.

$^1$H NMR (500 MHz, Chloroform-d) δ 0.21 (dq, J=4.7, 10.7 Hz, 3H), 0.26-0.41 (m, 1H), 0.44-0.76 (m, 4H), 0.82-1.03 (m, 7H), 1.02-1.20 (m, 1H), 1.31-1.44 (m, 1H), 1.46-1.68 (m, 1H), 1.78-2.01 (m, 1H), 2.95-3.45 (m, 4H), 4.00 (td, J=3.9, 10.3, 10.7 Hz, 1H), 4.28-4.48 (m, 1H), 6.98-7.18 (m, 1H), 7.96-8.33 (m, 1H).

LC-MS (METCR1410): 96% (UV), Rt=1.00-1.12 min (multiple peaks), m/z (ESI$^+$)=297.6 [M+H]$^+$

N-(Cyclopropylmethyl)-2-hydroxy-5-methyl-3-{N-[(oxan-4-yl)methyl]formamido}hexanamide (I-186)

The title compound was synthesized from N-(cyclopropylmethyl)-2-hydroxy-5-methyl-3-{[(oxan-4-yl)methyl]amino}hexanamide (I-114) in a similar manner to method C, general procedure 3 (general scheme 4) as a colourless viscous oil (400 mg, 77% purity, quantitative) used in the next step without further purification.

LC-MS (METCR1410): 76% (UV), Rt=0.96-1.04 min (multiple peaks), m/z (ESI$^+$)=341.2 [M+H]$^+$

N-(Cyclopropylmethyl)-2-hydroxy-5-methyl-3-(N{[(3S)-oxolan-3-yl]methyl}formamido)-hexanamide (I-187)

The title compound was synthesized from N-(cyclopropylmethyl)-2-hydroxy-5-methyl-3-({[(3S)-oxolan-3-yl]methyl}amino)hexanamide (I-115) in a similar manner to method C, general procedure 3 (general scheme 4) as a colourless viscous oil (310 mg, 80% purity by 1H NMR, 80%) used in the next step without further purification.

$^1$H NMR (250 MHz, Chloroform-d) δ 0.13-0.29 (m, 2H), 0.43-0.58 (m, 2H), 0.81-1.01 (m, 7H), 1.35-1.62 (m, 2H), 1.76-1.94 (m, 1H), 1.97-2.23 (m, 1H), 2.65-2.95 (m, 1H), 3.02-3.98 (m, 10H), 4.18-4.29 (m, 1H), 6.06 (d, J=3.0 Hz, 1H), 7.03-7.18 (m, 1H), 7.99-8.26 (m, 1H).
LC-MS (METCR0990): 96% (UV), Rt=1.35-1.55 min (multiple peaks), m/z (ESI$^+$)=327.0 [M+H]$^+$

N-(Cyclopropylmethyl)-2-hydroxy-5-methyl-3-(N{[(3R)-oxolan-3-yl]methyl}formamido)-hexanamide (I-188)

The title compound was synthesized from N-(cyclopropylmethyl)-2-hydroxy-5-methyl-3-({[(3R)-oxolan-3-yl]methyl}amino)hexanamide (I-116) in a similar manner to method C, general procedure 3 (general scheme 4) as a colourless viscous oil (277 mg, 80% purity by 1H NMR, 72%) used in the next step without further purification.
$^1$H NMR (250 MHz, Chloroform-d) δ 0.14-0.27 (m, 2H), 0.43-0.57 (m, 2H), 0.79-1.03 (m, 7H), 1.35-1.61 (m, 2H), 1.75-1.95 (m, 1H), 1.96-2.18 (m, 1H), 2.60-2.85 (m, 1H), 3.01-3.99 (m, 10H), 4.17-4.29 (m, 1H), 6.07 (d, J=2.9 Hz, 1H), 7.02-7.17 (m, 1H), 8.02-8.25 (m, 1H).
LC-MS (METCR0990): 96% (UV), Rt=1.35-1.55 min (multiple peaks), m/z (ESI$^+$)=327.0 [M+H]$^+$

N-(Cyclopropylmethyl)-2-hydroxy-3-[N-(3-methoxypropyl)formamido]-5-methylhexanamide (I-189)

The title compound was synthesized from N-(cyclopropylmethyl)-2-hydroxy-3-[(3-methoxypropyl)amino]-5-methylhexanamide (I-117) in a similar manner to method C, general procedure 3 (general scheme 4) as a colourless viscous oil (269 mg, 85% purity by $^1$H NMR, 100%) used in the next step without further purification.
$^1$H NMR (500 MHz, Chloroform-d) δ 0.16-0.28 (m, 2H), 0.45-0.56 (m, 2H), 0.85-0.92 (m, 6H), 0.92-1.10 (m, 1H), 1.33-1.59 (m, 2H), 1.73-1.99 (m, 3H), 2.01-2.10 (m, 1H), 3.07-3.20 (m, 2H), 3.21-3.45 (m, 6H), 3.49-3.91 (m, 2H), 4.24-4.34 (m, 1H), 7.01-7.18 (m, 1H), 8.01-8.26 (m, 1H).
LC-MS (METCR1410): 96% (UV), Rt=0.90-1.10 min (multiple peaks), m/z (ESI$^+$)=315.2 [M+H]$^+$

N-(Cyclopropylmethyl)-2-hydroxy-5-methyl-3-{N-[(oxolan-3-yl)methyl]formamido}-hexanamide (I-190)

The title compound was synthesized from N-(cyclopropylmethyl)-2-hydroxy-5-methyl-3-{[(oxolan-3-yl)methyl]amino}hexanamide (I-118) in a similar manner to method C, general procedure 3 (general scheme 4) as a colourless viscous oil (237 mg, 98% purity by $^1$H NMR, quantitative) used in the next step without further purification.
$^1$H NMR (500 MHz, Chloroform-d) δ 0.17-0.27 (m, 2H), 0.46-0.57 (m, 2H), 0.86-0.93 (m, 6H), 0.93-1.01 (m, 1H), 1.37-1.46 (m, 1H), 1.47-1.58 (m, 1H), 1.82-1.92 (m, 1H), 2.00-2.19 (m, 1H), 2.66-2.84 (m, 1H), 3.07-3.86 (m, 8H), 3.87-3.96 (m, 2H), 4.18-4.29 (m, 1H), 6.07 (d, J=6.0 Hz, 1H), 7.03-7.14 (m, 1H), 8.04 (s, 1H).
LC-MS (METCR1410): 100% (UV), Rt=0.90-1.10 min (two peaks), m/z (ESI$^+$)=327.2 [M+H]$^+$

N-(Cyclopropylmethyl)-2-hydroxy-5-methyl-3-{N-[(oxolan-2-yl)methyl]formamido}-hexanamide (I-191)

The title compound was synthesized from N-(cyclopropylmethyl)-2-hydroxy-5-methyl-3-{[(oxolan-2-yl)methyl]amino}hexanamide (I-119) in a similar manner to method C, general procedure 3 (general scheme 4) as a pale yellow solid (176 mg, 99% purity, 93%) used in the next step without further purification.
$^1$H NMR (500 MHz, Chloroform-d) δ 0.14-0.26 (m, 2H), 0.44-0.56 (m, 2H), 0.80-1.02 (m, 7H), 1.07-1.57 (m, 4H), 1.61-2.31 (m, 4H), 2.89-3.46 (m, 3H), 3.53-4.42 (m, 5H), 5.42-6.19 (m, 1H), 7.10-7.26 (m, 1H), 8.01-8.30 (m, 1H).
LC-MS (METCR1410): 99% (UV), Rt=0.92-1.08 min (multiple peaks), m/z (ESI$^+$)=327.2 [M+H]$^+$

3-Cyclopropyl-N-(cyclopropylmethyl)-2-hydroxy-3-{N-[(oxan-4-yl)methyl]formamido}-propanamide (I-192)

The title compound was synthesized from 3-cyclopropyl-N-(cyclopropylmethyl)-2-hydroxy-3-{[(oxan-4-yl)methyl]amino}propanamide (I-120) in a similar manner to method C, general procedure 3 (general scheme 4) as a colourless viscous oil (321 mg, 95% purity by 1H NMR, 72%) used in the next step without further purification.
$^1$H NMR (500 MHz, Chloroform-d) δ 0.18-0.34 (m, 4H), 0.46-0.63 (m, 4H), 0.93-1.04 (m, 1H), 1.15-1.32 (m, 2H), 1.57-1.63 (m, 2H), 1.64-1.72 (m, 1H), 1.85-1.99 (m, 1H), 3.01-3.26 (m, 5H), 3.38 (tdd, J=2.0, 5.33, 11.6 Hz, 2H), 3.98 (dd, J=3.7, 11.6 Hz, 2H), 4.23-4.27 (m, 1H), 6.30-6.40 (m, 1H), 7.18-7.23 (m, 1H), 7.94-8.53 (m, 1H).
LC-MS (METCR1410): 97% (UV), Rt=0.84-0.92 min (two peaks), m/z (ESI$^+$)=325.5 [M+H]$^+$

3-(N-Benzylformamido)-3-cyclopropyl-N-(cyclopropylmethyl)-2-hydroxypropanamide (I-193)

The title compound was synthesized from 3-(benzylamino)-3-cyclopropyl-N-(cyclopropylmethyl)-2-hydroxypropanamide (I-121) in a similar manner to method C, general procedure 3 (general scheme 4) as a colourless viscous oil (273 mg, 95% purity by $^1$H NMR, 89%) used in the next step without further purification.
$^1$H NMR (500 MHz, Chloroform-d) δ −0.43-0.14 (m, 1H), 0.08-0.15 (m, 1H), 0.17-0.34 (m, 3H), 0.40-0.54 (m, 3H), 0.86-1.00 (m, 1H), 1.61-1.66 (m, 1H), 2.93-3.09 (m, 2H), 3.10-3.20 (m, 1H), 4.23 (m, 1H), 4.39-5.14 (m, 2H), 6.12-6.19 (m, 1H), 6.87-7.18 (m, 1H), 7.25-7.40 (m, 5H), 8.29-8.54 (m, 1H).
LC-MS (METCR1410): 99% (UV), Rt=0.96-1.08 min (multiple peaks), m/z (ESI$^+$)=317.5 [M+H]$^+$

N-(Cyclopropylmethyl)-2-hydroxy-3-{N-[(oxan-4-yl)methyl]formamido}-5-phenylpentanamide (I-194)

The title compound was synthesized from N-(cyclopropylmethyl)-2-hydroxy-3-{[(oxan-4-yl)methyl]amino}-5-phenylpentanamide (I-124) in a similar manner to method C, general procedure 3 (general scheme 4) as a yellow viscous oil (310 mg, 95% purity by $^1$H NMR, quantitative) used in the next step without further purification.
$^1$H NMR (500 MHz, Chloroform-d) δ 0.18-0.25 (m, 2H), 0.43-0.57 (m, 2H), 0.91-1.01 (m, 1H), 1.18-1.24 (m, 1H), 1.46-1.65 (m, 3H), 1.81-1.94 (m, 1H), 1.99-2.08 (m, 1H), 2.13-2.27 (m, 1H), 2.49-2.69 (m, 2H), 2.87-3.23 (m, 4H), 3.26-3.43 (m, 2H), 3.78-4.00 (m, 3H), 4.25-4.32 (m, 1H), 6.24 (m, 1H), 7.05-7.18 (m, 3H), 7.18-7.22 (m, 1H), 7.26-7.31 (m, 2H), 7.97-8.34 (m, 1H).
LC-MS (METCR1410): 99% (UV), Rt=0.96-1.12 min (multiple peaks), m/z (ESI$^+$)=389.3 [M+H]$^+$

N-[(3-Chlorophenyl)methyl]-2-hydroxy-3-(N-methylformamido)butanamide (I-195)

The title compound was synthesized from N-[(3-chlorophenyl)methyl]-2-hydroxy-3-(methylamino)butanamide (I-125) in a similar manner to method C, general procedure 3 (general scheme 4) as a colourless viscous oil (296 mg, 95% purity by $^1$H NMR, 93%) used in the next step without further purification.

$^1$H NMR (500 MHz, Chloroform-d) δ 1.22-1.32 (m, 3H), 2.88-3.07 (m, 3H), 3.98 (m, 1H), 4.37-4.51 (m, 3H), 6.12 (s, 1H), 7.10-7.19 (m, 1H), 7.21-7.30 (m, 3H), 7.36-7.49 (m, 1H), 7.98-8.19 (m, 1H).

LC-MS (METCR1278): 100% (UV), Rt=1.50-1.70 min (multiple peaks), m/z (ESI$^+$)=285.0/287.0 [M+H]$^+$

3-(N-Benzylformamido)-N-(cyclopropylmethyl)-2-hydroxy-5-methoxypentanamide (I-196)

The title compound was synthesized from 3-(benzylamino)-N-(cyclopropyl-methyl)-2-hydroxy-5-methoxypentanamide (I-122) in a similar manner to method C, general procedure 3 (general scheme 4) as a yellow viscous oil (153 mg) used in the next step without further purification.

3-(N-Benzylformamido)-N-(cyclopropylmethyl)-2-hydroxy-3-(oxan-4-yl)propanamide (I-197)

The title compound was synthesized from 3-(benzylamino)-N-(cyclopropyl-methyl)-2-hydroxy-3-(oxan-4-yl)propanamide (I-123) in a similar manner to method C, general procedure 3 (general scheme 4) as a colourless viscous oil (101 mg) used in the next step without further purification.

General Procedure 4 (General Scheme 4): Oxidation

Method A: Dess-Martin Oxidation

N-[(3-Chlorophenyl)methyl]-3-[N-(2-methoxyphenyl)formamido]-2-oxobutanamide (FP 1)

To a stirred solution of N-[(3-chlorophenyl)methyl]-2-hydroxy-3-[N-(2-methoxyphenyl)formamido]butanamide (I-126, 75% purity, 60 mg, 0.12 mmol) in DCM (1 mL) was added DMP (76 mg, 0.18 mmol). The reaction was stirred at RT for 1 h. The solution was washed with saturated NaHCO$_3$ (3 mL) and the aqueous layer extracted with DCM (2×5 mL). The combined organic layer was dried over sodium sulfate, filtered and concentrated in vacuo. The crude material was purified by preparative LC (acidic pH, standard elution method) to afford 11 mg of N-[(3-chloro-phenyl)methyl]-3-[N-(2-methoxyphenyl)formamido]-2-oxobutanamide as a yellow viscous oil (100% purity, 25%).

$^1$H NMR (500 MHz, Chloroform-d) δ 1.31-1.51 (m, 3H), 3.59-3.89 (m, 3H), 4.42-4.57 (m, 2H), 4.98-5.49 (m, 1H), 6.95-7.06 (m, 2H), 7.11-7.18 (m, 1H), 7.19 (dt, J=2.0, 6.6 Hz, 1H), 7.22-7.33 (m, 3H), 7.36 (ddd, J=1.7, 7.6, 8.2 Hz, 1H), 7.56 (dd, J=1.7, 7.8 Hz, 1H), 7.97-8.65 (m, 1H).

LC-MS (METCR1416): 100% (UV), Rt=4.17 min, m/z (ESI$^+$)=375.0/377.0 [M+H]$^+$

(3R)—N-[(3-chlorophenyl)methyl]-3-[N-(2-methoxyphenyl)formamido]-2-oxobutanamide and (3S)—N-[(3-chlorophenyl)methyl]-3-[N-(2-methoxyphenyl)formamido]-2-oxobutanamide (FP 2-3) ((R) and (S) assignments arbitrary)

N-[(3-Chlorophenyl)methyl]-3-[N-(2-methoxyphenyl)formamido]-2-oxobutanamide (FP 1, 96% purity, 140 mg, 0.36 mmol) was purified by chiral separation on SFC [Column: YMC Amylose-C (20 mm×250 mm, 5 μm) at 40° C.; Isocratic eluent: 30:70 MeOH/CO$_2$; Flow rate: 50 mL/min; Detector wavelength; 210 nm; Dilution solvent: MeOH; Injection volume: 500 μL]. The samples were redissolved in DCM (2 mL) and transferred to barcoded vials. The solvent was removed under a stream of air and the residues dried in vacuo at 40° C. to afford 32 mg of Enantiomer 1 (FP 2) as a yellow viscous oil (74% ee, 17%) and 30 mg of Enantiomer 2 (FP 3) as a yellow viscous oil (73% ee, 15%).

Enantiomer 1 (FP 2)

$^1$H NMR (500 MHz, Chloroform-d) δ 1.36 (d, J=7.0 Hz, 3H), 3.83 (s, 3H), 4.43-4.56 (m, 2H), 5.05 (q, J=7.0 Hz, 1H), 6.98 (dd, J=8.3, 1.1 Hz, 1H), 7.02 (td, J=7.6, 1.2 Hz, 1H), 7.12-7.17 (m, 1H), 7.17-7.22 (m, 1H), 7.24-7.28 (m, 2H), 7.28-7.32 (m, 1H), 7.34-7.39 (m, 1H), 7.56 (dd, J=7.8, 1.7 Hz, 1H), 8.02 (s, 1H).

LC-MS (MET-uPLC-AB-101): 95% (UV), Rt=3.41 min, m/z (ESI$^+$)=375.0/377.0 [M+H]$^+$ LC-MS (CAM-F1): 86% (UV), Rt=5.02 min, 74% ee Enantiomer 2 (FP 3)

$^1$H NMR (500 MHz, Chloroform-d) δ 1.36 (d, J=7.0 Hz, 3H), 3.83 (s, 3H), 4.44-4.56 (m, 2H), 5.05 (q, J=7.0 Hz, 1H), 6.98 (dd, J=8.3, 1.1 Hz, 1H), 7.02 (td, J=7.6, 1.2 Hz, 1H), 7.11-7.17 (m, 1H), 7.17-7.21 (m, 1H), 7.24-7.28 (m, 2H), 7.28-7.31 (m, 1H), 7.34-7.38 (m, 1H), 7.56 (dd, J=7.7, 1.7 Hz, 1H), 8.02 (s, 1H).

LC-MS (MET-uPLC-AB-101): 94% (UV), Rt=3.41 min, m/z (ESI$^+$)=375.1/377.0 [M+H]$^+$ LC-MS (CAM-F1): 84% (UV), Rt=6.66 min, 73% ee

N-[(3-Chlorophenyl)methyl]-3-[N-(3-methoxyphenyl)formamido]-2-oxo butanamide (FP 4)

The title compound was synthesized from N-[(3-chlorophenyl)methyl]-2-hydroxy-3-[N-(3-methoxyphenyl)formamido]butanamide (I-127) in a similar manner to method A, general procedure 4 (general scheme 4) as a colourless viscous oil (90 mg, 96% purity, 33%) after purification by flash column chromatography on normal phase silica (10 g SNAP KP-SIL cartridge, 0-50% EtOAc in heptane gradient).

$^1$H NMR (500 MHz, Chloroform-d) δ 1.47 (d, J=6.9 Hz, 3H), 3.84 (s, 3H), 4.42-4.54 (m, 2H), 4.94 (q, J=6.9 Hz, 1H), 6.90-6.93 (m, 1H), 6.96-7.00 (m, 2H), 7.06-7.13 (m, 1H), 7.16-7.20 (m, 1H), 7.24-7.26 (m, 1H), 7.26-7.28 (m, 1H), 7.28-7.30 (m, 1H), 7.31-7.37 (m, 1H), 8.19 (s, 1H).

LC-MS (MET-uPLC-AB-101): 96% (UV), Rt=3.43 min, m/z (ESI$^+$)=375.0/377.0 [M+H]$^+$

N-[(3-Chlorophenyl)methyl]-3-[N-(4-methoxyphenyl)formamido]-2-oxobutanamide (FP 5)

The title compound was synthesized from N-[(3-chlorophenyl)methyl]-2-hydroxy-3-[N-(4-methoxyphenyl)formamido]butanamide (I-128) in a similar manner to method A, general procedure 4 (general scheme 4) as a yellow viscous oil (156 mg, 99% purity, 58%) after purification by flash column chromatography on normal phase silica (10 g SNAP KP-SIL cartridge, 0-40% EtOAc in heptane gradient).

$^1$H NMR (500 MHz, Chloroform-d) δ 1.43 (d, J=6.9 Hz, 3H), 3.83 (s, 3H), 4.43-4.55 (m, 2H), 4.91 (q, J=6.9 Hz, 1H), 6.92-6.97 (m, 2H), 7.08-7.15 (m, 1H), 7.16-7.20 (m, 1H), 7.24-7.28 (m, 2H), 7.28-7.30 (m, 1H), 7.32-7.38 (m, 2H), 8.11 (s, 1H).

LC-MS (MET-uPLC-AB-101): 99% (UV), Rt=3.39 min, m/z (ESI$^+$)=375.0/377.0 [M+H]$^+$

N-[(3-Chlorophenyl)methyl]-2-oxo-3-(N-phenylformamido)butanamide (FP 6)

The title compound was synthesized from N-[(3-chlorophenyl)methyl]-2-hydroxy-3-(N-phenylformamido)butanamide (I-129) in a similar manner to method A, general procedure 4 (general scheme 4) as a yellow viscous oil (83 mg, 95% purity, 36%) after purification by flash column chromatography on normal phase silica (10 g SNAP KP-SIL cartridge, 0-40% EtOAc in heptane gradient).

$^1$H NMR (500 MHz, Chloroform-d) δ 1.47 (d, J=6.9 Hz, 3H), 4.42-4.55 (m, 2H), 4.94 (q, J=6.9 Hz, 1H), 7.08-7.15 (m, 1H), 7.16-7.20 (m, 1H), 7.24-7.28 (m, 2H), 7.28-7.30 (m, 1H), 7.36-7.40 (m, 1H), 7.40-7.48 (m, 4H), 8.18 (s, 1H).

LC-MS (MET-uPLC-AB-101): 95% (UV), Rt=3.37 min, m/z (ESI$^+$)=345.0/347.0 [M+H]$^+$

N-[(3-Chlorophenyl)methyl]-3-[N-(5-fluoro-2-methoxyphenyl)formamido]-2-oxobutanamide (FP 7)

The title compound was synthesized from N-[(3-chlorophenyl)methyl]-3-[N-(5-fluoro-2-methoxyphenyl)formamido]-2-hydroxybutanamide (I-130) in a similar manner to method A, general procedure 4 (general scheme 4) as a yellow viscous oil (87 mg, 95% purity, 38%) after purification by flash column chromatography on normal phase silica (10 g SNAP KP-SIL cartridge, 0-40% EtOAc in heptane gradient).

$^1$H NMR (500 MHz, Chloroform-d) δ 1.34-1.53 (m, 3H), 3.59-3.83 (m, 3H), 4.41-4.57 (m, 2H), 4.97-5.45 (m, 1H), 6.84-6.94 (m, 1H), 6.99-7.10 (m, 1H), 7.10-7.16 (m, 1H), 7.16-7.21 (m, 1H), 7.25-7.28 (m, 2H), 7.29-7.31 (m, 1H), 7.41 (dd, J=3.1, 8.5 Hz, 1H), 8.00-8.59 (m, 1H).

LC-MS (MET-uPLC-AB-101): 95% (UV), Rt=3.49 min, m/z (ESI$^+$)=393.0/395.0 [M+H]$^+$

N-[(3-Chlorophenyl)methyl]-3-[N-(4-fluoro-2-methoxyphenyl)formamido]-2-oxobutanamide (FP 8)

The title compound was synthesized from N-[(3-chlorophenyl)methyl]-3-[N-(4-fluoro-2-methoxyphenyl)formamido]-2-hydroxybutanamide (I-131) in a similar manner to method A, general procedure 4 (general scheme 4) as an off-white powder (100 mg, 99% purity, 30%) after purification by flash column chromatography on normal phase silica (10 g SNAP KP-SIL cartridge, 0-100% EtOAc in heptane gradient) followed by trituration in heptane.

$^1$H NMR (500 MHz, Chloroform-d) δ 1.36-1.50 (m, 3H), 3.46-3.88 (m, 3H), 4.41-4.56 (m, 2H), 4.96-5.59 (m, 1H), 6.66-6.80 (m, 2H), 7.10-7.19 (m, 2H), 7.25-7.28 (m, 2H), 7.28-7.30 (m, 1H), 7.57 (t, J=8.8 Hz, 1H), 8.00-8.58 (m, 1H).

LC-MS (MET-uPLC-AB-101): 99% (UV), Rt=3.53 min, m/z (ESI$^+$)=393.0/395.1 [M+H]$^+$

N-[(3-Chlorophenyl)methyl]-3-[N-(2-methoxyphenyl)formamido]-3-methyl-2-oxobutanamide (FP 9)

The title compound was synthesized from N-[(3-chlorophenyl)methyl]-2-hydroxy-3-[N-(2-methoxyphenyl)formamido]-3-methylbutanamide (I-132) in a similar manner to method A, general procedure 4 (general scheme 4) as a brown solid (45 mg, 99% purity, 19%) after purification by flash column chromatography on normal phase silica (10 g SNAP KP-SIL cartridge, 0-40% EtOAc in heptane gradient).

$^1$H NMR (500 MHz, Chloroform-d) δ 1.32 (s, 3H), 1.67 (s, 3H), 3.85 (s, 3H), 4.48 (d, J=6.3 Hz, 2H), 6.99 (dd, J=8.3, 1.1 Hz, 1H), 7.00-7.05 (m, 1H), 7.10-7.18 (m, 1H), 7.18-7.21 (m, 1H), 7.23-7.29 (m, 2H), 7.30-7.33 (m, 1H), 7.36-7.41 (m, 1H), 7.71 (dd, J=7.7, 1.7 Hz, 1H), 7.93 (s, 1H).

LC-MS (MET-uPLC-AB-101): 99% (UV), Rt=3.79 min, m/z (ESI$^+$)=389.1/391.0 [M+H]$^+$

N-[(3-Chlorophenyl)methyl]-3-[N-(2-methoxyphenyl)formamido]-2-oxo-3-phenylpropanamide (FP 10)

The title compound was synthesized from N-[(3-chlorophenyl)methyl]-2-hydroxy-3-[N-(2-methoxyphenyl)formamido]-3-phenylpropanamide (I-133) in a similar manner to method A, general procedure 4 (general scheme 4) as a brown glass (124 mg, 98% purity, 50%) after purification by flash column chromatography on normal phase silica (10 g SNAP KP-SIL cartridge, 0-40% EtOAc in heptane gradient).

$^1$H NMR (500 MHz, Chloroform-d) δ 3.54 (s, 3H), 4.40-4.52 (m, 2H), 6.48-6.54 (m, 1H), 6.67 (dd, J=8.3, 1.0 Hz, 1H), 6.90 (td, J=7.6, 1.2 Hz, 1H), 7.13-7.23 (m, 8H), 7.23-7.26 (m, 3H), 7.46 (dd, J=7.8, 1.7 Hz, 1H), 8.14-8.43 (m, 1H).

LC-MS (MET-uPLC-AB-101): 98% (UV), Rt=3.75 min, m/z (ESI$^+$)=437.0/439.0 [M+H]$^+$

N-[2-(3-Chlorophenyl)propan-2-yl]-3-[N-(2-methoxyphenyl)formamido]-2-oxobutanamide (FP 11)

The title compound was synthesized from N-[2-(3-chlorophenyl)propan-2-yl]-2-hydroxy-3-[N-(2-methoxyphenyl)formamido]butanamide (I-134) in a similar manner to method A, general procedure 4 (general scheme 4) as an off-white powder (70 mg, 97% purity, 34%) after purification by flash column chromatography on normal phase silica (10 g SNAP KP-SIL cartridge, 0-100% EtOAc in heptane gradient) followed by trituration in heptane.

$^1$H NMR (500 MHz, Chloroform-d) δ 1.31-1.49 (m, 3H), 1.70 (s, 3H), 1.74 (s, 3H), 3.70-3.88 (m, 3H), 4.78-5.39 (m, 1H), 6.93-6.98 (m, 2H), 7.05 (s, 1H), 7.18-7.22 (m, 1H), 7.23-7.27 (m, 1H), 7.27-7.34 (m, 2H), 7.37-7.43 (m, 2H), 7.99-8.56 (m, 1H).

LC-MS (MET-uPLC-AB-101): 97% (UV), Rt=3.77 min, m/z (ESI$^+$)=403.1/405.1 [M+H]$^+$

N-[(3-Chlorophenyl)methyl]-3-[N-(2-methoxyphenyl)formamido]-2-oxopentanamide (FP 12)

The title compound was synthesized from N-[(3-chlorophenyl)methyl]-2-hydroxy-3-[N-(2-methoxyphenyl)formamido]pentanamide (I-135) in a similar manner to method A, general procedure 4 (general scheme 4) as a yellow viscous oil (53 mg, 96% purity, 42%) after purification by flash column chromatography on normal phase silica (10 g SNAP KP-SIL cartridge, 0-40% EtOAc in heptane gradient).

¹H NMR (500 MHz, Chloroform-d) δ 0.89-1.13 (m, 3H), 1.70-1.81 (m, 1H), 1.90-2.01 (m, 1H), 3.56-3.82 (m, 3H), 4.46-4.54 (m, 2H), 4.98 (t, J=6.7 Hz, 1H), 6.88-6.99 (m, 1H), 7.00-7.06 (m, 1H), 7.13-7.22 (m, 2H), 7.23-7.31 (m, 3H), 7.31-7.37 (m, 1H), 7.58 (dd, J=1.7, 7.8 Hz, 1H), 8.04-8.63 (m, 1H).

LC-MS (MET-uPLC-AB-101): 96% (UV), Rt=3.54 min, m/z (ESI$^+$)=389.1/391.1 [M+H]$^+$

N-[(3-Chlorophenyl)methyl]-3-[N-(2-methoxyphenyl)formamido]-5-methyl-2-oxohexanamide (FP 13)

The title compound was synthesized from N-[(3-chlorophenyl)methyl]-2-hydroxy-3-[N-(2-methoxyphenyl)formamido]-5-methylhexanamide (I-136) in a similar manner to method A, general procedure 4 (general scheme 4) as an off-white powder (39 mg, 97% purity, 28%) after purification by flash column chromatography on normal phase silica (10 g SNAP KP-SIL cartridge, 0-40% EtOAc in heptane gradient) followed by trituration in heptane.

¹H NMR (500 MHz, Chloroform-d) δ 0.73-1.02 (m, 6H), 1.46-1.64 (m, 2H), 1.80-1.96 (m, 1H), 3.52-3.84 (m, 3H), 4.44-4.57 (m, 2H), 5.16-5.39 (m, 1H), 6.87-6.99 (m, 1H), 6.99-7.06 (m, 1H), 7.11-7.23 (m, 2H), 7.23-7.32 (m, 3H), 7.31-7.38 (m, 1H), 7.54 (dd, J=1.6, 7.8 Hz, 1H), 8.04-8.65 (m, 1H).

LC-MS (MET-uPLC-AB-101): 97% (UV), Rt=3.93 min, m/z (ESI$^+$)=417.1/419.1 [M+H]$^+$

3-[N-(2-Methoxyphenyl)formamido]-2-oxobutanamide (FP 14)

The title compound was synthesized from 2-hydroxy-3-[N-(2-methoxyphenyl) formamido]butanamide (I-137) in a similar manner to method A, general procedure 4 (general scheme 4) as a yellow oil (5 mg, 98% purity, 26%) after purification by flash column chromatography on normal phase silica (10 g SNAP KP-SIL cartridge, 0-100% EtOAc in heptane gradient).

¹H NMR (500 MHz, Chloroform-d) δ 1.31-1.48 (m, 3H), 3.67-3.86 (m, 3H), 5.02-5.44 (m, 1H), 5.44-5.68 (m, 1H), 6.54-6.86 (m, 1H), 6.96-7.00 (m, 1H), 7.02 (td, J=1.3, 7.6 Hz, 1H), 7.29-7.39 (m, 1H), 7.53 (dd, J=1.7, 7.7 Hz, 1H), 8.00-8.63 (m, 1H).

LC-MS (MET-uPLC-AB-101): 98% (UV), Rt=1.94 min, m/z (ESI$^+$)=251.2 [M+H]$^+$

3-(N-Cyclohexylformamido)-N-(2-methylpropyl)-2-oxobutanamide (FP 15)

The title compound was synthesized from 3-(N-cyclohexylformamido)-2-hydroxy-N-(2-methylpropyl)butanamide (I-138) in a similar manner to method A, general procedure 4 (general scheme 4) as a colourless oil (72 mg, 96% purity, 29%) after purification by flash column chromatography on normal phase silica (25 g SNAP KP-SIL cartridge, 0-100% EtOAc in heptane gradient) followed by preparative LC (acidic pH, standard elution method).

¹H NMR (500 MHz, Chloroform-d) δ 0.85-0.98 (m, 6H), 1.08-1.21 (m, 1H), 1.22-1.40 (m, 2H), 1.44-1.84 (m, 7H), 1.84-1.94 (m, 2H), 2.02-2.12 (m, 2H), 3.03-3.24 (m, 2H), 3.31-4.18 (m, 1H), 4.23-5.20 (m, 1H), 6.59-7.00 (m, 1H), 8.02-8.26 (m, 1H).

LC-MS (MET-uPLC-AB-101): 96% (UV), Rt=3.09 min, m/z (ESI$^+$)=283.2 [M+H]$^+$

3-[N-(cyclopropylmethyl)formamido]-N-(2-methylpropyl)-2-oxobutanamide (FP 16)

The title compound was synthesized from 3-[N-(cyclopropylmethyl)formamido]-2-hydroxy-N-(2-methylpropyl)butanamide (I-139) in a similar manner to method A, general procedure 4 (general scheme 4) as a yellow oil (27 mg, 94% purity, 9%) after purification by flash column chromatography on normal phase silica (10 g SNAP KP-SIL cartridge, 0-100% EtOAc in heptane gradient) followed by preparative LC (acidic pH, standard elution method).

¹H NMR (500 MHz, Chloroform-d) δ 0.17-0.36 (m, 2H), 0.39-0.74 (m, 2H), 0.82-1.14 (m, 7H), 1.45-1.57 (m, 3H), 1.74-1.88 (m, 1H), 3.03-3.36 (m, 4H), 4.36-5.23 (m, 1H), 6.64-6.99 (m, 1H), 7.94-8.31 (m, 1H).

LC-MS (MET-uPLC-AB-101): 94% (UV), Rt=2.5 min, m/z (ESI$^+$)=255.2 [M+H]$^+$

N-[(3-Chlorophenyl)methyl]-3-(N-cyclohexylformamido)-2-oxobutanamide (FP 17)

The title compound was synthesized from N-[(3-chlorophenyl)methyl]-3-(N cyclohexylformamido)-2-hydroxybutanamide (I-140) in a similar manner to method A, general procedure 4 (general scheme 4) as a colourless viscous oil (16 mg, 94% purity, 21%) after purification by flash column chromatography on normal phase silica (10 g SNAP KP-SIL cartridge, 0-50% EtOAc in heptane gradient) followed by preparative LC (acidic pH, standard elution method).

¹H NMR (500 MHz, Chloroform-d) δ 1.07-1.21 (m, 1H), 1.28-1.39 (m, 2H), 1.43-1.66 (m, 5H), 1.66-1.73 (m, 1H), 1.78-1.93 (m, 2H), 2.01-2.11 (m, 2H), 3.30-4.15 (m, 1H), 4.21-5.21 (m, 1H), 4.36-4.54 (m, 2H), 6.89-7.02 (m, 1H), 7.12-7.17 (m, 1H), 7.21-7.31 (m, 3H), 8.01-8.27 (m, 1H).

LC-MS (MET-uPLC-AB-101): 94% (UV), Rt=3.56 min, m/z (ESI$^+$)=351.1/353.0 [M+H]$^+$

N-[(3-Chlorophenyl)methyl]-3-[N-(cyclohexylmethyl)formamido]-2-oxobutanamide (FP 18)

The title compound was synthesized from N-[(3-chlorophenyl)methyl]-3-[N-(cyclohexylmethyl)formamido]-2-hydroxybutanamide (I-141) in a similar manner to method A, general procedure 4 (general scheme 4) as a colourless viscous oil (34 mg, 96% purity, 26%) after purification by flash column chromatography on normal phase silica (10 g SNAP KP-SIL cartridge, 0-40% EtOAc in heptane gradient) followed by preparative LC (acidic pH, standard elution method).

¹H NMR (500 MHz, Chloroform-d) δ 0.82-0.96 (m, 2H), 1.10-1.36 (m, 3H), 1.44-1.56 (m, 3H), 1.61-1.82 (m, 6H), 2.96-3.18 (m, 1H), 3.25-3.36 (m, 1H), 4.22-5.11 (m, 1H), 4.38-4.49 (m, 2H), 6.96-7.05 (m, 1H), 7.12-7.17 (m, 1H), 7.23-7.30 (m, 3H), 7.83-8.30 (m, 1H).

LC-MS (MET-uPLC-AB-101): 96% (UV), Rt=3.89 min, m/z (ESI$^+$)=365.1/367.1 [M+H]$^+$

N-[(3-Chlorophenyl)methyl]-3-[N-(2-methoxyphenyl)formamido]-2-oxopropanamide (FP 19)

The title compound was synthesized from N-[(3-chlorophenyl)methyl]-2-hydroxy-3-[N-(2-methoxyphenyl)formamido]propanamide (I-142) in a similar manner to method A, general procedure 4 (general scheme 4) as a yellow viscous oil (107 mg, 93% purity by 1H NMR, 52%) after purification by flash column chromatography on normal phase silica (25 g SNAP Ultra cartridge, 10-100% EtOAc in heptane gradient) followed by preparative LC (acidic pH, standard elution method).

$^1$H NMR (500 MHz, Chloroform-d) δ 3.78-3.88 (m, 3H), 4.45 (d, J=6.3 Hz, 2H), 4.99-5.13 (m, 2H), 6.92-7.02 (m, 2H), 7.11-7.23 (m, 2H), 7.26-7.30 (m, 4H), 7.30-7.36 (m, 1H), 8.22-8.34 (m, 1H)

LC-MS (METCR1600): 92% (UV), Rt=4.58 min, m/z (ESI$^+$)=361.1/363.1 [M+H]$^+$

3-(N-Benzylformamido)-N-[(3-chlorophenyl)methyl]-2-oxobutanamide (FP 20)

The title compound was synthesized from 3-(N-benzylformamido)-N-[(3-chlorophenyl)methyl]-2-hydroxybutanamide (I-143) in a similar manner to method A, general procedure 4 (general scheme 4) as a yellow viscous oil (88 mg, 100% purity, 53%) after purification by flash column chromatography on normal phase silica (10 g SNAP KP-SIL cartridge, 0-45% EtOAc in heptane gradient) then on reverse phase silica (12 g SNAP Ultra C18 cartridge, acidic pH, standard elution method).

$^1$H NMR (500 MHz, Chloroform-d) δ 1.13-1.48 (m, 3H), 4.16-5.19 (m, 5H), 6.62-7.06 (m, 1H), 7.12-7.31 (m, 6H), 7.32-7.43 (m, 3H), 8.14-8.48 (m, 1H).

LC-MS (METCR1600): 100% (UV), Rt=4.20-5.00 min (two peaks), m/z (ESI$^+$)=359.1/361.1 [M+H]$^+$

N-[(3-Chlorophenyl)methyl]-2-oxo-3-[N-(propan-2-yl)formamido]butanamide (FP 21)

The title compound was synthesized from N-[(3-chlorophenyl)methyl]-2-hydroxy-3-[N-(propan-2-yl)formamido]butanamide (I-144) in a similar manner to method A, general procedure 4 (general scheme 4) as a yellow viscous oil (87 mg, 100% purity, 52%) after purification by flash column chromatography on normal phase silica (10 g SNAP KP-SIL cartridge, 0-45% EtOAc in heptane gradient).

$^1$H NMR (500 MHz, Chloroform-d) δ 1.00-1.45 (m, 6H), 1.45-1.60 (m, 3H), 3.84 (hept, J=6.8 Hz, 1H), 4.19-5.19 (m, 3H), 6.91-7.04 (m, 1H), 7.12-7.19 (m, 1H), 7.21-7.32 (m, 3H), 8.02-8.26 (m, 1H).

LC-MS (METCR1600): 100% (UV), Rt=4.38 min, m/z (ESI$^+$)=311.1/313.2 [M+H]$^+$

N-[(3-Chlorophenyl)methyl]-3-[N-(oxan-4-yl)formamido]-2-oxobutanamide (FP 22)

The title compound was synthesized from N-[(3-chlorophenyl)methyl]-2-hydroxy-3-[N-(oxan-4-yl)formamido]butanamide (I-145) in a similar manner to method A, general procedure 4 (general scheme 4) as an off-white powder (20 mg, 90% purity, 11%) after purification by flash column chromatography on normal phase silica (10 g SNAP KP-SIL cartridge, 0-100% EtOAc in heptane gradient) followed by preparative LC (neutral pH, standard elution method) and trituration in heptane.

$^1$H NMR (500 MHz, Chloroform-d) δ 1.45-1.64 (m, 3H), 1.86-2.10 (m, 4H), 3.37-3.50 (m, 2H), 3.59-3.69 (m, 1H), 3.93-4.14 (m, 2H), 4.20-5.19 (m, 1H), 4.37-4.53 (m, 2H), 6.93-7.03 (m, 1H), 7.11-7.18 (m, 1H), 7.20-7.32 (m, 3H), 8.05-8.26 (m, 1H).

LC-MS (MET-uPLC-AB-101): 90% (UV), Rt=2.58 min, m/z ((ESI$^+$)=353.1/355.1 [M+H]$^+$

N-[(3-Chlorophenyl)methyl]-3-[N-(2,2-dimethylpropyl)formamido]-2-oxobutanamide (FP 23)

The title compound was synthesized from N-[(3-chlorophenyl)methyl]-3-[N-(2,2-dimethylpropyl)formamido]-2-hydroxybutanamide (I-146) in a similar manner to method A, general procedure 4 (general scheme 4) as a colourless viscous oil (64 mg, 98% purity, 29%) after purification by flash column chromatography on normal phase silica (10 g SNAP KP-SIL cartridge, 0-40% EtOAc in heptane gradient) followed by preparative LC (acidic pH, standard elution method).

$^1$H NMR (500 MHz, DMSO-d6) δ 0.83-0.97 (m, 9H), 1.31-1.61 (m, 3H), 2.81-3.16 (m, 1H), 3.18-3.33 (m, 1H), 4.22-4.89 (m, 3H), 7.18-7.25 (m, 1H), 7.27-7.39 (m, 3H), 7.90-8.20 (m, 1H), 9.00-9.44 (m, 1H).

LC-MS (MET-uPLC-AB-101): 98% (UV), Rt=3.56 min, m/z (ESI$^+$)=339.2/341.2 [M+H]$^+$

N-[(3-Chlorophenyl)methyl]-3-{N[(oxan-4-yl)methyl]formamido}-2-oxobutanamide (FP 24)

The title compound was synthesized from N-[(3-chlorophenyl)methyl]-2-hydroxy-3-{N-[(oxan-4-yl)methyl]formamido}butanamide (I-147) in a similar manner to method A, general procedure 4 (general scheme 4) as a yellow viscous oil (75 mg, 96% purity, 39%) after purification by flash column chromatography on normal phase silica (10 g SNAP KP-SIL cartridge, 0-40% EtOAc in heptane gradient).

$^1$H NMR (500 MHz, Chloroform-d) δ 1.19-1.32 (m, 2H), 1.44-1.57 (m, 3H), 1.63-1.71 (m, 2H), 1.77-2.02 (m, 1H), 3.04-3.23 (m, 1H), 3.25-3.44 (m, 3H), 3.90-4.04 (m, 2H), 4.25-5.14 (m, 1H), 4.38-4.49 (m, 2H), 6.98-7.08 (m, 1H), 7.12-7.17 (m, 1H), 7.23-7.31 (m, 3H), 7.85-8.31 (m, 1H).

LC-MS (MET-uPLC-AB-101): 96% (UV), Rt=2.72 min, m/z (ESI$^+$)=367.1/369.1 [M+H]$^+$

N-(Cyclohexylmethyl)-3-[N-(2-methoxyphenyl)formamido]-2-oxobutanamide (FP 25)

The title compound was synthesized from N-(cyclohexylmethyl)-2-hydroxy-3-[N-(2-methoxyphenyl)formamido]butanamide (I-148) in a similar manner to method A, general procedure 4 (general scheme 4) as an off-white powder (254 mg, 100% purity, 79%) after trituration in EtOAc and purification of the filtrate by flash column chromatography on normal phase silica (50 g SNAP KP-SIL cartridge, 0-100% TBME in heptane gradient).

$^1$H NMR (500 MHz, Chloroform-d) δ 0.90-1.01 (m, 2H), 1.10-1.29 (m, 3H), 1.32-1.50 (m, 3H), 1.50-1.54 (m, 1H), 1.63-1.69 (m, 1H), 1.69-1.78 (m, 4H), 3.09-3.27 (m, 2H), 3.68-3.87 (m, 3H), 5.02-5.45 (m, 1H), 6.81-6.91 (m, 1H), 6.95-7.00 (m, 1H), 7.00-7.07 (m, 1H), 7.32-7.39 (m, 1H), 7.55-7.64 (m, 1H), 7.96-8.61 (m, 1H).

LC-MS (MET-uPLC-AB-101): 100% (UV), Rt=3.58 min, m/z (ESI$^+$)=347.2 [M+H]$^+$

N-[2-(3-Chlorophenyl)propan-2-yl]-2-oxo-3-[N-(propan-2-yl)formamido]butanamide (FP 26)

The title compound was synthesized from N-[2-(3-chlorophenyl)propan-2-yl]-2-hydroxy-3-[N-(propan-2-yl)formamido]butanamide (I-149) in a similar manner to method A, general procedure 4 (general scheme 4) as a colourless viscous oil (40 mg, 97% purity, 35%) after purification by flash column chromatography on normal phase silica (10 g SNAP KP-SIL cartridge, 0-40% EtOAc in heptane gradient) followed by preparative LC (acidic pH, standard elution method).

$^1$H NMR (500 MHz, Chloroform-d) δ 1.01-1.33 (m, 6H), 1.45-1.54 (m, 3H), 1.62-1.70 (m, 3H), 1.74-1.76 (m, 3H), 3.71-4.01 (m, 1H), 4.12-4.54 (m, 1H), 6.67-6.99 (m, 1H), 7.20-7.23 (m, 1H), 7.25-7.28 (m, 2H), 7.35-7.39 (m, 1H), 8.10-8.26 (m, 1H).

LC-MS (MET-uPLC-AB-101): 97% (UV), Rt=3.28 min, m/z (ESI$^+$)=339.2/341.2 [M+H]$^+$

N[2-(3-Chlorophenyl)propan-2-yl]-3-(N-cyclohexylformamido)-2-oxobutanamide (FP 27)

The title compound was synthesized from N-[2-(3-chlorophenyl)propan-2-yl]-3-(N-cyclohexylformamido)-2-hydroxybutanamide (I-150) in a similar manner to method A, general procedure 4 (general scheme 4) as an off-white powder (19 mg, 98% purity, 18%) after purification by flash column chromatography on normal phase silica (10 g SNAP KP-SIL cartridge, 0-40% EtOAc in heptane gradient) followed by preparative LC (acidic pH, standard elution method).

$^1$H NMR (500 MHz, Chloroform-d) δ 1.03-1.18 (m, 1H), 1.24-1.35 (m, 2H), 1.39-1.55 (m, 5H), 1.64 (s, 3H), 1.64-1.70 (m, 1H), 1.72-1.77 (m, 3H), 1.80-1.89 (m, 3H), 1.90-1.96 (m, 1H), 3.21-4.13 (m, 1H), 4.15-5.15 (m, 1H), 6.81 (s, 1H), 7.20-7.24 (m, 1H), 7.24-7.28 (m, 2H), 7.32-7.37 (m, 1H), 8.08-8.28 (m, 1H).

LC-MS (MET-uPLC-AB-101): 98% (UV), Rt=3.89 min, m/z (ESI$^+$)=379.2/381.2 [M+H]$^+$

3-[N-(2-Methoxyphenyl)formamido]-2-oxo-N-(propan-2-yl)butanamide (FP 28)

The title compound was synthesized from 2-hydroxy-3-[N-(2-methoxyphenyl)-formamido]-N-(propan-2-yl)butanamide (I-152) in a similar manner to method A, general procedure 4 (general scheme 4) as a yellow viscous oil (108 mg, 97% purity, 56%) after purification by flash column chromatography on normal phase silica (10 g SNAP KP-SIL cartridge, 0-40% EtOAc in heptane gradient).

$^1$H NMR (500 MHz, Chloroform-d) δ 1.20-1.25 (m, 6H), 1.32-1.50 (m, 3H), 3.70-3.86 (m, 3H), 4.01-4.14 (m, 1H), 5.06-5.45 (m, 1H), 6.54-6.81 (m, 1H), 6.90-6.99 (m, 1H), 7.00-7.15 (m, 1H), 7.28-7.38 (m, 1H), 7.55-7.61 (m, 1H), 7.99-8.61 (m, 1H).

LC-MS (MET-uPLC-AB-101): 97% (UV), Rt=2.62 min, m/z (ESI$^+$)=293.1 [M+H]$^+$

3-[N-(2,2-Dimethylpropyl)formamido]-2-oxo-N-(propan-2-yl)butanamide (FP 29)

The title compound was synthesized from 3-[N-(2,2-dimethylpropyl)formamido]-2-hydroxy-N-(propan-2-yl)butanamide (I-153) in a similar manner to method A, general procedure 4 (general scheme 4) as an off-white solid (88 mg, 100% purity, 52%) after trituration in 1:1 EtOAc/heptane and purification of the filtrate by flash column chromatography on normal phase silica (50 g SNAP KP-SIL cartridge, 0-100% TBME in heptane gradient).

$^1$H NMR (500 MHz, Chloroform-d) δ 0.91-1.05 (m, 9H), 1.17-1.24 (m, 6H), 1.50-1.67 (m, 3H), 2.78-3.20 (m, 1H), 3.23-3.53 (m, 1H), 3.94-4.12 (m, 1H), 4.17-5.05 (m, 1H), 6.37-6.81 (m, 1H), 7.88-8.30 (m, 1H).

LC-MS (MET-uPLC-AB-101): 100% (UV), Rt=2.72 min, m/z (ESI$^+$)=257.2 [M+H]$^+$

N-(Cyclopropylmethyl)-4-methyl-3-[N-(2-methylpropyl)formamido]-2-oxopentanamide (FP 30)

The title compound was synthesized from N-(cyclopropylmethyl)-2-hydroxy-4-methyl-3-[N-(2-methylpropyl)formamido]pentanamide (I-155) in a similar manner to method A, general procedure 4 (general scheme 4) as a colourless glass (40 mg, 98% purity, 49%) after purification by preparative LC (acidic pH, standard elution method) followed by flash column chromatography on normal phase silica (10 g SNAP KP-SIL cartridge, 0-50% EtOAc in heptane gradient).

$^1$H NMR (500 MHz, Chloroform-d) δ 0.20-0.26 (m, 2H), 0.51-0.57 (m, 2H), 0.76-1.03 (m, 13H), 1.78-2.04 (m, 1H), 2.31-2.51 (m, 1H), 3.02-3.21 (m, 4H), 4.46-4.78 (m, 1H), 6.76-7.07 (m, 1H), 8.01-8.42 (m, 1H).

LC-MS (METCR1600): 98% (UV), Rt=4.59 min, m/z (ESI$^+$)=283.3 [M+H]$^+$

N-(Cyclopropylmethyl)-3-[N-(2,2-dimethylpropyl)formamido]-4-methyl-2-oxopentanamide (FP 31)

The title compound was synthesized from N-(cyclopropylmethyl)-3-[N-(2,2-dimethylpropyl)formamido]-2-hydroxy-4-methylpentanamide (I-156) in a similar manner to method A, general procedure 4 (general scheme 4) as a colourless glass (58 mg, 100% purity, 82%) after purification by flash column chromatography on normal phase silica (10 g SNAP KP-SIL cartridge, 0-50% EtOAc in heptane gradient).

$^1$H NMR (500 MHz, Chloroform-d) δ 0.20-0.26 (m, 2H), 0.49-0.57 (m, 2H), 0.86 (s, 6H), 0.96-1.07 (m, 10H), 2.31-2.54 (m, 1H), 2.82-3.45 (m, 4H), 4.35-4.90 (m, 1H), 6.82-7.13 (m, 1H), 8.00-8.56 (m, 1H).

LC-MS (METCR1600): 100% (UV), Rt=4.8 min, m/z (ESI$^+$)=297.4 [M+H]$^+$

(3R)—N-(Cyclopropylmethyl)-3-[N-(2,2-dimethylpropyl)formamido]-4-methyl-2-oxopentanamide and (3S)—N-(cyclopropylmethyl)-3-[N-(2,2-dimethylpropyl)formamido]-4-methyl-2-oxopentanamide (FP 32-33) ((R) and (S) assignments arbitrary)

N-(cyclopropylmethyl)-3-[N-(2,2-dimethylpropyl)formamido]-4-methyl-2-oxopentanamide (FP 31) (100% purity, 40.8 mg, 0.138 mmol) was purified by chiral separation on Gilson LC [Column: Chiralpakas (250 mm×20 mm, 10 μM) at RT; Isocratic eluent: 85:15 heptane:EtOH; Flow rate: 9 mL/min; Detector wavelength; 210/254 nm; Injection volume: 300-1000 μL] to afford 8.9 mg of enantiomer 1 (FP 32) as a yellow viscous oil (95% ee, 20%) and 10.1 mg of enantiomer 2 (FP 33) as a yellow viscous oil (99% ee, 24%).

Enantiomer 1 (FP 32)

$^1$H NMR (500 MHz, Chloroform-d) δ 0.19-0.28 (m, 2H), 0.49-0.60 (m, 2H), 0.88 (s, 6H), 0.95-1.10 (m, 10H), 2.29-2.58 (m, 1H), 2.83-3.46 (m, 4H), 4.34-4.93 (m, 1H), 6.80-7.08 (m, 1H), 7.99-8.58 (m, 1H).

LC-MS (METCR1416): 97% (UV), Rt=3.97 min, m/z (ESI$^+$)=297.5 [M+H]$^+$

LC-MS (CAM-F2): 95% (UV), Rt=15.24 min, 95% ee

Enantiomer 2 (FP 33)

$^1$H NMR (500 MHz, Chloroform-d) δ 0.24 (dq, J=4.8, 15.4 Hz, 2H), 0.47-0.61 (m, 2H), 0.88 (s, 6H), 0.93-1.13 (m, 10 OH), 2.29-2.61 (m, 1H), 2.82-3.46 (m, 4H), 4.32-4.95 (m, 1H), 6.80-7.08 (m, 1H), 7.99-8.59 (m, 1H).

LC-MS (METCR1416): 99% (UV), Rt=3.97 min, m/z (ESI$^+$)=297.5 [M+H]$^+$

LC-MS (CAM-F2): 99% (UV), Rt=6.66 min, 99% ee

N-(Cyclopropylmethyl)-4-methyl-3-{N-[(oxan-4-yl)methyl]formamido}-2-oxopentanamide (FP 34)

The title compound was synthesized from N-(cyclopropylmethyl)-2-hydroxy-4-methyl-3-{N-[(oxan-4-yl)methyl]

formamido}pentanamide (I-157) in a similar manner to method A, general procedure 4 (general scheme 4) as a colourless glass (41 mg, 100% purity, 51%) after purification by flash column chromatography on normal phase silica (10 g SNAP KP-SIL cartridge, 0-50% EtOAc in heptane gradient).

$^1$H NMR (500 MHz, Chloroform-d) δ 0.19-0.27 (m, 2H), 0.50-0.58 (m, 2H), 0.90-1.04 (m, 7H), 1.16-1.66 (m, 4H), 1.80-2.00 (m, 1H), 2.30-2.51 (m, 1H), 3.02-3.42 (m, 6H), 3.86-4.00 (m, 2H), 4.43-4.82 (m, 1H), 6.80-7.08 (m, 1H), 7.98-8.40 (m, 1H).

LC-MS (METCR1600): 100% (UV), Rt=4.06 min, m/z (ESI$^+$)=325.3 [M+H]$^+$

N-[(3-Chlorophenyl)methyl]-3-[N-(2-methoxyphenyl)formamido]-4-methyl-2-oxopentanamide (FP 35)

The title compound was synthesized from N-[(3-chlorophenyl)methyl]-2-hydroxy-3-[N-(2-methoxyphenyl)formamido]-4-methylpentanamide (I-158) in a similar manner to method A, general procedure 4 (general scheme 4) as a yellow viscous oil (202 mg, 95% purity by $^1$H NMR, 73%) after purification by flash column chromatography on normal phase silica (10 g SNAP Ultra cartridge, 7-58% EtOAc in heptane gradient) then on reverse phase silica (10 g SNAP Ultra C18 cartridge, acidic pH, standard elution method).

$^1$H NMR (500 MHz, Chloroform-d) δ 0.83-0.97 (m, 3H), 1.02-1.24 (m, 3H), 2.26-2.42 (m, 1H), 3.45-3.84 (m, 3H), 4.42-4.59 (m, 2H), 4.87-5.11 (m, 1H), 6.86-7.07 (m, 2H), 7.09-7.30 (m, 5H), 7.30-7.79 (m, 2H), 8.00-8.90 (m, 1H).

LC-MS (METCR1416): 100% (UV), Rt=4.37 min, m/z (ESI$^+$)=403.1/405.1 [M+H]$^+$

3-(N-Cyclohexylformamido)-2-oxo-N-(propan-2-yl)butanamide (FP 36)

The title compound was synthesized from 3-(N-cyclohexylformamido)-2-hydroxy-N-(propan-2-yl)butanamide (I-159) in a similar manner to method A, general procedure 4 (general scheme 4) as a yellow viscous oil (127 mg, 97% purity, 43%) after purification by flash column chromatography on normal phase silica (10 g SNAP KP-SIL cartridge, 0-40% EtOAc in heptane gradient) followed by a second flash column chromatography on normal phase silica (10 g SNAP KP-SIL cartridge, 0-35% EtOAc in heptane gradient).

$^1$H NMR (500 MHz, Chloroform-d) δ 1.16-1.24 (m, 6H), 1.28-1.40 (m, 2H), 1.44-1.51 (m, 3H), 1.52-1.63 (m, 3H), 1.66-1.73 (m, 1H), 1.76-1.93 (m, 2H), 2.03-2.12 (m, 2H), 3.29-4.17 (m, 1H), 3.93-4.09 (m, 1H), 4.25-5.19 (m, 1H), 6.36-6.78 (m, 1H), 8.04-8.24 (m, 1H).

LC-MS (MET-uPLC-AB-101): 97% (UV), Rt=2.72 min, m/z (ESI$^+$)=269.2 [M+H]$^+$

3-(N-Benzylformamido)-N-(cyclopropyylmethyl)-2-oxobutanamide (FP 37)

The title compound was synthesized from 3-(N-benzylformamido)-M (cyclopropylmethyl)-2-hydroxybutanamide (I-160) in a similar manner to method A, general procedure 4 (general scheme 4) as a colourless oil (58.8 mg, 95% purity, 16%) after purification twice by flash column chromatography on normal phase silica (10 g SNAP KP-SIL cartridge, 0-100% EtOAc in heptane gradient).

$^1$H NMR (500 MHz, Chloroform-d) δ 0.17-0.27 (m, 2H), 0.51-0.57 (m, 2H), 0.83-1.02 (m, 1H), 1.16-1.45 (m, 3H), 2.93-3.22 (m, 2H), 4.24-5.18 (m, 3H), 6.49-6.87 (m, 1H), 7.20-7.30 (m, 2H), 7.32-7.41 (m, 3H), 8.15-8.45 (m, 1H).

LC-MS (MET-uPLC-AB-101): 95% (UV), Rt=2.68-2.74 min, m/z (ESI$^+$)=289.1 [M+H]$^+$

3-[N-(Cyclohexylmethyl)formamido]-N-(cyclopropylmethyl)-2-oxobutanamide (FP 38)

The title compound was synthesized from 3-[N-(cyclohexylmethyl)formamido]-N-(cyclopropylmethyl)-2-hydroxybutanamide (I-161) in a similar manner to method A, general procedure 4 (general scheme 4) as a colourless oil (17 mg, 89% purity by 1H NMR, 51%) after purification by flash column chromatography on normal phase silica (10 g SNAP KP-SIL cartridge, 0-100% EtOAc in heptane gradient).

$^1$H NMR (500 MHz, Chloroform-d) δ 0.18-0.28 (m, 2H), 0.48-0.60 (m, 2H), 0.81-1.03 (m, 3H), 1.12-1.36 (m, 3H), 1.43-1.56 (m, 3H), 1.61-1.82 (m, 6H), 2.94-3.21 (m, 3H), 3.26-3.36 (m, 1H), 4.26-5.11 (m, 1H), 6.71-7.04 (m, 1H), 7.83-8.30 (m, 1H).

LC-MS (MET-uPLC-AB-101): 97% (UV), Rt=3.31 min, m/z (ESI$^+$)=295.2 [M+H]$^+$ tert-Butyl 4-[(N-{1-[(cyclopropylmethyl)carbamoyl]-1-oxopropan-2-yl}formamido) methyl]piperidine-1-carboxylate (FP 39)

The title compound was synthesized from tert-butyl 4-[(N-{1-[(cyclopropyl methyl)carbamoyl]-1-hydroxypropan-2-yl}formamido)methyl]piperidine-1-carboxylate (I-162) in a similar manner to method A, general procedure 4 (general scheme 4) as a colourless viscous oil (26 mg, 92% purity by $^1$H NMR, 57%) after purification by flash column chromatography on normal phase silica (25 g SNAP KP-SIL cartridge, 0-50% EtOAc in heptane gradient) followed by preparative LC (acidic pH, standard elution method).

$^1$H NMR (500 MHz, Chloroform-d) δ 0.18-0.28 (m, 2H), 0.48-0.60 (m, 2H), 0.92-1.01 (m, 1H), 1.02-1.17 (m, 2H), 1.43-1.55 (m, 12H), 1.70-1.80 (m, 2H), 1.81-1.91 (m, 1H), 2.57-2.80 (m, 2H), 3.04-3.39 (m, 4H), 3.94-4.26 (m, 2H), 4.27-5.15 (m, 1H), 6.70-7.01 (m, 1H), 7.82-8.31 (m, 1H).

LC-MS (MET-uPLC-AB-101): 97% (UV), Rt=3.14 min, m/z (ESI$^+$)=396.2 [M+H]$^+$

3-(N-Cyclohexylformamido)-N-(cyclopropylmethyl)-2-oxobutanamide (FP 40)

The title compound was synthesized from 3-(N-cyclohexylformamido)-N-(cyclo-propylmethyl)-2-hydroxybutanamide (I-163) in a similar manner to method A, general procedure 4 (general scheme 4) as a yellow viscous oil (91 mg, 100% purity, 35%) after purification by flash column chromatography on normal phase silica (10 g SNAP KP-SIL cartridge, 0-35% EtOAc in heptane gradient) then on reverse phase silica (12 g SNAP Ultra C18 cartridge, acidic pH, standard elution method).

$^1$H NMR (500 MHz, Chloroform-d) δ 0.15-0.31 (m, 2H), 0.45-0.63 (m, 2H), 0.90-1.41 (m, 4H), 1.43-2.16 (m, 10H), 3.04-3.21 (m, 2H), 3.30-4.20 (m, 1H), 4.23-5.21 (m, 1H), 6.62-7.07 (m, 1H), 8.01-8.26 (m, 1H).

LC-MS (METCR1600): 100% (UV), Rt=4.37 min, m/z (ESI$^+$)=281.3 [M+H]$^+$

N-(Cyclopropylmethyl)-3-[N-(2,2-dimethylpropyl)formamido]-2-oxobutanamide (FP 41)

The title compound was synthesized from N-(cyclopropylmethyl)-3-[N-(2,2-dimethylpropyl)formamido]-2-hydroxybutanamide (I-164) in a similar manner to method A, general procedure 4 (general scheme 4) as a yellow powder (52 mg, 99% purity, 26%) after purification by flash column chromatography on normal phase silica (10 g SNAP KP-SIL cartridge, 0-35% EtOAc in heptane gradient) then on reverse phase silica (12 g SNAP Ultra C18 cartridge, acidic pH, standard elution method).

$^1$H NMR (500 MHz, Chloroform-d) δ 0.19-0.29 (m, 2H), 0.48-0.62 (m, 2H), 0.88-1.08 (m, 10 OH), 1.46-1.70 (m, 3H), 2.79-3.53 (m, 4H), 4.18-5.05 (m, 1H), 6.71-7.08 (m, 1H), 7.87-8.34 (m, 1H).

LC-MS (METCR1600): 99% (UV), Rt=4.4 min, m/z (ESI$^+$)=269.3 [M+H]$^+$

3-(N-Cyclohexylformamido)-N-cyclopropyl-2-oxobutanamide (FP 42)

The title compound was synthesized from 3-(N-cyclohexylformamido)-N-cyclopropyl-2-hydroxybutanamide (I-165) in a similar manner to method A, general procedure 4 (general scheme 4) as a colourless viscous oil (66 mg, 97% purity by $^1$H NMR, 41%) after purification by flash column chromatography on normal phase silica (10 g SNAP KP-SIL cartridge, 0-35% EtOAc in heptane gradient) followed by preparative LC (acidic pH, standard elution method).

$^1$H NMR (500 MHz, Chloroform-d) δ 0.52-0.65 (m, 2H), 0.76-0.91 (m, 2H), 1.08-1.21 (m, 1H), 1.28-1.40 (m, 2H), 1.42-1.66 (m, 5H), 1.66-1.74 (m, 1H), 1.77-1.94 (m, 2H), 1.98-2.18 (m, 2H), 2.65-2.85 (m, 1H), 3.31-4.17 (m, 1H), 4.20-5.19 (m, 1H), 6.60-6.98 (m, 1H), 8.02-8.23 (m, 1H).

LC-MS (Achiral SFC): 100% (UV), Rt=1.27 min, m/z (ESI$^+$)=555.3 [2M+Na]$^+$

3-[N-(Cyclohexylmethyl)formamido]-N-cyclopropyl-2-oxobutanamide (FP 43)

The title compound was synthesized from 3-[N-(cyclohexylmethyl)formamido]-N-cyclopropyl-2-hydroxybutanamide (I-166) in a similar manner to method A, general procedure 4 (general scheme 4) as a colourless viscous oil (57 mg, 100% purity, 32%) after purification by flash column chromatography on normal phase silica (10 g SNAP KP-SIL cartridge, 0-35% EtOAc in heptane gradient) followed by preparative LC (acidic pH, standard elution method).

$^1$H NMR (500 MHz, Chloroform-d) δ 0.51-0.64 (m, 2H), 0.74-0.85 (m, 2H), 0.85-0.96 (m, 2H), 1.10-1.35 (m, 3H), 1.42-1.54 (m, 3H), 1.61-1.66 (m, 1H), 1.66-1.83 (m, 5H), 2.68-2.82 (m, 1H), 2.93-3.18 (m, 1H), 3.27-3.37 (m, 1H), 4.23-5.09 (m, 1H), 6.64-6.97 (m, 1H), 7.81-8.30 (m, 1H).

LC-MS (Achiral SFC): 100% (UV), Rt=1.25 min, m/z (ESI$^+$)=583.4 [2M+Na]$^+$

3-(N-Benzylformamido)-N-cyclopropyl-2-oxobutanamide (FP 44)

The title compound was synthesized from 3-(N-benzylformamido)-N-cyclopropyl-2-hydroxybutanamide (I-167) in a similar manner to method A, general procedure 4 (general scheme 4) as a colourless viscous oil (22 mg, 100% purity, 12%) after purification by flash column chromatography on normal phase silica (10 g SNAP KP-SIL cartridge, 0-40% EtOAc in heptane gradient) followed by preparative LC (acidic pH, standard elution method).

$^1$H NMR (500 MHz, Chloroform-d) δ 0.45-0.62 (m, 2H), 0.76-0.87 (m, 2H), 1.13-1.43 (m, 3H), 2.57-2.76 (m, 1H), 4.19-5.16 (m, 3H), 6.37-6.79 (m, 1H), 7.19-7.29 (m, 2H), 7.32-7.42 (m, 3H), 8.13-8.44 (m, 1H).

LC-MS (Achiral SFC): 100% (UV), Rt=1.2 min, m/z (ESI$^+$)=571.3 [2M+Na]$^+$

3-[N-(2,2-Dimethylpropyl)formamido]-N-(2-methylpropyl)-2-oxobutanamide (FP 45)

The title compound was synthesized from 3-[N-(2,2-dimethylpropyl)formamido]-2-hydroxy-N-(2-methylpropyl)butanamide (I-168) in a similar manner to method A, general procedure 4 (general scheme 4) as an off-white powder (30 mg, 100% purity, 12%) after purification by flash column chromatography on normal phase silica (10 g SNAP KP-SIL cartridge, 0-50% EtOAc in heptane gradient) followed by trituration in heptane.

$^1$H NMR (500 MHz, Chloroform-d) δ 0.89-1.11 (m, 15H), 1.51-1.69 (m, 3H), 1.79-1.88 (m, 1H), 2.81-3.22 (m, 3H), 3.25-3.56 (m, 1H), 4.17-5.11 (m, 1H), 6.65-7.04 (m, 1H), 7.88-8.36 (m, 1H).

LC-MS (MET-uPLC-AB-101): 100% (UV), Rt=3.09 min, m/z (ESI$^+$)=271.2 [M+H]$^+$

N-(2-Methylpropyl)-2-oxo-3-[N-(2,2,2-trifluoroethyl)formamido]butanamide (FP 46)

The title compound was synthesized from 2-hydroxy-N-(2-methylpropyl)-3-[N-(2,2,2-trifluoroethyl)formamido]butanamide (I-169) in a similar manner to method A, general procedure 4 (general scheme 4) as an off-white solid (102 mg, 100% purity, 52%) after purification by flash column chromatography on normal phase silica (10 g SNAP KP-SIL cartridge, 0-35% EtOAc in heptane gradient) followed by trituration in 1:1 EtOAc/heptane.

$^1$H NMR (500 MHz, Chloroform-d) δ 0.90-0.95 (m, 6H), 1.51-1.64 (m, 3H), 1.76-1.89 (m, 1H), 3.05-3.18 (m, 2H), 3.86-4.06 (m, 1H), 4.09-4.24 (m, 1H), 4.33-5.18 (m, 1H), 6.69-7.00 (m, 1H), 7.98-8.31 (m, 1H).

LC-MS (MET-uPLC-AB-101): 100% (UV), Rt=2.61 min, m/z (ESI$^+$)=283.1 [M+H]$^+$

3-(N-Benzylformamido)-N-(2-methylpropyl)-2-oxobutanamide (FP 47)

The title compound was synthesized from 3-(N-benzylformamido)-2-hydroxy-N-(2-methylpropyl)butanamide (I-170) in a similar manner to method A, general procedure 4 (general scheme 4) as a yellow viscous oil (64 mg, 100% purity, 41%) after purification by flash column chromatography on normal phase silica (10 g SNAP KP-SIL cartridge, 0-40% EtOAc in heptane gradient).

$^1$H NMR (500 MHz, Chloroform-d) δ 0.85-0.95 (m, 6H), 1.15-1.44 (m, 3H), 1.69-1.87 (m, 1H), 2.89-3.18 (m, 2H), 4.28-5.17 (m, 3H), 6.46-6.80 (m, 1H), 7.21-7.29 (m, 2H), 7.32-7.41 (m, 3H), 8.14-8.45 (m, 1H).

LC-MS (Achiral SFC): 100% (UV), Rt=1.1 min, m/z (ESI$^+$)=291.2 [M+H]$^+$

N-(Cyclohexylmethyl)-2-oxo-3-[N-(propan-2-yl)formamido]butanamide (FP 48)

The title compound was synthesized from N-(cyclohexylmethyl)-2-hydroxy-3-[N-(propan-2-yl)formamido]butanamide (I-171) in a similar manner to method A, general procedure 4 (general scheme 4) as a yellow viscous oil (107 mg, 96% purity, 32%) after purification by flash column chromatography on normal phase silica (10 g SNAP KP-SIL cartridge, 0-40% EtOAc in heptane gradient).

$^1$H NMR (500 MHz, Chloroform-d) δ 0.84-0.92 (m, 1H), 0.92-1.00 (m, 2H), 1.13-1.29 (m, 4H), 1.38-1.59 (m, 9H), 1.63-1.78 (m, 4H), 3.04-3.21 (m, 2H), 3.77-5.19 (m, 2H), 6.61-7.05 (m, 1H), 8.04-8.28 (m, 1H).

LC-MS (MET-uPLC-AB-101): 96% (UV), Rt=3.06 min, m/z (ESI$^+$)=283.2 [M+H]$^+$

N-(Cyclohexylmethyl)-3-{N-[(oxan-4-yl)methyl]formamido}-2-oxobutanamide (FP 49)

The title compound was synthesized from N-(cyclohexylmethyl)-2-hydroxy-3-{N[(oxan-4-yl)methyl]formamido}butanamide (I-172) in a similar manner to method A, general procedure 4 (general scheme 4) as an off-white solid (180 mg, 97% purity, 44%) after purification by flash column chromatography on normal phase silica (10 g SNAP KP-SIL cartridge, 0-35% EtOAc in heptane gradient) followed by trituration in heptane.

$^1$H NMR (500 MHz, Chloroform-d) δ 0.80-0.93 (m, 2H), 1.02-1.68 (m, 16H), 1.71-1.93 (m, 1H), 2.98-3.40 (m, 6H), 3.85-3.98 (m, 2H), 4.20-5.06 (m, 1H), 6.57-6.91 (m, 1H), 7.74-8.26 (m, 1H).

LC-MS (MET-uPLC-AB-101): 97% (UV), Rt=2.89 min, m/z (ESI$^+$)=339.2 [M+H]$^+$

N-(Cyclohexylmethyl)-2-oxo-3-[N-(2,2,2-trifluoroethyl)formamido]butanamide (FP 50)

The title compound was synthesized from N-(cyclohexylmethyl)-2-hydroxy-3-[N-(2,2,2-trifluoroethyl)formamido]butanamide (I-173) in a similar manner to method A, general procedure 4 (general scheme 4) as an off-white solid (18 mg, 96% purity, 10%) after purification by flash column chromatography on normal phase silica (10 g SNAP KP-SIL cartridge, 0-60% EtOAc in heptane gradient) followed by preparative LC (acidic pH, standard elution method).

$^1$H NMR (500 MHz, Chloroform-d) δ 0.84-1.01 (m, 2H), 1.10-1.30 (m, 3H), 1.42-1.77 (m, 9H), 3.00-3.23 (m, 2H), 3.85-4.05 (m, 1H), 4.07-4.24 (m, 1H), 4.34-5.18 (m, 1H), 6.69-6.99 (m, 1H), 7.95-8.31 (m, 1H).

LC-MS (METCR1600): 96% (UV), Rt=4.71 min, m/z (ESI$^+$)=323.2 [M+H]$^+$

N-(Cyclohexylmethyl)-3-[N-(cyclopropylmethyl)formamido]-2-oxobutanamide (FP 51)

The title compound was synthesized from N-(cyclohexylmethyl)-3-[N-(cyclopropylmethyl)formamido]-2-hydroxybutanamide (I-174) in a similar manner to method A, general procedure 4 (general scheme 4) as a yellow viscous oil (92 mg, 97% purity by $^1$H NMR, 52%) after purification by flash column chromatography on normal phase silica (10 g SNAP KP-SIL cartridge, 0-35% EtOAc in heptane gradient).

$^1$H NMR (500 MHz, Chloroform-d) δ 0.20-0.34 (m, 2H), 0.39-0.72 (m, 2H), 0.87-0.99 (m, 2H), 1.05-1.27 (m, 4H), 1.45-1.55 (m, 4H), 1.63-1.76 (m, 5H), 3.04-3.18 (m, 2H), 3.19-3.35 (m, 2H), 4.36-5.21 (m, 1H), 6.65-6.96 (m, 1H), 7.95-8.29 (m, 1H).

LC-MS (Achiral SFC): 100% (UV), Rt=1.21 min, m/z (ESI$^+$)=295.2 [M+H]$^+$ 3-(N-Cyclohexylformamido)-N-(cyclohexylmethyl)-2-oxobutanamide (FP 52)

The title compound was synthesized from 3-(N-cyclohexylformamido)-N-(cyclohexylmethyl)-2-hydroxybutanamide (I-175) in a similar manner to method A, general procedure 4 (general scheme 4) as a colourless viscous oil (70 mg, 97% purity, 43%) after purification by flash column chromatography on normal phase silica (10 g SNAP KP-SIL cartridge, 0-35% EtOAc in heptane gradient).

$^1$H NMR (500 MHz, Chloroform-d) δ 0.81-0.98 (m, 2H), 1.09-1.27 (m, 4H), 1.29-1.39 (m, 2H), 1.44-1.67 (m, 7H), 1.67-1.76 (m, 5H), 1.77-1.93 (m, 2H), 2.02-2.13 (m, 2H), 3.03-3.23 (m, 2H), 3.31-4.16 (m, 1H), 4.24-5.19 (m, 1H), 6.57-6.98 (m, 1H), 8.02-8.25 (m, 1H).

LC-MS (MET-uPLC-AB-101): 97% (UV), Rt=3.73 min, m/z (ESI$^+$)=323.2 [M+H]$^+$ tert-Butyl 4-[(N-{1-[(cyclohexylmethyl)carbamoyl]-1-oxopropan-2-yl}formamido)-methyl]piperidine-1-carboxylate (FP 53)

The title compound was synthesized from tert-butyl 4-[(N-{1-[(cyclohexyl-methyl)carbamoyl]-1-hydroxypropan-2-yl}formamido)methyl]piperidine-1-carboxylate (I-176) in a similar manner to method A, general procedure 4 (general scheme 4) as an off-white powder (210 mg, 100% purity, 84%) after purification by flash column chromatography on normal phase silica (10 g SNAP KP-SIL cartridge, 0-70% EtOAc in heptane gradient) followed by trituration in heptane.

$^1$H NMR (500 MHz, Chloroform-d) δ 0.85-1.00 (m, 2H), 1.03-1.29 (m, 5H), 1.43-1.56 (m, 15H), 1.63-1.79 (m, 6H), 1.80-1.92 (m, 1H), 2.57-4.23 (m, 7H), 4.25-5.13 (m, 1H), 6.64-6.97 (m, 1H), 7.82-8.29 (m, 1H).

LC-MS (METCR1600): 100% (UV), Rt=4.39 min, m/z (ESI$^+$)=438.4 [M+H]$^+$ tert-Butyl N-[(1s,4s)-4-(N{1-[(cyclohexylmethyl)carbamoyl]-1-oxopropan-2-yl}-formamido)cyclohexyl]carbamate (FP 54)

The title compound was synthesized from tert-butyl N-[(1s,4s)-4-(N-{1-[(cyclohexylmethyl)carbamoyl]-1-hydroxypropan-2-yl}formamido)cyclohexyl]carbamate (I-177) in a similar manner to method A, general procedure 4 (general scheme 4) as an off-white solid (252 mg, 96% purity, 41%) after trituration in DCM and purification of the filtrate by flash column chromatography on normal phase silica (25 g SNAP KP-SIL cartridge, 0-100% TBME in heptane gradient).

$^1$H NMR (250 MHz, Chloroform-d) δ 0.78-1.07 (m, 3H), 1.10-1.37 (m, 4H), 1.42-1.55 (m, 12H), 1.62-1.88 (m, 9H), 1.92-2.11 (m, 3H), 2.99-3.29 (m, 2H), 3.38-3.52 (m, 1H), 3.72-3.97 (m, 1H), 4.14-5.24 (m, 2H), 6.59-7.04 (m, 1H), 8.01-8.27 (m, 1H).

LC-MS (METCR1600): 96% (UV), Rt=3.83 min, m/z (ESI$^+$)=438.4 [M+H]$^+$ 3-(N-Cyclohexylformamido)-N-[2-(cyclohexyloxy)ethyl]-2-oxobutanamide (FP 55)

The title compound was synthesized from 3-(N-cyclohexylformamido)-N-[2-(cyclohexyloxy)ethyl]-2-hydroxybutanamide (I-178) in a similar manner to method A, general procedure 4 (general scheme 4) as a yellow gum (40 mg, 95% purity by $^1$H NMR, 16%) after purification by flash column chromatography on normal phase silica (25 g SNAP KP-SIL cartridge, 0-100% TBME in heptane gradient).

$^1$H NMR (500 MHz, Chloroform-d) δ 1.11-1.39 (m, 8H), 1.44-1.50 (m, 3H), 1.50-1.57 (m, 3H), 1.63-1.76 (m, 3H), 1.79-1.95 (m, 4H), 2.00-2.14 (m, 2H), 3.20-3.27 (m, 1H), 3.30-3.59 (m, 5H), 4.26-5.21 (m, 1H), 7.02 (s, 1H), 7.98-8.30 (m, 1H).

LC-MS (METCR1400): 86% (UV), Rt=4.15 min, m/z (ESI$^+$)=353.5 [M+H]$^+$

Methyl 2-[3-(N-benzylformamido)-2-oxobutanamido]acetate (FP 56)

The title compound was synthesized from methyl 2-[3-(N-benzylformamido)-2-hydroxybutanamido]acetate (I-179) in a similar manner to method A, general procedure 4 (general scheme 4) as a colourless viscous oil (13 mg, 98% purity, 4%) after purification by preparative LC (acidic pH, standard elution method) followed by a second preparative LC (basic pH, standard elution method).

$^1$H NMR (500 MHz, Chloroform-d) δ 1.18-1.44 (m, 3H), 3.66-3.80 (m, 3H), 3.81-5.13 (m, 5H), 6.83-7.20 (m, 1H), 7.20-7.26 (m, 1H), 7.27-7.42 (m, 4H), 8.15-8.44 (m, 1H).

LC-MS (METCR1600): 98% (UV), Rt=3.30-4.00 min (multiple peaks), m/z (ESI$^+$)=307.5 [M+H]$^+$

3-(N-Benzylformamido)-2-oxo-N-(propan-2-yl)butanamide (FP 57)

The title compound was synthesized from 3-(N-benzylformamido)-2-hydroxy-N-(propan-2-yl)butanamide (I-180) in a similar manner to method A, general procedure 4 (general scheme 4) as a yellow viscous oil (51 mg, 100% purity, 42%) after purification by flash column chromatography on normal phase silica (10 g SNAP KP-SIL cartridge, 0-35% EtOAc in heptane gradient) followed by preparative LC (acidic pH, standard elution method).

$^1$H NMR (500 MHz, Chloroform-d) δ 1.10-1.22 (m, 6H), 1.16-1.43 (m, 3H), 3.86-4.08 (m, 1H), 4.27-4.62 (m, 1H), 4.34-5.17 (m, 1H), 4.64-4.80 (m, 1H), 6.27-6.60 (m, 1H), 7.20-7.29 (m, 2H), 7.32-7.41 (m, 3H), 8.14-8.45 (m, 1H).

LC-MS (METCR1600): 100% (UV), Rt=3.70-4.30 min (multiple peaks), m/z (ESI$^+$)=277.5 [M+H]$^+$

N-(Cyclopropylmethyl)-3-{N-[(oxan-4-yl)methyl]formamido}-2-oxohexanamide (FP 58)

The title compound was synthesized from N-(cyclopropylmethyl)-2-hydroxy-3-{N[(oxan-4-yl)methyl]formamido}hexanamide (I-181) in a similar manner to method A, general procedure 4 (general scheme 4) as a colourless viscous oil (10 mg, 98% purity, 5%) after purification twice by flash column chromatography on normal phase silica (10 g SNAP KP-SIL cartridge, 0-40% EtOAc in heptane gradient).

$^1$H NMR (500 MHz, Chloroform-d) δ 0.17-0.28 (m, 2H), 0.48-0.58 (m, 2H), 0.91-1.00 (m, 4H), 1.19-2.18 (m, 9H), 3.03-3.32 (m, 5H), 3.36-3.45 (m, 1H), 3.87-3.96 (m, 1H), 3.96-4.02 (m, 1H), 4.38-5.03 (m, 1H), 6.76-7.10 (m, 1H), 7.88-8.34 (m, 1H).

LC-MS (METCR1600): 98% (UV), Rt=4.01 min, m/z (ESI$^+$)=325.3 [M+H]$^+$ tert-Butyl 4-[(N-{1-[(cyclohexylmethyl)carbamoyl]-1-oxobutan-2-yl}formamido)methyl]-piperidine-1-carboxylate (FP 59)

The title compound was synthesized from tert-butyl 4-[(N-{1-[(cyclohexyl-methyl)carbamoyl]-1-hydroxybutan-2-yl}formamido)methyl]piperidine-1-carboxylate (I-182) in a similar manner to method A, general procedure 4 (general scheme 4) as an off-white powder (445 mg, 95% purity by $^1$H NMR, 73%) after purification by flash column chromatography on normal phase silica (25 g SNAP KP-SIL cartridge, 0-70% EtOAc in heptane gradient).

$^1$H NMR (500 MHz, Chloroform-d) δ 0.89-0.97 (m, 2H), 0.98-1.02 (m, 3H), 1.04-1.26 (m, 5H), 1.42-1.46 (m, 9H), 1.47-1.56 (m, 2H), 1.58-1.90 (m, 8H), 2.00-2.20 (m, 1H), 2.53-2.79 (m, 2H), 3.04-3.31 (m, 4H), 3.97-4.22 (m, 2H), 4.23-4.96 (m, 1H), 6.68-6.99 (m, 1H), 7.90-8.33 (m, 1H).

LC-MS (MET-uPLC-AB-101): 89% (UV), Rt=4.04 min, m/z (ESI$^+$)=452.3 [M+H]$^+$

3-(N-Cyclohexylformamido)-N-(cyclohexylmethyl)-2-oxopentanamide (FP 60)

The title compound was synthesized from 3-(N-cyclohexylformamido)-N-(cyclohexylmethyl)-2-hydroxypentanamide (I-183) in a similar manner to method A, general procedure 4 (general scheme 4) as a brown viscous oil (45 mg, 95% purity by $^1$H NMR, 9%) after purification by flash column chromatography on normal phase silica (25 g SNAP KP-SIL cartridge, 0-100% EtOAc in heptane gradient then 0-20% MeOH in EtOAc gradient) followed by preparative LC (acidic pH, standard elution method).

$^1$H NMR (500 MHz, Chloroform-d) δ 0.86-0.96 (m, 2H), 0.96-1.05 (m, 3H), 1.06-1.56 (m, 10 OH), 1.56-1.75 (m, 6H), 1.75-1.83 (m, 1H), 1.83-2.10 (m, 3H), 2.10-2.19 (m, 1H), 3.02-3.19 (m, 2H), 3.20-4.19 (m, 1H), 4.27-4.98 (m, 1H), 6.68-7.04 (m, 1H), 8.11-8.23 (m, 1H).

LC-MS (METCR1416): 89% (UV), Rt=4.76 min, m/z (ESI$^+$)=337.5 [M+H]$^+$ tert-Butyl 3-[(NM{1-[(cyclohexylmethyl)carbamoyl]-1-oxobutan-2-yl}formamido)methyl]-azetidine-1-carboxylate (FP 61)

The title compound was synthesized from tert-butyl 3-[(N-{1-[(cyclohexyl-methyl)carbamoyl]-1-hydroxybutan-2-yl}formamido)methyl]azetidine-1-carboxylate (I-184) in a similar manner to method A, general procedure 4 (general scheme 4) as a colourless gum (90 mg, 95% purity by 1H NMR, 43%) after purification by flash column chromatography on normal phase silica (25 g SNAP KP-SIL cartridge, 0-100% TBME in heptane gradient).

$^1$H NMR (500 MHz, Chloroform-d) δ 0.74-1.02 (m, 5H), 1.08-1.33 (m, 4H), 1.37-1.48 (m, 10H), 1.63-1.78 (m, 6H), 2.01-2.22 (m, 1H), 2.66-3.03 (m, 1H), 3.07-3.23 (m, 2H), 3.48-3.72 (m, 3H), 3.89-4.95 (m, 3H), 6.61-7.03 (m, 1H), 7.99-8.25 (m, 1H).

LC-MS (METCR1600): 92% (UV), Rt=3.85 min, m/z (ESI$^+$)=424.3 [M+H]$^+$

N-(Cyclopropylmethyl)-3-[N-(cyclopropylmethyl)formamido]-5-methyl-2-oxohexanamide (FP 62)

The title compound was synthesized from N-(cyclopropylmethyl)-3-[N-(cyclopropylmethyl)formamido]-2-hydroxy-5-methylhexanamide (I-185) in a similar manner to method A, general procedure 4 (general scheme 4) as a yellow viscous oil (46 mg, 95% purity by $^1$H NMR, 25%) after purification by flash column chromatography on normal phase silica (10 g SNAP KP-SIL cartridge, 0-40% EtOAc in heptane gradient) followed by preparative LC (acidic pH, standard elution method).

$^1$H NMR (500 MHz, Chloroform-d) δ −0.07-0.10 (m, 4H), 0.18-0.28 (m, 1H), 0.28-0.37 (m, 2H), 0.39-0.48 (m, 1H), 0.61-0.90 (m, 8H), 1.31-2.01 (m, 3H), 2.77-4.98 (m, 5H), 6.58-6.82 (m, 1H), 7.86-8.12 (m, 1H).
LC-MS (METCR1600): 93% (UV), Rt=4.6 min, m/z (ESI$^+$)=295.3 [M+H]$^+$ N-(Cyclopropylmethyl)-5-methyl-3-{N-[(oxan-4-yl)methyl]formamido}-2-oxohexanamide (FP 63)

The title compound was synthesized from N-(cyclopropylmethyl)-2-hydroxy-5-methyl-3-{N-[(oxan-4-yl)methyl]formamido}hexanamide (I-186) in a similar manner to method A, general procedure 4 (general scheme 4) as a yellow viscous oil (85 mg, 92% purity by $^1$H NMR, 28%) after purification by flash column chromatography on normal phase silica (10 g SNAP KP-SIL cartridge, 0-60% EtOAc in heptane gradient) followed by preparative LC (acidic pH, standard elution method).
$^1$H NMR (500 MHz, Chloroform-d) δ 0.15-0.28 (m, 2H), 0.45-0.62 (m, 2H), 0.81-0.93 (m, 1H), 0.94-1.01 (m, 6H), 1.18-1.51 (m, 4H), 1.60-1.97 (m, 4H), 2.10-5.15 (m, 9H), 6.75-7.08 (m, 1H), 7.91-8.35 (m, 1H).
LC-MS (METCR1600): 96% (UV), Rt=4.27 min, m/z (ESI$^+$)=339.4 [M+H]$^+$ N-(Cyclopropylmethyl)-5-methyl-2-oxo-3-(N{[(3S)-oxolan-3-yl]methyl}formamido) hexanamide (FP 64)

The title compound was synthesized from N-(cyclopropylmethyl)-2-hydroxy-5-methyl-3-(N{[(3S)-oxolan-3-yl]methyl}formamido)hexanamide (I-187) in a similar manner to method A, general procedure 4 (general scheme 4) as a yellow viscous oil (25 mg, 95% purity by 1H NMR, 8%) after purification by flash column chromatography on normal phase silica (25 g SNAP KP-SIL cartridge, 0-100% TBME in heptane gradient) followed by trituration in EtOAc and preparative LC (acidic pH, standard elution method).
$^1$H NMR (500 MHz, Chloroform-d) δ 0.13-0.30 (m, 2H), 0.46-0.61 (m, 2H), 0.87-1.04 (m, 7H), 1.34-1.74 (m, 3H), 1.76-1.97 (m, 1H), 2.05-2.29 (m, 1H), 2.33-2.81 (m, 1H), 3.02-3.62 (m, 5H), 3.67-3.97 (m, 3H), 4.34-5.17 (m, 1H), 6.72-7.09 (m, 1H), 7.89-8.34 (m, 1H).
LC-MS (MET-uPLC-AB-102): 93% (UV), Rt=2.86 min, m/z (ESI$^+$)=325.2 [M+H]$^+$ N-(Cyclopropylmethyl)-5-methyl-2-oxo-3-(N-{[(3R)-oxolan-3-yl]methyl}formamido) hexanamide (FP 65)

The title compound was synthesized from N-(cyclopropylmethyl)-2-hydroxy-5-methyl-3-(N{[(3R)-oxolan-3-yl]methyl}formamido)hexanamide (I-188) in a similar manner to method A, general procedure 4 (general scheme 4) as a colourless viscous oil (22 mg, 98% purity, 8%) after purification by flash column chromatography on normal phase silica (25 g SNAP KP-SIL cartridge, 0-100% TBME in heptane gradient) followed by trituration in EtOAc and preparative LC (acidic pH, standard elution method).
$^1$H NMR (500 MHz, Chloroform-d) δ 0.13-0.33 (m, 2H), 0.45-0.62 (m, 2H), 0.84-1.06 (m, 7H), 1.31-1.75 (m, 3H), 1.75-1.99 (m, 1H), 2.04-2.28 (m, 1H), 2.34-2.74 (m, 1H), 3.04-3.59 (m, 5H), 3.69-3.99 (m, 3H), 4.34-5.16 (m, 1H), 6.71-7.11 (m, 1H), 7.89-8.34 (m, 1H).
LC-MS (MET-uPLC-AB-102): 98% (UV), Rt=2.86 min, m/z (ESI$^+$)=325.2 [M+H]$^+$ 3-Cyclopropyl-N-(cyclopropylmethyl)-3-{N-[(oxan-4-yl)methyl]formamido}-2-oxopropanamide (FP 66)

The title compound was synthesized from 3-cyclopropyl-N-(cyclopropylmethyl)-2-hydroxy-3-{N[(oxan-4-yl)methyl]formamido}propanamide (I-192) in a similar manner to method A, general procedure 4 (general scheme 4) as a colourless viscous oil (210 mg, 95% purity by $^1$H NMR, 66%) after purification by flash column chromatography on normal phase silica (10 g SNAP KP-SIL cartridge, 0-100% EtOAc in heptane gradient).
$^1$H NMR (500 MHz, Chloroform-d) δ 0.20-0.29 (m, 2H), 0.38-0.44 (m, 1H), 0.51-0.60 (m, 2H), 0.61-0.68 (m, 1H), 0.71-0.83 (m, 2H), 0.93-1.03 (m, 1H), 1.10-1.35 (m, 3H), 1.46-1.78 (m, 2H), 1.79-2.00 (m, 1H), 3.06-3.36 (m, 4H), 3.37-3.47 (m, 2H), 3.91-4.05 (m, 2H), 4.08-4.28 (m, 1H), 6.86-7.04 (m, 1H), 7.95-8.44 (m, 1H).
LC-MS (METCR1600): 100% (UV), Rt=3.76 min (two peaks), m/z (ESI$^+$)=323.2 [M+H]$^+$ 3-(N-Benzylformamido)-3-cyclopropyl-N-(cyclopropylmethyl)-2-oxopropanamide (FP 67)

The title compound was synthesized from 3-(N-benzylformamido)-3-cyclo-propyl-N-(cyclopropylmethyl)-2-hydroxypropanamide (I-193) in a similar manner to method A, general procedure 4 (general scheme 4) as a colourless viscous oil (213 mg, 96% purity by $^1$H NMR, 77%) after purification by flash column chromatography on normal phase silica (10 g SNAP KP-SIL cartridge, 0-50% EtOAc in heptane gradient).
$^1$H NMR (500 MHz, Chloroform-d) δ −0.19-0.17 (m, 1H), 0.17-0.29 (m, 2H), 0.32-0.74 (m, 5H), 0.85-1.02 (m, 1H), 1.05-1.27 (m, 1H), 2.96-3.11 (m, 1H), 3.10-3.24 (m, 1H), 4.07-4.21 (m, 1H), 4.30-4.81 (m, 2H), 6.54-6.94 (m, 1H), 7.20-7.26 (m, 2H), 7.26-7.34 (m, 2H), 7.35-7.40 (m, 1H), 8.19-8.55 (m, 1H).
LC-MS (METCR1600): 100% (UV), Rt=4.31 min, m/z (ESI$^+$)=315.2 [M+H]$^+$ N-(Cyclopropylmethyl)-3-{N-[(oxan-4-yl)methyl]formamido}-2-oxo-5-phenylpentanamide (FP 68)

The title compound was synthesized from N-(cyclopropylmethyl)-2-hydroxy-3-{N-[(oxan-4-yl)methyl]formamido}-5-phenylpentanamide (I-194) in a similar manner to method A, general procedure 4 (general scheme 4) as a yellow viscous oil (86 mg, 100% purity, 29%) after purification by flash column chromatography on normal phase silica (25 g SNAP KP-SIL cartridge, 0-70% EtOAc in heptane gradient) followed by preparative LC (acidic pH, standard elution method).
$^1$H NMR (500 MHz, Chloroform-d) δ 0.16-0.27 (m, 2H), 0.46-0.63 (m, 2H), 0.90-1.02 (m, 1H), 1.10-1.35 (m, 2H), 1.41-1.73 (m, 3H), 1.82-2.07 (m, 1H), 2.34-2.70 (m, 2H), 2.72-2.85 (m, 1H), 2.99-3.24 (m, 4H), 3.25-3.36 (m, 2H), 3.86-4.00 (m, 2H), 4.19-5.04 (m, 1H), 6.78-7.02 (m, 1H), 7.15-7.25 (m, 3H), 7.28-7.34 (m, 2H), 7.88-8.33 (m, 1H).
LC-MS (METCR1600): 100% (UV), Rt=4.49 min, m/z (ESI$^+$)=387.0 [M+H]$^+$ N-[(3-Chlorophenyl)methyl]-3-(N-methylformamido)-2-oxobutanamide (FP 69)

The title compound was synthesized from N-[(3-chlorophenyl)methyl]-2-hydroxy-3-(N-methylformamido)butanamide (I-195) in a similar manner to method A, general procedure 4 (general scheme 4) as a colourless viscous oil (42 mg, 95% purity by 1H NMR, 14%) after purification by flash column chromatography on normal phase silica (10 g SNAP KP-SIL cartridge, 0-70% EtOAc in heptane gradient) then trituration in 4:1 EtOAc/heptane, followed by preparative LC (acidic pH, standard elution method).

$^1$H NMR (500 MHz, DMSO-d6) δ 1.23-1.43 (m, 3H), 2.61-3.04 (m, 3H), 4.27-4.36 (m, 2H), 4.57-5.25 (m, 1H), 7.17-7.24 (m, 1H), 7.27-7.38 (m, 3H), 7.92-8.13 (m, 1H), 9.11-9.40 (m, 1H).

LC-MS (METCR1600): 100% (UV), Rt=3.45-4.10 min (multiple peaks), m/z (ESI$^+$)=283.2/285.1 [M+H]$^+$ 3-(N-Benzylformamido)-MN-(cyclopropylmethyl)-5-methoxy-2-oxopentanamide (FP 70)

The title compound was synthesized from 3-(N-benzylformamido)-N-(cyclo-propylmethyl)-2-hydroxy-5-methoxypentanamide (I-196) in a similar manner to method A, general procedure 4 (general scheme 4) as a yellow viscous oil (39 mg, 100% purity, 31%) after purification by flash column chromatography on normal phase silica (10 g SNAP KP-SIL cartridge, 0-70% EtOAc in heptane gradient) followed by preparative LC (acidic pH, standard elution method).

$^1$H NMR (500 MHz, Chloroform-d) δ 0.12-0.27 (m, 2H), 0.45-0.57 (m, 2H), 0.80-1.01 (m, 1H), 1.74-1.99 (m, 1H), 2.14-2.41 (m, 1H), 2.88-3.06 (m, 1H), 3.07-3.21 (m, 4H), 3.22-3.39 (m, 2H), 4.24-5.29 (m, 3H), 6.41-6.84 (m, 1H), 7.18-7.28 (m, 3H), 7.31-7.41 (m, 2H), 8.14-8.50 (m, 1H).

LC-MS (METCR1600): 100% (UV), Rt=4.19 min, m/z (ESI$^+$)=333.3 [M+H]$^+$ 3-(N-Benzylformamido)-N-(cyclopropylmethyl)-3-(oxan-4-yl)-2-oxopropanamide (FP 71)

The title compound was synthesized from 3-(N-benzylformamido)-M (cyclopropylmethyl)-2-hydroxy-3-(oxan-4-yl)propanamide (I-197) in a similar manner to method A, general procedure 4 (general scheme 4) as a colourless viscous oil (10 mg, 100% purity, 12%) after purification by preparative LC (acidic pH, standard elution method).

$^1$H NMR (500 MHz, Chloroform-d) δ 0.12-0.23 (m, 2H), 0.47-0.56 (m, 2H), 0.77-0.95 (m, 1H), 0.96-1.21 (m, 1H), 1.22-1.54 (m, 3H), 2.27-2.50 (m, 1H), 2.82-3.17 (m, 2H), 3.24-3.40 (m, 2H), 3.80-3.97 (m, 2H), 4.01-4.49 (m, 1H), 4.57-4.93 (m, 2H), 6.27-6.70 (m, 1H), 7.19-7.29 (m, 4H), 7.29-7.38 (m, 1H), 8.22-8.48 (m, 1H).

LC-MS (METCR1600): 100% (UV), Rt=4.17 min, m/z (ESI$^+$)=359.6 [M+H]$^+$

Method B: Addition of DMP at 0° C.

N-(Cyclopropylmethyl)-3-[N-(3-methoxypropyl)formamido]-5-methyl-2-oxohexanamide (FP 72)

To a stirred, ice cooled solution of N-(cyclopropylmethyl)-2-hydroxy-3-[N-(3-methoxypropyl)formamido]-5-methylhexanamide (I-189, 258 mg, 0.82 mmol) in DCM (2.5 mL), under nitrogen at 0° C., was added DMP (383 mg, 0.9 mmol). The reaction was stirred at RT for 2 h, diluted with DCM (5 mL) and quenched dropwise with saturated NaHCO$_3$(5 mL). The precipitate formed was filtered and washed with DCM (5 mL). The filtrate was passed through a Telos® hydrophobic frit and the organic phase was concentrated in vacuo. The crude material was dissolved in 4:1:5 MeCN:H$_2$O:DMSO (4 mL), filtered and purified by preparative LC (acidic pH, standard elution method) followed by flash column chromatography on normal phase silica (10 g SNAP KP-SIL cartridge, 80-100% TBME in heptane gradient). The material was dried in vacuo at 40° C. for 2 h to afford 75.6 mg of N-(cyclopropylmethyl)-3-[N-(3-methoxy propyl)formamido]-5-methyl-2-oxohexanamide as a colourless free-flowing oil (100% purity, 29%).

$^1$H NMR (500 MHz, Chloroform-d) δ 0.17-0.29 (m, 2H), 0.47-0.60 (m, 2H), 0.90-1.03 (m, 7H), 1.41-2.20 (m, 5H), 3.07-3.20 (m, 2H), 3.22-3.59 (m, 7H), 4.55-5.18 (m, 1H), 6.76-7.04 (m, 1H), 7.95-8.27 (m, 1H).

LC-MS (METCR1600): 100% (UV), Rt=4.3 min, m/z (ESI$^+$)=313.3 [M+H]$^+$

N-(Cyclopropylmethyl)-5-methyl-2-oxo-3-{N-[(oxolan-3-yl)methyl]formamido} hexanamide (FP 73)

The title compound was synthesized from N-(cyclopropylmethyl)-2-hydroxy-5-methyl-3-{N-[(oxolan-3-yl)methyl]formamido}hexanamide (I-190) in a similar manner to method B, general procedure 4 (general scheme 4) as a colourless viscous oil (108 mg, 96% purity by $^1$H NMR, 44%) after purification by preparative LC (acidic pH, standard elution method).

$^1$H NMR (500 MHz, Chloroform-d) δ 0.17-0.28 (m, 2H), 0.46-0.62 (m, 2H), 0.93-1.03 (m, 7H), 1.37-1.70 (m, 3H), 1.78-1.97 (m, 1H), 2.08-2.27 (m, 1H), 2.33-2.74 (m, 1H), 3.01-3.59 (m, 5H), 3.68-3.97 (m, 3H), 4.39-5.16 (m, 1H), 6.72-7.10 (m, 1H), 7.94-8.34 (m, 1H).

LC-MS (METCR1600): 99% (UV), Rt=4.12 min, m/z (ESI$^+$)=325.3 [M+H]$^+$

N-(Cyclopropylmethyl)-5-methyl-2-oxo-3-{N[(oxolan-2-yl)methyl]formamido} hexanamide (FP 74)

The title compound was synthesized from N-(cyclopropylmethyl)-2-hydroxy-5-methyl-3-{N-[(oxolan-2-yl)methyl]formamido}hexanamide (I-191) in a similar manner to method B, general procedure 4 (general scheme 4) as a colourless viscous oil (70 mg, 97% purity by $^1$H NMR, 40%) after purification by preparative LC (acidic pH, standard elution method).

$^1$H NMR (500 MHz, Chloroform-d) δ 0.19-0.27 (m, 2H), 0.50-0.58 (m, 2H), 0.90-1.03 (m, 7H), 1.37-1.71 (m, 3H), 1.71-2.00 (m, 3H), 2.01-2.60 (m, 1H), 3.05-3.89 (m, 6H), 3.98-4.23 (m, 1H), 4.65-5.20 (m, 1H), 6.75-7.12 (m, 1H), 8.01-8.36 (m, 1H).

LC-MS (METCR1600): 100% (UV), Rt=4.39 min, m/z (ESI$^+$)=325.3 [M+H]$^+$

Method C: Oxidation Using IBX

N-tert-Butyl-3-[N-(2-methoxyphenyl)formamido]-2-oxobutanamide (FP 75)

To a stirred solution of N-tert-butyl-2-hydroxy-3-[N-(2-methoxyphenyl)formamido]butanamide (I-151) (117 mg, 0.38 mmol) in MeCN (4 mL) was added IBX (212 mg, 0.76 mmol). The solution was stirred at RT for 1 h then heated at 80° C. for 1 h. IBX (70 mg, 0.19 mmol) was added and heating continued for 1 h. The mixture was cooled to RT and filtered. The filtrate was concentrated in vacuo and the crude residue was purified by preparative LC (acidic pH, standard elution method) to afford 67 mg of N-tert-butyl-3-[N-(2-methoxyphenyl)formamido]-2-oxobutanamide as a colourless viscous oil (95% purity, 55%).

¹H NMR (500 MHz, Chloroform-d) δ 1.31-1.40 (m, 3H), 1.39-1.44 (m, 9H), 3.70-3.85 (m, 3H), 5.05-5.46 (m, 1H), 6.60-6.84 (m, 1H), 6.91-7.06 (m, 2H), 7.28-7.39 (m, 1H), 7.10-7.59 (m, 1H), 7.98-8.60 (m, 1H).

LC-MS (MET-uPLC-AB-101): 95% (UV), Rt=3.05 min, m/z (ESI⁺)=307.1 [M+H]⁺

N-[4-(7-Chloro-1,2,3,4-tetrahydroisoquinolin-2-yl)-3,4-dioxobutan-2-yl]-N-(2-methoxy-phenyl)formamide (FP 76)

The title compound was synthesized from N-[4-(7-chloro-1,2,3,4-tetrahydro isoquinolin-2-yl)-3-hydroxy-4-oxobutan-2-yl]-N-(2-methoxyphenyl)formamide (I-154) in a similar manner to method C, general procedure 4 (general scheme 4) directly at 80 C and was obtained as a colourless glass (23 mg, 99% purity, 46%) after purification by preparative LC (acidic pH, standard elution method).

¹H NMR (500 MHz, Chloroform-d) δ 1.49-1.54 (m, 3H), 2.86-3.00 (m, 2H), 3.80-3.94 (m, 5H), 4.66-4.82 (m, 3H), 6.96-7.10 (m, 3H), 7.13-7.18 (m, 2H), 7.33 (tdd, J=1.7, 2.8, 8.2 Hz, 1H), 7.56 (ddd, J=1.6, 5.1, 6.8 Hz, 1H), 7.97-8.06 (m, 1H).

LC-MS (MET-uPLC-AB-101): 99% (UV), Rt=3.88 min, m/z (ESI⁺)=401.1/403.1 [M+H]⁺

General Procedure 5 (General Scheme 4): N-Methylation

N-[(3-Chlorophenyl)methyl]-3-[N-(2-methoxyphenyl)formamido]-N-methyl-2-oxobutanamide (FP 77)

To a stirred solution of N-[(3-chlorophenyl)methyl]-3-[N-(2-methoxyphenyl)-formamido]-2-oxobutanamide (FP 1, 104 mg, 0.27 mmol) in MeCN (4 mL), in a sealed tube under nitrogen, was added K₂CO₃ (55 mg, 0.4 mmol) followed by iodomethane (33 μL, 0.53 mmol). The reaction was stirred at RT for 18 h then at 50° C. for 3 h. The mixture was cooled and treated with sodium tert-butoxide (33 mg, 0.34 mmol) and iodomethane (33 μL, 0.53 mmol) and stirred at RT for 3 h. The mixture was diluted with EtOAc (10 mL), washed with water (10 mL) and the organic layer dried over sodium sulfate, filtered and concentrated in vacuo to give a crude material which was purified by preparative LC (acidic pH, standard elution method) to afford 10 mg of N-[(3-chlorophenyl)methyl]-3-[N-(2-methoxyphenyl)formamido]-N-methyl-2-oxobutanamide as a colourless oil (98% purity, 10%).

¹H NMR (500 MHz, Chloroform-d) δ 1.64-2.40 (m, 3H), 3.39-3.71 (m, 4H), 3.76-3.88 (m, 3H), 4.49 (dd, J=13.9, 5.6 Hz, 2H), 6.76-7.07 (m, 3H), 7.12-7.24 (m, 2H), 7.27-7.36 (m, 3H), 7.96-8.56 (m, 1H).

LC-MS (MET-uPLC-AB-101): 98% (UV), Rt=3.24 min, m/z (ESI⁺)=389.1/391.1 [M+H]⁺

Further compounds (FP 192-FP 194) were synthesised via general scheme 4 and these compounds are described in the additional compound section.

GENERAL SCHEME 5:

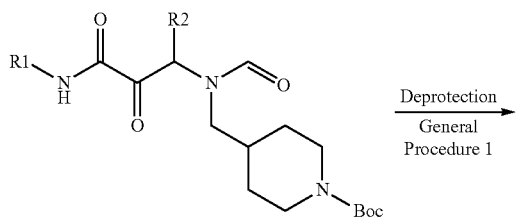

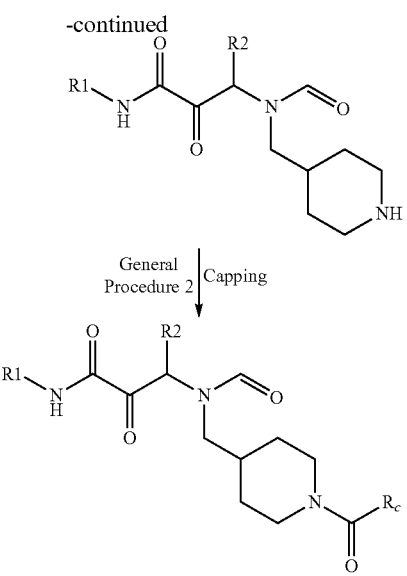

General Procedure 1 (General Scheme 5): Deprotection

N-(Cyclohexylmethyl)-2-oxo-3-[N-(piperdin-4-ylmethyl)formamido]butanamide (TFA salt) (I-198)

To a stirred solution of tert-butyl 4-[(N-{1-[(cyclohexylmethyl)carbamoyl]-1-oxopropan-2-yl}formamido)methyl]piperidine-1-carboxylate (FP 53, 89% purity, 140 mg, 0.28 mmol) in DCM (6 mL) was added TFA (145 μL, 1.88 mmol) and the mixture was stirred at RT for 30 min. TFA was added (66 μL, 0.86 mmol) and the reaction was stirred for 30 min and concentrated in vacuo to afford 150 mg of N-(cyclohexylmethyl)-2-oxo-3-[N-(piperidin-4-ylmethyl)formamido]butanamide (TFA salt) as an off white solid (72% purity, quantitative). The crude material was used in the next step without further purification.

LC-MS (METCR1410): 72% (UV), Rt=0.85 min, m/z (ESI⁺)=338.7 [M+H]⁺ (free amine)

N-(Cyclopropylmethyl)-2-oxo-3-[N-(piperidin-4-ylmethyl)formamido]butanamide TFA salt (I-199)

The title compound was synthesized from tert-butyl 4-[(N-{1-[(cyclopropyl-methyl)carbamoyl]-1-oxopropan-2-yl}formamido)methyl]piperidine-1-carboxylate (FP 39) in a similar manner to general procedure 1 (general scheme 5) as a yellow oil (616 mg) used in the next step without further purification.

General Procedure 2 (General Scheme 5): Capping

N-(Cyclohexylmethyl)-3-(AN{[1-(2-methylpropanoyl)piperidin-4-yl]methyl}formamido)-2-oxobutanamide (FP 78)

To a stirred, ice cooled solution of N-(cyclohexylmethyl)-2-oxo-3-[N-(piperidin-4-ylmethyl)formamido]butanamide (TFA salt, I-198, 72% purity, 150 mg, 0.32 mmol) and DIPEA (158 μL, 0.91 mmol) in DCM (3 mL) was added a solution of 2-methylpropanoyl chloride (37 μL, 0.35 mmol) in DCM (2 mL) dropwise over 5 min. The reaction was stirred at RT under nitrogen for 1 h, diluted with DCM (10 mL) and washed with saturated NaHCO₃ (10 mL) and water (10 mL). The organic layer was separated, dried over magnesium sulfate, filtered and concentrated in vacuo to give a crude material which was purified by flash column chromatography on normal phase silica (10 g SNAP KP-SIL silica cartridge, 0-100% EtOAc in heptane gradient) followed by preparative LC (acidic pH, standard elution method) to yield 11 mg of N-(cyclohexyl-methyl)-3-(N-{[1-(2-methylpropanoyl)piperidin-4-yl]methyl}formamido)-2-oxobutanamide as a yellow oil (94% purity, 8%).

¹H NMR (500 MHz, Chloroform-d) δ 0.86-0.99 (m, 2H), 1.07-1.15 (m, 8H), 1.17-1.26 (m, 3H), 1.41-1.59 (m, 4H), 1.67-1.89 (m, 7H), 1.90-2.02 (m, 1H), 2.38-2.62 (m, 1H), 2.69-2.83 (m, 1H), 2.90-3.43 (m, 5H), 3.89-5.14 (m, 3H), 6.65-6.99 (m, 1H), 7.78-8.33 (m, 1H).

LC-MS (METCR1600): 94% (UV), Rt=4.41 min, m/z (ESI⁺)=408.3 [M+H]⁺

3-{N-[(1-Acetylpiperidin-4-yl)methyl]formamido}-N-(cyclohexylmethyl)-2-oxobutanamide (FP 79)

The title compound was synthesized from N-(cyclohexylmethyl)-2-oxo-3-[N-(piperidin-4-ylmethyl)formamido]butanamide (TFA salt, 1-198) in a similar manner to general procedure 2 (general scheme 5) as a colourless oil (16 mg, 100% purity, 7%) after purification by flash column chromatography on normal phase silica (10 g SNAP KP-SIL silica cartridge, 0-100% EtOAc in heptane gradient) followed by preparative LC (acidic pH, standard elution method).

¹H NMR (500 MHz, Chloroform-d) δ 0.86-1.00 (m, 2H), 1.03-1.26 (m, 5H), 1.41-1.56 (m, 4H), 1.59-2.01 (m, 8H), 2.04-2.10 (m, 3H), 2.44-3.42 (m, 6H), 3.71-5.16 (m, 3H), 6.62-7.03 (m, 1H), 7.79-8.33 (m, 1H).

LC-MS (METCR1600): 100% (UV), Rt=3.96 min, m/z (ESI⁺)=380.3 [M+H]⁺

3-{N[(1-Benzoylpiperidin-4-yl)methyl]formamido}-N-(cyclopropylmethyl)-2-oxobutanamide (FP 80)

The title compound was synthesized from N-(cyclopropylmethyl)-2-oxo-3-[N-(piperidin-4-ylmethyl)formamido]butanamide (TFA salt, 1-199) in a similar manner to general procedure 2 (general scheme 5) as an off-white solid (28 mg, 95% purity, 33%) after purification by flash column chromatography on normal phase silica (10 g SNAP KP-SIL silica cartridge, 0-100% EtOAc in heptane gradient) followed by preparative LC (acidic pH, standard elution method).

¹H NMR (500 MHz, Chloroform-d) δ 0.15-0.28 (m, 2H), 0.48-0.61 (m, 2H), 0.90-1.00 (m, 1H), 1.07-1.31 (m, 2H), 1.44-1.56 (m, 3H), 1.67-2.06 (m, 3H), 2.71-3.25 (m, 5H), 3.29-3.95 (m, 2H), 4.27-5.16 (m, 2H), 6.73-7.03 (m, 1H), 7.34-7.42 (m, 5H), 7.84-8.30 (m, 1H).

LC-MS (Achiral SFC): 95% (UV), Rt=1.77 min, m/z (ESI⁺)=400.2 [M+H]⁺

3-{N-[(1-Cyclohexanecarbonylpiperidin-4-yl)methyl]formamido}-N-(cyclopropylmethyl)-2-oxobutanamide (FP 81)

The title compound was synthesized from N-(cyclopropylmethyl)-2-oxo-3-[N-(piperidin-4-ylmethyl)formamido]butanamide (TFA salt, 1-199) in a similar manner to general procedure 2 (general scheme 5) as an off-white solid (32 mg, 97% purity, 16%) after purification by flash column chromatography on normal phase silica (10 g SNAP KP-SIL silica cartridge, 0-100% EtOAc in heptane gradient) followed by preparative LC (acidic pH, standard elution method).

¹H NMR (500 MHz, Chloroform-d) δ 0.16-0.28 (m, 2H), 0.47-0.61 (m, 2H), 0.91-1.01 (m, 1H), 1.01-1.16 (m, 2H), 1.19-1.31 (m, 3H), 1.42-1.50 (m, 3H), 1.50-1.85 (m, 9H), 1.92-1.99 (m, 1H), 2.37-2.63 (m, 2H), 2.88-3.22 (m, 4H), 3.24-3.46 (m, 1H), 3.82-5.16 (m, 3H), 6.72-7.03 (m, 1H), 7.83-8.29 (m, 1H).

LC-MS (Achiral SFC): 97% (UV), Rt=1.65 min, m/z (ESI⁺)=406.3 [M+H]⁺

GENERAL SCHEME 6:

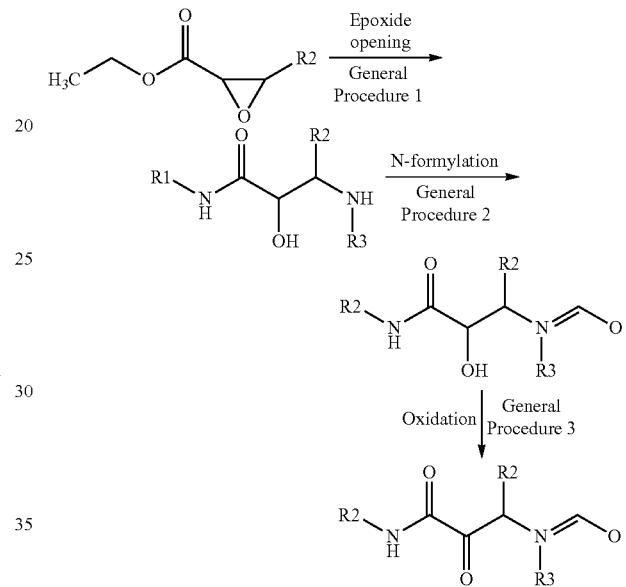

General Procedure 1 (General Scheme 6): Epoxide Opening

(2R,3S)-2-Hydroxy-N-(2-methoxyphenyl)-3-[(2-methoxyphenyl)amino]butanamide (I-200)

To a stirred solution of ethyl (2R,3R)-3-methyloxirane-2-carboxylate (200 mg, 1.54 mmol) and 2-methoxyaniline (1.4 mL, 12.29 mmol) was added titanium(IV) isopropoxide (686 µL, 2.31 mmol). The reaction mixture was stirred at RT for 3 h, quenched with 2N citric acid (3 mL) and the aqueous layer extracted with DCM (3×5 mL). The combined organic layers were washed with brine (5 mL), dried over sodium sulfate, filtered and concentrated in vacuo. The crude material was purified by flash column chromatography on normal phase silica (50 g SNAP KP-SIL silica cartridge, 10-55% EtOAc in heptane gradient) to afford 148 mg of (2R,3S)-2-hydroxy-N-(2-methoxyphenyl)-3-[(2-methoxyphenyl)amino]butanamide as a brown solid (95% purity by ¹H NMR, 28%).

¹H NMR (500 MHz, Chloroform-d) δ 1.32 (d, J=6.7 Hz, 3H), 3.84 (s, 3H), 3.84-3.87 (m, 1H), 3.88 (s, 3H), 3.93-4.07 (m, 1H), 4.36 (d, J=4.0 Hz, 1H), 6.76-6.85 (m, 2H), 6.85-6.93 (m, 3H), 6.96 (td, J=1.2, 7.8 Hz, 1H), 7.06 (td, J=1.6, 7.8 Hz, 1H), 8.33 (dd, J=1.6, 8.0 Hz, 1H), 9.11 (s, 1H).

LC-MS (METCR1410): 79% (UV), Rt=1.10 min, m/z (ESI⁺)=331.0 [M+H]⁺

General Procedure 2 (General Scheme 6): N-Formylation

(2R,3S)-2-Hydroxy-(2-methoxyphenyl)-3-[(2-methoxyphenyl)formamido]butanamide (I-201)

To a stirred suspension of (2R,3S)-2-hydroxy-N-(2-methoxyphenyl)-3-[(2-methoxyphenyl)amino]butanamide (I-200, 95% purity by $^1$H NMR, 145 mg, 0.42 mmol) and formic acid (107 μL, 2.71 mmol) was added acetic anhydride (1 mL). The mixture was stirred at RT for 4.5 h, quenched with saturated NaHCO$_3$ (5 mL) and the biphasic solution separated by passage through a Telos® hydrophobic frit. The aqueous layer was extracted with DCM (3×5 mL) and the combined organic layers were passed through a Telos® hydrophobic frit and concentrated in vacuo to afford 178 mg of (2R,3S)-2-hydroxy-N-(2-methoxyphenyl)-3-[N-(2-methoxyphenyl)formamido]butanamide as a dark oil (80% purity by 1H NMR, 96%) which was used in the next step without further purification.

$^1$H NMR (500 MHz, Chloroform-d) δ 1.66 (d, J=7.2 Hz, 3H), 3.74 (s, 3H), 3.91 (s, 3H), 4.28 (dd, J=4.2, 8.6 Hz, 1H), 4.40 (qd, J=4.3, 7.2 Hz, 1H), 6.87-7.00 (m, 5H), 7.06 (td, J=1.6, 7.9 Hz, 1H), 7.30 (ddd, J=1.6, 7.8, 15.7 Hz, 2H), 7.95 (s, 1H), 8.37 (dd, J=1.6, 8.0 Hz, 1H), 9.49 (s, 1H).

LC-MS (MET-μHPLC-AB-101): 96% (UV), Rt=2.81 min, m/z (ESI$^+$)=359.1 [M+H]$^+$

General Procedure 3 (General Scheme 6): Oxidation

(3S)—N-(2-Methoxyphenyl)-3-[N-(2-methoxyphenyl)formamido]-2-oxobutanamide (FP 82)

To a stirred solution of (2R,3S)-2-hydroxy-N-(2-methoxyphenyl)-3-[N-(2-methoxyphenyl)formamido]butanamide (I-201, 80% purity by $^1$H NMR, 175 mg, 0.39 mmol) in DCM (4.5 mL) was added DMP (249 mg, 0.59 mmol) and the reaction was stirred at RT for 14 h. The mixture was washed with saturated NaHCO$_3$(5 mL) and the aqueous layer extracted with DCM (3×7 mL). The combined organic layers were dried over sodium sulfate, filtered and concentrated in vacuo. The crude material was purified by flash column chromatography on normal phase silica (10 g SNAP KP-SIL silica cartridge, 0-45% EtOAc in heptane gradient) to afford 79.4 mg of (3S)—N-(2-methoxyphenyl)-3-[N-(2-methoxyphenyl)formamido]-2-oxobutanamide as an orange oil (98% purity, 56%).

$^1$H NMR (500 MHz, Chloroform-d) δ 1.33-1.54 (m, 3H), 3.57-3.85 (m, 3H), 3.89-3.95 (m, 3H), 5.28-5.60 (m, 1H), 6.87-6.96 (m, 1H), 6.95-7.01 (m, 2H), 7.04 (td, J=1.1, 7.6 Hz, 1H), 7.07-7.18 (m, 1H), 7.28-7.41 (m, 1H), 7.59 (dd, J=1.6, 7.7 Hz, 1H), 8.43 (dd, J=1.5, 8.0 Hz, 1H), 8.02-8.73 (m, 1H), 9.21-9.37 (m, 1H).

LC-MS (METCR1416): 98% (UV), Rt=4.26 min, m/z (ESI$^+$)=357.0 [M+H]$^+$

Route Via Ylide Formation: Synthesis of Intermediates (I-202-I-207)

GENERAL SCHEME 7:

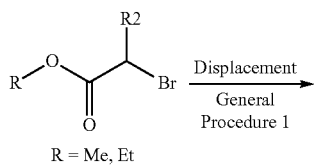

R = Me, Et

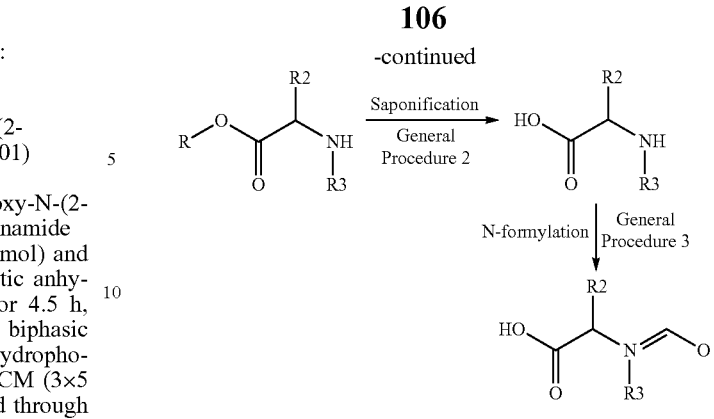

General Procedure 1 (General Scheme 7): Displacement

Methyl 2-[(2-methoxyphenyl)amino]propanoate (I-202)

To a stirred solution of 2-methoxyaniline (13.8 mL, 121.8 mmol) in DMF (188 mL) was added at RT methyl 2-bromopropanoate (13.6 mL, 121.8 mmol) followed by K$_2$CO$_3$ (33.7 g, 243.6 mmol) and KI (4.1 g, 24.36 mmol). The reaction was heated at 100° C. for 27 h, quenched with saturated NaHCO$_3$(100 mL) and the emulsion filtered. The solid was washed with EtOAc (2×200 mL) and water (2×200 mL). The organic layers were combined and washed with brine (150 mL), dried over sodium sulfate, filtered and concentrated in vacuo. The residue was purified by flash column chromatography on normal phase silica in 4 batches (340 g SNAP KP-SIL cartridge, 0-20% EtOAc in heptane gradient) to afford 23.19 g of methyl 2-[(2-methoxyphenyl)amino]propanoate as a viscous yellow oil (98% purity, 89%)

$^1$H NMR (500 MHz, Chloroform-d) δ 1.52 (d, J=6.9 Hz, 3H), 3.73 (s, 3H), 3.86 (s, 3H), 4.16 (p, J=7.0 Hz, 1H), 4.70 (d, J=6.4 Hz, 1H), 6.53 (dd, J=1.4, 7.8 Hz, 1H), 6.71 (td, J=1.5, 7.7 Hz, 1H), 6.79 (dd, J=1.3, 7.9 Hz, 1H), 6.84 (td, J=1.4, 7.6 Hz, 1H)

LC-MS (METCR1410): 98% (UV), Rt=1.08 min, m/z (ESI$^+$)=210.2 [M+H]$^+$

General Procedure 2 (General Scheme 7): Saponification

2-[(2-Methoxyphenyl)amino]propanoic acid (I-203)

To a stirred solution of methyl 2-[(2-methoxyphenyl)amino]propanoate (I-202, 7 g, 32.79 mmol) in 1:1:1 THF/water/MeOH (135 mL) was added lithium hydroxide hydrate (1:1:1, 2.52 g, 65.57 mmol) at RT. The reaction mixture was stirred for 2 h, concentrated in vacuo and the residue suspended in DCM (20 mL). The organic layer was separated and acidified to pH 1-2 with 1N HCl (70 mL) and the aqueous layer extracted with 1:1 IPA/CHCl$_3$ (4×100 mL). The organic layers were combined, washed with brine (50 mL), dried over sodium sulfate, filtered and concentrated in vacuo to afford 6.33 g of 2-[(2-methoxyphenyl)amino]propanoic acid as a grey-brown solid (98% purity, 97% yield) used in the next step without further purification.

$^1$H NMR (500 MHz, DMSO-d6) δ 1.38 (d, J=6.9 Hz, 3H), 3.79 (s, 3H), 4.03 (q, J=6.9 Hz, 1H), 6.48 (dd, J=1.4, 7.9 Hz, 1H), 6.59 (td, J=1.5, 7.7 Hz, 1H), 6.76 (td, J=1.3, 7.7 Hz, 1H), 6.83 (dd, J=1.3, 7.9 Hz, 1H).

LC-MS (METCR1410): 98% (UV), Rt=0.87 min, m/z (ESI+)=196.2 [M+H]+

General Procedure 3 (General Scheme 7):
N-Formylation

2-[N-(2-Methoxyphenyl)formamido]propanoic acid
(I-204)

To a stirred suspension of 2-[(2-methoxyphenyl)amino]propanoic acid (I-203, 3.27 g, 16.75 mmol) and formic acid (4.3 mL, 108.88 mmol) was added acetic anhydride (14.2 mL, 150.22 mmol) dropwise. The reaction mixture was stirred at RT for 5 h, quenched with ice and concentrated in vacuo. The residue was dissolved in Et$_2$O (15 mL) and sonicated for 10 min. The resulting precipitate was collected by filtration, washed with Et$_2$O (2×15 mL) and dried in vacuo to afford 2.62 g of 2-[N-(2-methoxyphenyl)formamido]propanoic acid as a brown solid (100% purity, 70%) used in the next step without further purification.

$^1$H NMR (250 MHz, Chloroform-d) δ 1.38 (d, J=7.3 Hz, 3H), 3.84 (s, 3H), 4.80 (q, J=7.3 Hz, 1H), 6.93-7.08 (m, 2H), 7.30-7.41 (m, 2H), 8.16 (s, 1H).

LC-MS (METCR1416): 100% (UV), Rt=0.87 min, m/z (ESI+)=224.1 [M+H]+

GENERAL SCHEME 8:

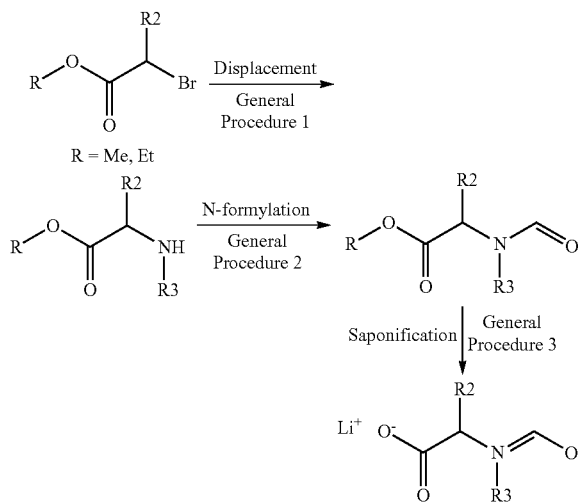

General Procedure 1 (General Scheme 8):
Displacement

Ethyl 2-(cyclohexylamino)propanoate (I-205)

To a stirred solution of cyclohexanamine (59 mL, 510 mmol) in EtOH (140 mL) was added ethyl 2-bromopropanoate (22 mL, 169 mmol). The reaction mixture was heated at reflux for 4 h, then concentrated in vacuo and the residue suspended in EtOAc (200 mL) and water (50 mL) then sonicated for 10 min. The solution was filtered and the organic layer was separated, dried over magnesium sulfate, filtered and concentrated in vacuo to give a brown oil. The aqueous layer was concentrated in vacuo. The residues from organic and aqueous phases were individually suspended in EtOAc (100 mL), sonicated for 10 min and filtered. The filtrates were combined and concentrated in vacuo to afford 34 g of ethyl 2-(cyclohexylamino)propanoate as a brown oil (90% purity by $^1$H NMR, 91%) used in the next step without further purification.

$^1$H NMR (250 MHz, Chloroform-d) δ 0.92-1.34 (m, 11H), 1.52-1.64 (m, 1H), 1.65-1.79 (m, 2H), 1.80-1.95 (m, 3H), 2.27-2.42 (m, 1H), 3.46 (q, J=7.0 Hz, 1H), 4.17 (q, J=7.1 Hz, 2H).

General Procedure 2 (General Scheme 8):
N-Formylation

Ethyl 2-(N-cyclohexylformamido)propanoate
(I-206)

Formic acid (6.9 mL, 175.62 mmol) was added dropwise at 0° C. to acetic anhydride (12.3 mL, 130.46 mmol). The solution was stirred at 50° C. for 1 h and the reaction mixture diluted with dry THF (50 mL) at RT. A solution of ethyl 2-(cyclohexyl-amino)propanoate (I-205, 10 g, 50.18 mmol) in dry THF (50 mL) was added at 0° C. The solution was stirred at RT for 1.5 h, concentrated in vacuo and diluted with EtOAc (60 mL) then washed with saturated NaHCO$_3$ (3×100 mL), water (100 mL) and brine (20 mL). The organic layer was separated, dried over magnesium sulfate and concentrated in vacuo to afford 8.7 g of ethyl 2-(N-cyclohexylformamido)propanoate as a brown viscous oil (95% purity, 72%) used in the next step without further purification.

$^1$H NMR (250 MHz, Chloroform-d) δ 1.00-1.19 (m, 1H), 1.21-1.28 (m, 3H), 1.29-1.44 (m, 2H), 1.44-1.50 (m, 3H), 1.51-1.56 (m, 1H), 1.59-1.68 (m, 1H), 1.78-1.92 (m, 3H), 1.93-2.06 (m, 1H), 3.24 (tt, J=3.5, 11.8 Hz, 1H), 3.98-4.33 (m, 4H), 8.11-8.24 (m, 1H).

LC-MS (METCR1410): 95% (UV), Rt=1.07 min, m/z (ESI+)=228.2 [M+H]+

General Procedure 3 (General Scheme 8):
Saponification 2-(N-Cyclohexylformamido)propanoic acid lithium salt (I-207)

To a stirred solution of ethyl 2-(N-cyclohexylformamido)propanoate (I-206, 95% purity, 8.7 g, 38.37 mmol) in a 2:2:1 mixture of THF/water/EtOH (50 mL) was added lithium hydroxide hydrate (1.83 g, 43.63 mmol). The mixture was stirred at RT for 2.5 h and concentrated in vacuo. The residue was suspended in Et$_2$O (100 mL) and concentrated in vacuo (process repeated×3) and the solid was dried in vacuo to afford 8.15 g of 2-(N-cyclohexylformamido)propanoic acid lithium salt as a gummy yellow solid (95% purity, quantitative) used in the step without further purification.

$^1$H NMR (500 MHz, DMSO-d6) δ 0.99-1.33 (m, 6H), 1.39-1.78 (m, 7H), 3.01-4.47 (m, 2H), 8.03-8.16 (m, 1H).

LC-MS (METCR1410): 95% (UV), Rt=0.87-0.89 min (two peaks), m/z (ESI+)=200.3 [M+H]+

Route Via Ylide Formation: Synthesis of Final Compounds (FP 83-115)

GENERAL SCHEME 9:

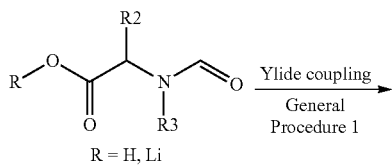

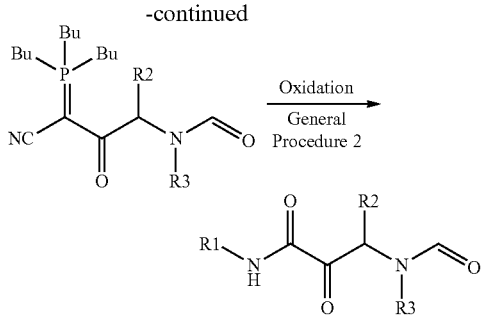

General Procedure 1 (General Scheme 9): Ylide Coupling

N-[4-Cyano-3-oxo-4-(tributyl-λ⁵-phosphanylidene)butan-2-yl]-N-(2-methoxyphenyl)-formamide (I-208)

To a stirred, ice cooled solution of 2-[N-(2-methoxyphenyl)formamido]propanoic acid (I-204, 500 mg, 2.24 mmol) and DIPEA (1.2 mL, 6.72 mmol) in dry 9:1 DCM/DMF (10 mL) at 0° C. was added HATU (2.56 g, 6.72 mmol) in one portion. The reaction mixture was stirred at 0° C. for 15 min and (tributyl-λ⁵-phosphanylidene)acetonitrile (1.8 mL, 6.72 mmol) added. The reaction was stirred at RT for 1.5 h, washed with water (3 mL) and the aqueous layer was extracted with DCM (2×5 mL). The combined organic layers were washed with brine (5 mL) then dried over sodium sulfate, filtered and concentrated in vacuo. The residue was purified by flash column chromatography on normal phase silica (340 g SNAP KP-SIL cartridge, 10-100% EtOAc in heptane gradient) to afford 1.11 g of N[4-cyano-3-oxo-4-(tributyl-λ⁵-phosphanylidene)butan-2-yl]-N-(2-methoxyphenyl)formamide as a brown sticky solid (94% purity by $^1$H NMR, quantitative).

$^1$H NMR (500 MHz, DMSO-d6) δ 0.81-1.07 (m, 12H), 1.28-1.52 (m, 12H), 2.02-2.15 (m, 6H), 3.69-3.87 (m, 3H), 4.47-5.22 (m, 1H), 6.83-7.00 (m, 1H), 7.06-7.16 (m, 1H), 7.24-7.40 (m, 1H), 6.99-7.64 (m, 1H), 7.87-8.41 (m, 1H)

LC-MS (METCR1410): 99% (UV), Rt=1.23 min, m/z (ESI$^+$)=447.5 [M+H]$^+$

N-[4-Cyano-3-oxo-4-(tributyl-λ⁵-phosphanylidene)butan-2-yl]-N-cyclohexylformamide (I-209)

To a stirred solution of 2-(N-cyclohexylformamido)propanoic acid lithium salt (I-207, 95% purity, 5.65 g, 26.16 mmol) and DIPEA (13.7 mL, 78.48 mmol) in dry DMF (50 mL) was added HATU (29.84 g, 78.48 mmol) at 0° C. The mixture was stirred at 0° C. for 1 h and (tributyl-λ⁵-phosphanylidene)acetonitrile (20.6 mL, 78.48 mmol) added. The reaction was stirred for 45 min at 0° C., then at RT for 18 h. The reaction was cooled (ice bath), quenched with water (200 mL) and stirred for 10 min. The aqueous layer was extracted with EtOAc (2×100 mL) and the combined organic layers washed with water and brine, dried over magnesium sulfate, filtered and concentrated in vacuo. The crude material was purified by flash column chromatography on normal phase silica in 2 batches (340 g SNAP KP-SIL cartridge, 0-100% EtOAc in heptane gradient) to give 22 g of brown gum. A portion of the material (6 g) was purified by flash column chromatography on reverse phase silica (400 g SNAP Ultra C18 cartridge, high pH, standard elution method) to afford 1.88 g of N-[4-cyano-3-oxo-4-(tributyl-λ⁵-phosphanylidene)butan-2-yl]-N-cyclohexylformamide as an off-white solid (100% purity, 17%).

$^1$H NMR (500 MHz, DMSO-d$_6$) δ 0.84-0.92 (m, 9H), 0.94-1.28 (m, 3H), 1.31-1.48 (m, 15H), 1.49-1.79 (m, 4H), 2.02-2.16 (m, 6H), 3.31 (s, 3H), 3.92 (td, J=5.7, 11.3 Hz, 1H), 4.35-5.21 (m, 1H), 8.11-8.29 (m, 1H).

LC-MS (METCR1410): 100% (UV), Rt=1.31 min, m/z (ESI$^+$)=423.8 [M+H]$^+$

The remaining material was purified twice by flash column chromatography on reverse phase silica (400 g SNAP Ultra C18 cartridge, high pH, standard elution method) to afford 5.78 g of N-[4-cyano-3-oxo-4-(tributyl-λ⁵-phosphanylidene)butan-2-yl]-N-cyclohexyl formamide as an off-white solid (97% purity, 51%).

$^1$H NMR (500 MHz, DMSO-d6) δ 0.84-0.90 (m, 9H), 0.97-1.30 (m, 3H), 1.31-1.46 (m, 15H), 1.50-1.80 (m, 4H), 2.04-2.15 (m, 6H), 3.32 (s, 3H), 3.91 (td, J=5.59, 11.30 Hz, 1H), 4.37-5.18 (m, 1H), 8.14-8.27 (m, 1H).

LC-MS (METCR1410): 97% (UV), Rt=1.25 min, m/z (ESI$^+$)=423.7 [M+H]$^+$

General Procedure 2 (General Scheme 9): Oxidation

Method A: Ozonolysis

N-[(3,5-Dichlorophenyl)methyl]-3-[N-(2-methoxyphenyl)formamido]-2-oxobutanamide (FP 83)

Ozone (ozone generator) was passed at −78° C. through a solution of N-[4-cyano-3-oxo-4-(tributyl-λ⁵-phosphanylidene)butan-2-yl]-N-(2-methoxyphenyl)formamide (I-208, 94% purity, 400 mg, 0.84 mmol) and 1-(3,5-dichlorophenyl)-methanamine (124 μL, 0.93 mmol) in DCM (12 mL) for 15 min. The solution was flushed with nitrogen and the mixture stirred at −78° C. under nitrogen for 1.5 h. The reaction was concentrated in vacuo to afford a gum which was purified by flash column chromatography on normal phase silica (50 g SNAP KP-SIL cartridge, 0-100% EtOAc in heptane gradient) to afford 82.7 mg of N-[(3,5-dichlorophenyl)methyl]-3-[N-(2-methoxyphenyl)formamido]-2-oxobutanamide as a viscous yellow oil (96% purity, 19%).

$^1$H NMR (500 MHz, Chloroform-d) δ 1.34-1.54 (m, 3H), 3.65-3.88 (m, 3H), 4.42-4.59 (m, 2H), 4.98-5.48 (m, 1H), 7.01 (dd, J=1.0, 8.3 Hz, 1H), 7.05 (td, J=1.2, 7.6 Hz, 1H), 7.17-7.21 (m, 1H), 7.22 (d, J=1.8 Hz, 2H), 7.30 (t, J=1.8 Hz, 1H), 7.39 (td, J=1.7, 8.2 Hz, 1H), 7.58 (dd, J=1.7, 7.8 Hz, 1H), 8.03-8.65 (m, 1H).

LC-MS (METCR1416): 96% (UV), Rt=4.43 min, m/z (ESI$^+$)=409.0/411.0 [M+H]$^+$

N-[1-(3-Chlorophenyl)ethyl]-3-[N-(2-methoxyphenyl)formamido]-2-oxobutanamide (FP 84)

The title compound was synthesized from N-[4-cyano-3-oxo-4-(tributyl-λ⁵-phosphanylidene)butan-2-yl]-N-(2-methoxyphenyl)formamide (I-208) in a similar manner to method A, general procedure 2 (general scheme 9) as a brown viscous oil (17.7 mg, 90% purity, 13%) after purification by preparative LC (acidic pH, standard elution method).

$^1$H NMR (500 MHz, Chloroform-d) δ 1.29-1.40 (m, 3H), 1.52-1.57 (m, 3H), 3.76-3.85 (m, 3H), 4.91-5.10 (m, 2H), 6.93-7.04 (m, 2H), 7.19-7.30 (m, 4H), 7.29-7.39 (m, 2H), 7.39-7.59 (m, 1H), 7.96-8.03 (m, 1H).

3-[N-(2-Methoxyphenyl)formamido]-N-[(3-methoxyphenyl)methyl]-2-oxobutanamide (FP 85)

The title compound was synthesized from N-[4-cyano-3-oxo-4-(tributyl-$\lambda^5$-phosphanylidene)butan-2-yl]-N-(2-methoxyphenyl)formamide (I-208) in a similar manner to method A, general procedure 2 (general scheme 9) as a yellow viscous oil (7 mg, 100% purity, 4%) after purification by flash column chromatography on normal phase silica (25 g SNAP KP-SIL cartridge, 0-40% EtOAc in heptane gradient) followed by preparative LC (acidic pH, standard elution method).

$^1$H NMR (500 MHz, Chloroform-d) δ 1.31-1.50 (m, 3H), 3.80 (s, 3H), 3.83 (s, 3H), 4.43-4.57 (m, 2H), 5.02-5.49 (m, 1H), 6.80-6.86 (m, 2H), 6.87-6.91 (m, 1H), 6.98 (dd, J=0.9, 8.3 Hz, 1H), 7.02 (td, J=1.2, 7.6 Hz, 1H), 7.07-7.16 (m, 1H), 7.26 (d, J=4.1 Hz, 1H), 7.32-7.39 (m, 1H), 7.54-7.61 (m, 1H), 7.97-8.65 (m, 1H).

LC-MS (METCR1416): 100% (UV), Rt=3.97 min, m/z (ESI$^+$)=371.0 [M+H]$^+$

N-[(2-Chlorophenyl)methyl]-3-[N-(2-methoxyphenyl)formamido]-2-oxobutanamide (FP 86)

The title compound was synthesized from N-[4-cyano-3-oxo-4-(tributyl-$\lambda^5$-phosphanylidene)butan-2-yl]-N-(2-methoxyphenyl)formamide (I-208) in a similar manner to method A, general procedure 2 (general scheme 9) as a yellow viscous oil (31.8 mg, 96% purity, 10%) after purification by flash column chromatography on normal phase silica (50 g SNAP KP-SIL cartridge, 0-100% EtOAc in heptane gradient) followed by preparative LC (acidic pH, standard elution method).

$^1$H NMR (500 MHz, Chloroform-d) δ 1.30-1.49 (m, 3H), 3.55-3.84 (m, 3H), 4.55-4.68 (m, 2H), 5.02-5.46 (m, 1H), 6.95-7.00 (m, 1H), 7.01 (td, J=1.2, 7.6 Hz, 1H), 7.20-7.26 (m, 3H), 7.32-7.43 (m, 3H), 7.55 (dd, J=1.6, 7.7 Hz, 1H), 7.97-8.64 (m, 1H).

LC-MS (METCR1416): 96% (UV), Rt=4.14 min, m/z (ESI$^+$)=375.0/377.0 [M+H]$^+$

3-[N-(2-Methoxyphenyl)formamido]-N-[(3-methylphenyl)methyl]-2-oxo butanamide (FP 87)

The title compound was synthesized from N-[4-cyano-3-oxo-4-(tributyl-$\lambda^5$-phosphanylidene)butan-2-yl]-N-(2-methoxyphenyl)formamide (I-208) in a similar manner to method A, general procedure 2 (general scheme 9) as a yellow viscous oil (50.4 mg, 100% purity, 17%) after purification by flash column chromatography on normal phase silica (50 g SNAP KP-SIL cartridge, 0-100% EtOAc in heptane gradient) followed by preparative LC (acidic pH, standard elution method).

$^1$H NMR (500 MHz, Chloroform-d) δ 1.35-1.52 (m, 3H), 2.34-2.39 (m, 3H), 3.63-3.87 (m, 3H), 4.51 (qd, J=6.1, 14.9 Hz, 2H), 5.07-5.52 (m, 1H), 7.00 (dd, J=1.0, 8.3 Hz, 1H), 7.04 (td, J=1.2, 7.6 Hz, 1H), 7.10-7.15 (m, 4H), 7.25 (t, J=7.6 Hz, 1H), 7.38 (td, J=1.7, 8.2 Hz, 1H), 7.60 (dd, J=1.7, 7.7 Hz, 1H), 8.00-8.66 (m, 1H).

LC-MS (METCR1416): 100% (UV), Rt=4.1 min, m/z (ESI$^+$)=355.1 [M+H]$^+$

N-Benzyl-3-[N-(2-methoxyphenyl)formamido]-2-oxobutanamide (FP 88)

The title compound was synthesized from N-[4-cyano-3-oxo-4-(tributyl-$\lambda^5$-phosphanylidene)butan-2-yl]-N-(2-methoxyphenyl)formamide (I-208) in a similar manner to method A, general procedure 2 (general scheme 9) as a yellow viscous oil (53.7 mg, 99% purity, 19%) after purification by flash column chromatography on normal phase silica (50 g SNAP KP-SIL cartridge, 0-100% EtOAc in heptane gradient).

$^1$H NMR (500 MHz, Chloroform-d) δ 1.34-1.53 (m, 3H), 3.57-3.88 (m, 3H), 4.47-4.62 (m, 2H), 5.06-5.53 (m, 1H), 7.00 (dd, J=0.9, 8.3 Hz, 1H), 7.04 (td, J=1.2, 7.6 Hz, 1H), 7.14 (s, 1H), 7.30-7.41 (m, 6H), 7.60 (dd, J=1.7, 7.8 Hz, 1H), 8.00-8.66 (m, 1H).

LC-MS (METCR1416): 99% (UV), Rt=4.01 min, m/z (ESI$^+$)=341.1 [M+H]$^+$

3-[N-(2-Methoxyphenyl)formamido]-2-oxo-A[(pyridin-3-yl)methyl]butanamide (FP 89)

The title compound was synthesized from N-[4-cyano-3-oxo-4-(tributyl-$\lambda^5$-phosphanylidene)butan-2-yl]-N-(2-methoxyphenyl)formamide (I-208) in a similar manner to method A, general procedure 2 (general scheme 9) as a yellow viscous oil (27 mg, 100% purity, 10%) after purification by flash column chromatography on normal phase silica (50 g SNAP KP-SIL cartridge, 50-100% EtOAc in heptane gradient then 20% MeOH in EtOAc) followed by trituration in MeCN and preparative LC (acidic pH, standard elution method).

$^1$H NMR (500 MHz, Chloroform-d) δ 1.28-1.53 (m, 3H), 3.58-3.86 (m, 3H), 4.48-4.65 (m, 2H), 5.01-5.45 (m, 1H), 6.96-7.05 (m, 2H), 7.21-7.25 (m, 1H), 7.31 (dd, J=4.9, 7.4 Hz, 1H), 7.36 (td, J=1.6, 8.2 Hz, 1H), 7.55 (dd, J=1.6, 7.7 Hz, 1H), 7.70 (d, J=7.8 Hz, 1H), 8.00 (s, 1H), 8.47-8.66 (m, 2H).

LC-MS (METCR1416): 100% (UV), Rt=2.78 min, m/z (ESI$^+$)=342.1 [M+H]$^+$

3-[N-(2-Methoxyphenyl)formamido]-2-oxo-N-[(pyridin-4-yl)methyl]butanamide (FP 90)

The title compound was synthesized from N-[4-cyano-3-oxo-4-(tributyl-$\lambda^5$-phosphanylidene)butan-2-yl]-N-(2-methoxyphenyl)formamide (I-208) in a similar manner to method A, general procedure 2 (general scheme 9) as a yellow viscous oil (27.3 mg, 100% purity, 10%) after purification by flash column chromatography on normal phase silica (50 g SNAP KP-SIL cartridge, 50-100% EtOAc in heptane gradient then 20% MeOH in EtOAc) followed by trituration in MeCN and preparative LC (acidic pH, standard elution method).

$^1$H NMR (500 MHz, Chloroform-d) δ 1.23-1.46 (m, 3H), 3.56-3.82 (m, 3H), 4.39-4.59 (m, 2H), 4.85-5.39 (m, 1H), 6.88-6.99 (m, 2H), 7.19-7.24 (m, 3H), 7.30 (td, J=1.7, 8.2 Hz, 1H), 7.49 (dd, J=1.6, 7.7 Hz, 1H), 7.94 (s, 1H), 8.51 (d, J=6.0 Hz, 2H).

LC-MS (METCR1416): 100% (UV), Rt=2.73 min, m/z (ESI$^+$)=342.2 [M+H]$^+$

N-[(4-Chlorophenyl)methyl]-3-[N-(2-methoxyphenyl)formamido]-2-oxobutanamide (FP 91)

The title compound was synthesized from N-[4-cyano-3-oxo-4-(tributyl-$\lambda^5$-phosphanylidene)butan-2-yl]-N-(2-methoxyphenyl)formamide (I-208) in a similar manner to method A, general procedure 2 (general scheme 9) as a yellow viscous oil (77.6 mg, 100% purity, 25%) after purification by flash column chromatography on normal phase silica (50 g SNAP KP-SIL cartridge, 0-100% EtOAc in heptane gradient) followed by preparative LC (acidic pH, standard elution method).

¹H NMR (500 MHz, Chloroform-d) δ 1.27-1.49 (m, 3H), 3.55-3.89 (m, 3H), 4.39-4.58 (m, 2H), 4.98-5.47 (m, 1H), 6.89-7.05 (m, 2H), 7.11-7.16 (m, 1H), 7.24 (d, J=8.4 Hz, 2H), 7.28-7.33 (m, 2H), 7.36 (td, J=1.7, 8.2 Hz, 1H), 7.56 (dd, J=1.6, 7.7 Hz, 1H), 7.95-8.62 (m, 1H).

LC-MS (METCR1416): 100% (UV), Rt=4.28 min, m/z (ESI$^+$)=375.1/377.1 [M+H]$^+$

3-[N-(2-Methoxyphenyl)formamido]-N-[(4-methoxyphenyl)methyl]-2-oxobutanamide (FP 92)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (33.3 mg, 100% purity, 10.7%) after purification by flash column chromatography on normal phase silica (50 g SNAP KP-SIL cartridge, 0-100% EtOAc in heptane gradient) followed by preparative LC (acidic pH, standard elution method).

¹H NMR (500 MHz, Chloroform-d) δ 1.32-1.49 (m, 3H), 3.60-3.80 (m, 3H), 3.80-3.86 (m, 3H), 4.33-4.55 (m, 2H), 5.04-5.49 (m, 1H), 6.85-6.91 (m, 2H), 6.96-7.09 (m, 3H), 7.21-7.25 (m, 2H), 7.34-7.40 (m, 1H), 7.57 (dd, J=1.7, 7.7 Hz, 1H), 8.00-8.63 (m, 1H).

LC-MS (METCR1416): 100% (UV), Rt=4.02 min, m/z (ESI$^+$)=371.2 [M+H]$^+$

N-[(3-Chloro-4-fluorophenyl)methyl]-3-[A (2-methoxyphenyl)formamido]-2-oxobutanamide (FP 93)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (47.1 mg, 100% purity, 14%) after purification by flash column chromatography on normal phase silica (50 g SNAP KP-SIL cartridge, 0-100% EtOAc in heptane gradient) followed by preparative LC (acidic pH, standard elution method).

¹H NMR (500 MHz, Chloroform-d) δ 1.35 (d, J=7.0 Hz, 3H), 3.83 (s, 3H), 4.47 (d, J=6.3 Hz, 2H), 5.02 (q, J=7.0 Hz, 1H), 6.99 (d, J=8.3 Hz, 1H), 7.03 (td, J=1.1, 7.6 Hz, 1H), 7.10 (t, J=8.6 Hz, 1H), 7.13-7.22 (m, 2H), 7.32-7.40 (m, 2H), 7.56 (dd, J=1.6, 7.7 Hz, 1H), 8.01 (s, 1H).

LC-MS (METCR1416): 100% (UV), Rt=4.31 min, m/z (ESI$^+$)=393.1/395.0 [M+H]$^+$

N-[(3-Chloro-5-fluorophenyl)methyl]-3-[N-(2-methoxyphenyl)formamido]-2-oxobutanamide (FP 94)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (47.9 mg, 100% purity, 14%) after purification by flash column chromatography on normal phase silica (50 g SNAP KP-SIL cartridge, 0-100% EtOAc in heptane gradient) followed by preparative LC (acidic pH, standard elution method).

¹H NMR (500 MHz, Chloroform-d) δ 1.31-1.52 (m, 3H), 3.63-3.88 (m, 3H), 4.40-4.57 (m, 2H), 4.99-5.47 (m, 1H), 6.94 (d, J=9.0 Hz, 1H), 6.96-7.06 (m, 3H), 7.10 (s, 1H), 7.16-7.22 (m, 1H), 7.36 (td, J=1.7, 8.2 Hz, 1H), 7.56 (dd, J=1.6, 7.8 Hz, 1H), 7.97-8.64 (m, 1H).

LC-MS (METCR1416): 100% (UV), Rt=4.37 min, m/z (ESI$^+$)=393.1/395.0 [M+H]$^+$

3-[N-(2-Methoxyphenyl)formamido]-N-[(2-methoxyphenyl)methyl]-2-oxobutanamide (FP 95)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (44.2 mg, 100% purity, 14%) after purification by flash column chromatography on normal phase silica (50 g SNAP KP-SIL cartridge, 0-100% TBME in heptane gradient) followed by preparative LC (acidic pH, standard elution method).

¹H NMR (500 MHz, Chloroform-d) δ 1.32-1.48 (m, 3H), 3.52-3.84 (m, 3H), 3.85-3.91 (m, 3H), 4.51 (qd, J=6.2, 14.5 Hz, 2H), 5.08-5.47 (m, 1H), 6.86-6.95 (m, 2H), 6.95-7.03 (m, 2H), 7.27-7.30 (m, 2H), 7.30-7.38 (m, 2H), 7.54 (dd, J=1.7, 7.7 Hz, 1H), 8.00 (m, 1H).

LC-MS (METCR1416): 100% (UV), Rt=4 min, m/z (ESI$^+$)=371.0 [M+H]$^+$

3-[N-(2-Methoxyphenyl)formamido]-2-oxo-N-[(pyridin-2-yl)methyl]butanamide (FP 96)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as an orange viscous oil (27.5 mg, 100% purity, 10%) after purification by flash column chromatography on normal phase silica (50 g SNAP KP-SIL cartridge, 0-100% TBME in heptane gradient) followed by preparative LC (acidic pH, standard elution method).

¹H NMR (500 MHz, Chloroform-d) δ 1.30-1.56 (m, 3H), 3.58-3.84 (m, 3H), 4.65 (d, J=5.6 Hz, 2H), 5.10-5.51 (m, 1H), 6.94-7.05 (m, 2H), 7.21 (dd, J=5.2, 7.1 Hz, 1H), 7.30 (d, J=7.8 Hz, 1H), 7.32-7.40 (m, 1H), 7.58 (dd, J=1.5, 7.7 Hz, 1H), 7.68 (td, J=1.6, 7.7 Hz, 1H), 7.88 (s, 1H), 8.00-8.67 (m, 2H).

LC-MS (METCR1416): 100% (UV), Rt=2.92 min, m/z (ESI$^+$)=342.1 [M+H]$^+$

N-[2-(3-Chlorophenyl)ethyl]-3-[N-(2-methoxyphenyl)formamido]-2-oxobutanamide (FP 97)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (42.3 mg, 96% purity, 12%) after purification by flash column chromatography on normal phase silica (50 g SNAP KP-SIL cartridge, 0-100% TBME in heptane gradient) followed by preparative LC (acidic pH, standard elution method).

¹H NMR (500 MHz, Chloroform-d) δ 1.28-1.49 (m, 3H), 2.85 (t, J=7.2 Hz, 2H), 3.58 (q, J=6.2, 6.7 Hz, 2H), 3.62-3.91 (m, 3H), 4.98-5.45 (m, 1H), 6.83-6.92 (m, 1H), 6.96-7.01 (m, 1H), 7.01-7.08 (m, 1H), 7.11 (d, J=7.2 Hz, 1H), 7.19-7.25 (m, 3H), 7.36 (td, J=1.7, 8.2 Hz, 1H), 7.54 (dd, J=1.7, 7.7 Hz, 1H), 7.96-8.61 (m, 1H).

LC-MS (METCR1416): 96% (UV), Rt=4.22 min, m/z (ESI$^+$)=389.0/391.0 [M+H]$^+$

3-[N-(2-Methoxyphenyl)formamido]-N-[(2-methylphenyl)methyl]-2-oxobutanamide (FP 98)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (94.8 mg, 96% purity, 31%) after purification by flash column chromatography on normal phase silica (50 g SNAP KP-SIL cartridge, 0-100% TBME in heptane gradient) followed by preparative LC (acidic pH, standard elution method).

$^1$H NMR (500 MHz, Chloroform-d) δ 1.21-1.43 (m, 3H), 2.22-2.31 (m, 3H), 3.50-3.79 (m, 3H), 4.32-4.52 (m, 2H), 4.97-5.42 (m, 1H), 6.85-6.99 (m, 3H), 7.07-7.18 (m, 3H), 7.19-7.21 (m, 1H), 7.27-7.32 (m, 1H), 7.51 (dd, J=1.7, 7.8 Hz, 1H), 7.91-8.58 (m, 1H).

LC-MS (METCR1416): 96% (UV), Rt=4.06 min, m/z (ESI$^+$)=355.3 [M+H]$^+$

N-[(2,6-Dimethylphenyl)methyl]-3-[N-(2-methoxyphenyl)formamido]-2-oxobutanamide (FP 99)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a brown viscous oil (31.5 mg, 100% purity, 10%) after purification by flash column chromatography on normal phase silica (50 g SNAP KP-SIL cartridge, 0-100% TBME in heptane gradient) followed by preparative LC (acidic pH, standard elution method).

$^1$H NMR (500 MHz, Chloroform-d) δ 1.30-1.49 (m, 3H), 2.35-2.40 (m, 6H), 3.58-3.89 (m, 3H), 4.48-4.60 (m, 2H), 5.07-5.48 (m, 1H), 6.69 (s, 1H), 6.95-7.01 (m, 1H), 7.01-7.08 (m, 3H), 7.13 (dd, J=6.9, 8.1 Hz, 1H), 7.36 (td, J=1.7, 8.2 Hz, 1H), 7.57 (dd, J=1.7, 7.7 Hz, 1H), 7.98-8.64 (m, 1H).

LC-MS (METCR1416): 100% (UV), Rt=4.47 min, m/z (ESI$^+$)=369.1 [M+H]$^+$

3-[N-(2-Methoxyphenyl)formamido]-N-(2-methylpropyl)-2-oxobutanamide (FP 100)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as an off-white powder (37 mg, 100% purity, 13%) after purification by flash column chromatography on normal phase silica (50 g SNAP KP-SIL cartridge, 0-100% TBME in heptane gradient) followed by preparative LC (acidic pH, standard elution method).

$^1$H NMR (500 MHz, Chloroform-d) δ 0.92-0.96 (m, 6H), 1.32-1.51 (m, 3H), 1.85 (dp, J=6.7, 13.5 Hz, 1H), 3.10-3.28 (m, 2H), 3.69-3.86 (m, 3H), 5.00-5.46 (m, 1H), 6.86 (s, 1H), 6.95-7.06 (m, 2H), 7.31-7.41 (m, 1H), 7.60 (dd, J=1.7, 7.8 Hz, 1H), 7.98-8.61 (m, 1H).

LC-MS (METCR1416): 100% (UV), Rt=3.81 min, m/z (ESI$^+$)=307.0 [M+H]$^+$

N-(2,2-Dimethylpropyl)-3-[N-(2-methoxyphenyl)formamido]-2-oxobutanamide (FP 101)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (65.5 mg, 100% purity, 23%) after purification by flash column chromatography on normal phase silica (50 g SNAP KP-SIL cartridge, 0-100% TBME in heptane gradient) followed by preparative LC (acidic pH, standard elution method).

$^1$H NMR (500 MHz, Chloroform-d) δ 0.91-0.98 (m, 9H), 1.33-1.52 (m, 3H), 3.14 (d, J=6.7 Hz, 2H), 3.71-3.86 (m, 3H), 4.99-5.46 (m, 1H), 6.86 (s, 1H), 6.91-7.15 (m, 2H), 7.28-7.39 (m, 1H), 7.60 (dd, J=1.7, 7.8 Hz, 1H), 7.99-8.61 (m, 1H).

LC-MS (METCR1416): 100% (UV), Rt=4.01 min, m/z (ESI$^+$)=321.1 [M+H]$^+$

N-[(2R)-Butan-2-yl]-3-[N-(2-methoxyphenyl)formamido]-2-oxobutanamide (FP 102)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (53 mg, 95% purity by $^1$H NMR, 18%) after purification by flash column chromatography on normal phase silica (50 g SNAP KP-SIL cartridge, 0-100% TBME in heptane gradient) followed by preparative LC (acidic pH, standard elution method).

$^1$H NMR (500 MHz, Chloroform-d) δ 0.90-0.95 (m, 3H), 1.17-1.21 (m, 3H), 1.35 (d, J=7.1 Hz, 3H), 1.46-1.57 (m, 2H), 3.83 (s, 3H), 3.87-3.96 (m, 1H), 5.00-5.45 (m, 1H), 6.56-6.64 (m, 1H), 6.96-6.99 (m, 1H), 7.02 (td, J=1.2, 7.6 Hz, 1H), 7.32-7.38 (m, 1H), 7.59 (dt, J=1.6, 7.8 Hz, 1H), 7.99-8.62 (m, 1H).

LC-MS (MET-uPLC-AB-101): 93% (UV), Rt=2.92 min, m/z (ESI$^+$)=307.2 [M+H]$^+$

3-[N-(2-Methoxyphenyl)formamido]-m[(oxan-4-yl)methyl]-2-oxobutanamide (FP 103)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as an off-white powder (66.3 mg, 100% purity, 21%) after purification by flash column chromatography on normal phase silica (50 g SNAP KP-SIL cartridge, 0-100% TBME in heptane gradient) followed by preparative LC (neutral pH, standard elution method).

$^1$H NMR (500 MHz, Chloroform-d) δ 1.28-1.50 (m, 5H), 1.57-1.69 (m, 2H), 1.76-1.87 (m, 1H), 3.24 (t, J=6.7 Hz, 2H), 3.30-3.41 (m, 2H), 3.69-3.86 (m, 3H), 3.94-4.01 (m, 2H), 4.99-5.44 (m, 1H), 6.85-6.95 (m, 1H), 6.96-7.00 (m, 1H), 7.02 (td, J=1.1, 7.6 Hz, 1H), 7.32-7.39 (m, 1H), 7.59 (dd, J=1.6, 7.8 Hz, 1H), 7.97-8.59 (m, 1H).

LC-MS (METCR1416): 100% (UV), Rt=3.43 min, m/z (ESI$^+$)=349.0 [M+H]$^+$

3-[N-(2-Methoxyphenyl)formamido]-2-oxo-N-[(pyrazin-2-yl)methyl]butanamide (FP 104)

The title compound was synthesized from A[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a cream powder (23.4 mg, 99% purity, 7%) after the following sequence of purifications: flash column chromatography on normal phase silica (50 g SNAP KP-SIL cartridge, 0-100%

TBME in heptane gradient then MeOH flush), flash column chromatography on irregular phase silica (28 g SNAP KP—NH cartridge, 0-15% MeOH in TBME gradient), preparative LC (neutral pH, standard elution method), preparative LC (acidic pH, standard elution method), recrystallization from 1:1 EtOAc/heptane.

$^1$H NMR (500 MHz, Chloroform-d) δ 1.31-1.49 (m, 3H), 3.63-3.91 (m, 3H), 4.63-4.76 (m, 2H), 5.05-5.49 (m, 1H), 6.97-7.00 (m, 1H), 7.00-7.05 (m, 1H), 7.33-7.40 (m, 1H), 7.57 (dd, J=1.6, 7.8 Hz, 1H), 7.70-7.79 (m, 1H), 8.02 (s, 1H), 8.48-8.58 (m, 2H), 8.61-8.66 (m, 1H).

LC-MS (MET-uPLC-AB-101): 99% (UV), Rt=2.20 min, m/z (ESI$^+$)=343.1 [M+H]$^+$

N-(Cyclopropylmethyl)-3-[N-(2-methoxyphenyl)formamido]-2-oxobutanamide (FP 105)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as an off-white powder (30.5 mg, 100% purity, 11%) after purification by flash column chromatography on normal phase silica (50 g SNAP KP-SIL cartridge, 0-100% TBME in heptane gradient) followed by preparative LC (acidic pH, standard elution method) and recrystallization from 1:1 EtOAc/heptane.

$^1$H NMR (500 MHz, Chloroform-d) δ 0.20-0.30 (m, 2H), 0.50-0.60 (m, 2H), 0.88-1.05 (m, 1H), 1.30-1.50 (m, 3H), 3.11-3.27 (m, 2H), 3.68-3.88 (m, 3H), 5.03-5.49 (m, 1H), 6.89-6.96 (m, 1H), 6.97-7.01 (m, 1H), 7.01-7.07 (m, 1H), 7.32-7.41 (m, 1H), 7.59 (dd, J=1.7, 7.7 Hz, 1H), 8.01-8.64 (m, 1H).

LC-MS (MET-uPLC-AB-101): 100% (UV), Rt=2.80 min, m/z (ESI$^+$)=305.1 [M+H]$^+$

N-[(2S)-Butan-2-yl]-3-[N-(2-methoxyphenyl)formamido]-2-oxobutanamide (FP 106)

The title compound was synthesized from N-[4-cyano-3-oxo-4-(tributyl-λ5-phosphanylidene)butan-2-yl]-N-(2-methoxyphenyl)formamide (I-208) in a similar manner to method A, general procedure 2 (general scheme 9) as a yellow viscous oil (22 mg, 95% purity by $^1$H NMR, 8%) after purification by flash column chromatography on normal phase silica (50 g SNAP KP-SIL cartridge, 0-100% TBME in heptane gradient) followed by preparative LC (acidic pH, standard elution method) repeated twice.

$^1$H NMR (500 MHz, Chloroform-d) δ 0.93-0.98 (m, 3H), 1.20-1.23 (m, 3H), 1.35-1.46 (m, 3H), 1.52-1.60 (m, 2H), 3.82-3.87 (m, 3H), 3.89-3.97 (m, 1H), 5.02-5.46 (m, 1H), 6.58-6.67 (m, 1H), 6.98-7.02 (m, 1H), 7.02-7.06 (m, 1H), 7.34-7.40 (m, 1H), 7.61 (dt, J=1.5, 7.8 Hz, 1H), 8.01-8.64 (m, 1H).

LC-MS (MET-uPLC-AB-101): 94% (UV), Rt=2.92 min, m/z (ESI$^+$)=307.2 [M+H]$^+$

3-[N-(2-Methoxyphenyl)formamido]-N-[(2R)-3-methylbutan-2-yl]-2-oxobutanamide (FP 107)

The title compound was synthesized from N-[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (19 mg, 96% purity, 6%) after purification by flash column chromatography on normal phase silica (50 g SNAP KP-SIL cartridge, 0-100% TBME in heptane gradient) followed by preparative LC (acidic pH, standard elution method).

$^1$H NMR (500 MHz, Chloroform-d) δ 0.91-0.95 (m, 6H), 1.13-1.16 (m, 3H), 1.35 (dd, J=1.7, 7.1 Hz, 3H), 1.69-1.83 (m, 1H), 3.46-3.84 (m, 3H), 3.85-3.90 (m, 1H), 5.00-5.13 (m, 1H), 6.58-6.72 (m, 1H), 6.95-7.00 (m, 1H), 7.00-7.06 (m, 1H), 7.32-7.38 (m, 1H), 7.60 (dd, J=1.5, 7.7 Hz, 1H), 7.95-8.62 (m, 1H).

LC-MS (MET-uPLC-AB-101): 96% (UV), Rt=3.19 min, m/z (ESI$^+$)=321.2 [M+H]$^+$

3-[N-(2-Methoxyphenyl)formamido]-N-[(2S)-3-methylbutan-2-yl]-2-oxobutanamide (FP 108)

The title compound was synthesized from N[4-cyano-3-oxo-4-(tributyl-λ$^5$-phosphanylidene)butan-2-yl]-N-(2-methoxyphenyl)formamide (I-208) in a similar manner to method A, general procedure 2 (general scheme 9) as a yellow viscous oil (19 mg, 95% purity, 6%) after purification by flash column chromatography on normal phase silica (50 g SNAP KP-SIL cartridge, 0-100% TBME in heptane gradient) followed by preparative LC (acidic pH, standard elution method).

$^1$H NMR (500 MHz, Chloroform-d) δ 0.91-0.95 (m, 6H), 1.13-1.17 (m, 3H), 1.33-1.37 (m, 3H), 1.71-1.81 (m, 1H), 3.83 (s, 3H), 3.84-3.89 (m, 1H), 5.00-5.12 (m, 1H), 6.59-6.71 (m, 1H), 6.95-6.99 (m, 1H), 7.02 (td, J=1.2, 7.6 Hz, 1H), 7.32-7.38 (m, 1H), 7.59 (dd, J=1.6, 7.7 Hz, 1H), 7.98-8.62 (m, 1H).

LC-MS (MET-uPLC-AB-101): 95% (UV), Rt=3.2 min, m/z (ESI$^+$)=321.2 [M+H]$^+$

3-(N-Cyclohexylformamido)-2-oxo-N-(2-phenoxyethyl)butanamide (FP 109)

The title compound was synthesized from N-[4-cyano-3-oxo-4-(tributyl-λ$^5$-phosphanylidene)butan-2-yl]-N-cyclohexylformamide (I-209) in a similar manner to method A, general procedure 2 (general scheme 9) as a brown gum (8.5 mg, 100% purity, 3%) after purification by flash column chromatography on normal phase silica (50 g SNAP KP-SIL cartridge, 0-100% TBME in heptane gradient) then on reverse phase silica (12 g SNAP Ultra C18 cartridge, acidic pH, standard elution method).

$^1$H NMR (250 MHz, Chloroform-d) δ 1.01-1.79 (m, 10H), 1.79-1.95 (m, 2H), 2.01-2.13 (m, 1H), 3.31 (tt, J=3.6, 12.0 Hz, 1H), 3.53-3.83 (m, 2H), 3.94-4.18 (m, 2H), 4.17-5.23 (m, 1H), 6.81-7.02 (m, 3H), 7.07 (t, J=5.9 Hz, 1H), 7.21-7.35 (m, 2H), 7.96-8.27 (m, 1H).

LC-MS (METCR1600): 100% (UV), Rt=4.77 min, m/z (ESI$^+$)=347.4 [M+H]$^+$

3-(N-Cyclohexylformamido)-2-oxo-N-(2,2,2-trifluoroethyl)butanamide (FP 110)

The title compound was synthesized from N-[4-cyano-3-oxo-4-(tributyl-λ$^5$-phosphanylidene)butan-2-yl]-N-cyclohexylformamide (I-209) in a similar manner to method A, general procedure 2 (general scheme 9) as a brown gum (30.3 mg, 100% purity, 8%) after purification by flash column chromatography on normal phase silica (50 g SNAP KP-SIL cartridge, 0-100% TBME in heptane gradient) then on reverse phase silica (12 g SNAP Ultra-C18 cartridge, acidic pH, standard elution method).

$^1$H NMR (500 MHz, Chloroform-d) δ 1.09-1.20 (m, 1H), 1.27-1.42 (m, 2H), 1.46 (d, J=6.7 Hz, 3H), 1.47-1.53 (m, 1H), 1.58-1.66 (m, 1H), 1.68-1.75 (m, 1H), 1.84-1.96 (m, 2H), 2.01-2.13 (m, 2H), 3.35 (tt, J=3.6, 12.1 Hz, 1H), 3.79-4.11 (m, 2H), 4.14-5.17 (m, 1H), 6.91 (s, 1H), 7.98-8.27 (m, 1H).

LC-MS (METCR1600): 100% (UV), Rt=4.43 min, m/z (ESI$^+$)=309.3 [M+H]$^+$

3-(N-Cyclohexylformamido)-N-(2,2-difluoroethyl)-2-oxobutanamide (FP 111)

The title compound was synthesized from N-[4-cyano-3-oxo-4-(tributyl-$\lambda^5$-phosphanylidene)butan-2-yl]-N-cyclohexylformamide (I-209) in a similar manner to method A, general procedure 2 (general scheme 9) as a yellow gum (76 mg, 98% purity by 1H NMR, 22%) after purification by flash column chromatography on normal phase silica (50 g SNAP KP-SIL cartridge, 0-100% TBME in heptane gradient) then on reverse phase silica (30 g SNAP Ultra C18 cartridge, acidic pH, standard elution method).

$^1$H NMR (500 MHz, Chloroform-d) δ 1.09-1.21 (m, 1H), 1.25-1.47 (m, 5H), 1.47-1.73 (m, 3H), 1.84-1.97 (m, 2H), 2.04-2.10 (m, 2H), 3.29-3.54 (m, 1H), 3.52-3.91 (m, 2H), 4.06-5.16 (m, 1H), 5.68-6.05 (m, 1H), 6.77-6.95 (m, 1H), 8.00-8.30 (m, 1H).

LC-MS (METCR1600): 100% (UV), Rt=4.13 min, m/z (ESI$^+$)=291.3 [M+H]$^+$

3-(N-Cyclohexylformamido)-N-[2-(oxan-4-yl)ethyl]-2-oxobutanamide (FP 112-1/2)

The title compound was synthesized from N-[4-cyano-3-oxo-4-(tributyl-$\lambda^5$-phosphanylidene)butan-2-yl]-N-cyclohexylformamide (I-209) in a similar manner to method A, general procedure 2 (general scheme 9) and obtained as a colourless gum in 2 batches, FP 112-1 (2.2 mg, 100% purity, 0.5%) and FP 112-2 (5.4 mg, 95% purity by 1H NMR, 2%), after purification by flash column chromatography on normal phase silica (50 g SNAP KP-SIL cartridge, 0-100% TBME in heptane gradient) then on reverse phase silica using basic conditions (12 g SNAP Ultra C18 cartridge, basic pH, standard elution method) and acidic conditions (12 g SNAP Ultra C18 cartridge, acidic pH, standard elution method).

FP 112-1
$^1$H NMR (500 MHz, Chloroform-d) δ 1.08-1.21 (m, 1H), 1.26-1.39 (m, 4H), 1.43-1.51 (m, 5H), 1.52-1.65 (m, 5H), 1.67-1.74 (m, 1H), 1.85-1.95 (m, 3H), 2.02-2.13 (m, 2H), 3.24-3.41 (m, 4H), 3.90-3.99 (m, 2H), 4.22-5.21 (m, 1H), 6.54-7.00 (m, 1H), 7.97-8.34 (m, 1H).

LC-MS (METCR1600): 100% (UV), Rt=4.13 min, m/z (ESI$^+$)=339.3 [M+H]$^+$

FP 112-2
$^1$H NMR (500 MHz, Chloroform-d) δ 1.10-1.21 (m, 1H), 1.22-1.40 (m, 4H), 1.40-1.76 (m, 12H), 1.86-1.94 (m, 2H), 2.03-2.14 (m, 2H), 3.25-3.43 (m, 4H), 3.89-4.01 (m, 2H), 4.20-5.19 (m, 1H), 6.54-6.94 (m, 1H), 8.02-8.26 (m, 1H).

LC-MS (METCR1600): 100% (UV), Rt=4.12 min, m/z (ESI$^+$)=339.3 [M+H]$^+$

Method B: Oxidation with m-CPBA

N-Benzyl-3-(N-cyclohexylformamido)-2-oxobutanamide (FP 113)

To a stirred, ice cooled solution of N-[4-cyano-3-oxo-4-(tributyl-$\lambda^5$-phosphanyl-idene)butan-2-yl]-N-cyclohexylformamide (I-209) (500 mg, 1.18 mmol) in dry MeOH (8 mL) was added at 0° C., m-CPBA (75%, 871 mg, 3.79 mmol) portion wise. The reaction was allowed to warm up to RT over 30 min and purged with nitrogen for 1.5 h. EtOAc (20 mL) was added and the mixture washed with 1:1:1 0.5M KI/NaHCO$_3$/NaS$_2$O$_3$ (2×25 mL). The organic layer was dried over sodium sulfate, filtered and concentrated in vacuo to give an orange oil which was dissolved in dry MeOH (8 mL). Benzylamine (258 μL, 2.37 mmol) was added and the reaction mixture stirred at RT for 18 h. The mixture was concentrated in vacuo and the crude material was purified by flash column chromatography on normal phase silica (25 g SNAP KP-SIL cartridge, 0-100% TBME in heptane gradient) followed by flash column chromatography on reverse phase silica (12 g SNAP KP-C18-HS cartridge, acidic pH, standard elution method). The gum obtained after purification was dried in vacuo for 6 h at 45° C. to afford 39.6 mg of N—benzyl-3-(N-cyclohexylformamido)-2-oxobutanamide as an off-white gum (100% purity, 11%).

$^1$H NMR (500 MHz, Chloroform-d) δ 1.10-1.21 (m, 1H), 1.24-1.40 (m, 2H), 1.43-1.50 (m, 3H), 1.50-1.57 (m, 1H), 1.68-1.74 (m, 1H), 1.85-1.94 (m, 2H), 2.03-2.12 (m, 2H), 3.28-4.19 (m, 1H), 4.24-5.20 (m, 3H), 6.94 (s, 1H), 7.25-7.40 (m, 6H), 8.02-8.30 (m, 1H).

LC-MS (METCR1600): 100% (UV), Rt=4.63 min, m/z (ESI$^+$)=317.3 [M+H]$^+$

4-{2-[3-(N-Cyclohexylformamido)-2-oxobutanamido]ethoxy}benzamide (FP 114)

To a stirred, ice cooled solution of N[4-cyano-3-oxo-4-(tributyl-$\lambda^5$-phosphanylidene)butan-2-yl]-N-cyclohexylformamide (I-209) (500 mg, 1.18 mmol) in dry MeOH (8 mL) was added at 0° C. m-CPBA (75%, 871 mg, 3.79 mmol) portion wise. The reaction was allowed to warm up to RT over 30 min and purged with nitrogen for 1.5 h. The mixture was diluted with EtOAc (20 mL) then washed with 1:1:1 0.5 M KI/NaHCO$_3$/NaS$_2$O$_3$ (2×25 mL). The organic layer was dried over sodium sulfate, filtered and concentrated in vacuo to give an orange oil which was dissolved in dry MeOH (8 mL). 4-(2-Aminoethoxy)benzamide (360 μL, 2.37 mmol) was added and the reaction mixture was stirred at RT for 18 h. DMF (2 mL) was added and the reaction was stirred at RT for 4 h then heated at 40° C. for 1.5 h. The mixture was cooled down and stirred at RT for 18 h. The suspension was diluted with EtOAc (20 mL) and washed with water (2×20 mL). The aqueous layer was extracted with 1:1 IPA/CHCl$_3$ then the combined organic layer were dried over magnesium sulfate, filtered and concentrated in vacuo. The crude material was purified by flash column chromatography on normal phase silica (50 g SNAP KP-SIL cartridge, 0-100% TBME in heptane gradient then MeOH flush) then on reverse phase silica (30 g SNAP KP-C18-HS cartridge, acidic pH, standard elution method). The gum obtained was triturated in Et$_2$O and the suspension was filtered to afford 5.7 mg of 4-{2-[3-(N-cyclohexylformamido)-2-oxobutanamido]ethoxy}benzamide as an off-white solid (96% purity, 1%).

$^1$H NMR (500 MHz, Chloroform-d) δ 1.10-1.19 (m, 1H), 1.24-1.39 (m, 3H), 1.42-1.47 (m, 3H), 1.49-1.61 (m, 2H), 1.85-1.95 (m, 2H), 2.02-2.11 (m, 2H), 3.25-3.38 (m, 1H), 3.60-3.81 (m, 2H), 4.04-4.19 (m, 2H), 4.23-5.21 (m, 1H), 5.48-6.11 (m, 2H), 6.86-6.98 (m, 2H), 7.01-7.11 (m, 1H), 7.71-7.83 (m, 2H), 7.95-8.30 (m, 1H).

LC-MS (METCR1600): 96% (UV), Rt=3.75 min, m/z (ESI$^+$)=390.2 [M+H]$^+$

GENERAL SCHEME 10:

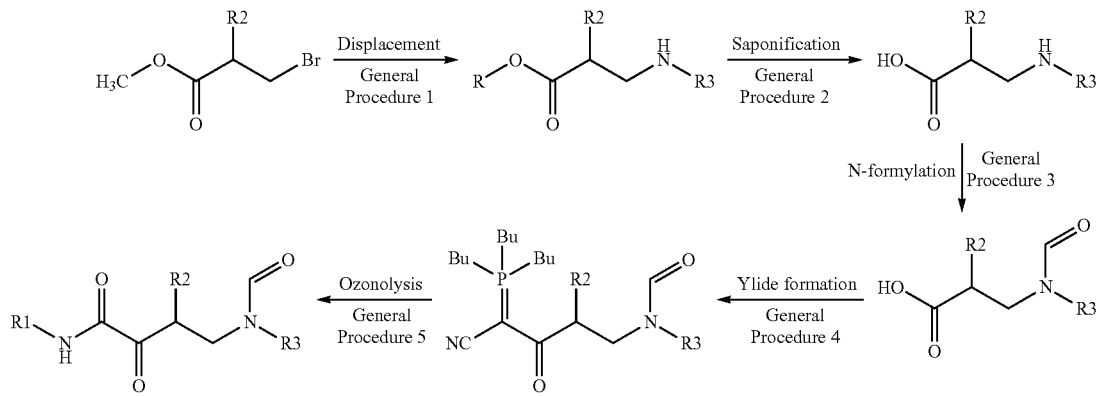

General Procedure 1 (General Scheme 10): Displacement

Methyl 3-[(2-methoxyphenyl)amino]propanoate (I-210)

To 2-methoxyaniline (517 µL, 4.58 mmol) was added methyl 3-bromopropanoate (500 µL, 4.58 mmol) and the mixture was heated at 100° C. in a microwave for 5 min. The reaction was diluted with DCM and filtered. The filtrate was concentrated in vacuo and the crude material was purified by flash column chromatography on normal phase silica (50 g SNAP KP-SIL cartridge, 0-50% EtOAc in heptane gradient) to afford 301 mg of methyl 3-[(2-methoxyphenyl)amino]propanoate as a red oil (100% purity, 31%).

$^1$H NMR (250 MHz, Chloroform-d) δ 2.67 (t, J=6.6 Hz, 2H), 3.48 (t, J=6.6 Hz, 2H), 3.70 (s, 3H), 3.84 (s, 3H), 4.77 (s, 1H), 6.57-6.95 (m, 4H).

LC-MS (METCR1410): 100% (UV), Rt=1.15 min, m/z (ESI$^+$)=209.9 [M+H]$^+$

General Procedure 2 (General Scheme 10): Saponification

3-[(2-Methoxyphenyl)amino]propanoic acid (I-211)

To a stirred solution of methyl 3-[(2-methoxyphenyl)amino]propanoate (I-210) (301 mg, 1.44 mmol) in EtOH (5 mL) was added 2M KOH (1.1 mL, 2.16 mmol) and the reaction was stirred at RT for 2.5 h. The mixture was acidified with 1M HCl to pH 1-2 and the aqueous layer was extracted with 1:1 IPA/CHCl$_3$ (3×25 mL). The combined organic layers were dried over magnesium sulfate, filtered and concentrated in vacuo to afford 349 mg of 3-[(2-methoxyphenyl)amino]propanoic acid as a grey glassy solid (100% purity, quantitative) used in the next step without further purification.

$^1$H NMR (250 MHz, DMSO-d6) δ 2.59 (t, J=6.9 Hz, 2H), 3.35 (t, J=6.9 Hz, 2H), 3.82 (s, 3H), 6.76-7.12 (m, 4H).

LC-MS (METCR1410): 100% (UV), Rt=0.70 min, m/z (ESI$^+$)=196.1 [M+H]$^+$

General Procedure 3 (General Scheme 10): N-Formylation

3-[N-(2-Methoxyphenyl)formamido]propanoic acid (I-212)

To a stirred suspension of 3-[(2-methoxyphenyl)amino]propanoic acid (I-211, 349 mg, 1.79 mmol) and formic acid (460 µL, 11.63 mmol) was added acetic anhydride (3 mL) dropwise and the reaction was stirred at RT for 6 h. Formic acid (100 µL, 2.54 mmol) was added and stirring continued at RT for 18 h. Formic acid (460 µL, 11.71 mmol) was added and the reaction was stirred at RT for 8 h. Formic acid (230 µl, 5.85 mmol) was added and the mixture was stirred at RT for 18 h. The solution was concentrated in vacuo and the residue dissolved in Et$_2$O. The solvent was removed in vacuo and the crude material was dissolved in DCM. The solution was concentrated in vacuo to afford 299 mg of 3-[N-(2-methoxyphenyl)formamido]propanoic acid as a brown gum (51% purity, 38%) used in the next step without purification LC-MS (METCR1410): 51% (UV), Rt=0.81 min, m/z (ESI$^+$)=224.1 [M+H]$^+$ General Procedure 4 (General Scheme 10): Ylide Formation N-[4-Cyano-3-oxo-4-(tributyl-λ$^5$-phosphanylidene)butyl]-N-(2-methoxyphenyl)formamide (I-213)

To a stirred, ice cooled solution of 3-[N-(2-methoxyphenyl)formamido]propanoic acid (I-212, 51% purity, 298 mg, 0.68 mmol) and DIPEA (356 µL, 2.04 mmol) in dry 9:1 DCM/DMF (10 mL) was added HATU (777 mg, 2.04 mmol) at 0° C. portion wise. The mixture was stirred at 0° C. for 1 h and (tributyl-λ$^5$-phosphanyl-idene)acetonitrile (429 µL, 1.57 mmol) added. The solution was stirred for 45 min at 0° C., then at RT for 6 h. The reaction was quenched with water (30 mL) and the aqueous layer was extracted with DCM (20 mL). The organic layer was washed with water (30 mL), dried over magnesium sulfate and concentrated in vacuo. The crude material was purified by flash column chromatography on normal phase silica (50 g SNAP KP-SIL cartridge, 0-100% TBME in heptane gradient) to afford 337 mg of N[4-cyano-3-oxo-4-(tributyl-λ$^5$-phosphanylidene)butyl]-N-(2-methoxyphenyl)formamide as an orange oil (83% purity by $^1$H NMR, 92%).

$^1$H NMR (500 MHz, Chloroform-d) δ 0.82-0.93 (m, 9H), 1.28-1.44 (m, 12H), 1.94-2.13 (m, 6H), 2.67-2.78 (m, 2H), 3.74-3.79 (m, 3H), 3.87-4.04 (m, 2H), 6.93-7.02 (m, 2H), 7.13-7.21 (m, 1H), 7.31 (m, 1H), 8.20 (m, 1H).

LC-MS (METCR1410): 97% (UV), Rt=1.25 min, m/z (ESI$^+$)=447.8 [M+H]$^+$

General Procedure 5 (General Scheme 10): Ozonolyals

N-[(3-Chlorophenyl)methyl]-4-[N-(2-methoxyphenyl)formamido]-2-oxobutanamide (FP 115)

Ozone (ozone generator) was passed at −78° C. through a solution of N-[4-cyano-3-oxo-4-(tributyl-$\lambda^5$-phosphanylidene)butyl]-N-(2-methoxyphenyl)formamide (I-213, 83% purity, 337 mg, 0.63 mmol) and 1-(3-chlorophenyl)methanamine (84 μL, 0.69 mmol) in DCM (10 mL) for 15 min. The solution was flushed with nitrogen and the mixture stirred at −78° C. under nitrogen for 1 h. The reaction was warmed up to RT, concentrated in vacuo to afford a gum which was purified by flash column chromatography on normal phase silica (50 g SNAP KP-SIL cartridge, 0-100% TBME in heptane gradient) followed by preparative LC (acidic pH, standard elution method) to afford 24.3 mg of N-[(3-chlorophenyl)methyl]-4-[N-(2-methoxyphenyl)formamido]-2-oxobutanamide as a yellow oil (100% purity, 10%).

$^1$H NMR (500 MHz, Chloroform-d) δ 3.07-3.21 (m, 2H), 3.69-3.86 (m, 3H), 3.92-4.08 (m, 2H), 4.43 (d, J=6.3 Hz, 2H), 6.93-7.01 (m, 2H), 7.07-7.20 (m, 3H), 7.26-7.30 (m, 3H), 7.33 (td, J=1.7, 8.1 Hz, 1H), 8.06-8.40 (m, 1H).

LC-MS (METCR1600): 100% (UV), Rt=4.52 min, m/z (ESI$^+$)=375.1/377.1 [M+H]$^+$

Route Via Ylide Formation: Synthesis of Final Products (FP 116 119)

General Procedure 1 (General Scheme 11): Reductive Amination

Methyl (2S)-2-(benzylamino)-3-[1-(triphenylmethyl)-1H-imidazol-4-yl]propanoate (I-214)

To a stirred, ice cooled solution of methyl (2S)-2-amino-3-[1-(triphenyl-methyl)-1H-imidazol-4-yl]propanoate hydrochloride (95%, 5 g, 10.6 mmol) in MeOH (50 mL), at 0° C. was added NaH (60% dispersion in oil, 424 mg, 10.6 mmol). The mixture was stirred at 0° C. for 5 min and benzaldehyde (1.3 mL, 12.72 mmol) added. The reaction was stirred at RT for 1.5 h, cooled to 0° C. and sodium borohydride (98%, 430 mg, 11.13 mmol) added. The reaction was stirred at 0° C. for 20 min, acidified to pH 5-6 with 10% HCl in DCM (200 mL) and 1M NaHCO$_3$(50 mL) added. The organic layer was separated, dried over sodium sulfate, filtered and concentrated in vacuo to give 5.55 g of methyl (2S)-2-(benzylamino)-3-[1-(triphenylmethyl)-1H-imidazol-4-yl]propanoate as a thick pale yellow oil (73% purity, 76%) used in the next step without further purification.

LC-MS (METCR1416): 73% (UV), Rt=3.70 min, m/z (ESI$^+$)=502.3 [M+H]$^+$

General Procedure 2 (General Scheme 11): N-Formylation Methyl (2S)-2-(N-benzylformamido)-3-[1-(triphenylmethyl)-1H-imidazol-4-yl]propanoate (I-215)

To acetic anhydride (1.9 mL, 20.5 mmol) was added formic acid (1.1 mL, 26.6 mmol) dropwise. The mixture was

GENERAL SCHEME 11:

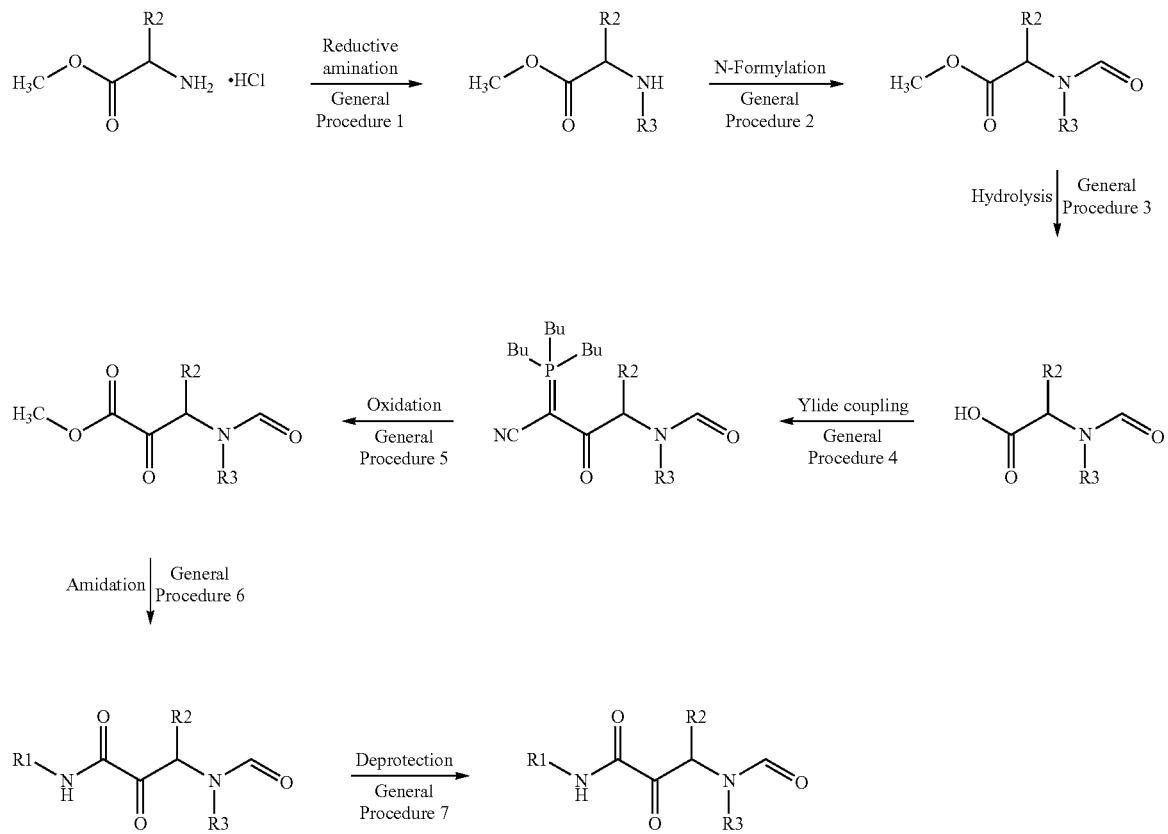

heated at 50° C. for 1 h and cooled to 0° C. The solution was diluted with dry THF (5 mL) and added dropwise to a stirred solution of methyl (2S)-2-(benzylamino)-3-[1-(triphenylmethyl)-1H-imidazol-4-yl]propanoate (I-214, 90% purity, 3.75 g, 6.73 mmol) in dry THF (35 mL) at 0° C. The reaction was stirred at RT for 1 h, diluted with EtOAc (50 mL). The organic layer was separated, washed with 1 M $NaHCO_3$ (2× 50 mL), water (50 mL) and brine (50 mL) and dried over sodium sulfate, filtered and concentrated in vacuo to give a yellow oil. The residue was suspended in heptane (2×100 mL) and concentrated in vacuo to afford 4 g of methyl (2S)-2-(N-benzylformamido)-3-[1-(triphenylmethyl)-1H-imidazol-4-yl]propanoate as a colourless foam (86% purity by 1H NMR, 97%) used in the next step without further purification.

$^1$H NMR (500 MHz, Chloroform-d) δ 2.81-3.22 (m, 2H), 3.33-3.47 (m, 3H), 3.89-4.45 (m, 2H), 4.51-4.67 (m, 1H), 6.19-6.59 (m, 1H), 6.95-7.39 (m, 21H), 8.00-8.14 (m, 1H).

LC-MS (METCR1416): 76% (UV), Rt=3.81 min, m/z $(ESI^+)$=530.3 $[M+H]^+$

General Procedure 3 (General Scheme 11): Hydrolysis (2S)-2-(N-Benzylformamido)-3-[1-(triphenylmethyl)-1H-imidazol-4-yl]propanoic acid (I-216)

To a stirred, ice cooled solution of methyl (2S)-2-(N-benzylformamido)-3-[1-(triphenylmethyl)-1H-imidazol-4-yl]propanoate (I-215, 86% purity by $^1$H NMR, 4 g, 6.5 mmol) in MeOH (150 mL) was added 0.1M LiOH (102 mL) and THF (75 mL). The mixture was cooled at 0-5° C. for 24 h, acidified to pH 4-5 with 1M HCl (9 mL) and THF and MeOH removed in vacuo. The residue was extracted with EtOAc (2×50 mL) and the combined organic layers washed with water (50 mL), dried over sodium sulfate, filtered and concentrated in vacuo to afford 3.66 g of (2S)-2-(N-benzylformamido)-3-[1-(triphenylmethyl)-1H-imidazol-4-yl]propanoic acid as a pale yellow foam (85% purity by $^1$H NMR, 89%) used in the next step without further purification.

$^1$H NMR (500 MHz, DMSO-d6) δ 3.17-3.60 (m, 1H), 2.85-4.16 (m, 3H), 4.47-4.60 (m, 2H), 6.35-6.54 (m, 1H), 6.97-7.46 (m, 21H), 8.10-8.20 (m, 1H).

LC-MS (METCR1410): 94% (UV), Rt=1.07 min, m/z $(ESI^+)$=516.3 $[M+H]^+$

General Procedure 4 (General Scheme 11): Ylide Coupling

N-Benzyl-[(2S)-4-cyano-3-oxo-4-(tributyl-$\lambda^5$-phosphanylidene)-1-[1-(triphenylmethyl)-1H-imidazol-4-yl]butan-2-yl]formamide (I-217)

To a stirred, ice cooled solution of (2S)-2-(N-benzylformamido)-3-[1-(triphenyl-methyl)-1H-imidazol-4-yl]propanoic acid (I-216, 85% purity by 1H NMR, 3.66 g, 6.03 mmol) and DIPEA (3.2 mL, 18.4 mmol) in 1:3 DMF/DCM (80 mL) was added HATU (3.57 g, 9.19 mmol). The mixture was stirred at 0° C. for 40 min and (tributyl-$\lambda^5$-phosphanylidene)-acetonitrile (2.1 mL, 7.96 mmol) added. The mixture was stirred at RT for 2 h and quenched with 1M $NaHCO_3$ (50 mL). The organic layer was washed with water (3×50 mL), brine (50 mL), dried over sodium sulfate, filtered and concentrated in vacuo to give a crude product which was purified by flash column chromatography on reverse phase (400 g SNAP Ultra C18 cartridge, acidic pH, standard elution method). Selected fractions were combined, treated with 1M $NaHCO_3$ and partially concentrated. The residual solution was extracted with EtOAc (2×50 mL) and the combined extracts washed with brine, dried over sodium sulfate, filtered and concentrated in vacuo to afford 4.2 g of N-benzyl-N-[(2S)-4-cyano-3-oxo-4-(tributyl-$\lambda^5$-phosphanylidene)-1-[1-(triphenylmethyl)-1H-imidazol-4-yl]butan-2-yl]formamide as a pale orange foam (87% purity by $^1$H NMR, 81%).

$^1$H NMR (500 MHz, Chloroform-d) δ 0.92 (t, 9H), 1.21-1.50 (m, 12H), 1.75-1.90 (m, 3H), 1.94-2.10 (m, 3H), 2.90 (d, J=7.6 Hz, 2H), 4.07-4.63 (m, 2H), 4.96 (t, J=7.5 Hz, 1H), 6.22-6.40 (m, 1H), 7.01-7.45 (m, 21H), 8.11-8.28 (m, 1H).

LC-MS (METCR1416): 99% (UV), Rt=4.49 min, m/z $(ESI^+)$=739.6 $[M+H]^+$

General Procedure 5 (General Scheme 11): Oxidation

Methyl (3S)-3-(N-benzylformamido)-2-oxo-4-[1-(triphenylmethyl)-1H-imidazol-4-yl]butanoate (I-218)

To a stirred, ice cooled solution of N-benzyl-N-[(2S)-4-cyano-3-oxo-4-(tributyl-$\lambda_5$-phosphanylidene)-1-[1-(triphenylmethyl)-1H-imidazol-4-yl]butan-2-yl]formamide (I-217, 87% purity by $^1$H NMR, 3.94 g, 4.64 mmol) in dry MeOH (50 mL) was added m-CPBA (75%, 3.42 g, 14.8 mmol) at 0° C., portion wise over 5 min. The reaction was stirred at RT for 30 min and purged with nitrogen. The mixture was diluted with EtOAc (300 mL), washed with 1:1:1 0.5M $KI/NaHCO_3/NaS_2O_3$ (3×100 mL) and brine (200 mL). The organic layer was dried over sodium sulfate, filtered and concentrated in vacuo to give 4 g of methyl (3S)-3-(N-benzylformamido)-2-oxo-4-[1-(triphenylmethyl)-1H-imidazol-4-yl]butanoate as a yellow gum (47% purity, 73%) used in the next step without further purification.

LC-MS (METCR1410): 47% (UV), Rt=1.05 min, m/z $(ESI^+)$=558.3 $[M+H]^+$

General Procedure 6 (General Scheme 11): Amide Formation (3S)-3-(N-Benzylformamido)-N-(cyclohexylmethyl)-2-oxo-4-[1-(triphenylmethyl)-1H-imidazol-4-yl]butanamide (FP 116)

To a stirred solution of methyl (3S)-3-(N-benzylformamido)-2-oxo-4-[1-(triphenylmethyl)-1H-imidazol-4-yl]butanoate (I-218, 800 mg, 0.90 mmol) in dry MeOH (5 mL) was added cyclohexylmethanamine (205 mg, 1.81 mmol). The mixture was stirred at RT for 2 h then C18 reverse phase silica (3 g) added and the suspension stirred at RT for 1 h. The mixture was concentrated in vacuo and purified by flash column chromatography on reverse phase silica (30 g SNAP Ultra C18 cartridge, high pH, standard elution method). Selected fractions were combined, diluted with EtOAc (100 mL), washed with water (3×50 mL) and brine (50 mL) and dried over sodium sulfate, filtered and concentrated in vacuo to afford 449 mg of (3S)-3-(N-benzylform-amido)-N-(cyclohexylmethyl)-2-oxo-4-[1-(triphenylmethyl)-1H-imidazol-4-yl]butanamide as a pale yellow foam (93% purity by $^1$H NMR, 72%).

$^1$H NMR (500 MHz, Chloroform-d) δ 0.76-0.98 (m, 2H), 1.05-1.23 (m, 3H), 1.30-1.51 (m, 1H), 1.52-1.74 (m, 5H), 2.76-3.38 (m, 4H), 4.06-4.17 (m, 1H), 4.42-4.73 (m, 1H), 4.89-5.54 (m, 1H), 6.34-6.75 (m, 2H), 7.01-7.20 (m, 10H), 7.21-7.39 (m, 11H), 7.94-8.30 (m, 1H).

LC-MS (METCR1600): 96% (UV), Rt=6.17 min, m/z (ESI+)=639.4 [M+H]+

(3S)-3-(N-Benzylformamido)-N-(cyclopropylmethyl)-2-oxo-4-[1-(triphenylmethyl)-1H-imidazol-4-yl]butanamide (FP 117)

The title compound was synthesized from methyl (3S)-3-(N-benzylform-amido)-2-oxo-4-[1-(triphenylmethyl)-1H-imidazol-4-yl]butanoate (I-218) in a similar manner to general procedure 6 (general scheme 11) as a colourless gum (116 mg, 90% purity by 1H NMR, 39%) after 2 purifications by flash column chromatography on reverse phase silica (30 g SNAP Ultra C18 cartridge, high pH, standard elution method) and extraction of selected fractions with EtOAc.

$^1$H NMR (500 MHz, Chloroform-d) δ −0.05-0.10 (m, 2H), 0.28-0.42 (m, 2H), 0.61-0.84 (m, 1H), 2.62-3.25 (m, 4H), 3.89-4.64 (m, 2H), 4.76-5.42 (m, 1H), 6.17-6.66 (m, 2H), 6.88-7.07 (m, 10H), 7.07-7.28 (m, 11H), 7.81-8.17 (m, 1H).

LC-MS (METCR1600): 94% (UV), Rt=5.60 min, m/z (ESI+)=597.3 [M+H]+

General Procedure 7 (General Scheme 11): Deprotection (3S)-3-(N-Benzylformamido)-N-(cyclohexylmethyl)-4-(1H-imidazol-4-yl)-2-oxobutanamide (FP 118)

To a stirred solution of (3S)-3-(N-benzylformamido)-N-(cyclohexylmethyl)-2-oxo-4-[1-(triphenylmethyl)-1H-imidazol-4-yl]butanamide (FP 116, 431 mg, 0.63 mmol) in dry DCM (10 mL) was added TFA (2.7 mL) and triethylsilane (298 μL, 1.87 mmol). The mixture was stirred at RT for 3 h, concentrated in vacuo to give a gum which was purified by flash column chromatography on reverse phase silica (30 g SNAP Ultra C18 cartridge, high pH, standard elution method). Selected fractions were diluted with EtOAc (20 mL), washed with water (3×20 mL) and brine (20 mL), dried over sodium sulfate, filtered and concentrated in vacuo to afford 227 mg of (3S)-3-(N-benzylform-amido)-N-(cyclohexylmethyl)-4-(1H-imidazol-4-yl)-2-oxobutanamide as a colourless foam (92% purity by $^1$H NMR, 84%).

$^1$H NMR (500 MHz, Chloroform-d) δ 0.84-0.98 (m, 2H), 1.10-1.25 (m, 3H), 1.33-1.52 (m, 1H), 1.57-1.75 (m, 5H), 2.71-3.24 (m, 4H), 4.19-5.51 (m, 4H), 6.45-6.85 (m, 2H), 7.17-7.25 (m, 2H), 7.30-7.42 (m, 3H), 7.52 (d, J=10.4 Hz, 1H), 8.06-8.29 (m, 1H).

LC-MS (METCR1600): 100% (UV), Rt=4.26 min, m/z (ESI+)=397.3 [M+H]+

(3S)-3-(N-Benzylformamido)-N-(cyclopropylmethyl)-4-(1H-imidazol-4-yl)-2-oxobutanamide (FP 119)

The title compound was synthesized from (3S)-3-(N-benzylformamido)-N-(cyclopropylmethyl)-2-oxo-4-[1-(triphenylmethyl)-1H-imidazol-4-yl]butanamide (FP 117) in a similar manner to general procedure 7 (general scheme 11) as a yellow foam (53.5 mg, 90% purity by $^1$H NMR, 45%) after purification by flash column chromatography on reverse phase silica (12 g SNAP Ultra C18 cartridge, high pH, standard elution method) and extraction of selected fractions with EtOAc.

$^1$H NMR (500 MHz, Chloroform-d) δ 0.13-0.26 (m, 2H), 0.44-0.56 (m, 2H), 0.79-0.99 (m, 1H), 2.71-3.27 (m, 4H), 4.15-5.51 (m, 4H), 6.49-6.95 (m, 2H), 7.16-7.24 (m, 2H), 7.29-7.41 (m, 3H), 7.53 (d, J=5.2 Hz, 1H), 8.07-8.31 (m, 1H).

LC-MS (METCR1600): 100% (UV), Rt=3.55 min, m/z (ESI+)=355.2 [M+H]+

Further compounds (FP195-FP201) were synthesised via a related route (General Scheme 11a) and these compounds are described in the additional compound section.

Route to Ethers: Synthesis of Final Compounds (FP 120-137)

GENERAL SCHEME 12:

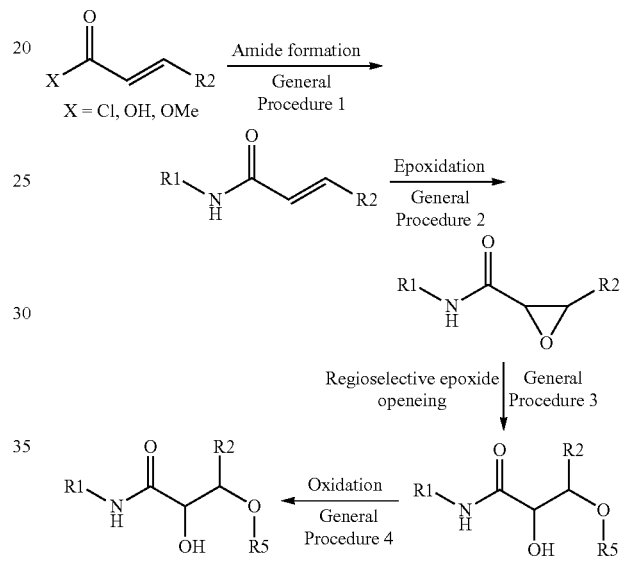

General Procedure 1 (General Scheme 12): Amide Formation

Method A: Amide Formation Using Acid Chloride (2E)-N-(Cyclobutylmethyl)but-2-enamide (I-219)

To a stirring solution of 1-cyclobutylmethanamine hydrochloride (1:1) (1 g, 8.22 mmol) and DIPEA (4.3 mL, 24.67 mmol) in DCM (10 mL) was added at 0° C. a solution of crotonoyl chloride (0.8 mL, 8.39 mmol) in DCM (10 mL) dropwise over 15 min. The reaction mixture was stirred at RT for 2 h and washed with water (2×30 mL). The organic layer was separated, dried over magnesium sulfate, filtered and concentrated in vacuo. The crude material was purified by recrystallization from 1:1 EtOAc/heptane to afford 870 mg of (2E)-N-(cyclopropylmethyl)but-2-enamide as a off-white solid (100% purity, 69%).

$^1$H NMR (250 MHz, Chloroform-d) δ 1.64-1.79 (m, 2H), 1.84 (dd, J=1.6, 6.9 Hz, 3H), 1.87-1.98 (m, 2H), 1.98-2.15 (m, 2H), 2.35-2.59 (m, 1H), 3.34 (dd, J=5.9, 7.2 Hz, 2H), 5.34 (br. s, 1H), 5.77 (dq, J=1.5, 15.2 Hz, 1H), 6.72-6.92 (m, 1H).

LC-MS (METCR1410): 100% (UV), Rt=0.98 min, m/z (ESI+)=154.1 [M+H]+

(2E)-N-(Cyclopentylmethyl)but-2-enamide (I-220)

The title compound was synthesized in a similar manner to method A, general procedure 1 (general scheme 12) as an off-white solid (725 mg, 96% purity, 56%) following recrystallization from 1:1 EtOAc/heptane.

$^1$H NMR (250 MHz, Chloroform-d) δ 1.07-1.31 (m, 2H), 1.48-1.64 (m, 4H), 1.67-1.80 (m, 2H), 1.85 (dd, J=1.6, 6.9 Hz, 3H), 1.97-2.12 (m, 1H), 3.25 (dd, J=6.0, 7.2 Hz, 2H), 5.41 (br. s, 1H), 5.78 (dq, J=1.5, 15.2 Hz, 1H), 6.73-6.91 (m, 1H).

LC-MS (METCR1410): 96% (UV), Rt=1.06 min, m/z (ESI$^+$)=168.1 [M+H]$^+$

Method B: Amide Formation Using Carboxylic Acid

N-(Cyclopropylmethyl)prop-2-enamide (I-221)

To a stirred solution of prop-2-enoic acid (4.8 mL, 69.38 mmol) in DCM (50 mL) was added 1-cyclopropylmethanamine (6.3 mL, 72.85 mmol) and DIPEA (24 mL, 138.77 mmol) followed by HATU (29 g, 76.32 mmol). The solution was stirred under nitrogen at RT for 18 h and washed with 2M HCl (100 mL). The organic layer was separated and washed with saturated $K_2CO_3$ (100 mL), dried over sodium sulfate, filtered and concentrated in vacuo. The crude material was purified by flash column chromatography on normal phase silica (100 g SNAP Ultra cartridge, 10-100% TBME in heptane then 0-20% MeOH in heptane gradient) to give an oil which was suspended in EtOAc (50 mL) and washed with water (2×30 mL). The organic layer was separated, dried over sodium sulfate, filtered and concentrated in vacuo to afford 4.59 g of N-(cyclopropylmethyl)prop-2-enamide as a yellow oil (70% purity by $^1$H NMR, 37%).

$^1$H NMR (250 MHz, Chloroform-d) δ 0.21 (q, J=4.8 Hz, 2H), 0.41-0.59 (m, 2H), 0.84-1.10 (m, 1H), 3.18 (dd, J=5.6, 7.1 Hz, 2H), 5.62 (dd, J=1.7, 10.0 Hz, 1H), 5.68-6.01 (m, 1H), 6.00-6.48 (m, 2H).

General Procedure 2 (General Scheme 12): Epoxide Formation

N-(Cyclobutylmethyl)-3-methyloxirane-2-carboxamide (I-222)

To a stirred solution of (2E)-N-(cyclobutylmethyl)but-2-enamide (I-219, 400 mg, 2.61 mmol) in DCM (15 mL) was added at 0° C. m-CPBA (70%, 1.93 g, 7.83 mmol) and the suspension stirred at RT for 18 h. m-CPBA (70%, 3.22 g, 13.05 mmol) was added and the mixture stirred at RT for 3 days. 30% $Na_2S_2O_3$ (30 mL) was added and the suspension was filtered through celite. The organic layer was washed with 0.5N NaOH (4×10 mL), water (20 mL), dried over sodium sulfate, filtered and concentrated in vacuo. The residue was purified by flash column chromatography on normal phase silica (25 g SNAP KP-SIL cartridge, 0-100% EtOAc in heptane gradient) to afford 182.3 mg of N-(cyclobutylmethyl)-3-methyloxirane-2-carboxamide as a colour oil (100% purity by 1H NMR, 83%).

$^1$H NMR (250 MHz, Chloroform-d) δ 1.39 (d, J=5.1 Hz, 3H), 1.56-1.75 (m, 2H), 1.80-1.97 (m, 2H), 1.97-2.11 (m, 2H), 2.41 (h, J=7.5 Hz, 1H), 2.98 (qd, J=2.1, 5.1 Hz, 1H), 3.19 (d, J=2.1 Hz, 1H), 3.21-3.29 (m, 2H), 6.08 (s, 1H).

LC-MS (METCR1410): 95% (UV), Rt=0.83 min, m/z (ESI$^+$)=170.4 [M+H]$^+$

N-(Cyclopentylmethyl)-3-methyloxirane-2-carboxamide (I-223)

The title compound was synthesized from (2E)-N-(cyclopentylmethyl)but-2-enamide (I-220) in a similar manner to general procedure 2 (general scheme 12) as a colourless oil (189.3 mg, 94% purity by $^1$H NMR, 81%) after purification by flash column chromatography on normal phase silica (25 g SNAP KP-SIL cartridge, 0-100% EtOAc in heptane gradient).

$^1$H NMR (250 MHz, Chloroform-d) δ 1.06-1.22 (m, 2H), 1.40 (d, J=5.1 Hz, 3H), 1.50-1.62 (m, 4H), 1.64-1.80 (m, 2H), 1.88-2.11 (m, 1H), 3.00 (qd, J=2.1, 5.1 Hz, 1H), 3.11-3.23 (m, 3H), 6.15 (s, 1H).

LC-MS (METCR1410): 64% (UV), Rt=0.97 min, m/z (ESI$^+$)=184.1 [M+H]$^+$

N-(Cyclopropylmethyl)oxirane-2-carboxamide (I-224)

The title compound was synthesized from N-(cyclopropylmethyl)prop-2-enamide (I-221) in a similar manner to general procedure 2 (general scheme 12) at 40 C and was obtained as a yellow oil (552 mg, 55% purity by 1H NMR, 6%) after purification by flash column chromatography on normal phase silica (25 g SNAP KP-SIL cartridge, 0-100% TBME in heptane gradient).

$^1$H NMR (250 MHz, Chloroform-d) δ 0.10-0.28 (m, 2H), 0.41-0.62 (m, 2H), 0.79-1.05 (m, 1H), 2.76 (dd, J=2.6, 5.6 Hz, 1H), 2.98 (dd, J=4.7, 5.5 Hz, 1H), 3.02-3.22 (m, 2H), 3.43 (dd, J=2.6, 4.6 Hz, 1H), 6.28 (dd, J=1.7, 17.0 Hz, 1H).

General Procedure 3 (General Scheme 12): Ring Opening

Method A: Addition of Ethoxyethane-Trifluoroborane at RT

3-(Cyclohexyloxy)-N-(cyclopropylmethyl)-2-hydroxybutanamide (I-225)

To a stirred solution of N-(cyclopropylmethyl)-3-methyloxirane-2-carboxamide (I-30, 86% purity, 300 mg, 1.66 mmol) and cyclohexanol (0.21 mL, 1.99 mmol) in DCM (5 mL) was added ethoxyethane-trifluoroborane (1:1, 209 µL, 1.66 mmol). The mixture was stirred for 3 days and concentrated in vacuo to give a yellow oil which was purified by flash column chromatography on normal phase silica (25 g SNAP KP-SIL cartridge, 0-80% EtOAc in heptane gradient) to afford 206 mg of 3-(cyclohexyloxy)-N-(cyclo-propylmethyl)-2-hydroxybutanamide as an off-white solid (100% purity by 1H NMR, 46%).

$^1$H NMR (250 MHz, Chloroform-d) δ 0.16-0.26 (m, 2H), 0.47-0.58 (m, 2H), 0.83-1.06 (m, 1H), 1.12 (d, J=6.2 Hz, 3H), 1.18-1.38 (m, 5H), 1.61-1.97 (m, 5H), 3.08-3.19 (m, 2H), 3.32-3.50 (m, 1H), 3.89 (p, J=6.2 Hz, 1H), 4.10 (d, J=5.1 Hz, 1H), 6.88 (s, 1H).

LC-MS (METCR1410): 64% (UV), Rt=1.06 min, m/z (ESI$^+$)=256.2 [M+H]$^+$

N-(Cyclopropylmethyl)-2-hydroxy-3-[(oxan-4-yl)methoxy]butanamide (I-226)

The title compound was synthesized from N-(cyclopropylmethyl)-3-methyl-oxirane-2-carboxamide (I-30) in a similar manner to method A, general procedure 3 (general scheme 12) as a colourless gum (236 mg, 98% purity, 51%)

after purification by flash column chromatography on normal phase silica (25 g SNAP KP-SIL cartridge, 0-40% EtOAc in heptane gradient then 0-40% MeOH in EtOAc gradient).

LC-MS (METCR1410): 98% (UV), Rt=0.89 min, m/z (ESI$^+$)=272.2 [M+H]$^+$

N-(Cyclopropylmethyl)-3-(2,2-dimethylpropoxy)-2-hydroxybutanamide (I-227)

The title compound was synthesized from N-(cyclopropylmethyl)-3-methyl-oxirane-2-carboxamide (I-30) in a similar manner to method A, general procedure 3 (general scheme 12) as an off-white solid (261.8 mg, 100% purity, 65%) after purification by flash column chromatography on normal phase silica (25 g SNAP KP-SIL cartridge, 0-100% TBME in heptane gradient).

$^1$H NMR (500 MHz, Chloroform-d) δ 0.21 (q, J=4.7 Hz, 2H), 0.48-0.54 (m, 2H), 0.92 (s, 9H), 0.93-1.00 (m, 1H), 1.14 (d, J=6.2 Hz, 3H), 3.07 (d, J=2.4 Hz, 1H), 3.08-3.15 (m, 2H), 3.16-3.23 (m, 2H), 3.67 (p, J=6.2 Hz, 1H), 4.14 (dd, J=2.3, 5.4 Hz, 1H), 6.87 (s, 1H).

LC-MS (METCR1410): 100% (UV), Rt=1.04-1.16 min (multiple peaks), m/z (ESI$^+$)=244.2 [M+H]$^+$

3-(Cyclohexylmethoxy)-N-(cyclopropylmethyl)-2-hydroxybutanamide (I-228)

The title compound was synthesized from N-(cyclopropylmethyl)-3-methyl-oxirane-2-carboxamide (I-30) in a similar manner to method A, general procedure 3 (general scheme 12) as an off-white solid (199 mg, 100% purity by $^1$H NMR, 44%) after purification by flash column chromatography on normal phase silica (25 g SNAP KP-SIL cartridge, 0-80% EtOAc in heptane gradient).

$^1$H NMR (250 MHz, Chloroform-d) δ 0.21 (q, J=4.6 Hz, 2H), 0.46-0.57 (m, 2H), 0.81-1.06 (m, 3H), 1.14 (d, J=6.2 Hz, 3H), 1.15-1.36 (m, 4H), 1.62-1.83 (m, 5H), 3.04 (s, 1H), 3.15 (ddd, J=3.5, 5.8, 7.1 Hz, 2H), 3.20-3.40 (m, 2H), 3.59-3.77 (m, 1H), 4.14 (d, J=5.3 Hz, 1H), 6.88 (br. s, 1H).

3-(Cyclohexyloxy)-2-hydroxy-N-(2-methylpropyl)butanamide (I-229)

The title compound was synthesized from 3-methyl-N-(2-methylpropyl)oxirane-2-carboxamide (I-32) in a similar manner to method A, general procedure 3 (general scheme 12) as an off-white crystalline solid (113 mg, 88% purity, 20%) after purification by flash column chromatography on normal phase silica (25 g SNAP KP-SIL cartridge, 0-100% EtOAc in heptane gradient).

$^1$H NMR (250 MHz, Chloroform-d) δ 0.93 (d, J=6.7 Hz, 6H), 1.10 (d, J=6.3 Hz, 3H), 1.16-1.39 (m, 6H), 1.65-1.98 (m, 5H), 2.92-3.09 (m, 2H), 3.15-3.30 (m, 1H), 3.34-3.50 (m, 1H), 3.84-4.00 (m, 1H), 4.15 (dd, J=2.0, 4.7 Hz, 1H), 6.82 (s, 1H).

LC-MS (METCR1410): 88% (UV), Rt=1.08-1.20 min (multiple peaks), m/z (ESI$^+$)=258.3 [M+H]$^+$

3-(Cyclohexyloxy)-2-hydroxy-N-(propan-2-yl)butanamide (I-230)

The title compound was synthesized from 3-methyl-N-(propan-2-yl)oxirane-2-carboxamide (I-39) in a similar manner to method A, general procedure 3 (general scheme 12) as an off-white solid (327 mg, 100% purity, 64%) after purification by flash column chromatography on normal phase silica (25 g SNAP KP-SIL cartridge, 0-100% EtOAc in heptane gradient).

$^1$H NMR (500 MHz, Chloroform-d) δ 1.10 (d, J=6.3 Hz, 3H), 1.17 (dd, J=12.1, 6.6 Hz, 6H), 1.24-1.30 (m, 5H), 1.50-1.57 (m, 1H), 1.70-1.78 (m, 2H), 1.85-1.93 (m, 2H), 3.34-3.44 (m, 1H), 3.55-3.65 (m, 1H), 3.82-3.94 (m, 1H), 4.05-4.15 (m, 2H), 6.54-6.64 (m, 1H).

LC-MS (METCR1410): 100% (UV), Rt=1.03 min, m/z (ESI$^+$)=244.2 [M+H]$^+$

N-(Cyclobutylmethyl)-3-(cyclohexyloxy)-2-hydroxybutanamide (I-231)

The title compound was synthesized from N-(cyclobutylmethyl)-3-methyl-oxirane-2-carboxamide (I-222) in a similar manner to method A, general procedure 3 (general scheme 12) as an off-white powder (200 mg, 90% purity by 1H NMR, 48%) after purification by flash column chromatography on normal phase silica (25 g SNAP KP-SIL cartridge, 0-100% EtOAc in heptane gradient).

$^1$H NMR (250 MHz, Chloroform-d) δ 1.09 (d, J=6.3 Hz, 3H), 1.16-1.34 (m, 5H), 1.67-1.77 (m, 4H), 1.79-1.95 (m, 4H), 2.01-2.16 (m, 2H), 2.38-2.59 (m, 1H), 3.02 (d, J=2.0 Hz, 1H), 3.15-3.29 (m, 1H), 3.29-3.46 (m, 2H), 3.80-3.97 (m, 1H), 4.12 (dd, J=1.7, 4.88 Hz, 1H), 6.73 (s, 1H).

LC-MS (METCR1410): 78% (UV), Rt=1.09 min, m/z (ESI$^+$)=270.2 [M+H]$^+$

3-(Cyclohexyloxy)-N-(cyclopentylmethyl)-2-hydroxybutanamide (I-232)

The title compound was synthesized from N-(cyclopentylmethyl)-3-methyl-oxirane-2-carboxamide (I-223) in a similar manner to method A, general procedure 3 (general scheme 12) as an off-white powder (213 mg, 95% purity by $^1$H NMR, 46%) after purification by flash column chromatography on normal phase silica (25 g SNAP KP-SIL cartridge, 0-100% EtOAc in heptane gradient).

$^1$H NMR (250 MHz, Chloroform-d) δ 1.10 (d, J=6.3 Hz, 3H), 1.15-1.36 (m, 7H), 1.48-1.63 (m, 5H), 1.67-1.93 (m, 6H), 1.95-2.13 (m, 1H), 3.01 (d, J=1.9 Hz, 1H), 3.07-3.22 (m, 1H), 3.24-3.36 (m, 1H), 3.36-3.47 (m, 1H), 3.83-3.99 (m, 1H), 4.09-4.20 (m, 1H), 6.79 (s, 1H).

LC-MS (METCR1410): 97% (UV), Rt=1.08-1.20 min (multiple peaks), m/z (ESI$^+$)=284.1 [M+H]$^+$

3-(Benzyloxy)-N-(cyclopropylmethyl)-2-hydroxypropanamide (I-233)

The title compound was synthesized from N-(cyclopropylmethyl)oxirane-2-carboxamide (I-224) in a similar manner to method A, general procedure 3 (general scheme 12) as a colourless oil (113.3 mg, 69% purity, 28%) after purification by flash column chromatography on normal phase silica (25 g SNAP KP-SIL cartridge, 0-100% TBME in heptane gradient).

LC-MS (METCR1410): 69% (UV), Rt=0.93 min, m/z (ESI$^+$)=250.5 [M+H]$^+$

3-(Cyclohexylmethoxy)-N-(cyclopropylmethyl)-2-hydroxypropanamide (I-234)

The title compound was synthesized from N-(cyclopropylmethyl)oxirane-2-carboxamide (I-224) in a similar manner to method A, general procedure 3 (general scheme 12) as a colourless oil (63.6 mg, 100% purity, 19%) after purification by flash column chromatography on normal phase silica (25 g SNAP KP-SIL cartridge, 0-100% TBME in heptane gradient).

¹H NMR (500 MHz, Chloroform-d) δ 0.21 (q, J=4.8 Hz, 2H), 0.48-0.57 (m, 2H), 0.87-1.02 (m, 3H), 1.09-1.32 (m, 3H), 1.52-1.64 (m, 1H), 1.64-1.78 (m, 5H), 3.13-3.18 (m, 2H), 3.31 (d, J=6.5 Hz, 2H), 3.58-3.70 (m, 2H), 4.17 (t, J=5.9 Hz, 1H), 6.85 (s, 1H).

LC-MS (METCR1410): 100% (UV), Rt=1.06 min, m/z (ESI$^+$)=256.5 [M+H]$^+$

N-(Cyclopropylmethyl)-2-hydroxy-5-methyl-3-[(oxan-4-yl)methoxy]hexanamide (I-235)

The title compound was synthesized from N-(cyclopropylmethyl)-3-(2-methylpropyl)oxirane-2-carboxamide (I-47) in a similar manner to method A, general procedure 3 (general scheme 12) as a yellow free-flowing oil (300 mg, 51% purity, 36%) after work-up. The crude material was used in the next step without purification.

LC-MS (METCR1410): 51% (UV), Rt=1.04 min, m/z (ESI$^+$)=314.5 [M+H]$^+$

Method B: Addition of Ethoxyethane-Trifluoroborane at RT and NaHCO₃ Wash after Purification by Column Chromatography

N-(Cyclobutylmethyl)-2-hydroxy-3-[(oxan-4-yl)methoxy]butanamide (I-236)

To a stirred solution of N-(cyclobutylmethyl)-3-methyl-oxirane-2-carboxamide (I-222, 182.4 mg, 1.08 mmol) and tetrahydro-2H-pyran-4-ylmethanol (181 μL, 1.62 mmol) in DCM (4 mL) was added ethoxyethane-trifluoroborane (1:1, 203 μL, 1.62 mmol) and the mixture was stirred at RT for 18 h. Tetrahydro-2H-pyran-4-ylmethanol (60 μL, 0.54 mmol) and ethoxyethane-trifluoroborane (1:1, 68 μL, 0.54 mmol) were added and the reaction stirred for 2 h. The mixture was concentrated in vacuo to give a yellow oil which was purified by flash column chromatography on normal phase silica (25 g SNAP KP-SIL cartridge, 0-100% EtOAc in heptane gradient then 0-40% MeOH in EtOAc gradient). The solid obtained was dissolved in DCM (20 mL) and washed with saturated NaHCO₃. The aqueous layer was extracted with DCM (20 mL) and the combined organic layers were dried over sodium sulfate, filtered and concentrated in vacuo. The resulting oil was dried in a vacuum oven for 8 h at 40° C. to afford 76.3 mg of N-(cyclobutylmethyl)-2-hydroxy-3-[(oxan-4-yl)methoxy]butanamide as a colourless oil (95% purity by ¹H NMR, 24%).

¹H NMR (250 MHz, Chloroform-d) δ 1.10 (d, J=6.3 Hz, 3H), 1.22-1.46 (m, 3H), 1.63-2.15 (m, 8H), 2.36-2.59 (m, 1H), 2.87 (d, J=2.3 Hz, 1H), 3.16-3.50 (m, 6H), 3.68-3.82 (m, 1H), 3.92-4.06 (m, 2H), 4.19 (dd, J=2.2, 4.6 Hz, 1H), 6.69 (s, 1H).

LC-MS (METCR1410): 72% (UV), Rt=0.95 min, m/z (ESI$^+$)=286.2 [M+H]$^+$

N-(Cyclopentylmethyl)-2-hydroxy-3-[(oxan-4-yl)methoxy]butanamide (I-237)

The title compound was synthesized from N-(cyclopentylmethyl)-3-methyl-oxirane-2-carboxamide (I-223) in a similar manner to method B, general procedure 3 (general scheme 12) as a colourless oil (54 mg, 97% purity by ¹H NMR, 17%) after purification by flash column chromatography on normal phase silica (25 g SNAP KP-SIL cartridge, 0-100% EtOAc in heptane gradient then 0-40% MeOH in EtOAc gradient) and washed with saturated NaHCO₃.

¹H NMR (250 MHz, Chloroform-d) δ 1.11 (d, J=6.3 Hz, 3H), 1.15-1.48 (m, 5H), 1.59-1.91 (m, 8H), 1.99-2.16 (m, 1H), 2.85 (d, J=2.2 Hz, 1H), 3.07-3.55 (m, 6H), 3.70-3.83 (m, 1H), 3.92-4.08 (m, 2H), 4.14-4.24 (m, 1H), 6.75 (s, 1H).

LC-MS (METCR1410): 100% (UV), Rt=0.97 min, m/z (ESI$^+$)=300.2 [M+H]$^+$

Method C: Addition of Ethoxyethane-Trifluoroborane at 0° C.

N-[(3-Chlorophenyl)methyl]-2-hydroxy-3-(2-methoxyphenoxy)butanamide (I-238)

To a stirred, ice cooled solution of N-[(3-chlorophenyl)methyl]-3-methyloxirane-2-carboxamide (I-27, 86% purity, 400 mg, 1.52 mmol) and 2-methoxyphenol (202 μL 1.83 mmol) in dry DCM (5 mL) was added at 0° C., ethoxyethane-trifluoro-borane (1:1) (192 μL, 1.52 mmol). The mixture was stirred at 0° C. for 15 min and at RT for 3 days. Water (3 mL) was added and the aqueous phase extracted with DCM (3×3 mL). The combined organic layers were washed with saturated NaHCO₃, dried over sodium sulfate, filtered and concentrated in vacuo. The crude material was purified by flash column chromatography on normal phase silica (10 g SNAP Ultra cartridge, 5-40% EtOAc in heptane gradient) to give 130 mg of N-[(3-chlorophenyl)methyl]-2-hydroxy-3-(2-methoxyphenoxy)butanamide as a yellow oil (85% purity, 21%).

¹H NMR (500 MHz, Chloroform-d) δ 1.40 (d, J=6.3 Hz, 3H), 3.79 (s, 3H), 3.84 (s, 1H), 4.27 (d, J=4.7 Hz, 1H), 4.43 (d, J=6.1 Hz, 2H), 4.54 (qd, J=4.9, 6.3 Hz, 1H), 6.88 (dd, J=1.4, 8.1 Hz, 1H), 6.93 (td, J=1.5, 7.7 Hz, 1H), 7.00-7.07 (m, 2H), 7.11 (dt, J=2.2, 5.9 Hz, 1H), 7.19-7.30 (m, 4H).

LC-MS (METCR1410): 85% (UV), Rt=1.12 min, m/z (ESI$^+$)=350.0/352.0 [M+H]$^+$

3-(Cyclopropylmethoxy)-N-(cyclopropylmethyl)-2-hydroxybutanamide (I-239)

The title compound was synthesized from N-(cyclopropylmethyl)-3-methyl-oxirane-2-carboxamide (I-30) in a similar manner to method C, procedure 3 (general scheme 12) as a colourless viscous oil (200 mg, 55% purity by 1H NMR, 38%) after work-up. The crude material was used in the next step without purification.

¹H NMR (500 MHz, Chloroform-d) δ −0.08-0.07 (m, 4H), 0.23-0.40 (m, 4H), 0.74 (ddtt, J=2.6, 4.8, 7.7, 12.6 Hz, 1H), 0.80-0.92 (m, 1H), 0.94 (d, J=6.3 Hz, 3H), 2.87-3.22 (m, 5H), 3.50-3.60 (m, 1H), 3.94 (d, J=5.3 Hz, 1H), 6.74 (s, 1H).

LC-MS (METCR1410): 57% (UV), Rt=0.88 min, m/z (ESI$^+$)=228.6 [M+H]$^+$

2-Hydroxy-3-(2-methoxyphenoxy)-N-(propan-2-yl)butanamide (I-240)

The title compound was synthesized from 3-methyl-N-(propan-2-yl)oxirane-2-carboxamide (I-39) in a similar manner to method C, general procedure 3 (general scheme 12) as a colourless viscous oil (430 mg, 80% purity by ¹H NMR, 51%) after purification by flash column chromatography on normal phase silica (25 g SNAP KP-SIL cartridge, 0-50% EtOAc in heptane gradient).

¹H NMR (500 MHz, Chloroform-d) δ 1.12 (d, J=6.6 Hz, 3H), 1.18 (d, J=6.5 Hz, 3H), 1.38 (d, J=6.3 Hz, 3H), 3.89 (s, 3H), 4.01-4.17 (m, 1H), 4.21 (d, J=4.5 Hz, 1H), 4.53-4.60 (m, 1H), 6.72 (d, J=6.9 Hz, 1H), 6.89-6.99 (m, 2H), 7.05 (ddd, J=1.5, 7.8, 18.4 Hz, 2H).

LC-MS (METCR1410): 93% (UV), Rt=1.02 min, m/z (ESI$^+$)=268.0 [M+H]$^+$

3-(Benzyloxy)-2-hydroxy-N-(propan-2-yl)butanamide (I-241)

The title compound was synthesized from 3-methyl-N-(propan-2-yl)oxirane-2-carboxamide (I-39) in a similar manner to method C, general procedure 3 (general scheme 12) as a colourless viscous oil (390 mg, 93% purity, 60%) after purification by flash column chromatography on normal phase silica (25 g SNAP KP-SIL cartridge, 0-60% EtOAc in heptane gradient).

¹H NMR (500 MHz, Chloroform-d) δ 1.15 (t, J=6.5 Hz, 6H), 1.22 (d, J=6.3 Hz, 3H), 3.88-3.98 (m, 1H), 4.05-4.13 (m, 1H), 4.20 (d, J=5.0 Hz, 1H), 4.52 (d, J=11.4 Hz, 1H), 4.66 (d, J=11.4 Hz, 1H), 6.59 (s, 1H), 7.30-7.42 (m, 5H).

LC-MS (METCR1410): 93% (UV), Rt=1.01 min, m/z (ESI$^+$)=252.2 [M+H]$^+$

Method D: Epoxide Opening at 60° C.

N-(Cyclopropylmethyl)-2-hydroxy-4-methyl-3-[(oxan-4-yl)methoxy]pentanamide (I-242)

To a stirred solution of N-(cyclopropylmethyl)-3-(propan-2-yl)oxirane-2-carboxamide (I-43, 300 mg, 1.64 mmol) and oxan-4-ylmethanol (1.5 mL, 9.5 mmol) was added ethoxyethane-trifluoroborane (1:1, 308 μL, 2.46 mmol). The mixture was heated in a sealed tube at 60° C. for 12 h. The reaction was cooled, diluted with EtOAc and washed with saturated NaHCO$_3$. The organic layer was washed with brine, dried over sodium sulfate, filtered and concentrated in vacuo. The crude material was purified by flash column chromatography on normal phase silica (25 g SNAP KP-SIL cartridge, 0-100% TBME in heptane gradient) to give 184 mg of N-(cyclopropylmethyl)-2-hydroxy-4-methyl-3-[(oxan-4-yl)methoxy]pentanamide as a colourless oil which crystallized upon standing (75% purity by 1H NMR, 17%).

¹H NMR (250 MHz, Chloroform-d) δ 0.22 (q, J=4.6 Hz, 2H), 0.46-0.59 (m, 2H), 0.87-1.07 (m, 7H), 1.21-1.47 (m, 4H), 1.52-1.73 (m, 2H), 3.11-3.21 (m, 1H), 3.27-3.48 (m, 5H), 3.91-4.06 (m, 5H), 6.69 (s, 1H).

LC-MS (METCR1410): Poor UV absorbance, Rt=1.06 min, m/z (ESI$^+$)=300.1 [M+H]$^+$

General Procedure 4 (General Scheme 12): Oxidation

3-(Cyclohexyloxy)-N-(cyclopropylmethyl)-2-oxobutanamide (FP 120)

To a stirred solution of 3-(cyclohexyloxy)-N-(cyclopropylmethyl)-2-hydroxy-butanamide (I-225, 206 mg, 0.81 mmol) in DCM (5 mL) was added DMP (342 mg, 0.81 mmol) and the reaction was stirred at RT for 64 h. The mixture was filtered and the filtrate washed with saturated NaHCO$_3$ (10 mL). The aqueous layer was extracted with DCM (2×10 mL) and the combined organic layers dried over sodium sulfate, filtered and concentrated in vacuo. The crude material was purified by flash column chromatography on normal phase silica (10 g SNAP KP-SIL cartridge, 0-100% EtOAc in heptane gradient) followed by preparative LC (acidic pH, standard elution method) to afford 40 mg of 3-(cyclohexyloxy)-N-(cyclopropylmethyl)-2-oxobutanamide as a colourless oil (100% purity, 20%).

¹H NMR (500 MHz, Chloroform-d) δ 0.21-0.31 (m, 2H), 0.52-0.62 (m, 2H), 0.94-1.06 (m, 1H), 1.19-1.29 (m, 3H), 1.29-1.38 (m, 2H), 1.42 (d, J=7.0 Hz, 3H), 1.51-1.57 (m, 1H), 1.70-1.80 (m, 2H), 1.85-1.97 (m, 2H), 3.10-3.24 (m, 2H), 3.24-3.35 (m, 1H), 5.08 (q, J=7.0 Hz, 1H), 7.05 (s, 1H).

LC-MS (METCR1600): 100% (UV), Rt=4.65 min, m/z (ESI$^+$)=254.3 [M+H]$^+$

N-(Cyclopropylmethyl)-3-[(oxan-4-yl)methoxy]-2-oxobutanamide (FP 121)

The title compound was synthesized from N-(cyclopropylmethyl)-2-hydroxy-3-[(oxan-4-yl)methoxy]butanamide (I-226) in a similar manner to general procedure 4 (general scheme 12) as a colourless oil (62.4 mg, 100% purity, 27%) after purification by flash column chromatography on normal phase silica (10 g SNAP KP-SIL cartridge, 0-100% TBME in heptane gradient).

¹H NMR (500 MHz, Chloroform-d) δ 0.25 (q, J=4.8 Hz, 2H), 0.53-0.60 (m, 2H), 0.93-1.05 (m, 1H), 1.32 (dtt, J=17.9, 11.8, 5.2 Hz, 2H), 1.42 (d, J=7.0 Hz, 3H), 1.64-1.69 (m, 2H), 1.81-1.93 (m, 1H), 3.11-3.20 (m, 2H), 3.23 (dd, J=8.9, 6.7 Hz, 1H), 3.34-3.43 (m, 3H), 3.96 (dd, J=11.2, 3.8 Hz, 2H), 4.90 (q, J=7.0 Hz, 1H), 7.00 (s, 1H).

LC-MS (METCR1600): 100% (UV), Rt=3.52 min, m/z (ESI$^+$)=270.3 [M+H]$^+$

N-(Cyclopropylmethyl)-3-(2,2-dimethylpropoxy)-2-oxobutanamide (FP 122)

The title compound was synthesized from N-(cyclopropylmethyl)-3-(2,2-dimethylpropoxy)-2-hydroxybutanamide (I-227) in a similar manner to general procedure 4 (general scheme 12) as a light yellow oil (197 mg, 100% purity, 76%) after purification by flash column chromatography on normal phase silica (10 g SNAP KP-SIL cartridge, 0-100% TBME in heptane gradient).

¹H NMR (500 MHz, Chloroform-d) δ 0.24 (q, J=4.8 Hz, 2H), 0.52-0.58 (m, 2H), 0.91 (s, 9H), 0.93-1.02 (m, 1H), 1.41 (d, J=7.0 Hz, 3H), 2.99 (d, J=8.6 Hz, 1H), 3.10-3.21 (m, 2H), 3.23 (d, J=8.6 Hz, 1H), 4.85 (q, J=7.0 Hz, 1H), 7.00 (s, 1H).

LC-MS (METCR1600): 100% (UV), Rt=4.92 min, m/z (ESI$^+$)=242.3 [M+H]$^+$

3-(Cyclohexylmethoxy)-N-(cyclopropylmethyl)-2-oxobutanamide (FP 123)

The title compound was synthesized from 3-(cyclohexylmethoxy)-N-(cyclo-propylmethyl)-2-hydroxybutanamide (I-228) in a similar manner to general procedure 4 (general scheme 12) as a colourless viscous oil (15 mg, 100% purity, 8%) after purification by flash column chromatography on normal phase silica (10 g SNAP KP-SIL cartridge, 0-60% EtOAc in heptane gradient) followed by preparative LC (acidic pH, standard elution method).

¹H NMR (500 MHz, Chloroform-d) δ 0.00-0.04 (m, 2H), 0.31-0.36 (m, 2H), 0.64-0.80 (m, 3H), 0.89-0.97 (m, 1H), 0.97-1.07 (m, 2H), 1.19 (d, J=7.0 Hz, 3H), 1.37-1.51 (m, 4H), 1.52-1.58 (m, 2H), 2.89-2.99 (m, 3H), 3.10 (dd, J=9.0, 6.5 Hz, 1H), 4.66 (q, J=7.0 Hz, 1H), 6.81 (s, 1H).

3-(Cyclohexyloxy)-N-(2-methylpropyl)-2-oxobutanamide (FP 124)

The title compound was synthesized from 3-(cyclohexyloxy)-2-hydroxy-N-(2-methylpropyl)butanamide (I-229) in a similar manner to general procedure 4 (general scheme 12) as a colourless gum (142 mg, 100% purity, 61%) after purification by flash column chromatography on normal phase silica (25 g SNAP KP-SIL cartridge, 0-100% EtOAc in heptane gradient).

$^1$H NMR (500 MHz, Chloroform-d) δ 0.94 (d, J=6.7 Hz, 6H), 1.14-1.35 (m, 5H), 1.39 (d, J=7.0 Hz, 3H), 1.49-1.55 (m, 1H), 1.69-1.76 (m, 2H), 1.79-1.88 (m, 2H), 1.89-1.96 (m, 1H), 3.07-3.22 (m, 2H), 3.23-3.36 (m, 1H), 5.05 (q, J=7.0 Hz, 1H), 6.97 (s, 1H).

LC-MS (METCR1600): 100% (UV), Rt=4.98 min, m/z (ESI$^+$)=256.3 [M+H]$^+$

3-(Cyclohexyloxy)-2-oxo-N-(propan-2-yl)butanamide (FP 125)

The title compound was synthesized from 3-(cyclohexyloxy)-2-hydroxy-N-(propan-2-yl)butanamide (I-230) in a similar manner to general procedure 4 (general scheme 12) as a yellow oil (109 mg, 100% purity, 40%) after purification by flash column chromatography on normal phase silica (10 g SNAP KP-SIL cartridge, 0-60% EtOAc in heptane gradient).

$^1$H NMR (500 MHz, Chloroform-d) δ 1.08-1.35 (m, 11H), 1.38 (d, J=7.0 Hz, 3H), 1.48-1.56 (m, 1H), 1.67-1.76 (m, 2H), 1.81-1.95 (m, 2H), 3.26 (ddd, J=13.5, 9.5, 3.9 Hz, 1H), 4.05 (ddt, J=13.2, 8.1, 6.6 Hz, 1H), 5.04 (q, J=7.0 Hz, 1H), 6.64-6.86 (s, 1H).

LC-MS (Achiral SFC): 100% (UV), Rt=1.02 min, m/z (ESI$^+$)=242.2 [M+H]$^+$

N-(Cyclobutylmethyl)-3-(cyclohexyloxy)-2-oxobutanamide (FP 126)

The title compound was synthesized from N-(cyclobutylmethyl)-3-(cyclohexyloxy)-2-hydroxybutanamide (I-231) in a similar manner to general procedure 4 (general scheme 12) as a colourless free-flowing oil (88 mg, 95% purity by $^1$H NMR, 44%) after trituration in 1:1 DCM/MeOH and purification of the filtrate by flash column chromatography on normal phase silica (25 g SNAP KP-SIL cartridge, 0-100 EtOAc in heptane gradient).

$^1$H NMR (500 MHz, Chloroform-d) δ 1.11-1.26 (m, 3H), 1.26-1.36 (m, 2H), 1.39 (d, J=7.0 Hz, 3H), 1.48-1.54 (m, 1H), 1.66-1.78 (m, 4H), 1.81-1.97 (m, 4H), 2.04-2.12 (m, 2H), 2.51 (p, J=7.6 Hz, 1H), 3.23-3.31 (m, 1H), 3.31-3.39 (m, 2H), 5.05 (q, J=7.0 Hz, 1H), 6.88 (s, 1H).

LC-MS (METCR1600): 100% (UV), Rt=5.08 min, m/z (ESI$^+$)=268.3 [M+H]$^+$

3-(Cyclohexyloxy)-N-(cyclopentylmethyl)-2-oxobutanamide (FP 127)

The title compound was synthesized from 3-(cyclohexyloxy)-N-(cyclopentylmethyl)-2-hydroxybutanamide (I-232) in a similar manner to general procedure 4 (general scheme 12) as a colourless free-flowing oil (151 mg, 100% purity, 71%) after trituration in 1:1 DCM/MeOH and purification of the filtrate by flash column chromatography on normal phase silica (25 g SNAP KP-SIL cartridge, 0-100 EtOAc in heptane gradient).

$^1$H NMR (500 MHz, Chloroform-d) δ 1.13-1.26 (m, 5H), 1.26-1.35 (m, 2H), 1.39 (d, J=7.0 Hz, 3H), 1.48-1.67 (m, 5H), 1.70-1.81 (m, 4H), 1.82-1.88 (m, 1H), 1.89-1.96 (m, 1H), 2.08 (hept, J=7.6 Hz, 1H), 3.19-3.34 (m, 3H), 5.05 (q, J=7.0 Hz, 1H), 6.95 (s, 1H).

LC-MS (METCR1600): 100% (UV), Rt=5.33 min, m/z (ESI$^+$)=282.3 [M+H]$^+$

3-(Benzyloxy)-N-(cyclopropylmethyl)-2-oxopropanamide (FP 128)

The title compound was synthesized from 3-(benzyloxy)-N-(cyclopropyl-methyl)-2-hydroxypropanamide (I-233) in a similar manner to general procedure 4 (general scheme 12) as an off-white solid (46 mg, 98% purity, 40%) after purification by flash column chromatography on normal phase silica (10 g SNAP KP-SIL cartridge, 0-100% EtOAc in heptane gradient).

$^1$H NMR (500 MHz, Chloroform-d) δ 0.24 (q, J=4.8 Hz, 2H), 0.53-0.60 (m, 2H), 0.92-1.03 (m, 1H), 3.14 (dd, J=7.1, 6.0 Hz, 2H), 4.65 (s, 2H), 4.81 (s, 2H), 7.02 (s, 1H), 7.28-7.41 (m, 5H).

LC-MS (METCR1600): 98% (UV), Rt=4 min, m/z (ESI$^+$)=248.3 [M+H]$^+$

3-(Cyclohexylmethoxy)-N-(cyclopropylmethyl)-2-oxopropanamide (FP 129)

The title compound was synthesized from 3-(cyclohexylmethoxy)-N-(cyclo-propylmethyl)-2-hydroxypropanamide (I-234) in a similar manner to general procedure 4 (general scheme 12) as an off-white solid (33 mg, 95% purity, 49%) after purification by flash column chromatography on normal phase silica (10 g SNAP KP-SIL cartridge, 0-100% EtOAc in heptane gradient).

$^1$H NMR (500 MHz, Chloroform-d) δ 0.24 (q, J=4.8 Hz, 2H), 0.53-0.59 (m, 2H), 0.89-1.03 (m, 3H), 1.11-1.31 (m, 3H), 1.63-1.75 (m, 4H), 1.75-1.82 (m, 2H), 3.15 (dd, J=7.1, 6.0 Hz, 2H), 3.33 (d, J=6.6 Hz, 2H), 4.79 (s, 2H), 7.02 (s, 1H).

LC-MS (METCR1600): 95% (UV), Rt=4.77 min, m/z (ESI$^+$)=254.3 [M+H]$^+$

N-(Cyclopropylmethyl)-5-methyl-3-[(oxan-4-yl)methoxy]-2-oxohexanamide (FP 130)

The title compound was synthesized from N-(cyclopropylmethyl)-2-hydroxy-5-methyl-3-[(oxan-4-yl)methoxy]hexanamide (I-235) in a similar manner to general procedure 4 (general scheme 12) as a colourless viscous oil (18 mg, 98% purity, 4%) after purification by flash column chromatography on normal phase silica (10 g SNAP KP-SIL cartridge, 0-40% EtOAc in heptane gradient).

$^1$H NMR (500 MHz, Chloroform-d) δ 0.22-0.26 (m, 2H), 0.53-0.58 (m, 2H), 0.94 (d, J=6.7 Hz, 3H), 0.99 (d, J=6.6 Hz, 3H), 1.32 (qd, J=4.6, 12.2 Hz, 2H), 1.44-1.50 (m, 1H), 1.58-1.64 (m, 3H), 1.68-1.74 (m, 1H), 1.83-1.96 (m, 2H), 3.06-3.20 (m, 3H), 3.33-3.43 (m, 3H), 3.90-4.01 (m, 2H), 4.87 (dd, J=3.0, 9.7 Hz, 1H), 6.95-7.06 (m, 1H).

LC-MS (METCR1600): 98% (UV), Rt=4.85 min, m/z (ESI$^+$)=312.3 [M+H]$^+$

N-(Cyclobutylmethyl)-3-[(oxan-4-yl)methoxy]-2-oxobutanamide (FP 131)

The title compound was synthesized from N-(cyclobutylmethyl)-2-hydroxy-3-[(oxan-4-yl)methoxy]butanamide (I-236) in a similar manner to general procedure 4 (general scheme 12) as a colourless gum (13 mg, 100% purity by $^1$H NMR, 16%) after purification by flash column chromatography on normal phase silica (10 g SNAP KP-SIL cartridge, 0-100% EtOAc in heptane gradient) followed by flash column chromatography on normal phase silica (10 g SNAP KP-SIL cartridge, 0-100% TBME in heptane gradient).

$^1$H NMR (250 MHz, Chloroform-d) δ 1.20-1.38 (m, 3H), 1.40 (d, J=7.0 Hz, 3H), 1.60-1.79 (m, 3H), 1.79-1.99 (m, 3H), 1.99-2.18 (m, 2H), 2.50 (hept, J=7.3 Hz, 1H), 3.15-3.28 (m, 1H), 3.28-3.45 (m, 5H), 3.89-4.06 (m, 2H), 4.89 (q, J=7.0 Hz, 1H), 6.86 (s, 1H).

LC-MS (MET-uHPLC-AB-102): 93% (UV), Rt=2.62 min, m/z (ESI$^+$)=284.2 [M+H]$^+$

N-(Cyclopentylmethyl)-3-[(oxan-4-yl)methoxy]-2-oxobutanamide (FP 132)

The title compound was synthesized from N-(cyclopentylmethyl)-2-hydroxy-3-[(oxan-4-yl)methoxy]butanamide (I-237) in a similar manner to general procedure 4 (general scheme 12) as a colourless gum (12 mg, 100% purity by $^1$H NMR, 22%) after purification by flash column chromatography on normal phase silica (10 g SNAP KP-SIL cartridge, 0-100% EtOAc in heptane gradient) followed by flash column chromatography on normal phase silica (10 g SNAP KP-SIL cartridge, 0-100% TBME in heptane gradient).

$^1$H NMR (250 MHz, Chloroform-d) δ 1.10-1.37 (m, 4H), 1.41 (d, J=7.0 Hz, 3H), 1.50-1.96 (m, 9H), 2.07 (hept, J=7.5 Hz, 1H), 3.16-3.30 (m, 3H), 3.32-3.46 (m, 3H), 3.87-4.02 (m, 2H), 4.90 (q, J=7.0 Hz, 1H), 6.93 (s, 1H).

LC-MS (MET-uHPLC-AB-102): 93% (UV), Rt=2.95 min, m/z (ESI$^+$)=298.2 [M+H]$^+$

N-[(3-Chlorophenyl)methyl]-3-(2-methoxyphenoxy)-2-oxobutanamide (FP 133)

The title compound was synthesized from N-[(3-chlorophenyl)methyl]-2-hydroxy-3-(2-methoxyphenoxy)butanamide (I-238) in a similar manner to general procedure 4 (general scheme 12) as a yellow viscous oil (68 mg, 98% purity, 61%) after purification by flash column chromatography on normal phase silica (10 g SNAP KP-SIL cartridge, 0-45% EtOAc in heptane gradient) then on reverse phase silica (10 g SNAP Ultra C18 cartridge, 10-100% ACN in heptane gradient).

$^1$H NMR (500 MHz, Chloroform-d) δ 1.65 (d, J=7.0 Hz, 3H), 3.80 (s, 3H), 4.48 (qd, J=6.2, 15.0 Hz, 2H), 5.75 (q, J=7.0 Hz, 1H), 6.84 (td, J=1.4, 7.7, 8.1 Hz, 1H), 6.89 (dd, J=1.5, 8.1 Hz, 2H), 6.98 (td, J=1.8, 7.4, 7.8 Hz, 1H), 7.16 (td, J=2.1, 4.1, 4.7 Hz, 1H), 7.26-7.33 (m, 4H).

LC-MS (METCR1600): 98% (UV), Rt=4.61 min, m/z (ESI$^+$)=348.1/350.1 [M+H]$^+$

3-(Cyclopropylmethoxy)-N-(cyclopropylmethyl)-2-oxobutanamide (FP 134)

The title compound was synthesized from 3-(cyclopropylmethoxy)-N-(cyclopropylmethyl)-2-hydroxybutanamide (I-239) in a similar manner to general procedure 4 (general scheme 12) as a yellow viscous oil (37 mg, 98% purity, 37%) after purification twice by flash column chromatography on normal phase silica (10 g SNAP KP-SIL cartridge, 0-60% EtOAc in heptane gradient) followed by preparative LC (basic pH, standard elution method).

$^1$H NMR (500 MHz, Chloroform-d) δ 0.16-0.26 (m, 4H), 0.50-0.58 (m, 4H), 0.94-1.02 (m, 1H), 1.02-1.10 (m, 1H), 1.43 (d, J=7.0 Hz, 3H), 3.11-3.21 (m, 2H), 3.26 (dd, J=7.3, 10.2 Hz, 1H), 3.36 (dd, J=6.7, 10.2 Hz, 1H), 4.97 (q, J=7.0 Hz, 1H), 7.02 (s, 1H).

LC-MS (METCR1600): 98% (UV), Rt=3.88 min, m/z (ESI$^+$)=226.3 [M+H]$^+$

3-(2-Methoxyphenoxy)-2-oxo-N-(propan-2-yl)butanamide (FP 135-1/2)

The title compound was synthesized from 2-hydroxy-3-(2-methoxyphenoxy)-N-(propan-2-yl)butanamide (I-240) in a similar manner to general procedure 4 (general scheme 12) in 2 batches as brown oils (FP 135-1, 21 mg, 96% purity, 5%) and (FP 135-2, 25 mg, 100% purity, 6%) after purification by flash column chromatography on normal phase silica (10 g SNAP KP-SIL cartridge, 0-40% EtOAc in heptane gradient) followed by preparative LC (acidic pH, standard elution method).

FP 135-1

$^1$H NMR (500 MHz, Chloroform-d) δ 1.22-1.26 (m, 6H), 1.66 (d, J=7.0 Hz, 3H), 3.85 (s, 3H), 4.05-4.16 (m, 1H), 5.77 (q, J=7.0 Hz, 1H), 6.78-6.84 (m, 1H), 6.84-6.93 (m, 3H), 6.96-7.02 (m, 1H).

LC-MS (METCR1600): 96% (UV), Rt=4.05 min, m/z (ESI$^+$)=266.3 [M+H]$^+$

FP 135-2

$^1$H NMR (500 MHz, Chloroform-d) δ 1.22-1.26 (m, 6H), 1.66 (d, J=7.0 Hz, 3H), 3.85 (s, 3H), 4.06-4.15 (m, 1H), 5.77 (q, J=7.0 Hz, 1H), 6.76-6.84 (m, 1H), 6.84-6.92 (m, 3H), 6.97-7.01 (m, 1H).

LC-MS (METCR1600): 100% (UV), Rt=4.04 min, m/z (ESI$^+$)=266.3 [M+H]$^+$

3-(Benzyloxy)-2-oxo-N-(propan-2-yl)butanamide (FP 136)

The title compound was synthesized from 3-(benzyloxy)-2-hydroxy-N-(propan-2-yl)butanamide (I-241) in a similar manner to general procedure 4 (general scheme 12) as an off-white powder (19 mg, 100% purity, 5%) after purification by flash column chromatography on normal phase silica (10 g SNAP KP-SIL cartridge, 0-60% EtOAc in heptane gradient) followed by preparative LC (acidic pH, standard elution method).

$^1$H NMR (500 MHz, Chloroform-d) δ 1.15-1.49 (m, 9H), 3.67-5.08 (m, 4H), 6.63-6.84 (m, 1H), 7.29-7.41 (m, 5H).

LC-MS (METCR1600): 100% (UV), Rt=4.3 min, m/z (ESI$^+$)=250.3 [M+H]$^+$

N-(Cyclopropylmethyl)-4-methyl-3-[(oxan-4-yl)methoxy]-2-oxopentanamide (FP 137)

The title compound was synthesized from N-(cyclopropylmethyl)-2-hydroxy-4-methyl-3-[(oxan-4-yl)methoxy]pentanamide (I-242) in a similar manner to general procedure 4 (general scheme 12) as a colourless viscous oil (41 mg, 97% purity, 21%) after purification by flash column chromatography on normal phase silica (10 g SNAP KP-SIL cartridge, 0-50% EtOAc in heptane gradient).

$^1$H NMR (500 MHz, Chloroform-d) δ 0.24 (q, J=4.9 Hz, 2H), 0.51-0.59 (m, 2H), 0.84 (d, J=6.9 Hz, 3H), 0.94-1.00 (m, 1H), 1.04 (d, J=6.8 Hz, 3H), 1.28-1.37 (m, 2H), 1.59-1.71 (m, 2H), 1.83-1.90 (m, 1H), 2.22-2.32 (m, 1H), 3.08-3.21 (m, 3H), 3.34-3.42 (m, 3H), 3.95 (d, J=11.4 Hz, 2H), 4.65 (d, J=4.2 Hz, 1H), 7.01 (s, 1H).

LC-MS (METCR1600): 97% (UV), Rt=4.61 min, m/z (ESI⁺)=298.3 [M+H]⁺

Route to Oxopyrrolidines: Synthesis of Final Products (FP 138-140)

GENERAL SCHEME 13:

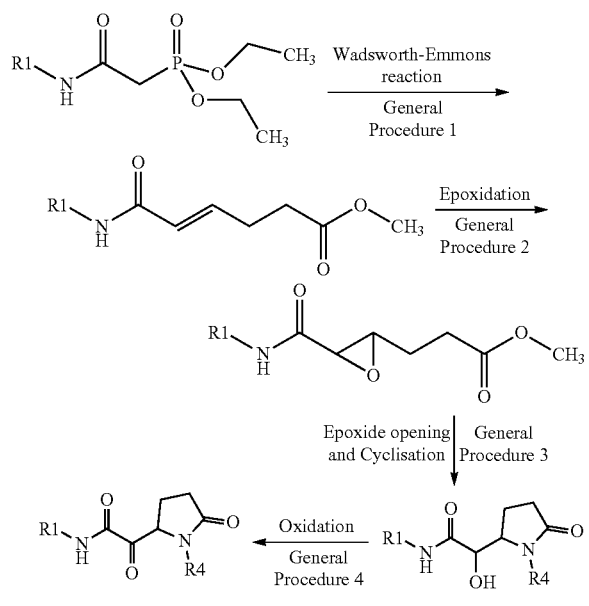

General Procedure 1 (General Scheme 13): Wadworth-Emmons Reaction

Methyl (4E)-5-[(cyclopropylmethyl)carbamoyl]pent-4-enoate (I-243)

To a cold, stirred solution of diethyl {[(cyclopropylmethyl)carbamoyl]methyl}phosphonate (I-24a, 91% purity, 1.0 g, 3.65 mmol) in dry THF (20 mL) under nitrogen was added NaH (60% dispersion in mineral oil, 300 mg, 7.50 mmol) portion wise over 5 min. The mixture was stirred at RT for 15 min and methyl 4-oxobutanoate (0.42 mL, 4.01 mmol) added. The mixture was stirred with cooling for 15 min and a precipitate formed. Water (20 mL) was added and the reaction acidified to pH 5 with 2N HCl. The aqueous layer was extracted with EtOAc (20 mL) and the organic layer was separated, dried over sodium sulfate, filtered and concentrated in vacuo. The crude residue was purified by flash column chromatography on normal phase silica (25 g SNAP KP-SIL cartridge, 0-60% EtOAc in heptane gradient) to afford 236 mg of methyl (4E)-5-[(cyclopropylmethyl)carbamoyl]pent-4-enoate as a pale yellow oil (86% purity, 26%).

¹H NMR (500 MHz, Chloroform-d) δ 0.20 (q, 4.7 Hz, 2H), 0.47-0.52 (m, 2H), 0.90-0.99 (m, 1H), 2.43-2.51 (m, 4H), 3.16 (dd, J=5.5, 7.1 Hz, 2H), 3.67 (s, 3H), 5.66-5.75 (m, 1H), 5.79-5.84 (m, 1H), 6.79 (dt, J=6.5, 15.3 Hz, 1H).

LC-MS (METCR1410): 86% (UV), Rt=0.85 min, m/z (ESI⁺)=212.3 [M+H]⁺

General Procedure 2 (General Scheme 13): Epoxidation

Methyl 3-{3-[(cyclopropylmethyl)carbamoyl]oxiran-2-yl}propanoate (I-244)

To a stirred solution of methyl (4E)-5-[(cyclopropylmethyl)carbamoyl]pent-4-enoate (I-243, 86% purity, 236 mg, 0.96 mmol) in DCM (10 mL) was added m-CPBA (70%, 950 mg, 3.85 mmol). The reaction was stirred at RT for 6 h then m-CPBA (70%, 950 mg, 2.92 mmol) added and stirring continued at RT for 3 days. The mixture was cooled in an ice bath and slowly quenched with 20% Na₂SO₃ (20 mL) with vigorous stirring. The organic layer was separated, washed with 0.5M NaOH (20 mL), dried over sodium sulfate, filtered and concentrated in vacuo. The crude residue was purified by flash column chromatography on normal phase silica (10 g SNAP KP-SIL cartridge, 0-80% EtOAc in heptane gradient) to afford 132 mg of methyl 3-{3-[(cyclopropylmethyl)carbamoyl]oxiran-2-yl}propanoate as an off-white solid (91% purity, 55%).

¹H NMR (250 MHz, Chloroform-d) δ 0.12-0.23 (m, 2H), 0.44-0.56 (m, 2H), 0.82-1.00 (m, 1H), 1.74-1.94 (m, 1H), 2.00-2.18 (m, 1H), 2.48 (t, J=7.3 Hz, 2H), 2.98-3.19 (m, 3H), 3.26 (d, J=2.1 Hz, 1H), 3.71 (s, 3H), 6.02-6.42 (m, 1H).

LC-MS (METCR1410): 91% (UV), Rt=0.82 min, m/z (ESI⁺)=228.2 [M+H]⁺

General Procedure 3 (General Scheme 13): Epoxide Opening and Cyclisation

2-(1-Benzyl-5-oxopyrrolidin-2-yl)-N-(cyclopropylmethyl)-2-hydroxyacetamide (I-245)

To a stirred solution of methyl 3-{3-[(cyclopropylmethyl)carbamoyl]oxiran-2-yl}propanoate (I-244, 91% purity, 128 mg, 0.51 mmol) in MeOH (2 mL) was added benzylamine (60 μL, 0.55 mmol). The mixture was stirred at RT for 20 h. Benzylamine (60 μL, 0.55 mmol) was added and the solution was stirred at 55° C. for 20 h. Benzylamine (120 μL, 1.10 mmol) was added and the mixture was stirred at 55° C. for 5 h. The reaction mixture was cooled and concentrated in vacuo to give a colourless oil which was suspended in water (10 mL) and extracted into DCM (3×10 mL). The combined organic extracts were dried over sodium sulfate, filtered and concentrated in vacuo. The crude residue was purified by flash column chromatography on normal phase silica (10 g SNAP KP-SIL cartridge, 0-100% EtOAc in heptane gradient) to afford 138 mg of 2-(1-benzyl-5-oxopyrrolidin-2-yl)-N-(cyclopropylmethyl)-2-hydroxyacetamide as a yellow oil (81% purity, 72%).

LC-MS (METCR1410): 81% (UV), Rt=0.89 min, m/z (ESI⁺)=303.1 [M+H]⁺

General Procedure 4 (General Scheme 13): Oxidation

2-(1-Benzyl-5-oxopyrrolidin-2-yl)-N-(cyclopropylmethyl)-2-oxoacetamide (FP 138)

To a solution of 2-(1-benzyl-5-oxopyrrolidin-2-yl)-N-(cyclopropylmethyl)-2-hydroxyacetamide (I-245, 81% purity, 138 mg, 0.37 mmol) in DCM (5 mL) was added DMP (160 mg, 0.38 mmol). The reaction was stirred at RT for 1 h, DMP (160 mg, 0.38 mmol) added and stirring at RT continued for 3 h. The mixture was filtered through a small pad of celite and washed with DCM (15 mL). The filtrate was washed with saturated NaHCO₃ (20 mL) and the aqueous phase separated and extracted with DCM (2×10 mL). The combined organic layers were dried over sodium sulfate, filtered and concentrated in vacuo. The crude residue was purified by flash column chromatography on normal phase silica (10 g SNAP KP-SIL cartridge, 0-70% EtOAc in heptane gradient) to afford 25 mg of 2-(1-benzyl-5-oxopyrrolidin-2-yl)-N-(cyclopropylmethyl)-2-oxoacetamide as a beige coloured solid (98% purity, 22%).

¹H NMR (500 MHz, Chloroform-d) δ 0.24 (q, J=4.8 Hz, 2H), 0.53-0.61 (m, 2H), 0.90-1.01 (m, 1H), 1.93-2.04 (m, 1H), 2.37-2.49 (m, 3H), 3.13 (dd, J=5.9, 7.1 Hz, 2H), 3.94 (d, J=14.9 Hz, 1H), 4.97-5.01 (m, 1H), 5.04 (d, J=14.9 Hz, 1H), 6.88-6.98 (m, 1H), 7.13-7.17 (m, 2H), 7.24-7.33 (m, 3H).

LC-MS (METCR1600): 98% (UV), Rt=3.89 min, m/z (ESI⁺)=301.2 [M+H]⁺

Further compounds (FP204-FP204xx) were synthesised via a related route (General Scheme 13a) and these compounds are described in the additional compound section.

GENERAL SCHEME 14:

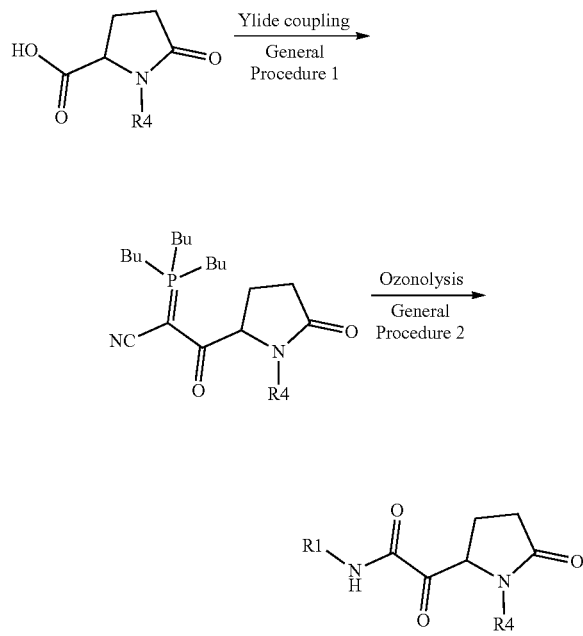

General Procedure 1 (General Scheme 14): Ylide Coupling

3-[(2S)-1-(2-Methoxyphenyl)-5-oxopyrrolidin-2-yl]-3-oxo-2-(tributyl-λ⁵-phosphanyl-idene)propanenitrile (I-246)

To a stirred, ice cooled solution of (2S)-1-(2-methoxyphenyl)-5-oxopyrrolidine-2-carboxylic acid (500 mg, 2.13 mmol) and DIPEA (1.11 mL, 6.38 mmol) in dry DMF (10 mL) was added HATU (2.42 g, 6.38 mmol) at 0° C. The reaction mixture was stirred at 0° C. for 1 h and (tributyl-λ⁵-phosphanylidene)acetonitrile (1.34 mL, 5.1 mmol) added. The reaction was stirred for 45 min at 0° C. then at RT for 3 h. The reaction mixture was washed with water (20 mL) and the aqueous layer extracted with DCM (2×20 mL). The combined organic layers were washed with water (30 mL), brine (30 mL) then dried over magnesium sulfate, filtered and concentrated in vacuo. The residue was purified by flash column chromatography on normal phase silica (50 g SNAP KP-SIL cartridge, 0-100% EtOAc in heptane gradient) to afford 1.01 g of 3-[(2S)-1-(2-methoxyphenyl)-5-oxopyrrolidin-2-yl]-3-oxo-2-(tributyl-λ⁵-phosphanylidene)propanenitrile as a brown oil (91%, quantitative).

¹H NMR (500 MHz, DMSO-d6) δ 0.79-0.99 (m, 9H), 1.20-1.33 (m, 12H), 1.83-1.92 (m, 1H), 1.95-2.06 (m, 6H), 2.31-2.47 (m, 3H), 3.80 (s, 3H), 5.06-5.10 (m, 1H), 6.81-6.90 (m, 1H), 7.06 (d, J=8.3 Hz, 1H), 7.13 (dd, J=1.6, 7.8 Hz, 1H), 7.21-7.28 (m, 1H).

LC-MS (METCR1410): 91% (UV), Rt=1.15 min, m/z (ESI⁺)=459.6 [M+H]⁺

General Procedure 2 (General Scheme 14): Ozonolysis

N-[(3-Chlorophenyl)methyl]-2-[(2S)-1-(2-methoxyphenyl)-5-oxopyrrolidin-2-yl]-2-oxoacetamide (FP 139)

Ozone (ozone generator) was passed at −78° C. through a solution of 3-[(2S)-1-(2-methoxyphenyl)-5-oxopyrrolidin-2-yl]-3-oxo-2-(tributyl-λ⁵-phosphanyl idene)propane-nitrile (I-246, 91% purity, 400 mg, 0.79 mmol) and 1-(3-chlorophenyl)methanamine (146 μL, 1.19 mmol) in DCM (12 mL) for 25 min. The solution was purged with nitrogen and the mixture stirred at −78° C. under nitrogen for 1 h. The reaction was concentrated in vacuo to afford a solid which was triturated in DCM. The filtrate was concentrated in vacuo and the residue purified by flash column chromatography on normal phase silica (50 g SNAP KP-SIL cartridge, 0-100% TBME in heptane gradient then 0-30% MeOH/TBME gradient) followed by preparative LC (acidic pH, standard elution method). The clear gum obtained was triturated in 1:1 EtOAc/heptane to afford 14.8 mg of N-[(3-chlorophenyl)methyl]-2-[(2S)-1-(2-methoxyphenyl)-5-oxopyrrolidin-2-yl]-2-oxoacetamide as a yellow gum (100% purity, 5%).

¹H NMR (500 MHz, Chloroform-d) δ 2.12 (dddd, J=3.8, 5.8, 7.5, 13.2 Hz, 1H), 2.50-2.61 (m, 2H), 2.72 (dq, J=9.7, 13.2 Hz, 1H), 3.80 (s, 3H), 4.35-4.51 (m, 2H), 5.76 (dd, J=3.7, 10.0 Hz, 1H), 6.88-6.93 (m, 1H), 6.98 (td, J=1.2, 7.7 Hz, 1H), 7.10-7.15 (m, 1H), 7.18 (t, J=6.2 Hz, 1H), 7.22-7.32 (m, 4H), 7.45-7.51 (m, 1H).

LC-MS (METCR1416): 100% (UV), Rt=4.33 min, m/z (ESI⁺)=387.2/389.2 [M+H]⁺

N-(cyclopropylmethyl)-2-[(2S)-1-(2-methoxyphenyl)-5-oxopyrrolidin-2-yl]-2-oxoacetamide (FP 140)

The title compound was synthesized from 3-[(2S)-1-(2-methoxyphenyl)-5-oxopyrrolidin-2-yl]-3-oxo-2-(tributyl-h-phosphanylidene)propanenitrile (I-246) in a similar manner to general procedure 1 (general scheme 14) and obtained as a clear gum (3.4 mg, 100% purity, 1%) after purification by flash column chromatography on normal phase silica (50 g SNAP KP-SIL cartridge, 0-100% TBME in heptane gradient then 0-60% MeOH in TBME gradient) followed by preparative LC (acidic pH, standard elution method).

¹H NMR (500 MHz, Chloroform-d) δ 0.18-0.28 (m, 2H), 0.50-0.59 (m, 2H), 0.90-1.00 (m, 1H), 2.05-2.14 (m, 1H), 2.49-2.60 (m, 2H), 2.64-2.78 (m, 1H), 3.06-3.19 (m, 2H), 3.81 (s, 3H), 5.75 (dd, J=3.6, 10.0 Hz, 1H), 6.90 (dd, J=1.0, 8.3 Hz, 1H), 6.99 (td, J=1.2, 7.7 Hz, 2H), 7.22-7.25 (m, 1H), 7.50 (dd, J=1.7, 7.8 Hz, 1H).

LC-MS (METCR1416): 100% (UV), Rt=3.65 min, m/z (ESI⁺)=317.3 [M+H]⁺

Epoxide Route: Synthesis of Final Products (FP 141-177)

GENERAL SCHEME 15:

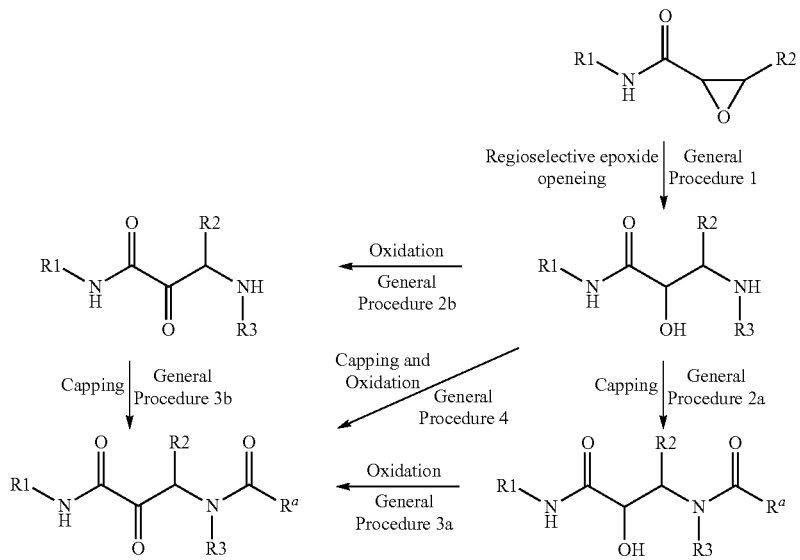

General Procedure 1 (General Scheme 15): Regioselective Epoxide Opening

Method A: Epoxide Opening Without Titanium(IV) Isopropoxide

2-Hydroxy-N-(2-methylpropyl)-3-{[(oxan-4-yl)methyl]amino}butanamide (I-247)

To a stirred solution of 3-methyl-N-(2-methylpropyl)oxirane-2-carboxamide (I-32, 350 mg, 2.23 mmol) in EtOH (4 mL) was added oxan-4-ylmethanamine (313 μL, 2.67 mmol) and the reaction heated in a sealed tube at 60° C. for 18 h. Oxan-4-ylmethanamine (783 μL, 6.68 mmol) was added and the mixture heated at 60° C. for 4 h. The solution was concentrated in vacuo to give an oil which was dissolved in EtOAc (25 mL). The solution was diluted with heptane (10 mL) and cooled in an ice bath. The resulting precipitate was collected by filtration and dried in vacuo at 40° C. to afford 650 mg of 2-hydroxy-N-(2-methylpropyl)-3-{[(oxan-4-yl)methyl]amino}butanamide as an off-white solid (93% purity, quantitative).

¹H NMR (500 MHz, Chloroform-d) δ 0.86 (d, J=6.7 Hz, 6H), 0.97 (d, J=6.5 Hz, 3H), 1.15-1.29 (m, 3H), 1.54 (d, J=13.2 Hz, 2H), 1.58-1.64 (m, 2H), 1.72 (dt, J=6.7, 13.5 Hz, 1H), 2.41 (dd, J=7.0, 11.9 Hz, 1H), 2.60 (dd, J=5.9, 11.9 Hz, 1H), 2.94-3.14 (m, 3H), 3.28-3.35 (m, 2H), 3.91 (dd, J=3.8, 11.3 Hz, 2H), 3.99 (d, J=4.8 Hz, 1H), 7.10 (s, 1H).

LC-MS (METCR1410): 93% (UV), Rt=0.64 min, m/z (ESI⁺)=273.5 [M+H]⁺

Method B: Epoxide Opening with 33% Methylamine in EtOH

N-(Cyclohexylmethyl)-2-hydroxy-3-(methylamino)butanamide (I-248)

N-(cyclohexylmethyl)-3-methyl-oxirane-2-carboxamide (I-34, 86% purity, 1 g, 4.36 mmol) in 33% methylamine in EtOH (11.4 mL, 91.88 mmol) was stirred in a sealed tube at RT for 18 h. The reaction mixture was concentrated in vacuo to give a solid which was dissolved in hot EtOAc (10 mL). The solution was diluted with heptane (15 mL) and cooled over 1 h. The resulting precipitate was collected via filtration and dried in vacuo at 40° C. for 1 h to afford 930 mg of N-(cyclohexylmethyl)-2-hydroxy-3-(methylamino)butanamide as an off-white solid (100% purity, 93%).

¹H NMR (500 MHz, DMSO-d6) δ 0.82 (d, J=6.5 Hz, 3H), 0.84-0.90 (m, 2H), 1.09-1.21 (m, 3H), 1.37-1.49 (m, 2H), 1.57-1.69 (m, 5H), 2.28 (s, 3H), 2.75 (qd, J=3.3, 6.5 Hz, 1H), 2.90 (dt, J=6.5, 12.9 Hz, 1H), 2.98 (dt, J=6.6, 13.1 Hz, 1H), 3.99 (d, J=3.2 Hz, 1H), 5.31 (s, 1H), 7.68 (t, J=5.9 Hz, 1H).

LC-MS (METCR1410): 100% (UV), Rt=0.73 min, m/z (ESI⁺)=229.2 [M+H]⁺

Method C: Epoxide Opening with 2M Methylamine in MeOH

N-(Cyclopropylmethyl)-2-hydroxy-3-(methylamino)butanamide (I-249)

N-(cyclopropylmethyl)-3-methyloxirane-2-carboxamide (I-30, 86% purity, 700 mg, 3.88 mmol) in 2M methylamine in MeOH (9.7 mL, 19.40 mmol) was stirred in a sealed tube at RT for 20 h. 2M methylamine in MeOH (5 mL) was added and the reaction heated at 50° C. for 24 h. The mixture was concentrated in vacuo to give a solid which was dissolved in hot EtOAc (10 mL). The solution was diluted with heptane (20 mL) and cooled. The resulting precipitate was collected via filtration and dried in vacuo at 40° C. for 18 h to afford 482 mg of N-(cyclopropylmethyl)-2-hydroxy-3-(methylamino)butanamide as an off-white solid (95% purity by ¹H NMR, 63%).

¹H NMR (500 MHz, Chloroform-d) δ 0.14-0.28 (m, 2H), 0.44-0.57 (m, 2H), 0.89-1.00 (m, 1H), 1.01-1.25 (m, 3H), 1.79-2.38 (m, 3H), 2.38-2.50 (m, 3H), 2.91-4.14 (m, 4H).

LC-MS (METCR0990): 71% (UV), Rt=1.16 min, m/z (ESI⁺)=187.2 [M+H]⁺

Method D: Epoxide Opening with 7N Ammonia in MeOH

3-Amino-N-(cyclopropylmethyl)-2-hydroxybutanamide (I-250)

N-(Cyclopropylmethyl)-3-methyloxirane-2-carboxamide (I-30, 85% purity, 2.8 g, 15.34 mmol) in 7M ammonia in MeOH (7.8 mL) was heated to 70° C. for 18 h in a sealed tube (×4 reactions in parallel). The reactions were combined and concentrated in vacuo. The crude material was purified by flash column chromatography on normal phase silica (50 g SNAP KP-SIL cartridge, 0-20% 7M ammonia (solution in MeOH) in DCM gradient) to afford 1.82 g of 3-amino-N-(cyclopropylmethyl)-2-hydroxybutanamide as a pale yellow viscous oil which solidified upon standing to an off-white crystalline solid (98% purity, 68%).

¹H NMR (500 MHz, Chloroform-d) δ 0.16-0.26 (m, 2H), 0.45-0.56 (m, 2H), 0.89-1.02 (m, 1H), 1.07 (d, J=6.5 Hz, 3H), 3.08-3.22 (m, 2H), 3.31-3.41 (m, 1H), 3.87 (d, J=5.1 Hz, 1H), 7.30 (br. s, 1H).

LC-MS (METCR0990): 98% (UV), Rt=1.09 min, m/z (ESI⁺)=173.2 [M+H]⁺

3-Amino-N-(cyclopropylmethyl)-2-hydroxypentanamide (I-251)

The title compound was synthesized from N-(cyclopropylmethyl)-3-ethyloxirane-2-carboxamide (I-41) in a similar manner to method D, general procedure 1 (general scheme 15) as an off-white solid (300 mg, 65% purity by ¹H NMR, 39%) after trituration in heptane.

¹H NMR (500 MHz, Chloroform-d) δ 0.15-0.24 (m, 2H), 0.44-0.52 (m, 2H), 0.87-1.00 (m, 4H), 1.23-1.58 (m, 3H), 2.84-3.07 (m, 2H), 3.10-3.23 (m, 3H), 4.03 (d, J=4.7 Hz, 1H), 7.48 (t, J=5.6 Hz, 1H).

3-Amino-N-(cyclopropylmethyl)-2-hydroxy-4-methylpentanamide (I-252)

The title compound was synthesized from N-(cyclopropylmethyl)-3-(propan-2-yl)oxirane-2-carboxamide (I-43) in a similar manner to method D, general procedure 1 (general scheme 15) as an off-white solid (426 mg, 90% purity by ¹H NMR, 35%) after purification by flash column chromatography on normal phase silica (50 g SNAP KP-SIL cartridge, 0-75% 1.4N ammonia (solution in 5:1 DCM/MeOH) in DCM gradient).

¹H NMR (250 MHz, Chloroform-d) δ 0.09-0.29 (m, 2H), 0.40-0.57 (m, 2H), 0.80-1.00 (m, 7H), 1.86-2.01 (m, 1H), 2.18 (dtd, J=4.2, 6.9, 13.7 Hz, 3H), 2.66 (dd, J=4.2, 8.3 Hz, 1H), 3.06-3.17 (m, 2H), 3.77 (d, J=8.3 Hz, 1H), 8.32 (s, 1H)

LC-MS (METCR1410): 100% (UV), Rt=0.42 min, m/z (ESI⁺)=201.4 [M+H]⁺

3-Amino-N-(cyclopropylmethyl)-2-hydroxyhexanamide (I-253)

The title compound was synthesized from N-(cyclopropylmethyl)-3-propyloxirane-2-carboxamide (I-44) in a similar manner to method D, general procedure 1 (general scheme 15) as an off-white solid (350 mg, 70% purity by ¹H NMR, 47%) after trituration in heptane.

¹H NMR (500 MHz, Chloroform-d) δ 0.18-0.23 (m, 2H), 0.47-0.52 (m, 2H), 0.88 (t, J=7.0 Hz, 1H), 0.96 (t, J=7.5 Hz, 3H), 1.01 (td, J=5.6, 7.5 Hz, 1H), 1.23-1.30 (m, 2H), 1.37 (ddd, J=7.3, 9.1, 14.1 Hz, 1H), 1.65 (dtt, J=3.7, 7.5, 15.0 Hz, 1H), 2.55 (s, 2H), 3.04 (dt, J=4.5, 9.1 Hz, 1H), 3.09-3.18 (m, 2H), 3.95 (d, J=5.4 Hz, 1H), 7.56 (t, J=4.9 Hz, 1H).

General Procedure 2a (General Scheme 15): Capping

Method A: Addition of Acid Chloride at RT

N-[(3-Chlorophenyl)methyl]-2-hydroxy-3-[N-(2-methoxyphenyl)propanamido]butanamide (I-254)

To N-[(3-chlorophenyl)methyl]-2-hydroxy-3-[(2-methoxyphenyl)amino]butanamide (I-54, 100 mg, 0.29 mmol) and DIPEA (71 µL, 0.43 mmol) in DCM (3 mL) was added propanoyl chloride (31.8 mg, 0.34 mmol) and the mixture stirred for 2 h. Water (4 mL) was added and the aqueous phase extracted with DCM (3×5 mL). The combined organic phases were washed with saturated NaHCO₃, dried over sodium sulfate, filtered and concentrated in vacuo. The crude material was purified by flash column chromatography on normal phase silica (10 g SNAP KP-SIL cartridge, 0-100% EtOAc in heptane gradient) to afford 59 mg of N-[(3-chlorophenyl)methyl]-2-hydroxy-3-[N-(2-methoxyphenyl)propanamido]butanamide as a yellow oil (91% purity, 46%).

¹H NMR (250 MHz, DMSO-d6) δ 0.58-1.21 (m, 6H), 1.73-1.86 (m, 2H), 3.76-3.83 (m, 3H), 4.26 (d, J=6.1 Hz, 2H), 4.35-4.48 (m, 1H), 4.63-4.81 (m, 1H), 5.58-6.07 (m, 1H), 6.92-7.57 (m, 8H), 8.40 (t, J=6.0 Hz, 1H).

LC-MS (METCR1410): 91% (UV), Rt=1.16 min, m/z (ESI⁺)=405.1/407.1 [M+H]⁺

N-[(3-Chlorophenyl)methyl]-2-hydroxy-3-[N-(2-methoxyphenyl)-2-methylpropanamido]butanamide (I-255)

The title compound was synthesized from N-[(3-chlorophenyl)methyl]-2-hydroxy-3-[(2-methoxyphenyl)amino] butanamide (I-54) in a similar manner to method A, general procedure 2a (general scheme 15) as a yellow oil (231 mg, 64% purity, 82%) after purification by flash column chromatography on normal phase silica (10 g SNAP KP-SIL cartridge, 0-100% EtOAc in heptane gradient).

¹H NMR (500 MHz, DMSO-d6) δ 0.62-1.07 (m, 9H), 2.04-2.15 (m, 1H), 3.79 (d, J=18.2 Hz, 3H), 4.72 (qd, J=4.0, 7.1 Hz, 4H), 5.68-6.11 (m, 1H), 6.92-7.03 (m, 1H), 7.07-7.14 (m, 1H), 7.16-7.63 (m, 6H), 8.39 (t, J=6.3 Hz, 1H).

LC-MS (METCR1410): 64% (UV), Rt=1.22 min, m/z (ESI⁺)=419.5/421.1 [M+H]⁺

N-[(3-Chlorophenyl)methyl]-2-hydroxy-3-[N-(2-methoxyphenyl)butanamido]butanamide (I-256)

The title compound was synthesized from N-[(3-chlorophenyl)methyl-2-hydroxy-3-[(2-methoxyphenyl)amino]butanamide (I-54) in a similar manner to method A, general procedure 2a (general scheme 15) as a yellow oil (122 mg, 76% purity, 64%) after purification by flash column chromatography on normal phase silica (10 g SNAP KP-SIL cartridge, 0-100% EtOAc in heptane gradient).

$^1$H NMR (250 MHz, DMSO-d6) δ 0.56-1.22 (m, 6H), 1.32-1.49 (m, 2H), 1.69-1.83 (m, 2H), 3.72-3.87 (m, 3H), 4.11-4.84 (m, 4H), 5.61-6.14 (m, 1H), 6.88-7.60 (m, 8H), 8.41 (t, J=6.0 Hz, 1H).

LC-MS (METCR1410): 76% (UV), Rt=1.21 min, m/z (ESI$^+$)=419.2/421.1 [M+H]$^+$

Method B: Addition of Acid Chloride at 0° C.

N-(Cyclohexylmethyl)-3-(N,2-dimethylpropanamido)-2-hydroxybutanamide (I-257)

To an ice-cooled solution of N-(cyclohexylmethyl)-2-hydroxy-3-(methyl-amino)butanamide (I-248, 300 mg, 1.31 mmol) and DIPEA (0.65 mL, 3.72 mmol) in DCM (8 mL) was added at 0° C. a solution of 2-methylpropanoyl chloride (0.15 mL, 1.45 mmol) in DCM (2 mL) dropwise over 5 min. The solution was stirred for 1 h at RT, diluted with DCM (10 mL), washed with saturated NaHCO$_3$ (20 mL) and water (20 mL). The organic layer was separated, dried over sodium sulfate and concentrated in vacuo to give 420 mg of N-(cyclohexylmethyl)-3-(N,2-dimethylpropanamido)-2-hydroxybutanamide as a brown solid (73% purity, 78%). The crude material was used in the next step without further purification.

$^1$H NMR (250 MHz, DMSO-d6) δ 0.63-1.76 (m, 20H), 2.58-3.09 (m, 6H), 3.83-4.95 (m, 2H), 5.79 (dd, J=6.3, 13.1 Hz, 1H), 7.73 (dd, J=6.1, 55.7 Hz, 1H).

LC-MS (METCR1410): 73% (UV), Rt=1.03 min, m/z (ESI$^+$)=299.1 [M+H]$^+$

N-(Cyclohexylmethyl)-2-hydroxy-3-(N-methylpropanamido)butanamide (I-258)

The title compound was synthesized from N-(cyclohexylmethyl)-2-hydroxy-3-(methylamino)butanamide (I-248) in a similar manner to method B, general procedure 2a (general scheme 15) as an off-white solid (180 mg, 92% purity, 44%) after purification by flash column chromatography on normal phase silica (10 g SNAP KP-SIL cartridge, 0-60% EtOAc in heptane gradient).

$^1$H NMR (250 MHz, DMSO-d6) δ 0.66-1.76 (m, 17H), 2.12-2.37 (m, 2H), 2.58-3.08 (m, 5H), 3.77-6.89 (m, 3H), 7.53-7.94 (m, 1H).

LC-MS (METCR1416): 92% (UV), Rt=3.51 min, m/z (ESI$^+$)=285.3 [M+H]$^+$

N-(Cyclohexylmethyl)-3-(1-cyclopropyl-N-methylformamido)-2-hydroxybutanamide (I-259)

The title compound was synthesized from N-(cyclohexylmethyl)-2-hydroxy-3-(methylamino)butanamide (I-248) in a similar manner to method B, general procedure 2a (general scheme 15) as a brown solid (430 mg, 90% purity, 99%). The crude material was used in the next step without further purification.

$^1$H NMR (250 MHz, DMSO-d6) δ 0.49-2.03 (m, 19H), 2.63-3.20 (m, 5H), 3.88-4.78 (m, 2H), 5.70-5.99 (m, 1H), 7.54-7.97 (m, 1H).

LC-MS (METCR1410): 90% (UV), Rt=1.07 min, m/z (ESI$^+$)=297.2 [M+H]$^+$

N-(Cyclohexylmethyl)-2-hydroxy-3-[N-methyl-1-(5-methyl-1,2-oxazol-3-yl)formamido]-butanamide (I-260)

The title compound was synthesized from N-(cyclohexylmethyl)-2-hydroxy-3-(methylamino)butanamide (I-248) in a similar manner to method B, general procedure 2a (general scheme 15) as a colourless viscous oil (510 mg, 80% purity by $^1$H NMR, 97%). The crude material was used in the next step without further purification.

$^1$H NMR (500 MHz, Chloroform-d) δ 0.81-1.40 (m, 10H), 1.40-1.59 (m, 1H), 1.57-1.80 (m, 4H), 2.42-2.55 (m, 3H), 2.98-3.36 (m, 5H), 3.89-4.82 (m, 2H), 6.20-6.50 (m, 1H), 6.95-7.22 (m, 1H).

LC-MS (METCR1410): 97% (UV), Rt=1.04 min, m/z (ESI$^+$)=338.1 [M+H]$^+$

N-(Cyclohexylmethyl)-2-hydroxy-3-(2-methoxy-N-methylacetamido)butanamide (I-261)

The title compound was synthesized from N-(cyclohexylmethyl)-2-hydroxy-3-(methylamino) butanamide (I-248) in a similar manner to method B, general procedure 2a (general scheme 15) as a colourless viscous oil (500 mg, 79% purity, quantitative). The crude material was used in the next step without further purification.

$^1$H NMR (500 MHz, Chloroform-d) δ 0.82-1.37 (m, 10H), 1.36-1.55 (m, 1H), 1.58-1.77 (m, 3H), 2.97-3.52 (m, 8H), 3.95-4.30 (m, 4H), 6.08 (s, 1H), 7.03 (s, 1H).

LC-MS (METCR1410): 79% (UV), Rt=1 min, m/z (ESI$^+$)=301.2 [M+H]$^+$

N-(Cyclopropylmethyl)-2-hydroxy-3-(N-methyl-1-phenylformamido) butanamide (I-262)

The title compound was synthesized from N-(cyclopropylmethyl)-2-hydroxy-3-(methylamino)butanamide (I-249) in a similar manner to method B, general procedure 2a (general scheme 15) as a colourless oil (249 mg, 80% purity by 1H NMR, 80%). The crude material was used in the next step without further purification.

$^1$H NMR (500 MHz, Chloroform-d) δ 0.23 (q, J=4.7 Hz, 2H), 0.46-0.60 (m, 2H), 0.90-1.05 (m, 1H), 1.28-1.44 (m, 3H), 2.91-3.07 (m, 3H), 3.07-3.71 (m, 2H), 4.09-4.94 (m, 2H), 6.77-7.25 (m, 1H), 7.35-7.51 (m, 5H), 7.50-8.21 (m, 1H).

LC-MS (METCR1410): 83% (UV), Rt=0.91 min, m/z (ESI$^+$)=291.1 [M+H]$^+$ 3-(1-Cyclohexyl-N-methylformamido)-N-(cyclopropylmethyl)-2-hydroxybutanamide (I-263)

The title compound was synthesized from N-(cyclopropylmethyl)-2-hydroxy-3-(methylamino)butanamide (I-249) in a similar manner to method B, general procedure 2a (general scheme 15) as an off-white solid (255 mg, 80% purity by 1H NMR, 80%). The crude material was used in the next step without further purification.

$^1$H NMR (500 MHz, Chloroform-d) δ 0.10-0.30 (m, 2H), 0.40-0.60 (m, 2H), 0.83-1.03 (m, 1H), 1.09-1.91 (m, 13H), 2.36-2.61 (m, 1H), 2.93-3.24 (m, 5H), 3.96-4.88 (m, 2H), 6.26-6.52 (m, 1H), 7.09 (s, 1H).

LC-MS (METCR1410): 97% (UV), Rt=1 min, m/z (ESI$^+$)=297.1 [M+H]$^+$

N-(Cyclopropylmethyl)-3-(N-2-dimethylpropanamido)-2-hydroxybutanamide (I-264)

The title compound was synthesized from N-(cyclopropylmethyl)-2-hydroxy-3-(methylamino)butanamide (I-249)

in a similar manner to method B, general procedure 2a (general scheme 15) as a colourless oil (220 mg, 74% purity by $^1$H NMR, 74%). The crude material was used in the next step without further purification.

$^1$H NMR (500 MHz, Chloroform-d) δ 0.12-0.30 (m, 2H), 0.43-0.57 (m, 2H), 0.83-1.03 (m, 1H), 1.05-1.31 (m, 9H), 2.72-2.91 (m, 1H), 2.98-3.23 (m, 5H), 3.96-4.90 (m, 2H), 6.33 (s, 1H), 7.09 (s, 1H).

LC-MS (METCR1410): 67% (UV), Rt=0.85 min, m/z (ESI$^+$)=257.2 [M+H]$^+$

Methyl N-{1-hydroxy-1-[(2-methylpropyl)carbamoyl]propan-2-yl}-N-[(oxan-4-yl)methyl]carbamate (I-265)

The title compound was synthesized from 2-hydroxy-N-(2-methylpropyl)-3-{[(oxan-4-yl)methyl]amino}butanamide (I-247) in a similar manner to method B, general procedure 2a (general scheme 15) as a brown solid (690 mg, 78% purity, 73%) after filtration. The crude material was used in the next step without further purification.

$^1$H NMR (250 MHz, Chloroform-d) δ 0.73-0.92 (m, 6H), 1.02-1.41 (m, 5H), 1.41-1.60 (m, 2H), 1.59-1.94 (m, 2H), 2.88-3.41 (m, 7H), 3.51-3.78 (m, 4H), 3.80-3.99 (m, 2H), 4.15-4.87 (m, 1H), 6.02-7.10 (m, 1H)

LC-MS (METCR1410): 78% (UV), Rt=1 min, m/z (ESI$^+$) =331.2 [M+H]$^+$

N-(Cyclopropylmethyl)-3-[(4-fluorophenyl)formamido]-2-hydroxybutanamide (I-266)

The title compound was synthesized from 3-amino-N-(cyclopropylmethyl)-2-hydroxybutanamide (I-250) in a similar manner to method B, general procedure 2a (general scheme 15) as a colourless viscous oil (360 mg, 28% purity, 31%) after purification by flash column chromatography on normal phase silica (100 g SNAP KP-SIL cartridge, 0-70% EtOAc in heptane gradient).

LC-MS (METCR1410): 28% (UV), Rt=0.93 min, m/z (ESI$^+$)=295.1 [M+H]$^+$

N-(Cyclopropylmethyl)-2-hydroxy-3-(phenylformamido)hexanamide (I-267)

The title compound was synthesized from 3-amino-N-(cyclopropylmethyl)-2-hydroxyhexanamide (I-253) in a similar manner to method B, general procedure 2a (general scheme 15) as an off-white powder (240 mg, 98% purity, 44%) after filtration. The crude material was used in the next step without further purification.

$^1$H NMR (500 MHz, Chloroform-d) δ −0.07-0.04 (m, 2H), 0.21-0.31 (m, 2H), 0.68-0.75 (m, 1H), 0.82 (t, J=7.4 Hz, 3H), 1.21-1.40 (m, 2H), 1.55-1.67 (m, 1H), 1.76-1.88 (m, 1H), 2.90-3.01 (m, 2H), 4.06-4.12 (m, 1H), 4.15 (s, 1H), 5.49 (s, 1H), 6.39 (d, J=7.1 Hz, 1H), 6.83-6.99 (m, 1H), 7.30 (t, J=7.6 Hz, 2H), 7.32-7.44 (m, 1H), 7.52-7.68 (m, 2H).

LC-MS (METCR1410): 98% (UV), Rt=0.89-1.00 min (multiple peaks), m/z (ESI$^+$)=305.6 [M+H]$^+$ N-(Cyclopropylmethyl)-2-hydroxy-3-(phenylformamido)pentanamide (I-268)

The title compound was synthesized from 3-amino-N-(cyclopropylmethyl)-2-hydroxypentanamide (I-251) in a similar manner to method B, general procedure 2a (general scheme 15) as an off-white powder (107 mg, 97% purity, 34%) after filtration. The crude material was used in the next step without further purification.

$^1$H NMR (500 MHz, Chloroform-d) δ −0.07-0.05 (m, 2H), 0.24-0.31 (m, 2H), 0.69-0.78 (m, 1H), 0.90 (t, J=7.4 Hz, 3H), 1.67-1.77 (m, 1H), 1.78-1.92 (m, 1H), 2.91-3.03 (m, 2H), 3.96-4.05 (m, 1H), 4.17 (d, J=4.4 Hz, 1H), 5.50 (d, J=5.7 Hz, 1H), 6.44 (d, J=7.0 Hz, 1H), 6.93 (s, 1H), 7.31 (t, J=7.6 Hz, 2H), 7.34-7.45 (m, 1H), 7.56-7.70 (m, 2H).

LC-MS (METCR1410): 97% (UV), Rt=0.92 min, m/z (ESI$^+$)=291.2 [M+H]$^+$

N-(Cyclopropylmethyl)-2-hydroxy-3-[(2-methylphenyl)formamido]butanamide (I-269)

The title compound was synthesized from 3-amino-N-(cyclopropylmethyl)-2-hydroxybutanamide (I-250) in a similar manner to method B, general procedure 2a (general scheme 15) as an off-white powder (410 mg, 90% purity by $^1$H NMR, 79%) after filtration. The crude material was used in the next step without further purification.

$^1$H NMR (500 MHz, DMSO-d6) δ −0.06-0.06 (m, 2H), 0.14-0.27 (m, 2H), 0.84 (d, J=6.9 Hz, 3H), 2.16 (s, 3H), 2.76-2.86 (m, 2H), 3.37 (s, 1H), 3.92 (dd, J=3.4, 5.4 Hz, 1H), 4.10-4.25 (m, 1H), 5.56 (d, J=5.5 Hz, 1H), 7.00-7.08 (m, 2H), 7.10-7.21 (m, 2H), 7.61-7.70 (m, 1H), 7.75 (d, J=8.1 Hz, 1H).

LC-MS (METCR1410): 84% (UV), Rt=0.90 min, m/z (ESI$^+$)=291.1 [M+H]$^+$

N-(Cyclopropylmethyl)-2-hydroxy-3-[(4-methylphenyl)formamido]butanamide (I-270)

The title compound was synthesized from 3-amino-N-(cyclopropylmethyl)-2-hydroxybutanamide (I-250) in a similar manner to method B, general procedure 2a (general scheme 15) as an off-white powder (320 mg, 90% purity, 61%) after purification by flash column chromatography on normal phase silica (25 g SNAP KP-SIL cartridge, 0-60% EtOAc in heptane gradient).

$^1$H NMR (500 MHz, DMSO-d6) δ −0.05-0.04 (m, 2H), 0.15-0.23 (m, 2H), 0.72-0.80 (m, 1H), 0.86 (d, J=6.9 Hz, 3H), 2.18 (s, 3H), 2.81 (qt, J=6.4, 13.4 Hz, 2H), 3.92 (dd, J=3.4, 5.0 Hz, 1H), 4.15-4.23 (m, 1H), 5.59 (d, J=5.2 Hz, 1H), 7.09 (d, J=8.0 Hz, 2H), 7.60 (d, J=8.2 Hz, 2H), 7.65 (t, J=6.0 Hz, 1H), 7.80 (d, J=8.0 Hz, 1H).

LC-MS (METCR1410): 83% (UV), Rt=0.93 min, m/z (ESI$^+$)=291.1 [M+H]$^+$ 3-(Cyclohexylformamido)-N-(cyclopropylmethyl)-2-hydroxybutanamide (I-271)

The title compound was synthesized from 3-amino-N-(cyclopropylmethyl)-2-hydroxy-butanamide (I-250) in a similar manner to method B, general procedure 2a (general scheme 15) as an off-white solid (19 mg, 87% purity, 17%) after purification by flash column chromatography on normal phase silica (10 g SNAP KP-SIL cartridge, 0-60% EtOAc in heptane gradient).

LC-MS (METCR1410): 87% (UV), Rt=0.92 min, m/z (ESI$^+$)=283.2 [M+H]$^+$

A second batch was collected as an off-white solid (27 mg, 100% purity, 28%) after filtration from the aqueous layer and was used in the next step without further purification.

$^1$H NMR (250 MHz, Chloroform-d) δ −0.24-0.07 (m, 2H), 0.20-0.41 (m, 2H), 0.61-0.80 (m, 1H), 0.99-1.22 (m, 10H), 1.54-1.71 (m, 4H), 1.79-1.97 (m, 1H), 2.81-3.03 (m, 2H), 3.85-4.07 (m, 2H), 5.37-5.90 (m, 1H), 6.70-6.87 (m, 1H).

LC-MS (METCR1410): 100% (UV) Rt=0.98 min, m/z (ESI$^+$)=283.2 [M+H]$^+$

N-(Cyclopropylmethyl)-3-[(2,6-dichlorophenyl)formamido]-2-hydroxybutanamide (I-272)

The title compound was synthesized from 3-amino-N-(cyclopropylmethyl)-2-hydroxybutanamide (I-250) in a similar manner to method B, general procedure 2a (general scheme 15) as an off-white powder (349 mg, 98% purity, 63%) after filtration and trituration in water and DCM. The crude material was used in the next step without further purification.

$^1$H NMR (250 MHz, Methanol-d4) δ 0.19-0.32 (m, 2H), 0.41-0.59 (m, 2H), 0.95-1.10 (m, 1H), 1.16 (d, J=6.9 Hz, 3H), 3.02-3.17 (m, 2H), 4.31 (d, J=2.9 Hz, 1H), 4.49-4.68 (m, 1H), 7.32-7.51 (m, 3H).

LC-MS (METCR1410): 98% (UV), Rt=0.96 min, m/z (ESI$^+$)=345.1/346.9 [M+H]$^+$

N-(Cyclopropylmethyl)-3-[(2-fluorophenyl)formamido]-2-hydroxybutanamide (I-273)

The title compound was synthesized from 3-amino-N-(cyclopropylmethyl)-2-hydroxybutanamide (I-250) in a similar manner to method B, general procedure 2a (general scheme 15) as an off-white powder (261 mg, 95% purity by $^1$H NMR, 54%) after filtration and trituration in water and DCM. The crude material was used in the next step without further purification.

$^1$H NMR (250 MHz, Methanol-d4) δ 0.15-0.30 (m, 2H), 0.41-0.55 (m, 2H), 0.89-1.11 (m, 1H), 1.17 (d, J=6.9 Hz, 3H), 3.02-3.15 (m, 2H), 4.26 (d, J=3.1 Hz, 1H), 4.49-4.60 (m, 1H), 7.12-7.37 (m, 2H), 7.45-7.62 (m, 1H), 7.79 (t, J=7.1 Hz, 1H).

LC-MS (METCR1410): 94% (UV), Rt=0.92 min, m/z (ESI$^+$)=295.1 [M+H]$^+$

N-(Cyclopropylmethyl)-2-hydroxy-4-methyl-3-(phenylformamido)pentanamide (I-274)

The title compound was synthesized from 3-amino-N-(cyclopropylmethyl)-2-hydroxy-4-methylpentanamide (I-252) in a similar manner to method B, general procedure 2a (general scheme 15) as an off-white powder (156.2 mg, 97% purity, 50%) after filtration and trituration in water and DCM. The crude material was used in the next step without further purification.

$^1$H NMR (250 MHz, Methanol-d4) δ 0.11-0.23 (m, 2H), 0.35-0.47 (m, 2H), 0.88-1.06 (m, 7H), 2.18 (dq, J=6.8, 13.5 Hz, 1H), 2.96-3.15 (m, 2H), 4.15-4.37 (m, 2H), 7.38-7.60 (m, 3H), 7.76-7.91 (m, 2H).

LC-MS (METCR1410): 97% (UV), Rt=0.98 min, m/z (ESI$^+$)=305.6 [M+H]$^+$

3-[(2-Bromophenyl)formamido]-N-(cyclopropylmethyl)-2-hydroxybutanamide (I-275)

The title compound was synthesized from 3-amino-N-(cyclopropylmethyl)-2-hydroxybutanamide (I-250) in a similar manner to method B, general procedure 2a (general scheme 15) as an off-white powder (312 mg, 95% purity by $^1$H NMR, 72%) after filtration and trituration in water and DCM.

$^1$H NMR (500 MHz, Chloroform-d) δ 0.17-0.26 (m, 2H), 0.46-0.55 (m, 2H), 0.90-1.01 (m, 1H), 1.41 (d, J=7.1 Hz, 3H), 3.07-3.20 (m, 2H), 4.33 (dd, J=1.7, 5.5 Hz, 1H), 4.42 (pd, J=1.9, 7.1 Hz, 1H), 5.04 (d, J=5.6 Hz, 1H), 6.44 (d, J=6.7 Hz, 1H), 6.97 (s, 1H), 7.30 (td, J=1.8, 7.7 Hz, 1H), 7.36 (td, J=1.1, 7.5 Hz, 1H), 7.51 (dd, J=1.8, 7.8 Hz, 1H), 7.60 (dd, J=1.0, 8.0 Hz, 1H).

LC-MS (METCR1410): 89% (UV), Rt=0.91 min, m/z (ESI$^+$)=355.1/356.7 [M+H]$^+$

N-(Cyclopropylmethyl)-2-hydroxy-3-(2-phenylacetamido)butanamide (I-276)

The title compound was synthesized from 3-amino-N-(cyclopropylmethyl)-2-hydroxybutanamide (I-250) in a similar manner to method B, general procedure 2a (general scheme 15) as an off-white powder (72 mg, 98% purity, 42%) after purification by recrystallization from 3:1 EtOAc/heptane and trituration in heptane.

$^1$H NMR (500 MHz, DMSO-d6) δ 0.11-0.21 (m, 2H), 0.31-0.41 (m, 2H), 0.88-0.98 (m, 4H), 2.89-3.01 (m, 2H), 3.39-3.48 (m, 2H), 3.95 (dd, J=3.0, 5.7 Hz, 1H), 4.09-4.19 (m, 1H), 5.77 (d, J=5.7 Hz, 1H), 7.17-7.24 (m, 1H), 7.24-7.31 (m, 4H), 7.80 (t, J=6.0 Hz, 1H), 7.89 (d, J=8.2 Hz, 1H).

LC-MS (METCR1410): 98% (UV), Rt=0.91 min, m/z (ESI$^+$)=291.1 [M+H]$^+$

N-(Cyclopropylmethyl)-2-hydroxy-3-[(2-methoxyphenyl)formamido]butanamide (I-277)

The title compound was synthesized from 3-amino-N-(cyclopropylmethyl)-2-hydroxybutanamide (I-250) in a similar manner to method B, general procedure 2a (general scheme 15) after work-up as an orange viscous oil (198 mg, 81% purity, 90%). The crude material was used in the next step without further purification.

$^1$H NMR (500 MHz, DMSO-d6) δ 0.12-0.24 (m, 2H), 0.31-0.44 (m, 2H), 0.91-0.99 (m, 1H), 1.01 (d, J=6.8 Hz, 3H), 2.95-3.04 (m, 2H), 3.92 (s, 3H), 4.01-4.06 (m, 1H), 4.34-4.41 (m, 1H), 5.94 (d, J=5.7 Hz, 1H), 7.03-7.08 (m, 1H), 7.16 (d, J=8.2 Hz, 1H), 7.49 (ddd, J=1.9, 7.4, 8.4 Hz, 1H), 7.89 (dd, J=1.8, 7.7 Hz, 1H), 7.91-7.96 (m, 1H), 8.26 (d, J=8.3 Hz, 1H).

LC-MS (METCR1410): 81% (UV), Rt=0.93 min, m/z (ESI$^+$)=307.4 [M+H]$^+$

Method C: Addition of Acid Chloride at 0° C.

3-[(2-Chlorophenyl)formamido]-N-(cyclopropylmethyl)-2-hydroxybutanamide (I-278)

To a stirred, ice-cooled solution of 3-amino-N-(cyclopropylmethyl)-2-hydroxybutanamide (I-250, 100 mg, 0.58 mmol) and DIPEA (121 μL, 0.70 mmol) in DCM (3.5 mL) was added dropwise at 0° C. 2-chlorobenzoyl chloride (72 μL, 0.57 mmol). The reaction was stirred for 1 h at RT. Saturated NaHCO$_3$(3 mL) was added and the precipitate formed (A) was filtered off and washed with DCM (2×3 mL), 1M HCl (3 mL) and water (3 mL). The combined filtrates were separated through a Telos® hydrophobic frit and the aqueous layer extracted with DCM (2×3 mL). The combined organic layers were washed with 1N HCl (3 mL), filtered through a Telos® hydrophobic frit and concentrated in vacuo to give a solid (B). Solids A and B were suspended in DCM, combined and concentrated in vacuo to afford 198 mg of 3-[(2-chlorophenyl) formamido]-N-(cyclopropylmethyl)-2-hydroxybutanamide as an off-white solid (91% purity, quantitative).

$^1$H NMR (500 MHz, DMSO-d6) δ 0.13-0.23 (m, 2H), 0.32-0.43 (m, 2H), 0.91-0.99 (m, 1H), 1.01 (d, J=6.9 Hz, 3H), 2.93-3.04 (m, 2H), 4.06-4.11 (m, 1H), 4.28-4.39 (m, 1H), 5.72 (d, J=3.9 Hz, 1H), 7.36-7.49 (m, 4H), 7.84 (t, J=5.9 Hz, 1H), 8.16 (d, J=8.1 Hz, 1H).

LC-MS (METCR1410): 91% (UV), Rt=0.89 min, m/z (ESI$^+$)=311.1/313.1 [M+H]$^+$

3-[(4-Chlorophenyl)formamido]-N-(cyclopropylmethyl)-2-hydroxybutanamide (I-279)

The title compound was synthesized from 3-amino-N-(cyclopropylmethyl)-2-hydroxybutanamide (I-250) in a similar manner to method C, general procedure 2a (general scheme 15) as an off-white solid (263 mg, 97% purity, 94%) after work-up. The crude material was used in the next step without further purification.

$^1$H NMR (500 MHz, DMSO-d6) δ 0.11-0.21 (m, 2H), 0.31-0.41 (m, 2H), 0.88-1.00 (m, 1H), 1.04 (d, J=6.9 Hz, 3H), 2.90-3.04 (m, 2H), 4.09 (dd, J=3.4, 5.5 Hz, 1H), 4.31-4.42 (m, 1H), 5.76 (d, J=5.5 Hz, 1H), 7.51-7.56 (m, 2H), 7.83 (t, J=5.9 Hz, 1H), 7.86-7.93 (m, 2H), 8.18 (d, J=7.9 Hz, 1H).

LC-MS (METCR1410): 97% (UV), Rt=0.96 min, m/z (ESI$^+$)=311.1/313.1 [M+H]$^+$

N-(Cyclopropylmethyl)-2-hydroxy-3-[(3-methylphenyl)formamido]butanamide (I-280)

The title compound was synthesized from 3-amino-N-(cyclopropylmethyl)-2-hydroxybutanamide (I-250) in a similar manner to method C described for the general procedure 2a (general scheme 15) as an off-white solid (159 mg, 97% purity, 91%) after work-up. The crude material was used in the next step without further purification.

$^1$H NMR (500 MHz, DMSO-d6) δ 0.10-0.23 (m, 2H), 0.30-0.43 (m, 2H), 0.88-1.00 (m, 1H), 1.04 (d, J=6.9 Hz, 3H), 2.36 (s, 3H), 2.92-3.03 (m, 2H), 4.09 (dd, J=3.3, 5.4 Hz, 1H), 4.32-4.42 (m, 1H), 5.76 (d, J=5.4 Hz, 1H), 7.31-7.35 (m, 2H), 7.62-7.67 (m, 1H), 7.69 (br. s, 1H), 7.83 (t, J=5.9 Hz, 1H), 8.00 (d, J=8.0 Hz, 1H).

LC-MS (METCR1410): 97% (UV), Rt=0.94 min, m/z (ESI$^+$)=291.1 [M+H]$^+$

3-[(3-Chlorophenyl)formamido]-N-(cyclopropylmethyl)-2-hydroxybutanamide (I-281)

The title compound was synthesized from 3-amino-N-(cyclopropylmethyl)-2-hydroxybutanamide (I-250) in a similar manner to method C, general procedure 2a (general scheme 15) as an off-white solid (296 mg, 96% purity, quantitative) after work-up. The crude material was used in the next step without purification.

$^1$H NMR (500 MHz, DMSO-d6) δ 0.10-0.22 (m, 2H), 0.30-0.43 (m, 2H), 0.83-1.00 (m, 4H), 2.58-2.77 (m, 4H), 2.86-3.03 (m, 3H), 3.96 (dd, J=3.0, 5.8 Hz, 1H), 4.12-4.20 (m, 1H), 5.75 (d, J=5.8 Hz, 1H), 7.80 (t, J=5.9 Hz, 1H), 7.86 (d, J=8.0 Hz, 1H).

LC-MS (METCR1410): 96% (UV), Rt=0.96 min, m/z (ESI$^+$)=311.5/313.1 [M+H]$^+$

Method D: Formation of Acid Chloride In Situ

N-(cyclopropylmethyl)-3-[(4,4-difluorocyclohexyl)formamido]-2-hydroxybutanamide (I-282)

To a stirred, ice-cooled solution of 4,4-difluorocyclohexanecarboxylic acid (122 mg, 0.74 mmol) in DCM (1 mL) at 0° C. was added oxalyl chloride (63 μL, 0.66 mmol) dropwise. The reaction mixture was stirred at RT for 1 h to give the acid chloride in solution which was used in the next step. To 3-amino-N-(cyclopropylmethyl)-2-hydroxybutanamide (I-250, 116 mg, 0.67 mmol) and DIPEA (141 μL, 0.81 mmol) in DCM (1 mL) at 0° C. was added dropwise 4,4-difluorocyclohexane-1-carbonyl chloride in DCM. The reaction mixture was stirred at RT for 1 h and saturated NaHCO$_3$(2 mL) and DCM (10 mL) added. The phases were separated through a Telos® hydrophobic frit and the aqueous phase was extracted with DCM (2×2 mL). The combined organic layers were washed with 1M HCl (2 mL), filtered through a Telos® hydrophobic frit and the filtrate concentrated in vacuo to obtain a solid which was purified by preparative LC (acidic pH, standard elution method) to afford 76.2 mg of N-(cyclopropylmethyl)-3-[(4,4-difluorocyclohexyl)formamido]-2-hydroxybutanamide as an off-white crystalline solid (100% purity, 36%).

$^1$H NMR (500 MHz, DMSO-d6) δ 0.11-0.21 (m, 2H), 0.31-0.42 (m, 2H), 0.87-0.98 (m, 4H), 1.53-1.65 (m, 2H), 1.67-1.84 (m, 4H), 1.99-2.09 (m, 2H), 2.23-2.34 (m, 1H), 2.90-3.01 (m, 2H), 3.92 (dd, J=3.2, 5.2 Hz, 1H), 4.07-4.18 (m, 1H), 5.71 (d, J=5.4 Hz, 1H), 7.61 (d, J=8.2 Hz, 1H), 7.79 (t, J=6.0 Hz, 1H).

LC-MS (METCR1410): 100% (UV), Rt=0.91 min, m/z (ESI$^+$)=319.1 [M+H]$^+$

N-(Cyclopropylmethyl)-3-[(3,3-difluorocyclobutyl)formamido]-2-hydroxybutanamide (I-283)

The title compound was synthesized from 3-amino-N-(cyclopropylmethyl)-2-hydroxybutanamide (I-250) in a similar manner to method D, general procedure 2a (general scheme 15) as an off-white solid (166 mg, 97% purity, 64%) which was used in the next step without further purification.

$^1$H NMR (500 MHz, DMSO-d6) δ 0.10-0.22 (m, 2H), 0.30-0.43 (m, 2H), 0.83-1.00 (m, 4H), 2.58-2.77 (m, 4H), 2.86-3.03 (m, 3H), 3.96 (dd, J=3.0, 5.8 Hz, 1H), 4.12-4.20 (m, 1H), 5.75 (d, J=5.8 Hz, 1H), 7.80 (t, J=5.9 Hz, 1H), 7.86 (d, J=8.0 Hz, 1H).

LC-MS (METCR1410): 97% (UV), Rt=0.86 min, m/z (ESI$^+$)=291.4 [M+H]$^+$

Method E: HATU Coupling 3-(N-Cyclohexyl-2-methanesulfonamidoacetamido)-N-(cyclohexylmethyl)-2-hydroxy-butanamide (I-284)

To N-(methylsulfonyl)glycine (77.5 mg, 0.51 mmol) and 3-(cyclohexylamino)-N-(cyclohexylmethyl)-2-hydroxybutanamide (I-103, 150 mg, 0.51 mmol) in dry DMF (3.5 mL) was added DIPEA (176 μL, 1.01 mmol) and HATU (212 mg, 0.56 mmol) and the mixture stirred for 18 h. Water (20 mL) was added and the aqueous phase extracted with DCM (20 mL). The organic layer was washed with water (20 mL) and brine (20 mL), dried over sodium sulfate and concentrated in vacuo to obtain a crude orange oil which was purified by flash column chromatography on normal phase silica (10 g SNAP KP-SIL catridge, 0-5% MeOH in DCM gradient).

The resulting product was then dissolved in 4:1 MeCN/H₂O, filtered and purified by preparative LC (acidic pH, standard elution method). The pure fractions were combined and neutralized with saturated NaHCO₃ to pH 7-8. An equal volume of DCM was added and the mixture separated through a Telos® hydrophobic frit. The aqueous layer was extracted with DCM and the combined organic filtrates were concentrated in vacuo to afford 55.8 mg of 3-(N-cyclohexyl-2-methanesulfonamidoacetamido)-N-(cyclohexylmethyl)-2-hydroxy-butanamide as a colourless glass (98% purity, 25%).

¹H NMR (500 MHz, Chloroform-d) δ 0.86-1.00 (m, 2H), 1.09-1.38 (m, 9H), 1.44-1.53 (m, 1H), 1.58-1.77 (m, 9H), 1.84-1.97 (m, 3H), 2.98 (s, 3H), 3.05-3.18 (m, 2H), 3.33 (tt, J=3.7, 11.9 Hz, 1H), 3.94-4.06 (m, 2H), 4.14 (s, 1H), 4.18 (q, J=7.2 Hz, 1H), 5.26-5.34 (m, 1H), 6.21 (s, 1H), 6.99-7.13 (m, 1H).

LC-MS (METCR1410): 98% (UV), Rt=1.17 min, m/z (ESI⁺)=432.6 [M+H]⁺

Method F: Addition of Acid Chloride at 0° C. and In Situ Hydrolysis

N-[(3-Chlorophenyl)methyl]-2-hydroxy-3-(N-methyl-1-phenylformamido)butanamide (I-285)

To a stirred, ice cooled, solution of N-[(3-chlorophenyl)methyl]-2-hydroxy-3-(methylamino)butanamide (I-125, 260 mg, 1.01 mmol) and DIPEA (0.5 mL, 2.87 mmol) in DCM (8 mL) was added a solution of benzoyl chloride (0.13 mL, 1.12 mmol) in DCM (2 mL) dropwise over 5 min. The reaction was stirred for 0.5 h at RT. The solution was diluted with DCM (10 mL) and washed with saturated NaHCO₃ (20 mL) and water (20 mL). The organic layer was separated, dried over sodium sulfate and concentrated in vacuo to give a yellow oil which was dissolved in 1:1 MeOH/THF (10 mL) and 2N NaOH (3 mL) was added. The mixture was stirred for 1 h, partitioned between EtOAc (15 mL) and water (15 mL) and the aqueous layer extracted with EtOAc (2×10 mL). The combined organic layers were dried over sodium sulfate and concentrated in vacuo to give a yellow solid which was suspended in hot EtOAc (8 mL). The suspension was diluted with heptane (20 mL) and allowed to cool for 5 min. The suspension was filtered to afford a 180 mg of N-[(3-chlorophenyl)methyl]-2-hydroxy-3-(N-methyl-1-phenylformamido)butanamide as an off-white solid (100% purity, 49%).

¹H NMR (250 MHz, DMSO-d6) δ 1.01-1.20 (m, 3H), 2.74-2.97 (m, 3H), 3.90-4.89 (m, 4H), 6.06 (s, 1H), 7.16-7.45 (m, 9H), 8.38-8.55 (m, 1H).

LC-MS (METCR1278): 100% (UV), Rt=1.86 min, m/z (ESI⁺)=361.3/363.3 [M+H]⁺

General Procedure 3a (General Scheme 15): Oxidation

Method A: Addition of DMP at RT

N-[(3-Chlorophenyl)methyl]-3-[N-(2-methoxyphenyl)propanamido]-2-oxobutanamide (FP 141)

To N-[(3-chlorophenyl)methyl]-2-hydroxy-3-[N-(2-methoxyphenyl)propanamido]butanamide (I-254, 85% purity, 59 mg, 0.12 mmol) in DCM (3 mL) was added DMP (53 mg, 0.12 mmol)) and the mixture stirred for 1 h. The reaction was quenched with saturated NaHCO₃ (5 mL) and the aqueous layer extracted with DCM (3×5 mL). The combined organic layers were dried over sodium sulfate, filtered and concentrated in vacuo. The crude material was purified by flash column chromatography on normal phase silica (10 g SNAP KP-SIL cartridge, 0-100% EtOAc in heptane gradient) to afford 29.9 mg of N-[(3-chlorophenyl)methyl]-3-[N-(2-methoxyphenyl)propanamido]-2-oxobutanamide as a yellow oil (97% purity, 60%).

¹H NMR (500 MHz, Chloroform-d) δ 0.89-0.99 (m, 3H), 1.02-1.40 (m, 3H), 1.87-2.07 (m, 2H), 3.82-3.85 (m, 3H), 4.32-5.47 (m, 3H), 6.94-7.07 (m, 2H), 7.16-7.28 (m, 4H), 7.31-7.40 (m, 2H), 7.41-7.87 (m, 1H).

LC-MS (MET-uPLC-AB-101): 97% (UV), Rt=3.77 min, m/z (ESI⁺)=403.0/405.0 [M+H]⁺

N-[(3-Chlorophenyl)methyl]-3-[N-(2-methoxyphenyl)-2-methylpropanamido]-2-oxobutanamide (FP 142)

The title compound was synthesized from N-[(3-chlorophenyl)methyl]-2-hydroxy-3-[N-(2-methoxyphenyl)-2-methylpropanamido]butanamide (I-255) in a similar manner to method A, general procedure 3a (general scheme 15) as an off-white powder (56 mg, 97% purity, 36%) after purification by flash column chromatography on normal phase silica (10 g SNAP KP-SIL cartridge, 0-100% EtOAc in heptane gradient).

¹H NMR (500 MHz, Chloroform-d) δ 0.79-1.43 (m, 9H), 2.26 (dq, J=6.8, 13.5 Hz, 1H), 3.79-3.88 (m, 3H), 4.38-4.64 (m, 2H), 4.21-6.45 (m, 1H), 6.94-7.09 (m, 2H), 7.12 (t, J=6.2 Hz, 1H), 7.26 (s, 3H), 7.31-7.41 (m, 2H), 7.41-7.97 (m, 1H).

LC-MS (MET-uPLC-AB-101): 97% (UV), Rt=4.03 min, m/z (ESI⁺)=417.1/419.1 [M+H]⁺

N-[(3-Chlorophenyl)methyl]-3-[N-(2-methoxyphenyl)butanamido]-2-oxobutanamide (FP 143)

The title compound was synthesized from N-[(3-chlorophenyl)methyl]-2-hydroxy-3-[N-(2-methoxyphenyl)butanamido]butanamide (I-256) in a similar manner to method A, general procedure 3a (general scheme 15) as a colourless viscous oil (44 mg, 99% purity, 42%) after purification by flash column chromatography on normal phase silica (10 g SNAP KP-SIL cartridge, 0-100% EtOAc in heptane gradient).

¹H NMR (500 MHz, Chloroform-d) δ 0.75-0.83 (m, 3H), 1.02-1.43 (m, 3H), 1.44-1.58 (m, 2H), 1.86-2.04 (m, 2H), 3.83-3.89 (m, 3H), 4.32-6.50 (m, 3H), 6.96-7.12 (m, 2H), 7.19 (t, J=5.8 Hz, 1H), 7.21-7.32 (m, 3H), 7.33-7.93 (m, 3H).

LC-MS (MET-uPLC-AB-101): 99% (UV), Rt=3.98 min, m/z (ESI⁺)=417.1/419.0 [M+H]⁺

N-(Cyclohexylmethyl)-3-(N,2-dimethylpropanamido)-2-oxobutanamide (FP 144)

The title compound was synthesized from N-(cyclohexylmethyl)-3-(N,2-dimethylpropanamido)-2-hydroxybutanamide (I-257) in a similar manner to method A, general procedure 3a (general scheme 15) as an off-white powder (114 mg, 97% purity, 36%) after purification by flash column chromatography on normal phase silica (10 g SNAP KP-SIL cartridge, 0-30% EtOAc in heptane gradient) followed by trituration in heptane.

¹H NMR (500 MHz, Chloroform-d) δ 0.90-0.99 (m, 2H), 1.04-1.10 (m, 6H), 1.14-1.27 (m, 3H), 1.40 (d, J=6.8 Hz, 3H), 1.46-1.55 (m, 1H), 1.64-1.69 (m, 1H), 1.70-1.77 (m, 4H), 2.74 (hept, 1H), 3.05-3.14 (m, 2H), 3.22 (s, 3H), 4.07 (q, J=6.7 Hz, 1H), 6.72-6.80 (m, 1H).

LC-MS (MET-uPLC-AB-101): 97% (UV), Rt=3.18 min, m/z (ESI$^+$)=297.2 [M+H]$^+$

N-(Cyclohexylmethyl)-3-(N-methylpropanamido)-2-oxobutanamide (FP 145)

The title compound was synthesized from N-(cyclohexylmethyl)-2-hydroxy-3-(N-methylpropanamido)butanamide (I-258) in a similar manner to method A, general procedure 3a (general scheme 15) as an off-white powder (46 mg, 98% purity, 27%) after purification by flash column chromatography on normal phase silica (10 g SNAP KP-SIL cartridge, 0-40% EtOAc in heptane gradient) followed by trituration in heptane.

$^1$H NMR (500 MHz, Chloroform-d) δ 0.87-1.00 (m, 2H), 1.09 (t, J=7.4 Hz, 3H), 1.14-1.28 (m, 3H), 1.41 (d, J=6.8 Hz, 3H), 1.46-1.54 (m, 1H), 1.64-1.70 (m, 1H), 1.70-1.76 (m, 4H), 2.30 (q, J=7.5 Hz, 2H), 3.06-3.16 (m, 2H), 3.17 (s, 3H), 4.18 (q, J=6.8 Hz, 1H), 6.72-6.82 (m, 1H).

LC-MS (MET-uPLC-AB-101): 98% (UV), Rt=2.9 min, m/z (ESI$^+$)=283.2 [M+H]$^+$

N-(Cyclohexylmethyl)-3-(1-cyclopropyl-N-methylformamido)-2-oxobutanamide (FP 146)

The title compound was synthesized from N-(cyclohexylmethyl)-3-(1-cyclo-propyl-N-methylformamido)-2-hydroxybutanamide (I-259) in a similar manner to method A, general procedure 3a (general scheme 15) as an off-white powder (134 mg, 97% purity, 34%) after purification by flash column chromatography on normal phase silica (10 g SNAP KP-SIL cartridge, 0-40% EtOAc in heptane gradient).

$^1$H NMR (500 MHz, Chloroform-d) δ 0.76-0.83 (m, 2H), 0.81-0.89 (m, 1H), 0.91-1.01 (m, 3H), 1.14-1.29 (m, 3H), 1.41 (d, J=6.8 Hz, 3H), 1.45-1.53 (m, 1H), 1.65-1.77 (m, 6H), 3.03-3.12 (m, 1H), 3.12-3.19 (m, 1H), 3.35 (s, 3H), 4.21 (q, J=6.8 Hz, 1H), 6.67-6.81 (m, 1H).

LC-MS (MET-uPLC-AB-101): 97% (UV), Rt=3.03 min, m/z (ESI$^+$)=295.2 [M+H]$^+$

N-(Cyclohexylmethyl)-3-[N-methyl-1-(5-methyl-1,2-oxazol-3-yl)formamido]-2-oxobutanamide (FP 147)

The title compound was synthesized from N-(cyclohexylmethyl)-2-hydroxy-3-[N-methyl-1-(5-methyl-1,2-oxazol-3-yl)formamido]butanamide (I-260) in a similar manner to method A, general procedure 3a (general scheme 15) as a colourless viscous oil (201 mg, 96% purity, 43%) after purification by flash column chromatography on normal phase silica (10 g SNAP KP-SIL cartridge, 0-40% EtOAc in heptane gradient).

$^1$H NMR (500 MHz, Chloroform-d) δ 0.87-1.05 (m, 2H), 1.08-1.32 (m, 3H), 1.47-1.61 (m, 4H), 1.63-1.78 (m, 5H), 2.44-2.49 (m, 3H), 3.03-3.53 (m, 5H), 4.44-6.00 (m, 1H), 6.17-6.41 (m, 1H), 6.68-6.99 (m, 1H).

LC-MS (MET-uPLC-AB-101): 96% (UV), Rt=3.25 min, m/z (ESI$^+$)=336.1 [M+H]$^+$

N-(Cyclohexylmethyl)-3-(2-methoxy-N-methylacetamido)-2-oxobutanamide (FP 148)

The title compound was synthesized from N-(cyclohexylmethyl)-2-hydroxy-3-(2-methoxy-N-methylacetamido)butanamide (I-261) in a similar manner to method A, general procedure 3a (general scheme 15) as an off-white powder (67 mg, 98% purity, 17%) after purification by flash column chromatography on normal phase silica (10 g SNAP KP-SIL cartridge, 0-40% EtOAc in heptane gradient).

$^1$H NMR (500 MHz, Chloroform-d) δ 0.85-1.03 (m, 2H), 1.11-1.30 (m, 3H), 1.41-1.55 (m, 4H), 1.64-1.79 (m, 5H), 2.90-3.20 (m, 5H), 3.29-3.43 (m, 3H), 4.01-6.60 (m, 3H), 6.66-6.99 (m, 1H).

LC-MS (MET-uPLC-AB-101): 98% (UV), Rt=2.61 min, m/z (ESI$^+$)=299.1 [M+H]$^+$

N-(Cyclopropylmethyl)-3-(N-methyl-1-phenylformamido)-2-oxobutanamide (FP 149)

The title compound was synthesized from N-(cyclopropylmethyl)-2-hydroxy-3-(N-methyl-1-phenylformamido)butanamide (I-262) in a similar manner to method A, general procedure 3a (general scheme 15) as a light yellow oil (121.2 mg, 93% purity, 45%) after purification by flash column chromatography on normal phase silica (10 g SNAP KP-SIL cartridge, 0-100% EtOAc in heptane gradient) followed by trituration in heptane.

$^1$H NMR (500 MHz, Chloroform-d) δ 0.23 (q, J=4.8 Hz, 2H), 0.52 (q, J=5.1 Hz, 2H), 0.94-1.02 (m, 1H), 1.56 (d, J=6.8 Hz, 3H), 3.08-3.25 (m, 5H), 4.46 (q, J=6.8 Hz, 1H), 6.89 (s, 1H), 7.36-7.46 (m, 5H).

LC-MS (MET-uPLC-AB-101): 93% (UV), Rt=2.58 min, m/z (ESI$^+$)=289.1 [M+H]$^+$

3-(1-Cyclohexyl-N-methylformamido)-N-(cyclopropylmethyl)-2-oxobutanamide (FP 150)

The title compound was synthesized from 3-(1-cyclohexyl-N-methylform-amido)-N-(cyclopropylmethyl)-2-hydroxybutanamide (I-263) in a similar manner to method A, general procedure 3a (general scheme 15) as an off-white powder (86.7 mg, 95% purity by $^1$H NMR, 33%) after purification by flash column chromatography on normal phase silica (10 g SNAP KP-SIL cartridge, 0-100% EtOAc in heptane gradient).

$^1$H NMR (500 MHz, Chloroform-d) δ 0.18-0.26 (m, 2H), 0.47-0.56 (m, 2H), 0.88-1.03 (m, 1H), 1.17-1.48 (m, 8H), 1.64-1.83 (m, 5H), 2.42 (tt, J=11.4, 3.3 Hz, 1H), 3.04-3.18 (m, 2H), 3.20 (s, 3H), 4.13 (q, J=6.8 Hz, 1H), 6.82 (s, 1H).

LC-MS (METCR1416): 91% (UV), Rt=3.91 min, m/z (ESI$^+$)=295.10 [M+H]$^+$

N-(Cyclopropylmethyl)-3-(N,2-dimethylpropanamido)-2-oxobutanamide (FP 151)

The title compound was synthesized from N-(cyclopropylmethyl)-3-(N,2-dimethylpropanamido)-2-hydroxybutanamide (I-264) in a similar manner to method A, general procedure 3a (general scheme 15) as an off-white solid (69.9 mg, 96% purity, 31%) after purification by flash column chromatography on normal phase silica (10 g SNAP KP-SIL cartridge, 0-100% EtOAc in heptane gradient).

$^1$H NMR (500 MHz, Chloroform-d) δ 0.18-0.23 (m, 2H), 0.47-0.55 (m, 2H), 0.90-1.00 (m, 1H), 1.02-1.09 (m, 6H), 1.39 (d, J=6.8 Hz, 3H), 2.73 (p, J=6.7 Hz, 1H), 3.04-3.16 (m, 2H), 3.20 (s, 3H), 4.12 (q, J=6.8 Hz, 1H), 6.80 (s, 1H).

LC-MS (METCR1600): 96% (UV), Rt=3.74 min, m/z (ESI$^+$)=255.2 [M+H]$^+$

Methyl N-{1-[(2-methylpropyl)carbamoyl]-1-oxopropan-2-yl}-N-[(oxan-4-yl)methyl]carbamate (FP 152)

The title compound was synthesized from methyl N-{1-hydroxy-1-[(2-methyl-propyl)carbamoyl]propan-2-yl}-M

[(oxan-4-yl)methyl]carbamate (I-265) in a similar manner to method A, general procedure 3a (general scheme 15) as an off-white powder (210 mg, 97% purity, 38%) after purification by flash column chromatography on normal phase silica (10 g SNAP KP-SIL cartridge, 0-100% TBME in heptane gradient).

$^1$H NMR (500 MHz, Chloroform-d) δ 0.92 (d, J=6.7 Hz, 6H), 1.26-1.37 (m, 2H), 1.44 (d, J=6.9 Hz, 3H), 1.60-1.68 (m, 2H), 1.75-1.84 (m, 1H), 1.85-1.95 (m, 1H), 3.01-3.11 (m, 1H), 3.13-3.20 (m, 1H), 3.27-3.34 (m, 2H), 3.34-3.45 (m, 2H), 3.64 (s, 3H), 3.93-4.01 (m, 2H), 4.27 (q, J=6.7 Hz, 1H), 6.53-6.79 (m, 1H).

LC-MS (METCR1600): 97% (UV), Rt=4.10 min, m/z (ESI$^+$)=329.3 [M+H]$^+$

N-(Cyclopropylmethyl)-3-[(4-fluorophenyl)formamido]-2-oxobutanamide (FP 153)

The title compound was synthesized from N-(cyclopropylmethyl)-3-[(4-fluoro-phenyl)formamido]-2-hydroxybutanamide (I-266) in a similar manner to method A, general procedure 3a (general scheme 15) as an off-white powder (8 mg, 97% purity, 7%) after purification by flash column chromatography on normal phase silica (10 g SNAP KP-SIL cartridge, 0-60% EtOAc in heptane gradient) followed by preparative LC (acidic pH, standard elution method) and trituration in heptane.

$^1$H NMR (500 MHz, Chloroform-d) δ 0.23-0.28 (m, 2H), 0.52-0.60 (m, 2H), 0.94-1.05 (m, 1H), 1.58 (d, J=7.2 Hz, 3H), 3.15-3.23 (m, 2H), 5.48 (p, J=7.2 Hz, 1H), 6.78-6.87 (m, 1H), 6.95-7.05 (m, 1H), 7.08-7.16 (m, 2H), 7.78-7.88 (m, 2H).

LC-MS (METCR1600): 97% (UV), Rt=3.84 min, m/z (ESI$^+$)=293.2 [M+H]$^+$

N-(Cyclopropylmethyl)-2-oxo-3-(phenylformamido)hexanamide (FP 154)

The title compound was synthesized from N-(cyclopropylmethyl)-2-hydroxy-3-(phenylformamido)hexanamide (I-267) in a similar manner to method A, general procedure 3a (general scheme 15) as an off-white solid (85 mg, 97% purity, 35%) after purification by flash column chromatography on normal phase silica (10 g SNAP KP-SIL cartridge, 0-45% EtOAc in heptane gradient).

$^1$H NMR (500 MHz, Chloroform-d) δ 0.18-0.29 (m, 2H), 0.50-0.61 (m, 2H), 0.93-1.03 (m, 4H), 1.39-1.52 (m, 2H), 1.70-1.83 (m, 1H), 1.98-2.11 (m, 1H), 3.11-3.23 (m, 2H), 5.41-6.53 (m, 1H), 6.85-6.95 (m, 1H), 6.95-7.07 (m, 1H), 7.40-7.48 (m, 2H), 7.48-7.55 (m, 1H), 7.77-7.88 (m, 2H).

LC-MS (METCR1600): 97% (UV), Rt=4.33 min, m/z (ESI$^+$)=303.3 [M+H]$^+$

N-(Cyclopropylmethyl)-2-oxo-3-(phenylformamido)pentanamide (FP 155)

The title compound was synthesized from N-(cyclopropylmethyl)-2-hydroxy-3-(phenylformamido)pentanamide (I-268) in a similar manner to method A, general procedure 3a (general scheme 15) as an off-white solid (34 mg, 96% purity, 31%) after purification by flash column chromatography on normal phase silica (10 g SNAP KP-SIL cartridge, 0-60% EtOAc in heptane gradient).

$^1$H NMR (500 MHz, Chloroform-d) δ 0.19-0.29 (m, 2H), 0.50-0.60 (m, 2H), 0.94-1.06 (m, 4H), 1.81-1.92 (m, 1H), 2.11-2.22 (m, 1H), 3.14-3.22 (m, 2H), 5.38-6.50 (m, 1H), 6.87-6.96 (m, 1H), 6.97-7.07 (m, 1H), 7.42-7.48 (m, 2H), 7.48-7.56 (m, 1H), 7.77-7.86 (m, 2H).

LC-MS (METCR1600): 96% (UV), Rt=4.04 min, m/z (ESI$^+$)=289.2 [M+H]$^+$

N-(Cyclopropylmethyl)-3-[(2-methylphenyl)formamido]-2-oxobutanamide (FP 156)

The title compound was synthesized from N-(cyclopropylmethyl)-2-hydroxy-3-[(2-methylphenyl)formamido]butanamide (I-269) in a similar manner to method A, general procedure 3a (general scheme 15) as an off-white solid (91 mg, 100% purity, 24%) after purification by flash column chromatography on normal phase silica (10 g SNAP KP-SIL cartridge, 0-45% EtOAc in heptane gradient).

$^1$H NMR (500 MHz, Chloroform-d) δ 0.19-0.31 (m, 2H), 0.50-0.62 (m, 2H), 0.93-1.05 (m, 1H), 1.56 (d, J=7.2 Hz, 3H), 2.45 (s, 3H), 3.15-3.21 (m, 2H), 5.47 (p, J=7.2 Hz, 1H), 6.34-6.45 (m, 1H), 6.96-7.08 (m, 1H), 7.19-7.24 (m, 2H), 7.31-7.35 (m, 1H), 7.40-7.43 (m, 1H).

LC-MS (METCR1600): 100% (UV), Rt=3.88 min, m/z (ESI$^+$)=289.3 [M+H]$^+$ (3S)—N-(Cyclopropylmethyl)-3-[(2-methylphenyl)formamido]-2-oxobutanamide and (3R)—N-(Cyclopropylmethyl)-3-[(2-methylphenyl)formamido]-2-oxobutanamide (FP 157-158) ((R) and (S) assignments arbitrary)

N-(Cyclopropylmethyl)-3-[(2-methylphenyl)formamido]-2-oxobutanamide (FP 156) (65.2 mg, 0.23 mmol) was purified by chiral separation on Gilson LC [Column: Chiralcel OJ-H (20 mm×250 mm, 5 μm) at RT; Isocratic eluent: 9:1 heptane/IPA; Flow rate: 15 mL/min; Detector wavelength; 210/254 nm; Dilution solvent: IPA; Injection volume: 500-1000 μL] to afford 11.5 mg of Enantiomer 2 (FP158) as an off-white powder (>99% ee, 17%). The mixed fractions were re-purified in the same conditions to give 10.3 mg of Enantiomer 1 (FP 157) as an off-white solid (86% ee, 13%).

Enantiomer 1 (FP 157)

$^1$H NMR (500 MHz, Chloroform-d) δ 0.19-0.32 (m, 2H), 0.50-0.64 (m, 2H), 0.94-1.06 (m, 1H), 1.57 (d, J=7.2 Hz, 3H), 2.45 (s, 3H), 3.13-3.25 (m, 2H), 5.48 (p, J=7.2 Hz, 1H), 6.38 (d, J=6.7 Hz, 1H), 7.00 (br. s, 1H), 7.19-7.24 (m, 2H), 7.30-7.35 (m, 1H), 7.40-7.44 (m, 1H).

LC-MS (MET-uPLC-AB-102): 96% (UV), Rt=2.55 min, m/z (ESI$^+$)=289.1 [M+H]$^+$

LC-MS (CAM-1): 93% (UV), Rt=10.38 min, 86% ee

Enantiomer 2 (FP 158)

$^1$H NMR (500 MHz, Chloroform-d) δ 0.22-0.35 (m, 2H), 0.52-0.66 (m, 2H), 0.98-1.07 (m, 1H), 1.60 (d, J=7.2 Hz, 3H), 2.48 (s, 3H), 3.15-3.28 (m, 2H), 5.50 (p, J=7.2 Hz, 1H), 6.41 (d, J=6.6 Hz, 1H), 7.03 (br. s, 1H), 7.22-7.27 (m, 2H), 7.33-7.38 (m, 1H), 7.42-7.46 (m, 1H).

LC-MS (MET-uPLC-AB-102): 97% (UV), Rt=2.55 min, m/z (ESI$^+$)=289.1 [M+H]$^+$

LC-MS (CAM-2): 99% (UV), Rt=6.11 min, >99% ee

N-(Cyclopropylmethyl)-3-[(4-methylphenyl)formamido]-2-oxobutanamide (FP 159)

The title compound was synthesized from N-(cyclopropylmethyl)-2-hydroxy-3-[(4-methylphenyl)formamido]butanamide (I-270) in a similar manner to method A, general procedure 3a (general scheme 15) as an off-white solid (46 mg, 97% purity, 16%) after purification by flash column chromatography on normal phase silica (10 g SNAP KP-SIL cartridge, 0-45% EtOAc in heptane gradient).

$^1$H NMR (500 MHz, Chloroform-d) δ 0.20-0.30 (m, 2H), 0.51-0.59 (m, 2H), 0.94-1.03 (m, 1H), 1.57 (d, J=7.2 Hz, 3H), 2.40 (s, 3H), 3.15-3.23 (m, 2H), 5.47 (p, J=7.2 Hz, 1H), 6.76-6.88 (m, 1H), 6.96-7.06 (m, 1H), 7.24 (d, J=8.1 Hz, 2H), 7.70 (d, J=8.1 Hz, 2H).

LC-MS (METCR1600): 97% (UV), Rt=3.98 min, m/z (ESI$^+$)=289.3 [M+H]$^+$

N-[(3-Chlorophenyl)methyl]-3-(N-methyl-1-phenylformamido)-2-oxobutanamide (FP 160)

The title compound was synthesized from N-[(3-chlorophenyl)methyl]-2-hydroxy-3-(N-methyl-1-phenylformamido)butanamide (I-285) in a similar manner to method A, general procedure 3a (general scheme 15) as a yellow viscous oil (117 mg, 95% purity, 64%) after purification by flash column chromatography on normal phase silica (10 g SNAP KP-SIL cartridge, 0-40% EtOAc in heptane gradient).

$^1$H NMR (500 MHz, DMSO-d6) δ 1.40 (d, J=6.7 Hz, 3H), 2.77-3.04 (m, 3H), 4.20-4.34 (m, 1H), 4.41 (dd, J=6.7, 15.2 Hz, 1H), 4.46-6.07 (m, 1H), 7.16-7.26 (m, 3H), 7.26-7.37 (m, 3H), 7.39-7.47 (m, 3H), 9.06-9.36 (m, 1H).

LC-MS (MET-uPLC-AB-101): 95% (UV), Rt=3.25 min, m/z (ESI$^+$)=359.1/361.0 [M+H]$^+$

3-(Cyclohexylformamido)-N-(cyclopropylmethyl)-2-oxobutanamide (FP 161)

The title compound was synthesized from 3-(cyclohexylformamido)-N-(cyclo-propylmethyl)-2-hydroxybutanamide (I-271) in a similar manner to method A, general procedure 3a (general scheme 15) as a brown gum (13 mg, 99% purity, 29%) after purification by flash column chromatography on normal phase silica (10 g SNAP KP-SIL cartridge, 0-100% TBME in heptane gradient).

$^1$H NMR (500 MHz, Chloroform-d) δ 0.18-0.28 (m, 2H), 0.49-0.59 (m, 2H), 0.91-1.03 (m, 1H), 1.15-1.33 (m, 4H), 1.36-1.50 (m, 4H), 1.64-1.69 (m, 1H), 1.74-1.81 (m, 2H), 1.81-1.91 (m, 2H), 2.12 (tt, J=3.5, 11.7 Hz, 1H), 3.11-3.22 (m, 2H), 5.23 (p, J=7.2 Hz, 1H), 6.10 (d, J=6.3 Hz, 1H), 6.96 (s, 1H).

LC-MS (METCR1600): 99% (UV), Rt=3.97 min, m/z (ESI$^+$)=281.3 [M+H]$^+$

Method B: Addition of DMP at RT and Multiple Extractions/Purifications

3-(N-Cyclohexyl-2-methanesulfonamidoacetamido)-N-(cyclohexylmethyl)-2-oxobutanamide (FP 162)

To a stirred solution of 3-(N-cyclohexyl-2-methanesulfonamidoacetamido)-N-(cyclohexylmethyl)-2-hydroxybutanamide (I-284, 98% purity, 47.6 mg, 0.11 mmol) in DCM (2 mL) was added DMP (56.2 mg, 0.13 mmol) and the reaction stirred for 5 min. Saturated NaHCO$_3$(2 mL) was added and the phases separated through a Telos® hydrophobic frit. The aqueous layer was extracted with DCM (2 mL×2) and the combined organic layers concentrated in vacuo. The crude residue was dissolved in 4:1:1 MeCN/H$_2$O/DMSO (1.1 mL), filtered twice and purified by preparative LC (acidic pH, standard elution method). The pure fractions were combined and neutralized to pH 7-8 with saturated NaHCO$_3$and extracted with DCM. The organic phase was concentrated in vacuo. The solid obtained was dried in a vac oven at 40° C. for 10 min to afford 15.5 mg of 3-(N-cyclohexyl-2-methanesulfonamidoacetamido)-(cyclohexylmethyl)-2-oxobutanamide as an off-white powder (100% purity, 33%).

$^1$H NMR (500 MHz, Chloroform-d) δ 0.78-1.54 (m, 15H), 1.61-2.24 (m, 9H), 2.87-3.23 (m, 5H), 3.38-3.70 (m, 1H), 3.87-4.03 (m, 1H), 4.13-4.60 (m, 2H), 5.10-6.34 (m, 1H), 6.52-6.74 (m, 1H).

LC-MS (MET-uPLC-AB-102): 100% (UV), Rt=3.61 min, m/z (ESI$^+$)=447.3 [M+H+NH$_3$]$^+$

Method C: Addition of DMP at 0° C.

N-(Cyclopropylmethyl)-3-[(2,6-dichlorophenyl)formamido]-2-oxobutanamide (FP 163)

To a stirred, ice cooled solution of N-(cyclopropylmethyl)-3-[(2,6-dichloro-phenyl)formamido]-2-hydroxybutanamide (I-272, 349 mg, 1.01 mmol) in DCM (10 mL) at 0° C. was added DMP (514.5 mg, 1.21 mmol). The mixture was stirred at RT for 18 h, saturated NaHCO$_3$(10 mL) added and the reaction stirred for 20 min. The suspension was filtered and the biphasic filtrate separated. The aqueous layer was extracted with DCM (10 mL) and the combined organic phases dried over sodium sulfate, filtered and concentrated in vacuo. The crude product was dissolved in 1:1 MeCN/H$_2$O, filtered twice and purified on preparative LC (acidic pH standard elution method) to afford 208 mg of N-(cyclopropylmethyl)-3-[(2,6-dichlorophenyl)formamido]-2-oxobutanamide as a cream solid (97% purity, 58%).

$^1$H NMR (500 MHz, Chloroform-d) δ 0.23 (p, J=4.9 Hz, 2H), 0.50-0.58 (m, 2H), 0.93-1.03 (m, 1H), 1.60 (d, J=7.2 Hz, 3H), 3.12-3.22 (m, 2H), 5.57 (p, J=7.2 Hz, 1H), 6.52 (d, J=7.1 Hz, 1H), 7.01 (s, 1H), 7.22-7.25 (m, 1H), 7.29-7.31 (m, 2H).

LC-MS (MET-uPLC-AB-102): 97% (UV), Rt=2.64 min, m/z (ESI$^+$)=343.0/345.0 [M+H]$^+$

N-(Cyclopropylmethyl)-3-[(2-fluorophenyl)formamido]-2-oxobutanamide (FP 164)

The title compound was synthesized from N-(cyclopropylmethyl)-3-[(2-fluoro-phenyl)formamido]-2-hydroxybutanamide (I-273) in a similar manner to method C, general procedure 3a (general scheme 15) as a cream powder (144 mg, 100% purity, 59%) after purification by preparative LC (acidic pH, standard elution method).

$^1$H NMR (500 MHz, Chloroform-d) δ 0.19-0.30 (m, 2H), 0.50-0.58 (m, 2H), 0.94-1.04 (m, 1H), 1.58 (d, J=7.2 Hz, 3H), 3.13-3.25 (m, 2H), 5.48-5.62 (m, 1H), 7.01 (s, 1H), 7.10-7.19 (m, 1H), 7.24-7.28 (m, 1H), 7.33-7.43 (m, 1H), 7.44-7.54 (m, 1H), 8.07 (td, J=1.9, 7.9 Hz, 1H).

LC-MS (MET-uPLC-AB-102): 100% (UV), Rt=2.48 min, m/z (ESI$^+$)=293.1 [M+H]$^+$

N-(Cyclopropylmethyl)-4-methyl-2-oxo-3-(phenylformamido)pentanamide (FP 165)

The title compound was synthesized from N-(cyclopropylmethyl)-2-hydroxy-4-methyl-3-(phenylformamido)pentanamide (I-274) in a similar manner to method C, general procedure 3a (general scheme 15) as an off-white powder (50 mg, 100% purity, 33%) after purification by preparative LC (acidic pH, standard elution method).

$^1$H NMR (500 MHz, Chloroform-d) δ 0.22-0.27 (m, 2H), 0.53-0.60 (m, 2H), 0.92-1.03 (m, 4H), 1.08 (d, J=6.8 Hz, 3H), 2.41-2.54 (m, 1H), 3.11-3.25 (m, 2H), 5.37 (dd, J=5.7, 8.7 Hz, 1H), 6.96-7.06 (m, 2H), 7.42-7.48 (m, 2H), 7.50-7.55 (m, 1H), 7.80-7.84 (m, 2H).
LC-MS (MET-uPLC-AB-102): 100% (UV), Rt=3.12 min, m/z (ESI$^+$)=303.1 [M+H]$^+$ 3-[(2-Bromophenyl)formamido]-N-(cyclopropylmethyl)-2-oxobutanamide (FP 166)

The title compound was synthesized from 3-[(2-bromophenyl)formamido]-N-(cyclopropylmethyl)-2-hydroxybutanamide (I-275) in a similar manner to method C, general procedure 3a (general scheme 15) as an off-white powder (64 mg, 99% purity, 21%) after purification by preparative LC (acidic pH, standard elution method).
$^1$H NMR (500 MHz, Chloroform-d) δ 0.20-0.31 (m, 2H), 0.51-0.61 (m, 2H), 0.95-1.05 (m, 1H), 1.60 (d, J=7.2 Hz, 3H), 3.14-3.24 (m, 2H), 5.54 (p, J=7.2 Hz, 1H), 6.71 (d, J=6.5 Hz, 1H), 7.03 (s, 1H), 7.27-7.32 (m, 1H), 7.37 (td, J=1.1, 7.5 Hz, 1H), 7.56 (dd, J=1.7, 7.6 Hz, 1H), 7.60 (dd, J=1.0, 8.0 Hz, 1H).
LC-MS (MET-uPLC-AB-102): 99% (UV), Rt=2.56 min, m/z (ESI$^+$)=353.0/355.0 [M+H]$^+$ N-(Cyclopropylmethyl)-2-oxo-3-(2-phenylacetamido)butanamide (FP 167)

The title compound was synthesized from N-(cyclopropylmethyl)-2-hydroxy-3-(2-phenylacetamido)butanamide (I-276) in a similar manner to method C, general procedure 3a (general scheme 15) as an off-white powder (26.5 mg, 98% purity, 38%) after purification by preparative LC (acidic pH, standard elution method).
$^1$H NMR (500 MHz, Chloroform-d) δ 0.16-0.29 (m, 2H), 0.47-0.61 (m, 2H), 0.91-1.00 (m, 1H), 1.39 (d, J=7.2 Hz, 3H), 3.07-3.21 (m, 2H), 3.59 (s, 2H), 5.27 (p, J=7.2 Hz, 1H), 6.02 (d, J=6.0 Hz, 1H), 6.92 (br. s, 1H), 7.27-7.33 (m, 3H), 7.34-7.40 (m, 2H).
LC-MS (METCR1600): 98% (UV), Rt=3.76 min, m/z (ESI$^+$)=289.2 [M+H]$^+$ N-(Cyclopropylmethyl)-3-[(2-methoxyphenyl)formamido]-2-oxobutanamide (FP 168)

The title compound was synthesized from N-(cyclopropylmethyl)-2-hydroxy-3-[(2-methoxyphenyl)formamido]butanamide (I-277) in a similar manner to method C, general procedure 3a (general scheme 15) as a colourless viscous oil (52 mg, 97% purity, 32%) after purification by preparative LC (acidic pH, standard elution method).
$^1$H NMR (500 MHz, Chloroform-d) δ 0.20-0.30 (m, 2H), 0.49-0.60 (m, 2H), 0.92-1.05 (m, 1H), 1.57 (d, J=7.2 Hz, 3H), 3.12-3.25 (m, 2H), 4.02 (s, 3H), 5.49 (p, J=7.2 Hz, 1H), 6.96-7.11 (m, 3H), 7.46 (ddd, J=1.9, 7.4, 8.4 Hz, 1H), 8.17 (dd, J=1.8, 7.8 Hz, 1H), 8.57 (d, J=5.5 Hz, 1H).
LC-MS (METCR1600): 97% (UV), Rt=3.93 min, m/z (ESI$^+$)=305.5 [M+H]$^+$ 3-[(2-Chlorophenyl)formamido]-(cyclopropylmethyl)-2-oxobutanamide (FP 169)

The title compound was synthesized from 3-[(2-chlorophenyl)formamido]-N-(cyclopropylmethyl)-2-hydroxybutanamide (I-278) in a similar manner to method C, general procedure 3a (general scheme 15) as an off-white powder (25.6 mg, 100% purity, 14%) after purification by preparative LC (acidic pH, standard elution method).
$^1$H NMR (500 MHz, Chloroform-d) δ 0.19-0.32 (m, 2H), 0.50-0.64 (m, 2H), 0.94-1.06 (m, 1H), 1.60 (d, J=7.2 Hz, 3H), 3.13-3.26 (m, 2H), 5.55 (p, J=7.2 Hz, 1H), 6.84-7.09 (m, 2H), 7.31-7.44 (m, 3H), 7.69 (dd, J=1.7, 7.6 Hz, 1H).
LC-MS (METCR1600): 100% (UV), Rt=3.80 min, m/z (ESI$^+$)=309.4/311.4 [M+H]$^+$ 3-[(4-Chlorophenyl)formamido]-N-(cyclopropylmethyl)-2-oxobutanamide (FP 170)

The title compound was synthesized from 3-[(4-chlorophenyl)formamido]-N-(cyclopropylmethyl)-2-hydroxybutanamide (I-279) in a similar manner to method C, general procedure 3a (general scheme 15) as an off-white powder (45.3 mg, 100% purity, 18%) after purification by flash column chromatography on normal phase silica (10 g SNAP KP-SIL cartridge, 40-100% TBME in heptane gradient then 0-10% MeOH in DCM gradient) followed by preparative LC (acidic pH, standard elution method).
$^1$H NMR (500 MHz, Chloroform-d) δ 0.19-0.32 (m, 2H), 0.50-0.63 (m, 2H), 0.93-1.05 (m, 1H), 1.58 (d, J=7.2 Hz, 3H), 3.13-3.25 (m, 2H), 5.48 (p, J=7.2 Hz, 1H), 6.86 (d, J=6.5 Hz, 1H), 6.93-7.09 (m, 1H), 7.40-7.45 (m, 2H), 7.73-7.77 (m, 2H).
LC-MS (METCR1600): 100% (UV), Rt=4.12 min, m/z (ESI$^+$)=309.4/311.4 [M+H]$^+$ N-(Cyclopropylmethyl)-3-[(3-methylphenyl)formamido]-2-oxobutanamide (FP 171)

The title compound was synthesized from N-(cyclopropylmethyl)-2-hydroxy-3-[(3-methylphenyl)formamido]butanamide (I-280) in a similar manner to method C, general procedure 3a (general scheme 15) as an off-white powder (45.1 mg, 100% purity, 29%) after purification by preparative LC (acidic pH, standard elution method) followed by flash column chromatography on normal phase silica (10 g SNAP KP-SIL cartridge, 0-5% MeOH in DCM gradient).
$^1$H NMR (500 MHz, Chloroform-d) δ 0.19-0.32 (m, 2H), 0.49-0.63 (m, 2H), 0.93-1.05 (m, 1H), 1.58 (d, J=7.3 Hz, 3H), 2.41 (s, 3H), 3.14-3.24 (m, 2H), 5.48 (p, J=7.2 Hz, 1H), 6.82 (br. d, J=6.7 Hz, 1H), 6.94-7.11 (m, 1H), 7.30-7.35 (m, 2H), 7.56-7.60 (m, 1H), 7.63 (br. s, 1H).
LC-MS (METCR1600): 100% (UV), Rt=4.01 min, m/z (ESI$^+$)=289.5 [M+H]$^+$ 3-[(3-Chlorophenyl)formamido]-N-(cyclopropylmethyl)-2-oxobutanamide (FP 172)

The title compound was synthesized from 3-[(3-chlorophenyl)formamido]-N-(cyclopropylmethyl)-2-hydroxybutanamide (I-281) in a similar manner to method C, general procedure 3a (general scheme 15) as an off-white powder (102.4 mg, 98% purity, 36%) after purification by flash column chromatography on normal phase silica (10 g SNAP KP-SIL cartridge, 0-10% MeOH in DCM gradient) followed by preparative LC (acidic pH, standard elution method).
$^1$H NMR (500 MHz, Chloroform-d) δ 0.19-0.32 (m, 2H), 0.50-0.64 (m, 2H), 0.93-1.06 (m, 1H), 1.58 (d, J=7.2 Hz, 3H), 3.13-3.26 (m, 2H), 5.48 (p, J=7.2 Hz, 1H), 6.85 (d, J=6.7 Hz, 1H), 6.93-7.10 (m, 1H), 7.39 (t, J=7.9 Hz, 1H), 7.49 (ddd, J=1.0, 2.0, 8.0 Hz, 1H), 7.67 (dt, J=1.2, 7.7 Hz, 1H), 7.80 (t, J=1.8 Hz, 1H).
LC-MS (METCR1600): 98% (UV), Rt=4.12 min, m/z (ESI$^+$)=309.4/311.4 [M+H]$^+$

N-(Cyclopropylmethyl)-3-[(4,4-difluorocyclohexyl) formamido]-2-oxobutanamide (FP 173)

The title compound was synthesized from N-(cyclopropylmethyl)-3-[(4,4-difluorocyclohexyl)formamido]-2-hydroxybutanamide (I-282) in a similar manner to method C, general procedure 3a (general scheme 15) as an off-white powder (21.5 mg, 100% purity, 29%) after purification by preparative LC (acidic pH, standard elution method).

$^1$H NMR (500 MHz, Chloroform-d) δ 0.18-0.31 (m, 2H), 0.49-0.63 (m, 2H), 0.92-1.04 (m, 1H), 1.46 (d, J=7.2 Hz, 3H), 1.67-1.91 (m, 4H), 1.90-2.00 (m, 2H), 2.11-2.30 (m, 3H), 3.10-3.23 (m, 2H), 5.25 (p, J=7.2 Hz, 1H), 6.13 (d, J=6.4 Hz, 1H), 6.82-7.08 (m, 1H).

LC-MS (METCR1600): 100% (UV), Rt=3.83 min, m/z (ESI$^+$)=317.2 [M+H]$^+$

N-(Cyclopropylmethyl)-3-[(3,3-difluorocyclobutyl) formamido]-2-oxobutanamide (FP 174)

The title compound was synthesized from N-(cyclopropylmethyl)-3-[(3,3-difluorocyclobutyl)formamido]-2-hydroxybutanamide (I-283) in a similar manner to method C, general procedure 3a (general scheme 15) as an off-white powder (29.5 mg, 100% purity, 18%) after purification by preparative LC (acidic pH, standard elution method).

$^1$H NMR (500 MHz, Chloroform-d) δ 0.18-0.32 (m, 2H), 0.49-0.63 (m, 2H), 0.93-1.04 (m, 1H), 1.47 (d, J=7.2 Hz, 3H), 2.66-2.95 (m, 5H), 3.11-3.23 (m, 2H), 5.30 (p, J=7.2 Hz, 1H), 6.13 (d, J=6.3 Hz, 1H), 6.96 (br. s, 1H).

LC-MS (METCR1600): 100% (UV), Rt=3.57 min, m/z (ESI$^+$)=289.4 [M+H]$^+$

General Procedure 2b (General Scheme 15): Oxidation

N-[(3-Chlorophenyl)methyl]-3-[(2-methoxyphenyl) amino]-2-oxobutanamide (I-286)

To a stirred, ice cooled, solution of N-[(3-chlorophenyl)methyl]-2-hydroxy-3-[(2-methoxyphenyl)amino]butanamide (I-54, 300 mg, 0.86 mmol) and DIPEA (0.6 mL, 3.44 mmol) in DCM (6 mL) at 0° C. was added sulfur trioxide-pyridine complex (274 mg, 1.72 mmol) in DMSO (1 mL) and the reaction stirred at 0° C. for 30 min. Sulfur trioxide-pyridine complex (274 mg, 1.72 mmol) was added and the mixture stirred at 0° C. for 30 min. The solution was diluted with EtOAc (8 mL) and saturated NH$_4$Cl (6 mL) added. The aqueous layer was extracted with EtOAc (2×8 mL) and the combined organic layers washed with brine (6 mL), dried over sodium sulfate, filtered and concentrated in vacuo. The crude product was purified by flash column chromatography on reverse phase silica (12 g SNAP Ultra C18 cartridge, 10-100% ACN in water gradient) to afford 62.2 mg of N-[(3-chlorophenyl)methyl]-3-[(2-methoxyphenyl)amino]-2-oxobutanamide as a yellow oil (97% purity, 71%).

$^1$H NMR (500 MHz, Chloroform-d) δ 1.53 (d, J=7.0 Hz, 3H), 3.86 (s, 3H), 4.42-4.52 (m, 2H), 4.78-6.12 (m, 1H), 5.17 (q, J=7.0 Hz, 1H), 6.59 (dd, J=1.3, 7.8 Hz, 1H), 6.71 (td, J=1.5, 7.8 Hz, 1H), 6.79 (dd, J=1.3, 8.0 Hz, 1H), 6.83 (td, J=1.4, 7.6 Hz, 1H), 7.10-7.16 (m, 1H), 7.19 (s, 1H), 7.24-7.26 (m, 1H), 7.26-7.30 (m, 2H).

LC-MS (METCR1600): 97% (UV), Rt=5.10 min, m/z (ESI$^+$)=347.2/349.1 [M+H]$^+$

General Procedure 3b (General Scheme 15): Capping

N-[(3-Chlorophenyl)methyl]-3-[2-methoxy-N-(2-methoxyphenyl)acetamido]-2-oxobutanamide (FP 175)

To a stirred solution of N-[(3-chlorophenyl)methyl]-3-[(2-methoxyphenyl) amino]-2-oxobutanamide (I-286, 56 mg, 0.16 mmol) and DIPEA (40 μL, 0.24 mmol) in DCM (3 mL) was added methoxyacetyl chloride (18 μL, 0.19 mmol) dropwise. The reaction was stirred for 30 min and saturated NaHCO$_3$ (3 mL) added. The aqueous layer was extracted with DCM (3×5 mL) and the combined organic layers were dried over sodium sulfate, filtered and concentrated in vacuo. The crude material was purified by flash column chromatography (10 g SNAP KP-SIL cartridge, 0-100% EtOAc in heptane gradient) to afford 56 mg of N-[(3-chlorophenyl)methyl]-3-[2-methoxy-N-(2-methoxyphenyl) acetamido]-2-oxobutanamide as a yellow oil (98% purity, 81%).

$^1$H NMR (500 MHz, DMSO-d6) δ 0.88-1.31 (m, 3H), 3.01-3.18 (m, 3H), 3.46-3.55 (m, 1H), 3.56-3.70 (m, 1H), 3.79-3.87 (m, 3H), 4.27-4.43 (m, 2H), 4.45-6.44 (m, 1H), 7.01-7.10 (m, 1H), 7.14-7.20 (m, 1H), 7.24-7.75 (m, 6H), 9.10-9.32 (m, 1H).

LC-MS (MET-uPLC-AB-101): 98% (UV), Rt=3.42 min, m/z (ESI$^+$)=419.1/421.1 [M+H]$^+$

General Procedure 4 (General Scheme 15): Capping/Oxidation

Method A: Capping with Acid Chloride Followed by Oxidation Using DMP

N-(Cyclohexylmethyl)-3-(N-methyl-1-phenylformamido)-2-oxobutanamide (FP 176)

To a stirred, ice cooled, solution of N-(cyclohexylmethyl)-2-hydroxy-3-(methylamino)butanamide (I-248, 95% purity, 300 mg, 1.25 mmol) and DIPEA (0.62 mL, 3.54 mmol) in DCM (8 mL) at 0° C. was added a solution of benzoyl chloride (0.16 mL, 1.38 mmol) in DCM (2 mL) dropwise over 5 min. The reaction was stirred for 4 h, diluted with DCM (10 mL) then washed with saturated NaHCO$_3$ (20 mL) and water (20 mL). The organic layer was separated, dried over sodium sulfate and concentrated in vacuo to give 600 mg of a brown viscous oil which was used in the next step without further purification.

To a stirred solution of the crude oil, prepared above, in DCM (5 mL) was added at RT, DMP (306 mg, 0.72 mmol) and the mixture was stirred for 1 h. The reaction mixture was washed with saturated NaHCO$_3$ (10 mL) and the aqueous layer extracted with DCM (2×10 mL). The combined organic layers were dried over sodium sulfate and concentrated in vacuo. The crude material was purified by flash column chromatography on normal phase silica (10 g SNAP KP-SIL cartridge, 0-40% EtOAc in heptane gradient) to afford 38 mg of N-(cyclohexylmethyl)-3-(N-methyl-1-phenylform-amido)-2-oxobutanamide as a colourless oil (97% purity, 16%).

$^1$H NMR (500 MHz, Chloroform-d) δ 0.85-0.98 (m, 2H), 1.07-1.25 (m, 3H), 1.45-1.56 (m, 4H), 1.62-1.76 (m, 5H), 3.05-3.21 (m, 5H), 4.38 (q, J=6.8 Hz, 1H), 6.74-6.86 (m, 1H), 7.37-7.45 (m, 5H).

LC-MS (MET-uPLC-AB-101): 97% (UV), Rt=3.43 min, m/z (ESI+)=331.2 [M+H]+

Method B: HATU Coupling Followed by Oxidation Using Sulfur Trioxide Pyridine Complex N-(Cyclohexylmethyl)-3-[2-(dimethylamino)-N-methylacetamido]-2-oxobutanamide (FP 177)

To a stirred suspension of N,N-dimethylglycine (86 mg, 0.83 mmol) and N-(cyclohexylmethyl)-2-hydroxy-3-(methylamino)butanamide (I-248, 95% purity, 200 mg, 0.83 mmol) in DCM (5 mL) was added DIPEA (0.29 mL, 1.67 mmol) and HATU (350 mg, 0.92 mmol). The reaction was stirred for 45 min, cooled in an ice batch and a solution of sulfur trioxide-pyridine complex (264 mg, 1.66 mmol) in DMSO (2 mL) added. The mixture was stirred with cooling for 45 min then at RT and DIPEA (0.29 mL, 1.67 mmol) added. The reaction was stirred at RT for 2 h then sulfur trioxide pyridine complex (264 mg, 1.66 mmol) added. After 18 h, DIPEA (0.29 mL, 1.67 mmol) and sulfur trioxide pyridine complex (264 mg, 1.66 mmol) in DMSO (1 mL) were added and the mixture was stirred for 4 h. Sulfur trioxide pyridine complex (264 mg, 1.66 mmol) was added and stirring continued for 1.5 h. The reaction was diluted with DCM (5 mL) and washed with water (5×10 mL). The organic layer was dried over sodium sulfate, filtered and concentrated in vacuo to give a dark oil which was purified by preparative LC (high pH, standard elution method). The material was then loaded onto a 2 g Isolute SCX-2 cartridge and eluted with EtOAc followed by 10% MeOH in EtOAc and 10% 7N methanolic ammonia in EtOAc. The pure fractions were combined and concentrated in vacuo to afford 27 mg of N-(cyclohexylmethyl)-3-[2-(dimethylamino)-N—methylacetamido]-2-oxobutanamide as a yellow oil (85% purity by 1H NMR, 9%).

$^1$H NMR (500 MHz, Chloroform-d) δ 0.87-1.00 (m, 2H), 1.11-1.28 (m, 3H), 1.38-1.48 (m, 3H), 1.50-1.76 (m, 6H), 1.90-2.27 (m, 6H), 2.83-3.39 (m, 7H), 4.15-6.37 (m, 1H), 6.73-7.00 (m, 1H).

LC-MS (METCR1600): 97% (UV), Rt=4.25 min, m/z (ESI+)=312.3 [M+H]+

Further compounds (FP205-FP214) were synthesised via general scheme 15 and these compounds are described in the additional compound section.

Di-Hydroozaxole Route: Synthesis of Final Products (FP 178-184)

GENERAL SCHEME 16:

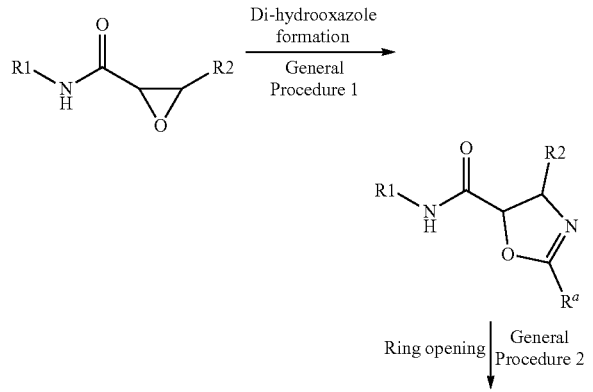

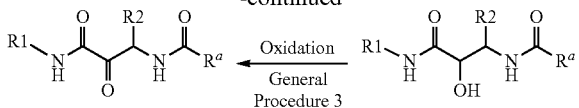

General Procedure 1 (General Scheme 16): Di-Hydroozaxole Formation

N-(Cyclopropylmethyl)-4-methyl-2-phenyl-4,5-dihydro-1,3-oxazole-5-carboxamide (I-287)

To a vigorously stirred solution of N-(cyclopropylmethyl)-3-methyloxirane-2-carboxamide (I-30, 200 mg, 1.29 mmol) in DCM (15 mL) was added benzonitrile (0.66 mL, 6.44 mmol) followed by ethoxyethane-trifluoroborane (1:1, 0.81 mL, 6.44 mmol) dropwise over 5 min. The mixture was stirred for 18 h. Saturated NaHCO$_3$(10 mL) was added and the mixture was stirred vigorously for 45 min. The organic layer was separated, dried through a Telos® hydrophobic frit and concentrated in vacuo. The crude material was purified by flash column chromatography on normal phase silica (10 g SNAP KP-SIL cartridge, 0-100% EtOAc in heptane gradient) to afford 70.5 mg of N-(cyclopropylmethyl)-4-methyl-2-phenyl-4,5-dihydro-1,3-oxazole-5-carboxamide as a yellow oil (92% purity, 19%).

$^1$H NMR (500 MHz, Chloroform-d) δ 0.21-0.31 (m, 2H), 0.49-0.60 (m, 2H), 0.95-1.06 (m, 1H), 1.34 (d, J=6.9 Hz, 3H), 3.15-3.23 (m, 1H), 3.23-3.32 (m, 1H), 4.71-4.82 (m, 1H), 5.12 (d, J=10.1 Hz, 1H), 6.50 (s, 1H), 7.47-7.54 (m, 2H), 7.55-7.62 (m, 1H), 8.05 (d, J=7.5 Hz, 2H).

LC-MS (METCR1410): 92% (UV), Rt=0.97 min, m/z (ESI+)=259.4 [M+H]+

N-(Cyclohexylmethyl)-4-methyl-2-phenyl-4,5-dihydro-1,3-oxazole-5-carboxamide (I-288)

The title compound was synthesized from N-(cyclohexylmethyl)-3-methyl-oxirane-2-carboxamide (I-34) in a similar manner to general procedure 1 (general scheme 16) as a yellow oil (28.2 mg, 100% purity, 12%) after purification by flash column chromatography on normal phase silica (10 g SNAP KP-SIL cartridge, 0-100% EtOAc in heptane gradient).

$^1$H NMR (500 MHz, Chloroform-d) δ 0.87-0.99 (m, 2H), 1.11-1.26 (m, 4H), 1.27 (d, J=7.0 Hz, 3H), 1.44-1.54 (m, 1H), 1.61-1.77 (m, 4H), 3.11-3.25 (m, 2H), 4.70 (dq, J=6.9, 10.1 Hz, 1H), 5.05 (d, J=10.1 Hz, 1H), 6.42 (s, 1H), 7.45 (t, J=7.6 Hz, 2H), 7.50-7.57 (m, 1H), 7.95-8.01 (m, 2H).

LC-MS (METCR1410): 100% (UV), Rt=1.13 min, m/z (ESI+)=301.5 [M+H]+

General Procedure 2 (General Scheme 16): Ring Opening

N-(Cyclopropylmethyl)-2-hydroxy-3-(phenylformamido)butanamide (I-289)

To a stirred solution of N-(cyclopropylmethyl)-4-methyl-2-phenyl-4,5-dihydro-1,3-oxazole-5-carboxamide (I-287, 92% purity, 70.5 mg, 0.25 mmol) in EtOH (5 mL) was added 1M HCl (1 mL). The reaction was heated at 80° C. in a sealed tube for 2 h. The mixture was allowed to cool and was concentrated in vacuo. The residue was dissolved in DCM (5 mL) and washed with saturated NaHCO$_3$(5 mL). The organic layer was dried through a Telos® hydrophobic frit and concentrated in vacuo. The residue was dried in vacuo at 40° C. to afford 64.5 mg of N-(cyclopropylmethyl)-2-hydroxy-3-(phenylformamido)butanamide as an off-white solid (78% purity by ¹H NMR, 14%). The crude material was used in the next step without further purification.

¹H NMR (500 MHz, Chloroform-d) δ 0.10-0.22 (m, J=5.0 Hz, 2H), 0.37-0.48 (m, 2H), 0.85-0.93 (m, 1H), 1.44 (d, J=7.1 Hz, 3H), 3.06-3.17 (m, 2H), 4.28 (d, J=1.6 Hz, 1H), 4.39 (qd, J=1.7, 7.1 Hz, 1H), 6.59 (d, J=6.7 Hz, 1H), 7.05 (s, 1H), 7.44 (t, J=7.6 Hz, 2H), 7.50-7.57 (m, 1H), 7.73-7.80 (m, 2H).

LC-MS (METCR1410): 80% (UV), Rt=0.77 min, m/z (ESI⁺)=277.5 [M+H]⁺

N-(Cyclohexylmethyl)-2-hydroxy-3-(phenylformamido)butanamide (I-290)

The title compound was synthesized from N-(cyclohexylmethyl)-4-methyl-2-phenyl-4,5-dihydro-1,3-oxazole-5-carboxamide (I-288) in a similar manner to general procedure 2 (general scheme 16) as an off-white solid (59.7 mg, 58% purity, 14%) after work-up. The crude material was used in the next step without further purification.

¹H NMR (500 MHz, Chloroform-d) δ 0.78-0.98 (m, 2H), 0.99-1.27 (m, 4H), 1.39 (d, J=6.4 Hz, 1H), 1.48 (d, J=7.1 Hz, 3H), 1.53-1.77 (m, 4H), 3.07-3.22 (m, 2H), 4.26 (d, J=1.4 Hz, 1H), 4.38 (td, J=1.6, 7.1 Hz, 1H), 6.62 (d, J=6.2 Hz, 1H), 6.98 (s, 1H), 7.40-7.65 (m, 3H), 7.72-7.80 (m, 2H).

LC-MS (METCR1410): 50% (UV), Rt=0.93 min (double peak), m/z (ESI⁺)=319.4 [M+H]⁺

General Procedure 3 (General Scheme 16): Oxidation

N-(Cyclopropylmethyl)-2-oxo-3-(phenylformamido)butanamide (FP 178)

To N-(cyclopropylmethyl)-2-hydroxy-3-(phenylformamido)butanamide (I-289, 78% purity by ¹H NMR, 64.5 mg, 0.19 mmol) in DCM (6 mL) was added DMP (99 mg, 0.23 mmol) and the reaction stirred for 18 h. DMP (99 mg, 0.23 mmol) was added and the reaction stirred for 2 h. Saturated NaHCO₃ (6 mL) was added and the aqueous phase extracted with DCM (3 mL). The combined organic layers were dried through a Telos® hydrophobic frit and concentrated in vacuo. The crude material was purified by flash column chromatography on normal phase silica (10 g SNAP KP-SIL cartridge, 0-100% EtOAc in heptane gradient) followed by trituration in water. The resulting solid was dried in vacuo for 18 h to afford 45.1 mg of N-(cyclopropylmethyl)-2-oxo-3-(phenylformamido)butanamide as an off-white solid (97% purity, 68%).

¹H NMR (500 MHz, Chloroform-d) δ 0.90-1.02 (m, 2H), 1.10-1.29 (m, 3H), 1.51 (dt, J=3.4, 11.4 Hz, 1H), 1.58 (d, J=7.2 Hz, 3H), 1.69 (dd, J=11.0, 27.9 Hz, 5H), 3.11-3.24 (m, 2H), 5.47 (p, J=7.2 Hz, 1H), 6.88 (d, J=7.1 Hz, 1H), 6.91-6.99 (m, 1H), 7.45 (t, J=7.5 Hz, 2H), 7.52 (t, J=7.4 Hz, 1H), 7.77-7.85 (m, 2H).

LC-MS (METCR1600): 97% (UV), Rt=3.75 min, m/z (ESI⁺)=275.3 [M+H]⁺

N-(Cyclohexylmethyl)-2-oxo-3-(phenylformamido)butanamide (FP 179)

The title compound was synthesized from N-(cyclohexylmethyl)-2-hydroxy-3-(phenylformamido)butanamide (I-290) in a similar manner to general procedure 3 (general scheme 2) as an off-white solid (13.3 mg, 100% purity, 45%) after purification by flash column chromatography on normal phase silica (10 g SNAP KP-SIL cartridge, 0-100% EtOAc in heptane gradient) followed by trituration in acetonitrile.

¹H NMR (500 MHz, Chloroform-d) δ 0.26 (q, J=4.8 Hz, 2H), 0.53-0.60 (m, 2H), 0.94-1.06 (m, 1H), 1.58 (d, J=7.2 Hz, 3H), 3.19 (ddd, J=2.5, 5.9, 7.9 Hz, 2H), 5.50 (p, J=7.2 Hz, 1H), 6.86 (d, J=6.2 Hz, 1H), 7.01 (s, 1H), 7.45 (t, J=7.6 Hz, 2H), 7.50-7.56 (m, 1H), 7.78-7.84 (m, 2H).

LC-MS (METCR1600): 100% (UV), Rt=4.58 min, m/z (ESI⁺)=317.3 [M+H]⁺

GENERAL SCHEME 17:

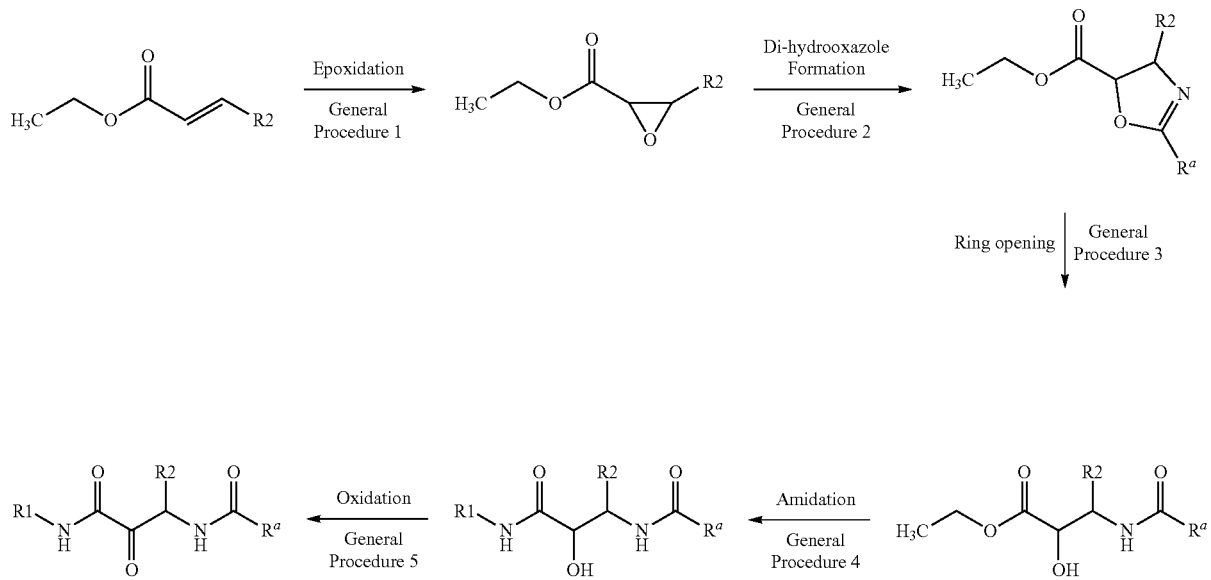

General Procedure 1 (General Scheme 17): Epoxidation

Ethyl 3-methyloxirane-2-carboxylate (I-291)

To a stirred solution of ethyl (2E)-but-2-enoate (5 g, 43.8 mmol) in DCM was added m-CPBA (70%, 11.88 g, 48.19 mmol) portion wise. The reaction was stirred at 40° C. for 18 h, filtered and m-chlorobenzoic acid was washed with cold DCM. The filtrate was washed successively with 1M Na$_2$CO$_3$, water and brine, dried over sodium sulfate and concentrated in vacuo. The crude material was purified by flash column chromatography on normal phase silica (100 g SNAP KP-SIL cartridge, 10-60% EtOAc in heptane gradient) to afford 1.79 g of ethyl 3-methyloxirane-2-carboxylate as a pale yellow oil (95% purity by $^1$H NMR, 31%).

$^1$H NMR (500 MHz, Chloroform-d) δ 1.30 (t, J=7.1 Hz, 3H), 1.40 (d, J=5.1 Hz, 3H), 3.17 (d, J=1.9 Hz, 1H), 3.23 (qd, J=1.9, 5.1 Hz, 1H), 4.23 (qq, J=7.1, 10.8 Hz, 2H).

Ethyl 3-ethyloxirane-2-carboxylate (I-292)

The title compound was synthesized from ethyl (2E)-pent-2-enoate in a similar manner to general procedure 1 (general scheme 17) at RT for 1 week and was obtained as an orange oil (7.1 g, 74% purity by 1H NMR, 47%) after trituration in EtOAc.

$^1$H NMR (500 MHz, Chloroform-d) δ 1.01 (t, J=7.5 Hz, 3H), 1.29 (t, J=7.1 Hz, 3H), 1.57-1.75 (m, 2H), 3.14 (ddd, J=1.9, 4.8, 5.9 Hz, 1H), 3.22 (d, J=1.9 Hz, 1H), 4.22 (qq, J=7.1, 10.8 Hz, 2H).

Ethyl 3-propyloxirane-2-carboxylate (I-293)

The title compound was synthesized from ethyl (2E)-hex-2-enoate in a similar manner to general procedure 1 (general scheme 17) at RT for 1 week and obtained as an orange oil (1.8 g, 90% purity by 1H NMR, 15%) after flash column chromatography on normal phase silica (100 g SNAP KP-SIL cartridge, 0-100% EtOAc in heptane gradient).

$^1$H NMR (500 MHz, Chloroform-d) δ 0.91 (t, J=7.3 Hz, 3H), 1.23 (t, J=7.1 Hz, 3H), 1.40-1.60 (m, 4H), 3.08 (ddd, J=1.9, 4.8, 6.4 Hz, 1H), 3.14 (d, J=1.9 Hz, 1H), 4.12-4.21 (m, 2H).

LC-MS (METCR1410): 61% (UV), Rt=0.96 min, m/z (ESI$^+$)=159.5 [M+H]$^+$

General Procedure 2 (General Scheme 17): Di-Hydrooxazole Formation

Ethyl 4-methyl-2-phenyl-4,5-dihydro-1,3-oxazole-5-carboxylate (I-294)

To a vigorously stirred solution of ethyl 3-methyloxirane-2-carboxylate (I-291) (1.09 g, 8.38 mmol) in DCM (40 mL) was added benzonitrile (4.29 mL, 41.88 mmol) followed by ethoxyethane-trifluoroborane (1:1, 5.3 mL, 41.88 mmol) dropwise over 5 min. The reaction was stirred for 1 h, saturated NaHCO$_3$ (40 mL) was added and the mixture stirred vigorously for 30 min. The aqueous layer was separated and extracted with DCM (2×20 mL). The organic layers were combined, dried over sodium sulfate and concentrated in vacuo. The crude material was purified by flash column chromatography on normal phase silica (100 g SNAP KP-SIL cartridge, 0-20% EtOAc in heptane gradient) to afford 961 mg of ethyl 4-methyl-2-phenyl-4,5-dihydro-1,3-oxazole-5-carboxylate as a viscous light yellow oil (96% purity, 47%).

$^1$H NMR (500 MHz, Chloroform-d) δ 1.29-1.36 (m, 6H), 4.29 (q, J=7.1 Hz, 2H), 4.71 (dq, J=6.9, 10.2 Hz, 1H), 5.13 (d, J=10.2 Hz, 1H), 7.40-7.47 (m, 2H), 7.46-7.55 (m, 1H), 7.98-8.04 (m, 2H).

LC-MS (METCR1410): 96% (UV), Rt=1.10 min, m/z (ESI$^+$)=234.1 [M+H]$^+$

Ethyl 4-ethyl-2-phenyl-4,5-dihydro-1,3-oxazole-5-carboxylate (I-295)

The title compound was synthesized from ethyl 3-ethyloxirane-2-carboxylate (I-292) in a similar manner to general procedure 2 (general scheme 17) as a yellow oil (448 mg, 95% purity, 50%) after purification by flash column chromatography on normal phase silica (50 g SNAP KP-SIL cartridge, 0-35% EtOAc in heptane gradient).

$^1$H NMR (250 MHz, Chloroform-d) δ 1.13 (t, J=7.33 Hz, 3H), 1.31 (t, J=7.14 Hz, 3H), 1.39-1.83 (m, 2H), 4.17-4.34 (m, 2H), 4.37-4.55 (m, 1H), 5.11 (d, J=10.22 Hz, 1H), 7.34-7.57 (m, 3H), 7.91-8.06 (m, 2H).

LC-MS (METCR1410): 95% (UV), Rt=1.17 min, m/z (ESI$^+$)=248.2 [M+H]$^+$

Ethyl 2-phenyl-4-propyl-4,5-dihydro-1,3-oxazole-5-carboxylate (I-296)

The title compound was synthesized from ethyl 3-propyloxirane-2-carboxylate (I-293) in a similar manner to general procedure 2 (general scheme 17) as a colourless viscous oil (518 mg, 92% purity, 58%) after purification by flash column chromatography on normal phase silica (50 g SNAP KP-SIL cartridge, 0-20% EtOAc in heptane gradient).

$^1$H NMR (250 MHz, Chloroform-d) δ 0.89-1.03 (m, 3H), 1.31 (t, J=7.14 Hz, 3H), 1.43-1.78 (m, 4H), 4.27 (q, J=7.10 Hz, 2H), 4.46-4.59 (m, 1H), 5.10 (d, J=10.22 Hz, 1H), 7.34-7.56 (m, 3H), 7.95-8.02 (m, 2H).

LC-MS (METCR1410): 92% (UV), Rt=1.24 min, m/z (ESI$^+$)=262.2 [M+H]$^+$

General Procedure 3 (General Scheme 17): Ring Opening

Ethyl 2-hydroxy-3-(phenylformamido)butanoate (I-297)

To a stirred solution of ethyl 4-methyl-2-phenyl-4,5-dihydro-1,3-oxazole-5-carboxylate (I-294, 961 mg, 3.96 mmol) in EtOH (5 mL) was added 1N HCl (2 mL). The reaction was stirred at 70° C. in a sealed tube for 18 h, cooled to RT and concentrated in vacuo. The residue was dissolved in DCM (5 mL), washed with saturated NaHCO$_3$ (5 mL) and the aqueous layer extracted with DCM (5 mL). The combined organic layers were dried over sodium sulfate and concentrated in vacuo to afford 950 mg of ethyl 2-hydroxy-3-(phenylformamido)butanoate as a colourless viscous oil, which solidified upon standing overnight (96% purity, 92%). The crude material was used in the next step without further purification.

$^1$H NMR (500 MHz, DMSO-d6) δ 1.10-1.16 (m, 6H), 4.03-4.10 (m, 2H), 4.10-4.15 (m, 1H), 4.24-4.35 (m, 1H), 5.63 (d, J=6.4 Hz, 1H), 7.42-7.48 (m, 2H), 7.48-7.55 (m, 1H), 7.81-7.86 (m, 2H), 8.22 (d, J=8.3 Hz, 1H).

LC-MS (METCR1410): 96% (UV), Rt=0.80-0.95 min (two peaks), m/z (ESI⁺)=252.2 [M+H]⁺

Ethyl 2-hydroxy-3-(phenylformamido)pentanoate (I-298)

The title compound was synthesized from ethyl 4-ethyl-2-phenyl-4,5-dihydro-1,3-oxazole-5-carboxylate (I-295) in a similar manner to general procedure 3 (general scheme 17) as an off-white solid (443 mg, 94% purity, 91%) after work-up. The crude material was used in the next step without further purification.

¹H NMR (250 MHz, Chloroform-d) δ 0.99 (t, J=7.4 Hz, 3H), 1.32 (t, J=7.2 Hz, 3H), 1.39-1.76 (m, 2H), 3.23 (s, 1H), 4.22-4.40 (m, 3H), 4.44-4.60 (m, 1H), 6.36 (d, J=9.0 Hz, 1H), 7.39-7.59 (m, 3H), 7.75-7.85 (m, 2H).

LC-MS (METCR1410): 94% (UV), Rt=0.84-0.96 min (two peaks), m/z (ESI⁺)=266.5 [M+H]⁺

Ethyl 2-hydroxy-3-(phenylformamido)hexanoate (I-299)

The title compound was synthesized from ethyl 2-phenyl-4-propyl-4,5-dihydro-1,3-oxazole-5-carboxylate (I-296) in a similar manner to procedure 3 (general scheme 17) as an off-white solid (447 mg, 99% purity, 87%) after work-up. The crude material was used in the next step without further purification.

¹H NMR (250 MHz, Chloroform-d) δ 0.93 (t, J=7.1 Hz, 3H), 1.20-1.69 (m, 8H), 4.28 (td, J=1.3, 7.1 Hz, 2H), 4.39 (d, J=3.1 Hz, 1H), 4.60 (tt, J=3.2, 10.1 Hz, 1H), 6.38 (d, J=9.1 Hz, 1H), 7.37-7.61 (m, 3H), 7.72-7.90 (m, 2H).

LC-MS (METCR1410): 12% (UV), Rt=0.88-1.00 min (two peaks), m/z (ESI⁺)=280.5 [M+H]⁺

General Procedure 4 (General Scheme 17): Amide Formation

N-(Cyclopentylmethyl)-2-hydroxy-3-(phenylformamido)butanamide (I-300)

To a stirred solution of 1-cyclopentylmethanamine hydrochloride (1:1, 121 mg, 0.90 mmol) and DABCO (50 mg, 0.45 mmol) in THF (1.5 mL) was added DABAL-Me3 [1,4-diazabicyclo[2.2.2]octane-trimethylaluminum] (1:2), 230 mg, 0.90 mmol]. The reaction was heated at 40° C. in a sealed tube for 1 h, ethyl 2-hydroxy-3-(phenylform-amido)butanoate (I-297, 150 mg, 0.6 mmol) was added and the reaction heated at 70° C. for 2 h. The reaction was cooled to RT and 2N HCl (2 mL) added dropwise. The precipitate formed was filtered and washed with DCM (4 mL). The biphasic filtrate was passed through a Telos® hydrophobic frit and the aqueous layer was washed with DCM (2×2 mL). The organic layers and precipitate were combined and concentrated in vacuo. The crude material was purified by flash column chromatography on normal phase silica (10 g SNAP KP-SIL cartridge, 0-10% MeOH in DCM gradient) to afford 165 mg of N-(cyclopentylmethyl)-2-hydroxy-3-(phenylform-amido)butanamide as an off-white solid (100% purity, 94%).

¹H NMR (500 MHz, DMSO-d6) δ 1.04 (d, J=6.9 Hz, 3H), 1.12-1.22 (m, 2H), 1.40-1.64 (m, 6H), 2.04 (hept, J=7.6 Hz, 1H), 2.92-3.13 (m, 2H), 4.09 (dd, J=3.5, 5.2 Hz, 1H), 4.33-4.40 (m, 1H), 5.74 (d, J=5.4 Hz, 1H), 7.43-7.48 (m, 2H), 7.49-7.54 (m, 1H), 7.77 (t, J=6.0 Hz, 1H), 7.84-7.88 (m, 2H), 8.06 (d, J=7.9 Hz, 1H).

LC-MS (METCR1410): 100% (UV), Rt=1.00 min, m/z (ESI⁺)=305.2 [M+H]⁺

N-(Cyclobutylmethyl)-2-hydroxy-3-(phenylformamido)butanamide (I-301)

The title compound was synthesized from ethyl 2-hydroxy-3-(phenylform-amido)butanoate (I-297) in a similar manner to general procedure 4 (general scheme 17) as an off-white solid (149 mg, 100% purity, 90%) after purification by flash column chromatography on normal phase silica (10 g SNAP KP-SIL cartridge, 10-100% MeOH in DCM gradient).

¹H NMR (500 MHz, DMSO-d6) δ 1.02 (d, J=6.9 Hz, 3H), 1.59-1.69 (m, 2H), 1.73-1.83 (m, 2H), 1.88-1.96 (m, 2H), 2.43 (dt, J=7.6, 15.2 Hz, 1H), 3.13 (ddt, J=6.4, 12.9, 66.9 Hz, 2H), 4.09 (s, 1H), 4.32-4.40 (m, 1H), 5.74 (d, J=4.1 Hz, 1H), 7.42-7.48 (m, 2H), 7.49-7.54 (m, 1H), 7.75 (t, J=6.0 Hz, 1H), 7.83-7.89 (m, 2H), 8.05 (d, J=7.9 Hz, 1H).

LC-MS (METCR1410): 100% (UV), Rt=0.94 min, m/z (ESI⁺) 291.2 [M+H]⁺

2-Hydroxy-N-(2-methylpropyl)-3-(phenylformamido)butanamide (I-302)

The title compound was synthesised from ethyl 2-hydroxy-3-(phenylform-amido)butanoate (I-297) in a similar manner to general procedure 4 (general scheme 17) without addition of DABCO, as an off-white solid (160 mg, 90% purity by ¹H NMR, 90%) after purification by flash column chromatography on normal phase silica (10 g SNAP KP-SIL cartridge, 0-10% MeOH in DCM gradient).

¹H NMR (500 MHz, DMSO-d6) δ 0.80-0.84 (m, 6H), 1.04 (d, J=6.9 Hz, 3H), 1.68-1.79 (m, 1H), 2.82-3.04 (m, 2H), 4.11 (dd, J=3.4, 5.5 Hz, 1H), 4.31-4.43 (m, 1H), 5.73-6.77 (m, 1H), 7.45 (t, J=7.4 Hz, 2H), 7.49-7.54 (m, 1H), 7.76 (t, J=6.1 Hz, 1H), 7.84-7.88 (m, 2H), 8.06 (d, J=8.0 Hz, 1H).

LC-MS (METCR1410): 100% (UV), Rt=0.91 min, m/z (ESI⁺)=279.2 [M+H]⁺

N-Cyclopropyl-2-hydroxy-3-(phenylformamido)pentanamide (I-303)

The title compound was synthesized from ethyl 2-hydroxy-3-(phenylformamido)-pentanoate (I-298) in a similar manner to general procedure 4 (general scheme 17) as an off-white powder (135 g, 97% purity, 63%) following trituration with Et₂O and DCM.

¹H NMR (250 MHz, Chloroform-d) δ 0.32-0.55 (m, 2H), 0.64-0.79 (m, 2H), 1.03 (t, J=7.4 Hz, 3H), 1.76-2.06 (m, 2H), 2.59-2.76 (m, 1H), 4.01-4.16 (m, 1H), 4.26 (d, J=5.5 Hz, 1H), 5.56 (d, J=5.7 Hz, 1H), 6.59 (d, J=7.9 Hz, 1H), 7.10 (s, 1H), 7.37-7.61 (m, 3H), 7.66-7.85 (m, 2H).

LC-MS (METCR1410): 97% (UV), Rt=0.89 min, m/z (ESI⁺)=277.1 [M+H]⁺

N-Cyclopropyl-2-hydroxy-3-(phenylformamido)hexanamide (I-304)

The title compound was synthesized from ethyl 2-hydroxy-3-(phenylform-amido)hexanoate (I-299) in a similar manner to general procedure 4 (general scheme 17) as an off-white solid (137 mg, 97% purity, 52%) after purification by flash column chromatography on normal phase silica (25 g SNAP KP-SIL cartridge, 0-20% 4/1 DCM/MeOH solution in DCM gradient).

¹H NMR (250 MHz, Chloroform-d) δ 0.25-0.58 (m, 2H), 0.67-0.84 (m, 2H), 0.96 (t, J=7.3 Hz, 3H), 1.33-1.54 (m, 2H), 1.68-1.85 (m, 1H), 1.89-2.10 (m, 1H), 2.60-2.80 (m, 1H), 4.12-4.32 (m, 2H), 5.66 (d, J=5.8 Hz, 1H), 6.50 (d, J=6.7 Hz, 1H), 6.99 (s, 1H), 7.39-7.61 (m, 3H), 7.69-7.86 (m, 2H).

LC-MS (METCR1410): 97% (UV), Rt=0.97 min, m/z (ESI$^+$)=291.2 [M+H]$^+$

General Procedure 5 (General Scheme 17): Oxidation

N-(Cyclopentylmethyl)-2-oxo-3-(phenylformamido) butanamide (FP 180)

To a stirred, ice cooled solution of N-(cyclopentylmethyl)-2-hydroxy-3-(phenyl-formamido)butanamide (I-300, 100 mg, 0.33 mmol) in DCM (4 mL) at 0° C. was added DMP (153 mg, 0.36 mmol). The reaction was warmed to RT and stirred for 60 h. DMP (77 mg, 0.18 mmol) was added and the reaction stirred for 1 h. Saturated NaHCO$_3$(3 mL) was added and the white precipitate formed filtered and washed with DCM (2×3 mL). The biphasic filtrate was separated and the aqueous layer was extracted with DCM (2×3 mL). The combined organic layers were dried over sodium sulfate, filtered and concentrated in vacuo to give a crude residue which was dissolved in 4:1:5 MeCN/H$_2$O/DMSO (1.1 mL), filtered and purified by preparative LC (acidic pH, standard elution method) to afford 35.1 mg of N-(cyclopentylmethyl)-2-oxo-3-(phenylformamido)butanamide as an off-white powder (100% purity, 35%).

$^1$H NMR (500 MHz, Chloroform-d) δ 1.16-1.28 (m, 2H), 1.48-1.52 (m, 1H), 1.56-1.60 (m, 4H), 1.59-1.70 (m, 2H), 1.73-1.83 (m, 2H), 2.09 (hept, J=7.6 Hz, 1H), 3.23-3.32 (m, 2H), 4.28 (p, J=7.1 Hz, 1H), 6.88 (d, J=7.0 Hz, 1H), 6.94 (br. s, 1H), 7.41-7.48 (m, 2H), 7.48-7.56 (m, 1H), 7.78-7.83 (m, 2H).

LC-MS (METCR1600): 100% (UV), Rt=4.28 min, m/z (ESI$^+$)=303.3 [M+H]$^+$

N-(Cyclobutylmethyl)-2-oxo-3-(phenylformamido) butanamide (FP 181)

The title compound was synthesized from N-(cyclobutylmethyl)-2-hydroxy-3-(phenylformamido)butanamide (I-301) in a similar manner to general procedure 5 (general scheme 17) as an off-white powder (23.5 mg, 95% purity by 1H NMR, 22%) after purification by preparative LC (acidic pH, standard elution method).

$^1$H NMR (500 MHz, Chloroform-d) δ 1.57 (d, J=7.2 Hz, 3H under H$_2$O), 1.65-1.76 (m, 2H), 1.82-1.99 (m, 2H), 2.03-2.13 (m, 2H), 2.52 (hept, J=7.6 Hz, 1H), 3.30-3.40 (m, 2H), 5.48 (p, J=7.2 Hz, 1H), 6.80-6.95 (m, 2H), 7.44 (t, J=7.5 Hz, 2H), 7.52 (t, J=7.4 Hz, 1H), 7.80 (d, J=7.3 Hz, 2H).

LC-MS (METCR1600): 100% (UV), Rt=4.06 min, m/z (ESI$^+$)=289.3 [M+H]$^+$

N-(2-Methylpropyl)-2-oxo-3-(phenylformamido) butanamide (FP 182)

The title compound was synthesized from 2-hydroxy-N-(2-methylpropyl)-3-(phenylformamido)butanamide (I-302) in a similar manner to general procedure 5 (general scheme 17) as an off-white powder (18 mg, 100% purity, 99%) after purification by preparative LC (acidic pH, standard elution method).

$^1$H NMR (500 MHz, Chloroform-d) δ 0.94 (dd, J=0.9, 6.7 Hz, 6H), 1.58 (d, J=7.2 Hz, 3H), 1.80-1.89 (m, 1H), 3.16 (t, J=6.6 Hz, 2H), 5.47 (p, J=7.2 Hz, 1H), 6.90 (d, J=6.2 Hz, 1H), 6.97 (br. s, 1H), 7.44 (t, J=7.5 Hz, 2H), 7.52 (t, J=7.4 Hz, 1H), 7.77-7.83 (m, 2H).

LC-MS (METCR1600): 100% (UV), Rt=3.92 min, m/z (ESI$^+$)=277.2 [M+H]$^+$

N-Cyclopropyl-2-oxo-3-(phenylformamido)pentanamide (FP 183)

The title compound was synthesized from N-cyclopropyl-2-hydroxy-3-(phenyl-formamido)pentanamide (I-303) in a similar manner to general procedure 5 (general scheme 17) as an off-white powder (9.3 mg, 99% purity, 7%) after purification by preparative LC (acidic pH, standard elution method).

$^1$H NMR (500 MHz, Chloroform-d) δ 0.56-0.66 (m, 2H), 0.81-0.91 (m, 2H), 1.00 (t, J=7.4 Hz, 3H), 1.79-1.93 (m, 1H), 2.09-2.22 (m, 1H), 2.76-2.84 (m, 1H), 5.37-5.45 (m, 1H), 6.85-7.00 (m, 2H), 7.41-7.48 (m, 2H), 7.49-7.56 (m, 1H), 7.77-7.84 (m, 2H).

LC-MS (MET-uPLC-AB-102): 99% (UV), Rt=2.31 min, m/z (ESI$^+$)=275.1 [M+H]$^+$

N-Cyclopropyl-2-oxo-3-(phenylformamido)hexanamide (FP 184)

The title compound was synthesized from N-cyclopropyl-2-hydroxy-3-(phenylformamido)hexanamide (I-304) in a similar manner to general procedure 5 (general scheme 17) in 1:1 DCM/1,2-DCE and obtained as an off-white powder (41.3 mg, 99% purity, 31%) after purification by filtration and trituration in water and DCM.

$^1$H NMR (500 MHz, DMSO-d6) δ 0.53-0.61 (m, 2H), 0.62-0.70 (m, 2H), 0.92 (t, J=7.3 Hz, 3H), 1.32-1.44 (m, 1H), 1.44-1.57 (m, 1H), 1.65 (dtd, J=4.8, 9.5, 13.8 Hz, 1H), 1.72-1.84 (m, 1H), 2.72-2.80 (m, 1H), 5.14 (ddd, J=4.0, 6.7, 10.4 Hz, 1H), 7.47 (t, J=7.5 Hz, 2H), 7.51-7.58 (m, 1H), 7.83-7.91 (m, 2H), 8.71 (d, J=6.0 Hz, 2H).

LC-MS (MET-uPLC-AB-102): 99% (UV), Rt=2.63 min, m/z (ESI$^+$)=289.1 [M+H]$^+$

Ozonolysis Route: Synthesis of Final Products (FP 185-186)

GENERAL SCHEME 18:

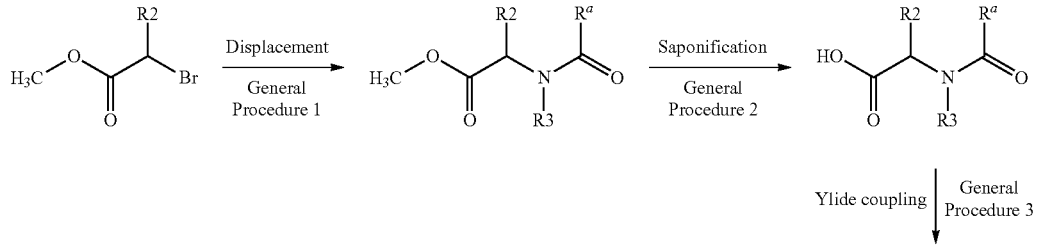

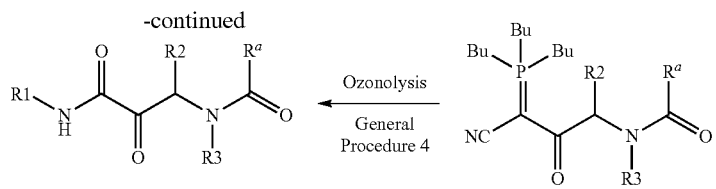

General Procedure 1 (General Scheme 18): Displacement

Methyl 2-[N-(2-methoxyphenyl)acetamido]propanoate (I-305)

To a stirred, ice cooled solution of N-(2-methoxyphenyl) acetamide (2 g, 12.11 mmol) in dry DMF (20 mL) at 0° C. was added NaH (60% in mineral oil, 697 mg, 29.06 mmol) followed by methyl 2-bromopropanoate (3.2 mL, 29.06 mmol). The reaction was allowed to reach RT and stirred for 18 h. The mixture was poured over ice and the solution extracted with EtOAc (75 mL). The organic layer was separated, washed with water (3×75 mL) and brine (50 mL), dried over magnesium sulfate, filtered and concentrated in vacuo. The crude material was purified by flash column chromatography on normal phase silica (340 g SNAP KP-SIL cartridge, 0-100% EtOAc in heptane gradient) to afford 2.54 g of methyl 2-[N-(2-methoxyphenyl)acetamido]propanoate as a yellow oil (83% purity, 69%).

$^1$H NMR (500 MHz, Chloroform-d) δ 1.03-1.60 (m, 3H), 3.72-3.78 (m, 3H), 3.80-3.86 (m, 3H), 4.06-6.19 (m, 1H), 6.94-7.04 (m, 2H), 7.28-7.39 (m, 1H), 7.46 (dd, J=1.7, 7.7 Hz, 1H).

LC-MS (METCR1410): 83% (UV), Rt=1.00 min, m/z (ESI$^+$)=252.1 [M+H]$^+$

Methyl 2-(2-oxopiperidin-1-yl)propanoate (I-306)

The title compound was synthesized in a similar manner to general procedure 1 (general scheme 18) as a yellow free-flowing oil (1.63 g, 95% purity by $^1$H NMR, 42%) after purification by flash column chromatography on normal phase silica (50 g SNAP KP-SIL cartridge, 0-60% EtOAc in heptane gradient).

$^1$H NMR (500 MHz, Chloroform-d) δ 1.39 (d, J=7.4 Hz, 3H), 1.74-1.87 (m, 4H), 1.76-1.81 (m, 3H), 2.35-2.48 (m, 2H), 3.19-3.32 (m, 2H), 3.70 (s, 3H), 5.20 (q, J=7.4 Hz, 1H).

LC-MS (METCR1410): 60% (UV), Rt=0.76 min, m/z (ESI$^+$)=186.3 [M+H]$^+$

General Procedure 2 (General Scheme 18): Saponification

2-[N-(2-methoxyphenyl)acetamido]propanoic acid (I-307)

To methyl 2-[N-(2-methoxyphenyl)acetamido]propanoate (I-305, 500 mg, 1.95 mmol) in 1:1:1 THF/water/MeOH (10 mL) was added lithium hydroxide hydrate (164 mg, 3.90 mmol) and the reaction stirred for 2 h, then concentrated in vacuo to 2 mL. The residual solution was acidified with 2N HCl (10 mL) to pH 1-2. The aqueous layer was extracted with 1:1 IPA/CHCl$_3$ (4×10 mL). The combined organic layers were dried over sodium sulfate, filtered and concentrated in vacuo to afford 439 mg of 2-[N-(2-methoxyphenyl) acetamido]propanoic acid as an off-white solid (97% purity, 92%). The crude material was used in the next step without further purification.

$^1$H NMR (500 MHz, Chloroform-d) δ 1.16-1.31 (m, 3H), 1.82-1.91 (m, 3H), 3.79-3.92 (m, 3H), 4.70-4.85 (m, 1H), 6.97-7.06 (m, 2H), 7.14-7.26 (m, 1H), 7.37-7.42 (m, 1H).

LC-MS (METCR1410): 97% (UV), Rt=0.90 min, m/z (ESI$^+$)=238.0 [M+H]+

2-(2-Oxopiperidin-1-yl)propanoic acid (I-308)

The title compound was synthesized from methyl 2-(2-oxopiperidin-1-yl)-propanoate (I-306) in a similar manner to general procedure 2 (general scheme 18) as a colourless gum (1.01 g, 100% purity, 67%) after work-up. The crude material was used in the next step without purification.

$^1$H NMR (250 MHz, Chloroform-d) δ 1.35 (d, J=7.3 Hz, 3H), 1.57-1.88 (m, 4H), 2.28-2.51 (m, 2H), 3.14-3.45 (m, 2H), 4.87 (q, J=7.2 Hz, 1H).

LC-MS (METCR1410): 100% (UV), Rt=0.62 min, m/z (ESI$^+$)=172.3 [M+H]$^+$

General Procedure 3 (General Scheme 18): Ylide Formation

N-[4-Cyano-3-oxo-4-(tributyl-λ$^5$-phosphanylidene) butan-2-yl]-N-(2-methoxyphenyl) acetamide (I-309)

To a stirred, ice cooled solution of 2-[N-(2-methoxyphenyl)acetamido]-propanoic acid (I-307, 435 mg, 1.83 mmol) and DIPEA (958 μL, 5.5 mmol) in dry 9/1 DCM/DMF (10 mL) at 0° C. was added HATU (2.09 g, 5.5 mmol) in one portion. The reaction was stirred at 0° C. for 15 min then (tributyl-As-phosphanylidene)acetonitrile (1.44 mL, 5.5 mmol) added. The mixture was stirred at 0° C. for 15 min then at RT for 1.5 h. Water (3 mL) was added and the aqueous layer was extracted with DCM (2×5 mL). The combined organic layers were washed with brine (5 mL), dried over sodium sulfate, filtered and concentrated in vacuo. The crude material was purified by flash column chromatography on normal phase silica (340 g SNAP KP-SIL cartridge, 10-100% EtOAc in heptane gradient) followed by flash column chromatography on reverse phase silica (120 g SNAP C18 KP—HS cartridge, 0-100% ACN in water gradient) to afford 196 mg of N-[4-cyano-3-oxo-4-(tributyl-λ$^5$-phosphanylidene)butan-2-yl]-N-(2-methoxyphenyl)acetamide as a brown oil (89% purity, 21%).

$^1$H NMR (500 MHz, Chloroform-d) δ 0.80-0.97 (m, 12H), 1.31-1.56 (m, 12H), 1.66 (s, 3H), 1.93-2.09 (m, 6H), 3.74 (s, 3H), 5.33 (q, J=7.4 Hz, 1H), 6.82-6.91 (m, 2H), 7.20-7.27 (m, 1H), 7.56 (dd, J=1.7, 7.7 Hz, 1H).

LC-MS (METCR1410): 89% (UV), Rt=1.27 min, m/z (ESI$^+$)=461.6 [M+H]$^+$

3-Oxo-4-(2-oxopiperidin-1-yl)-2-(tributyl-λ$^5$-phosphanylidene)pentanenitrile (I-310)

The title compound was synthesized from 2-(2-oxopiperidin-1-yl)propanoic acid (I-308) in a similar manner to general procedure 3 (general scheme 18) as a brown oil (1.15 g, 90% purity by ¹H NMR, 45%) after purification by flash column chromatography on normal phase silica (50 g SNAP KP-SIL cartridge, 0-100% EtOAc in heptane gradient).

¹H NMR (500 MHz, Chloroform-d) δ 0.91-0.95 (m, 9H), 1.30 (d, J=7.1 Hz, 3H), 1.40-1.56 (m, 12H), 1.73-1.91 (m, 4H), 2.01-2.16 (m, 6H), 2.34-2.51 (m, 2H), 3.31 (t, J=5.9 Hz, 2H), 5.24 (q, J=7.0 Hz, 1H).

LC-MS (METCR1410): 67% (UV), Rt=1.13 min, m/z (ESI⁺)=395.6 [M+H]⁺

General Procedure 4 (General Scheme 18): Ozonolysis

N-[(3-Chlorophenyl)methyl]-3-[N-(2-methoxyphenyl)acetamido]-2-oxobutanamide (FP 185)

Ozone (ozone generator) was passed at −78° C. through a solution of N-[4-cyano-3-oxo-4-(tributyl-λ⁵-phosphanylidene)butan-2-yl]-N-(2-methoxyphenyl)acetamide (I-309, 89% purity, 196 mg, 0.38 mmol) in DCM (5 mL) for 15 min. The solution was purged with nitrogen for 15 min and 1-(3-chlorophenyl)methanamine (56 µL, 0.45 mmol) added. The mixture was stirred at −78° C. under nitrogen for 1 h, warmed to RT and concentrated in vacuo to give an oil which was purified by flash column chromatography on normal phase silica (10 g SNAP KP-SIL cartridge, 10-100% EtOAc in heptane gradient) to afford 28.2 mg of N-[(3-chlorophenyl)methyl]-3-[N-(2-methoxy-phenyl)acetamido]-2-oxobutanamide as a viscous yellow oil (97% purity, 19%).

¹H NMR (500 MHz, Chloroform-d) δ 1.02-1.41 (m, 3H), 1.71-1.78 (m, 3H), 3.83-3.86 (m, 3H), 4.43-4.52 (m, 1H), 4.52-4.59 (m, 1H), 4.34-5.49 (m, 1H), 6.95-7.08 (m, 2H), 7.11-7.30 (m, 4H), 7.31-7.40 (m, 2H), 7.39-7.88 (m, 1H).

LC-MS (METCR1416): 97% (UV), Rt=4.24 min, m/z (ESI⁺)=389.0/391.0 [M+H]⁺

N-(Cyclohexylmethyl)-2-oxo-3-(2-oxopiperidin-1-yl)butanamide (FP 186)

The title compound was synthesized from 3-oxo-4-(2-oxopiperidin-1-yl)-2-(tributyl-λ⁵-phosphanylidene)pentanenitrile (I-310) in a similar manner to general procedure 4 (general scheme 18) as a yellow oil (22 mg, 96% purity, 8%) after purification by flash column chromatography on normal phase silica (25 g SNAP KP-SIL cartridge, 0-50% EtOAc in heptane gradient) followed by preparative LC (acidic pH, standard elution method).

¹H NMR (500 MHz, Chloroform-d) δ 0.87-0.98 (m, 2H), 1.09-1.26 (m, 3H), 1.40 (d, J=6.8 Hz, 3H), 1.44-1.53 (m, 1H), 1.63-1.67 (m, 1H), 1.67-1.74 (m, 4H), 1.74-1.85 (m, 3H), 1.85-1.95 (m, 1H), 2.21-2.36 (m, 2H), 3.11 (t, J=6.7 Hz, 2H), 3.39-3.48 (m, 1H), 3.56-3.69 (m, 1H), 4.04 (q, J=6.8 Hz, 1H), 6.73 (s, 1H).

LC-MS (MET-uHPLC-AB-101): 96% (UV), Rt=2.84 min, m/z (ESI⁺)=295.2 [M+H]⁺

Route to Sulfonamides: Synthesis of Final Products (FP 187-191)

GENERAL SCHEME 19:

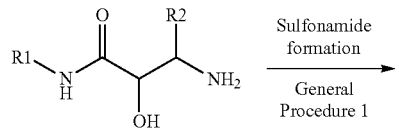

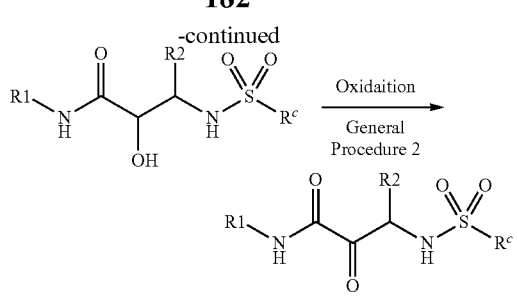

General Procedure 1 (General Scheme 19): Sulfonamide Formation

3-Benzenesulfonamido-N-(cyclopropylmethyl)-2-hydroxybutanamide (I-311)

To a stirred, ice cooled solution of 3-amino-N-(cyclopropylmethyl)-2-hydroxy-butanamide (I-250, 100 mg, 0.58 mmol) and DIPEA (121 µL, 0.70 mmol) in DCM (1 mL) was added at 0° C. benzenesulfonyl chloride (73 µL, 0.57 mmol) dropwise. The reaction was stirred at RT for 1 h, saturated NaHCO₃ (2 mL), then DCM (2 mL) added and the mixture filtered through a Telos® hydrophobic frit. The aqueous layer was extracted with DCM (2×2 mL) and the combined organic layers washed with 1N HCl (2 mL), passed through a Telos® hydrophobic frit and the filtrate concentrated in vacuo to give a crude product which was recrystallized from 3:1 EtOAc/heptane (2 mL). The white precipitate formed was filtered off, washed with heptane (2×1 mL) and dried in vacuo to afford 106 mg of 3-benzenesulfonamido-N-(cyclopropylmethyl)-2-hydroxybutanamide as an off-white solid (92% purity, 54%).

¹H NMR (500 MHz, DMSO-d6) δ 0.07-0.17 (m, 2H), 0.27-0.38 (m, 2H), 0.67 (d, J=6.8 Hz, 3H), 0.83-0.95 (m, 1H), 2.83-2.96 (m, 2H), 3.49-3.60 (m, 1H), 3.90 (dd, J=2.7, 5.8 Hz, 1H), 5.90 (d, J=5.8 Hz, 1H), 7.55-7.67 (m, 4H), 7.75-7.86 (m, 3H).

LC-MS (METCR1410): 92% (UV), Rt=0.91 min, m/z (ESI⁺)=313.0 [M+H]⁺

N-(Cyclopropylmethyl)-2-hydroxy-3-(phenylmethanesulfonamido)butanamide (I-312)

The title compound was synthesized from 3-amino-N-(cyclopropylmethyl)-2-hydroxybutanamide (I-250) in a similar manner to general procedure 1 (general scheme 19) as an off-white solid (230 mg, 84% purity by 1H NMR, 68%) after filtration. The crude material was used in the next step without further purification.

¹H NMR (500 MHz, DMSO-d6) δ 0.15-0.18 (m, 2H), 0.35-0.39 (m, 2H), 0.87-0.98 (m, 4H), 2.92-2.99 (m, 2H), 3.73 (td, J=2.8, 7.7 Hz, 1H), 4.00 (dd, J=3.0, 5.7 Hz, 1H), 4.32 (s, 2H), 5.80 (d, J=5.7 Hz, 1H), 6.92 (d, J=8.2 Hz, 1H), 7.31-7.40 (m, 5H), 7.83 (t, J=6.0 Hz, 1H).

LC-MS (METCR1410): 94% (UV), Rt=0.94 min, m/z (ESI⁺)=327.1 [M+H]⁺

N-(Cyclopropylmethyl)-2-hydroxy-3-(4-methylbenzenesulfonamido) butanamide (I-313)

The title compound was synthesized from 3-amino-N-(cyclopropylmethyl)-2-hydroxybutanamide (I-250) in a similar manner to general procedure 1 (general scheme 19)

as an off-white solid (150 mg, 97% purity, 38%) after filtration. The crude material was used in the next step without further purification.

$^1$H NMR (500 MHz, DMSO-d6) δ 0.08-0.18 (m, 2H), 0.27-0.37 (m, 2H), 0.67 (d, J=6.8 Hz, 3H), 0.84-0.92 (m, 1H), 2.37 (s, 3H), 2.89 (hept, J=6.8 Hz, 2H), 3.51 (pd, J=2.7, 6.9 Hz, 1H), 3.89 (dd, J=2.7, 5.8 Hz, 1H), 5.87 (d, J=5.8 Hz, 1H), 7.38 (d, J=8.0 Hz, 2H), 7.49 (d, J=7.8 Hz, 1H), 7.64-7.73 (m, 2H), 7.77 (t, J=6.0 Hz, 1H).

LC-MS (METCR1410): 97% (UV), Rt=0.97 min, m/z (ESI$^+$)=327.4 [M+H]$^+$

N-(Cyclopropylmethyl)-2-hydroxy-3-(2-methylbenzenesulfonamido)butanamide (I-314)

The title compound was synthesized from 3-amino-N-(cyclopropylmethyl)-2-hydroxybutanamide (I-250) in a similar manner to general procedure 1 (general scheme 19) as an off-white solid (180 mg, 97% purity, 46%) after filtration. The crude material was used in the next step without further purification.

$^1$H NMR (500 MHz, DMSO-d6) δ 0.08-0.17 (m, 2H), 0.27-0.38 (m, 2H), 0.75 (d, J=6.8 Hz, 3H), 0.85-0.92 (m, 1H), 2.58 (s, 3H), 2.81-2.93 (m, 2H), 3.45-3.57 (m, 1H), 3.82-3.93 (m, 1H), 5.78-5.95 (m, 1H), 7.35-7.40 (m, 2H), 7.51 (t, J=7.4 Hz, 1H), 7.60 (d, J=6.0 Hz, 1H), 7.78 (t, J=5.9 Hz, 1H), 7.85 (d, J=7.8 Hz, 1H).

LC-MS (METCR1410): 97% (UV), Rt=0.95 min, m/z (ESI$^+$)=327.4 [M+H]$^+$

3-(2-Chlorobenzenesulfonamido)-N-(cyclopropylmethyl)-2-hydroxybutanamide (I-315)

The title compound was synthesized from 3-amino-N-(cyclopropylmethyl)-2-hydroxybutanamide (I-250) in a similar manner to general procedure 1 (general scheme 19) as an off-white solid (160 mg, 85% purity, 47%) after purification by flash column chromatography on normal phase silica (10 g SNAP KP-SIL cartridge, 0-60% EtOAc in heptane gradient).

$^1$H NMR (500 MHz, Chloroform-d) δ −0.05-0.06 (m, 2H), 0.22-0.32 (m, 2H), 0.61-0.77 (m, 4H), 2.83-3.01 (m, 2H), 3.57-3.71 (m, 1H), 4.10 (dd, J=2.8, 5.2 Hz, 1H), 4.44-4.53 (m, 1H), 5.70 (d, J=8.5 Hz, 1H), 6.97 (t, J=5.7 Hz, 1H), 7.19-7.27 (m, 1H), 7.27-7.37 (m, 2H), 7.90-7.97 (m, 1H).

LC-MS (METCR1410): 85% (UV), Rt=1.00 min, m/z (ESI$^+$)=345.2/347.2 [M+H]$^+$

General Procedure 2 (General Scheme 19): Oxidation

Method A: Addition of DMP at 0° C.

3-Benzenesulfonamido-N-(cyclopropylmethyl)-2-oxobutanamide (FP 187)

To a stirred, ice cooled solution of 3-benzenesulfonamido-N-(cyclopropyl-methyl)-2-hydroxybutanamide (I-311, 92% purity, 104 mg, 0.31 mmol) in DCM (4 mL) was added DMP (156 mg, 0.37 mmol) at 0° C. The reaction was stirred for 18 h at RT, saturated NaHCO$_3$(3 mL) added and the biphasic mixture separated through a Telos® hydrophobic frit. The aqueous layer was extracted with DCM (2×3 mL) and the combined organic layers concentrated in vacuo. The crude residue was dissolved in 4:1:1 MeCN/H$_2$O/DMSO (1.1 mL), filtered twice and purified by preparative LC (acidic pH, standard elution method) to afford 30 mg of 3-benzenesulfonamido-N-(cyclopropyl-methyl)-2-oxobutanamide as an off-white powder (98% purity, 31%).

$^1$H NMR (500 MHz, Chloroform-d) δ 0.15-0.28 (m, 2H), 0.48-0.62 (m, 2H), 0.86-0.98 (m, 1H), 1.39 (d, J=7.2 Hz, 3H), 3.03-3.15 (m, 2H), 4.79 (dq, J=7.2, 9.2 Hz, 1H), 5.52 (d, J=9.3 Hz, 1H), 6.75 (br. s, 1H), 7.46-7.52 (m, 2H), 7.53-7.58 (m, 1H), 7.81-7.87 (m, 2H).

LC-MS (METCR1600): 98% (UV), Rt=3.81 min, m/z (ESI$^+$)=311.2 [M+H]$^+$

Method B: Addition of DMP at RT

N-(Cyclopropylmethyl)-2-oxo-3-(phenylmethanesulfonamido)butanamide (FP 188)

To N-(cyclopropylmethyl)-2-hydroxy-3-(phenylmethanesulfonamido)butanamide (I-312, 80% purity by 1H NMR, 230 mg, 0.56 mmol) in DCM (5 mL) was added DMP (239 mg, 0.56 mmol) and the reaction stirred for 18 h. The mixture was diluted with DCM (10 mL) and washed with saturated NaHCO$_3$(15 mL). The organic layer was separated, dried over magnesium sulfate, filtered and concentrated in vacuo. The crude material was purified by flash column chromatography on normal phase silica (10 g SNAP KP-SIL cartridge, 0-70% EtOAc in heptane gradient) to afford 78 mg of A (cyclopropylmethyl)-2-oxo-3-(phenyl-methanesulfonamido)butanamide as an off-white solid (95% purity by $^1$H NMR, 41%).

$^1$H NMR (500 MHz, Chloroform-d) δ 0.20-0.31 (m, 2H), 0.54-0.64 (m, 2H), 0.92-1.05 (m, 1H), 1.35 (d, J=7.2 Hz, 3H), 3.11-3.19 (m, 2H), 4.23-4.34 (m, 2H), 4.60 (dq, J=7.2, 8.8 Hz, 1H), 5.04 (d, J=8.8 Hz, 1H), 6.92-7.00 (m, 1H), 7.34-7.45 (m, 5H).

LC-MS (METCR1600): 94% (UV), Rt=3.95 min, m/z (ESI$^+$)=325.0 [M+H]$^+$

N-(Cyclopropylmethyl)-3-(4-methylbenzenesulfonamido)-2-oxobutanamide (FP 189)

The title compound was synthesized from N-(cyclopropylmethyl)-2-hydroxy-3-(4-methylbenzenesulfonamido)butanamide (I-313) in a similar manner to method B, general procedure 2 (general scheme 19) as an off-white powder (14 mg, 95% purity by $^1$H NMR, 9%) after purification by flash column chromatography on normal phase silica (10 g SNAP KP-SIL cartridge, 0-100% EtOAc in heptane gradient) followed by preparative LC (acidic pH, standard elution method).

$^1$H NMR (500 MHz, Chloroform-d) δ 0.16-0.28 (m, 2H), 0.51-0.60 (m, 2H), 0.86-0.99 (m, 1H), 1.39 (d, J=7.2 Hz, 3H), 2.40 (s, 3H), 3.03-3.16 (m, 2H), 4.76 (dq, J=7.2, 9.2 Hz, 1H), 5.47 (d, J=9.3 Hz, 1H), 6.65-6.85 (m, 1H), 7.26-7.29 (m, 2H), 7.68-7.77 (m, 2H).

LC-MS (METCR1600): 93% (UV), Rt=4.13 min, m/z (ESI$^+$)=325.1 [M+H]$^+$

N-(Cyclopropylmethyl)-3-(2-methylbenzenesulfonamido)-2-oxobutanamide (FP 190)

The title compound was synthesized from N-(cyclopropylmethyl)-2-hydroxy-3-(2-methylbenzenesulfonamido)butanamide (I-314) in a similar manner to method B, general procedure 2 (general scheme 19) as a colourless viscous oil (10 mg, 100% purity, 9%) after purification by flash column chromatography on normal phase silica (10 g SNAP KP-SIL cartridge, 0-100% EtOAc in heptane gradient) followed by preparative LC (acidic pH, standard elution method).

$^1$H NMR (500 MHz, Chloroform-d) δ 0.18-0.24 (m, 2H), 0.51-0.57 (m, 2H), 0.87-0.98 (m, 1H), 1.37 (d, J=7.3 Hz, 3H), 2.65 (s, 3H), 3.06-3.12 (m, 2H), 4.70 (dq, J=7.2, 9.4 Hz, 1H), 5.61 (d, J=9.4 Hz, 1H), 6.74-6.88 (m, 1H), 7.26-7.31 (m, 2H), 7.43 (td, J=1.3, 7.6 Hz, 1H), 7.92-7.96 (m, 1H).

LC-MS (METCR1600): 100% (UV), Rt=4.17 min, m/z (ESI$^+$)=325.2 [M+H]$^+$ 3-(2-Chlorobenzenesulfonamido)-N-(cyclopropylmethyl)-2-oxobutanamide (FP 191)

The title compound was synthesized from 3-(2-chlorobenzenesulfonamido)-N-(cyclopropylmethyl)-2-hydroxybutanamide (I-315) in a similar manner to method B, general procedure 2 (general scheme 19) as a yellow viscous oil (11 mg, 95% purity, 8%) after purification by flash column chromatography on normal phase silica (10 g SNAP KP-SIL cartridge, 0-100% EtOAc in heptane gradient) followed by flash column chromatography on reverse phase silica (12 g SNAP Ultra C18 cartridge, acidic pH, standard elution method) then trituration in heptane and concentration of the filtrate.

$^1$H NMR (500 MHz, DMSO-d6) δ 0.12-0.17 (m, 2H), 0.35-0.40 (m, 2H), 0.88-0.95 (m, 1H), 1.21 (d, J=7.3 Hz, 3H), 2.88-3.00 (m, 2H), 4.77-4.88 (m, 1H), 7.46-7.55 (m, 1H), 7.60-7.65 (m, 2H), 7.90-7.95 (m, 1H), 8.44-8.52 (m, 1H), 8.75-8.84 (m, 1H).

LC-MS (METCR1600): 95% (UV), Rt=1.49 min, m/z (ESI$^+$)=344.9/346.9 [M+H]$^+$

Compounds Synthesised Using the Method Described in General Scheme 4 (FP 192 to FP 194)

General Procedure 2 (General Scheme 4): Regioselective Epoxide Opening

Method C: Epoxide Opening without Titanium(IV)Isopropoxide

N-(Cyclopropylmethyl)-3-[(4,4-difluorocyclohexyl)amino]-2-hydroxybutanamide (I-316)

The title compound was synthesised from N-(cyclopropylmethyl)-3-methyloxirane-2-carboxamide (I-30) in a similar manner to method C, general procedure 2 (general scheme 4) at 70° C. and was obtained as an off-white powder (293 mg, 90% purity by $^1$H NMR, 62%) after purification by trituration in 2:1 Et$_2$O/heptane followed by flash column chromatography on normal phase silica (25 g SNAP KP-SIL cartridge, 0-6% MeOH in DCM gradient) then trituration in 1:1 MeCN/H$_2$O followed by flash column chromatography on reverse phase silica (30 g SNAP C18 cartridge, acidic pH, standard elution method).

$^1$H NMR (500 MHz, DMSO-d6) δ 0.13-0.23 (m, 2H), 0.33-0.42 (m, 2H), 0.89-0.96 (m, 1H), 1.00 (d, J=6.6 Hz, 3H), 1.48-1.62 (m, 2H), 1.77-1.92 (m, 2H), 1.93-2.14 (m, 5H), 2.91-3.03 (m, J=6.3 Hz, 3H), 3.08-3.17 (m, 2H), 4.23 (d, J=2.6 Hz, 1H), 8.03 (t, J=5.9 Hz, 1H).

LC-MS (METCR1410): 100% (UV), Rt=0.69 min, m/z (ESI$^+$)=291.5 [M+H]$^+$

N-(Cyclohexylmethyl)-2-hydroxy-3-[(2-oxo-1,2-dihydropyridin-4-yl)amino]butanamide (I-317)

The title compound was synthesised from N-(cyclohexylmethyl)-3-methyloxirane-2-carboxamide (I-34) in a similar manner to method C, general procedure 2 (general scheme 4) at 115° C. in a Biotage Horizon microwave and was obtained as a colourless gummy solid (86 mg, 80% purity by 1H NMR, 11%) after purification by flash column chromatography on normal phase silica (50 g SNAP Ultra cartridge, 0-100% TBME in heptane gradient then 0-60% MeOH in TBME gradient).

$^1$H NMR (250 MHz, Chloroform-d) δ 0.70-1.04 (m, 2H), 1.04-1.41 (m, 4H), 1.45-1.78 (m, 8H), 2.85-3.01 (m, 1H), 3.05-3.28 (m, 2H), 4.19-4.28 (m, 1H), 4.36 (s, 2H), 4.97-5.31 (m, 1H), 5.97-6.07 (m, 1H), 6.16-6.30 (m, 1H), 6.88-7.06 (m, 1H), 7.65-7.78 (m, 1H).

LC-MS (METCR1410): 96% (UV), Rt=0.84 min, m/z (ESI$^+$)=308.4 [M+H]$^+$ 3-(Benzylamino)-N-(cyclopropylmethyl)-2-hydroxypropanamide (I-318)

The title compound was synthesised from N-(cyclopropylmethyl)oxirane-2-carboxamide (I-224) in a similar manner to method C, general procedure 2 (general scheme 4) at 70° C. and was obtained as an off-white powder (558 mg, 100% purity, 63%) after purification by flash column chromatography on normal phase silica (50 g SNAP KP-SIL cartridge, 0-10% MeOH in DCM gradient) followed by flash column chromatography on reverse phase silica (30 g SNAP Ultra C18 cartridge, acidic pH, standard elution method).

$^1$H NMR (500 MHz, Chloroform-d) δ 0.16-0.26 (m, 2H), 0.45-0.56 (m, 2H), 0.89-1.01 (m, 1H), 2.95-3.07 (m, 2H), 3.08-3.19 (m, 2H), 3.76-3.84 (m, 2H), 4.01 (t, J=6.0 Hz, 1H), 7.26-7.36 (m, 6H).

LC-MS (METCR1410): 100% (UV), Rt=0.72 min, m/z (ESI$^+$)=249.1 [M+H]$^+$

N-(Cyclopropylmethyl)-2-hydroxy-3-{[(oxan-4-yl)methyl]amino}butanamide (I-319)

The title compound was synthesised from N-(cyclopropylmethyl)-3-methyloxirane-2-carboxamide (I-30) in a similar manner to method C, general procedure 2 (general scheme 4) at 70° C. and was obtained as an off-white powder (494 mg, 100% purity, 68%) after purification by trituration in 4:1 EtOAc/heptane.

$^1$H NMR (500 MHz, DMSO-d6) δ 0.12-0.18 (m, 2H), 0.30-0.42 (m, 2H), 0.84 (d, J=6.5 Hz, 3H), 0.87-1.01 (m, 1H), 1.08-1.19 (m, 2H), 1.54-1.66 (m, 3H), 2.38-2.44 (m, 2H), 2.80-2.87 (m, 1H), 2.96 (dp, J=6.9, 21.1 Hz, 2H), 3.22-3.29 (m, 2H), 3.79-3.86 (m, 2H), 3.95 (s, 1H), 5.36 (s, 1H), 7.79 (t, J=5.3 Hz, 1H).

LC-MS (METCR1410): 100% (ELS), Rt=0.40-0.70 min, m/z (ESI$^+$)=271.2 [M+H]$^+$

General Procedure 3 (General Scheme 4): N-Formylation

Method C: Pre-Formation of Mixed Anhydride

N-(Cyclopropylmethyl)-3-[N-(4,4-difluorocyclohexyl)formamido]-2-hydroxybutanamide (I-320)

The title compound was synthesised from N-(cyclopropylmethyl)-3-[(4,4-difluorocyclohexyl)amino]-2-hydroxybutanamide (I-316) in a similar manner to method C, general procedure 3 (general scheme 4) as a colourless gum (80 mg, 80% purity by $^1$H NMR, 20%) after purification by trituration in DCM followed by purification of the filtrate by flash chromatography on normal phase silica (25 g SNAP KP-SIL cartridge, 0-5% MeOH in DCM gradient).

$^1$H NMR (250 MHz, Chloroform-d) δ 0.04-0.30 (m, 2H), 0.38-0.60 (m, 2H), 0.82-1.06 (m, 1H), 1.12-1.35 (m, 3H), 1.66-2.00 (m, 6H), 2.01-2.32 (m, 3H), 3.00-3.22 (m, 2H), 3.40-3.59 (m, 1H), 3.99 (q, J=6.9 Hz, 1H), 7.09 (s, 1H), 8.05-8.39 (m, 1H).

LC-MS (METCR1410): 91% (UV), Rt=1.35-1.60 min (multiple peaks), m/z (ESI$^+$)=319.2 [M+H]$^+$

N-(Cyclohexylmethyl)-2-hydroxy-3-[N-(2-oxo-1,2-dihydropyridin-4-yl)formamido]butanamide (I-321)

The title compound was synthesised from N-(cyclohexylmethyl)-2-hydroxy-3-[(2-oxo-1,2-dihydropyridin-4-yl)amino]butanamide (I-317) in a similar manner to method C, general procedure 3 (general scheme 4) as an off-white powder (60 mg, 68% purity, 56%) after purification by used in the step without further purification.

$^1$H NMR (500 MHz, Chloroform-d) δ 0.69-0.82 (m, 3H), 0.97-1.10 (m, 4H), 1.18-1.23 (m, 2H), 1.50-1.56 (m, 4H), 1.58-1.60 (m, 3H), 2.87-2.96 (m, 1H), 3.03-3.15 (m, 2H), 6.87 (d, J=1.3 Hz, 1H), 7.13 (t, J=6.2 Hz, 1H), 7.65-7.73 (m, 1H), 7.97 (d, J=5.9 Hz, 1H), 8.41-8.52 (m, 1H), 9.84-9.93 (m, 1H).

LC-MS (METCR1410): 68% (UV), Rt=0.99 min, m/z (ESI$^+$)=336.2 [M+H]$^+$

3-(N-Benzylformamido)-N-(cyclopropylmethyl)-2-hydroxypropanamide (I-322)

The title compound was synthesised from 3-(benzylamino)-N-(cyclopropyl-methyl)-2-hydroxypropanamide (I-318) in a similar manner to method C, general procedure 3 (general scheme 4) as an off-white powder (590 mg, 94% purity, 90%) after purification by trituration in 1:1 TBME/heptane.

$^1$H NMR (500 MHz, Chloroform-d) δ 0.17-0.27 (m, 2H), 0.46-0.57 (m, 2H), 0.91-1.01 (m, 1H), 3.08-3.17 (m, 2H), 3.62-4.24 (m, 3H), 4.42-4.59 (m, 2H), 4.60-5.49 (m, 1H), 7.11-7.20 (m, 1H), 7.20-7.25 (m, 2H), 7.29-7.40 (m, 3H), 8.20-8.35 (m, 1H).

LC-MS (METCR1410): 94% (UV), Rt=0.90-1.00 min (multiple peaks), m/z (ESI$^+$)=277.1 [M+H]$^+$

General Procedure 4 (General Scheme 4): Oxidation

Method A

N-(Cyclohexylmethyl)-2-oxo-3-[N-(2-oxo-1,2-dihydropyridin-4-yl)formamido]butanamide (FP 192)

The title compound was synthesised from N-(cyclohexylmethyl)-2-hydroxy-3-[N-(2-oxo-1,2-dihydropyridin-4-yl)formamido]butanamide (I-321) in a similar manner to method A, general procedure 4 (general scheme 4) as a colourless viscous oil (11 mg, 100% purity, 27%) after purification by flash column chromatography on normal phase silica (10 g SNAP KP-SIL cartridge, 0-100% EtOAc in heptane gradient) followed by flash column chromatography on normal phase silica (10 g SNAP KP-SIL cartridge, 0-100% TBME in heptane gradient).

$^1$H NMR (500 MHz, Chloroform-d) δ 0.80-1.02 (m, 2H), 1.11-1.28 (m, 4H), 1.49-1.56 (m, 1H), 1.57-1.63 (m, 2H), 1.64-1.77 (m, 5H), 3.13-3.26 (m, 2H), 5.96-6.12 (m, 1H), 6.45-8.90 (m, 6H).

LC-MS (METCR1600): 100% (UV), Rt=4.35 min, m/z (ESI)$^+$=334.4 [M+H]$^+$

3-(N-Benzylformamido)-N-(cyclopropylmethyl)-2-oxopropanamide (FP 193)

The title compound was synthesised from 3-(N-benzylformamido)-N-(cyclopropylmethyl)-2-hydroxypropanamide (I-322) in a similar manner to method A, general procedure 4 (general scheme 4) as a colourless viscous oil (15 mg, 95% purity, 18%) after purification by flash column chromatography on reverse phase silica (60 g SNAP Ultra C18 cartridge, acidic method, standard elution method) followed by preparative LC (acidic pH, early elution method).

$^1$H NMR (500 MHz, Chloroform-d) δ 0.18-0.29 (m, 2H), 0.48-0.60 (m, 2H), 0.90-1.02 (m, 1H), 3.10-3.16 (m, 2H), 4.47-4.54 (m, 2H), 4.59 (s, 2H), 6.80-7.01 (m, 1H), 7.16-7.23 (m, 2H), 7.26-7.40 (m, 3H), 8.10-8.43 (m, 1H).

LC-MS (MET-uPLC-AB-101): 95% (UV), Rt=2.05-2.50 min, m/z (ESI$^+$)=275.2 [M+H]$^+$

Method B: Addition of DMP at 0° C.

N-(Cyclopropylmethyl)-3-[N-(4,4-difluorocyclohexyl)formamido]-2-oxobutanamide (FP 194)

The title compound was synthesised from N-(cyclopropylmethyl)-3-[N-(4,4-difluorocyclohexyl)formamido]-2-hydroxybutanamide (I-320) in a similar manner to method B, general procedure 4 (general scheme 4) as a colourless gum (30 mg, 96% purity, 45%) after purification by preparative LC (acidic pH, standard elution method).

$^1$H NMR (500 MHz, Chloroform-d) δ 0.17-0.29 (m, 2H), 0.48-0.60 (m, 2H), 0.91-1.03 (m, 1H), 1.42-2.55 (m, 11H), 3.01-5.24 (m, 4H), 6.69-7.05 (m, 1H), 8.05-8.25 (m, 1H).

LC-MS (MET-uPLC-AB-102): 96% (UV), Rt=2.77 min, m/z (ESI$^+$)+=317.1 [M+H]$^+$

Route Via Sulfur Ylide Formation: Synthesis of Final Products (FP 195-FP 201)

The compounds below were synthesised using a modification of Scheme 11 as described in Scheme 11a.

GENERAL SCHEME 11a

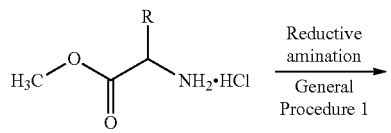

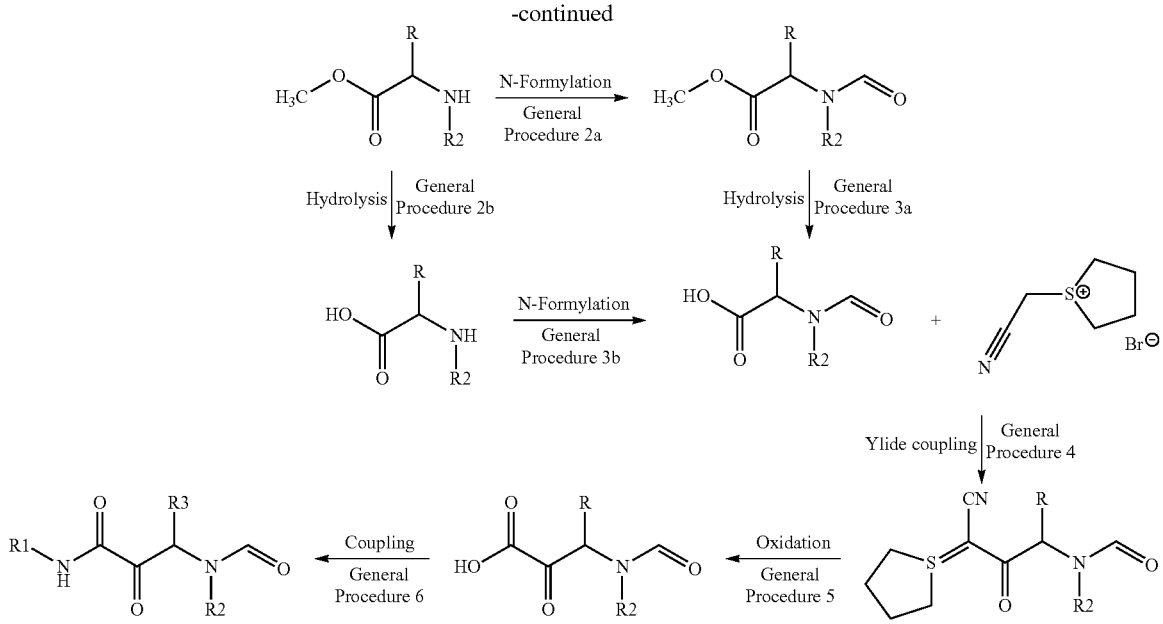

General Procedure 1 (General Scheme 11a): Reductive Amination

Methyl 2-(benzylamino)-3-methylbutanoate (I-323)

To a stirred suspension of methyl 2-amino-3-methylbutanoate hydrochloride (2.0 g, 11.93 mmol) in 1,2-DCE (40 mL) was added benzaldehyde (1.21 mL, 11.93 mmol) and the reaction was stirred at RT for 18 h. STAB (3.03 g, 14.32 mmol) was added portion wise (6 equal portions) and the reaction was then stirred for a further 18 h. The reaction mixture was slowly quenched with saturated NaHCO$_3$ (50 mL) and extracted with EtOAc (3×50 mL), the combined organic layers were dried in vacuo to obtain a crude product which was purified by flash column chromatography on normal phase silica (50 g SNAP KP-SIL cartridge, 0-10% MeOH in DCM gradient) to afford 879 mg of methyl 2-(benzylamino)-3-methylbutanoate as a yellow oil (86% purity by $^1$H NMR, 29%).

$^1$H NMR (500 MHz, Chloroform-d) δ 0.89-0.99 (m, 6H), 1.88-1.96 (m, 1H), 3.02 (d, J=6.1 Hz, 1H), 3.59 (d, J=13.1 Hz, 1H), 3.70-3.74 (m, 3H), 3.83 (d, J=13.1 Hz, 1H), 7.22-7.26 (m, 1H), 7.28-7.39 (m, 5H).

LC-MS (METCR1410): 99% (UV), Rt=0.71 min, m/z (ESI$^+$)=222.3[M+H]$^+$

Methyl 2-(benzylamino)-4-methylpentanoate (I-324)

The title compound was synthesised in a similar manner to general procedure 1 (general scheme 11a) as a yellow free-flowing oil (1.39 g, 86% purity by $^1$H NMR, 46%) after purification by flash column chromatography on normal phase silica (50 g SNAP KP-SIL cartridge, 0-10% MeOH in DCM gradient).

$^1$H NMR (500 MHz, Chloroform-d) δ 0.85 (d, J=6.6 Hz, 3H), 0.91 (d, J=6.6 Hz, 3H), 1.44-1.52 (m, 2H), 1.73-1.82 (m, 1H), 3.27-3.34 (m, 1H), 3.61 (d, J=13.0 Hz, 1H), 3.72 (s, 4H), 3.81 (d, J=13.0 Hz, 1H), 7.22-7.26 (m, 1H), 7.29-7.34 (m, 4H).

LC-MS (METCR1410): 88% (UV), Rt=0.80 min, m/z (ESI$^+$)=236.2 [M+H]$^+$

Ethyl 2-(benzylamino)-3-cyclobutylpropanoate (I-325)

The title compound was synthesised in a similar manner to general procedure 1 (general scheme 11a) as a yellow free-flowing oil (919 mg, 82% purity by 1H NMR, 49%) after purification by flash column chromatography on normal phase silica (25 g SNAP KP-SIL cartridge, 0-10% MeOH in DCM gradient).

$^1$H NMR (500 MHz, Chloroform-d) δ 1.26-1.32 (m, 3H), 1.49 (s, 1H), 1.61-1.91 (m, 5H), 1.93-2.11 (m, 2H), 2.39-2.49 (m, 1H), 3.16 (t, J=6.8 Hz, 1H), 3.58-3.62 (m, 1H), 3.79 (d, J=13.0 Hz, 1H), 4.14-4.21 (m, 2H), 7.21-7.26 (m, 1H), 7.27-7.36 (m, 4H).

LC-MS (METCR1410): 84% (UV), Rt=0.85 min, m/z (ESI$^+$)=262.6 [M+H]$^+$

Methyl 2-(benzylamino)propanoate (I-326)

The title compound was synthesised in a similar manner to general procedure 1 (general scheme 11a) as a yellow free-flowing oil (1.99 g, 94% purity, 54%) after purification by flash column chromatography on normal phase silica (50 g SNAP KP-SIL cartridge, 0-10% MeOH in DCM gradient).

$^1$H NMR (500 MHz, Chloroform-d) δ 1.26 (d, J=7.0 Hz, 3H), 3.33 (q, J=7.0 Hz, 1H), 3.61 (d, J=12.9 Hz, 1H), 3.66 (s, 3H), 3.74 (d, J=12.9 Hz, 1H), 7.15-7.31 (m, 5H).

LC-MS (METCR0990): 95% (UV), Rt=1.58 min, m/z (ESI$^+$)=194.2 [M+H]$^+$

General Procedure 2a (General Scheme 11a): N-Formylation

Method As Described in General Procedure 2 (General Scheme 11)

Methyl 2-(N-benzylformamido)propanoate (I-327)

The title compound was synthesised from methyl 2-(benzylamino)propanoate (I-326) in a similar manner to general procedure 2 (general scheme 11) as a yellow free-flowing oil (2.30 g, 93% purity, 100%) and used in the next step without further purification.

$^1$H NMR (500 MHz, Chloroform-d) δ 1.31-1.48 (m, 3H), 3.53-3.64 (m, 3H), 4.09-4.72 (m, 3H), 7.22-7.39 (m, 5H), 8.25-8.39 (m, 1H).

LC-MS (METCR1410): 93% (UV), Rt=0.95 min, m/z (ESI$^+$)=222.2 [M+H]$^+$

General Procedure 3a (General Scheme 11a): Hydrolysis

Method As Described in General Procedure 3 (General Scheme 11)

2-(N-Benzylformamido)propanoic acid (I-328)

The title compound was synthesised from methyl 2-(N-benzylformamido)propanoate (I-327) in a similar manner to general procedure 3 (general scheme 11) as a yellow viscous oil (2.05 g, 93% purity, 95%) and used in the next step without further purification.

$^1$H NMR (500 MHz, Chloroform-d) δ 1.32-1.47 (m, 3H), 4.11-4.46 (m, 1H), 4.46-4.72 (m, 2H), 7.22-7.40 (m, 5H), 8.23-8.41 (m, 1H).

LC-MS (METCR1410): 93% (UV), Rt=0.85 min, m/z (ESI$^+$)=208.2 [M+H]$^+$

General Procedure 2b (General Scheme 11a): Hydrolysis 2-(Benzylamino)-4-methylpentanoic acid (I-329)

To a stirred solution of methyl 2-(benzylamino)-4-methylpentanoate (I-324) (86% purity, 1.39 g, 5.1 mmol) dissolved in 1:1 MeOH/THF (28 mL) was added 1M LiOH solution (28 mL, 28 mmol) and the mixture was stirred at RT overnight. The mixture was diluted with water (100 mL), neutralised to pH-7 using 2M KHSO$_4$ and extracted with 1:1 IPA:CHCl$_3$ (3×100 mL). The combined organic layers were dried over sodium sulfate, filtered and concentrated in vacuo. The solid residue was sonicated with DCM, filtered, the resultant cake was washed with DCM then dried under suction to afford 931 mg of 2-(benzylamino)-4-methylpentanoic acid (I-329) as an off-white powder (96% purity, 80% yield by $^1$H NMR).

$^1$H NMR (500 MHz, DMSO-d6) δ 0.78 (d, J=6.6 Hz, 3H), 0.85 (d, J=6.6 Hz, 3H), 1.35-1.49 (m, J=7.0 Hz, 2H), 1.72-1.84 (m, 1H), 3.05 (t, J=7.1 Hz, 1H), 3.69 (d, J=13.4 Hz, 1H), 3.88 (d, J=13.4 Hz, 1H), 7.25-7.30 (m, 1H), 7.31-7.39 (m, 4H).

LC-MS (METCR1410): 96% (UV), Rt=0.72 min, m/z (ESI$^+$)=222.3 [M+H]$^+$ 2-(Benzylamino)-3-methylbutanoic acid (I-330)

The title compound was synthesised from methyl 2-(benzylamino)-3-methylbutanoate (I-323) in a similar manner to method general procedure 2b (general scheme 11a) as an off-white powder (341 mg, 100% purity, 48%) after purification by trituration in DCM.

$^1$H NMR (500 MHz, DMSO-d6) δ 0.85-0.93 (m, 6H), 1.82-1.96 (m, 1H), 2.83 (d, J=5.4 Hz, 1H), 3.61 (d, J=13.5 Hz, 1H), 3.86 (d, J=13.5 Hz, 1H), 7.23-7.28 (m, 1H), 7.29-7.38 (m, 4H).

LC-MS (METCR1410): 100% (UV), Rt=0.52 min, m/z (ESI$^+$)=208.3 [M+H]$^+$ 2-(Benzylamino)-3-cyclobutylpropanoic acid (I-331)

The title compound was synthesised from ethyl 2-(benzylamino)-3-cyclobutylpropanoate (I-325) in a similar manner to general procedure 2b (general scheme 11a) as an off-white powder (466 mg, 100% purity, 69%) after purification by trituration in water and DCM.

$^1$H NMR (500 MHz, DMSO-d6) δ 1.46-1.84 (m, 6H), 1.86-2.01 (m, 2H), 2.41-2.47 (m, 1H), 2.89-2.93 (m, 1H), 3.65-3.69 (m, 1H), 3.83-3.87 (m, 1H), 7.25-7.30 (m, 1H), 7.31-7.38 (m, 4H).

LC-MS (METCR1410): 100% (UV), Rt=0.76 min, m/z (ESI$^+$)=234.1 [M+H]$^+$

General Procedure 3b (General Scheme 11a): N-Formylation 2-(N-Benzylformamido)-4-methylpentanoic acid (I-332)

To acetic anhydride (0.99 mL, 10.5 mmol) was added formic acid (0.51 mL, 12.9 mmol) dropwise. The mixture was heated at 50° C. for 0.5 h and cooled to RT. The solution was diluted with dry THF (11 mL), cooled to 0° C. in an ice bath and a solution of 2-(benzylamino)-4-methylpentanoic acid (I-329) (96%, 931 mg, 4.04 mmol) in anhydrous THF (11 mL) was added. The reaction mixture was stirred at 50° C. for 1 h then left standing at RT for 18 h then quenched with water (80 mL) and extracted with EtOAc (50 mL). The organic layer was separated, washed with water (2×80 mL), dried over sodium sulfate, filtered, concentrated in vacuo and azeotroped with EtOAc:Heptane (1:4) to give 1.04 g of 2-(N-benzylformamido)-4-methylpentanoic acid (I-332) as a pale yellow viscous oil (96% purity, 99%) used in the next step without further purification.

$^1$H NMR (500 MHz, Chloroform-d) δ 0.67-0.86 (m, 6H), 1.35-1.51 (m, 1H), 1.59-1.89 (m, 2H), 4.00-4.63 (m, 3H), 7.23-7.40 (m, 5H), 8.30-8.38 (m, 1H).

LC-MS (METCR1410): 96% (UV), Rt=1.03 min, m/z (ESI$^+$)=250.1 [M+H]$^+$ 2-(N-Benzylformamido)-3-methylbutanoic acid (I-333)

The title compound was synthesised from 2-(benzylamino)-3-methylbutanoic acid (I-330) in a similar manner to general procedure 3b (general scheme 11a) as a colourless viscous oil (392 mg, 96% purity by $^1$H NMR, 97%) which was used in the next step without further purification.

$^1$H NMR (500 MHz, Chloroform-d) δ 0.74-0.86 (m, 3H), 0.91-1.06 (m, 3H), 2.23-2.62 (m, 1H), 3.47-3.96 (m, 1H), 4.37-4.52 (m, 1H), 4.55-4.70 (m, 1H), 7.21-7.31 (m, 4H), 7.31-7.39 (m, 1H), 8.27-8.45 (m, 1H).

LC-MS (METCR1410): 98% (UV), Rt=0.96 min, m/z (ESI$^+$)=236.1 [M+H]$^+$ 2-(N-Benzylformamido)-3-cyclobutylpropanoic acid (I-334)

The title compound was synthesised from 2-(benzylamino)-3-cyclobutylpropanoic acid (I-331) in a similar manner to general procedure 3b (general scheme 11a) as a colourless viscous oil (569 mg, 90% purity by 1H NMR, 98%) which was used in the next step without further purification.

$^1$H NMR (500 MHz, Chloroform-d) δ 1.21-1.59 (m, 3H), 1.69-2.28 (m, 7H), 3.81-4.23 (m, 1H), 4.36-4.68 (m, 2H), 7.24-7.40 (m, 5H), 8.27-8.35 (m, 1H).

LC-MS (METCR1410): 95% (UV), Rt=1.03 min, m/z (ESI$^+$)=262.1 [M+H]$^+$

General Procedure 4 (General Scheme 11a): Ylide Coupling

N-Benzyl-N-[1-cyano-5-methyl-2-oxo-1-(1λ$^4$-thiolan-1-ylidene)hexan-3-yl]formamide (I-335)

To a stirred solution of 2-(N-benzylformamido)-4-methylpentanoic acid (I-332) (96%, 1.04 g, 4.0 mmol), DIPEA (2.09 mL, 12.0 mmol) and HATU (1.67 g, 4.4 mmol) dissolved in DCM (20 mL) was added 1-(cyanomethyl)thiolan-1-ium bromide (90%, 1.20 g, 5.2 mmol, synthesised by the procedure outlined in WO2014/154829) and the mixture was stirred at RT for 2 h followed by standing at RT for 18 h. The reaction was quenched with 1M HCl (20 mL) and the layers were separated. The aqueous layer was washed with DCM (20 mL) and the organic layers combined, washed with saturated NaHCO$_3$ (20 mL) and brine (20 mL, filtered through a Telos® hydrophobic frit. The retained aqueous was washed with DCM (2 mL) and the organic filtrate concentrated in vacuo. The crude material was purified by flash column chromatography on normal phase silica (50 g SNAP KP-SIL cartridge 0-10% MeOH/EtOAc) gradient to give 1.59 g of N-benzyl-N-{1-cyano-5-methyl-2-oxo-1-[(1E)-1λ$^4$-thiolan-1-ylidene]hexan-3-yl}formamide (I-335) as a pale yellow viscous oil (89% purity by 1H NMR, 98%).

$^1$H NMR (500 MHz, Chloroform-d) δ 0.74-0.90 (m, 6H), 1.41-1.53 (m, 1H), 1.60-1.76 (m, 2H), 1.92-2.03 (m, 2H), 2.41-2.54 (m, 2H), 2.90-3.23 (m, 4H), 4.34-5.28 (m, 3H), 7.18-7.35 (m, 5H), 8.29-8.51 (m, 1H).

LC-MS (METCR1410): 100% (UV), Rt=0.99 min, m/z (ESI$^+$)=359.1 [M+H]$^+$

N-Benzyl-N-[1-cyano-4-methyl-2-oxo-1-(1λ$^5$-thiolan-1-ylidene)pentan-3-yl]formamide (I-336)

The title compound was synthesised from 2-(N-benzylformamido)-3-methylbutanoic acid (I-333) in a similar manner to general procedure 4 (general scheme 11a) as a yellow viscous oil (595 mg, 80% purity by $^1$H NMR, 86%) after purification by flash column chromatography on normal phase silica (25 g SNAP KP-SIL cartridge, 0-10% MeOH in EtOAc gradient).

$^1$H NMR (500 MHz, Chloroform-d) δ 0.82 (d, J=6.7 Hz, 3H), 0.90 (d, J=6.5 Hz, 3H), 1.90-2.00 (m, 2H), 2.32-2.50 (m, 3H), 2.76-2.95 (m, 2H), 3.04-3.14 (m, 2H), 3.89 (d, J=10.9 Hz, 1H), 4.42 (d, J=14.8 Hz, 1H), 4.63 (d, J=14.8 Hz, 1H), 7.17-7.22 (m, 1H), 7.23-7.30 (m, 2H), 7.31-7.36 (m, 2H), 8.48 (s, 1H).

LC-MS (METCR1410): 100% (UV), Rt=0.94 min, m/z (ESI$^+$)=345.1 [M+H]$^+$

N-Benzyl-N-[4-cyano-1-cyclobutyl-3-oxo-4-(1λ$^4$-thiolan-1-ylidene)butan-2-yl]formamide (I-337)

The title compound was synthesised from 2-(N-benzylformamido)-3-cyclobutylpropanoic acid (I-334) in a similar manner to general procedure 4 (general scheme 11a) as a colourless viscous oil (656 mg, 95% purity by $^1$H NMR, 86%) after purification by flash column chromatography on normal phase silica (25 g SNAP KP-SIL cartridge, 0-2.5% MeOH in EtOAc gradient).

$^1$H NMR (250 MHz, Chloroform-d) δ 1.41-1.66 (m, 4H), 1.72-1.81 (m, 1H), 1.82-1.92 (m, 3H), 1.93-1.99 (m, 1H), 2.01-2.07 (m, 1H), 2.12-2.26 (m, 1H), 2.37-2.57 (m, 2H), 2.85-3.00 (m, 2H), 3.08-3.22 (m, 2H), 4.21 (t, J=7.6 Hz, 1H), 4.37-4.65 (m, 2H), 7.16-7.35 (m, 5H), 8.24-8.47 (m, 1H).

LC-MS (METCR1410): 100% (UV), Rt=1.01 min, m/z (ESI$^+$)=371.1 [M+H]$^+$

N-Benzyl-N-[4-cyano-3-oxo-4-(λ$^4$-thiolan-1-ylidene)butan-2-yl]formamide (I-338)

The title compound was synthesised from 2-(N-benzylformamido)propanoic acid (I-328) in a similar manner to general procedure 4 (general scheme 11a) as a yellow viscous oil (2.80 g, 89% purity by 1H NMR, 86%) after purification by flash column chromatography on normal phase silica (50 g SNAP KP-SIL cartridge, 0-10% MeOH in EtOAc gradient).

$^1$H NMR (500 MHz, Chloroform-d) δ 1.18-1.50 (m, 3H), 1.93-2.03 (m, 2H), 2.41-2.61 (m, 2H), 2.92-3.30 (m, 4H), 4.42-4.94 (m, 3H), 7.26 (s, 5H), 8.22-8.53 (m, 1H).

LC-MS (METCR1410): 99% (UV), Rt=0.85 min, m/z (ESI$^+$)=317.0 [M+H]$^+$

General Procedure 5 (General Scheme 11a): Oxidation 3-(N-Benzylformamido)-5-methyl-2-oxohexanoic acid (I-339)

To a stirred solution of N-benzyl-N-[1-cyano-5-methyl-2-oxo-1-(1λ$^4$-thiolan-1-ylidene)hexan-3-yl]formamide (I-335) (600 mg, 89% purity, 0.84 mmol) in 2:1 THF:water (3 mL), under nitrogen was added Oxone (1.03 g, 1.49 mmol). The reaction mixture was stirred at RT for 1 h then diluted with EtOAc (5 mL) and the organic layer separated, the aqueous layer was extracted with ethyl acetate (1×5 mL). The organic fractions were combined, washed with water (1×5 mL) and brine (1×10 mL), dried over sodium sulfate, filtered and concentrated in vacuo to give 534 mg of 3-(N-benzylformamido)-5-methyl-2-oxohexanoic acid as a colourless oil (I-339) (70% purity by 1H NMR, 90%) used in the next step without further purification.

$^1$H NMR (500 MHz, Chloroform-d) δ 0.55-0.83 (m, 6H), 1.31-1.46 (m, 1H), 1.58-2.28 (m, 2H), 4.22-4.85 (m, 3H), 7.19-7.49 (m, 5H), 8.21-8.39 (m, 1H), 9.37 (s, 1H).

LC-MS (METCR1673): 85% (UV), Rt=1.27 min, m/z (ESI$^+$)=276.3 [M–H]$^+$ 3-(N-Benzylformamido)-4-methyl-2-oxopentanoic acid (I-340)

The title compound was synthesised from N-benzyl-N-[1-cyano-4-methyl-2-oxo-1-(1λ$^4$-thiolan-1-ylidene)pentan-3-yl]formamide (I-336) in a similar manner to general procedure 5 (general scheme 11a) after quenching the reaction with 1N HCl prior to work-up to give a yellow viscous oil (165 mg, 53% purity, 72%) and used in the next step without further purification.

$^1$H NMR (500 MHz, Chloroform-d) δ 0.78-1.03 (m, 6H), 2.34-2.47 (m, 1H), 4.07-4.75 (m, 3H), 7.18-7.42 (m, 5H), 8.19-8.50 (m, 1H).

LC-MS (METCR1410): 53% (UV), Rt=1.09 min, m/z (ESI+)=264.0 [M+H]+

3-(N-Benzylformamido)-4-cyclobutyl-2-oxobutanoic acid (I-341)

The title compound was synthesised from N-benzyl-N-[4-cyano-1-cyclobutyl-3-oxo-4-(1λ$^4$-thiolan-1-ylidene)butan-2-yl]formamide (I-337) in a similar manner to general procedure 5 (general scheme 11a) as a colourless viscous oil (284 mg, 72% purity, 84%) and used in the next step without further purification.

$^1$H NMR (250 MHz, DMSO-d6) δ 1.21-1.97 (m, 9H), 4.11-4.70 (m, 3H), 7.17-7.53 (m, 5H), 8.26-8.34 (m, 1H).

LC-MS (METCR0990): 72% (UV), Rt=1.29 min, m/z (ESI-)=288.3 [M−H]−

3-(N-Benzylformamido)-2-oxobutanoic acid (I-342)

The title compound was synthesised from N-benzyl-N-[4-cyano-3-oxo-4-(1λ$^4$-thiolan-1-ylidene)butan-2-yl]formamide (I-338) in a similar manner to general procedure 5 (general scheme 11a) after quenching the reaction with 1N HCl prior to work-up to give a yellow viscous oil (772 mg, 46% purity by $^1$H NMR, 67%) and used in the next step without further purification.

$^1$H NMR (500 MHz, DMSO-d6) δ 0.96-1.32 (m, 3H), 4.15-5.04 (m, 3H), 7.17-7.51 (m, 5H), 8.24-8.41 (m, 1H).

LC-MS (METCR1410): 81% (UV), Rt=0.70-0.90 min, m/z (ESI+)=236.1 [M+H]+

General Procedure 6 (General Scheme 11a): Amide Formation

Method A: T3P Coupling

3-(N-Benzylformamido)-N,5-dimethyl-2-oxohexanamide (FP 195)

To a stirred solution of 3-(N-benzylformamido)-5-methyl-2-oxohexanoic acid (I-339) (70%, 267 mg, 0.67 mmol) in THF (2 mL) was added T3P (50% in DMF, 802 µL, 1.35 mmol) and DIPEA (646 µL, 3.71 mmol), followed by methylamine hydrochloride (114 mg, 1.68 mmol). The reaction mixture was stirred for 30 min at RT then partitioned between EtOAc (5 mL) and water (2 mL). The organic layer was separated and the aqueous layer was extracted with EtOAc (2×5 mL). The organic layer was washed with brine (5 mL), dried over sodium sulfate, filtered and concentrated in vacuo. The crude product was purified by flash column chromatography on reverse phase silica (30 g SNAP KP-C18-HS cartridge, acidic pH, as per standard elution method except eluting with a 10-60% acetonitrile in water+0.1% formic acid gradient gradient). The relevant fractions were combined and extracted with DCM (2×15 mL). The organic fractions were passed through a Telos® hydrophobic frit and concentrated in vacuo to give 28 mg of 3-(N-benzylformamido)-N,5-dimethyl-2-oxohexanamide (FP195) as a yellow gum (98% purity, 14%).

$^1$H NMR (500 MHz, Chloroform-d) δ 0.54-0.86 (m, 6H), 1.17-2.09 (m, 3H), 2.70-2.87 (m, 3H), 4.20-5.10 (m, 3H), 6.28-6.74 (m, 1H), 7.20-7.42 (m, 5H), 8.19-8.44 (m, 1H).

LC-MS (METCR1416): 98% (UV), Rt=3.70 min, m/z (ESI+)=291.0 [M+H]+

3-(N-Benzylformamido)-4-cyclobutyl-N-methyl-2-oxobutanamide (FP 196)

The title compound was synthesised from 3-(N-benzylformamido)-4-cyclobutyl-2-oxobutanoic acid (I-341) in a similar manner to method A, general procedure 6 (general scheme 11) as an off-white gum (9 mg, 95% purity by $^1$H NMR, 8%) after purification by flash column chromatography on reverse phase silica (12 g SNAP KP-C18-HS cartridge, acidic pH, as per standard elution method except eluting with a 10-60% acetonitrile in water+0.1% formic acid gradient.

$^1$H NMR (500 MHz, Chloroform-d) δ 1.15-2.25 (m, 9H), 2.66-2.86 (m, 3H), 4.07-4.94 (m, 3H), 6.24-6.75 (m, 1H), 7.16-7.43 (m, 5H), 8.15-8.41 (m, 1H).

LC-MS (METCR1416): 93% (UV), Rt=3.79 min, m/z (ESI+)=303.1 [M+H]+

3-(N-Benzylformamido)-N,4-dimethyl-2-oxopentanamide (FP 197)

The title compound was synthesised from 3-(N-benzylformamido)-4-methyl-2-oxopentanoic acid (I-340) in a similar manner to method A, general procedure 6 (general scheme 11) as a yellow viscous oil (17 mg, 100% purity, 13%) after purification by flash column chromatography on normal phase silica (10 g SNAP KP-SIL cartridge, 0-100% EtOAc in heptane gradient).

$^1$H NMR (500 MHz, Chloroform-d) δ 0.81-1.00 (m, 6H), 2.38-2.55 (m, 1H), 2.67-2.86 (m, 3H), 4.02-4.99 (m, 3H), 6.12-6.59 (m, 1H), 7.21-7.43 (m, 5H), 8.28-8.58 (m, 1H).

LC-MS (METCR1603): 100% (UV), Rt=3.70 min, m/z (ESI+)=277.3 [M+H]+

Method B: Mixed Anhydride Method

3-(N-Benzylformamido)-4-methyl-2-oxopentanamide (FP 198)

To an ice cooled solution of 3-(N-benzylformamido)-4-methyl-2-oxopentanoic acid (I-340) (53% purity, 170 mg, 0.33 mmol) in MeOH (2 mL) was added acetyl chloride (50 µL, 0.66 mmol). The reaction was allowed to warm to RT and stirred for 1 h, then the solvent was removed in vacuo. The crude intermediate was redissolved in MeOH (2 mL), cooled to 0° C. and 7M ammonia in MeOH (0.71 mL, 5.0 mmol) was added. The reaction was stirred at RT for 1 h then concentrated in vacuo. The residue was purified by flash column chromatography on normal phase silica (10 g SNAP KP-SIL cartridge, 0-100% EtOAc in heptane gradient) to afford 35 mg of 3-(N-benzylformamido)-4-methyl-2-oxopentanamide as a yellow viscous oil (98% purity, 39%)

$^1$H NMR (500 MHz, Chloroform-d) δ 0.81-0.97 (m, 6H), 2.33-2.52 (m, 1H), 4.12-4.84 (m, 3H), 5.36-5.57 (m, 1H), 6.13-6.55 (m, 1H), 7.19-7.42 (m, 5H), 8.21-8.52 (m, 1H).

LC-MS (METCR1416): 98% (UV), Rt=3.33 min, m/z (ESI+)=263.2 [M+H]+

3-(N-Benzylformamido)-5-methyl-2-oxohexanamide (FP 199)

The title compound was synthesised from 3-(N-benzylformamido)-5-methyl-2-oxohexanoic acid (I-339) in a similar manner to method B, general procedure 6 (general scheme 11) as an off-white gum (7 mg, 95% purity by $^1$H NMR, 7%) after purification by flash column chromatography on normal phase silica (10 g SNAP KP-SIL cartridge, 0-50% EtOAc in heptane gradient).

$^1$H NMR (500 MHz, Chloroform-d) δ 0.57-0.86 (m, 6H), 1.18-1.41 (m, 1H), 1.46-2.09 (m, 2H), 4.27-5.10 (m, 3H), 5.32-5.50 (m, 1H), 6.26-6.63 (m, 1H), 7.21-7.40 (m, 5H), 8.19-8.45 (m, 1H).

LC-MS (METCR1416): 97% (UV), Rt=3.54-3.58 min (multiple peaks), m/z (ESI⁺)=277.1 [M+H]⁺

Method C: HATU Coupling

3-(N-Benzylformamido)-N-(cyclopentylmethyl)-2-oxobutanamide (FP 200)

To a stirred solution of 3-(N-benzylformamido)-2-oxobutanoic acid (I-342) (46% purity, 386 mg, 0.75 mmol), DIPEA (302 µL, 1.74 mmol) and HATU (344 mg, 0.91 mmol) dissolved in DCM (8 mL) was added 1-cyclopentylmethanamine hydrochloride (123 mg, 0.91 mmol) and the mixture was stirred at RT for 18 h. The reaction was then diluted with DCM (8 mL), quenched with 1M HCl (15 mL) and the 2 layers separated. The aqueous layer was extracted with DCM (8 mL), the combined organic layer was washed with saturated NaHCO₃ (8 mL), brine (8 mL), dried over anhydrous sodium sulfate, filtered and concentrated in vacuo. The residue was purified by flash column chromatography on normal phase silica (25 g SNAP KP-SIL cartridge, 0-5% MeOH in DCM gradient) followed by preparative LC (acidic pH, standard elution method) to afford 98 mg of 3-(N-benzylformamido)-N-(cyclopentylmethyl)-2-oxobutanamide (FP200) as a colourless viscous oil (98% purity, 40% yield).

¹H NMR (500 MHz, Chloroform-d) δ 1.08-1.45 (m, 5H), 1.55-1.81 (m, 6H), 1.92-2.12 (m, 1H), 3.00-3.29 (m, 2H), 4.26-5.17 (m, 3H), 6.32-6.87 (m, 1H), 7.18-7.43 (m, 5H), 8.13-8.45 (m, 1H).

LC-MS (MET-uPLC-AB-101): 98% (UV), Rt=3.30 min, m/z (ESI⁺)=317.2 [M+H]⁺

3-(N-Benzylformamido)-N-(cyclobutylmethyl)-2-oxobutanamide (FP 201)

The title compound was synthesised from 3-(N-benzylformamido)-2-oxobutanoic acid (I-342) in a similar manner to method C, general procedure 6 (general scheme 11) as a yellow viscous oil (22 mg, 97% purity, 9%) after purification by flash column chromatography on normal phase silica (25 g SNAP KP-SIL cartridge, 0-5% MeOH in DCM gradient) followed by preparative LC (acidic pH, standard elution method).

¹H NMR (500 MHz, Chloroform-d) δ 1.13-1.44 (m, 3H), 1.59-1.74 (m, 2H), 1.82-1.97 (m, 2H), 2.01-2.11 (m, 2H), 2.35-2.56 (m, 1H), 3.09-3.37 (m, 2H), 4.24-5.17 (m, 3H), 6.20-6.85 (m, 1H), 7.18-7.42 (m, 5H), 8.12-8.45 (m, 1H).

LC-MS (METCR1603): 97% (UV), Rt=3.63-3.77 min (multiple peaks), m/z (ESI⁺)=303.5 [M+H]⁺

Route to Oxopyrrolidines: Synthesis of Final Products (FP 202-FP 204)

The compounds below were synthesised using a modification of Scheme 13 as described in Scheme 13a.

GENERAL SCHEME 13a:
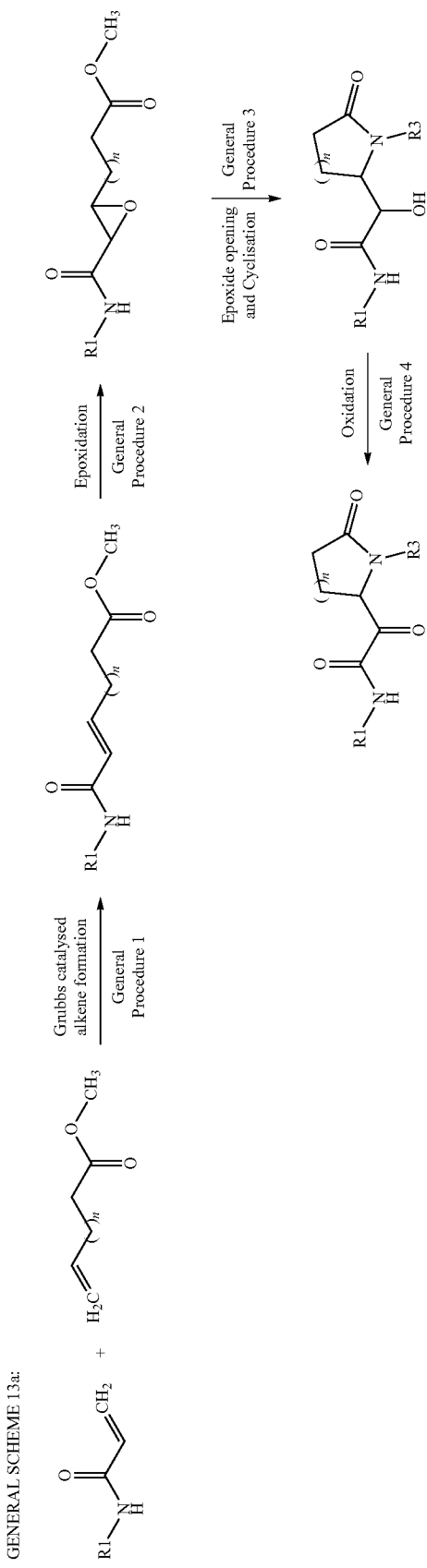
n = 0, 1

General Procedure 1 (General Scheme 13a):
Grubbs Catalysed Alkene Formation

Ethyl (4E)-5-[(cyclopropylmethyl)carbamoyl]pent-4-enoate (I-343)

To a stirring solution of N-(cyclopropylmethyl)prop-2-enamide prepared by the method described in Journal of the American Chemical Society, (2005), 127(42), 14942-14949 (85% purity by $^1$H NMR, 1.00 g, 6.79 mmol) and ethyl pent-4-enoate (1.0 mL, 7.02 mmol) in DCM (70 mL) was added Hoveyda-Grubbs catalyst $2^{nd}$ generation (132 mg, 0.21 mmol). The mixture was stirred at RT under nitrogen for 16 h then concentrated in vacuo. The crude residue was purified by flash column chromatography on normal phase silica (50 g SNAP KP-SIL cartridge, 0-50% EtOAc in heptane gradient) to afford 1.15 g of ethyl (4E)-5-(cyclopropylmethyl)carbamoyl]pent-4-enoate as a grey free flowing oil (80% purity by $^1$H NMR, 60%).

$^1$H NMR (500 MHz, Chloroform-d) δ 0.13-0.26 (m, 2H), 0.43-0.56 (m, 2H), 0.89-1.01 (m, 1H), 1.25 (t, J=7.1 Hz, 3H), 2.39-2.54 (m, 4H), 3.16 (dd, J=5.6, 7.2 Hz, 2H), 4.13 (q, J=7.1 Hz, 2H), 5.55-5.70 (m, 1H), 5.82 (dt, J=1.4, 15.2 Hz, 1H), 6.79 (dt, J=6.5, 15.3 Hz, 1H).

LC-MS (METCR1410): 91% (UV), Rt=0.93 min, m/z (ESI$^+$)=226.5 [M+H]$^+$

Methyl (5E)-6-[(cyclopropylmethyl)carbamoyl]hex-5-enoate (I-344)

The title compound was synthesised from N-(cyclopropylmethyl)prop-2-enamide prepared by the method described in Journal of the American Chemical Society, (2005), 127(42), 14942-14949 and methyl hex-5-enoate in a similar manner to general procedure 1 (general scheme 13a) as a grey solid (1.27 g, 80% purity by $^1$H NMR, 66%) after purification by flash column chromatography on normal phase silica (50 g SNAP KP-SIL cartridge, 0-50% EtOAc in heptane gradient).

$^1$H NMR (500 MHz, Chloroform-d) δ 0.16-0.24 (m, 2H), 0.48-0.54 (m, 2H), 0.91-1.01 (m, 1H), 1.79 (p, J=7.4 Hz, 2H), 2.22 (qd, J=1.4, 7.3 Hz, 2H), 2.34 (t, J=7.4 Hz, 2H), 3.15-3.19 (m, 2H), 3.67 (s, 3H), 5.50-5.61 (m, 1H), 5.79 (dt, J=1.5, 15.3 Hz, 1H), 6.79 (dt, J=6.9, 15.2 Hz, 1H).

LC-MS (METCR1410): 89% (UV), Rt=0.91 min, m/z (ESI$^+$)=226.5 [M+H]$^+$

General Procedure 2 (General Scheme 13a):
Epoxidation

General Method 2 is Same as for Scheme 13

Ethyl 3-{3-[(cyclopropylmethyl)carbamoyl]oxiran-2-yl}propanoate (I-345)

The title compound was synthesised from ethyl (4E)-5-[(cyclopropylmethyl)-carbamoyl]pent-4-enoate (I-343) in a similar manner to general procedure 2 (general scheme 13a) at 55° C. in 1,2-DCE as a yellow free-flowing oil (411 mg, 85% purity by $^1$H NMR, 36%) after purification by flash column chromatography on normal phase silica (25 g SNAP KP-SIL cartridge, 0-80% EtOAc in heptane gradient).

$^1$H NMR (500 MHz, Chloroform-d) δ 0.16-0.20 (m, 2H), 0.48-0.52 (m, 2H), 0.87-0.94 (m, 1H), 1.27 (t, J=7.1 Hz, 3H), 1.76-1.89 (m, 1H), 2.05-2.13 (m, 1H), 2.46 (t, J=7.3 Hz, 2H), 3.02-3.15 (m, 3H), 3.26 (d, J=2.1 Hz, 1H), 4.16 (q, J=7.1 Hz, 2H), 6.19 (s, 1H).

LC-MS (METCR1410): 62% (UV), Rt=0.91 min, m/z (ESI$^+$)=242.1 [M+H]$^+$

Methyl 4-{3-[(cyclopropylmethyl)carbamoyl]oxiran-2-yl}butanoate (I-346)

The title compound was synthesised from methyl (5E)-6-[(cyclopropylmethyl)-carbamoyl]hex-5-enoate (I-344) in a similar manner to general procedure 2 (general scheme 13a) as a yellow solid (423 mg, 85% purity by $^1$H NMR, 33%) at 55° C. in 1,2-DCE after purification by flash column chromatography on normal phase silica (25 g SNAP KP-SIL cartridge, 0-80% EtOAc in heptane gradient).

$^1$H NMR (500 MHz, Chloroform-d) δ 0.14-0.21 (m, 2H), 0.47-0.52 (m, 2H), 0.85-0.94 (m, 1H), 1.51-1.60 (m, 1H), 1.73-1.85 (m, 3H), 2.35-2.41 (m, 2H), 2.93-2.98 (m, 1H), 3.02-3.15 (m, 2H), 3.23 (d, J=2.1 Hz, 1H), 3.67 (s, 3H), 6.15-6.25 (m, 1H).

LC-MS (METCR1410): 60% (UV), Rt=0.89 min, m/z (ESI$^+$)=242.2 [M+H]$^+$

General Procedure 3 (General Scheme 13b):
Epoxide Opening and Cyclisation

General Method 3 is Same as for Scheme 13

2-[1-(Cyclohexylmethyl)-5-oxopyrrolidin-2-yl]-N-(cyclopropylmethyl)-2-hydroxyacetamide (I-347)

The title compound was synthesised from ethyl 3-{3-[(cyclopropylmethyl)-carbamoyl]oxiran-2-yl}propanoate (I-345) in a similar manner to general procedure 3 (general scheme 13a) at 70° C. in EtOH as a yellow viscous oil (107 mg, 93% purity, 45%) after purification by flash column chromatography on normal phase silica (10 g SNAP KP-SIL cartridge, 0-100% EtOAc in heptane gradient followed by 0-15% MeOH in EtOAc gradient).

$^1$H NMR (500 MHz, Chloroform-d) δ 0.17-0.26 (m, 2H), 0.44-0.56 (m, 2H), 0.83-1.04 (m, 3H), 1.13-1.28 (m, 3H), 1.55-1.75 (m, 6H), 1.83-1.91 (m, 1H), 1.92-2.01 (m, 1H), 2.25-2.33 (m, 1H), 2.43-2.52 (m, 1H), 2.68 (dd, J=5.1, 13.9 Hz, 1H), 3.10-3.23 (m, 2H), 3.48 (dd, J=9.6, 13.9 Hz, 1H), 4.18-4.24 (m, 1H), 4.44 (d, J=1.6 Hz, 1H), 4.96-5.65 (m, 1H), 7.17 (t, J=5.5 Hz, 1H).

LC-MS (METCR1410): 93% (UV), Rt=0.97 min, m/z (ESI$^+$)=309.1 [M+H]+

2-{1-[(4-Chlorophenyl)methyl]-5-oxopyrrolidin-2-yl}-N-(cyclopropylmethyl)-2-hydroxyacetamide (I-348)

The title compound was synthesised from ethyl 3-{3-[(cyclopropylmethyl)-carbamoyl]oxiran-2-yl}propanoate (I-345) in a similar manner to general procedure 3 (general scheme 13a) at 70° C. in EtOH as a yellow viscous oil (119 mg, 96% purity, 48%) after purification by flash column chromatography on normal phase silica (10 g SNAP KP-SIL cartridge, 0-100% EtOAc in heptane gradient).

$^1$H NMR (500 MHz, Chloroform-d) δ 0.14-0.25 (m, 2H), 0.45-0.55 (m, 2H), 0.86-1.01 (m, 1H), 1.82-1.99 (m, 2H), 2.30-2.42 (m, 1H), 2.52-2.64 (m, 1H), 3.12 (t, J=6.4 Hz, 2H), 4.05-4.17 (m, 2H), 4.39 (d, J=1.9 Hz, 1H), 4.76 (d, J=15.1 Hz, 1H), 7.02 (t, J=5.6 Hz, 1H), 7.20-7.24 (m, 2H), 7.30-7.34 (m, 2H).

LC-MS (METCR1410): 96% (UV), Rt=0.98 min, m/z (ESI$^+$)=337.0/339.1 [M+H]$^+$

2-(1-Benzyl-6-oxopiperidin-2-yl)-N-(cyclopropylmethyl)-2-hydroxyacetamide (I-349)

The title compound was synthesised from methyl 4-{3-[(cyclopropylmethyl)-carbamoyl]oxiran-2-yl}butanoate (I-346) in a similar manner to general procedure 3 (general scheme 13a) at 60° C. as a brown viscous oil (318 mg, 50% purity, 34%) after purification by flash column chromatography on normal phase silica (25 g SNAP KP-SIL cartridge, 0-100% EtOAc in heptane gradient followed by 0-10% MeOH in EtOAc gradient).

$^1$H NMR (500 MHz, Chloroform-d) δ 0.14-0.24 (m, 2H), 0.46-0.54 (m, 2H), 0.89-0.97 (m, 1H), 1.40-1.57 (m, 1H), 1.58-1.66 (m, 1H), 1.68-1.83 (m, 2H), 2.19-2.36 (m, 1H), 2.39-2.54 (m, 1H), 3.05-3.18 (m, 2H), 3.90-3.95 (m, 1H), 4.30 (d, J=15.2 Hz, 1H), 4.42 (d, J=5.8 Hz, 1H), 4.48 (d, J=2.8 Hz, 1H), 5.06 (d, J=15.2 Hz, 1H), 7.27-7.35 (m, 5H).

LC-MS (METCR1410): 69% (UV), Rt=0.95 min, m/z (ESI$^+$)=317.1 [M+H]$^+$

General Procedure 4 (General Scheme 13b): Oxidation

General Method 4 is Same as for Scheme 13

2-[1-(Cyclohexylmethyl)-5-oxopyrrolidin-2-yl]-N-(cyclopropylmethyl)-2-oxoacetamide (FP 202)

The title compound was synthesised from 2-[1-(cyclohexylmethyl)-5-oxopyrrolidin-2-yl]-N-(cyclopropylmethyl)-2-hydroxyacetamide (I-347) in a similar manner to general procedure 4 (general scheme 13a) as an off-white solid (22 mg, 100% purity, 22%) after purification by preparative LC (acidic pH, standard elution method).

$^1$H NMR (500 MHz, Chloroform-d) δ 0.23-0.30 (m, 2H), 0.55-0.61 (m, 2H), 0.85-1.04 (m, 3H), 1.11-1.24 (m, 3H), 1.43-1.54 (m, 1H), 1.57-1.66 (m, 3H), 1.67-1.74 (m, 2H), 1.95-2.03 (m, 1H), 2.29-2.52 (m, 3H), 2.54 (dd, J=6.0, 14.0 Hz, 1H), 3.16-3.22 (m, 2H), 3.62 (dd, J=9.0, 14.0 Hz, 1H), 5.22 (dd, J=3.0, 10.0 Hz, 1H), 7.00-7.10 (br. s, 1H).

LC-MS (MET-uPLC-AB-102): 100% (UV), Rt=3.06 min, m/z (ESI$^+$)=307.2 [M+H]$^+$

2-{1-[(4-Chlorophenyl)methyl]-5-oxopyrrolidin-2-yl}-N-(cyclopropylmethyl)-2-oxoacetamide (FP 203)

The title compound was synthesised from 2-{1-[(4-chlorophenyl)methyl]-5-oxopyrrolidin-2-yl}-N-(cyclopropylmethyl)-2-hydroxyacetamide (I-348) in a similar manner to general procedure 4 (general scheme 13a) as a colourless viscous oil (28 mg, 96% purity, 24%) after purification by preparative LC (acidic pH, standard elution method).

$^1$H NMR (500 MHz, Chloroform-d) δ 0.20-0.28 (m, 2H), 0.54-0.61 (m, 2H), 0.90-1.03 (m, 1H), 1.93-2.02 (m, 1H), 2.38-2.48 (m, 3H), 3.07-3.19 (m, 2H), 3.97 (d, J=15.0 Hz, 1H), 4.93 (d, J=15.0 Hz, 1H), 4.95-5.02 (m, 1H), 6.87-6.97 (br. s, 1H), 7.07-7.13 (m, 2H), 7.25-7.29 (m, 2H).

LC-MS (MET-uPLC-AB-102): 96% (UV), Rt=2.96 min, m/z (ESI$^+$)=335.1/336.1 [M+H]$^+$

2-(1-Benzyl-6-oxopiperidin-2-yl)-N-(cyclopropylmethyl)-2-oxoacetamide (FP 204)

The title compound was synthesised from 2-(1-benzyl-6-oxopiperidin-2-yl)-N-(cyclopropylmethyl)-2-hydroxyacetamide (I-349) in a similar manner to general procedure 4 (general scheme 13a) as an off-white solid (62 mg, 100% purity, 39%) after purification by flash column chromatography on normal phase silica (10 g SNAP KP-SIL cartridge, 0-70% EtOAc in heptane gradient) followed by preparative LC (acidic pH, standard elution method).

$^1$H NMR (500 MHz, Chloroform-d) δ 0.20-0.27 (m, 2H), 0.53-0.61 (m, 2H), 0.91-1.00 (m, 1H), 1.47-1.56 (m, 1H), 1.70-1.80 (m, 1H), 2.02-2.19 (m, 2H), 2.39-2.50 (m, 1H), 2.50-2.59 (m, 1H), 3.04-3.19 (m, 2H), 3.88 (d, J=14.8 Hz, 1H), 5.09-5.19 (m, 2H), 6.82-6.91 (br. s, 1H), 7.16-7.21 (m, 2H), 7.22-7.31 (m, 3H).

LC-MS (MET-uPLC-AB-101): 100% (UV), Rt=2.63 min, m/z (ESI$^+$)+=315.1 [M+H]$^+$

Compounds Synthesised Using the Method Described in General Scheme 15 (FP 205-FP 214)

General Procedure 1 (General Scheme 15): Regioselective Epoxide Opening

3-Amino-N-(cyclohexylmethyl)-2-hydroxybutanamide (I-350)

The title compound was synthesised from N-(cyclohexylmethyl)-3-methyl-oxirane-2-carboxamide (I-34) in a similar manner to method D, general procedure 1 (general scheme 15) as an off-white crystalline solid (1.94 g, 100% purity, quantitative) after purification by flash column chromatography on normal phase silica (50 g SNAP Ultra cartridge, 0-15% 7N methanolic ammonia in DCM gradient).

$^1$H NMR (250 MHz, Chloroform-d) δ 0.81-1.02 (m, 2H), 1.04 (d, J=6.5 Hz, 3H), 1.10-1.31 (m, 3H), 1.38-1.54 (m, 1H), 1.58-1.79 (m, 5H), 2.95-3.22 (m, 2H), 3.22-3.39 (m, 1H), 3.88 (d, J=4.8 Hz, 1H), 7.30 (s, 1H).

LC-MS (METCR1410): 100% (UV), Rt=0.71 min, m/z (ESI$^+$)=215.6 [M+H]$^+$

3-Amino-N-(cyclohexylmethyl)-2-hydroxyhexanamide (I-351)

The title compound was synthesised from N-(cyclohexylmethyl)-3-propyloxirane-2-carboxamide (I-44) in a similar manner to method D, general procedure 1 (general scheme 15) as an orange powder (2.00 g, 90% purity by 1H NMR, 65%) after purification by trituration in EtOAc.

$^1$H NMR (500 MHz, Chloroform-d) δ 0.90-0.94 (m, 4H), 1.10-1.33 (m, 6H), 1.40-1.60 (m, 3H), 1.62-1.68 (m, 1H), 1.69-1.75 (m, 4H), 3.04-3.18 (m, 3H), 3.88 (d, J=5.6 Hz, 1H), 7.45-7.58 (m 1H).

LC-MS (METCR1410): 40% (UV), Rt=0.82 min, m/z (ESI$^+$)=243.2 [M+H]$^+$

3-Amino-N-(cyclohexylmethyl)-2-hydroxypentanamide (I-352)

The title compound was synthesised from N-(cyclohexylmethyl)-3-ethyloxirane-2-carboxamide (I-45) in a similar manner to method D, general procedure 1 (general scheme 15) as an off-white powder (1.54 g, 87% purity, 62%) after purification by flash column chromatography on normal phase silica (50 g SNAP KP-SIL cartridge, 0-10% 7N methanolic ammonia in DCM gradient).

$^1$H NMR (500 MHz, DMSO-d6) δ 0.77-0.92 (m, 5H), 1.05-1.21 (m, 3H), 1.30-1.53 (m, 3H), 1.55-1.70 (m, 5H), 2.66-2.72 (m, 1H), 2.85-2.98 (m, 2H), 3.73 (d, J=3.9 Hz, 1H), 5.35 (br. s, 1H), 7.69 (t, J=5.7 Hz, 1H).

LC-MS (METCR0990): 87% (UV), Rt=1.51 min, m/z (ESI$^+$)=229.4 [M+H]$^+$

General Procedure 2a (General Scheme 15): Capping

Method B

N-(Cyclohexylmethyl)-2-hydroxy-3-[(pyridin-4-yl)formamido]butanamide (I-353)

The title compound was synthesised from 3-amino-N-(cyclohexylmethyl)-2-hydroxybutanamide (I-350) in a similar manner to method B, general procedure 2a (general scheme 15) as an off-white powder (110 mg, 100% purity, 49%) after work-up. The crude material was used in the next step without further purification.

$^1$H NMR (500 MHz, DMSO-d6) δ 0.75-0.94 (m, 2H), 1.05 (d, J=6.9 Hz, 3H), 1.07-1.21 (m, 3H), 1.35-1.49 (m, 1H), 1.52-1.67 (m, 5H), 2.89 (dt, J=6.3, 12.9 Hz, 1H), 2.99 (dt, J=6.7, 13.2 Hz, 1H), 4.09 (dd, J=3.6, 5.7 Hz, 1H), 4.36 (td, J=3.6, 7.3 Hz, 1H), 5.76 (d, J=5.7 Hz, 1H), 7.73 (t, J=6.2 Hz, 1H), 7.75-7.81 (m, 2H), 8.40 (d, J=7.9 Hz, 1H), 8.61-8.75 (m, 2H).

LC-MS (METCR1410): 100% (UV), Rt=0.88 min, m/z (ESI$^+$)=320.1 [M+H]$^+$

N-(Cyclohexylmethyl)-2-hydroxy-3-[(pyridin-4-yl)formamido]pentanamide (I-354)

The title compound was synthesised from 3-amino-N-(cyclohexylmethyl)-2-hydroxypentanamide (I-352) in a similar manner to method B, general procedure 2a (general scheme 15) as an off-white powder (89 mg, 100% purity, 47%) after work-up. The crude material was used in the next step without further purification.

$^1$H NMR (500 MHz, DMSO-d6) δ 0.77-0.89 (m, 5H), 1.03-1.19 (m, 3H), 1.35-1.46 (m, 2H), 1.53-1.69 (m, 6H), 2.87-2.98 (m, 2H), 4.03 (d, J=4.1 Hz, 1H), 4.16-4.23 (m, 1H), 7.74 (t, J=6.0 Hz, 1H), 7.76-7.81 (m, 2H), 8.37 (d, J=8.5 Hz, 1H), 8.68-8.74 (m, 2H).

LC-MS (METCR0990): 100% (UV), Rt=1.52 min, m/z (ESI$^+$)=334.3 [M+H]$^+$

Method D: Formation of Acid Chloride In Situ

3-[(2-Chloro-6-methoxyphenyl)formamido]-N-(cyclopropylmethyl)-2-hydroxybutanamide (I-355)

The title compound was synthesised from 3-amino-N-(cyclopropylmethyl)-2-hydroxybutanamide (I-250) in a similar manner to method D, general procedure 2a (general scheme 15) as an off-white solid (76 mg, 86% purity, 33%) after work-up. The crude material was used in the next step without further purification.

$^1$H NMR (250 MHz, Chloroform-d) δ 0.14-0.27 (m, 2H), 0.45-0.57 (m, 2H), 0.87-1.03 (m, 1H), 1.36 (d, J=7.03 Hz, 3H), 3.00-3.30 (m, 2H), 3.83 (s, 3H), 4.33-4.51 (m, 2H), 4.98 (d, J=5.02 Hz, 1H), 6.14-6.28 (m, 1H), 6.79-6.85 (m, 1H), 6.87-6.96 (m, 1H), 6.99 (dd, J=0.75, 8.12 Hz, 1H), 7.23-7.32 (m, 1H).

LC-MS (METCR1410): 86% (UV), Rt=0.96 min, m/z (ESI$^+$)=341.1/343.1 [M+H]$^+$

Method E: HATU Coupling

N-(Cyclohexylmethyl)-2-hydroxy-3-[(4-methylpyridin-3-yl)formamido]butanamide (I-356)

The title compound was synthesised from 3-amino-N-(cyclohexylmethyl)-2-hydroxybutanamide (I-350) in a similar manner to method E, general procedure 2a (general scheme 15) as an off-white solid (112 mg, 93% purity, 67%) after work-up. The crude material was used in the next step without further purification.

$^1$H NMR (500 MHz, DMSO-d6) δ 0.81-0.90 (m, 2H), 1.01 (d, J=6.9 Hz, 3H), 1.11-1.21 (m, 3H), 1.40-1.49 (m, 1H), 1.57-1.69 (m, 5H), 2.35 (s, 3H), 2.88-3.03 (m, 2H), 4.10 (dd, J=3.6, 5.7 Hz, 1H), 4.30-4.37 (m, 1H), 5.74 (d, J=5.8 Hz, 1H), 7.27 (d, J=5.0 Hz, 1H), 7.74 (t, J=6.1 Hz, 1H), 8.23 (d, J=8.0 Hz, 1H), 8.45 (d, J=5.0 Hz, 1H), 8.51 (s, 1H).

LC-MS (METCR1410): 93% (UV), Rt=0.86 min, m/z (ESI$^+$)=334.1 [M+H]$^+$

N-(Cyclohexylmethyl)-2-hydroxy-3-[2-(piperidin-1-yl)acetamido]pentanamide (I-357)

The title compound was synthesised from 3-amino-N-(cyclohexylmethyl)-2-hydroxypentanamide (I-352) in a similar manner to method E, general procedure 2a (general scheme 15) as an off-white powder (133 mg, 100% purity, 66%) after purification by preparative LC (basic pH, early elution method).

$^1$H NMR (500 MHz, DMSO-d6) δ 0.78 (t, J=7.4 Hz, 3H), 0.81-0.91 (m, 2H), 1.06-1.21 (m, 3H), 1.30-1.47 (m, 5H), 1.47-1.57 (m, 4H), 1.58-1.70 (m, 5H), 2.34-2.43 (m, 4H), 2.82-2.90 (m, 2H), 2.93 (t, J=6.5 Hz, 2H), 3.87-3.93 (m, 1H), 3.98-4.05 (m, 1H), 5.71-5.79 (m, 1H), 7.41 (d, J=9.4 Hz, 1H), 7.74 (t, J=6.0 Hz, 1H).

LC-MS (METCR1602): 100% (UV), Rt=0.63 min, m/z (ESI$^+$)=354.4 [M+H]$^+$

N-(Cyclohexylmethyl)-2-hydroxy-3-[(pyridin-3-yl)formamido]pentanamide (I-358)

The title compound was synthesised from 3-amino-N-(cyclohexylmethyl)-2-hydroxypentanamide (I-352) in a similar manner to method E, general procedure 2a (general scheme 15) as an off-white powder (129 mg, 99% purity, 67%) after purification by preparative LC (basic pH, early elution method).

$^1$H NMR (500 MHz, DMSO-d6) δ 0.78-0.91 (m, 5H), 1.04-1.17 (m, 3H), 1.36-1.47 (m, 2H), 1.53-1.66 (m, 6H), 2.86-3.00 (m, 2H), 4.04 (dd, J=4.1, 5.8 Hz, 1H), 4.17-4.24 (m, 1H), 5.71-5.76 (m, 1H), 7.48-7.52 (m, 1H), 7.71 (t, J=6.1 Hz, 1H), 8.20 (dt, J=1.9, 7.9 Hz, 1H), 8.24 (d, J=8.6 Hz, 1H), 8.69 (dd, J=1.6, 4.8 Hz, 1H), 9.02 (d, J=2.1 Hz, 1H).

LC-MS (METCR1602): 99% (UV), Rt=0.51 min, m/z (ESI$^+$)=334.3 [M+H]$^+$

N-(Cyclohexylmethyl)-2-hydroxy-3-[(4-methylpyridin-3-yl)formamido]pentanamide (I-359)

The title compound was synthesised from 3-amino-N-(cyclohexylmethyl)-2-hydroxypentanamide (I-352) in a similar manner to method E, general procedure 2a (general scheme 15) as an off-white powder (119 mg, 99% purity, 59%) after purification by precipitation from 1:1 MeCN/H$_2$O. The crude material was used in the next step without further purification.

¹H NMR (500 MHz, DMSO-d6) δ 0.87 (t, J=7.4 Hz, 5H), 1.12 (q, J=11.1, 11.7 Hz, 3H), 1.36-1.54 (m, 3H), 1.56-1.69 (m, 5H), 2.35 (s, 3H), 2.89-3.00 (m, 2H), 4.03 (dd, J=4.2, 5.9 Hz, 1H), 4.13-4.20 (m, 1H), 5.74 (d, J=5.9 Hz, 1H), 7.27 (d, J=5.0 Hz, 1H), 7.72 (t, J=6.0 Hz, 1H), 8.15 (d, J=8.7 Hz, 1H), 8.45 (d, J=5.0 Hz, 1H), 8.50 (s, 1H).

LC-MS (METCR1602): 99% (UV), Rt=0.52 min, m/z (ESI⁺)=348.2 [M+H]⁺

N-(Cyclohexylmethyl)-2-hydroxy-3-[2-(4-methylpiperazin-1-yl)acetamido]hexanamide (I-360)

The title compound was synthesised from 3-amino-N-(cyclohexylmethyl)-2-hydroxyhexanamide (I-351) in a similar manner to method E, general procedure 2a (general scheme 15) as an orange viscous oil (300 mg, 30% purity, 38%) after purification by flash column chromatography on normal phase silica (25 g SNAP KP-SIL catridge, 0-100% EtOAc in heptane gradient then 0-20% MeOH in EtOAc gradient).

LC-MS (METCR1410): 30% (UV), Rt=3.34 min, m/z (ESI⁺)=383.2 [M+H]⁺

Method G: T3P Coupling with Carboxylic Acid

N-(Cyclohexylmethyl)-2-hydroxy-3-{[1-(2,2,2-trifluoroethyl)piperidin-4-yl]formamido}-butanamide (I-361)

To a solution of 1-(2,2,2-trifluoroethyl)piperidine-4-carboxylic acid (100 mg, 0.47 mmol) and 3-amino-N-(cyclohexylmethyl)-2-hydroxybutanamide (I-350), 203 mg, 0.95 mmol) in DMF (3 mL) was added DIPEA (167 µl, 0.95 mmol) followed by T3P (50% w/w in DMF, 0.7 mL, 1.18 mmol) and the mixture was stirred at RT for 1 h. The mixture was diluted with EtOAc (10 mL) and washed sequentially with saturated NaHCO₃(10 mL), water (10 mL) and brine (10 mL). The organic layer was separated, dried over sodium sulfate and concentrated in vacuo. The residue was purified by flash column chromatography on normal phase silica (25 g SNAP KP-SIL cartridge, 0-10% MeOH in DCM gradient) to afford 93 mg of N-(cyclohexylmethyl)-2-hydroxy-3-{[1-(2,2,2-trifluoroethyl)piperidin-4-yl]formamido} butanamide (I-361) as a colourless powder (95% purity by ¹H NMR, 46%).

¹H NMR (250 MHz, Chloroform-d) δ 0.79-1.07 (m, 3H), 1.07-1.29 (m, 4H), 1.36 (d, J=7.1 Hz, 3H), 1.42-1.52 (m, 1H), 1.70-1.83 (m, 7H), 2.04-2.18 (m, 1H), 2.41 (td, J=4.7, 11.0 Hz, 2H), 2.94-3.15 (m, 6H), 4.08-4.24 (m, 2H), 5.74 (dd, J=6.3, 130.0 Hz, 2H), 6.98 (t, J=6.5 Hz, 1H).

LC-MS (METCR1410): 93% (UV), Rt=0.93 min, m/z (ESI⁺)=408.2 [M+H]⁺

N-(Cyclohexylmethyl)-3-[2-(dimethylamino)acetamido]-2-hydroxyhexanamide (I-362)

The title compound was synthesised from 3-amino-N-(cyclohexylmethyl)-2-hydroxyhexanamide (I-351) in a similar manner to method G, general procedure 2a (general scheme 15) as an off-white powder (185 mg, 50% purity by 1H NMR, 34%) after purification by flash column chromatography on normal phase silica (10 g SNAP KP-SIL cartridge, 0-100% EtOAc in heptane gradient).

¹H NMR (500 MHz, Chloroform-d) δ 0.93 (d, J=4.5 Hz, 4H), 1.15-1.24 (m, 3H), 1.32 (ddt, J=3.8, 7.4, 14.9 Hz, 1H), 1.37-1.50 (m, 2H), 1.58-1.76 (m, 6H), 1.89 (dtd, J=5.0, 10.0, 14.9 Hz, 1H), 2.32 (s, 6H), 3.00 (d, J=4.0 Hz, 2H), 3.06-3.23 (m, 4H), 4.00 (dt, J=5.1, 10.1 Hz, 1H), 4.22 (s, 1H), 5.83 (s, 1H), 7.03 (d, J=15.1 Hz, 1H), 7.55 (d, J=6.7 Hz, 1H).

LC-MS (METCR1410): 35% (UV), Rt=0.88 min, m/z (ESI⁺)=328.8 [M+H]⁺

General Procedure 3a (General Scheme 15): Oxidation

Method A

N-(Cyclohexylmethyl)-2-oxo-3-[(pyridin-4-yl)formamido]butanamide (FP 205)

The title compound was synthesised from N-(cyclohexylmethyl)-2-hydroxy-3-[(pyridin-4-yl)formamido]butanamide (I-353) in a similar manner to method A, general procedure 3a (general scheme 15) as an off-white powder (69 mg, 99% purity, 62%) after purification by flash chromatography on normal phase silica (10 g SNAP KP-SIL cartridge, 1-8% MeOH in DCM gradient).

¹H NMR (500 MHz, DMSO-d6) δ 0.77-0.89 (m, 2H), 1.02-1.16 (m, 3H), 1.39 (d, J=7.3 Hz, 3H), 1.41-1.50 (m, 1H), 1.54-1.63 (m, 5H), 2.88-3.04 (m, 2H), 5.04-5.17 (m, 1H), 7.72-7.83 (m, 2H), 8.63 (t, J=6.1 Hz, 1H), 8.71-8.78 (m, 2H), 9.15 (d, J=6.2 Hz, 1H).

LC-MS (MET-uPLC-AB-102): 99% (UV), Rt=2.61 min, m/z (ESI⁺)=318.2 [M+H]⁺

N-(Cyclohexylmethyl)-2-oxo-3-{[1-(2,2,2-trifluoroethyl)piperidin-4-yl]formamido}-butanamide (FP 206)

The title compound was synthesised from N-(cyclohexylmethyl)-2-hydroxy-3-{[1-(2,2,2-trifluoroethyl)piperidin-4-yl]formamido}butanamide (I-361) in a similar manner to method A, general procedure 3a (general scheme 15) as a colourless powder (61 mg, 98% purity by ¹H NMR, 67%) after purification by flash chromatography on normal phase silica (10 g SNAP KP-SIL cartridge, 0-5% MeOH in DCM gradient) followed by trituration in DCM.

¹H NMR (500 MHz, Chloroform-d) δ 0.91-0.98 (m, 2H), 1.12-1.27 (m, 4H), 1.44 (d, J=7.2 Hz, 3H), 1.47-1.53 (m, 1H), 1.70-1.84 (m, 8H), 2.10-2.16 (m, 1H), 2.40 (td, J=2.8, 11.4 Hz, 2H), 2.94-3.01 (m, 4H), 3.13-3.17 (m, 2H), 5.23 (p, J=7.2 Hz, 1H), 6.16 (d, J=6.8 Hz, 1H), 6.90 (bs, 1H).

LC-MS (METCR1416): 100% (UV), Rt=3.25-3.50 min, m/z (ESI⁺)=406.2 [M+H]⁺

N-(Cyclohexylmethyl)-3-[2-(dimethylamino)acetamido]-2-oxohexanamide (FP 207)

The title compound was synthesised from N-(cyclohexylmethyl)-3-[2-(dimethylamino)acetamido]-2-hydroxyhexanamide (I-362) in a similar manner to method A, general procedure 3a (general scheme 15) as a colourless viscous oil (22 mg, 95% purity by ¹H NMR, 23%) after purification by flash chromatography on normal phase silica (10 g SNAP KP-SIL cartridge, 0-100% EtOAc in heptane gradient then 0-20% MeOH in EtOAc gradient).

¹H NMR (500 MHz, Chloroform-d) δ 0.90-0.99 (m, 5H), 1.10-1.27 (m, 4H), 1.38-1.45 (m, 2H), 1.46-1.54 (m, 1H), 1.58-1.67 (m, 2H), 1.68-1.75 (m, 3H), 1.93-2.01 (m, 1H), 2.35 (s, 6H), 2.92-3.10 (m, 2H), 3.10-3.20 (m, 2H), 5.31 (td, 1H), 6.86-6.95 (m, 1H), 7.60-7.69 (m, 1H).

LC-MS (METCR1603): 93% (UV), Rt=4.45 min, m/z (ESI⁺)=326.4 [M+H]⁺

N-(Cyclohexylmethyl)-2-oxo-3-[(pyridin-4-yl)formamido]pentanamide (FP 208)

The title compound was synthesised from N-(cyclohexylmethyl)-2-hydroxy-3-[(pyridin-4-yl)formamido]pentanamide (I-354) in a similar manner to method A, general procedure 3a (general scheme 15) as an off-white powder (45 mg, 97% purity, 49%) after purification by flash chromatography on normal phase silica (10 g SNAP KP-SIL cartridge, 0-5% MeOH in DCM gradient) followed by trituration in Et$_2$O.

$^1$H NMR (500 MHz, DMSO-d6) δ 0.77-0.89 (m, 2H), 0.98 (t, J=7.4 Hz, 3H), 1.02-1.16 (m, 3H), 1.40-1.51 (m, 1H), 1.52-1.64 (m, 5H), 1.63-1.76 (m, 1H), 1.84-1.96 (m, 1H), 2.90-3.03 (m, 2H), 5.00 (ddd, J=4.4, 6.7, 9.4 Hz, 1H), 7.74-7.80 (m, 2H), 8.64 (t, J=6.2 Hz, 1H), 8.71-8.77 (m, 2H), 9.06 (d, J=6.7 Hz, 1H).

LC-MS (MET-uPLC-AB-102): 97% (UV), Rt=2.92 min, m/z (ESI$^+$)=332.2 [M+H]$^+$

N-(Cyclohexylmethyl)-3-[(4-methylpyridin-3-yl)formamido]-2-oxobutanamide (FP 209)

The title compound was synthesised from N-(cyclohexylmethyl)-2-hydroxy-3-[(4-methylpyridin-3-yl)formamido]butanamide (I-356) in a similar manner to method A, general procedure 3a (general scheme 15) using 8:1 DCM:DMSO as solvent to give an off-white powder (42 mg, 96% purity, 23%) after purification by flash chromatography on normal phase silica (10 g SNAP KP-SIL cartridge, 0-100% EtOAc in heptane gradient then 0-10% MeOH in EtOAc gradient).

$^1$H NMR (500 MHz, Chloroform-d) δ 0.91-1.01 (m, 2H), 1.11-1.28 (m, 3H), 1.48-1.56 (m, 1H), 1.59 (d, J=7.2 Hz, 3H), 1.62-1.77 (m, 5H), 2.47 (s, 3H), 3.13-3.22 (m, 2H), 5.49 (p, J=7.2 Hz, 1H), 6.55 (d, J=6.9 Hz, 1H), 6.92-7.00 (m, 1H), 7.17 (d, J=5.1 Hz, 1H), 8.52 (d, J=5.0 Hz, 1H), 8.64 (s, 1H).

LC-MS (MET-uPLC-AB-102): 96% (UV), Rt=2.73 min, m/z (ESI$^+$)=332.3 [M+H]$^+$

N-(Cyclohexylmethyl)-2-oxo-3-[(pyridin-3-yl)formamido]pentanamide (FP 210)

The title compound was synthesised from N-(cyclohexylmethyl)-2-hydroxy-3-[(pyridin-3-yl)formamido]pentanamide (I-358) in a similar manner to method A, general procedure 3a (general scheme 15) as an off-white powder (71 mg, 97% purity, 58%) after purification by flash chromatography on normal phase silica (10 g SNAP KP-SIL cartridge, 0-10% MeOH in EtOAc gradient) followed by trituration in Et$_2$O.

$^1$H NMR (500 MHz, DMSO-d6) δ 0.77-0.88 (m, 2H), 0.99 (t, J=7.4 Hz, 3H), 1.03-1.16 (m, 3H), 1.40-1.50 (m, 1H), 1.51-1.64 (m, 5H), 1.65-1.75 (m, 1H), 1.85-1.95 (m, 1H), 2.92-3.01 (m, 2H), 4.99 (ddd, J=4.4, 6.7, 9.4 Hz, 1H), 7.53 (ddd, J=0.8, 4.8, 7.9 Hz, 1H), 8.20 (dt, J=1.8, 8.0 Hz, 1H), 8.64 (t, J=6.1 Hz, 1H), 8.72 (dd, J=1.7, 4.8 Hz, 1H), 8.98 (d, J=6.7 Hz, 1H), 9.02 (dd, J=0.7, 2.3 Hz, 1H).

LC-MS (METCR1603): 97% (UV), Rt=2.90 min, m/z (ESI$^+$)=332.2 [M+H]$^+$

N-(Cyclohexylmethyl)-3-[(4-methylpyridin-3-yl)formamido]-2-oxopentanamide (FP 211)

The title compound was synthesised from N-(cyclohexylmethyl)-2-hydroxy-3-[(4-methylpyridin-3-yl)formamido]pentanamide (I-359) in a similar manner to method A, general procedure 3a (general scheme 15) as an off-white powder (21 mg, 98% purity, 18%) after purification by flash chromatography on normal phase silica (10 g SNAP KP-SIL cartridge, 0-10% MeOH in EtOAc gradient) followed by trituration in Et$_2$O.

$^1$H NMR (500 MHz, DMSO-d6) δ 0.80-0.92 (m, 2H), 0.98 (t, J=7.4 Hz, 3H), 1.06-1.20 (m, 3H), 1.44-1.54 (m, 1H), 1.55-1.68 (m, 6H), 1.82-1.92 (m, 1H), 2.35 (s, 3H), 2.98 (t, J=6.7 Hz, 2H), 5.01 (ddd, J=4.3, 6.8, 9.3 Hz, 1H), 7.30 (d, J=5.0 Hz, 1H), 8.46-8.50 (m, 2H), 8.70 (t, J=6.1 Hz, 1H), 8.87 (d, J=6.8 Hz, 1H).

LC-MS (METCR1603): 98% (UV), Rt=3.04 min, m/z (ESI$^+$)=346.3 [M+H]$^+$

Method C: Addition of DMP at 0° C.

3-[(2-Chloro-6-methoxyphenyl)formamido]-N-(cyclopropylmethyl)-2-oxobutanamide (FP 212)

The title compound was synthesised from 3-[(2-chloro-6-methoxyphenyl)-formamido]-N-(cyclopropylmethyl)-2-hydroxybutanamide (I-355) in a similar manner to method C, general procedure 3a (general scheme 15) using 8:1 DCM:DMSO as solvent to give a yellow gummy solid (21 mg, 94% purity, 31%) after purification by preparative LC (acid pH method, early elution method).

$^1$H NMR (500 MHz, Chloroform-d) δ 0.23-0.27 (m, 2H), 0.54-0.59 (m, 2H), 0.94-1.05 (m, 1H), 1.59 (d, J=7.2 Hz, 3H), 3.19 (ddd, J=3.8, 5.9, 7.2 Hz, 2H), 3.82 (s, 3H), 5.58 (p, J=7.3 Hz, 1H), 6.49 (d, J=7.2 Hz, 1H), 6.80-6.84 (m, 1H), 6.97-7.00 (m, 1H), 7.00-7.03 (m, 1H), 7.24-7.29 (m, 1H).

LC-MS (MET-uPLC-AB-102): 94% (UV), Rt=2.49 min, m/z (ESI$^+$)=339.1/341.0 [M+H]$^+$

Method D: Swern Oxidation

N-(Cyclohexylmethyl)-2-oxo-3-[2-(piperidin-1-yl)acetamido]pentanamide (FP 213)

To a stirred solution of anhydrous DMSO (136 μL, 1.9 mmol) in anhydrous DCM (0.5 mL), under a nitrogen atmosphere, at −78° C. was added oxalyl chloride (81 μL, 0.95 mmol) dropwise. After 15 min, a solution of N-(cyclohexylmethyl)-2-hydroxy-3-[2-(piperidin-1-yl)acetamido]pentanamide (I-357) (67 mg, 0.19 mmol) in anhydrous DCM (0.5 mL) was added dropwise and after a further 15 min, DIPEA (495 μL, 2.84 mmol) was added dropwise then the reaction was stirred 30 min at −78° C. and slowly allowed to warm to RT. The mixture was diluted with DCM (2 mL) and quenched with water (2 mL). The aqueous phase was separated, washed with DCM (2×1 mL) then the organic phases were combined, washed with brine (2 mL) and the mixture filtered through a Telos® hydrophobic frit. The retained aqueous layer was washed with DCM (0.5 mL), the combined organic filtrate was concentrated in vacuo. The residue was purified by preparative LC (basic pH, early elution method) to afford 29 mg of N—[(3-chlorophenyl)methyl]-3-[(2-methoxyphenyl)amino]-2-oxobutanamide) as an off-white powder (95% purity by $^1$H NMR, 41%).

$^1$H NMR (500 MHz, DMSO-d6) δ 0.79-0.91 (m, 5H), 1.06-1.24 (m, 3H), 1.35-1.41 (m, 2H), 1.42-1.69 (m, 11H), 1.77-1.87 (m, 1H), 2.33-2.45 (m, 4H), 2.82-3.01 (m, 4H), 4.92 (td, J=4.7, 8.0 Hz, 1H), 7.95 (d, J=7.6 Hz, 1H), 8.67 (t, J=6.2 Hz, 1H).

LC-MS (METCR1603): 92% (UV), Rt=3.88 min, m/z (ESI$^+$)=352.3 [M+H]$^+$

N-(Cyclohexylmethyl)-3-[2-(4-methylpiperazin-1-yl)acetamido]-2-oxohexanamide (FP 214)

The title compound was synthesised from N-(cyclohexylmethyl)-2-hydroxy-3-[2-(4-methylpiperazin-1-yl)acetamido]hexanamide (I-360) in a similar manner to method D, general procedure 3a (general scheme 15) as a brown viscous oil (30 mg, 95% purity by 1H NMR, 32%) after purification by preparative LC (basic pH, early elution method) followed by ion-exchange flash chromatography (5 g Isolute SCX-2 cartridge, 0-20% MeOH in EtOAc gradient then 0-10% 7N methanolic ammonia in EtOAc gradient).

$^1$H NMR (500 MHz, Chloroform-d) δ 0.91-0.97 (m, 5H), 1.11-1.26 (m, 4H), 1.33-1.41 (m, 2H), 1.43-1.54 (m, 1H), 1.61-1.74 (m, 5H), 1.92-2.02 (m, 1H), 2.34 (s, 3H), 2.47-2.66 (m, 8H), 2.97-3.09 (m, 2H), 3.11-3.17 (m, 2H), 5.29 (td, J=4.5, 8.3 Hz, 1H), 6.87-6.98 (m, 1H), 7.62-7.70 (m, 1H).

LC-MS (METCR1603): 79% (UV), Rt=3.23 min, m/z (ESI$^+$)=381.3 [M+H]$^+$

Compounds Synthesised Using the Method Described in General Scheme 19 (FP 215-FP 223)

General Procedure 1 (General Scheme 19): Sulfonamide Formation

3-(4-Chlorobenzenesulfonamido)-N-(cyclopropylmethyl)-2-hydroxybutanamide (I-363)

The title compound was synthesised from 3-amino-N-(cyclopropylmethyl)-2-hydroxybutanamide (I-279) in a similar manner to general procedure 1 (general scheme 19) as an off-white crystalline solid (80 mg, 87% purity, 24%) after purification by flash column chromatography on normal phase silica (10 g SNAP KP-SIL cartridge, 0-100% EtOAc in heptane gradient).

$^1$H NMR (500 MHz, Chloroform-d) δ 0.11-0.23 (m, 2H), 0.44-0.51 (m, 2H), 0.85-0.93 (m, 4H), 3.00-3.18 (m, 2H), 3.79-3.89 (m, 1H), 4.29-4.35 (m, 1H), 4.68-4.85 (m, 1H), 5.90-6.03 (m, 1H), 7.07-7.15 (m, 1H), 7.46 (d, J=8.6 Hz, 2H), 7.86 (d, J=8.6 Hz, 2H).

LC-MS (METCR1410): 87% (UV), Rt=0.99 min, m/z (ESI$^+$)=347.0/349.1 [M+H]$^+$

3-Benzenesulfonamido-N-cyclopropylmethyl)-2-hydroxypentanamide (I-364)

The title compound was synthesised from 3-amino-N-(cyclopropylmethyl)-2-hydroxypentanamide (I-251) in a similar manner to general procedure 1 (general scheme 19) as an off-white powder (214 mg, 90% purity, 58%) after purification by flash column chromatography on normal phase silica (10 g SNAP KP-SIL cartridge, 0-100% EtOAc in heptane gradient).

$^1$H NMR (500 MHz, Chloroform-d) δ −0.05-0.03 (m, 2H), 0.22-0.31 (m, 2H), 0.40 (t, J=7.4 Hz, 3H), 0.66-0.78 (m, 1H), 1.12-1.33 (m, 2H), 2.81-2.99 (m, 2H), 3.37-3.48 (m, 1H), 4.11 (dd, J=2.6, 5.0 Hz, 1H), 4.68 (d, J=5.5 Hz, 1H), 5.71 (d, J=8.8 Hz, 1H), 7.03 (t, J=5.7 Hz, 1H), 7.26-7.32 (m, 2H), 7.32-7.40 (m, 1H), 7.72-7.79 (m, 2H).

LC-MS (METCR1410): 90% (UV), Rt=0.95 min, m/z (ESI$^+$)=327.4 [M+H]$^+$

3-Benzenesulfonamido-N-(cyclopropylmethyl)-2-hydroxyhexanamide (I-365)

The title compound was synthesised from 3-amino-N-(cyclopropylmethyl)-2-hydroxyhexanamide (I-253) in a similar manner to general procedure 1 (general scheme 19) as an off-white powder (229 mg, 93% purity, 66%) after purification by flash column chromatography on normal phase silica (10 g SNAP KP-SIL cartridge, 0-100% EtOAc in heptane gradient).

$^1$H NMR (500 MHz, Chloroform-d) δ 0.18-0.26 (m, 2H), 0.47-0.56 (m, 2H), 0.63 (t, J=7.3 Hz, 3H), 0.79-0.90 (m, 1H), 0.92-1.01 (m, 1H), 1.03-1.17 (m, 1H), 1.32-1.41 (m, 1H), 1.44-1.55 (m, 1H), 3.08-3.20 (m, 2H), 3.51-3.61 (m, 1H), 3.92 (d, J=6.6 Hz, 1H), 4.25 (dd, J=2.5, 6.6 Hz, 1H), 5.12 (d, J=8.5 Hz, 1H), 6.86-6.93 (m, 1H), 7.49-7.56 (m, 2H), 7.56-7.64 (m, 1H), 7.88-7.95 (m, 2H).

LC-MS (METCR1410): 93% (UV), Rt=1.03 min, m/z (ESI$^+$)=341.2 [M+H]$^+$

3-Benzenesulfonamido-N-(cyclohexylmethyl)-2-hydroxybutanamide (I-366)

The title compound was synthesised from 3-amino-N-(cyclohexylmethyl)-2-hydroxybutanamide (I-350) in a similar manner to general procedure 1 (general scheme 19) as an off-white solid (260 mg, 83% purity, 87%) after purification by flash column chromatography on normal phase silica (10 g SNAP KP-SIL cartridge, 0-100% EtOAc in heptane gradient).

$^1$H NMR (500 MHz, Chloroform-d) δ 0.86-0.95 (m, 2H), 0.97 (d, J=6.9 Hz, 3H), 1.11-1.22 (m, 3H), 1.40-1.47 (m, 2H), 1.62-1.73 (m, 4H), 3.01-3.07 (m, 1H), 3.09-3.15 (m, 1H), 3.74-3.83 (m, 1H), 4.04-4.19 (m, 1H), 4.22-4.30 (m, 1H), 5.35-5.54 (m, 1H), 6.86 (t, J=5.9 Hz, 1H), 7.49-7.53 (m, 2H), 7.56-7.60 (m, 1H), 7.90-7.93 (m, 2H).

LC-MS (METCR1410): 83% (UV), Rt=1.06 min, m/z (ESI$^+$)=355.4 [M+H]$^+$

N-(Cyclopropylmethyl)-3-(4-fluorobenzenesulfonamido)-2-hydroxybutanamide (I-367)

The title compound was synthesised from 3-amino-N-(cyclopropylmethyl)-2-hydroxybutanamide (I-279) in a similar manner to general procedure 1 (general scheme 19) as an off-white solid (280 mg, 89% purity, 65%) after purification by flash column chromatography on normal phase silica (10 g SNAP KP-SIL cartridge, 0-100% EtOAc in heptane gradient).

$^1$H NMR (500 MHz, Chloroform-d) δ 0.17-0.25 (m, 2H), 0.47-0.55 (m, 2H), 0.87-1.01 (m, 4H), 3.03-3.16 (m, 2H), 3.74-3.82 (m, 1H), 4.12 (d, J=6.0 Hz, 1H), 4.26-4.38 (m, 1H), 5.48 (d, J=8.6 Hz, 1H), 6.93 (t, J=5.5 Hz, 1H), 7.14-7.24 (m, 2H), 7.87-7.97 (m, 2H).

LC-MS (METCR1410): 89% (UV), Rt=0.97 min, m/z (ESI$^+$)=331.0 [M+H]$^+$

N-(Cyclopropylmethyl)-2-hydroxy-3-(2-methoxybenzenesulfonamido)butanamide (I-368)

The title compound was synthesised from 3-amino-N-(cyclopropylmethyl)-2-hydroxybutanamide (I-279) in a similar manner to general procedure 1 (general scheme 19) as an off-white solid (210 mg, 75% purity, 40%) after purification by flash column chromatography on normal phase silica (10 g SNAP KP-SIL cartridge, 0-100% EtOAc in heptane gradient).

$^1$H NMR (500 MHz, Chloroform-d) δ 0.12-0.27 (m, 2H), 0.44-0.55 (m, 2H), 0.90-0.97 (m, 1H), 1.00 (d, J=6.9 Hz, 3H), 3.06-3.16 (m, 2H), 3.46 (d, J=5.7 Hz, 1H), 3.58-3.74

(m, 1H), 4.00 (s, 3H), 4.15-4.20 (m, 1H), 5.17 (d, J=7.3 Hz, 1H), 6.65-6.76 (m, 1H), 7.01-7.13 (m, 2H), 7.52-7.62 (m, 1H), 7.88-7.97 (m, 1H).

LC-MS (METCR1410): 75% (UV), Rt=0.92 min, m/z (ESI$^+$)=343.4 [M+H]$^+$

N-(Cyclopropylmethyl)-2-hydroxy-3-(N-methylbenzenesulfonamido)butanamide (I-369)

The title compound was synthesised from N-(cyclopropylmethyl)-2-hydroxy-3-(methylamino)butanamide (I-278) in a similar manner to general procedure 1 (general scheme 19) as an off-white viscous oil (260 mg, 68% purity, 59%) after purification by flash column chromatography on normal phase silica (10 g SNAP KP-SIL cartridge, 0-100% EtOAc in heptane gradient).

$^1$H NMR (500 MHz, Chloroform-d) δ 0.21-0.26 (m, 2H), 0.51-0.56 (m, 2H), 0.84-0.92 (m, 1H), 1.01 (d, J=7.2 Hz, 3H), 2.86 (s, 3H), 3.12-3.17 (m, 2H), 3.77 (d, J=5.1 Hz, 1H), 4.12-4.18 (m, 2H), 6.73-6.85 (m, 1H), 7.52-7.56 (m, 2H), 7.58-7.63 (m, 1H), 7.79-7.84 (m, 2H).

LC-MS (METCR1410): 68% (UV), Rt=0.98 min, m/z (ESI$^+$)=327.4 [M+H]$^+$

3-(N-Benzylmethanesulfonamido)-N-(cyclopropyl-methyl)-2-hydroxybutanamide (I-370)

The title compound was synthesised from 3-(benzylamino)-N-(cyclopropyl-methyl)-2-hydroxybutanamide (I-86) in a similar manner to general procedure 1 (general scheme 19) as a colourless gum (88 mg, 80% purity, 17%) after purification by flash column chromatography on normal phase silica (10 g SNAP KP-SIL cartridge, 20-100% TBME in heptane gradient).

$^1$H NMR (500 MHz, DMSO-d6) δ 0.13-0.21 (m, 2H), 0.32-0.42 (m, 2H), 0.95 (d, J=7.0 Hz, 4H), 2.93 (s, 3H), 2.96 (td, J=3.6, 6.5 Hz, 2H), 4.17-4.28 (m, 2H), 4.52 (s, 2H), 6.01 (d, J=4.9 Hz, 1H), 7.20-7.26 (m, 1H), 7.29-7.39 (m, 4H), 7.96 (t, J=5.8 Hz, 1H).

LC-MS (METCR1410): 80% (UV), Rt=1.00 min, m/z (ESI$^+$)=341.0 [M+H]$^+$

N-(Cyclopropylmethyl)-2-hydroxy-3-{N-[(oxan-4-yl)methyl] methanesulfonamido}-butanamide (I-371)

The title compound was synthesised from N-(cyclopropylmethyl)-2-hydroxy-3-{[(oxan-4-yl)methyl] amino}butanamide (I-319) in a similar manner to general procedure 1 (general scheme 19) as a yellow crystalline solid (136 mg, 86% purity, 36%) after work-up. The crude material was used in the next step without further purification.

LC-MS (METCR1410): 86% (UV), Rt=0.87 min, m/z (ESI$^+$)=349.2 [M+H]$^+$

General Procedure 2 (General Scheme 19): Oxidation

3-(4-Chlorobenzenesulfonamido)-N-(cyclopropylmethyl)-2-oxobutanamide (FP 215)

The title compound was synthesised from 3-(4-chlorobenzenesulfonamido)-N-(cyclopropylmethyl)-2-hydroxybutanamide (I-363) in a similar manner to method B, general procedure 2 (general scheme 19) as a colourless oil (9 mg, 95% purity by $^1$H NMR, 11%) after purification by flash column chromatography on normal phase silica (10 g SNAP KP-SIL cartridge, 0-100% TBME in heptane gradient) followed by preparative LC (acidic pH, standard elution method).

$^1$H NMR (500 MHz, Chloroform-d) δ 0.20-0.24 (m, 2H), 0.53-0.59 (m, 2H), 0.88-0.97 (m, 1H), 1.40 (d, J=7.2 Hz, 3H), 3.05-3.14 (m, 2H), 4.73-4.86 (m, 1H), 5.59 (d, J=9.1 Hz, 1H), 6.80 (br. s, 1H), 7.43-7.47 (m, 2H), 7.75-7.80 (m, 2H).

LC-MS (METCR1600): 91% (UV), Rt=4.22 min, m/z (ESI$^+$)=345.0/347.0 [M+H]$^+$

3-Benzenesulfonamido-N-(cyclopropylmethyl)-2-oxopentanamide (FP 216)

The title compound was synthesised from 3-benzenesulfonamido-N-(cyclopropylmethyl)-2-hydroxypentanamide (I-364) in a similar manner to method B, general procedure 2 (general scheme 19) as an off-white powder (13 mg, 98% purity, 7%) after purification by flash column chromatography on normal phase silica (10 g SNAP KP-SIL cartridge, 0-100% TBME in heptane gradient) followed by preparative LC (acidic pH, standard elution method).

$^1$H NMR (500 MHz, Chloroform-d) δ 0.16-0.22 (m, 2H), 0.49-0.57 (m, 2H), 0.86-0.94 (m, 4H), 1.54-1.67 (m, 1H), 1.80-1.93 (m, 1H), 2.99-3.14 (m, 2H), 4.60-4.69 (m, 1H), 5.56 (d, J=9.8 Hz, 1H), 6.74 (br. s, 1H), 7.43-7.50 (m, 2H), 7.51-7.56 (m, 1H), 7.77-7.86 (m, 2H).

LC-MS (METCR1600): 98% (UV), Rt=4.26 min, m/z (ESI$^+$)=325.1 [M+H]$^+$

3-Benzenesulfonamido-N-(cyclopropylmethyl)-2-oxohexanamide (FP 217)

The title compound was synthesised from 3-benzenesulfonamido-N-(cyclopropylmethyl)-2-hydroxyhexanamide (I-365) in a similar manner to method B, general procedure 2 (general scheme 19) as an off-white powder (17 mg, 100% purity, 7%) after purification by flash column chromatography on normal phase silica (10 g SNAP KP-SIL cartridge, 0-100% TBME in heptane gradient) followed by preparative LC (acidic pH, standard elution method).

$^1$H NMR (500 MHz, Chloroform-d) δ 0.17-0.24 (m, 2H), 0.50-0.59 (m, 2H), 0.86 (t, J=7.3 Hz, 3H), 0.88-0.95 (m, 1H), 1.30-1.45 (m, 2H), 1.47-1.54 (m, 1H), 1.70-1.80 (m, 1H), 3.00-3.14 (m, 2H), 4.63-4.73 (m, 1H), 5.47 (d, J=10.1 Hz, 1H), 6.69 (br. s, 1H), 7.45-7.49 (m, 2H), 7.51-7.57 (m, 1H), 7.80-7.87 (m, 2H).

LC-MS (METCR1600): 100% (UV), Rt=4.52 min, m/z (ESI$^+$)=339.1 [M+H]$^+$

3-Benzenesulfonamido-N-(cyclohexylmethyl)-2-oxobutanamide (FP 218)

The title compound was synthesised from 3-benzenesulfonamido-N-(cyclohexylmethyl)-2-hydroxybutanamide (I-366) in a similar manner to method B, general procedure 2 (general scheme 19) as an off-white powder (61 mg, 98% purity, 28%) after purification by flash column chromatography on normal phase silica (10 g SNAP KP-SIL cartridge, 0-100% TBME in heptane gradient) followed by preparative LC (acidic pH, standard elution method).

$^1$H NMR (500 MHz, Chloroform-d) δ 0.90 (qd, J=3.2, 12.1 Hz, 2H), 1.09-1.27 (m, 3H), 1.39 (d, J=7.2 Hz, 3H), 1.41-1.48 (m, 1H), 1.61-1.69 (m, 3H), 1.70-1.77 (m, 2H), 3.00-3.14 (m, 2H), 4.75-4.85 (m, 1H), 5.53 (d, J=9.3 Hz, 1H), 6.70 (br. s, 1H), 7.45-7.50 (m, 2H), 7.52-7.57 (m, 1H), 7.82-7.86 (m, 2H).

LC-MS (METCR1600): 98% (UV), Rt=4.69 min, m/z (ESI$^+$)=353.1 [M+H]$^+$

N-(Cyclopropylmethyl)-3-(4-fluorobenzenesulfonamido)-2-oxobutanamide (FP 219)

The title compound was synthesised from N-(cyclopropylmethyl)-3-(4-fluorobenzenesulfonamido)-2-hydroxybutanamide (I-367) in a similar manner to method B, general procedure 2 (general scheme 19) as a colourless oil (57 mg, 100% purity, 23%) after purification by flash column chromatography on normal phase silica (50 g SNAP KP-SIL cartridge, 0-100% TBME in heptane gradient) followed by preparative LC (acidic pH, standard elution method).

$^1$H NMR (500 MHz, Chloroform-d) δ 0.16-0.25 (m, 2H), 0.47-0.59 (m, 2H), 0.87-0.97 (m, 1H), 1.38 (d, J=7.3 Hz, 3H), 3.04-3.15 (m, 2H), 4.75-4.84 (m, 1H), 5.67 (d, J=9.3 Hz, 1H), 6.85 (br. s, 1H), 7.12-7.19 (m, 2H), 7.81-7.89 (m, 2H).

LC-MS (METCR1600): 100% (UV), Rt=3.96 min, m/z (ESI$^+$)=329.1 [M+H]$^+$

N-(Cyclopropylmethyl)-3-(2-methoxybenzenesulfonamido)-2-oxobutanamide (FP 220)

The title compound was synthesised from N-(cyclopropylmethyl)-2-hydroxy-3-(2-methoxybenzenesulfonamido) butanamide (I-368) in a similar manner to method B, general procedure 2 (general scheme 19) as a colourless oil (42 mg, 95% purity by $^1$H NMR, 25%) after purification by flash column chromatography on normal phase silica (10 g SNAP KP-SIL cartridge, 0-100% TBME in heptane gradient) followed by preparative LC (acidic pH, standard elution method).

$^1$H NMR (500 MHz, Chloroform-d) δ 0.16-0.24 (m, 2H), 0.49-0.58 (m, 2H), 0.84-0.97 (m, 1H), 1.40 (d, J=7.3 Hz, 3H), 3.03-3.12 (m, 2H), 3.96 (s, 3H), 4.80-4.92 (m, 1H), 5.90 (d, J=8.2 Hz, 1H), 6.80 (br. s, 1H), 6.94-6.98 (m, 1H), 7.02 (td, J=0.9, 7.7 Hz, 1H), 7.45-7.54 (m, 1H), 7.86 (dd, J=1.7, 7.8 Hz, 1H).

LC-MS (METCR1600): 92% (UV), Rt=3.94 min, m/z (ESI$^+$)=341.1 [M+H]$^+$

N-(Cyclopropylmethyl)-3-(N-methylbenzenesulfonamido)-2-oxobutanamide (FP 221)

The title compound was synthesised from N-(cyclopropylmethyl)-2-hydroxy-3-(N-methylbenzenesulfonamido) butanamide (I-369) in a similar manner to method B, general procedure 2 (general scheme 19) as a yellow viscous oil (71 mg, 100% purity, 42%) after purification by preparative LC (acidic pH, early elution method).

$^1$H NMR (500 MHz, Chloroform-d) δ 0.17-0.26 (m, 2H), 0.47-0.58 (m, 2H), 0.89-1.00 (m, 1H), 1.31 (d, J=7.3 Hz, 3H), 2.92 (s, 3H), 3.09-3.20 (m, 2H), 5.47 (q, J=7.3 Hz, 1H), 6.80-6.94 (br. s, 1H), 7.46-7.52 (m, 2H), 7.53-7.58 (m, 1H), 7.75-7.84 (m, 2H).

LC-MS (METCR1600): 100% (UV), Rt=4.34 min, m/z (ESI$^+$)=325.1 [M+H]$^+$

3-(N-Benzylmethanesulfonamido)-N-(cyclopropylmethyl)-2-oxobutanamide (FP 222)

The title compound was synthesised from 3-(N-benzylmethanesulfonamido)-N-(cyclopropylmethyl)-2-hydroxybutanamide (I-370) in a similar manner to method B, general procedure 2 (general scheme 19) as a green powder (82 mg, 100% purity, 76%) after purification by flash column chromatography on normal phase silica (10 g SNAP KP-SIL cartridge, 10-100% EtOAc in heptane gradient).

$^1$H NMR (500 MHz, DMSO-d6) δ 0.18-0.22 (m, 2H), 0.37-0.43 (m, 2H), 0.92-1.01 (m, 1H), 1.26 (d, J=7.2 Hz, 3H), 2.95 (s, 3H), 3.01 (t, J=6.5 Hz, 2H), 4.39 (d, J=16.4 Hz, 1H), 4.53 (d, J=16.3 Hz, 1H), 5.13 (q, J=7.2 Hz, 1H), 7.25-7.29 (m, 1H), 7.30-7.40 (m, 4H), 8.77 (t, J=5.9 Hz, 1H).

LC-MS (METCR1603): 100% (UV), Rt=4.27 min, m/z (ESI$^+$)=339.2 [M+H]$^+$

N-(Cyclopropylmethyl)-3-{N-[(oxan-4-yl)methyl]methanesulfonamido}-2-oxobutanamide (FP 223)

The title compound was synthesised from N-(cyclopropylmethyl)-2-hydroxy-3-{N-[(oxan-4-yl)methyl]methanesulfonamido}butanamide (I-371) in a similar manner to method B, general procedure 2 (general scheme 19) as a yellow viscous oil (55 mg, 98% purity, 47%) after purification by preparative LC (acidic pH, standard elution method) followed by flash column chromatography on normal phase silica (5 g Biotage Flash Si II cartridge, 20-100% EtOAc in heptane gradient).

$^1$H NMR (500 MHz, DMSO-d6) δ 0.13-0.21 (m, 2H), 0.36-0.41 (m, 2H), 0.90-0.99 (m, 1H), 1.02-1.16 (m, 2H), 1.35 (d, J=7.1 Hz, 3H), 1.58-1.66 (m, 2H), 1.79-1.88 (m, 1H), 2.97 (s, 3H), 2.98-3.06 (m, 4H), 3.22-3.29 (m, 2H), 3.78-3.87 (m, 2H), 5.00 (q, J=7.1 Hz, 1H), 8.70 (t, J=5.9 Hz, 1H).

LC-MS (MET-uPLC-AB-102): 98% (UV), Rt=2.44 min, m/z (ESI$^+$)=347.2 [M+H]$^+$

Route to Oxopyrrolidines: Synthesis of Final Products (FP 224-FP 369)

GENERAL SCHEME 20
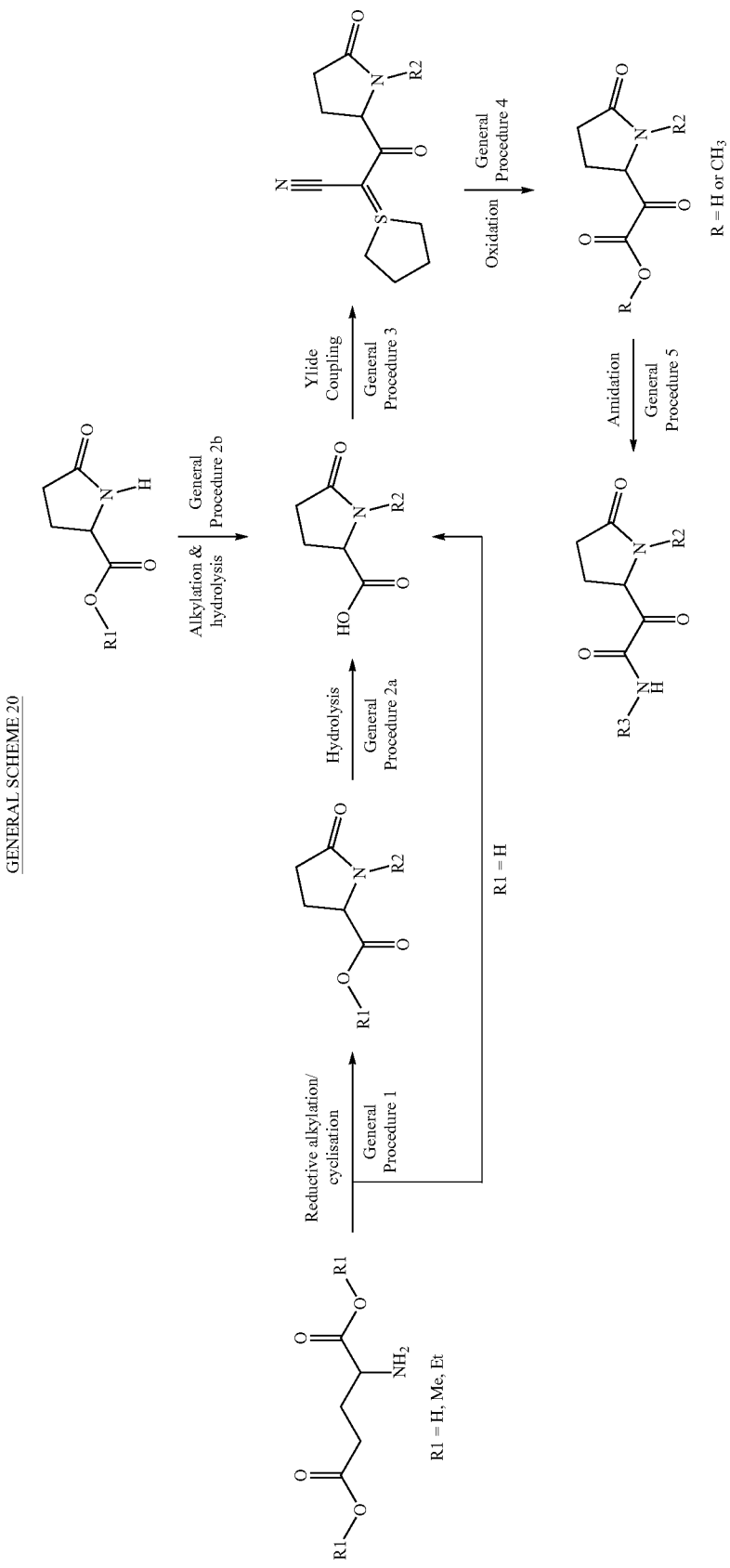

General Procedure 1 (General Scheme 20): Reductive Amination/Cyclisation

Method A: Cyclisation of Glutamic Acids Using Sodium Borohydride

1-[(4-Methyl-1,3-thiazol-2-yl)methyl]-5-oxopyrrolidine-2-carboxylic acid (I-372)

Glutamic acid monohydrate (5.9 g, 35.73 mmol) was dissolved in 2M NaOH for 4 h. The mixture was washed with EtOAc (3×20 mL), the aqueous layer was acidified to ~pH 4 using concentrated HCl and the resultant precipitate filtered off, washed with $Et_2O$ (70 mL) and air dryed overnight. The solid was suspended in EtOH (30 mL) and concentrated in vacuo. The residue was azeotroped 3 more times with EtOH (3×30 mL) then suspended in EtOH (85 mL) and stirred at reflux for 5 h. The reaction mixture was then allowed to cool to RT and concentrated in vacuo to give 6.07 g of 1-[(4-methyl-1,3-thiazol-2-yl)methyl]-5-oxopyrrolidine-2-carboxylic acid (I-372) as an orange solid (100% purity, 71%) which was used in general procedure 3 without further purification.

$^1$H NMR (500 MHz, Chloroform-d) δ 2.15-2.25 (m, 1H), 2.29-2.42 (m, 2H), 2.43 (s, 3H), 2.48-2.59 (m, 1H), 4.13-4.21 (m, 1H), 4.62 (d, J=15.5 Hz, 1H), 5.29 (d, J=15.5 Hz, 1H), 6.91 (s, 1H).

LC-MS (METCR1410): 100% (UV), Rt=0.68 min, m/z (ESI$^+$)=241.1 [M+H]$^+$

1-Benzyl-5-oxopyrrolidine-2-carboxylic acid (I-373)

The title compound was synthesised in a similar manner to method A, general procedure 1 (general scheme 20) as an off-white solid (6.13 g, 98% purity, 75%) which was used in general procedure 3 without further purification.

$^1$H NMR (500 MHz, Chloroform-d) δ 2.14-2.21 (m, 1H), 2.26-2.35 (m, 1H), 2.45-2.52 (m, 1H), 2.57-2.67 (m, 1H), 3.98 (d, J=14.9 Hz, 1H), 4.02 (dd, J=3.0, 9.4 Hz, 1H), 5.15 (d, J=14.9 Hz, 1H), 7.21-7.25 (m, 2H), 7.27-7.36 (m, 3H).

LC-MS (METCR1410): 98% (UV), Rt=0.81 min, m/z (ESI$^+$)=220.2 [M+H]$^+$

1-[(4-Chloro-3-fluorophenyl)methyl]-5-oxopyrrolidine-2-carboxylic acid (I-374)

The title compound was synthesised in a similar manner to method A, general procedure 1 (general scheme 20) as a colourless solid (1.50 g, 99% purity by 1H NMR, 20%) which was used in the next step without further purification.

$^1$H NMR (250 MHz, Chloroform-d) δ 2.19-2.69 (m, 4H), 3.99-4.08 (m, 2H), 5.01 (d, J=15.2 Hz, 1H), 6.95-7.09 (m, 2H), 7.35 (t, J=7.8 Hz, 1H).

LC-MS (METCR1410): 98% (UV), Rt=0.94 min, m/z (ESI$^+$)=272.0/274.0 [M+H]$^+$

1-[(4-Cyanophenyl)methyl]-5-oxopyrrolidine-2-carboxylic acid (I-375)

The title compound was synthesised in a similar manner to method A, general procedure 1 (general scheme 20) as a colourless powder (980 mg, 95% purity, 14%) which was used in the next step without further purification.

$^1$H NMR (250 MHz, Chloroform-d) δ 2.21-2.66 (m, 4H), 4.02 (dd, J=3.1, 8.8 Hz, 1H), 4.14 (d, J=15.4 Hz, 1H), 5.06 (d, J=15.4 Hz, 1H), 7.36 (d, J=8.2 Hz, 2H), 7.63 (d, J=8.2 Hz, 2H).

LC-MS (METCR1410): 95% (UV), Rt=0.78 min, m/z (ESI$^+$)=245.1 [M+H]$^+$

1-[(4-Chloro-2-fluorophenyl)methyl]-5-oxopyrrolidine-2-carboxylic acid (I-376)

The title compound was synthesised in a similar manner to method A, general procedure 1 (general scheme 20) as a colourless powder (738 mg, 95% purity by $^1$H NMR, 9%) which was used in the next step without further purification.

$^1$H NMR (250 MHz, Chloroform-d) δ 2.17-2.60 (m, 4H), 4.09 (dd, J=3.3, 8.8 Hz, 1H), 4.21 (d, J=15.0 Hz, 1H), 4.93 (d, J=15.1 Hz, 1H), 7.04-7.15 (m, 2H), 7.24-7.31 (m, 1H).

LC-MS (METCR1410): 100% (UV), Rt=0.92 min, m/z (ESI$^+$)=272.0/274.0 [M+H]$^+$

1-[(3-Chlorophenyl)methyl]-5-oxopyrrolidine-2-carboxylic acid (I-377)

The title compound was synthesised in a similar manner to method A, general procedure 1 (general scheme 20) as an off-white powder (2.7 g, 95% purity, 33%) which was used in the next step without further purification.

$^1$H NMR (500 MHz, DMSO-d6) δ 1.90-2.02 (m, 1H), 2.26-2.37 (m, 3H), 3.94-4.01 (m, 2H), 4.78 (d, J=15.5 Hz, 1H), 7.16-7.20 (m, 1H), 7.28 (s, 1H), 7.31-7.38 (m, 2H), 13.01 (br. s, 1H).

LC-MS (METCR1410): 95% (UV), Rt=0.92 min, m/z (ESI$^+$)=254.0, 256.1 [M+H]$^+$

1-[(3-Methylphenyl)methyl]-5-oxopyrrolidine-2-carboxylic acid (I-378)

The title compound was synthesised in a similar manner to method A, general procedure 1 (general scheme 20) as an off-white powder (1.0 g, 98% purity, 50%) which was used in the next step without further purification.

$^1$H NMR (500 MHz, DMSO-d6) δ 1.91-1.98 (m, 1H), 2.19-2.27 (m, 1H), 2.28 (s, 3H), 2.29-2.36 (m, 2H), 3.80-3.89 (m, 2H), 4.85 (d, J=15.1 Hz, 1H), 6.94-7.01 (m, 2H), 7.06-7.11 (m, 1H), 7.21 (t, J=7.6 Hz, 1H).

LC-MS (METCR1410): 98% (UV), Rt=0.89 min, m/z (ESI$^+$)=234.1 [M+H]$^+$

1-[(4-Chlorophenyl)methyl]-5-oxopyrrolidine-2-carboxylic acid (I-379)

The title compound was synthesised in a similar manner to method A, general procedure 1 (general scheme 20) as an off-white solid (15.3 g, 99% purity, 55%) which was used in the next step without further purification.

$^1$H NMR (500 MHz, DMSO-d6) δ 1.93-2.00 (m, 1H), 2.24-2.39 (m, 3H), 3.92-4.00 (m, 2H), 4.79 (d, J=15.3 Hz, 1H), 7.24 (d, J=8.2 Hz, 2H), 7.39 (d, J=8.2 Hz, 2H).

LC-MS (METCR1410): 99% (UV), Rt=0.92 min, m/z (ESI$^+$)=254.0/256.0 [M+H]$^+$

1-[(4-Fluorophenyl)methyl]-5-oxopyrrolidine-2-carboxylic acid (I-380)

The title compound was synthesised in a similar manner to method A, general procedure 1 (general scheme 20) as an off-white solid (11.0 g, 95% purity by $^1$H NMR, 40%) which was used in the next step without further purification.

$^1$H NMR (500 MHz, Chloroform-d) δ 2.10-2.19 (m, 1H), 2.23-2.33 (m, 1H), 2.40-2.49 (m, 1H), 2.50-2.67 (m, 1H), 3.93-4.00 (m, 2H), 5.03 (d, J=14.8 Hz, 1H), 6.93-7.05 (m, 2H), 7.14-7.23 (m, 2H).

LC-MS (METCR1603): 99% (UV), Rt=1.72 min, m/z (ESI⁺)=238.1 [M+H]⁺

1-[(2-Chlorophenyl)methyl]-5-oxopyrrolidine-2-carboxylic acid (I-381)

The title compound was synthesised in a similar manner to method A, general procedure 1 (general scheme 20) as an off-white solid (15.3 g, 100% purity, 55%) which was used in the next step without further purification.

¹H NMR (500 MHz, Chloroform-d) δ 2.06-2.20 (m, 1H), 2.26-2.38 (m, 1H), 2.39-2.50 (m, 1H), 2.50-2.64 (m, 1H), 4.01-4.08 (m, 1H), 4.24 (d, J=14.8 Hz, 1H), 5.10 (d, J=14.9 Hz, 1H), 7.20-7.25 (m, 2H), 7.27-7.32 (m, 1H), 7.32-7.37 (m, 1H).

LC-MS (METCR1410): 100% (UV), Rt=0.88 min, m/z (ESI⁺)=254.0/256.0 [M+H]⁺

1-[(2-Methylphenyl)methyl]-5-oxopyrrolidine-2-carboxylic acid (I-382)

The title compound was synthesised in a similar manner to method A, general procedure 1 (general scheme 20) as a tan solid (9.7 g, 98% purity, 37%) which was used in the next step without further purification.

¹H NMR (500 MHz, Chloroform-d) δ 2.09-2.21 (m, 1H), 2.21-2.37 (m, 4H), 2.42-2.53 (m, 1H), 2.56-2.67 (m, 1H), 3.93 (dd, J=2.5, 9.4 Hz, 1H), 4.08 (d, J=14.9 Hz, 1H), 5.09 (d, J=14.9 Hz, 1H), 7.07-7.25 (m, 4H).

LC-MS (METCR1410): 98% (UV), Rt=0.88 min, m/z (ESI⁺)=234.0 [M+H]⁺

1-[(4-Methylphenyl)methyl]-5-oxopyrrolidine-2-carboxylic acid (I-383)

The title compound was synthesised in a similar manner to method A, general procedure 1 (general scheme 20) as an off-white solid (18.2 g, 95% purity by 1H NMR, 68%) which was used in the next step without further purification.

¹H NMR (500 MHz, Chloroform-d) δ 2.11-2.19 (m, 1H), 2.24-2.32 (m, 1H), 2.33 (s, 3H), 2.42-2.50 (m, 1H), 2.54-2.65 (m, 1H), 3.91 (d, J=14.7 Hz, 1H), 4.01 (dd, J=3.1, 9.4 Hz, 1H), 5.12 (d, J=14.8 Hz, 1H), 7.09-7.15 (m, 4H).

LC-MS (METCR1410): 86% (UV), Rt=0.90 min, m/z (ESI⁺)=234.2 [M+H]⁺

(2R)-1-[(4-Chlorophenyl)methyl]-5-oxopyrrolidine-2-carboxylic acid (I-384)

The title compound was synthesised in a similar manner to method A general procedure 1a (general scheme 20) as an off-white solid (28.1 g, 91% purity, 99%) which was used in the next step without further purification.

¹H NMR (500 MHz, Chloroform-d) δ 2.14-2.24 (m, 1H), 2.25-2.39 (m, 1H), 2.41-2.54 (m, 1H), 2.54-2.68 (m, 1H), 3.98-4.05 (m, 2H), 5.04 (d, J=15.0 Hz, 1H), 7.15-7.20 (m, 2H), 7.27-7.33 (m, 2H).

LC-MS (METCR1410): 91% (UV), Rt=0.93 min, m/z (ESI⁺)=254.1/256.0 [M+H]⁺

5-Oxo-1-[(1-oxo-2,3-dihydro-1H-isoindol-5-yl)methyl]pyrrolidine-2-carboxylic acid (I-385)

The title compound was synthesised in a similar manner to method A, general procedure 1 (general scheme 20) as an off-white powder (900 mg, 90% purity by ¹H NMR, 54%) which was used in the next step without further purification.

¹H NMR (250 MHz, DMSO-d6) δ 1.90-2.00 (m, 1H), 2.22-2.36 (m, 3H), 3.90-3.95 (m, 1H), 4.05 (d, J=15.6 Hz, 1H), 4.34 (s, 2H), 4.92 (d, J=15.5 Hz, 1H), 7.30 (d, J=8.3 Hz, 1H), 7.39 (s, 1H), 7.61 (d, J=7.8 Hz, 1H), 8.50 (s, 1H).

LC-MS (METCR1410): 82% (UV), Rt=0.56 min, m/z (ESI⁺)=275.1 [M+H]⁺

5-Oxo-1-[(1,3-thiazol-2-yl)methyl]pyrrolidine-2-carboxylic acid (I-386)

The title compound was synthesised in a similar manner to method A, general procedure 1 (general scheme 20) as a colourless solid (988 mg, 99% purity by ¹H NMR, 51%) which was used in the next step without further purification.

¹H NMR (250 MHz, Chloroform-d) δ 2.18-2.62 (m, 4H). 4.17 (dd, J=4.3, 8.5 Hz, 1H), 4.73 (d, J=15.5 Hz, 1H), 5.36 (d, J=15.5 Hz, 1H), 7.41 (d, J=3.3 Hz, 1H), 7.75 (d, J=3.4 Hz, 1H).

LC-MS (METCR1410): 100% (UV), Rt=0.45 min, m/z (ESI⁺)=227.1 [M+H]⁺

(2R)-1-Benzyl-5-oxopyrrolidine-2-carboxylic acid (I-387)

The title compound was synthesised in a similar manner to method A, general procedure 1 (general scheme 20) as an off-white powder (20.5 g, 90% purity by 1H NMR, quantitative) which was used in the next step without further purification.

¹H NMR (500 MHz, DMSO-d6) δ 1.81-1.89 (m, 1H), 2.16-2.34 (m, 3H), 3.63 (dd, J=3.0, 8.8 Hz, 1H), 3.91 (d, J=15.1 Hz, 1H), 4.86 (d, J=15.1 Hz, 1H), 7.16 (d, J=7.2 Hz, 2H), 7.22-7.27 (m, 1H), 7.28-7.34 (m, 2H).

LC-MS (METCR1410): 100% (UV), Rt=0.83 min, m/z (ESI⁺)=220.2 [M+H]⁺

Method B: Cyclisation of Glutamic Esters Using NaBH₄

Methyl 1-[(3-carbamoylphenyl)methyl]-5-oxopyrrolidine-2-carboxylate (I-388)

To a stirred suspension of dimethyl glutamate hydrochloride (5.0 g, 23.62 mmol) in 1:1 anhydrous DCM:anhydrous MeOH (80 mL) was added TEA (3.6 mL 25.99 mmol), MgSO₄ (4.27 g, 35.44 mmol) and 3-formylbenzamide (3.52 g, 23.62 mmol) and the mixture was stirred at RT for 67 h. The suspension was filtered and the solid was washed with DCM (3×15 mL). The filtrates were combined, concentrated in vacuo and the residue was dissolved in dry MeOH (60 mL). The solution was cooled to 0° C., treated with sodium borohydride (447 mg, 11.81 mmol) in one portion then allowed to warm up and stirred at RT for 18 h. The reaction mixture was concentrated in vacuo and the residue was partitioned between water (30 mL) and DCM (50 mL). The aqueous layer was extracted with DCM (3×50 mL) and the combined organic layers were dried over sodium sulfate, filtered and concentrated in vacuo. The residue was suspended in MeOH (50 mL), concentrated H₂SO₄(5 drops) was added and the suspension was stirred at reflux for 19 h then concentrated in vacuo. The residue was purified by flash column chromatography on normal phase silica (100 g SNAP KP-SIL cartridge, 0-15% MeOH in EtOAc gradient) to afford 4.16 g of methyl 1-[(3-carbamoylphenyl)methyl]-5-oxopyrrolidine-2-carboxylate as a viscous yellow oil (94% purity by ¹H NMR, 60%).

¹H NMR (500 MHz, Chloroform-d) δ 2.10 (ddt, J=3.3, 9.6, 13.1 Hz, 1H), 2.28 (dq, J=9.3, 13.3 Hz, 1H), 2.43 (ddd, J=3.6, 9.7, 17.0 Hz, 1H), 2.58 (dt, J=9.2, 18.2 Hz, 1H), 3.66 (s, 3H), 4.00 (dd, J=3.0, 9.2 Hz, 1H), 4.14 (d, J=15.1 Hz, 1H), 4.97 (d, J=15.0 Hz, 1H), 5.80 (s, 1H), 6.27 (s, 1H), 7.37-7.44 (m, 2H), 7.67 (s, 1H), 7.74 (dt, J=1.7, 7.2 Hz, 1H).

LC-MS (METCR1410): 97% (UV), Rt=0.75 min, m/z (ESI⁺)=277.0 [M+H]⁺

Methyl 1-[(4-carbamoylphenyl)methyl]-5-oxopyrrolidine-2-carboxylate (I-389)

The title compound was synthesised in a similar manner to method B, general procedure 1 (general scheme 20) as a pale-yellow powder (4.5 g, 91% purity by 1H NMR, 64%) after purification by flash column chromatography on normal phase silica (100 g SNAP Ultra cartridge, 0-15% MeOH in EtOAc gradient).

¹H NMR (500 MHz, Chloroform-d) δ 2.11 (ddt, J=3.5, 9.6, 13.2 Hz, 1H), 2.28 (dq, J=9.3, 13.3 Hz, 1H), 2.44 (ddd, J=3.7, 9.7, 17.0 Hz, 1H), 2.59 (dt, J=9.4, 17.8 Hz, 1H), 3.68 (s, 3H), 3.98 (dd, J=3.1, 9.2 Hz, 1H), 4.09 (d, J=15.1 Hz, 1H), 5.03 (d, J=15.1 Hz, 1H), 5.64 (s, 1H), 6.10 (s, 1H), 7.30 (d, J=8.1 Hz, 2H), 7.74-7.80 (m, 2H).

LC-MS (METCR1410): 97% (UV), Rt=0.75 min, m/z (ESI⁺)=277.0 [M+H]⁺

Methyl 1-(cyclopentylmethyl)-5-oxopyrrolidine-2-carboxylate (I-390)

The title compound was synthesised in a similar manner to method B, general procedure 1 (general scheme 20) as a yellow oil (2.13 g, 93% purity, 37%) after purification by flash column chromatography on normal phase silica (100 g SNAP Ultra cartridge, 0-20% MeOH in EtOAc gradient).

¹H NMR (500 MHz, DMSO-d6) δ 1.04-1.16 (m, 2H), 1.41-1.61 (m, 5H), 1.62-1.69 (m, 1H), 1.92-1.98 (m, 1H), 2.00-2.07 (m, 1H), 2.18-2.33 (m, 3H), 2.74 (dd, J=6.5, 13.6 Hz, 1H), 3.41 (dd, J=9.1, 13.7 Hz, 1H), 3.69 (s, 3H), 4.29-4.35 (m, 1H).

LC-MS (METCR1410): 93% (UV), Rt=1.01 min, m/z (ESI⁺)=226.2 [M+H]⁺

Method C: Cyclisation of Glutamic Esters Using STAB

Methyl 5-oxo-1-(2-phenylethyl)pyrrolidine-2-carboxylate (I-391)

To a stirring mixture of 1,5-dimethyl 2-aminopentanedioate hydrochloride (2.84 g, 13.40 mmol) and 2-phenylacetaldehyde (1.5 mL, 13.42 mmol) in 1,2-DCE (40 mL) was added TEA (2 mL, 14.35 mmol). The mixture was stirred at RT under nitrogen for 1 h. STAB (4.25 g, 20.06 mmol) was then added portion wise and the mixture stirred at RT for 17 h under nitrogen. The reaction was diluted with DCM (25 mL) and washed with water (2×65 mL). The organic layer was separated, dried over sodium sulfate, filtered and concentrated in vacuo. The residue was purified by flash column chromatography on normal phase silica (50 g SNAP KP-SIL cartridge, 0-100% EtOAc in heptane gradient) to afford 516 mg of methyl 5-oxo-1-(2-phenylethyl)pyrrolidine-2-carboxylate as an off-white solid (100% purity, 16%).

¹H NMR (500 MHz, Chloroform-d) δ 1.98-2.06 (m, 1H), 2.15-2.25 (m, 1H), 2.28-2.37 (m, 1H), 2.43-2.52 (m, 1H), 2.75-2.83 (m, 1H), 2.84-2.93 (m, 1H), 3.08-3.16 (m, 1H), 3.74 (s, 3H), 3.93-3.96 (m, 1H), 3.96-4.02 (m, 1H), 7.17-7.24 (m, 3H), 7.27-7.31 (m, 2H).

LC-MS (METCR1603): 100% (UV), Rt=3.72 min, m/z (ESI⁺)=248.1 [M+H]⁺

Methyl 1-[2-(oxan-4-yl)ethyl]-5-oxopyrrolidine-2-carboxylate (I-392)

The title compound was synthesised in a similar manner to method C, general procedure 1 (general scheme 20) as a yellow viscous oil (1.01 g, 96% purity, 38%) after purification by flash column chromatography on normal phase silica (50 g SNAP KP-SIL cartridge, 0-100% EtOAc in heptane gradient).

¹H NMR (500 MHz, Chloroform-d) δ 1.19-1.32 (m, 2H), 1.36-1.50 (m, 3H), 1.54-1.67 (m, 2H), 2.04-2.13 (m, 1H), 2.24-2.39 (m, 2H), 2.42-2.54 (m, 1H), 2.89-2.98 (m, 1H), 3.33 (tt, J=2.4, 11.8 Hz, 2H), 3.64-3.73 (m, 1H), 3.75 (s, 3H), 3.88-3.94 (m, 2H), 4.15-4.20 (m, 1H).

LC-MS (METCR1410): 96% (UV), Rt=0.84 min, m/z (ESI⁺)=256.1 [M+H]⁺

Methyl 1-[(3-methyl-1,2-oxazol-5-yl)methyl]-5-oxopyrrolidine-2-carboxylate (I-393)

The title compound was synthesised in a similar manner to method C, general procedure 1 (general scheme 20) as a yellow viscous oil (680 mg, 75% purity, 24%) after purification by flash column chromatography on normal phase silica (50 g SNAP KP-SIL cartridge, 0-100% EtOAc in heptane gradient).

¹H NMR (500 MHz, Chloroform-d) δ 2.09-2.15 (m, 1H), 2.27 (s, 3H), 2.35-2.41 (m, 2H), 2.46-2.55 (m, 1H), 3.76 (s, 3H), 4.21 (d, J=16.0 Hz, 1H), 4.23-4.26 (m, 1H), 5.00 (d, J=16.0 Hz, 1H), 6.03 (s, 1H).

LC-MS (METCR1410): 75% (UV), Rt=0.78 min, m/z (ESI⁺)=239.2 [M+H]⁺

Methyl 1-[(5-methylthiophen-2-yl)methyl]-5-oxopyrrolidine-2-carboxylate (I-394)

The title compound was synthesised in a similar manner to method C, general procedure 1 (general scheme 20) after precipitation from Et₂O as a tan powder (1.80 g, 100% purity, 50%)

¹H NMR (500 MHz, Chloroform-d) δ 2.02-2.10 (m, 1H), 2.20-2.30 (m, 1H), 2.34-2.41 (m, 1H), 2.42 (s, 3H), 2.47-2.56 (m, 1H), 3.73 (s, 3H), 4.06-4.17 (m, 2H), 5.08 (d, J=15.3 Hz, 1H), 6.51-6.60 (m, 1H), 6.68 (d, J=3.4 Hz, 1H).

LC-MS (METCR0990): 100% (UV), Rt=1.53 min, m/z (ESI⁺)=254.2 [M+H]⁺

Method D: Cyclisation of Glutamic Acids Using NaCNBH₃

Ethyl 1-[(oxan-4-yl)methyl]-5-oxopyrrolidine-2-carboxylate (I-395)

To a stirred suspension of DL-glutamic acid monohydrate (1.0 g, 6.06 mmol) and NaBH₃CN (571 mg, 9.08 mmol) in MeOH (10 mL) at RT was added tetrahydro-2H-pyran-4-carbaldehyde (0.69 mL, 6.66 mmol) and the reaction mixture was stirred for 18 h. The precipitate was filtered off and washed with MeOH (2×10 mL). The combined filtrate was concentrated in vacuo and the residue was suspended in EtOH (15 mL) and stirred at reflux for 18 h. The mixture was cooled to RT, concentrated H₂SO₄ (20 drops) was added and the reaction was heated at reflux for further 18 h then cooled and concentrated in vacuo. The residue was purified by flash column chromatography on normal phase silica (25 g SNAP KP-SIL cartridge, 0-100% TBME in heptane gradient) to afford 261 mg of ethyl 5-oxo-1-[(4-sulfamoylphenyl) methyl]pyrrolidine-2-carboxylate as a viscous colourless oil (95% purity by $^1$H NMR, 16%).

$^1$H NMR (500 MHz, DMSO-d6) δ 1.00-1.10 (m, 1H), 1.11-1.19 (m, 1H), 1.21 (t, J=7.1 Hz, 3H), 1.40-1.46 (m, 1H), 1.48-1.54 (m, 1H), 1.69-1.79 (m, 1H), 1.90-1.99 (m, 1H), 2.19-2.35 (m, 3H), 2.71 (dd, J=6.3, 13.8 Hz, 1H), 3.22 (td, J=2.2, 11.7 Hz, 2H), 3.37 (dd, J=8.6, 13.8 Hz, 1H), 3.78-3.84 (m, 2H), 4.12-4.19 (m, 2H), 4.25-4.29 (m, 1H).

General Procedure 2a (General Scheme 20): Hydrolysis

Method A: Isolation of Carboxylic Acid

1-[(4-Carbamoylphenyl)methyl]-5-oxopyrrolidine-2-carboxylic acid (I-396)

To a stirred solution of methyl 1-[(4-carbamoylphenyl) methyl]-5-oxopyrrolidine-2-carboxylate (I-389), 91%, 4.58 g, 15.08 mmol) in 2:2:1 THF:water:MeOH (45 mL) was added lithium hydroxide hydrate (949 mg, 22.62 mmol) and the suspension was stirred at RT for 2 h. The reaction was acidified to pH 2 with 1N HCl (20 mL) then extracted with 1:1 IPA/CHCl3 (3×30 mL). The organic layers were combined, dried over sodium sulfate and concentrated in vacuo to afford 3.29 g of 1-[(4-carbamoylphenyl)methyl]-5-oxopyrrolidine-2-carboxylic acid as an off-white solid (99% purity by 1H NMR, 82%).

$^1$H NMR (500 MHz, DMSO-d6) δ 1.92-2.02 (m, 1H), 2.25-2.39 (m, 3H), 3.94 (dd, J=3.1, 8.7 Hz, 1H), 3.98 (d, J=15.5 Hz, 1H), 4.87 (d, J=15.5 Hz, 1H), 7.27 (d, J=8.2 Hz, 2H), 7.33 (s, 1H), 7.82 (d, J=8.2 Hz, 2H), 7.94 (s, 1H), 13.03 (s, 1H).

LC-MS (METCR0990): 100% (UV), Rt=0.25 min, m/z (ESI$^+$)=263.2 [M+H]$^+$

1-[(3-Carbamoylphenyl)methyl]-5-oxopyrrolidine-2-carboxylic acid (I-397)

The title compound was synthesised from methyl 1-[(3-carbamoylphenyl)-methyl]-5-oxopyrrolidine-2-carboxylate (I-388) in a similar manner to method A, general procedure 2a (general scheme 20) as an off-white powder (3.92 g, 79% purity, 83%) which was used in the next step without further purification.

$^1$H NMR (500 MHz, DMSO-d6) δ 1.93-2.01 (m, 1H), 2.24-2.36 (m, 3H), 3.89-3.99 (m, 2H), 4.90 (d, J=15.3 Hz, 1H), 7.35 (d, J=7.7 Hz, 1H), 7.36 (s, 1H), 7.41 (t, J=7.6 Hz, 1H), 7.69 (s, 1H), 7.77 (d, J=7.7 Hz, 1H), 7.96 (s, 1H).

LC-MS (METCR0990): 100% (UV), Rt=0.30 min, m/z (ESI$^+$)=263.2 [M+H]$^+$

1-[2-(Oxan-4-yl)ethyl]-5-oxopyrrolidine-2-carboxylic acid (I-398)

The title compound was synthesised from methyl 1-[2-(oxan-4-yl)ethyl]-5-oxopyrrolidine-2-carboxylate (I-392) in a similar manner to method A, general procedure 2a (general scheme 20) as a yellow solid (639 mg, 90% purity, 63%) which was used in the next step without further purification.

$^1$H NMR (500 MHz, Chloroform-d) δ 1.21-1.38 (m, 2H), 1.41-1.53 (m, 3H), 1.57-1.69 (m, 2H), 2.13-2.23 (m, 1H), 2.30-2.47 (m, 2H), 2.50-2.62 (m, 1H), 2.97-3.07 (m, 1H), 3.37 (tdd, J=2.3, 3.7, 11.8 Hz, 2H), 3.70-3.79 (m, 1H), 3.92-3.99 (m, 2H), 4.20-4.24 (m, 1H).

LC-MS (METCR1410): 97% (UV), Rt=0.70 min, m/z (ESI$^+$)=242.1 [M+H]$^+$ 1-(Cyclopentylmethyl)-5-oxopyrrolidine-2-carboxylic acid (I-399)

The title compound was synthesised from methyl 1-(cyclopentylmethyl)-5-oxopyrrolidine-2-carboxylate (I-390) in a similar manner to method A, general procedure 2a (general scheme 20) except extracting the product into EtOAc to afford a colourless viscous oil (971 mg, 94% purity, 95%) which was used in the next step without further purification.

$^1$H NMR (500 MHz, DMSO-d6) δ 1.04-1.19 (m, 2H), 1.42-1.61 (m, 5H), 1.63-1.71 (m, 1H), 1.89-1.97 (m, 1H), 2.02-2.09 (m, 1H), 2.18-2.31 (m, 3H), 2.74 (dd, J=6.3, 13.6 Hz, 1H), 3.44 (dd, J=9.2, 13.6 Hz, 1H), 4.15-4.21 (m, 1H), 12.96 (br. s, 1H).

LC-MS (METCR1410): 94% (UV), Rt=0.86 min, m/z (ESI-)=210.3 [M–H]$^-$

1-[(5-Methylthiophen-2-yl)methyl]-5-oxopyrrolidine-2-carboxylic acid (I-400)

The title compound was synthesised from methyl 1-[(5-methylthiophen-2-yl)methyl]-5-oxopyrrolidine-2-carboxylate (I-394) in a similar manner to method A, general procedure 2a (general scheme 20) by filtration of the acidified aqueous precipitate to afford a tan powder (1.25 g, 93% purity, 76%) which was used in the next step without further purification.

$^1$H NMR (500 MHz, Chloroform-d) δ 2.13-2.22 (m, 1H), 2.28-2.38 (m, 1H), 2.40-2.52 (m, 4H), 2.55-2.65 (m, 1H), 4.09-4.20 (m, 2H), 5.18 (d, J=15.4 Hz, 1H), 6.52-6.62 (m, 1H), 6.74 (d, J=3.4 Hz, 1H).

LC-MS (METCR1410): 93% (UV), Rt=0.87 min, m/z (ESI$^+$)=240.1 [M+H]$^+$

Method B: Isolation of Carboxylic Acid Lithium Salt

Lithium(1+) ion 1-[(3-methyl-1,2-oxazol-5-yl) methyl]-5-oxopyrrolidine-2-carboxylate (I-401)

To a stirring solution of methyl 1-[(3-methylisoxazol-5-yl)methyl]-5-oxopyrrolidine-2-carboxylate (I-393), 75% purity, 675 mg, 2.12 mmol) in 1:1:1 THF:water:MeOH (15 mL) was added lithium hydroxide monohydrate (140 mg, 3.34 mmol) and the resulting mixture stirred at RT for 1 h. The reaction mixture was concentrated in vacuo to give a yellow solid that was triturated in 4:1 heptane/EtOAc (10 mL). The solvent was decanted and the residue dried in vacuo to afford 644 mg of lithium(1+)ion 1-[(3-methyl-1,2-oxazol-5-yl)methyl]-5-oxopyrrolidine-2-carboxylate as a yellow solid (74% purity, 97%)

$^1$H NMR (500 MHz, Deuterium Oxide) δ 1.96-2.03 (m, 1H), 2.28 (s, 3H), 2.38-2.44 (m, 1H), 2.47-2.58 (m, 2H), 4.06-4.11 (m, 1H), 4.30 (d, J=16.2 Hz, 1H), 4.89 (d, J=16.2 Hz, 1H), 6.28 (s, 1H).

LC-MS (METCR1410): 74% (UV), Rt=0.40-0.61 min (2 peaks), m/z (ESI$^+$)=225.2 [M+H]$^+$ Lithium(1+) ion 1-[(oxan-4-yl)methyl]-5-oxopyrrolidine-2-carboxylate (I-402)

The title compound was synthesised from ethyl 1-[(oxan-4-yl)methyl]-5-oxopyrrolidine-2-carboxylate (I-395) in a similar manner to method B, general procedure 2a (general scheme 20) as an off-white powder (288 mg, 80% purity, quantitative) which was used in the next step without further purification.

$^1$H NMR (250 MHz, DMSO-d6) δ 0.92-1.26 (m, 2H), 1.33-1.54 (m, 2H), 1.62-1.86 (m, 2H), 1.89-2.20 (m, 3H), 2.70-2.83 (m, 1H), 3.13-3.26 (m, 3H), 3.65 (dd, J=3.9, 8.1 Hz, 1H), 3.73-3.86 (m, 2H).

LC-MS (METCR1410): 100% (UV), Rt=0.30-0.55 min (multiple peaks), m/z (ESI-)=226.2 [M−H]$^−$

Lithium(1+) ion 5-oxo-1-(2-phenylethyl)pyrrolidine-2-carboxylate (I-403)

The title compound was synthesised from methyl 5-oxo-1-(2-phenylethyl)pyrrolidine-2-carboxylate (I-391) in a similar manner to method B, general procedure 2a (general scheme 20) as a yellow solid (548 mg, 94% purity, quantitative) which was used in the next step without further purification.

$^1$H NMR (500 MHz, Methanol-d4) δ 1.91-1.99 (m, 1H), 2.13-2.25 (m, 2H), 2.36-2.46 (m, 1H), 2.71-2.80 (m, 1H), 2.81-2.90 (m, 1H), 3.11-3.18 (m, 1H), 3.85-3.91 (m, 1H), 3.91-3.95 (m, 1H), 7.12-7.17 (m, 1H), 7.17-7.20 (m, 2H), 7.21-7.25 (m, 2H).

LC-MS (METCR1603): 94% (UV), Rt=1.10-1.80 min (multiple peaks), m/z (ESI$^+$)=234.2 [M+H]$^+$

General Procedure 2b (General Scheme 20): Alkylation & Hydrolysis

1-(Cyclopropylmethyl)-5-oxopyrrolidine-2-carboxylic acid (I-404)

To an ice cooled solution of methyl 5-oxopyrrolidine-2-carboxylate (1.0 g, 6.99 mmol) in DMF (6 mL) was added NaH (60% dispersion in mineral oil, 419 mg, 10.48 mmol) and the reaction mixture stirred at RT for 20 min. after which (bromomethyl)-cyclopropane (852 µL, 8.38 mmol) was added and the reaction mixture stirred at RT for 1 h. The mixture was quenched with water (10 mL) and diluted with DCM (20 mL). The aqueous phase was separated, extracted with DCM (3×5 mL), then acidified to pH ~1 and extracted with DCM (3×10 mL). The combined organic extracts were then concentrated in vacuo to afford 320 mg of 1-(cyclopropylmethyl)-5-oxopyrrolidine-2-carboxylic acid as a dark brown viscous oil (81% purity by NMR, 20%) which was used in the next step without any further purification.

$^1$H NMR (500 MHz, Chloroform-d) δ 0.12-0.20 (m, 1H), 0.20-0.26 (m, 1H), 0.42-0.51 (m, 1H), 0.51-0.61 (m, 1H), 0.81-0.94 (m, 1H), 2.12-2.23 (m, 1H), 2.34-2.51 (m, 2H), 2.51-2.65 (m, 1H), 2.82 (dd, J=7.8, 14.3 Hz, 1H), 3.66 (dd, J=6.7, 14.3 Hz, 1H), 4.40-4.51 (m, 1H), 8.04 (br s, 1H).

LC-MS (METCR0990): 100% (UV), Rt=0.25-1.00 min (broad peak), m/z (ESI$^+$)=184.1 [M+H]$^+$

General Procedure 3 (General Scheme 20): Ylide Coupling

Method A: Coupling Using Carboxylic Acid

Method as Described in General Procedure 4 (General Scheme 11a): Ylide Coupling

3-[(2R)-1-Benzyl-5-oxopyrrolidin-2-yl]-3-oxo-2-(1λ'-thiolan-1-ylidene)propanenitrile (I-405)

The title compound was synthesised from (2R)-1-benzyl-5-oxopyrrolidine-2-carboxylic acid (I-387) in a similar manner to general procedure 4 (general scheme 11a) as a cream glass (2.96 g, 100% purity, 99%) after purification by flash column chromatography on normal phase silica (100 g SNAP Ultra cartridge, 2-20% MeOH in EtOAc gradient).

$^1$H NMR (500 MHz, Chloroform-d) δ 1.94 (ddt, J=3.9, 9.8, 13.4 Hz, 1H), 1.99-2.11 (m, 2H), 2.20-2.31 (m, 1H), 2.40 (ddd, J=4.2, 9.9, 16.7 Hz, 1H), 2.48-2.66 (m, 3H), 3.11-3.21 (m, 2H), 3.26-3.37 (m, 2H), 4.10 (d, J=14.9 Hz, 1H), 4.43 (dd, J=3.5, 9.0 Hz, 1H), 4.83 (d, J=14.9 Hz, 1H), 7.19-7.26 (m, 3H), 7.27-7.32 (m, 2H).

LC-MS (METCR1410): 100% (UV), Rt=0.83 min, m/z (ESI$^+$)=329.0 [M+H]$^+$

4-({2-[2-Cyano-2-(1λ$^4$-thiolan-1-ylidene)acetyl]-5-oxopyrrolidin-1-yl}methyl)benzamide (I-406)

The title compound was synthesised from 1-[(4-carbamoylphenyl)methyl]-5-oxopyrrolidine-2-carboxylic acid (I-396) in a similar manner to general procedure 4 (general scheme 11a) as a light pink gummy solid (1.54 g, 56% purity by 1H NMR, 19%) after purification by flash column chromatography on normal phase silica (100 g SNAP Ultra cartridge, 0-20% MeOH in EtOAc gradient).

$^1$H NMR (500 MHz, Chloroform-d) δ 1.96 (ddt, J=4.0, 9.8, 17.0 Hz, 1H), 2.00-2.09 (m, 2H), 2.25 (dq, J=8.8, 13.0 Hz, 1H), 2.40 (ddd, J=4.1, 9.9, 16.8 Hz, 1H), 2.44-2.56 (m, 2H), 2.63 (dt, J=9.2, 17.6 Hz, 1H), 3.01-3.15 (m, 2H), 3.32 (dq, J=6.9, 12.4 Hz, 2H), 4.30 (d, J=15.2 Hz, 1H), 4.42 (dd, J=3.4, 8.9 Hz, 1H), 4.71 (d, J=15.2 Hz, 1H), 5.70 (s, 1H), 6.39 (s, 1H), 7.32 (d, J=8.2 Hz, 2H), 7.76 (d, J=8.2 Hz, 2H).

LC-MS (METCR1410): 98% (UV), Rt=0.71 min, m/z (ESI$^+$)=372.1 [M+H]$^+$

3-({2-[2-Cyano-2-(1λ$^4$-thiolan-1-ylidene)acetyl]-5-oxopyrrolidin-1-yl}methyl)benzamide (I-407)

The title compound was synthesised from 1-[(3-carbamoylphenyl)methyl]-5-oxopyrrolidine-2-carboxylic acid (I-397) in a similar manner to general procedure 4 (general scheme 11a) as a light pink powder (1.96 g, 69% purity by $^1$H NMR, 31%) after purification by flash column chromatography on normal phase silica (100 g SNAP Ultra cartridge, 0-20% MeOH in EtOAc gradient).

$^1$H NMR (500 MHz, Chloroform-d) δ 1.97 (ddt, J=3.8, 9.9, 13.3 Hz, 1H), 2.00-2.10 (m, 2H), 2.21 (ddd, J=8.6, 12.9, 18.6 Hz, 1H), 2.40 (ddd, J=4.1, 10.0, 16.8 Hz, 1H), 2.44-2.57 (m, 2H), 2.70 (dt, J=9.4, 17.5 Hz, 1H), 3.01-3.17 (m, 2H), 3.24-3.37 (m, 2H), 4.36-4.43 (m, 2H), 4.65 (d, J=14.9 Hz, 1H), 5.55 (s, 1H), 6.66 (s, 1H), 7.41 (t, J=7.6 Hz, 1H), 7.43-7.49 (m, 1H), 7.65 (s, 1H), 7.77 (dt, J=1.4, 7.6 Hz, 1H).

LC-MS (METCR1410): 100% (UV), Rt=0.73 min, m/z (ESI$^+$)=372.1 [M+H]$^+$

3-(1-Benzyl-5-oxopyrrolidin-2-yl)-3-oxo-2-(1λ$^4$-thiolan-1-ylidene) (I-408)

The title compound was synthesised from 1-benzyl-5-oxopyrrolidine-2-carboxylic acid (I-373) in a similar manner to general procedure 4 (general scheme 11a) as a colourless gum (1.41 g, 90% purity by 1H NMR, 91%) after purification by flash column chromatography on normal phase silica (50 g SNAP KP-SIL cartridge, 0-100% EtOAc in heptane gradient followed by a 0-15% MeOH in EtOAc gradient).

$^1$H NMR (500 MHz, Chloroform-d) δ 1.89-1.98 (m, 1H), 1.99-2.11 (m, 2H), 2.19-2.30 (m, 1H), 2.33-2.44 (m, 1H), 2.48-2.65 (m, 3H), 3.10-3.21 (m, 2H), 3.25-3.37 (m, 2H), 4.09 (d, J=14.8 Hz, 1H), 4.42 (dd, J=3.5, 8.9 Hz, 1H), 4.83 (d, J=14.9 Hz, 1H), 7.20-7.26 (m, 3H), 7.27-7.32 (m, 2H).

LC-MS (METCR1410): 99% (UV), Rt=0.83 min, m/z (ESI$^+$)=329.0 [M+H]$^+$

3-[(2S)-1-Benzyl-5-oxopyrrolidin-2-yl]-3-oxo-2-(1λ$^4$-thiolan-1-ylidene)propanenitrile (I-409)

The title compound was synthesised in a similar manner to general procedure 4 (general scheme 11a) as a brown gum (657 mg, 89% purity by 1H NMR, 78%) after purification by flash column chromatography on normal phase silica (25 g SNAP KP-SIL cartridge, 0-100% EtOAc in heptane gradient followed by a 0-20% MeOH in EtOAc gradient).

$^1$H NMR (500 MHz, Chloroform-d) δ 1.89-1.98 (m, 1H), 2.00-2.11 (m, 2H), 2.20-2.30 (m, 1H), 2.34-2.44 (m, 1H), 2.49-2.65 (m, 3H), 3.11-3.21 (m, 2H), 3.27-3.36 (m, 2H), 4.08-4.12 (m, 1H), 4.43 (dd, J=3.5, 8.9 Hz, 1H), 4.83 (d, J=14.9 Hz, 1H), 7.21-7.27 (m, 3H), 7.27-7.32 (m, 2H).

LC-MS (METCR1410): 98% (UV), Rt=0.83 min, m/z (ESI$^+$)=329.1 [M+H]$^+$

3-{1-[(4-Chloro-3-fluorophenyl)methyl]-5-oxopyrrolidin-2-yl}-3-oxo-2-(1λ$^4$-thiolan-1-ylidene)propanenitrile (I-410)

The title compound was synthesised from 1-[(4-chloro-3-fluorophenyl)methyl]-5-oxopyrrolidine-2-carboxylic acid (I-374) in a similar manner to general procedure 4 (general scheme 11a) as a colourless powder (1.57 g, 97% purity, 73%) after purification by flash column chromatography on normal phase silica (50 g SNAP KP-SIL cartridge, 0-10% MeOH in EtOAc gradient).

$^1$H NMR (250 MHz, Chloroform-d) δ 1.90-2.13 (m, 3H), 2.23-2.46 (m, 2H), 2.48-2.68 (m, 3H), 3.13-3.25 (m, 2H), 3.30-3.43 (m, 2H), 4.12 (d, J=15.2 Hz, 1H), 4.41 (dd, J=3.5, 8.7 Hz, 1H), 4.72 (d, J=15.2 Hz, 1H), 6.95-7.09 (m, 2H), 7.32 (t, J=7.8 Hz, 1H).

LC-MS (METCR1410): 97% (UV), Rt=0.94 min, m/z (ESI$^+$)=381.0/383.1 [M+H]$^+$

4-({2-[2-Cyano-2-(1λ$^4$-thiolan-1-ylidene)acetyl]-5-oxopyrrolidin-1-yl}methyl)benzonitrile (I-411)

The title compound was synthesised from 1-[(4-cyanophenyl)methyl]-5-oxopyrrolidine-2-carboxylic acid (I-375) in a similar to manner general procedure 4 (general scheme 11a) as a colourless powder (1.16 g, 96% purity, 79%) after purification by flash column chromatography on normal phase silica (50 g SNAP KP-SIL cartridge, 0-10% MeOH in EtOAc gradient).

$^1$H NMR (250 MHz, Chloroform-d) δ 1.96-2.14 (m, 3H), 2.27-2.47 (m, 2H), 2.51-2.68 (m, 3H), 3.11-3.21 (m, 2H), 3.30-3.41 (m, 2H), 4.19 (d, J=15.6 Hz, 1H), 4.43 (dd, J=3.5, 8.7 Hz, 1H), 4.81 (d, J=15.6 Hz, 1H), 7.36 (d, J=8.4 Hz, 2H), 7.60 (d, J=8.3 Hz, 2H).

LC-MS (METCR1410): 96% (UV), Rt=0.83 min, m/z (ESI$^+$)=354.1 [M+H]$^+$

3-{1-[(4-Chloro-2-fluorophenyl)methyl]-5-oxopyrrolidin-2-yl}-3-oxo-2-(1λ$^4$-thiolan-1-ylidene)propanenitrile (I-412)

The title compound was synthesised from 1-[(4-chloro-2-fluorophenyl)methyl]-5-oxopyrrolidine-2-carboxylic acid (I-376) in a similar manner to general procedure 4 (general scheme 11a) as a colourless crystalline solid (855 mg, 90% purity by $^1$H NMR, 74%) after purification by flash column chromatography on normal phase silica (50 g SNAP KP-SIL cartridge, 0-10% MeOH in EtOAc gradient).

$^1$H NMR (250 MHz, Chloroform-d) δ 1.85-1.97 (m, 1H), 2.06-2.26 (m, 2H), 2.26-2.47 (m, 2H), 2.47-2.68 (m, 3H), 3.21-3.45 (m, 4H), 4.14 (d, J=15.1 Hz, 1H), 4.42 (dd, J=3.9, 8.5 Hz, 1H), 4.78 (d, J=15.1 Hz, 1H), 7.00-7.15 (m, 2H), 7.23-7.29 (m, 1H).

LC-MS (METCR1410): 94% (UV), Rt=0.93 min, m/z (ESI$^+$)=381.2/383.0 [M+H]$^+$

3-{1-[2-(Oxan-4-yl)ethyl]-5-oxopyrrolidin-2-yl}-3-oxo-2-(1λ$^4$-thiolan-1-ylidene)propane-nitrile (I-413)

The title compound was synthesised from 1-[2-(oxan-4-yl)ethyl]-5-oxopyrrolidine-2-carboxylic acid (I-398) in a similar manner to general procedure 4 (general scheme 11a) as a brown viscous oil (756 mg, 92% purity by 1H NMR, 77%) after purification by flash column chromatography on normal phase silica (25 g SNAP KP-SIL cartridge, 0-100% EtOAc in heptane gradient followed by a 0-20% MeOH in EtOAc gradient).

$^1$H NMR (500 MHz, Chloroform-d) δ 1.19-1.34 (m, 2H), 1.40-1.47 (m, 3H), 1.56-1.62 (m, 1H), 1.63-1.69 (m, 1H), 1.88-1.97 (m, 1H), 2.06-2.17 (m, 2H), 2.23-2.37 (m, 2H), 2.43-2.54 (m, 1H), 2.55-2.69 (m, 2H), 2.77-2.86 (m, 1H), 3.29-3.40 (m, 4H), 3.41-3.49 (m, 2H), 3.71 (dt, J=7.8, 14.0 Hz, 1H), 3.88-3.95 (m, 2H), 4.55-4.61 (m, 1H).

LC-MS (METCR1410): 100% (UV), Rt=0.78 min, m/z (ESI$^+$)=351.1 [M+H]$^+$

3-{1-[(3-Chlorophenyl)methyl]-5-oxopyrrolidin-2-yl}-3-oxo-2-(1λ$^4$-thiolan-1-ylidene)propanenitrile (I-414)

The title compound was synthesised from 1-[(3-chlorophenyl)methyl]-5-oxopyrrolidine-2-carboxylic acid (I-377) in a similar manner to general procedure 4 (general scheme 11a) as a colourless gum (2.00 g, 99% purity, 92%) after purification by flash column chromatography on normal phase silica (100 g SNAP Ultra cartridge, 0-100% EtOAc in heptane gradient followed by a 0-20% MeOH in EtOAc gradient).

$^1$H NMR (500 MHz, DMSO-d6) δ 1.78-1.85 (m, 1H), 1.94-2.09 (m, 2H), 2.15-2.35 (m, 5H), 3.00-3.13 (m, 2H), 3.52-3.59 (m, 2H), 3.84 (d, J=15.4 Hz, 1H), 4.24 (dd, J=3.5, 8.8 Hz, 1H), 4.68 (d, J=15.4 Hz, 1H), 7.13-7.18 (m, 1H), 7.23-7.26 (m, 1H), 7.31-7.37 (m, 2H).

LC-MS (METCR1410): 99% (UV), Rt=0.96 min, m/z (ESI$^+$)=363.1 [M+H]$^+$

3-{1-[(3-Methylphenyl)methyl]-5-oxopyrrolidin-2-yl}-3-oxo-2-(1λ$^4$-thiolan-1-ylidene)propanenitrile (I-415)

The title compound was synthesised from 1-[(3-methylphenyl)methyl]-5-oxopyrrolidine-2-carboxylic acid (I-378) in a similar manner to general procedure 4 (general scheme 11a) as an orange gum (854 mg, 85% purity by $^1$H NMR, 50%) after purification by flash column chromatography on normal phase silica (100 g SNAP KP-SIL cartridge, 100% EtOAc in heptane gradient followed by a 0-20% MeOH in EtOAc gradient).

$^1$H NMR (500 MHz, Chloroform-d) δ 1.60 (s, 3H), 1.89-1.96 (m, 1H), 2.02-2.11 (m, 2H), 2.21-2.30 (m, 1H), 2.36-2.43 (m, 1H), 2.51-2.63 (m, 3H), 3.16-3.22 (m, 2H), 3.30-3.38 (m, 2H), 4.00 (d, J=14.8 Hz, 1H), 4.42 (dd, J=3.6, 9.0 Hz, 1H), 4.84 (d, J=14.8 Hz, 1H), 6.99-7.08 (m, 3H), 7.18 (t, J=7.5 Hz, 1H).
LC-MS (METCR1410): 99% (UV), Rt=0.90 min, m/z (ESI$^+$)=343.0 [M+H]$^+$

3-[1-(Cyclopentylmethyl)-5-oxopyrrolidin-2-yl]-3-oxo-2-(1$\lambda^4$-thiolan-1-ylidene)-propanenitrile (I-416)

The title compound was synthesised from 1-(cyclopentylmethyl)-5-oxopyrrolidine-2-carboxylic acid (I-399) in a similar manner to general procedure 4 (general scheme 11a) as a brown gum (1.72 g, 70% purity by $^1$H NMR, 87%) after azeotroping with EtOAc.
$^1$H NMR (500 MHz, DMSO-d6) δ 1.06-1.15 (m, 2H), 1.22-1.29 (m, 6H), 1.42-1.61 (m, 5H), 1.63-1.71 (m, 1H), 1.74-1.83 (m, 1H), 2.00-2.08 (m, 2H), 2.11-2.26 (m, 2H), 2.26-2.35 (m, 2H), 2.52-2.58 (m, 1H), 3.39 (dd, J=9.2, 13.6 Hz, 1H), 4.40-4.51 (m, 1H).
LC-MS (METCR1410): 95% (UV), Rt=0.89 min, m/z (ESI$^+$)=321.1 [M+H]$^+$

3-{1-[(4-Chlorophenyl)methyl]-5-oxopyrrolidin-2-yl}-3-oxo-2-(1$\lambda^4$-thiolan-1-ylidene)-propanenitrile (I-417)

The title compound was synthesised from 1-[(4-chlorophenyl)methyl]-5-oxopyrrolidine-2-carboxylic acid (I-379) in a similar manner to general procedure 4 (general scheme 11a) as an orange gum (2.34 g, 81% purity by 1H NMR, 71%) after purification by flash column chromatography on normal phase silica (100 g SNAP KP-SIL cartridge, 0-100% EtOAc in heptane gradient followed by a 0-25% MeOH in EtOAc gradient).
$^1$H NMR (500 MHz, DMSO-d6) δ 1.78-1.84 (m, 1H), 2.00-2.07 (m, 2H), 2.15-2.22 (m, 1H), 2.25-2.33 (m, 4H), 3.02-3.12 (m, 2H), 3.53-3.59 (m, 2H), 3.81 (d, J=15.3 Hz, 1H), 4.22 (dd, J=3.5, 8.8 Hz, 1H), 4.68 (d, J=15.3 Hz, 1H), 7.20-7.23 (m, 2H), 7.37-7.40 (m, 2H).
LC-MS (METCR1410): 94% (UV), Rt=0.92 min, m/z (ESI$^+$)=363.0/365.0 [M+H]$^+$

3-{1-[(4-Fluorophenyl)methyl]-5-oxopyrrolidin-2-yl}-3-oxo-2-(1$\lambda^4$-thiolan-1-ylidene)-propanenitrile (I-418)

The title compound was synthesised from 1-[(4-fluorophenyl)methyl]-5-oxopyrrolidine-2-carboxylic acid (I-380) in a similar manner to general procedure 4 (general scheme 11a) as an orange viscous oil (2.41 g, 90% purity by 1H NMR, 87%) after purification by flash column chromatography on normal phase silica (50 g SNAP KP-SIL cartridge, 0-100% EtOAc in heptane gradient followed by a 0-25% MeOH in EtOAc gradient).
$^1$H NMR (500 MHz, Chloroform-d) δ 1.89-1.95 (m, 1H), 2.03-2.10 (m, 2H), 2.20-2.28 (m, 1H), 2.34-2.41 (m, 1H), 2.49-2.63 (m, 3H), 3.13-3.20 (m, 2H), 3.32-3.39 (m, 2H), 4.07 (d, J=14.9 Hz, 1H), 4.39 (dd, J=3.4, 8.9 Hz, 1H), 4.74 (d, J=14.9 Hz, 1H), 6.93-7.02 (m, 2H), 7.16-7.24 (m, 2H).
LC-MS (METCR1410): 99% (UV), Rt=0.88 min, m/z (ESI$^+$)=347.1 [M+H]$^+$

3-{1-[(2-Chlorophenyl)methyl]-5-oxopyrrolidin-2-yl}-3-oxo-2-(1$\lambda^4$-thiolan-1-ylidene)-propanenitrile (I-419)

The title compound was synthesised from 1-[(2-chlorophenyl)methyl]-5-oxopyrrolidine-2-carboxylic acid (I-381) in a similar manner to general procedure 4 (general scheme 11a) as an orange gum (1.22 g, 95% purity by 1H NMR, 73%) after purification by flash column chromatography on normal phase silica (50 g SNAP KP-SIL cartridge, 0-100% EtOAc in heptane gradient followed by 0-20% MeOH in EtOAc).
$^1$H NMR (500 MHz, Chloroform-d) δ 1.90-1.99 (m, 1H), 2.02-2.13 (m, 2H), 2.24-2.35 (m, 1H), 2.36-2.44 (m, 1H), 2.50-2.63 (m, 3H), 3.20-3.33 (m, 2H), 3.33-3.42 (m, 2H), 4.20 (d, J=15.4 Hz, 1H), 4.43 (dd, J=3.7, 8.9 Hz, 1H), 4.98 (d, J=15.4 Hz, 1H), 7.18-7.24 (m, 2H), 7.26-7.29 (m, 1H), 7.31-7.35 (m, 1H).
LC-MS (METCR1410): 100% (UV), Rt=0.88 min, m/z (ESI$^+$)=363.0 [M+H]$^+$

3-{1-[(2-Methylphenyl)methyl]-5-oxopyrrolidin-2-yl}-3-oxo-2-(1$\lambda^4$-thiolan-1-ylidene)-propanenitrile (I-420)

The title compound was synthesised from 1-[(2-methylphenyl)methyl]-5-oxopyrrolidine-2-carboxylic acid (I-382) in a similar manner to general procedure 4 (general scheme 11a) as an orange gum (923 mg, 96% purity by $^1$H NMR, 59%) after purification by flash column chromatography on normal phase silica (50 g SNAP KP-SIL cartridge, 0-100% EtOAc in heptane gradient followed by 0-20% MeOH in EtOAc gradient).
$^1$H NMR (500 MHz, Chloroform-d) δ 1.91 (ddt, J=3.6, 9.8, 13.1 Hz, 1H), 2.00-2.10 (m, 2H), 2.21-2.28 (m, 1H), 2.29 (s, 3H), 2.35-2.43 (m, 1H), 2.47-2.63 (m, 3H), 3.09-3.21 (m, 2H), 3.28-3.35 (m, 2H), 4.18 (d, J=14.9 Hz, 1H), 4.33 (dd, J=3.2, 9.0 Hz, 1H), 4.80 (d, J=14.9 Hz, 1H), 7.09-7.15 (m, 3H), 7.15-7.19 (m, 1H).
LC-MS (METCR1603): 100% (UV), Rt=3.11 min, m/z (ESI$^+$)=343.2 [M+H]$^+$

3-{1-[(4-Methylphenyl)methyl]-5-oxopyrrolidin-2-yl}-3-oxo-2-(1$\lambda^4$-thiolan-1-ylidene)-propanenitrile (I-421)

The title compound was synthesised from 1-[(4-methylphenyl)methyl]-5-oxopyrrolidine-2-carboxylic acid (I-383) in a similar manner to general procedure 4 (general scheme 11a) as an orange viscous oil (1.14 g, 85% purity by 1H NMR, 67%) after purification by flash column chromatography on normal phase silica (100 g SNAP-KP-SIL cartridge, 0-100% EtOAc in heptane gradient followed by 0-20% MeOH in EtOAc gradient).
$^1$H NMR (500 MHz, Chloroform-d) δ 1.87-1.95 (m, 1H), 2.01-2.10 (m, 2H), 2.17-2.28 (m, 1H), 2.31 (s, 3H), 2.33-2.41 (m, 1H), 2.49-2.62 (m, 3H), 3.14-3.22 (m, 2H), 3.29-3.38 (m, 2H), 3.99 (d, J=14.8 Hz, 1H), 4.39 (dd, J=3.5, 9.0 Hz, 1H), 4.82 (d, J=14.8 Hz, 1H), 7.05-7.14 (m, 4H).
LC-MS (METCR1410): 100% (UV), Rt=0.90 min, m/z (ESI$^+$)=343.1 [M+H]$^+$

3-{1-[(4-Methyl-1,3-thiazol-2-yl)methyl]-5-oxopyrrolidin-2-yl}-3-oxo-2-(1$\lambda^4$-thiolan-1-ylidene)propanenitrile (I-422)

The title compound was synthesised from 1-[(4-methyl-1,3-thiazol-2-yl)methyl]-5-oxopyrrolidine-2-carboxylic acid (I-372) in a similar manner to general procedure 4 (general scheme 11a) as an orange gum (6.31 g, 62% purity by $^1$H NMR, 90%) after purification by flash column chromatography on normal phase silica (325 g SNAP-KP-SIL cartridge, 0-100% EtOAc in heptane gradient followed by 0-20% MeOH in EtOAc gradient).

$^1$H NMR (500 MHz, Chloroform-d) δ 1.89-1.98 (m, 1H), 2.01-2.15 (m, 3H), 2.29-2.35 (m, 1H), 2.37-2.39 (m, 3H), 2.41-2.49 (m, 1H), 2.52-2.60 (m, 2H), 3.27-3.36 (m, 2H), 3.39-3.47 (m, 2H), 4.16 (d, J=15.9 Hz, 1H), 4.54-4.61 (m, 1H), 5.17 (d, J=15.9 Hz, 1H), 6.79 (s, 1H).

LC-MS (METCR1410): 99% (UV), Rt=0.79 min, m/z (ESI$^+$)=350.1 [M+H]$^+$

3-[(2R)-1-[(4-Chlorophenyl)methyl]-5-oxopyrrolidin-2-yl]-3-oxo-2-(1λ$^4$-thiolan-1-ylidene)propanenitrile (I-423)

The title compound was synthesised from (2R)-1-[(4-chlorophenyl)methyl]-5-oxopyrrolidine-2-carboxylic acid (I-384) in a similar manner to general procedure 4 (general scheme 11a) as an orange gum (3.70 g, 79% purity by 1H NMR, 75%) after purification by flash column chromatography on normal phase silica (340 g SNAP KP-SIL cartridge, 0-100% EtOAc in heptane gradient followed by a 0-20% MeOH in EtOAc gradient).

$^1$H NMR (500 MHz, Chloroform-d) δ 1.89-1.98 (m, 1H), 2.04-2.11 (m, 2H), 2.18-2.30 (m, 1H), 2.33-2.42 (m, 1H), 2.46-2.66 (m, 3H), 3.07-3.18 (m, 2H), 3.28-3.39 (m, 2H), 4.19 (d, J=15.0 Hz, 1H), 4.41 (dd, J=3.3, 8.9 Hz, 1H), 4.66 (d, J=15.0 Hz, 1H), 7.17-7.21 (m, 2H), 7.24-7.28 (m, 2H).

LC-MS (METCR1410): 100% (UV), Rt=0.92 min, m/z (ESI$^+$)=363.0 [M+H]$^+$

3-Oxo-3-{5-oxo-1 [(1-oxo-2,3-dihydro-1H-isoindol-5-yl)methyl]pyrrolidin-2-yl}-2-(1λ$^4$-thiolan-1-ylidene)propanenitrile (I-424)

The title compound was synthesised from 5-oxo-1-[(1-oxo-2,3-dihydro-1H-isoindol-5-yl)methyl]pyrrolidine-2-carboxylic acid (I-385) in a similar manner to general procedure 4 (general scheme 11a) except extracting with IPA:CHCl$_3$ (1:3) to afford a yellow viscous oil (530 mg, 80% purity by 1H NMR, 37%) after purification by flash column chromatography on normal phase silica (25 g SNAP KP-SIL cartridge, 0-20% MeOH in DCM gradient).

$^1$H NMR (250 MHz, Chloroform-d) δ 1.91-2.16 (m, 4H), 2.18-2.43 (m, 2H), 2.44-2.73 (m, 4H), 3.29-3.42 (m, 2H), 4.29 (d, J=15.1 Hz, 1H), 4.44-4.52 (m, 3H), 4.86 (d, J=15.2 Hz, 1H), 6.62 (b.s, 1H), 7.36 (d, J=7.7 Hz, 1H), 7.42 (s, 1H), 7.81 (d, J=7.8 Hz, 1H).

LC-MS (METCR1410): 92% (UV), Rt=0.70 min, m/z (ESI$^+$)=384.1 [M+H]$^+$

3-Oxo-3-{5-oxo-1-[(1,3-thiazol-2-yl)methyl]pyrrolidin-2-yl}-2-(1λ$^4$-thiolan-1-ylidene)-propanenitrile (I-425)

The title compound was synthesised from 5-oxo-1-[(1,3-thiazol-2-yl)methyl]-pyrrolidine-2-carboxylic acid (I-386) in a similar manner to general procedure 4 (general scheme 11a) except extracting with IPA:CHCl$_3$ (1:3) to afford a yellow viscous oil (587 mg, 80% purity by 1H NMR, 33%) after purification by flash column chromatography on normal phase silica (25 g SNAP KP-SIL cartridge, 0-15% MeOH in EtOAc gradient).

$^1$H NMR (250 MHz, Chloroform-d) δ 1.87-1.99 (m, 1H), 2.03-2.16 (m, 2H), 2.28-2.61 (m, 5H), 3.29-3.45 (m, 4H), 4.29 (d, J=15.9 Hz, 1H), 4.56-4.64 (m, 1H), 5.20 (d, J=15.9 Hz, 1H), 7.28 (d, J=3.3 Hz, 1H), 7.66 (d, J=3.3 Hz, 1H).

LC-MS (METCR1410): 100% (UV), Rt=0.72 min, m/z (ESI$^+$)=336.0 [M+H]$^+$

3-[1-(Cyclopropylmethyl)-5-oxopyrrolidin-2-yl]-3-oxo-2-(1λ$^4$-thiolan-1-ylidene)-propanenitrile (I-426)

The title compound was synthesised from 1-(cyclopropylmethyl)-5-oxopyrrolidine-2-carboxylic acid (I-404) in a similar manner to general procedure 4 (general scheme 11a) as a brown viscous oil (410 mg, 94% purity, 82%) after purification by flash column chromatography on normal phase silica (25 g SNAP KP-SIL cartridge, 0-100% EtOAc in heptane gradient followed by 0-50% MeOH in EtOAc gradient) followed by ion-exchange flash chromatography (5 g Isolute SCX-2 cartridge, 1:1 DCM/MeOH eluent).

$^1$H NMR (500 MHz, Chloroform-d) δ 0.14-0.24 (m, 2H), 0.45-0.54 (m, 1H), 0.57-0.67 (m, 1H), 0.80-0.94 (m, 1H), 1.97-2.05 (m, 1H), 2.11-2.23 (m, 2H), 2.36-2.48 (m, 1H), 2.51-2.75 (m, 5H), 3.30-3.42 (m, 2H), 3.54-3.61 (m, 2H), 3.63 (dd, J=6.8, 14.3 Hz, 1H), 4.91 (dd, J=3.4, 9.2 Hz, 1H).

LC-MS (METCR1410): 94% (UV), Rt=0.79 min, m/z (ESI$^+$)=293.1 [M+H]$^+$

3-{1-[(5-Methylthiophen-2-yl)methyl]-5-oxopyrrolidin-2-yl}-3-oxo-2-(1λ$^4$-thiolan-1-ylidene)propanenitrile (I-427)

The title compound was synthesised from 1-[(5-methylthiophen-2-yl)methyl]-5-oxopyrrolidine-2-carboxylic acid (I-400) in a similar manner to general procedure 4 (general scheme 11a) as a yellow viscous oil (1.80 g, 80% purity by $^1$H NMR, 86%) after purification by flash column chromatography on normal phase silica (10 g SNAP KP-SIL cartridge, 0-100% EtOAc in heptane gradient followed by 0-50% MeOH in EtOAc gradient).

$^1$H NMR (500 MHz, Chloroform-d) δ 1.81-1.93 (m, 1H), 2.20-2.36 (m, 2H), 2.39 (s, 3H), 2.42-2.65 (m, 3H), 3.06-3.18 (m, 1H), 3.19-3.33 (m, 2H), 3.38-3.51 (m, 2H), 3.62-3.75 (m, 1H), 4.00 (dd, J=2.8, 15.3 Hz, 1H), 4.41-4.57 (m, 1H), 4.97 (dd, J=4.3, 15.3 Hz, 1H), 6.52 (s, 1H), 6.65 (s, 1H).

LC-MS (METCR1410): 99% (UV), Rt=0.89 min, m/z (ESI$^+$)=349.1 [M+H]$^+$

3-Oxo-3-(5-oxo-1-phenylpyrrolidin-2-yl)-2-(1λ$^4$-thiolan-1-ylidene)propanenitrile (I-428)

The title compound was synthesised in a similar manner to general procedure 4 (general scheme 11a) as an off-white foam (1.43 g, 99% purity, 92%) after purification by flash column chromatography on normal phase silica (50 g SNAP Ultra cartridge, 0-20% MeOH in EtOAc gradient).

$^1$H NMR (500 MHz, Chloroform-d) δ 2.00-2.14 (m, 3H), 2.43-2.63 (m, 4H), 2.71-2.82 (m, 1H), 3.20-3.32 (m, 2H), 3.32-3.41 (m, 2H), 5.18 (dd, J=8.7, 3.9 Hz, 1H), 7.13-7.18 (m, 1H), 7.31-7.40 (m, 2H), 7.47-7.54 (m, 2H).

LC-MS (METCR1410): 99% (UV), Rt=0.82 min, m/z (ESI$^+$)=315.1 [M+H]$^+$

Method B: Coupling Using Carboxylic Acid Lithium Salt

3-{1-[(Oxan-4-yl)methyl]-5-oxopyrrolidin-2-yl}-3-oxo-2-(1λ$^4$-thiolan-1-ylidene)propane-nitrile (I-429)

To a stirred solution of 5-oxo-1-(tetrahydropyran-4-ylmethyl)pyrrolidine-2-carboxylic acid (I-402) (80% purity, 287 mg, 1.01 mmol), DIPEA (387 µL, 2.22 mmol) and HATU (461 mg, 1.21 mmol) dissolved in DCM (5 mL) was added 1-(cyanomethyl)-thiolan-1-ium bromide (90% purity, 304 mg, 1.31 mmol, synthesised by the procedure outlined in WO2014/154829)) and the mixture was stirred at RT for 18 h. The reaction mixture was then cooled to 0° C. and quenched with 1N HCl (4 mL). The phases were separated, the aqueous layer washed with DCM (8 mL) and the organic layers combined, washed with 1M HCl (2×8 mL), saturated NaHCO$_3$(8 mL), brine (8 mL), then dried over sodium sulfate, filtered and concentrated in vacuo. The residue was purified by flash column chromatography on normal phase silica (25 g SNAP KP-SIL cartridge, 0-100% EtOAc in heptane gradient followed by a 0-20% MeOH in EtOAc gradient) to afford 95 mg of 3-{1-[(oxan-4-yl)methyl]-5-oxopyrrolidin-2-yl}-3-oxo-2-(1λ$^4$-thiolan-1-ylidene)propane-nitrile (I-429) as a colourless viscous oil (98% purity, 27%).

$^1$H NMR (500 MHz, DMSO-d6) δ 1.01-1.11 (m, 1H), 1.12-1.19 (m, 1H), 1.41-1.48 (m, 1H), 1.48-1.54 (m, 1H), 1.67-1.85 (m, 2H), 1.99-2.10 (m, 2H), 2.14-2.26 (m, 3H), 2.27-2.35 (m, 2H), 3.10-3.25 (m, 5H), 3.35-3.47 (m, 1H), 3.55-3.65 (m, 2H), 3.77-3.85 (m, 2H), 4.38-4.45 (m, 1H).

LC-MS (METCR1410): 98% (UV), Rt=0.73 min, m/z (ESI$^+$)=337.1 [M+H]$^+$

3-{1-[(3-Methyl-1,2-oxazol-5-yl)methyl]-5-oxopyrrolidin-2-yl}-3-oxo-2-(1λ$^4$-thiolan-1-ylidene)propanenitrile (I-430)

The title compound was synthesised from lithium(1+) ion 1-[(3-methyl-1,2-oxazol-5-yl)methyl]-5-oxopyrrolidine-2-carboxylate (I-401) in a similar manner to method B, general procedure 3 (general scheme 20) as a brown viscous oil (480 mg, 66% purity by $^1$H NMR, 46%) after purification by flash column chromatography on normal phase silica (50 g SNAP KP-SIL cartridge, 0-100% EtOAc in heptane gradient followed by 0-20% MeOH in EtOAc gradient).

$^1$H NMR (500 MHz, Chloroform-d) δ 1.93-2.00 (m, 1H), 2.06-2.14 (m, 2H), 2.26 (s, 3H), 2.30-2.41 (m, 2H), 2.46-2.55 (m, 1H), 2.55-2.66 (m, 2H), 3.33-3.40 (m, 2H), 3.40-3.48 (m, 2H), 4.20 (d, J=16.0 Hz, 1H), 4.56-4.60 (m, 1H), 4.85 (d, J=16.0 Hz, 1H), 6.02 (s, 1H).

LC-MS (METCR1410): 97% (UV), Rt=0.73 min, m/z (ESI$^+$)=334.1 [M+H]$^+$

3-Oxo-3-[5-oxo-1-(2-phenylethyl)pyrrolidin-2-yl]-2-(1λ$^4$-thiolan-1-ylidene)propanenitrile (I-431)

The title compound was synthesised from lithium(1+) ion 5-oxo-1-(2-phenylethyl)pyrrolidine-2-carboxylate (I-403) in a similar manner to method B, general procedure 3 (general scheme 20) as an orange viscous oil (358 mg, 90% purity by $^1$H NMR, 44%) after purification by flash column chromatography on normal phase silica (25 g SNAP KP-SIL cartridge, 0-100% EtOAc in heptane gradient followed by a 0-20% MeOH in EtOAc gradient).

$^1$H NMR (500 MHz, Chloroform-d) δ 1.85-1.93 (m, 1H), 2.05-2.16 (m, 2H), 2.18-2.35 (m, 2H), 2.44-2.53 (m, 1H), 2.56-2.67 (m, 2H), 2.74-2.83 (m, 1H), 2.84-2.92 (m, 1H), 2.97-3.06 (m, 1H), 3.29-3.39 (m, 2H), 3.39-3.48 (m, 2H), 3.92-4.00 (m, 1H), 4.49 (dd, J=3.7, 8.7 Hz, 1H), 7.19-7.24 (m, 3H), 7.27-7.31 (m, 2H).

LC-MS (METCR1603): 100% (UV), Rt=3.22 min, m/z (ESI$^+$)=343.1 [M+H]$^+$

General Procedure 4 (General Scheme 20): Oxidation

Method As Described in General Procedure 6 (General Scheme 11a): Oxidation

Method A: Oxone Oxidation to Ketoacid 2-(1-Benzyl-5-oxopyrrolidin-2-yl)-2-oxoacetic acid (I-432)

The title compound was synthesised from 3-(1-benzyl-5-oxopyrrolidin-2-yl)-3-oxo-2-(1λ$^4$-thiolan-1-ylidene)propanenitrile (I-408) in a similar manner to general procedure 6 (general scheme 11a) after quenching the reaction with 1N HCl prior to extraction to afford a yellow viscous oil (1.12 g, 50% purity estimated by $^1$H NMR, 59%) which was used crude in the next step without purification. 2-[(2R)-1-Benzyl-5-oxopyrrolidin-2-yl]-2-oxoacetic acid (I-433)

The title compound was synthesised from 3-[(2R)-1-benzyl-5-oxopyrrolidin-2-yl]-3-oxo-2-(1λ$^4$-thiolan-1-ylidene)propanenitrile (I-405) in a similar manner to general procedure 5 (general scheme 11a) after quenching the reaction with 1N HCl prior to extraction to afford a yellow viscous oil (587 mg, 60% purity estimated by $^1$H NMR 71%) which was used crude in the next step without purification.

2-[(2S)-1-Benzyl-5-oxopyrrolidin-2-yl]-2-oxoacetic acid (I-434)

The title compound was synthesised from 3-[(2S)-1-benzyl-5-oxopyrrolidin-2-yl]-3-oxo-2-(1λ$^4$-thiolan-1-ylidene)propanenitrile (I-409) in a similar manner to general procedure 6 (general scheme 11a) after quenching the reaction with 1N HCl prior to extraction to afford a yellow viscous oil (511 mg, 50% purity estimated by $^1$H NMR, 58%) which was used crude in the next step without purification.

2-{1-[(4-Chloro-3-fluorophenyl)methyl]-5-oxopyrrolidin-2-yl}-2-oxoacetic acid (I-435)

The title compound was synthesised from 3-{1-[(4-chloro-3-fluorophenyl)-methyl]-5-oxopyrrolidin-2-yl}-3-oxo-2-(1λ$^4$-thiolan-1-ylidene)propanenitrile (I-410) in a similar manner to general procedure 6 (general scheme 11a) after quenching the reaction with 1N HCl prior to extraction to afford a colourless viscous oil (221 mg, 50% purity estimated by $^1$H NMR, 70%) which was used crude in the next step without purification.

2-{1-[(4-Cyanophenyl)methyl]-5-oxopyrrolidin-2-yl}-2-oxoacetic acid (I-436)

The title compound was synthesised from 4-({2-[2-cyano-2-(1λ$^4$-thiolan-1-ylidene)acetyl]-5-oxopyrrolidin-1-yl}methyl)benzonitrile (I-411) in a similar manner to general procedure 6 (general scheme 11a) after quenching the reaction with 1N HCl prior to extraction to afford a colourless viscous oil (195 mg, 50% purity estimated by $^1$H NMR, 63%) which was used crude in the next step without purification.

2-{1-[(4-Chlorophenyl)methyl]-5-oxopyrrolidin-2-yl}-2-oxoacetic acid (I-437)

The title compound was synthesised from 3-{1-[(4-chlorophenyl)methyl]-5-oxopyrrolidin-2-yl}-3-oxo-2-(1λ$^4$-thio-

2-{1-[(3-Chlorophenyl)methyl]-5-oxopyrrolidin-2-yl}-2-oxoacetic acid (I-438)

The title compound was synthesised from 3-{1-[(3-chlorophenyl)methyl]-5-oxopyrrolidin-2-yl}-3-oxo-2-(1$\lambda^4$-thiolan-1-ylidene)propanenitrile (I-414) in a similar manner to general procedure 6 (general scheme 11a) after quenching the reaction with 1N HCl prior to extraction to afford a yellow gum (198 mg, 55% purity estimated by $^1$H NMR, 71%) which was used crude in the next step without purification.

2-{1-[(Oxan-4-yl)methyl]-5-oxopyrrolidin-2-yl}-2-oxoacetic acid (I-439)

The title compound was synthesised from 3-{1-[(oxan-4-yl)methyl]-5-oxo-pyrrolidin-2-yl}-3-oxo-2-(1$\lambda^4$-thiolan-1-ylidene)propanenitrile (I-429) in a similar manner to general procedure 6 (general scheme 11a) after quenching the reaction with 1N HCl prior to extraction with 1:1 IPA:CHCl$_3$ to afford a colourless viscous oil (62 mg, 40% purity estimated by $^1$H NMR, 35%) which was used crude in the next step without purification.

2-[1-(Cyclopentylmethyl)-5-oxopyrrolidin-2-yl]-2-oxoacetic acid (I-440)

The title compound was synthesised from 3-[1-(cyclopentylmethyl)-5-oxo-pyrrolidin-2-yl]-3-oxo-2-(1$\lambda^4$-thiolan-1-ylidene)propanenitrile (I-416) in a similar manner to general procedure 6 (general scheme 11a) after quenching the reaction with 1N HCl prior to extraction to afford an off-white gum (316 mg, 55% purity estimated by $^1$H NMR, 83%) which was used crude in the next step without purification.

2-{1-[(4-Fluorophenyl)methyl]-5-oxopyrrolidin-2-yl}-2-oxoacetic acid (I-441)

The title compound was synthesised from 3-{1-[(4-fluorophenyl)methyl]-5-oxopyrrolidin-2-yl}-3-oxo-2-(1$\lambda^4$-thiolan-1-ylidene)propanenitrile (I-418) in a similar manner to general procedure 6 (general scheme 11a) after quenching the reaction with 1N HCl prior to extraction to afford a colourless viscous oil (2.10 g, 60% purity estimated by $^1$H NMR, 76%) which was used crude in the next step without purification.

2-Oxo-2-[5-oxo-1-(2-phenylethyl)pyrrolidin-2-yl]acetic acid (I-442)

The title compound was synthesised from 3-oxo-3-[5-oxo-1-(2-phenylethyl)-pyrrolidin-2-yl]-2-(1$\lambda^4$-thiolan-1-ylidene)propanenitrile (I-431) in a similar manner to general procedure 6 (general scheme 11a) after quenching the reaction with 1N HCl prior to extraction to afford an orange free-flowing oil (330 mg, 70% purity estimated by $^1$H NMR, 93%) which was used crude in the next step without purification.

2-{1-[(2-Chlorophenyl)methyl]-5-oxopyrrolidin-2-yl}-2-oxoacetic acid (I-443)

The title compound was synthesised from 3-{1-[(2-chlorophenyl)methyl]-5-oxopyrrolidin-2-yl}-3-oxo-2-(1$\lambda^4$-thiolan-1-ylidene)propanenitrile (I-419) in a similar manner to general procedure 6 (general scheme 11a) after quenching the reaction with 1N HCl prior to extraction to afford a off-white viscous oil (563 mg, 70% purity estimated by $^1$H NMR, 89%) which was used crude in the next step without purification.

2-{1-[(2-Methylphenyl)methyl]-5-oxopyrrolidin-2-yl}-2-oxoacetic acid (I-444)

The title compound was synthesised from 3-{1-[(2-methylphenyl)methyl]-5-oxopyrrolidin-2-yl}-3-oxo-2-(1$\lambda^4$-thiolan-1-ylidene)propanenitrile (I-420) in a similar manner to general procedure 6 (general scheme 11a) after quenching the reaction with 1N HCl prior to extraction to afford a off-white viscous oil (462 mg, 70% purity estimated by $^1$H NMR, 88%) which was used crude in the next step without purification.

2-{1-[(3-Methylphenyl)methyl]-5-oxopyrrolidin-2-yl}-2-oxoacetic acid (I-445)

The title compound was synthesised from 3-{1-[(3-methylphenyl)methyl]-5-oxopyrrolidin-2-yl}-3-oxo-2-(1A'$^4$-thiolan-1-ylidene)propanenitrile (I-415) in a similar manner to general procedure 6 (general scheme 11a) after quenching the reaction with 1N HCl prior to extraction to afford an off-white viscous oil (380 mg, 60% purity estimated by $^1$H NMR, 88%) which was used crude in the next step without purification.

2-{1-[(4-Methylphenyl)methyl]-5-oxopyrrolidin-2-yl}-2-oxoacetic acid (I-446)

The title compound was synthesised from 3-{1-[(4-methylphenyl)methyl]-5-oxopyrrolidin-2-yl}-3-oxo-2-(1$\lambda^4$-thiolan-1-ylidene)propanenitrile (I-421) in a similar manner to general procedure 6 (general scheme 11a) after quenching the reaction with 1N HCl prior to extraction to afford an orange viscous oil (384 mg, 50% purity estimated by $^1$H NMR, 85%) which was used crude in the next step without purification.

2-[(2R)-1-[(4-Chlorophenyl)methyl]-5-oxopyrrolidin-2-yl]-2-oxoacetic acid (I-447)

The title compound was synthesised from 3-[(2R)-1-[(4-chlorophenyl)methyl]-5-oxopyrrolidin-2-yl]-3-oxo-2-(1$\lambda^4$-thiolan-1-ylidene)propanenitrile (I-423) in a similar manner to general procedure 6 (general scheme 11a) after quenching the reaction with 1N HCl prior to extraction to afford an orange crystalline solid (3.17 g, 55% purity estimated by 1H NMR, 77%) which was used crude in the next step without purification.

2-{1-[(4-Chloro-2-fluorophenyl)methyl]-5-oxopyrrolidin-2-yl}-2-oxoacetic acid (I-448)

The title compound was synthesised from 3-{1-[(4-chloro-2-fluorophenyl)-methyl]-5-oxopyrrolidin-2-yl}-3-oxo-2-(1$\lambda^4$-thiolan-1-ylidene)propanenitrile (I-412) in a similar manner to general procedure 6 (general scheme 11a)

after quenching the reaction with 1N HCl prior to extraction to afford a colourless viscous oil (173 mg, 75% purity estimated by $^1$H NMR, 82%) which was used crude in the next step without purification.

2-Oxo-2-{5-oxo-1-[(1-oxo-2,3-dihydro-1H-isoindol-5-yl)methyl]pyrrolidin-2-yl}acetic acid

I-449

The title compound was synthesised from 3-oxo-3-{5-oxo-1-[(1-oxo-2,3-dihydro-1H-isoindol-5-yl)methyl]pyrrolidin-2-yl}-2-(1λ$^4$-thiolan-1-ylidene)propanenitrile (I-424) in a similar manner to general procedure 6 (general scheme 11a) after quenching the reaction with 1N HCl prior to extraction with 1:1 IPA:CHCl3 to afford a colourless viscous oil (261 mg, 50% purity estimated by $^1$H NMR, 78%) which was used crude in the next step without purification.

2-{1-[(4-Carbamoylphenyl)methyl]-5-oxopyrrolidin-2-yl}-2-oxoacetic acid (I-450)

The title compound was synthesised from 4-({2-[2-cyano-2-(1λ$^4$-thiolan-1-ylidene)acetyl]-5-oxopyrrolidin-1-yl}methyl)benzamide (I-406) in a similar manner to general procedure 6 (general scheme 11a) after quenching the reaction with 1N HCl prior to extraction with 1:1 IPA:CHCl3 to afford a pale-yellow foamy solid (436 mg, 40% purity estimated by 1H NMR, 52%) which was used crude in the next step without purification.

2-{1-[(3-Carbamoylphenyl)methyl]-5-oxopyrrolidin-2-yl}-2-oxoacetic acid (I-451)

The title compound was synthesised from 3-({2-[2-cyano-2-(1λ$^4$-thiolan-1-ylidene)acetyl]-5-oxopyrrolidin-1-yl}methyl)benzamide (I-407) in a similar manner to general procedure 6 (general scheme 11a) after quenching the reaction with 1N HCl prior to extraction with 1:1 IPA:CHCl3 to afford a pale-yellow solid (722 mg, 47% purity estimated by $^1$H NMR, 74%) which was used in the next step without purification.

2-[1-(Cyclopropylmethyl)-5-oxopyrrolidin-2-yl]-2-oxoacetic acid (I-452)

The title compound was synthesised from 3-[1-(cyclopropylmethyl)-5-oxopyrrolidin-2-yl]-3-oxo-2-(1λ$^4$-thiolan-1-ylidene)propanenitrile (I-426) in a similar manner to general procedure 6 (general scheme 11a) after quenching the reaction with 1N HCl prior to extraction with 1:1 IPA:CHCl$_3$ to afford a yellow viscous oil (210 mg, 40% purity estimated by 1H NMR, 30%) which was used crude in the next step without purification.

2-{1-[(5-Methylthiophen-2-yl)methyl]-5-oxopyrrolidin-2-yl}-2-oxoacetic acid (I-453)

The title compound was synthesised from 3-{1-[(5-methylthiophen-2-yl)methyl]-5-oxopyrrolidin-2-yl}-3-oxo-2-(1λ$^4$-thiolan-1-ylidene)propanenitrile (I-427) in a similar manner to general procedure 6 (general scheme 11a) after quenching the reaction with 1N HCl prior to extraction to afford a yellow viscous oil (400 mg, 50% purity estimated by $^1$H NMR, 69%) which was used crude in the next step without purification.

2-Oxo-2-(5-oxo-1-phenylpyrrolidin-2-yl)acetic acid (I-454)

The title compound was synthesised from 3-oxo-3-(5-oxo-1-phenylpyrrolidin-2-yl)-2-(1λ$^4$-thiolan-1-ylidene)propanenitrile (I-428) in a similar manner to general procedure 6 (general scheme 11a) after quenching the reaction with 1N HCl prior to extraction to afford a yellow gum (1.54 g, 50% purity estimated by 1H NMR, 72%) which was used crude in the next step without purification.

2-{1-[2-(Oxan-4-yl)ethyl]-5-oxopyrrolidin-2-yl}-2-oxoacetic acid (I-455)

The title compound was synthesised 3-{1-[2-(oxan-4-yl)ethyl]-5-oxopyrrolidin-2-yl}-3-oxo-2-(1λ$^4$-thiolan-1-ylidene)propanenitrile (I-413) in a similar manner to general procedure 6 (general scheme 11a) after quenching the reaction with 1N HCl prior to extraction to afford a yellow gum (435 mg) which was used crude in the next step without purification.

Method B: m CPBA Oxidation to Ketoester

Methyl 2-{1-[(4-methyl-1,3-thiazol-2-yl)methyl]-5-oxopyrrolidin-2-yl}-2-oxoacetate (I-456)

To an ice-cooled stirred solution of 3-{1-[(4-methyl-1,3-thiazol-2-yl)methyl]-5-oxopyrrolidin-2-yl}-3-oxo-2-[(1E)-1λ$^4$-thiolan-1-ylidene]propanenitrile (I-422, 62% purity, 1.0 g, 1.77 mmol) in anhydrous MeOH (15 mL) was added m-CPBA (70% purity, 875 mg, 3.55 mmol) and the mixture was stirred at RT for 2 h under nitrogen. Further m-CPBA (400 mg, 2.32 mmol) was added and stirring continued at RT for a further 1 h. The reaction mixture was diluted with EtOAc (50 mL) and washed with 1M Na$_2$S$_2$O$_3$ (40 mL) followed by saturated NaHCO$_3$ (40 mL). The organic layer was separated, dried over sodium sulfate, filtered and concentrated in vacuo to give 403 mg of methyl 2-{1-[(4-methyl-1,3-thiazol-2-yl)methyl]-5-oxopyrrolidin-2-yl}-2-oxoacetate as an orange oil (50% purity estimated by $^1$H NMR, 40%) which was used crude in the next step without purification.

Methyl 2-oxo-2-{5-oxo-1-[(1,3-thiazol-2-yl)methyl]pyrrolidin-2-yl}acetate (I-457)

The title compound was synthesised from 3-oxo-3-{5-oxo-1-[(1,3-thiazol-2-yl)methyl]pyrrolidin-2-yl}-2-(1λ$^4$-thiolan-1-ylidene)propanenitrile (I-425) in a similar manner to method B, general procedure 4 (general scheme 20) as a colourless viscous oil (164 mg, 50% purity estimated by 1H NMR, 65%) which was used crude in the next step without purification.

General Procedure 5 (General Scheme 20): Amination

Method A: T3P Coupling

Method As Described in Method A, General Procedure 6 (General Scheme 11a): Coupling 2-[(2R)-1-Benzyl-5-oxopyrrolidin-2-yl]-N-(cyclopropylmethyl)-2-oxoacetamide (FP 224)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine to give an off-white solid (45 mg, 100% purity, 27%) after purification by preparative LC (acidic pH, standard elution method).

$^1$H NMR (500 MHz, Chloroform-d) δ 0.21-0.27 (m, 2H), 0.54-0.60 (m, 2H), 0.91-1.02 (m, 1H), 1.92-2.03 (m, 1H), 2.38-2.49 (m, 3H), 3.13 (dd, J=5.9, 7.2 Hz, 2H), 3.94 (d, J=14.9 Hz, 1H), 4.95-5.01 (m, 1H), 5.04 (d, J=14.9 Hz, 1H), 6.87-6.98 (m, 1H), 7.13-7.18 (m, 2H), 7.24-7.32 (m, 3H).

LC-MS (METCR1603): 100% (UV), Rt=3.63 min, m/z (ESI$^+$)=301.3 [M+H]$^+$

2-[(2S)-1-Benzyl-5-oxopyrrolidin-2-yl]-N-(cyclopropylmethyl)-2-oxoacetamide (FP 225)

The title compound was synthesised from 2-[(2S)-1-benzyl-5-oxopyrrolidin-2-yl]-2-oxoacetic acid (I-434) in a similar manner method A, general procedure 6 (general scheme 11a) using the free-base form of the amine to give an off-white solid (59 mg, 100% purity, 39%) after purification by preparative LC (acidic pH, standard elution method).

$^1$H NMR (500 MHz, Chloroform-d) δ 0.19-0.29 (m, 2H), 0.53-0.62 (m, 2H), 0.91-1.01 (m, 1H), 1.93-2.03 (m, 1H), 2.38-2.49 (m, 3H), 3.13 (dd, J=5.9, 7.1 Hz, 2H), 3.94 (d, J=14.9 Hz, 1H), 4.95-5.01 (m, 1H), 5.04 (d, J=14.9 Hz, 1H), 6.88-6.98 (m, 1H), 7.13-7.17 (m, 2H), 7.23-7.32 (m, 3H).

LC-MS (METCR1603): 100% (UV), Rt=3.66 min, m/z (ESI$^+$)=301.3 [M+H]$^+$

2-(1-Benzyl-5-oxopyrrolidin-2-yl)-2-oxo-N-[2-(pyridin-4-yl)ethyl]acetamide (FP 226)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine to give a yellow viscous oil (39 mg, 97% purity, 44%) after purification by flash column chromatography on normal phase silica (10 g SNAP KP-SIL cartridge, 0-5% MeOH in EtOAc gradient).

$^1$H NMR (500 MHz, Chloroform-d) δ 1.87-1.93 (m, 1H), 2.38-2.47 (m, 3H), 2.85 (t, J=7.2 Hz, 2H), 3.57 (q, J=7.1 Hz, 2H), 3.92 (d, J=14.9 Hz, 1H), 4.91-4.96 (m, 1H), 5.00 (d, J=14.9 Hz, 1H), 6.94-7.00 (m, 1H), 7.10-7.14 (m, 4H), 7.25-7.30 (m, 3H), 8.51-8.57 (m, 2H).

LC-MS (METCR1603): 97% (UV), Rt=3.22 min, m/z (ESI$^+$)=352.3 [M+H]$^+$

2-(1-Benzyl-5-oxopyrrolidin-2-yl)-2-oxo-N-[2-(pyrazin-2-yl)ethyl]acetamide (FP 227)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine to give a yellow viscous oil (54 mg, 98% purity, 37%) after purification by flash column chromatography on normal phase silica (10 g SNAP KP-SIL cartridge, 0-5% MeOH in EtOAc gradient).

$^1$H NMR (500 MHz, Chloroform-d) δ 1.91-1.97 (m, 1H), 2.39-2.47 (m, 3H), 3.05-3.08 (m, 2H), 3.74 (q, J=6.2 Hz, 2H), 3.90 (d, J=14.9 Hz, 1H), 4.94-4.98 (m, 1H), 5.04 (d, J=14.9 Hz, 1H), 7.12-7.15 (m, 2H), 7.24-7.30 (m, 3H), 7.62-7.70 (m, 1H), 8.46-8.50 (m, 2H), 8.54 (dd, J=1.6, 2.4 Hz, 1H).

LC-MS (METCR1603): 98% (UV), Rt=3.06 min, m/z (ESI$^+$)=353.2 [M+H]$^+$

2-(1-Benzyl-5-oxopyrrolidin-2-yl)-2-oxo-N-[3-(pyridin-4-yl)propyl]acetamide (FP 228)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine to give a yellow viscous oil (29 mg, 90% purity by $^1$H NMR, 12%) after purification by flash column chromatography on normal phase silica (10 g SNAP KP-SIL cartridge, 0.5-20% MeOH in DCM gradient).

$^1$H NMR (500 MHz, Chloroform-d) δ 1.86-2.01 (m, 3H), 2.38-2.50 (m, 3H), 2.61-2.68 (m, 2H), 3.31 (qd, J=2.1, 7.0 Hz, 2H), 3.94 (d, J=14.9 Hz, 1H), 4.95-4.99 (m, 1H), 5.01 (d, J=14.9 Hz, 1H), 6.91 (t, J=5.4 Hz, 1H), 7.10-7.16 (m, 4H), 7.22-7.32 (m, 3H), 8.52 (d, J=5.7 Hz, 2H).

LC-MS (METCR1603): 96% (UV), Rt=3.03 min, m/z (ESI$^+$)=366.5 [M+H]$^+$

2-(1-Benzyl-5-oxopyrrolidin-2-yl)-2-oxo-N-[3-(1,3-thiazol-2-yl)propyl]acetamide (FP 229)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine to give a yellow viscous oil (70 mg, 98% purity by $^1$H NMR, 24%) after purification by flash column chromatography on normal phase silica (25 g SNAP KP-SIL cartridge, 20-100% EtOAc in heptane gradient).

$^1$H NMR (500 MHz, Chloroform-d) δ 1.91-2.01 (m, 1H), 2.03-2.12 (m, 2H), 2.36-2.50 (m, 3H), 3.10 (t, J=7.1 Hz, 2H), 3.35-3.44 (m, 2H), 3.92 (d, J=14.9 Hz, 1H), 4.93-4.99 (m, 1H), 5.04 (d, J=14.9 Hz, 1H), 7.12-7.17 (m, 2H), 7.20-7.32 (m, 4H), 7.51-7.56 (m, 1H), 7.72 (d, J=3.3 Hz, 1H).

LC-MS (METCR1603): 100% (UV), Rt=3.49 min, m/z (ESI$^+$)=372.2 [M+H]$^+$

2-(1-Benzyl-5-oxopyrrolidin-2-yl)-2-oxo-N-[(pyridin-2-yl)methyl]acetamide (FP 230)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine to give a yellow gum (7 mg, 97% purity by $^1$H NMR, 3%) after purification by flash column chromatography on normal phase silica (25 g SNAP KP-SIL cartridge, 20-100% EtOAc in heptane gradient followed by 0-5% MeOH in EtOAc gradient).

$^1$H NMR (500 MHz, Chloroform-d) δ 1.96-2.06 (m, 1H), 2.39-2.49 (m, 3H), 3.93 (d, J=14.9 Hz, 1H), 4.55 (d, J=5.3 Hz, 2H), 4.96-5.04 (m, 1H), 5.07 (d, J=14.9 Hz, 1H), 7.13-7.17 (m, 2H), 7.19-7.31 (m, 5H), 7.69 (td, J=7.7, 1.7 Hz, 1H), 8.04-8.10 (m, 1H), 8.56-8.62 (m, 1H).

LC-MS (METCR1603): 100% (UV), Rt=3.30 min, m/z (ESI$^+$)=338.3 [M+H]$^+$

2-(1-Benzyl-5-oxopyrrolidin-2-yl)-N-[3-(3,5-dimethyl-1H-1,2,4-triazol-1-yl)propyl]-2-oxoacetamide (FP 231)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine to give a yellow gum (54 mg, 95% purity by $^1$H NMR, 19%) after purification by flash column chromatography on normal phase silica (10 g SNAP KP-SIL cartridge, 0-15% MeOH in EtOAc gradient).

$^1$H NMR (250 MHz, Chloroform-d) δ 1.89-2.01 (m, 1H), 2.02-2.11 (m, 2H), 2.29-2.50 (m, 9H), 3.35 (q, J=6.4 Hz, 2H), 3.91 (d, J=14.9 Hz, 1H), 4.04 (t, J=6.3 Hz, 2H), 4.88-4.97 (m, 1H), 5.04 (d, J=14.9 Hz, 1H), 7.10-7.22 (m, 2H), 7.22-7.33 (m, 3H), 7.44-7.57 (m, 1H).

LC-MS (METCR1603): 100% (UV), Rt=3.00 min, m/z (ESI$^+$)=384.3 [M+H]$^+$

2-{1-[(4-Chloro-3-fluorophenyl)methyl]-5-oxopyrrolidin-2-yl}-N-cyclopropyl-2-oxoacetamide (FP 232)

The title compound was synthesised from 2-{1-[(4-chloro-3-fluorophenyl)-methyl]-5-oxopyrrolidin-2-yl}-2-oxoacetic acid (I-435) in a similar manner to method A, general procedure 6 (general scheme 11a) using the free-base form of the amine in DMF as solvent to give a colourless crystalline solid (62 mg, 99% purity, 49%) after purification by flash column chromatography on normal phase silica (10 g SNAP KP-SIL cartridge, 50-100% EtOAc in heptane gradient).

$^1$H NMR (500 MHz, Chloroform-d) δ 0.58-0.62 (m, 2H), 0.85-0.89 (m, 2H), 1.99-2.05 (m, 1H), 2.41-2.50 (m, 3H), 2.74-2.80 (m, 1H), 3.93 (d, J=15.2 Hz, 1H), 4.91 (d, J=15.2 Hz, 1H), 4.98-5.01 (m, 1H), 6.86-6.92 (m, 2H), 6.97 (dd, J=1.9, 9.5 Hz, 1H), 7.32 (t, J=7.8 Hz, 1H).

LC-MS (MET-uPLC-AB-102): 99% (UV), Rt=2.71 min, m/z (ESI$^+$)=339.1/341.1 [M+H]$^+$

2-{1-[(4-Cyanophenyl)methyl]-5-oxopyrrolidin-2-yl}-N-(cyclopropylmethyl)-2-oxoacetamide (FP 233)

The title compound was synthesised from 2-{1-[(4-cyanophenyl)methyl]-5-oxopyrrolidin-2-yl}-2-oxoacetic acid (I-436) in a similar manner to method A, general procedure 6 (general scheme 11a) using the free-base form of the amine in DMF as solvent to give a colourless glass (78 mg, 99% purity, 66%) after purification by flash column chromatography on normal phase silica (10 g SNAP KP-SIL cartridge, 50-100% EtOAc in heptane gradient) followed by azeotroping with chloroform (×2).

$^1$H NMR (500 MHz, Chloroform-d) δ 0.22-0.27 (m, 2H), 0.55-0.61 (m, 2H), 0.93-1.00 (m, 1H), 2.00-2.07 (m, 1H), 2.42-2.51 (m, 3H), 3.11-3.16 (m, 2H), 4.02 (d, J=15.5 Hz, 1H), 4.99-5.05 (m, 2H), 6.91-7.02 (m, 1H), 7.30 (d, J=7.6 Hz, 2H), 7.61 (dd, J=1.5, 8.2 Hz, 2H).

LC-MS (MET-uPLC-AB-102): 99% (UV), Rt=2.40 min, m/z (ESI$^+$)=326.1 [M+H]$^+$

2-{1-[(4-Chloro-2-fluorophenyl)methyl]-5-oxopyrrolidin-2-yl}-N-cyclopropyl-2-oxoacetamide (FP 234)

The title compound was synthesised from 2-{1-[(4-chloro-2-fluorophenyl)-methyl]-5-oxopyrrolidin-2-yl}-2-oxoacetic acid (I-448) in a similar manner to method A, general procedure 6 (general scheme 11a) using the free-base form of the amine in DMF as solvent to give a colourless powder (75 mg, 97% purity, 50%) after purification by flash column chromatography on normal phase silica (10 g SNAP KP-SIL cartridge, 50-100% EtOAc in heptane gradient).

$^1$H NMR (500 MHz, Chloroform-d) δ 0.60-0.64 (m, 2H), 0.86-0.90 (m, 2H), 1.94-2.00 (m, 1H), 2.35-2.50 (m, 3H), 2.76-2.82 (m, 1H), 4.08 (d, J=15.1 Hz, 1H), 4.83-4.88 (m, 1H), 5.02 (dd, J=3.9, 9.5 Hz, 1H), 6.92 (br.s, 1H), 7.05 (dd, J=2.0, 9.6 Hz, 1H), 7.10 (dd, J=1.8, 8.2 Hz, 1H), 7.24 (t, J=8.1 Hz, 1H).

LC-MS (MET-uPLC-AB-102): 97% (UV), Rt=2.69 min, m/z (ESI$^+$)=339.1/341.1 [M+H]$^+$

2-{1-[(4-Chlorophenyl)methyl]-5-oxopyrrolidin-2-yl}-N-[(oxan-4-yl)methyl]-2-oxoacetamide (FP 235)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine to give an off-white glass (24 mg, 100% purity, 8%) after purification by preparative LC (acidic pH, standard elution method).

$^1$H NMR (500 MHz, Chloroform-d) δ 1.29-1.38 (m, 2H), 1.56-1.60 (m, 2H), 1.75-1.79 (m, 1H), 1.95-1.99 (m, 1H), 2.42-2.48 (m, 3H), 3.16-3.23 (m, 2H), 3.38 (dt, J=2.0, 11.8 Hz, 2H), 3.97-4.02 (m, 3H), 4.90 (d, J=15.0 Hz, 1H), 4.97-5.00 (m, 1H), 6.90-6.96 (m, 1H), 7.09-7.12 (m, 2H), 7.26-7.29 (m, 2H).

LC-MS (METCR1603): 100% (UV), Rt=3.61 min, m/z (ESI$^+$)=379.1/381.1 [M+H]$^+$

2-[(2R)-1-Benzyl-5-oxopyrrolidin-2-yl]-N-cyclopropyl-2-oxoacetamide (FP 236)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give an off-white crystalline solid (57 mg, 100% purity, 25%) after purification by flash column chromatography on normal phase silica (25 g SNAP KP-SIL cartridge, 100% TBME) followed by trituration in diethyl ether.

$^1$H NMR (500 MHz, DMSO-d6) δ 0.57-0.69 (m, 4H), 1.87-1.95 (m, 1H), 2.16-2.26 (m, 1H), 2.27-2.40 (m, 2H), 2.71-2.79 (m, 1H), 3.86 (d, J=15.2 Hz, 1H), 4.81 (d, J=15.2 Hz, 1H), 4.85-4.91 (m, 1H), 7.17-7.20 (m, 2H), 7.24-7.28 (m, 1H), 7.29-7.34 (m, 2H), 8.81 (d, J=5.2 Hz, 1H).

LC-MS (MET-uPLC-AB-102): 100% (UV), Rt=2.20 min, m/z (ESI$^+$)=287.1 [M+H]$^+$

2-[(2R)-1-Benzyl-5-oxopyrrolidin-2-yl]-N-cyclobutyl-2-oxoacetamide (FP 237)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine to give an off-white powder (11 mg, 95% purity, 4%) after purification by flash column chromatography on normal phase silica (25 g SNAP KP-SIL cartridge, 50-100% TBME in heptane gradient) followed by preparative LC (basic pH, early elution method) then preparative LC (acidic pH, early elution method).

$^1$H NMR (500 MHz, DMSO-d6) δ 1.58-1.67 (m, 2H), 1.86-1.93 (m, 1H), 2.04-2.14 (m, 4H), 2.17-2.26 (m, 1H), 2.26-2.36 (m, 2H), 3.87 (d, J=15.2 Hz, 1H), 4.17-4.27 (m,

1H), 4.78-4.83 (m, 1H), 4.86 (dd, J=2.9, 9.8 Hz, 1H), 7.17-7.20 (m, 2H), 7.23-7.28 (m, 1H), 7.28-7.34 (m, 2H), 8.99 (d, J=8.1 Hz, 1H).

LC-MS (MET-uPLC-AB-102): 95% (UV), Rt=2.65 min, m/z (ESI$^+$)=301.1 [M+H]$^+$

2-[(2R)-1-Benzyl-5-oxopyrrolidin-2-yl]-2-oxo-N-(propan-2-yl)acetamide (FP 238)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give an off-white powder (13 mg, 96% purity, 5%) after purification by flash column chromatography on normal phase silica (25 g SNAP KP-SIL cartridge, 50-100% TBME in heptane gradient) followed by preparative LC (basic pH, early elution method) then preparative LC (acidic pH, early elution method).

$^1$H NMR (500 MHz, DMSO-d6) δ 1.10 (d, J=6.6 Hz, 6H), 1.85-1.94 (m, 1H), 2.17-2.40 (m, 3H), 3.83-3.94 (m, 2H), 4.82 (d, J=15.2 Hz, 1H), 4.84-4.90 (m, 1H), 7.16-7.20 (m, 2H), 7.23-7.28 (m, 1H), 7.29-7.35 (m, 2H), 8.59 (d, J=8.3 Hz, 1H).

LC-MS (MET-uPLC-AB-102): 96% (UV), Rt=2.46 min, m/z (ESI$^+$)=289.1 [M+H]$^+$

2-[(2R)-1-Benzyl-5-oxopyrrolidin-2-yl]-N-cyclopentyl-2-oxoacetamide (FP 239)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a colourless gum (21 mg, 100% purity, 8%) after purification by flash column chromatography on normal phase silica (25 g SNAP KP-SIL cartridge, 50-100% TBME in heptane gradient) followed by trituration Et$_2$O and preparative LC (basic pH, early elution method) then preparative LC (acidic pH, early elution method).

$^1$H NMR (500 MHz, DMSO-d6) δ 1.45-1.57 (m, 4H), 1.60-1.71 (m, 2H), 1.74-1.85 (m, 2H), 1.87-1.95 (m, 1H), 2.19-2.28 (m, 1H), 2.28-2.40 (m, 2H), 3.88 (d, J=15.2 Hz, 1H), 3.97-4.08 (m, 1H), 4.83 (d, J=15.2 Hz, 1H), 4.85-4.90 (m, 1H), 7.16-7.22 (m, 2H), 7.24-7.29 (m, 1H), 7.29-7.36 (m, 2H), 8.69 (d, J=7.8 Hz, 1H).

LC-MS (MET-uPLC-AB-102): 100% (UV), Rt=2.89 min, m/z (ESI$^+$)=315.2 [M+H]$^+$

2-{1-[(3-Chlorophenyl)methyl]-5-oxopyrrolidin-2-yl}-N-cyclopropyl-2-oxoacetamide (FP 240)

The title compound was synthesised from 2-{1-[(3-chlorophenyl)methyl]-5-oxopyrrolidin-2-yl}-2-oxoacetic acid (I-438) in a similar manner to method A, general procedure 6 (general scheme 11a) using the free-base form of the amine in DMF as solvent to give a colourless gum (65 mg, 99% purity, 52%) after purification by flash column chromatography on normal phase silica (10 g SNAP KP-SIL cartridge, 50-100% EtOAc in heptane gradient).

$^1$H NMR (500 MHz, DMSO-d6) δ 0.57-0.70 (m, 4H), 1.89-1.96 (m, 1H), 2.14-2.24 (m, 1H), 2.27-2.43 (m, 2H), 2.72-2.80 (m, 1H), 3.94 (d, J=15.4 Hz, 1H), 4.73 (d, J=15.4 Hz, 1H), 4.95 (dd, J=3.0, 10.1 Hz, 1H), 7.16-7.20 (m, 1H), 7.28-7.37 (m, 3H), 8.80 (d, J=5.2 Hz, 1H).

LC-MS (MET-uPLC-AB-102): 99% (UV), Rt=2.58 min, m/z (ESI$^+$)=321.1, 323.1 [M+H]$^+$

N-(Cyclopropylmethyl)-2-{1-[(4-fluorophenyl)methyl]-5-oxopyrrolidin-2-yl}-2-oxoacetamide (FP 241)

The title compound was synthesised from 2-{1-[(4-fluorophenyl)methyl]-5-oxopyrrolidin-2-yl}-2-oxoacetic acid (I-441) in a similar manner to method A, general procedure 6 (general scheme 11a) using the free-base form of the amine to give a colourless glass (27 mg, 100% purity, 13%) after purification by preparative LC (acidic pH, standard elution method).

$^1$H NMR (500 MHz, Chloroform-d) δ 0.19-0.27 (m, 2H), 0.52-0.62 (m, 2H), 0.92-1.01 (m, 1H), 1.94-2.03 (m, 1H), 2.37-2.48 (m, 3H), 3.13 (t, J=6.5 Hz, 2H), 3.96 (d, J=14.9 Hz, 1H), 4.94 (d, J=15.0 Hz, 1H), 4.96-5.03 (m, 1H), 6.90-7.00 (m, 3H), 7.10-7.17 (m, 2H).

LC-MS (METCR1603): 100% (UV), Rt=3.78 min, m/z (ESI$^+$)=319.2 [M+H]$^+$

N-Cyclopropyl-2-{1-[(4-fluorophenyl)methyl]-5-oxopyrrolidin-2-yl}-2-oxoacetamide (FP 242)

The title compound was synthesised from 2-{1-[(4-fluorophenyl)methyl]-5-oxopyrrolidin-2-yl}-2-oxoacetic acid (I-441) in a similar manner to method A, general procedure 6 (general scheme 11a) using the free-base form of the amine in DMF as solvent to give an off-white solid (100 mg, 100% purity, 29%) after purification by preparative LC (acidic pH, standard elution method).

$^1$H NMR (500 MHz, Chloroform-d) δ 0.56-0.64 (m, 2H), 0.84-0.89 (m, 2H), 1.93-2.02 (m, 1H), 2.40-2.48 (m, 3H), 2.72-2.81 (m, 1H), 3.95 (d, J=14.9 Hz, 1H), 4.92 (d, J=14.9 Hz, 1H), 4.95-5.01 (m, 1H), 6.84 (s, 1H), 6.95-7.01 (m, 2H), 7.10-7.17 (m, 2H).

LC-MS (METCR1603): 100% (UV), Rt=3.42 min, m/z (ESI$^+$)=305.2 [M+H]$^+$

2-{1-[(4-Chlorophenyl)methyl]-5-oxopyrrolidin-2-yl}-N-(2-acetamidoethyl)-2-oxoacetamide (FP 243)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine in DMF as solvent to give a yellow viscous oil (17 mg, 100% purity, 8%) after purification by preparative LC (acidic pH, standard elution method).

$^1$H NMR (500 MHz, Chloroform-d) δ 1.96-2.01 (m, 4H), 2.39-2.48 (m, 3H), 3.38-3.45 (m, 4H), 3.94 (d, J=15.1 Hz, 1H), 4.89-4.98 (m, 2H), 5.97-6.07 (m, 1H), 7.07-7.12 (m, 2H), 7.23-7.29 (m, 2H), 7.63-7.71 (m, 1H).

LC-MS (METCR1603): 100% (UV), Rt=3.13 min, m/z (ESI$^+$)=366.1/368.1 [M+H]$^+$

N-(Cyclohexylmethyl)-2-oxo-2-{5-oxo-1-[(1-oxo-2,3-dihydro-1H-isoindol-5-yl)methyl]-pyrrolidin-2-yl}acetamide (FP 244)

The title compound was synthesised from 2-oxo-2-{5-oxo-1-[(1-oxo-2,3-dihydro-1H-isoindol-5-yl)methyl]pyrrolidin-2-yl}acetic acid (I-449) in a similar manner to method A, general procedure 6 (general scheme 11a) using the free-base form of the amine in DMF as solvent to give a colourless glass (22 mg, 83% purity, 11%) after purification by flash column chromatography on normal phase silica (10 g SNAP KP-SIL cartridge, 0-20% MeOH in TBME gradient) followed by preparative LC (basic pH, standard elution method).

$^1$H NMR (500 MHz, Chloroform-d) δ 0.88-0.99 (m, 2H), 1.11-1.24 (m, 3H), 1.44-1.54 (m, 1H), 1.67-1.77 (m, 5H), 1.97-2.04 (m, 1H), 2.42-2.52 (m, 3H), 3.12 (t, J=6.6 Hz, 2H), 4.05 (d, J=15.2 Hz, 1H), 4.42 (s, 2H), 5.01-5.07 (m, 1H), 5.09 (d, J=15.2 Hz, 1H), 6.75 (s, 1H), 6.92 (br t, J=6.0 Hz, 1H), 7.24-7.29 (m, 1H), 7.32 (s, 1H), 7.79 (d, J=7.8 Hz, 1H).

LC-MS (METCR1603): 83% (UV), Rt=3.55 min, m/z (ESI$^+$)=398.2 [M+H]$^+$

N-(Cyclohexylmethyl)-2-{1-[2-(oxan-4-yl)ethyl]-5-oxopyrrolidin-2-yl}-2-oxoacetamide (FP 245)

The title compound was synthesised from 2-{1-[2-(oxan-4-yl)ethyl]-5-oxopyrrolidin-2-yl}-2-oxoacetic acid (I-455) in a similar manner to method A, general procedure 6 (general scheme 11a) using the free-base form of the amine in DMF as solvent to give a yellow gum (27 mg, 100% purity, 4%) after purification by preparative LC (acidic pH, standard elution method).

$^1$H NMR (500 MHz, Chloroform-d) δ 0.92-1.02 (m, 2H), 1.12-1.78 (m, 16H), 1.93-2.00 (m, 1H), 2.30-2.52 (m, 3H), 2.80-2.89 (m, 1H), 3.18 (t, J=6.6 Hz, 2H), 3.30-3.39 (m, 2H), 3.70-3.79 (m, 1H), 3.89-3.96 (m, 2H), 5.23 (dd, J=3.2, 10.0 Hz, 1H), 6.99 (t, J=5.4 Hz, 1H).

LC-MS (METCR1603): 100% (UV), Rt=4.04 min, m/z (ESI$^+$)=365.3 [M+H]$^+$

2-(1-Benzyl-5-oxopyrrolidin-2-yl)-N-(1-methylcyclopropyl)-2-oxoacetamide (FP 246)

The title compound was synthesised from 2-(1-benzyl-5-oxopyrrolidin-2-yl)-2-oxoacetic acid (I-432) in a similar manner to method A, general procedure 6 (general scheme 11a) using DMF as solvent to afford an off-white solid (118 mg, 100% purity, 32%) after purification by flash column chromatography on normal phase silica (10 g SNAP KP-SIL cartridge, 0-80% EtOAc in heptane gradient) followed by preparative LC (acidic pH, standard elution method).

$^1$H NMR (500 MHz, Chloroform-d) δ 0.67-0.74 (m, 2H), 0.74-0.80 (m, 2H), 1.37 (s, 3H), 1.91-2.00 (m, 1H), 2.36-2.51 (m, 3H), 3.96 (d, J=14.9 Hz, 1H), 4.93-5.01 (m, 2H), 7.04 (s, 1H), 7.12-7.16 (m, 2H), 7.23-7.31 (m, 3H).

LC-MS (MET-uPLC-AB-102): 100% (UV), Rt=2.53 min, m/z (ESI$^+$)=301.1 [M+H]$^+$

2-{1-[(4-Chlorophenyl)methyl]-5-oxopyrrolidin-2-yl}-2-oxo-N-[(6-oxo-1,6-dihydropyridin-2-yl)methyl]acetamide (FP 247)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the bis-hydrochloride form of the amine in DMF as solvent to give an off-white powder (14 mg, 98% purity by $^1$H NMR, 10%) after purification by preparative LC (acidic pH, standard elution method).

$^1$H NMR (500 MHz, Chloroform-d) δ 1.91-2.09 (m, 1H), 2.29-2.52 (m, 3H), 3.89 (d, J=15.0 Hz, 1H), 4.29-4.46 (m, 2H), 4.82-5.00 (m, 2H), 6.32 (d, J=6.8 Hz, 1H), 6.62 (d, J=9.1 Hz, 1H), 7.04-7.10 (m, 2H), 7.19-7.25 (m, 2H), 7.50 (dd, J=6.8, 9.2 Hz, 1H), 8.46 (t, J=6.4 Hz, 1H), 13.38 (s, 1H).

LC-MS (METCR1603): 100% (UV), Rt=3.16 min, m/z (ESI$^+$)=388.1/390.1 [M+H]$^+$

N-(Cyclohexylmethyl)-2-{1-[(oxan-4-yl)methyl]-5-oxopyrrolidin-2-yl}-2-oxoacetamide (FP 248)

The title compound was synthesised from 2-{1-[(oxan-4-yl)methyl]-5-oxopyrrolidin-2-yl}-2-oxoacetic acid (I-439) in a similar manner to method A, general procedure 6 (general scheme 11a) using the free-base form of the amine in DMF as solvent to give an off-white gum (5 mg, 95% purity, 14%) after purification by preparative LC (acidic pH, early elution method).

$^1$H NMR (500 MHz, Chloroform-d) δ 0.91-1.03 (m, 2H), 1.12-1.37 (m, 6H), 1.45-1.55 (m, 2H), 1.65-1.83 (m, 6H), 1.96-2.04 (m, 1H), 2.29-2.53 (m, 3H), 2.58-2.65 (m, 1H), 3.18 (t, J=6.6 Hz, 2H), 3.33 (tt, J=2.3, 11.7 Hz, 2H), 3.65 (dd, J=8.3, 14.1 Hz, 1H), 3.92-3.98 (m, 2H), 5.23 (dd, J=2.9, 10.0 Hz, 1H), 6.92-7.05 (m, 1H).

LC-MS (MET-uPLC-AB-102): 95% (UV), Rt=2.93 min, m/z (ESI$^+$)=351.2 [M+H]$^+$

3-[(2-{[(Cyclohexylmethyl)carbamoyl]carbonyl}-5-oxopyrrolidin-1-yl)methyl]benzamide (FP 249)

The title compound was synthesised from 2-{1-[(3-carbamoylphenyl)methyl]-5-oxopyrrolidin-2-yl}-2-oxoacetic acid (I-451) in a similar manner to method A, general procedure 6 (general scheme 11a) using the free-base form of the amine in DMF as solvent to give an off-white powder (22 mg, 98% purity by $^1$H NMR, 20%) after purification by preparative LC (acidic pH, early elution method).

$^1$H NMR (500 MHz, Chloroform-d) δ 0.87 (qd, J=2.9, 12.2 Hz, 2H), 1.02-1.23 (m, 3H), 1.35-1.47 (m, 1H), 1.57-1.71 (m, 5H), 1.88-1.94 (m, 1H), 2.31-2.45 (m, 3H), 3.04 (t, J=6.6 Hz, 2H), 4.00 (d, J=15.0 Hz, 1H), 4.91 (d, J=15.0 Hz, 1H), 4.93-4.97 (m, 1H), 5.46 (s, 1H), 6.12 (s, 1H), 6.81 (t, J=6.1 Hz, 1H), 7.26-7.30 (m, 1H), 7.33 (t, J=7.6 Hz, 1H), 7.53-7.56 (m, 1H), 7.63-7.68 (m, 1H).

LC-MS (METCR1603): 100% (UV), Rt=3.65 min, m/z (ESI$^+$)=403.2 [M+H+NH$_3$]$^+$

3-[(2-{[(Cyclopropylmethyl)carbamoyl]carbonyl}-5-oxopyrrolidin-1-yl)methyl]benzamide (FP 250)

The title compound was synthesised from 2-{1-[(3-carbamoylphenyl)methyl]-5-oxopyrrolidin-2-yl}-2-oxoacetic acid (I-451) in a similar manner to method A, general procedure 6 (general scheme 11a) using the free-base form of the amine in DMF as solvent to give an off-white foamy solid (17 mg, 96% purity by 1H NMR, 11%) after purification by preparative LC (acidic pH, early elution method).

$^1$H NMR (500 MHz, Chloroform-d) δ 0.24 (q, J=4.9 Hz, 2H), 0.53-0.62 (m, 2H), 0.91-1.02 (m, 1H), 1.96-2.03 (m, 1H), 2.39-2.50 (m, 3H), 3.12 (dd, J=5.9, 7.2 Hz, 2H), 4.06 (d, J=15.0 Hz, 1H), 4.95-5.05 (m, 2H), 5.50 (s, 1H), 6.18 (s, 1H), 6.90-6.98 (m, 1H), 7.33-7.38 (m, 1H), 7.41 (t, J=7.6 Hz, 1H), 7.60-7.63 (m, 1H), 7.71-7.74 (m, 1H).

LC-MS (METCR1603): 92% (UV), Rt=2.89 min, m/z (ESI$^+$)=361.2 [M+H+NH$_3$]$^+$

N-Cyclopropyl-2-oxo-2-[5-oxo-1-(2-phenylethyl)pyrrolidin-2-yl]acetamide (FP 251)

The title compound was synthesised from 2-oxo-2-[5-oxo-1-(2-phenylethyl)-pyrrolidin-2-yl]acetic acid (I-442) in a similar manner to method A, general procedure 6 (general scheme 11a) using the free-base form of the amine in DMF as solvent to give an orange gum (30 mg, 97% purity, 24%) after purification by preparative LC (acidic pH, standard elution method).

$^1$H NMR (500 MHz, Chloroform-d) δ 0.55-0.69 (m, 2H), 0.83-0.92 (m, 2H), 1.87-1.96 (m, 1H), 2.21-2.47 (m, 3H), 2.71-2.92 (m, 3H), 2.95-3.17 (m, 1H), 3.99 (ddd, J=6.3, 8.7, 14.5 Hz, 1H), 4.94-5.08 (m, 1H), 6.92 (s, 1H), 7.16-7.23 (m, 3H), 7.26-7.30 (m, 2H).

LC-MS (METCR1603): 97% (UV), Rt=3.51 min, m/z (ESI$^+$)=301.2 [M+H]$^+$

4-[(2-{[(Cyclohexylmethyl)carbamoyl]carbonyl}-5-oxopyrrolidin-1-yl)methyl]benzamide (FP 252)

The title compound was synthesised from 2-{1-[(4-carbamoylphenyl)methyl]-5-oxopyrrolidin-2-yl}-2-oxoacetic acid (I-450) in a similar manner to method A, general procedure 6 (general scheme 11a) using the free-base form of the amine in DMF as solvent to give a cream powder (50 mg, 99% purity by $^1$H NMR, 15%) after purification by preparative LC (acidic pH, early elution method).

$^1$H NMR (500 MHz, Chloroform-d) δ 0.88-0.99 (m, 2H), 1.10-1.29 (m, 4H), 1.44-1.54 (m, 1H), 1.69-1.77 (m, 4H), 1.95-2.05 (m, 1H), 2.40-2.51 (m, 3H), 3.12 (t, J=6.6 Hz, 2H), 4.00 (d, J=15.2 Hz, 1H), 4.97-5.03 (m, 1H), 5.04 (d, J=15.2 Hz, 1H), 5.73 (s, 1H), 6.17 (s, 1H), 6.94 (t, J=6.0 Hz, 1H), 7.22-7.26 (m, 2H), 7.73-7.77 (m, 2H).

LC-MS (METCR1603): 100% (UV), Rt=3.57 min, m/z (ESI$^+$)=403.2 [M+H+NH$_3$]$^+$

N-(Cyclopropylmethyl)-2-oxo-2-[5-oxo-1-(2-phenylethyl)pyrrolidin-2-yl] (FP 253)

The title compound was synthesised from 2-oxo-2-[5-oxo-1-(2-phenylethyl)-pyrrolidin-2-yl]acetic acid (I-442) in a similar manner to method A, general procedure 6 (general scheme 11a) using the free-base form of the amine in DMF as solvent to give a beige solid (30 mg, 100% purity, 27%) after purification by preparative LC (acidic pH, standard elution method).

$^1$H NMR (500 MHz, Chloroform-d) δ 0.20-0.31 (m, 2H), 0.52-0.64 (m, 2H), 0.91-1.05 (m, 1H), 1.87-1.98 (m, 1H), 2.24-2.45 (m, 3H), 2.77 (ddd, J=6.3, 8.5, 14.0 Hz, 1H), 2.86 (ddd, J=6.6, 8.7, 15.2 Hz, 1H), 3.03 (ddd, J=6.6, 8.4, 14.4 Hz, 1H), 3.11-3.21 (m, 2H), 4.01 (ddd, J=6.3, 8.7, 14.5 Hz, 1H), 5.00-5.05 (m, 1H), 6.97-7.05 (m, 1H), 7.14-7.24 (m, 3H), 7.26-7.31 (m, 2H).

LC-MS (METCR1603): 100% (UV), Rt=3.81 min, m/z (ESI$^+$)=315.3 [M+H]$^+$

N-Cyclopentyl-2-[1-(cyclopropylmethyl)-5-oxopyrrolidin-2-yl]-2-oxoacetamide (FP 254)

The title compound was synthesised from 2-[1-(cyclopropylmethyl)-5-oxopyrrolidin-2-yl]-2-oxoacetic acid (I-452) in a similar manner to method A, general procedure 6 (general scheme 11a) using the free-base form of the amine in DMF as solvent to give an off-white gum (6 mg, 95% purity by 1H NMR, 12%) after purification by preparative LC (acidic pH, early elution method).

$^1$H NMR (500 MHz, Chloroform-d) δ 0.10 (dtt, J=4.9, 9.3, 18.5 Hz, 2H), 0.37-0.45 (m, 1H), 0.48-0.57 (m, 1H), 0.72-0.82 (m, 1H), 1.42-1.51 (m, 2H), 1.55-1.68 (m, 2H), 1.68-1.78 (m, 2H), 1.91-1.99 (m, 1H), 2.00-2.09 (m, 1H), 2.32-2.44 (m, 2H), 2.44-2.54 (m, 1H), 2.86 (dd, J=7.3, 14.3 Hz, 1H), 3.46 (dd, J=7.1, 14.3 Hz, 1H), 4.21 (h, J=7.1 Hz, 1H), 5.42 (dd, J=3.2, 10.0 Hz, 1H), 6.89 (d, J=6.9 Hz, 1H).

LC-MS (MET-uPLC-AB-102): 100% (UV), Rt=2.66 min, m/z (ESI$^+$)=279.1 [M+H]$^+$

N-(Cyclopentylmethyl)-2-[1-(cyclopropylmethyl)-5-oxopyrrolidin-2-yl]-2-oxoacetamide (FP 255)

The title compound was synthesised from 2-[1-(cyclopropylmethyl)-5-oxopyrrolidin-2-yl]-2-oxoacetic acid (I-452) in a similar manner to method A, general procedure 6 (general scheme 11a) using the free-base form of the amine in DMF as solvent to give a colourless viscous oil (6 mg, 100% purity, 12%) after purification by preparative LC (acidic pH, early elution method).

$^1$H NMR (500 MHz, Chloroform-d) δ 0.03-0.16 (m, 2H), 0.37-0.45 (m, 1H), 0.49-0.56 (m, 1H), 0.72-0.82 (m, 1H), 1.17-1.26 (m, 2H), 1.52-1.70 (m, 4H), 1.73-1.83 (m, 2H), 1.91-1.99 (m, 1H), 2.09 (hept, J=7.6 Hz, 1H), 2.33-2.44 (m, 2H), 2.44-2.55 (m, 1H), 2.87 (dd, J=7.3, 14.3 Hz, 1H), 3.21-3.33 (m, 2H), 3.47 (dd, J=7.0, 14.3 Hz, 1H), 5.43 (dd, J=3.3, 9.9 Hz, 1H), 7.00 (br. s, 1H).

LC-MS (MET-uPLC-AB-102): 100% (UV), Rt=3.07 min, m/z (ESI$^+$)=293.2 [M+H]$^+$

2-{1-[(4-Chlorophenyl)methyl]-5-oxopyrrolidin-2-yl}-N-(2-hydroxyethyl)-2-oxoacetamide (FP 256)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine in DMF as solvent to give a colourless viscous oil (24 mg, 100% purity, 18%) after purification by preparative LC (acidic pH, standard elution method).

$^1$H NMR (250 MHz, DMSO-d6) δ 1.82-2.03 (m, 1H), 2.08-2.42 (m, 3H), 3.09-3.43 (m, 2H), 3.51 (q, J=5.9 Hz, 1H), 3.67-4.14 (m, 2H), 4.34-4.99 (m, 2H), 7.17-7.29 (m, 2H), 6.68-8.44 (m, 1H), 7.29-7.42 (m, 2H).

LC-MS (METCR1603): 100% (UV), Rt=3.00-3.20 min, m/z (ESI$^+$)=325.1/327.1 [M+H]$^+$

2-{1-[(4-Chlorophenyl)methyl]-5-oxopyrrolidin-2-yl}-2-oxo-N-[2-(propan-2-ylsulfanyl)-ethyl]acetamide (FP 257)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine in DMF as solvent to give a yellow viscous oil (191 mg, 98% purity, 54%) after purification by preparative LC (acidic pH, early elution method).

$^1$H NMR (500 MHz, Chloroform-d) δ 1.28 (d, J=6.7 Hz, 6H), 1.94-2.03 (m, 1H), 2.38-2.48 (m, 3H), 2.68-2.72 (m, 2H), 2.91-2.98 (m, 1H), 3.47 (qd, J=2.0, 6.5 Hz, 2H), 3.94 (d, J=15.0 Hz, 1H), 4.93-4.98 (m, 2H), 7.08-7.12 (m, 2H), 7.16-7.23 (m, 1H), 7.26-7.29 (m, 2H).

LC-MS (MET-uPLC-AB-102): 98% (UV), Rt=3.35 min, m/z (ESI$^+$)=383.1/385.1 [M+H]$^+$

2-{1-[(4-Chlorophenyl)methyl]-5-oxopyrrolidin-2-yl}-N-[(2R)-1-hydroxypropan-2-yl]-2-oxoacetamide (FP 258)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using DMF as solvent to afford a colourless viscous oil (18 mg, 99% purity by $^1$H NMR, 9%) after purification by preparative LC (acidic pH, standard elution method).

$^1$H NMR (500 MHz, DMSO-d6) δ 0.93-1.23 (m, 3H), 1.67-2.45 (m, 4H), 3.37-5.01 (m, 6H), 7.01-7.30 (m, 3H), 7.31-7.46 (m, 2H), 8.10-8.55 (m, 1H).

LC-MS (METCR1603): 100% (UV), Rt=3.00-3.60 min, m/z (ESI$^+$)=339.2/341.2 [M+H]$^+$ 2-{1-[(4-Chlorophenyl)methyl]-5-oxopyrrolidin-2-yl}-N-[(2R)-2-hydroxypropyl]-2-oxoacetamide (FP 259)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine in DMF as solvent to give a colourless viscous oil (26 mg, 99% purity by $^1$H NMR, 13%) after purification by preparative LC (acidic pH, standard elution method).

$^1$H NMR (500 MHz, DMSO-d6) δ 0.91-1.18 (m, 3H), 1.77-2.46 (m, 4H), 2.74-3.21 (m, 2H), 3.62-4.29 (m, 2H), 4.28-4.98 (m, 2H), 6.96-7.12 (m, 1H), 7.12-7.30 (m, 2H), 7.32-7.45 (m, 2H), 7.96-8.64 (m, 1H).

LC-MS (METCR1603): 100% (UV), Rt=3.10-3.60 min, m/z (ESI$^+$)=339.2/341.2 [M+H]$^+$ 2-{1-[(2-Chlorophenyl)methyl]-5-oxopyrrolidin-2-yl}-N-cyclopropyl-2-oxoacetamide (FP 260)

The title compound was synthesised from 2-{1-[(2-chlorophenyl)methyl]-5-oxopyrrolidin-2-yl}-2-oxoacetic acid (I-443) in a similar manner to method A, general procedure 6 (general scheme 11a) using the free-base form of the amine in DMF as solvent to give an off-white gum (125 mg, 98% purity, 29%) after purification by preparative LC (acidic pH, standard elution method).

$^1$H NMR (500 MHz, Chloroform-d) δ 0.57-0.64 (m, 2H), 0.83-0.89 (m, 2H), 1.93-2.00 (m, 1H), 2.31-2.53 (m, 3H), 2.73-2.82 (m, 1H), 4.16 (d, J=15.1 Hz, 1H), 4.97-5.05 (m, 2H), 6.94 (s, 1H), 7.20-7.25 (m, 2H), 7.25-7.30 (m, 1H), 7.30-7.35 (m, 1H).

LC-MS (METCR1603): 98% (UV), Rt=3.58 min, m/z (ESI$^+$)=321.2/323.2 [M+H]$^+$

N-Cyclopropyl-2-{1-[(2-methylphenyl)methyl]-5-oxopyrrolidin-2-yl}-2-oxoacetamide (FP 261)

The title compound was synthesised from 2-{1-[(2-methylphenyl)methyl]-5-oxopyrrolidin-2-yl}-2-oxoacetic acid (I-444) in a similar manner to method A, general procedure 6 (general scheme 11a) using the free-base form of the amine in DMF as solvent to give a yellow gum (97 mg, 100% purity, 27%) after purification by preparative LC (acidic pH, standard elution method).

$^1$H NMR (500 MHz, Chloroform-d) δ 0.49-0.62 (m, 2H), 0.77-0.87 (m, 2H), 1.89-2.01 (m, 1H), 2.23 (s, 3H), 2.34-2.48 (m, 3H), 2.65-2.74 (m, 1H), 4.16 (d, J=14.8 Hz, 1H), 4.81 (d, J=14.8 Hz, 1H), 4.87-4.92 (m, 1H), 6.79 (s, 1H), 6.94-6.99 (m, 1H), 7.06-7.11 (m, 1H), 7.11-7.14 (m, 1H), 7.14-7.19 (m, 1H).

LC-MS (METCR1603): 100% (UV), Rt=3.49 min, m/z (ESI$^+$)=301.2 [M+H]$^+$

2-[(2R)-1-Benzyl-5-oxopyrrolidin-2-yl]-N-(2-cyanoethyl)-2-oxoacetamide (FP 262)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a colourless gum (67 mg, 99% purity, 23%) after purification by flash column chromatography on normal phase silica (25 g SNAP KP-SIL cartridge, 10-100% MeOH in TBME gradient) followed by preparative LC (acidic pH, early elution method).

$^1$H NMR (500 MHz, Chloroform-d) δ 1.94-2.02 (m, 1H), 2.38-2.51 (m, 3H), 2.61-2.67 (m, 2H), 3.54-3.60 (m, 2H), 3.97-4.02 (m, 1H), 4.92-4.96 (m, 1H), 4.97-5.02 (m, 1H), 7.12-7.17 (m, 2H), 7.18-7.24 (m, 1H), 7.26-7.34 (m, 3H).

LC-MS (MET-uPLC-AB-102): 99% (UV), Rt=1.89 min, m/z (ESI$^+$)=300.1 [M+H]$^+$

2-[(2R)-1-Benzyl-5-oxopyrrolidin-2-yl]-N-(2-cyano-2,2-dimethylethyl)-2-oxoacetamide (FP 263)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a yellow viscous oil (124 mg, 97% purity by $^1$H NMR, 61%) after purification by flash column chromatography on normal phase silica (10 g SNAP Ultra cartridge, 0-70% EtOAc in heptane gradient).

$^1$H NMR (500 MHz, Chloroform-d) δ 1.33-1.37 (m, 6H), 1.92-1.99 (m, 1H), 2.39-2.50 (m, 3H), 3.35-3.45 (m, 2H), 4.01 (d, J=14.8 Hz, 1H), 4.93-4.97 (m, 1H), 5.00 (d, J=14.8 Hz, 1H), 7.11-7.19 (m, 3H), 7.25-7.33 (m, 3H).

LC-MS (METCR1603): 100% (UV), Rt=3.48 min, m/z (ESI$^+$)=328.3 [M+H]$^+$

N-(Cyclopropylmethyl)-2-oxo-2-(5-oxo-1-phenylpyrrolidin-2-yl)acetamide (FP 264)

The title compound was synthesised from 2-oxo-2-(5-oxo-1-phenylpyrrolidin-2-yl)acetic acid (I-454) in a similar manner to method A, general procedure 6 (general scheme 11a) using the free-base form of the amine in DMF as solvent to give a yellow gum (27 mg, 99% purity, 18%) after purification by flash column chromatography on normal phase silica (25 g SNAP Ultra cartridge, 0-100% EtOAc in heptane gradient) followed by preparative LC (acidic pH, early elution method).

$^1$H NMR (500 MHz, Chloroform-d) δ 0.21-0.27 (m, 2H), 0.53-0.59 (m, 2H), 0.91-1.02 (m, 1H), 2.07-2.14 (m, 1H), 2.57-2.70 (m, 3H), 3.15-3.20 (m, 2H), 5.83-5.89 (m, 1H), 6.98 (s, 1H), 7.13-7.20 (m, 1H), 7.30-7.38 (m, 2H), 7.41-7.45 (m, 2H).

LC-MS (METCR1603): 99% (UV), Rt=2.37 min, m/z (ESI$^+$)=287.1 [M+H]$^+$

2-[(2R)-1-Benzyl-5-oxopyrrolidin-2-yl]-N-ethyl-2-oxoacetamide (FP 265)

The title compound was synthesised from 2-[(2R)-1-benzyl-5-oxopyrrolidin-2-yl]-2-oxoacetic acid (I-433) in a similar manner to method A, general procedure 6 (general scheme 11a) using ethylamine as a 70% aqueous solution and DMF as solvent to give a yellow powder (75 mg, 98% purity, 17%) after purification by flash column chromatography on normal phase silica (25 g SNAP KP-SIL cartridge, 0-100% EtOAc in heptane gradient) followed by further purification by flash column chromatography on normal phase silica (10 g SNAP KP-SIL cartridge, 0-100% TBME in heptane gradient followed by isocratic 100% TBME).

$^1$H NMR (500 MHz, Chloroform-d) δ 1.13 (t, J=7.3 Hz, 3H), 1.86-1.96 (m, 1H), 2.31-2.43 (m, 3H), 3.22-3.29 (m, 2H), 3.86 (d, J=14.9 Hz, 1H), 4.89-4.94 (m, 1H), 4.96 (d, J=14.9 Hz, 1H), 6.68-6.82 (m, 1H), 7.05-7.10 (m, 2H), 7.17-7.25 (m, 3H).

LC-MS (MET-uPLC-AB-102): 98% (UV), Rt=2.14 min, m/z (ESI$^+$)=275.0 [M+H]$^+$

2-[(2R)-1-Benzyl-5-oxopyrrolidin-2-yl]-N-(2,2-difluoroethyl)-2-oxoacetamide (FP 266)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a yellow powder (168 mg, 98% purity, 40%) after purification by flash column chromatography on normal phase silica (25 g SNAP KP-SIL cartridge, 0-100% TBME in heptane gradient followed by isocratic 100% TBME).

$^1$H NMR (500 MHz, Chloroform-d) δ 1.95-2.03 (m, 1H), 2.42-2.53 (m, 3H), 3.68 (tddd, J=14.8, 6.5, 3.8, 1.5 Hz, 2H), 4.02 (d, J=14.9 Hz, 1H), 4.95-4.99 (m, 1H), 5.01 (d, J=14.9 Hz, 1H), 5.87 (tt, J=55.3, 3.8 Hz, 1H), 7.03-7.12 (m, 1H), 7.14-7.20 (m, 2H), 7.27-7.35 (m, 3H).

LC-MS (MET-uPLC-AB-102): 98% (UV), Rt=2.22 min, m/z (ESI$^+$)=311.0 [M+H]$^+$

2-[(2R)-1-Benzyl-5-oxopyrrolidin-2-yl]-N-[(1R,2S)-2-fluorocyclopropyl]-2-oxoacetamide (FP260)

The title compound was synthesised from 2-[(2R)-1-benzyl-5-oxopyrrolidin-2-yl]-2-oxoacetic acid (I-433) in a similar manner to method A, general procedure 6 (general scheme 11a) using the tosylate salt of the amine in DMF as solvent to give a yellow gum (113 mg, 99% purity, 37%) after purification by flash column chromatography on normal phase silica (10 g SNAP KP-SIL cartridge, 0-100% TBME in heptane gradient followed by isocratic 100% TBME).

$^1$H NMR (500 MHz, Chloroform-d) δ 0.94 (dddd, J=25.1, 8.7, 5.7, 3.1 Hz, 1H), 1.10-1.21 (m, 1H), 1.87-1.98 (m, 1H), 2.33-2.43 (m, 3H), 2.80 (dq, J=10.2, 5.3 Hz, 1H), 3.87 (d, J=14.9 Hz, 1H), 4.65 (dtd, J=63.6, 5.9, 3.1 Hz, 1H), 4.87-4.92 (m, 1H), 4.96 (d, J=14.9 Hz, 1H), 6.94 (s, 1H), 7.06-7.10 (m, 2H), 7.17-7.26 (m, 3H).

LC-MS (MET-uPLC-AB-102): 99% (UV), Rt=2.12 min, m/z (ESI$^+$)=305.0 [M+H]$^+$

2-[(2R)-1-Benzyl-5-oxopyrrolidin-2-yl]-N-(3,3-difluorocyclobutyl)-2-oxoacetamide (FP 268)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a yellow powder (240 mg, 99% purity, 37%) after purification by flash column chromatography on normal phase silica (25 g SNAP KP-SIL cartridge, 0-100% TBME in heptane gradient followed by isocratic 100% TBME) followed by further purification by flash column chromatography on normal phase silica (10 g SNAP KP-SIL cartridge, 0-100% TBME in heptane gradient and isocratic 100% TBME).

$^1$H NMR (500 MHz, Chloroform-d) δ 1.89 (ddt, J=12.4, 5.0, 3.6 Hz, 1H), 2.30-2.43 (m, 3H), 2.44-2.56 (m, 2H), 2.90-3.01 (m, 2H), 3.91 (d, J=14.9 Hz, 1H), 4.15 (dddd, J=11.9, 7.1, 5.2, 2.4 Hz, 1H), 4.86-4.94 (m, 2H), 7.01 (d, J=7.1 Hz, 1H), 7.04-7.10 (m, 2H), 7.17-7.26 (m, 3H).

LC-MS (MET-uPLC-AB-102): 99% (UV), Rt=2.63 min, m/z (ESI$^+$)=337.1 [M+H]$^+$

N-Cyclopropyl-2-{1-[(3-methylphenyl)methyl]-5-oxopyrrolidin-2-yl}-2-oxoacetamide (FP 269)

The title compound was synthesised from 2-{1-[(3-methylphenyl)methyl]-5-oxopyrrolidin-2-yl}-2-oxoacetic acid (I-445) in a similar manner to method A, general procedure 6 (general scheme 11a) using the free-base form of the amine in DMF as solvent to give a yellow gum (106 mg, 97% purity, 39%) after purification by preparative LC (acidic pH, standard elution method).

$^1$H NMR (500 MHz, Chloroform-d) δ 0.57-0.62 (m, 2H), 0.83-0.89 (m, 2H), 1.88-2.03 (m, 1H), 2.31 (s, 3H), 2.36-2.52 (m, 3H), 2.70-2.80 (m, 1H), 3.87 (d, J=14.8 Hz, 1H), 4.91-5.05 (m, 2H), 6.84-6.90 (m, 1H), 6.90-6.97 (m, 2H), 7.04-7.10 (m, 1H), 7.14-7.20 (m, 1H).

LC-MS (METCR1603): 97% (UV), Rt=3.56 min, m/z (ESI$^+$)=301.2 [M+H]$^+$

N-Cyclopropyl-2-{1-[(4-methylphenyl)methyl]-5-oxopyrrolidin-2-yl}-2-oxoacetamide (FP 270)

The title compound was synthesised from 2-{1-[(4-methylphenyl)methyl]-5-oxopyrrolidin-2-yl}-2-oxoacetic acid (I-446) in a similar manner method A, general procedure 6 (general scheme 11a) using the free-base form of the amine in DMF as solvent to give an off-white solid (68 mg, 98% purity, 30%) after purification by preparative LC (acidic pH, standard elution method).

$^1$H NMR (250 MHz, DMSO-d6) δ 0.52-0.76 (m, 4H), 1.85-2.01 (m, 1H), 2.19-2.39 (m, 6H), 2.64-2.84 (m, 1H), 3.84 (d, J=15.0 Hz, 1H), 4.66-4.88 (m, 2H), 6.99-7.20 (m, 4H), 8.46 (s, 1H).

LC-MS (METCR1603): 98% (UV), Rt=2.51 min, m/z (ESI$^+$)=301.1 [M+H]$^+$

2-[(2R)-1-Benzyl-5-oxopyrrolidin-2-yl]-N-[(1R,2R)-2-methylcyclopropyl]-2-oxoacetamide (FP 271)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a colourless glass (45 mg, 100% purity, 15%) after purification by flash column chromatography on normal phase silica (25 g SNAP KP-SIL cartridge, 0-100% TBME in heptane gradient followed by isocratic 100% TBME) followed by further purification by flash column chromatography on normal phase silica (10 g SNAP KP-SIL cartridge, 0-100% TBME in heptane gradient and isocratic elution 100% TBME) then preparative LC (acidic pH, early elution method).

$^1$H NMR (500 MHz, Chloroform-d) δ 0.63 (q, J=6.2 Hz, 1H), 0.73 (dddd, J=9.4, 5.5, 3.9, 1.5 Hz, 1H), 0.89-0.98 (m, 1H), 1.10 (dd, J=6.1, 1.5 Hz, 3H), 1.91-2.02 (m, 1H), 2.37-2.49 (m, 4H), 3.92 (dd, J=14.9, 3.6 Hz, 1H), 4.94-5.04 (m, 2H), 6.78-6.88 (m, 1H), 7.11-7.16 (m, 2H), 7.23-7.32 (m, 3H).

LC-MS (MET-uPLC-AB-102): 100% (UV), Rt=2.78 min, m/z (ESI$^+$)=301.1 [M+H]$^+$

2-[(2R)-1-Benzyl-5-oxopyrrolidin-2-yl]-N-[(1R,2S)-2-hydroxycyclohexyl]-2-oxoacetamide (FP 272) and 2-[(2R)-1-benzyl-5-oxopyrrolidin-2-yl]-N-[(1 S,2R)-2-hydroxycyclohexyl]-2-oxoacetamide (FP 273)

The title compounds were synthesised from 2-[(2R)-1-benzyl-5-oxopyrrolidin-2-yl]-2-oxoacetic acid (I-433) in a similar manner to method A, general procedure 6 (general scheme 11a) using cis-2-amino-cyclohexanol in DMF as solvent, after purification by preparative LC (acidic pH, standard elution method, twice) to afford the two isolated diastereoisomers (note—diastereoisomers were arbitrarily assigned):

2-[(2R)-1-Benzyl-5-oxopyrrolidin-2-yl]-N-[(1R,2S)-2-hydroxycyclohexyl]-2-oxoacetamide (FP 272)

The title compound was obtained as an off-white solid (24 mg, 93% purity, 4%) $^1$H NMR (500 MHz, DMSO-d6) δ 1.10-1.45 (m, 4H), 1.50-1.61 (m, 2H), 1.66-1.86 (m, 3H), 2.09 (dd, J=16.2, 9.5 Hz, 1H), 2.28 (dd, J=12.8, 9.3 Hz, 1H), 2.41-2.47 (m, 1H), 3.06-3.14 (m, 1H), 3.74-3.84 (m, 2H), 4.18 (d, J=2.5 Hz, 1H), 4.90 (d, J=15.0 Hz, 1H), 6.93 (s, 1H), 7.13-7.21 (m, 2H), 7.22-7.27 (m, 1H), 7.28-7.35 (m, 2H), 8.46 (d, J=4.6 Hz, 1H).
LC-MS (MET-uPLC-AB-102): 93% (UV), Rt=2.24 min, m/z (ESI$^+$)=345.2 [M+H]$^+$ 2-[(2R)-1-Benzyl-5-oxopyrrolidin-2-yl]-N-[(1 S,2R)-2-hydroxycyclohexyl]-2-oxoacetamide (FP 273)

The title compound was obtained as an off-white solid (31 mg, 92% purity, 6%)
$^1$H NMR (500 MHz, DMSO-d6) δ 1.13-1.41 (m, 3H), 1.41-1.50 (m, 1H), 1.52-1.63 (m, 1H), 1.63-1.83 (m, 4H), 1.85-1.94 (m, 1H), 2.09-2.18 (m, 1H), 2.41-2.48 (m, 1H), 3.09-3.17 (m, 1H), 3.82 (d, J=8.3 Hz, 1H), 4.27 (d, J=2.8 Hz, 1H), 4.42 (d, J=15.0 Hz, 1H), 4.95 (d, J=15.1 Hz, 1H), 7.14-7.22 (m, 2H), 7.23-7.28 (m, 1H), 7.30-7.36 (m, 2H), 8.22 (d, J=4.1 Hz, 1H).
LC-MS (MET-uPLC-AB-102): 92% (UV), Rt=2.33 min, m/z (ESI$^+$)=345.1 [M+H]$^+$ 2-{1-[(4-Chlorophenyl)methyl]-5-oxopyrrolidin-2-yl}-N-(2-hydroxy-2-methylpropyl)-2-oxoacetamide (FP 274)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine in DMF as solvent to give an off-white solid (51 mg, 88% purity, 10%) after purification by flash column chromatography on normal phase silica (25 g SNAP KP-SIL cartridge, 0-20% MeOH in DCM gradient) followed by preparative LC (acidic pH, standard elution method) and further purification by preparative LC (acidic pH, early elution method).
$^1$H NMR (500 MHz, DMSO-d6) δ 1.04-1.07 (m, 6H), 1.89-1.97 (m, 1H), 2.19-2.40 (m, 3H), 3.04-3.15 (m, 2H), 3.96 (d, J=15.4 Hz, 1H), 4.59 (s, 1H), 4.75 (d, J=15.4 Hz, 1H), 4.91 (dd, J=10.0, 3.1 Hz, 1H), 7.22-7.26 (m, 2H), 7.35-7.40 (m, 2H), 8.32 (t, J=6.2 Hz, 1H).

LC-MS (MET-uPLC-AB-102): 88% (UV), Rt=2.34 min, m/z (ESI$^+$)=353.1 [M+H]$^+$

2-{1-[(4-Chlorophenyl)methyl]-5-oxopyrrolidin-2-yl}-N-(3-hydroxypropyl)-2-oxoacetamide (FP 275)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine in DMF as solvent to give an off-white solid (45 mg, 100% purity, 9%) after purification by flash column chromatography on normal phase silica (25 g SNAP KP-SIL cartridge, 0-20% MeOH in EtOAc gradient) followed by preparative LC (acidic pH, early elution method).
$^1$H NMR (500 MHz, DMSO-d6) δ 1.57-1.66 (m, 2H), 1.86-1.95 (m, 1H), 2.16-2.40 (m, 3H), 3.17 (q, J=6.5 Hz, 2H), 3.41 (q, J=6.2 Hz, 2H), 3.94 (d, J=15.4 Hz, 1H), 4.48 (t, J=5.1 Hz, 1H), 4.73 (d, J=15.4 Hz, 1H), 4.92 (dd, J=10.0, 3.0 Hz, 1H), 7.20-7.26 (m, 2H), 7.34-7.40 (m, 2H), 8.71 (t, J=6.0 Hz, 1H)
LC-MS (MET-uPLC-AB-102): 100% (UV), Rt=2.09 min, m/z (ESI$^+$)=339.1 [M+H]$^+$ 2-{1-[(4-Chlorophenyl)methyl]-5-oxopyrrolidin-2-yl}-N-{[1-(hydroxymethyl)cyclopropyl]-methyl}-2-oxoacetamide (FP 276)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine in DMF as solvent to give an off-white solid (28 mg, 97% purity, 5%) after purification by preparative LC (acidic pH, early elution method) followed by flash column chromatography on normal phase silica (25 g SNAP KP-SIL cartridge, 0-10% MeOH in DCM gradient).
$^1$H NMR (500 MHz, DMSO-d6) δ 0.32-0.37 (m, 2H), 0.37-0.45 (m, 2H), 1.87-1.95 (m, 1H), 2.15-2.43 (m, 4H), 3.10-3.22 (m, 2H), 3.22-3.29 (m, 2H), 3.95 (d, J=15.4 Hz, 1H), 4.60 (t, J=5.7 Hz, 1H), 4.73 (d, J=15.4 Hz, 1H), 4.91 (dd, J=10.0, 3.1 Hz, 1H), 7.21-7.27 (m, 2H), 7.34-7.41 (m, 2H), 8.63 (t, J=6.0 Hz, 1H).
LC-MS (MET-uPLC-AB-102): 97% (UV), Rt=2.40 min, m/z (ESI$^+$)=365.1 [M+H]$^+$ N-Cyclopropyl-2-{1-[(5-methylthiophen-2-yl)methyl]-5-oxopyrrolidin-2-yl}-2-oxoacetamide (FP 277)

The title compound was synthesised from 2-{1-[(5-methylthiophen-2-yl)methyl]-5-oxopyrrolidin-2-yl}-2-oxoacetic acid (I-453) in a similar manner to method A, general procedure 6 (general scheme 11a) using the free-base form of the amine in DMF as solvent to give a yellow viscous oil (30 mg, 99% purity, 26%) after purification by preparative LC (acidic pH, standard elution method).
$^1$H NMR (500 MHz, Chloroform-d) δ 0.55-0.66 (m, 2H), 0.82-0.92 (m, 2H), 1.91-2.00 (m, 1H), 2.35-2.51 (m, 6H), 2.71-2.86 (m, 1H), 4.08 (d, J=15.3 Hz, 1H), 4.96-5.13 (m, 2H), 6.49-6.55 (m, 1H), 6.60 (d, J=3.3 Hz, 1H), 6.94 (s, 1H).
LC-MS (MET-uPLC-AB-102): 99% (UV), Rt=2.35 min, m/z (ESI$^+$)=307.1 [M+H]$^+$ N-Ethyl-2-{1-[(5-methylthiophen-2-yl)methyl]-5-oxopyrrolidin-2-yl}-2-oxoacetamide (FP 278)

The title compound was synthesised from 2-{1-[(5-methylthiophen-2-yl)methyl]-5-oxopyrrolidin-2-yl}-2-oxoacetic acid (I-453) in a similar manner to method A, general procedure 6 (general scheme 11a) using ethylamine (2M solution of in THF) and DMF as solvent to give a yellow viscous oil (12 mg, 100% purity, 11%) after purification by preparative LC (acidic pH, standard elution method).

$^1$H NMR (500 MHz, Chloroform-d) δ 1.21 (t, J=7.3 Hz, 3H), 1.89-2.01 (m, 1H), 2.35-2.51 (m, 6H), 3.30-3.40 (m, 2H), 4.08 (d, J=15.4 Hz, 1H), 5.01-5.12 (m, 2H), 6.47-6.57 (m, 1H), 6.61 (d, J=3.4 Hz, 1H), 6.91 (s, 1H).

LC-MS (METCR1603): 100% (UV), Rt=3.46 min, m/z (ESI$^+$)=295.2 [M+H]$^+$

2-[1-(Cyclopentylmethyl)-5-oxopyrrolidin-2-yl]-N-cyclopropyl-2-oxoacetamide (FP 279)

The title compound was synthesised from 2-[1-(cyclopentylmethyl)-5-oxopyrrolidin-2-yl]-2-oxoacetic acid (I-440) in a similar manner to method A, general procedure 6 (general scheme 11a) using the free-base form of the amine in DMF as solvent to give a colourless gum (22 mg, 100% purity, 22%) after purification by preparative LC (acidic pH, early elution method).

$^1$H NMR (500 MHz, Chloroform-d) δ 0.61-0.66 (m, 2H), 0.85-0.93 (m, 2H), 1.09-1.23 (m, 2H), 1.43-1.76 (m, 6H), 1.93-2.05 (m, 2H), 2.27-2.52 (m, 3H), 2.71 (dd, J=6.3, 13.9 Hz, 1H), 2.78-2.86 (m, 1H), 3.67 (dd, J=9.3, 13.9 Hz, 1H), 5.27 (dd, J=3.2, 9.9 Hz, 1H), 6.97 (br. s, 1H).

LC-MS (MET-uPLC-AB-102): 100% (UV), Rt=2.37 min, m/z (ESI$^+$)=279.1 [M+H]$^+$

2-[1-(Cyclopentylmethyl)-5-oxopyrrolidin-2-yl]-N-(cyclopropylmethyl)-2-oxoacetamide (FP 280)

The title compound was synthesised from 2-[1-(cyclopentylmethyl)-5-oxopyrrolidin-2-yl]-2-oxoacetic acid (I-440) in a similar manner to method A, general procedure 6 (general scheme 11a) using the free-base form of the amine in DMF as solvent to give a colourless gum (33 mg, 100% purity, 31%) after purification by preparative LC (acidic pH, early elution method).

$^1$H NMR (500 MHz, Chloroform-d) δ 0.26 (q, J=4.8 Hz, 2H), 0.52-0.63 (m, 2H), 0.94-1.05 (m, 1H), 1.11-1.24 (m, 2H), 1.45-1.77 (m, 6H), 1.93-2.07 (m, 2H), 2.28-2.53 (m, 3H), 2.73 (dd, J=6.4, 13.9 Hz, 1H), 3.14-3.24 (m, 2H), 3.68 (dd, J=9.3, 13.9 Hz, 1H), 5.25-5.31 (m, 1H), 7.06 (br. s, 1H).

LC-MS (MET-uPLC-AB-102): 100% (UV), Rt=2.76 min, m/z (ESI$^+$)=293.1 [M+H]$^+$

2-[(2R)-1-Benzyl-5-oxopyrrolidin-2-yl]-N-methyl-2-oxoacetamide (FP 281)

The title compound was synthesised from 2-[(2R)-1-benzyl-5-oxopyrrolidin-2-yl]-2-oxoacetic acid (I-433) in a similar manner to method A, general procedure 6 (general scheme 11a) using methylamine (2M solution in THF) and DMF as solvent to give a yellow viscous oil (63 mg, 99% purity, 35%) after purification by preparative LC (acidic pH, standard elution method).

$^1$H NMR (500 MHz, Chloroform-d) δ 1.92-2.02 (m, 1H), 2.36-2.50 (m, 3H), 2.86 (d, J=5.2 Hz, 3H), 3.92 (d, J=14.9 Hz, 1H), 4.93-5.00 (m, 1H), 5.03 (d, J=14.9 Hz, 1H), 6.93 (s, 1H), 7.06-7.19 (m, 2H), 7.20-7.36 (m, 3H).

LC-MS (MET-uPLC-AB-102): 99% (UV), Rt=1.79 min, m/z (ESI$^+$)=261.0 [M+H]$^+$

2-[(2R)-1-Benzyl-5-oxopyrrolidin-2-yl]-N-(2-fluoroethyl)-2-oxoacetamide (FP 282)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a pale yellow solid (127 mg, 97% purity, 25%) after purification by flash column chromatography on normal phase silica (25 g SNAP KP-SIL cartridge, 0-100% TBME in heptane gradient followed by isocratic 100% TBME).

$^1$H NMR (500 MHz, Chloroform-d) δ 1.93-2.04 (m, 1H), 2.38-2.50 (m, 3H), 3.54-3.59 (m, 1H), 3.59-3.65 (m, 1H), 3.96 (d, J=14.9 Hz, 1H), 4.51 (dt, J=47.1, 4.8 Hz, 2H), 4.94-4.99 (m, 1H), 5.02 (d, J=14.9 Hz, 1H), 7.11-7.18 (m, 2H), 7.24-7.33 (m, 3H).

LC-MS (MET-uPLC-AB-102): 97% (UV), Rt=1.98 min, m/z (ESI$^+$)=293.1 [M+H]$^+$

2-[(2R)-1-[(4-Chlorophenyl)methyl]-5-oxopyrrolidin-2-yl]-N-methyl-2-oxoacetamide (FP 283)

The title compound was synthesised from 2-[(2R)-1-[(4-chlorophenyl)methyl]-5-oxopyrrolidin-2-yl]-2-oxoacetic acid (I-447) in a similar manner to method A, general procedure 6 (general scheme 11a) using methylamine (2M solution in THF) and DMF as solvent to give an off-white solid (136 mg, 100% purity, 47%) after purification by flash column chromatography on normal phase silica (25 g SNAP KP-SIL cartridge, 0-100% EtOAc in heptane gradient).

$^1$H NMR (500 MHz, Chloroform-d) δ 1.91-2.06 (m, 1H), 2.37-2.50 (m, 3H), 2.88 (d, J=5.2 Hz, 3H), 3.94 (d, J=15.0 Hz, 1H), 4.91-5.01 (m, 2H), 6.85 (s, 1H), 7.05-7.14 (m, 2H), 7.20-7.32 (m, 2H).

LC-MS (METCR1603): 100% (UV), Rt=3.40 min, m/z (ESI$^+$)=295.1 [M+H]$^+$

2-[(2R)-1-[(4-Chlorophenyl)methyl]-5-oxopyrrolidin-2-yl]-N-cyclopropyl-2-oxoacetamide (FP 284)

The title compound was synthesised from 2-[(2R)-1-[(4-chlorophenyl)methyl]-5-oxopyrrolidin-2-yl]-2-oxoacetic acid (I-433) in a similar manner to method A, general procedure 6 (general scheme 11a) using the free-base form of the amine in DMF as solvent to give an off-white crystalline solid (179 mg, 100% purity, 57%) after purification by flash column chromatography on normal phase silica (25 g SNAP KP-SIL cartridge, 0-100% EtOAc in heptane gradient).

$^1$H NMR (500 MHz, Chloroform-d) δ 0.52-0.66 (m, 2H), 0.78-0.94 (m, 2H), 1.88-2.08 (m, 1H), 2.35-2.52 (m, 3H), 2.69-2.82 (m, 1H), 3.96 (d, J=15.0 Hz, 1H), 4.90 (d, J=15.0 Hz, 1H), 4.95-5.00 (m, 1H), 6.84 (s, 1H), 7.07-7.12 (m, 2H), 7.25-7.29 (m, 2H).

LC-MS (METCR1603): 100% (UV), Rt=3.68 min, m/z (ESI$^+$)=321.1 [M+H]$^+$

2-[(2R)-1-[(4-Chlorophenyl)methyl]-5-oxopyrrolidin-2-yl]-N-ethyl-2-oxoacetamide (FP 285)

The title compound was synthesised from 2-[(2R)-1-[(4-chlorophenyl)methyl]-5-oxopyrrolidin-2-yl]-2-oxoacetic acid (I-433) in a similar manner to method A, general procedure 6 (general scheme 11a) using a 70% aqueous solution of ethylamine and DMF as solvent to give an off-white solid (37 mg, 100% purity, 12%) after purification by flash column chromatography on normal phase silica (25 g SNAP Ultra cartridge, 0-100% EtOAc in heptane gradient) followed by preparative LC (acidic pH, standard elution method).

$^1$H NMR (500 MHz, Chloroform-d) δ 1.20 (t, J=7.3 Hz, 3H), 1.90-2.05 (m, 1H), 2.36-2.50 (m, 3H), 3.26-3.39 (m, 2H), 3.95 (d, J=15.0 Hz, 1H), 4.93 (d, J=15.0 Hz, 1H), 4.95-5.01 (m, 1H), 6.73-6.92 (m, 1H), 7.06-7.13 (m, 2H), 7.23-7.31 (m, 2H).

LC-MS (METCR1603): 100% (UV), Rt=3.67 min, m/z (ESI$^+$)=309.1 [M+H]$^+$

2-[(2R)-1-Benzyl-5-oxopyrrolidin-2-yl]-2-oxo-N-[2-(propan-2-yloxy)ethyl]acetamide (FP 286)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a yellow oil (113 mg, 95% purity by 1H NMR, 67%) after purification by flash column chromatography on reverse phase silica (12 g SNAP Ultra C18 cartridge, basic pH, standard elution method).

$^1$H NMR (500 MHz, Chloroform-d) δ 1.17 (d, J=6.1 Hz, 3H), 1.17 (d, J=6.1 Hz, 3H), 1.93-2.03 (m, 1H), 2.37-2.50 (m, 3H), 3.40-3.47 (m, 2H), 3.47-3.54 (m, 2H), 3.60 (hept, J=6.1 Hz, 1H), 3.91 (d, J=14.9 Hz, 1H), 4.93-5.00 (m, 1H), 5.07 (d, J=14.9 Hz, 1H), 7.12-7.17 (m, 2H), 7.21 (br. s, 1H), 7.24-7.34 (m, 3H).

LC-MS (METCR1603): 97% (UV), Rt=3.65 min, m/z (ESI$^+$)=333.2 [M+H]$^+$

2-[(2R)-1-Benzyl-5-oxopyrrolidin-2-yl]-N-[(3-methyl-1,2,4-oxadiazol-5-yl)methyl]-2-oxoacetamide (FP 287)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a yellow oil (72 mg, 95% purity by $^1$H NMR, 42%) after purification by flash column chromatography on reverse phase silica (12 g SNAP Ultra C18 cartridge, basic pH, standard elution method) followed by normal phase silica (10 g SNAP KP-SIL cartridge, 10-100% EtOAc in heptane gradient).

$^1$H NMR (500 MHz, Chloroform-d) δ 1.96-2.03 (m, 1H), 2.41 (s, 3H), 2.42-2.50 (m, 3H), 3.98 (d, J=14.9 Hz, 1H), 4.67 (d, J=6.0 Hz, 1H), 4.67 (d, J=6.0 Hz, 1H), 4.93-4.98 (m, 1H), 5.02 (d, J=14.9 Hz, 1H), 7.13-7.17 (m, 2H), 7.23-7.33 (m, 3H), 7.42 (t, J=5.1 Hz, 1H).

LC-MS (METCR1603): 98% (UV), Rt=3.19 min, m/z (ESI$^+$)=343.1 [M+H]$^+$

2-[(2R)-1-Benzyl-5-oxopyrrolidin-2-yl]-2-oxo-N-propylacetamide (FP 288)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give an off-white solid (92 mg, 97% purity, 65%) after purification by flash column chromatography on normal phase silica (25 g SNAP Ultra cartridge, 0-100% EtOAc in heptane gradient).

$^1$H NMR (500 MHz, Chloroform-d) δ 0.94 (t, J=7.4 Hz, 3H), 1.53-1.61 (m, 2H), 1.88-2.04 (m, 1H), 2.36-2.51 (m, 3H), 3.18-3.29 (m, 2H), 3.94 (d, J=14.9 Hz, 1H), 4.95-5.00 (m, 1H), 5.03 (d, J=14.9 Hz, 1H), 6.79-6.91 (m, 1H), 7.13-7.17 (m, 2H), 7.24-7.32 (m, 3H).

LC-MS (METCR1603): 97% (UV), Rt=3.61 min, m/z (ESI$^+$)=289.1 [M+H]$^+$

2-[(2R)-1-Benzyl-5-oxopyrrolidin-2-yl]-N-[(5-methyl-1,2-oxazol-3-yl)methyl]-2-oxoacetamide (FP 289)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a colourless gum (33 mg, 98% purity, 20%) after purification by flash column chromatography on normal phase silica (10 g SNAP KP-SIL cartridge, 100% TBME) followed by preparative LC (acidic pH, early elution method).

$^1$H NMR (500 MHz, Chloroform-d) δ 1.96-2.01 (m, 1H), 2.39-2.50 (m, 6H), 3.94 (d, J=14.9 Hz, 1H), 4.43-4.51 (m, 2H), 4.93-4.99 (m, 1H), 5.03 (d, J=14.9 Hz, 1H), 5.90-5.95 (m, 1H), 7.12-7.17 (m, 2H), 7.23-7.33 (m, 4H).

LC-MS (MET-uPLC-AB-102): 98% (UV), Rt=2.28 min, m/z (ESI$^+$)=342.2 [M+H]$^+$

2-[(2R)-1-Benzyl-5-oxopyrrolidin-2-yl]-N-[(1-cyanocyclopropyl)methyl]-2-oxoacetamide (FP 290)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a colourless gum (22 mg, 99% purity, 14%) after purification by flash column chromatography on normal phase silica (10 g SNAP KP-SIL cartridge, 50-100% TBME in heptane, then 0-10% MeOH in TBME gradient) followed by preparative LC (acidic pH, early elution method).

$^1$H NMR (500 MHz, Chloroform-d) δ 1.02-1.11 (m, 2H), 1.28-1.37 (m, 2H), 1.95-2.01 (m, 1H), 2.38-2.51 (m, 3H), 3.33 (dd, J=6.4, 14.4 Hz, 1H), 3.41 (dd, J=6.5, 14.4 Hz, 1H), 3.99 (d, J=14.9 Hz, 1H), 4.93-4.98 (m, 1H), 5.01 (d, J=14.9 Hz, 1H), 7.13-7.19 (m, 2H), 7.21-7.26 (m, 1H), 7.27-7.34 (m, 3H).

LC-MS (MET-uPLC-AB-102): 99% (UV), Rt=2.19 min, m/z (ESI$^+$)=326.2 [M+H]$^+$

2-[(2R)-1-Benzyl-5-oxopyrrolidin-2-yl]-N-{bicyclo[1.1.1]pentan-1-yl}-2-oxoacetamide (FP 291)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford an off-white solid (102 mg, 99% purity, 68%) after purification by flash column chromatography on normal phase silica (25 g SNAP Ultra cartridge, 0-100% EtOAc in heptane gradient) followed by flash column chromatography on normal phase silica (10 g SNAP Ultra cartridge, 0-100% EtOAc in heptane gradient).

$^1$H NMR (500 MHz, Chloroform-d) δ 1.93-2.03 (m, 1H), 2.13 (s, 6H), 2.35-2.48 (m, 3H), 2.51 (s, 1H), 3.92 (d, J=14.9 Hz, 1H), 4.93-4.99 (m, 1H), 5.01 (d, J=14.9 Hz, 1H), 7.13-7.16 (m, 2H), 7.16-7.20 (m, 1H), 7.23-7.28 (m, 2H), 7.29-7.32 (m, 1H).

LC-MS (METCR1603): 99% (UV), Rt=2.79 min, m/z (ESI$^+$)=313.1 [M+H]$^+$

2-[(2R)-1-Benzyl-5-oxopyrrolidin-2-yl]-2-oxo-N-[2-(2-oxopiperidin-1-yl)ethyl]acetamide (FP 292)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a yellow viscous oil (49 mg, 95% purity, 11%) after purification by flash column chromatography on reverse phase silica (30 g SNAP Ultra-C18 cartridge, basic pH, standard elution method) followed by flash column chromatography on reverse phase silica (12 g SNAP Ultra-C18 cartridge, basic pH, standard elution method).

$^1$H NMR (500 MHz, Chloroform-d) δ 1.71-1.87 (m, 4H), 1.92-2.03 (m, 1H), 2.33-2.49 (m, 5H), 3.28-3.37 (m, 2H), 3.39-3.47 (m, 2H), 3.51-3.58 (m, 2H), 3.88 (d, J=15.0 Hz, 1H), 4.88-4.95 (m, 1H), 5.08 (d, J=15.0 Hz, 1H), 7.11-7.17 (m, 2H), 7.21-7.33 (m, 3H), 7.92 (br. s, 1H).

LC-MS (METCR1603): 100% (UV), Rt=3.21 min, m/z (ESI$^+$)=372.1 [M+H]$^+$

2-[(2R)-1-Benzyl-5-oxopyrrolidin-2-yl]-N-[2-(3-methyl-1,2,4-oxadiazol-5-yl)ethyl]-2-oxoacetamide (FP 293)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a yellow viscous oil (52 mg, 96% purity, 30%) after purification by flash column chromatography on normal phase silica (10 g SNAP KP-SIL cartridge, 0-10% MeOH in DCM gradient) followed by preparative LC (acidic pH, early elution method).

$^1$H NMR (500 MHz, Chloroform-d) δ 1.93-2.00 (m, 1H), 2.38-2.48 (m, 6H), 3.05-3.11 (m, 2H), 3.75 (q, J=6.3 Hz, 2H), 3.94 (d, J=14.9 Hz, 1H), 4.92-4.98 (m, 1H), 5.02 (d, J=14.9 Hz, 1H), 7.12-7.16 (m, 2H), 7.22-7.31 (m, 3H), 7.51 (t, J=5.8 Hz, 1H).

LC-MS (MET-uPLC-AB-102): 96% (UV), Rt=2.14 min, m/z (ESI$^+$)=357.2 [M+H]$^+$

2-[(2R)-1-Benzyl-5-oxopyrrolidin-2-yl]-N-(3-fluorocyclobutyl)-2-oxoacetamide (FP 294)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford an off-white powder (60 mg, 98% purity, 15%) after purification by flash column chromatography on normal phase silica (25 g SNAP KP-SIL cartridge, 50-100% TBME in heptane gradient) followed by preparative LC (acidic pH, early elution method).

$^1$H NMR (500 MHz, Chloroform-d) δ 1.92-1.99 (m, 1H), 2.13-2.49 (m, 5H), 2.63-2.92 (m, 2H), 3.86-4.56 (m, 2H), 4.74-5.29 (m, 3H), 6.88-6.99 (m, 1H), 7.13-7.16 (m, 2H), 7.24-7.32 (m, 3H).

LC-MS (MET-uPLC-AB-102): 98% (UV), Rt=2.37 min, m/z (ESI$^+$)=319.1 [M+H]$^+$

2-[(2R)-1-Benzyl-5-oxopyrrolidin-2-yl]-N-(2,2-difluoropropyl)-2-oxoacetamide (FP 295)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford an off-white crystalline solid (117 mg, 100% purity, 76%) after purification by flash column chromatography on normal phase silica (25 g SNAP Ultra cartridge, 0-100% EtOAc in heptane gradient).

$^1$H NMR (500 MHz, Chloroform-d) δ 1.62 (t, J=18.4 Hz, 3H), 1.91-2.02 (m, 1H), 2.37-2.52 (m, 3H), 3.65 (td, J=6.6, 13.7 Hz, 2H), 3.98 (d, J=14.8 Hz, 1H), 4.92-4.98 (m, 1H), 5.01 (d, J=14.8 Hz, 1H), 7.06-7.13 (m, 1H), 7.12-7.18 (m, 2H), 7.24-7.33 (m, 3H).

LC-MS (METCR1603): 100% (UV), Rt=3.58 min, m/z (ESI$^+$)=325.1 [M+H]$^+$

2-[(2R)-1-Benzyl-5-oxopyrrolidin-2-yl]-N-[(1-methyl-1H-pyrazol-5-yl)methyl]-2-oxoacetamide (FP 296)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give an off-white crystalline solid (54 mg, 100% purity, 33%) after purification by flash column chromatography on normal phase silica (10 g SNAP Ultra cartridge, 0-100% EtOAc in heptane gradient).

$^1$H NMR (500 MHz, Chloroform-d) δ 1.89-2.04 (m, 1H), 2.35-2.54 (m, 3H), 3.83 (s, 3H), 3.98 (d, J=14.9 Hz, 1H), 4.41-4.55 (m, 2H), 4.92-5.03 (m, 2H), 6.20 (d, J=1.9 Hz, 1H), 6.98-7.07 (m, 1H), 7.11-7.16 (m, 2H), 7.22-7.32 (m, 3H), 7.43 (d, J=1.9 Hz, 1H).

LC-MS (METCR1603): 100% (UV), Rt=3.15 min, m/z (ESI$^+$)=341.2 [M+H]$^+$

2-[(2R)-1-Benzyl-5-oxopyrrolidin-2-yl]-N-{2-oxaspiro[3.3]heptan-6-yl}-2-oxoacetamide (FP 297)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a yellow viscous oil (29 mg, 95% purity by 1H NMR, 17%) after purification by flash column chromatography on reverse phase silica (12 g SNAP Ultra-C18 cartridge, basic pH, standard elution method).

$^1$H NMR (500 MHz, Chloroform-d) δ 1.89-1.98 (m, 1H), 2.11-2.20 (m, 2H), 2.35-2.49 (m, 3H), 2.65-2.74 (m, 2H), 3.92 (d, J=14.9 Hz, 1H), 4.13 (h, J=8.2 Hz, 1H), 4.62 (s, 2H), 4.73 (s, 2H), 4.92-4.96 (m, 1H), 5.00 (d, J=14.9 Hz, 1H), 6.95 (d, J=7.9 Hz, 1H), 7.11-7.15 (m, 2H), 7.23-7.32 (m, 3H).

LC-MS (METCR1603): 98% (UV), Rt=3.2 min, m/z (ESI$^+$)=343.2 [M+H]$^+$

2-[(2R)-1-Benzyl-5-oxopyrrolidin-2-yl]-2-oxo-N-[(pyrimidin-2-yl)methyl]acetamide (FP 298)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a colourless viscous oil (16 mg, 91% purity, 9%) after purification by preparative LC (acidic pH, standard elution method) followed by flash column chromatography on normal phase silica (10 g SNAP KP-SIL cartridge, 0-8% MeOH in DCM gradient).

$^1$H NMR (500 MHz, Chloroform-d) δ 1.97-2.07 (m, 1H), 2.39-2.51 (m, 3H), 3.89-3.98 (m, 1H), 4.69 (d, J=5.1 Hz, 2H), 4.97-5.04 (m, 1H), 5.08 (d, J=14.9 Hz, 1H), 7.12-7.18 (m, 2H), 7.19-7.32 (m, 4H), 8.06-8.14 (m, 1H), 8.74 (d, J=4.9 Hz, 2H).

LC-MS (METCR1603): 91% (UV), Rt=2.98 min, m/z (ESI+)=339.1 [M+H]+

N-(3-{2-[(2R)-1-Benzyl-5-oxopyrrolidin-2-yl]-2-oxoacetamido}propyl)-2-methylpropan-amide (FP 299)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford as a colourless viscous oil (53 mg, 95% purity, 28%) after purification by flash column chromatography on reverse phase silica (12 g SNAP Ultra-C18 cartridge, basic pH, standard elution method).

$^1$H NMR (500 MHz, Chloroform-d) δ 1.17 (d, J=6.9 Hz, 6H), 1.67 (p, J=6.2 Hz, 2H), 1.90-2.01 (m, 1H), 2.31-2.51 (m, 4H), 3.19-3.37 (m, 4H), 3.93 (d, J=14.9 Hz, 1H), 4.89-5.01 (m, 1H), 5.07 (d, J=15.0 Hz, 1H), 5.76-5.91 (m, 1H), 7.12-7.19 (m, 2H), 7.21-7.35 (m, 3H), 7.61-7.75 (m, 1H).

LC-MS (METCR1603): 95% (UV), Rt=3.27 min, m/z (ESI+)=374.3 [M+H]+

2-[(2R)-1-Benzyl-5-oxopyrrolidin-2-yl]-2-oxo-N-[(3R)-2-oxoazepan-3-yl]acetamide (FP 300)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give an off-white solid (73 mg, 96% purity, 23%) after purification by flash column chromatography on normal phase silica (25 g SNAP KP-SIL cartridge, 50-100% EtOAc in heptane gradient).

$^1$H NMR (500 MHz, DMSO-d6) δ 1.13-1.26 (m, 1H), 1.33-1.46 (m, 1H), 1.60-1.71 (m, 1H), 1.71-1.79 (m, 1H), 1.83-1.92 (m, 2H), 1.92-2.01 (m, 1H), 2.18-2.40 (m, 3H), 3.01-b3.12 (m, 1H), 3.15-3.24 (m, 1H), 3.90 (d, J=15.2 Hz, 1H), 4.37 (dd, J=10.5, 6.3 Hz, 1H), 4.77-4.89 (m, 2H), 7.16-7.21 (m, 2H), 7.22-7.27 (m, 1H), 7.27-7.34 (m, 2H), 8.02-8.09 (m, 1H), 8.33 (d, J=6.3 Hz, 1H).

LC-MS (MET-uPLC-AB-102): 96% (UV), Rt=2.02 min, m/z (ESI+)=358.2 [M+H]+

2-[(2R)-1-Benzyl-5-oxopyrrolidin-2-yl]-2-oxo-N-[3-(propan-2-yloxy)propyl]acetamide (FP 301)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a pale yellow oil (104 mg, 100% purity, 42%) after purification by preparative LC (acidic pH, early elution method).

$^1$H NMR (500 MHz, Chloroform-d) δ 1.18-1.23 (m, 6H), 1.76-1.84 (m, 2H), 1.92-2.03 (m, 1H), 2.36-2.49 (m, 3H), 3.40 (q, J=5.7 Hz, 2H), 3.54-3.63 (m, 3H), 3.88 (d, J=14.9 Hz, 1H), 4.92-5.00 (m, 1H), 5.08 (d, J=14.9 Hz, 1H), 7.12-7.17 (m, 2H), 7.22-7.33 (m, 3H), 7.77-7.85 (m, 1H).

LC-MS (MET-uPLC-AB-102): 100% (UV), Rt=2.72 min, m/z (ESI+)=347.3 [M+H]+

2-[(2R)-1-Benzyl-5-oxopyrrolidin-2-yl]-N-[2-(2-ethoxyethoxy)ethyl]-2-oxoacetamide (FP 302)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a yellow viscous oil (119 mg, 100% purity, 46%) after purification by flash column chromatography on normal phase silica (10 g SNAP KP-SIL cartridge, 0-65% EtOAc in heptane gradient).

$^1$H NMR (500 MHz, Chloroform-d) δ 1.24 (t, J=7.0 Hz, 3H), 1.93-2.04 (m, 1H), 2.37-2.49 (m, 3H), 3.45-3.51 (m, 2H), 3.56 (q, J=7.0 Hz, 2H), 3.58-3.62 (m, 4H), 3.62-3.65 (m, 2H), 3.89 (d, J=14.9 Hz, 1H), 4.93-4.99 (m, 1H), 5.08 (d, J=14.9 Hz, 1H), 7.13-7.17 (m, 2H), 7.23-7.32 (m, 3H), 7.32-7.41 (m, 1H).

LC-MS (METCR1603): 100% (UV), Rt=3.45 min, m/z (ESI+)=363.2 [M+H]+

2-[(2R)-1-Benzyl-5-oxopyrrolidin-2-yl]-N-(3-cyano-cyclobutyl)-2-oxoacetamide (FP 303)

The title compound was synthesised from 2-[(2R)-1-benzyl-5-oxopyrrolidin-2-yl]-2-oxoacetic acid (I-433) a similar manner to method A, general procedure 6 (general scheme 11a) using DMF as solvent to afford an off-white gum (44 mg, 99% purity, 14%) after purification by flash column chromatography on normal phase silica (10 g SNAP KP-SIL cartridge, 0-5% MeOH in DCM gradient) followed by preparative LC (acidic pH, early elution method).

$^1$H NMR (500 MHz, Chloroform-d) δ 1.91-1.98 (m, 1H), 2.36-2.49 (m, 5H), 2.78-2.90 (m, 3H), 3.98 (d, J=14.9 Hz, 1H), 4.29-4.39 (m, 1H), 4.91-5.00 (m, 2H), 7.02 (br. d, J=8.0 Hz, 1H), 7.11-7.16 (m, 2H), 7.24-7.32 (m, 3H).

LC-MS (MET-uPLC-AB-102): 99% (UV), Rt=2.16 min, m/z (ESI+)=326.2 [M+H]+

N-(4-{2-[(2R)-1-Benzyl-5-oxopyrrolidin-2-yl]-2-oxoacetamido}butyl)-2-methylpropan-amide (FP 304)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a yellow gum (127 mg, 97% purity, 44%) after purification by flash column chromatography on normal phase silica (10 g SNAP KP-SIL cartridge, 0-100% EtOAc in heptane gradient).

$^1$H NMR (500 MHz, Chloroform-d) δ 1.15 (d, J=6.9 Hz, 6H), 1.46-1.62 (m, 4H), 1.92-2.03 (m, 1H), 2.29-2.38 (m, 1H), 2.38-2.49 (m, 3H), 3.23-3.34 (m, 4H), 3.92 (d, J=14.9 Hz, 1H), 4.93-5.00 (m, 1H), 5.03 (d, J=14.9 Hz, 1H), 5.52-5.61 (m, 1H), 6.98-7.07 (m, 1H), 7.12-7.17 (m, 2H), 7.22-7.33 (m, 3H).

LC-MS (MET-uPLC-AB-102): 97% (UV), Rt=2.20 min, m/z (ESI+)=388.3 [M+H]+

(1s,3s)-3-{2-[(2R)-1-Benzyl-5-oxopyrrolidin-2-yl]-2-oxoacetamido}-N-(propan-2-yl)cyclobutane-1-carboxamide (FP 305)

The title compound was synthesised from 2-[(2R)-1-benzyl-5-oxopyrrolidin-2-yl]-2-oxoacetic acid (I-433) and (1s,3s)-3-amino-N-(propan-2-yl)cyclobutane-1-carboxamide (preparation analogous to WO2015154039) in a similar manner to method A, general procedure 6 (general scheme 11a) using the free-base form of the amine in DMF as solvent to give an off-white powder (15 mg, 99% purity by 1H NMR, 18%) after purification by preparative LC (acidic pH, standard elution method).

$^1$H NMR (500 MHz, Chloroform-d) δ 1.16 (dd, J=1.8, 6.6 Hz, 6H), 1.92-2.01 (m, 1H), 2.21-2.30 (m, 2H), 2.37-2.49

(m, 3H), 2.53-2.66 (m, 3H), 3.93 (d, J=14.9 Hz, 1H), 4.03-4.16 (m, 1H), 4.27-4.39 (m, 1H), 4.92-4.98 (m, 1H), 5.04 (d, J=14.9 Hz, 1H), 5.34 (br d, J=7.4 Hz, 1H), 7.10-7.18 (m, 2H), 7.24-7.33 (m, 3H), 7.53 (br d, J=8.9 Hz, 1H).

LC-MS (METCR1603): 100% (UV), Rt=3.37 min, m/z (ESI$^+$)=386.3 [M+H]$^+$ (1r,3r)-3-{2-[(2R)-1-Benzyl-5-oxopyrrolidin-2-yl]-2-oxoacetamido}-N-(propan-2-yl)cyclobutane-1-carboxamide (FP 306)

The title compound was synthesised from 2-[(2R)-1-benzyl-5-oxopyrrolidin-2-yl]-2-oxoacetic acid (I-433) and (1r,3r)-3-amino-N-(propan-2-yl)cyclobutane-1-carboxamide hydrochloride (preparation analogous to WO2015154039) in a similar manner to method A, general procedure 6 (general scheme 11a) using DMF as solvent to afford an off-white powder (12 mg, 100% purity, 6%) after purification by preparative LC (acidic pH, standard elution method).

$^1$H NMR (500 MHz, Chloroform-d) δ 1.15 (d, J=6.6 Hz, 6H), 1.91-2.00 (m, 1H), 2.19-2.29 (m, 2H), 2.36-2.49 (m, 3H), 2.61-2.70 (m, 2H), 2.81-2.94 (m, 1H), 3.94 (d, J=14.8 Hz, 1H), 4.05-4.17 (m, 1H), 4.48-4.59 (m, 1H), 4.92-5.04 (m, 2H), 5.19 (br d, J=6.9 Hz, 1H), 6.98 (br d, J=7.9 Hz, 1H), 7.11-7.17 (m, 2H), 7.24-7.31 (m, 3H).

LC-MS (METCR1603): 100% (UV), Rt=3.34 min, m/z (ESI$^+$)=386.3 [M+H]$^+$

Method B: HATU Coupling

Method as Described in Method C, General Procedure 6 (General Scheme 11a): Coupling 2-(1-Benzyl-5-oxopyrrolidin-2-yl)-N-(2-cyclopropylethyl)-2-oxoacetamide (FP 307)

The title compound was synthesised from 2-(1-benzyl-5-oxopyrrolidin-2-yl)-2-oxoacetic acid (I-432) in a similar manner to method C, general procedure 6 (general scheme 11a) using the free-base form of the amine in DMF as solvent to give a yellow viscous oil (17 mg, 97% purity, 11%) after purification by flash column chromatography on normal phase silica (10 g SNAP KP-SIL cartridge, 0-100% EtOAc in heptane gradient) followed by preparative LC (acidic pH, standard elution method).

$^1$H NMR (500 MHz, Chloroform-d) δ 0.04-0.11 (m, 2H), 0.45-0.52 (m, 2H), 0.61-0.71 (m, 1H), 1.44 (q, J=7.0 Hz, 2H), 1.92-2.02 (m, 1H), 2.38-2.49 (m, 3H), 3.31-3.42 (m, 2H), 3.93 (d, J=14.9 Hz, 1H), 4.94-5.00 (m, 1H), 5.03 (d, J=14.9 Hz, 1H), 6.93-7.02 (m, 1H), 7.12-7.17 (m, 2H), 7.22-7.32 (m, 3H).

LC-MS (METCR1603): 97% (UV), Rt=3.95 min, m/z (ESI$^+$)=315.2 [M+H]$^+$ 2-(1-Benzyl-5-oxopyrrolidin-2-yl)-2-oxo-N-(propan-2-yl)acetamide (FP 308)

The title compound was synthesised from 2-(1-benzyl-5-oxopyrrolidin-2-yl)-2-oxoacetic acid (I-432) in a similar manner to method C, general procedure 6 (general scheme 11a) using the free-base form of the amine in DMF as solvent to give an off-white powder (35 mg, 100% purity, 20%) after purification by flash column chromatography on normal phase silica (25 g SNAP KP-SIL cartridge, 25-100% EtOAc in heptane gradient) followed by preparative LC (acidic pH, early elution method).

$^1$H NMR (500 MHz, DMSO-d6) δ 1.10 (d, J=6.6 Hz, 6H), 1.86-1.94 (m, 1H), 2.17-2.27 (m, 1H), 2.28-2.38 (m, 2H), 3.84-3.94 (m, 2H), 4.82 (d, J=15.2 Hz, 1H), 4.84-4.90 (m, 1H), 7.16-7.20 (m, 2H), 7.24-7.28 (m, 1H), 7.29-7.36 (m, 2H), 8.58 (d, J=8.3 Hz, 1H).

LC-MS (METCR1603): 100% (UV), Rt=3.55 min, m/z (ESI$^+$)=289.2 [M+H]$^+$

Method C: Isobutyryl Chloroformate Method 2-(1-Benzyl-5-oxopyrrolidin-2-yl)-2-oxo-N-(propan-2-yl)acetamide (FP 309)

To a solution of crude 2-(1-benzyl-5-oxopyrrolidin-2-yl)-2-oxoacetic acid ((I-432, 60% purity, 160 mg, 0.39 mmol) and DIPEA (130 μL, 0.75 mmol) in 1,2-DCE (2 mL) was added isobutyl chloroformate (100 μL, 0.77 mmol) and the mixture stirred at RT for 1 h in a sealed tube. Cyclopropylamine (260 μL, 3.75 mmol) was added and the mixture stirred at RT for 18 h. The reaction mixture was diluted with DCM (5 mL) and washed with 1M HCl (10 mL). The organic layer was separated, dried over sodium sulfate, filtered and concentrated in vacuo. The residue was purified by flash column chromatography on normal phase silica (10 g SNAP KP-SIL cartridge, 0-100% EtOAc in heptane gradient) to afford 31 mg of 2-(1-benzyl-5-oxopyrrolidin-2-yl)-2-oxo-N-(propan-2-yl)acetamide as a viscous yellow oil (97% purity, 27%).

$^1$H NMR (500 MHz, Chloroform-d) δ 0.53-0.65 (m, 2H), 0.82-0.89 (m, 2H), 1.90-2.02 (m, 1H), 2.38-2.48 (m, 3H), 2.69-2.79 (m, 1H), 3.94 (d, J=14.9 Hz, 1H), 4.94-5.03 (m, 2H), 6.85 (s, 1H), 7.10-7.19 (m, 2H), 7.23-7.34 (m, 3H).

LC-MS (METCR1603): 97% (UV), Rt=3.28 min, m/z (ESI$^+$)=287.2 [M+H]$^+$

Method D: Displacement of Methyl Ketoester

2-[1-(Cyclopentylmethyl)-5-oxopyrrolidin-2-yl]-N-cyclopropyl-2-oxoacetamide (FP 310)

To a stirring solution of methyl 2-{1-[(4-methyl-1,3-thiazol-2-yl)methyl]-5-oxopyrrolidin-2-yl}-2-oxoacetate (I-456, 50% purity, 1.01 g, 1.79 mmol) in MeOH (25 mL) was added cyclopentylmethanamine (610 μL, 5.38 mmol) and the mixture was stirred at RT under nitrogen for 2 h. The reaction mixture was concentrated in vacuo and purified by flash column chromatography on normal phase silica (50 g SNAP Ultra column, 0-100% EtOAc in heptane gradient) followed by preparative LC (acidic pH, standard elution method) to afford 91 mg of 2-[1-(cyclopentylmethyl)-5-oxopyrrolidin-2-yl]-N-cyclopropyl-2-oxoacetamide as a viscous yellow oil (98% purity, 7%).

$^1$H NMR (500 MHz, Chloroform-d) δ 1.16-1.26 (m, 2H), 1.52-1.70 (m, 4H), 1.74-1.83 (m, 2H), 1.96-2.05 (m, 1H), 2.05-2.12 (m, 1H), 2.36-2.38 (m, 3H), 2.38-2.58 (m, 3H), 3.22-3.28 (m, 2H), 4.29 (d, J=15.7 Hz, 1H), 5.17-5.25 (m, 2H), 6.81-6.84 (m, 1H), 6.92-6.99 (m, 1H).

LC-MS (METCR1603): 98% (UV), Rt=3.79 min, m/z (ESI$^+$)=350.2 [M+H]$^+$

4-[(2-{[(Cyclohexylmethyl)carbamoyl]carbonyl}-5-oxopyrrolidin-1-yl)methyl]benzamide (FP 311)

The title compound was synthesised from methyl 2-oxo-2-{5-oxo-1-[(1,3-thiazol-2-yl)methyl]pyrrolidin-2-yl}acetate (I-457) in a similar manner to method D, general procedure 5 (general scheme 20) as a colourless viscous oil (43 mg, 95% purity, 19%) after purification by flash column chromatography on normal phase silica (10 g SNAP KP-SIL cartridge, 0-100% EtOAc in heptane gradient) followed by preparative LC (acidic pH, standard elution method).

$^1$H NMR (500 MHz, Chloroform-d) δ 0.91-0.99 (m, 2H), 1.14-1.28 (m, 3H), 1.47-1.55 (m, 1H), 1.67-1.76 (m, 5H), 1.99-2.04 (m, 1H), 2.38-2.57 (m, 3H), 3.10-3.20 (m, 2H), 4.39 (d, J=15.8 Hz, 1H), 5.20-5.27 (m, 2H), 6.97 (br t, 1H), 7.30 (d, J=3.3 Hz, 1H), 7.66 (d, J=3.3 Hz, 1H).

LC-MS (MET-uPLC-AB-102): 95% (UV), Rt=2.86 min, m/z (ESI$^+$)=350.1 [M+H]$^+$

2-{1-[(4-Chlorophenyl)methyl]-5-oxopyrrolidin-2-yl}-N-(3-hydroxypropyl)-2-oxoacetamide (FP 312)

The title compound was synthesised from methyl 2-{1-[(4-methyl-1,3-thiazol-2-yl)methyl]-5-oxopyrrolidin-2-yl}-2-oxoacetate (I-456) in a similar manner to method D, general procedure 5 (general scheme 20) as an orange gum (24 mg, 94% purity by $^1$H NMR, 5%) after purification by flash column chromatography on normal phase silica (25 g SNAP-KP-SIL column, 0-100% EtOAc in heptane gradient) followed by preparative LC (acidic pH, standard elution method).

$^1$H NMR (500 MHz, Chloroform-d) δ 0.20-0.30 (m, 2H), 0.52-0.62 (m, 2H), 0.91-1.06 (m, 1H), 1.97-2.06 (m, 1H), 2.37 (s, 3H), 2.38-2.58 (m, 3H), 3.05-3.26 (m, 2H), 4.30 (d, J=15.7 Hz, 1H), 5.19 (d, J=15.7 Hz, 1H), 5.21-5.25 (m, 1H), 6.82 (s, 1H), 6.94-7.14 (m, 1H).

LC-MS (MET-uPLC-AB-102): 100% (UV), Rt=3.18 min, m/z (ESI$^+$)=322.2 [M+H]$^+$

2-[1-(Cyclopentylmethyl)-5-oxopyrrolidin-2-yl]-N-(cyclopropylmethyl)-2-oxoacetamide (FP 313)

The title compound was synthesised from methyl 2-{1-[(4-methyl-1,3-thiazol-2-yl)methyl]-5-oxopyrrolidin-2-yl}-2-oxoacetate (I-456) in a similar manner to method D, general procedure 5 (general scheme 20) as an orange viscous oil (94 mg, 97% purity, 7%) after purification by flash column chromatography on normal phase silica (50 g SNAP KP-SIL cartridge, 0-100% EtOAc in heptane gradient then 0-20% MeOH in EtOAc gradient) followed by preparative LC (acidic pH, standard elution method).

$^1$H NMR (500 MHz, Chloroform-d) δ 0.88-1.03 (m, 2H), 1.10-1.31 (m, 3H), 1.46-1.57 (m, 1H), 1.64-1.79 (m, 5H), 1.96-2.06 (m, 1H), 2.37-2.38 (m, 3H), 2.38-2.58 (m, 3H), 3.09-3.22 (m, 2H), 4.30 (d, J=15.7 Hz, 1H), 5.16-5.26 (m, 2H), 6.80-6.85 (m, 1H), 6.93-7.01 (m, 1H).

LC-MS (METCR1603): 97% (UV), Rt=4.05 min, m/z (ESI$^+$)=264.1 [M+H]$^+$

GENERAL SCHEME 21 (Cyclic amides, sulfonamides and ureas)

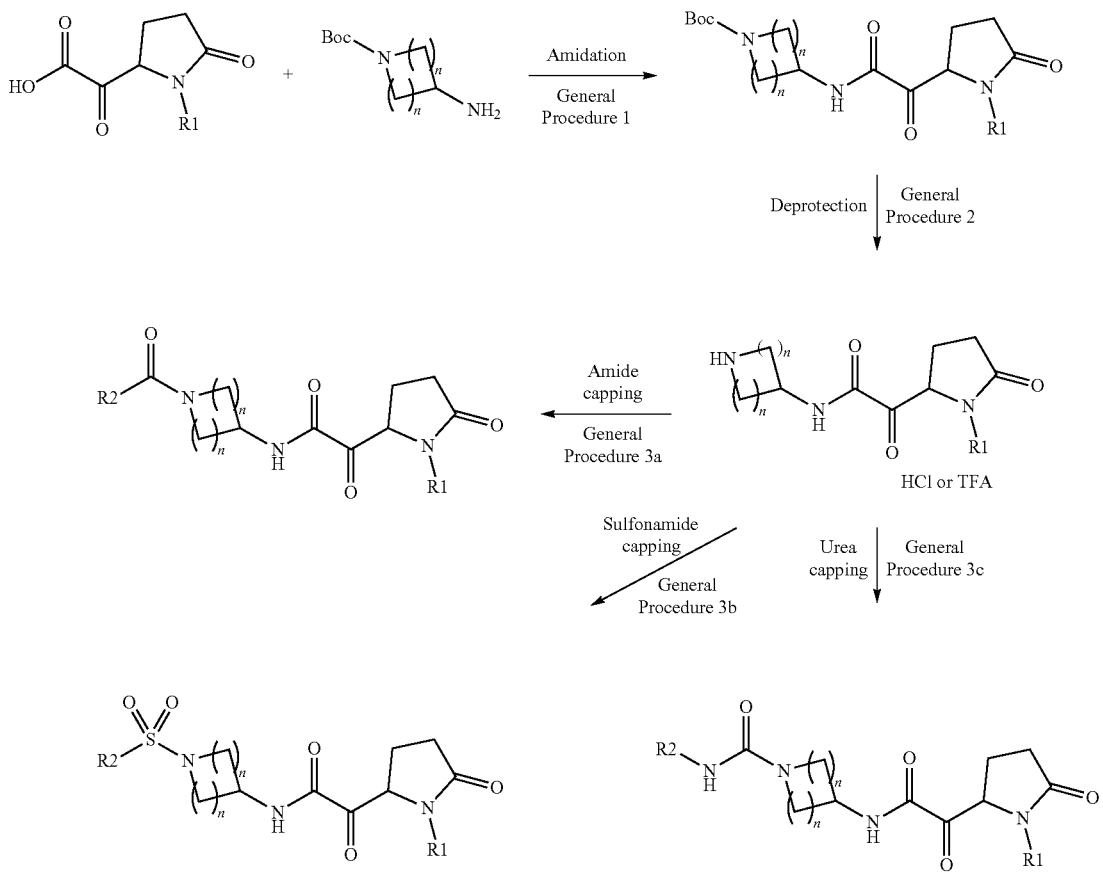

General Procedure 1 (General Scheme 21): Amination

Method A: T3P Coupling

Method a as Described in General Procedure 6 (General Scheme 11a): Coupling

Tert-butyl 4-{2-[(2R)-1-benzyl-5-oxopyrrolidin-2-yl]-2-oxoacetamido}piperidine-1-carboxylate (I-458)

The title compound was synthesised from 2-[(2R)-1-benzyl-5-oxopyrrolidin-2-yl]-2-oxoacetic acid (I-433) in a similar manner to method A, general procedure 6 (general scheme 11a) using DMF as solvent to afford a colourless glass (243 mg, 100% purity, 79%) after purification by flash column chromatography on normal phase silica (25 g SNAP Ultra cartridge, 0-100% EtOAc in heptane gradient).

$^1$H NMR (500 MHz, Chloroform-d) δ 1.31-1.43 (m, 2H), 1.46 (s, 9H), 1.80-1.91 (m, 2H), 1.91-2.01 (m, 1H), 2.33-2.50 (m, 3H), 2.77-2.95 (m, 2H), 3.76-3.89 (m, 1H), 3.95 (d, J=14.9 Hz, 1H), 3.99-4.18 (m, 2H), 4.94-5.03 (m, 2H), 6.74 (d, J=8.3 Hz, 1H), 7.11-7.17 (m, 2H), 7.22-7.33 (m, 3H).

LC-MS (METCR1603): 100% (UV), Rt=4.21 min, m/z (ESI$^+$)=430.2 [M+H]$^+$

Tert-butyl 3-{2-[(2R)-1-benzyl-5-oxopyrrolidin-2-yl]-2-oxoacetamido}azetidine-1-carboxylate (I-459)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give an off-white solid (904 mg, 98% purity, 70%) after purification by flash column chromatography on normal phase silica (50 g SNAP KP-SIL cartridge, 50-100% EtOAc in heptane gradient).

$^1$H NMR (500 MHz, Chloroform-d) δ 1.45 (s, 9H), 1.91-1.99 (m, 1H), 2.37-2.50 (m, 3H), 3.74-3.81 (m, 2H), 4.00 (d, J=14.9 Hz, 1H), 4.22-4.29 (m, 2H), 4.51-4.61 (m, 1H), 4.91-5.00 (m, 2H), 7.10-7.18 (m, 3H), 7.26-7.32 (m, 3H).

LC-MS (MET-uPLC-AB-102): 98% (UV), Rt=2.84 min, m/z (ESI$^+$)=419.3 [M+H+NH$_3$]$^+$

General Procedure 2 (General Scheme 21): Deprotection

Method A: HCl Deprotection

4-{2-[(2R)-1-Benzyl-5-oxopyrrolidin-2-yl]-2-oxoacetamido}piperidin-1-ium chloride (I-460)

To a stirred solution of tert-butyl N-{6-[2-(1-benzyl-5-oxopyrrolidin-2-yl)-2-oxoacetamido]hexyl}carbamate (I-458), 85% purity, 233 mg, 0.46 mmol) in DCM (6 mL) was added 4M HCl in dioxane (2.9 mL) and the resulting mixture was stirred at RT for 1 h. The reaction was concentrated in vacuo to give 231 mg of 4-[2-(1-benzyl-5-oxopyrrolidin-2-yl)-2-oxoacetamido]piperidin-1-ium chloride as an off-white glass (72% purity by 1H NMR, 98%) which was used in the next step without purification.

$^1$H NMR (500 MHz, Chloroform-d) δ 1.91-2.09 (m, 3H), 2.10-2.21 (m, 2H), 2.35-2.55 (m, 3H), 2.92-3.10 (m, 2H), 3.47-3.63 (m, 2H), 3.89-4.04 (m, 2H), 4.90-4.97 (m, 1H), 5.01 (d, J=14.8 Hz, 1H), 7.14 (s, 1H), 7.15 (s, 1H), 7.21-7.33 (m, 4H), 9.44-9.86 (m, 2H).

LC-MS (METCR1410): 81% (UV), Rt=0.56-0.76 min, m/z (ESI$^+$)=330.1 [M+H]$^+$

Method B: TFA Deprotection

3-{2-[(2R)-1-Benzyl-5-oxopyrrolidin-2-yl]-2-oxoacetamido}azetidin-1-ium trifluoroacetate (I-461)

To a stirred solution of tert-butyl 3-{2-[(2R)-1-benzyl-5-oxopyrrolidin-2-yl]-2-oxoacetamido}azetidine-1-carboxylate (I-459, 265 mg, 0.66 mmol) in DCM (5 mL) was added TFA (2.2 mL, 28.84 mmol) and the reaction was stirred at RT for 1 h then concentrated in vacuo to afford 274 mg of 3-{2-[(2R)-1-benzyl-5-oxopyrrolidin-2-yl]-2-oxoacetamido}azetidin-1-ium trifluoroacetate (I-461) as a yellow viscous oil (100% estimated purity, 100%) which was used in the next step without purification.

General Procedure 3a (General Scheme 21): Amide Capping

2-[(2R)-1-Benzyl-5-oxopyrrolidin-2-yl]-N-[1-(2,2-dimethylpropanoyl)piperidin-4-yl]-2-oxoacetamide (FP 314)

To an ice-cooled stirred solution of 4-{2-[(2R)-1-benzyl-5-oxopyrrolidin-2-yl]-2-oxoacetamido}piperidin-1-ium chloride (I-460, 82% purity, 130 mg, 0.29 mmol) and DIPEA (120 μL, 0.69 mmol) in DCM (2.5 mL) was added 2,2-dimethylpropanoyl chloride (40 μL, 0.33 mmol) dropwise. The reaction mixture was allowed to warm to RT and stirred for 45 min then diluted with DCM (2.5 mL), washed with saturated NaHCO$_3$ (3×5 mL). The combined aqueous layers were extracted with DCM (3 mL), then the combined organic layers were dried over sodium sulphate, filtered and concentrated in vacuo. The residue was purified by flash column chromatography on normal phase silica (10 g SNAP KP-SIL cartridge, 0-100% EtOAc in heptane gradient) to afford 82 mg of 2-[(2R)-1-benzyl-5-oxopyrrolidin-2-yl]-N-[1-(2,2-dimethylpropanoyl) piperidin-4-yl]-2-oxoacetamide as an off-white solid (100% purity, 68%).

$^1$H NMR (500 MHz, Chloroform-d) δ 1.28 (s, 9H), 1.34-1.45 (m, 2H), 1.91-1.99 (m, 3H), 2.37-2.49 (m, 3H), 2.89-2.99 (m, 2H), 3.87-3.99 (m, 2H), 4.34-4.42 (m, 2H), 4.94-5.02 (m, 2H), 6.74 (d, J=8.2 Hz, 1H), 7.12-7.17 (m, 2H), 7.24-7.32 (m, 3H).

LC-MS (METCR1603): 100% (UV), Rt=3.73 min, m/z (ESI$^+$)=414.3 [M+H]$^+$

2-[(2R)-1-Benzyl-5-oxopyrrolidin-2-yl]-N-[1-(2-methylpropanoyl)piperidin-4-yl]-2-oxoacetamide (FP 315)

The title compound was synthesised from 4-{2-[(2R)-1-benzyl-5-oxopyrrolidin-2-yl]-2-oxoacetamido}piperidin-1-ium chloride (I-460) in a similar manner to general procedure 3a (general scheme 21) as an off-white powder (86 mg, 96% purity, 91%) after purification by flash column chromatography on normal phase silica (10 g SNAP Ultra cartridge, 0-100% EtOAc in heptane gradient).

$^1$H NMR (500 MHz, Chloroform-d) δ 1.10-1.16 (m, 6H), 1.30-1.48 (m, 2H), 1.86-2.07 (m, 3H), 2.36-2.51 (m, 3H), 2.67-2.76 (m, 1H), 2.76-2.84 (m, 1H), 3.06-3.22 (m, 1H), 3.86-4.01 (m, 3H), 4.55-4.65 (m, 1H), 4.93-5.05 (m, 2H), 6.71-6.80 (m, 1H), 7.11-7.18 (m, 2H), 7.22-7.33 (m, 3H).

LC-MS (METCR1603): 96% (UV), Rt=3.38 min, m/z (ESI⁺)=400.1 [M+H]⁺

2-[(2R)-1-Benzyl-5-oxopyrrolidin-2-yl]-N-[1-(2-methylpropanoyl)azetidin-3-yl]-2-oxoacetamide (FP 316)

The title compound was synthesised from 3-{2-[(2R)-1-benzyl-5-oxopyrrolidin-2-yl]-2-oxoacetamido}azetidin-1-ium trifluoroacetate (I-461) in a similar manner to general procedure 3a (general scheme 21) using TEA as base to give a pale yellow powder (98 mg, 100% purity, 40%) after purification by flash column chromatography on normal phase silica (5 g TELOS silica cartridge, 0-100% EtOAc in heptane gradient).

¹H NMR (500 MHz, Chloroform-d) δ 1.10 (d, J=6.8 Hz, 6H), 1.92-2.00 (m, 1H), 2.36-2.50 (m, 4H), 3.84-3.91 (m, 1H), 3.96-4.05 (m, 2H), 4.29-4.37 (m, 1H), 4.43-4.50 (m, 1H), 4.59-4.68 (m, 1H), 4.90-5.01 (m, 2H), 7.11-7.17 (m, 2H), 7.22-7.33 (m, 4H).

LC-MS (MET-uPLC-AB-102): 100% (UV), Rt=2.13 min, m/z (ESI⁺)=372.3 [M+H]⁺

2-[(2R)-1-Benzyl-5-oxopyrrolidin-2-yl]-N-[1-(3-methylbutanoyl)azetidin-3-yl]-2-oxoacetamide (FP 317)

The title compound was synthesised from 3-{2-[(2R)-1-benzyl-5-oxopyrrolidin-2-yl]-2-oxoacetamido}azetidin-1-ium trifluoroacetate (I-461) in a similar manner to general procedure 3a (general scheme 21) using TEA as base to give a pale yellow solid (28 mg, 98% purity, 28%) after purification by flash column chromatography on normal phase silica (10 g SNAP Ultra cartridge, 0-100% EtOAc in heptane gradient then 0-20% MeOH in EtOAc gradient) followed by preparative LC (acidic pH, early elution method).

¹H NMR (500 MHz, Chloroform-d) δ 0.91-0.99 (m, 6H), 1.92-2.00 (m, 3H), 2.07-2.18 (m, 1H), 2.36-2.52 (m, 3H), 3.88 (dd, J=10.2, 5.3 Hz, 1H), 3.94-4.04 (m, 2H), 4.30-4.37 (m, 1H), 4.44 (t, J=8.4 Hz, 1H), 4.56-4.67 (m, 1H), 4.90-5.00 (m, 2H), 7.10-7.18 (m, 2H), 7.23-7.33 (m, 4H).

LC-MS (MET-uPLC-AB-102): 98% (UV), Rt=2.38 min, m/z (ESI⁺)=386.3 [M+H]⁺

2-[(2R)-1-Benzyl-5-oxopyrrolidin-2-yl]-N-(1-cyclobutanecarbonylazetidin-3-yl)-2-oxoacetamide (FP318)

The title compound was synthesised from 3-{2-[(2R)-1-benzyl-5-oxopyrrolidin-2-yl]-2-oxoacetamido}azetidin-1-ium trifluoroacetate (I-461) in a similar manner to general procedure 3a (general scheme 21) using TEA as base to give an off-white solid (23 mg, 99% purity, 28%) after purification by flash column chromatography on normal phase silica (25 g SNAP KP-SIL cartridge, 0-100% EtOAc in heptane gradient then 0-20% MeOH in EtOAc gradient) followed by preparative LC (acidic pH, early elution method).

¹H NMR (500 MHz, Chloroform-d) δ 1.83-2.03 (m, 3H), 2.04-2.15 (m, 2H), 2.25-2.37 (m, 2H), 2.37-2.51 (m, 3H), 2.97-3.07 (m, 1H), 3.81-3.95 (m, 2H), 4.01 (d, J=14.9 Hz, 1H), 4.28-4.41 (m, 2H), 4.55-4.67 (m, 1H), 4.89-5.00 (m, 2H), 7.10-7.22 (m, 3H), 7.24-7.33 (m, 3H).

LC-MS (MET-uPLC-AB-102): 99% (UV), Rt=2.28 min, m/z (ESI⁺)=384.3 [M+H]⁺

2-[(2R)-1-Benzyl-5-oxopyrrolidin-2-yl]-N-(1-cyclopentanecarbonylazetidin-3-yl)-2-oxoacetamide (FP 319)

The title compound was synthesised from 3-{2-[(2R)-1-benzyl-5-oxopyrrolidin-2-yl]-2-oxoacetamido}azetidin-1-ium trifluoroacetate (I-461) in a similar manner to general procedure 3a (general scheme 21) using TEA as base to give an off-white solid (36 mg, 97% purity, 49%) after purification by flash column chromatography on normal phase silica (25 g SNAP KP-SIL cartridge, 0-100% EtOAc in heptane gradient then 0-20% MeOH in EtOAc gradient).

¹H NMR (500 MHz, Chloroform-d) δ 1.67-1.88 (m, 8H), 1.93-2.01 (m, 1H), 2.37-2.50 (m, 3H), 2.50-2.59 (m, 1H), 3.82-3.90 (m, 1H), 3.95-4.05 (m, 2H), 4.29-4.37 (m, 1H), 4.42-4.50 (m, 1H), 4.58-4.68 (m, 1H), 4.90-4.99 (m, 2H), 7.14 (d, J=6.8 Hz, 2H), 7.21 (d, J=7.5 Hz, 1H), 7.26-7.32 (m, 3H).

LC-MS (MET-uPLC-AB-102): 97% (UV), Rt=2.49 min, m/z (ESI⁺)=398.3 [M+H]⁺

General Procedure 3b (General Scheme 21): Sulfonamide Capping

2-[(2R)-1-Benzyl-5-oxopyrrolidin-2-yl]-N-[1-(cyclopropanesulfonyl)piperidin-4-yl]-2-oxoacetamide (FP 320)

To an ice-cooled stirred solution of 4-{2-[(2R)-1-benzyl-5-oxopyrrolidin-2-yl]-2-oxoacet-amido}piperidin-1-ium chloride (I-460, 82% purity, 130 mg, 0.29 mmol) and DIPEA (120 μL, 0.69 mmol) in DCM (2.5 mL) was added cyclopropanesulfonyl chloride (33 μL, 0.32 mmol) dropwise. The reaction mixture was allowed to warm to RT and stirred for 1.5 h. Further cyclopropanesulfonyl chloride (15 μL, 0.15 mmol) and DIPEA (20 μL, 0.12 mmol) were added and the reaction stirred at RT for 1.5 h. The mixture was diluted with DCM (2.5 mL) and washed with saturated NaHCO₃ (3×5 mL). The combined aqueous layers were washed with DCM (3 mL), the combined organic layers were dried over sodium sulfate, filtered and concentrated in vacuo. The residue was purified by flash column chromatography on normal phase silica (10 g SNAP Ultra cartridge, 0-100% EtOAc in heptane gradient) to afford 94 mg of 2-[(2R)-1-benzyl-5-oxopyrrolidin-2-yl]-N-[1-(cyclopropanesulfonyl) piperidin-4-yl]-2-oxoacetamide (EV-BC0006-002) as an off-white solid (100% purity, 74%).

¹H NMR (500 MHz, Chloroform-d) δ 0.95-1.05 (m, 2H), 1.13-1.21 (m, 2H), 1.54-1.65 (m, 2H), 1.91-2.04 (m, 3H), 2.26 (tt, J=4.8, 8.0 Hz, 1H), 2.38-2.51 (m, 3H), 2.89-3.00 (m, 2H), 3.77-3.87 (m, 3H), 3.97 (d, J=14.9 Hz, 1H), 4.94-5.03 (m, 2H), 6.78 (d, J=8.2 Hz, 1H), 7.12-7.18 (m, 2H), 7.24-7.33 (m, 3H).

LC-MS (METCR1603): 100% (UV), Rt=3.59 min, m/z (ESI⁺)=434.2 [M+H]⁺

2-[(2R)-1-Benzyl-5-oxopyrrolidin-2-yl]-N-[1-(cyclopentanesulfonyl)piperidin-4-yl]-2-oxoacetamide (FP 321)

The title compound was synthesised from 4-{2-[(2R)-1-benzyl-5-oxopyrrolidin-2-yl]-2-oxoacetamido}piperidin-1-ium chloride (I-460) in a similar manner to general procedure 3b (general scheme 21) as an off-white powder (50 mg, 99% purity, 48%) after purification by flash column chromatography on normal phase silica (10 g SNAP Ultra cartridge, 0-100% EtOAc in heptane gradient).

¹H NMR (500 MHz, Chloroform-d) δ 1.51-1.68 (m, 4H), 1.74-1.85 (m, 2H), 1.90-2.04 (m, 7H), 2.35-2.50 (m, 3H), 2.89-2.99 (m, 2H), 3.42 (p, J=8.1 Hz, 1H), 3.77-3.89 (m, 3H), 3.97 (d, J=14.9 Hz, 1H), 4.91-5.04 (m, 2H), 6.77 (d, J=8.3 Hz, 1H), 7.10-7.19 (m, 2H), 7.23-7.33 (m, 3H).

LC-MS (METCR1603): 99% (UV), Rt=3.97 min, m/z (ESI⁺)=462.1 [M+H]⁺

2-[(2R)-1-Benzyl-5-oxopyrrolidin-2-yl]-N-[1-(cyclopentanesulfonyl)azetidin-3-yl]-2-oxoacetamide (FP322)

The title compound was synthesised from 3-{2-[(2R)-1-benzyl-5-oxopyrrolidin-2-yl]-2-oxoacetamido}azetidin-1-ium trifluoroacetate (I-461) in a similar manner to general procedure 3b (general scheme 21) using TEA as base to give a pale yellow powder (115 mg, 95% purity, 53%) after purification by flash column chromatography on normal phase silica (10 g SNAP KP-SIL cartridge, 0-100% EtOAc in heptane gradient).

¹H NMR (500 MHz, Chloroform-d) δ 1.60-1.68 (m, 2H), 1.75-1.84 (m, 2H), 1.91-2.05 (m, 5H), 2.35-2.51 (m, 3H), 3.34-3.44 (m, 1H), 3.95 (ddd, J=8.8, 6.5, 2.7 Hz, 2H), 4.00 (d, J=14.9 Hz, 1H), 4.12 (t, J=8.1 Hz, 2H), 4.60-4.70 (m, 1H), 4.89-5.00 (m, 2H), 7.11-7.17 (m, 2H), 7.20-7.32 (m, 4H).

LC-MS (METCR1603): 95% (UV), Rt=3.82 min, m/z (ESI⁺)=434.2 [M+H]⁺

2-[(2R)-1-Benzyl-5-oxopyrrolidin-2-yl]-2-oxo-N-[1-(propane-2-sulfonyl)piperidin-4-yl]acetamide (FP 323)

The title compound was synthesised from 4-{2-[(2R)-1-benzyl-5-oxopyrrolidin-2-yl]-2-oxoacetamido}piperidin-1-ium chloride (I-460) in a similar manner to general procedure 3b (general scheme 21) as an off-white crystalline solid (30 mg, 100% purity, 24%) after purification by flash column chromatography on normal phase silica (10 g SNAP Ultra cartridge, 0-100% EtOAc in heptane gradient).

¹H NMR (500 MHz, Chloroform-d) δ 1.34 (d, J=6.8 Hz, 6H), 1.50-1.62 (m, 2H), 1.91-2.01 (m, 3H), 2.37-2.49 (m, 3H), 2.95-3.04 (m, 2H), 3.18 (hept, J=6.9 Hz, 1H), 3.79-3.89 (m, 3H), 3.97 (d, J=14.9 Hz, 1H), 4.93-5.03 (m, 2H), 6.77 (d, J=8.2 Hz, 1H), 7.11-7.17 (m, 2H), 7.23-7.33 (m, 3H).

LC-MS (METCR1603): 100% (UV), Rt=3.68 min, m/z (ESI⁺)=436.3 [M+H]⁺

General Procedure 3c (General Scheme 21): Isocyanate Capping

4-{2-[(2R)-1-Benzyl-5-oxopyrrolidin-2-yl]-2-oxoacetamido}-N-cyclobutylpiperidine-1-carboxamide (FP 324)

To a stirred solution of 4-{2-[(2R)-1-benzyl-5-oxopyrrolidin-2-yl]-2-oxoacetamido}piperidin-1-ium chloride (I-460, 80% purity, 150 mg, 0.33 mmol) and TEA (92 μL, 0.66 mmol) in DCM (2 mL) was added isocyanatocyclobutane (40 μL, 0.4 mmol). The reaction mixture was stirred at RT for 1 h then concentrated in vacuo. The residue was purified by flash column chromatography on normal phase silica (25 g SNAP Ultra cartridge, 0-100% ethyl acetate in heptane gradient followed by a 0-10% MeOH in EtOAc gradient) to afford 99 mg of 4-{2-[(2R)-1-benzyl-5-oxopyrrolidin-2-yl]-2-oxoacetamido}-N-cyclobutylpiperidine-1-carboxamide as an off-white crystalline solid (100% purity, 71%).

¹H NMR (500 MHz, Chloroform-d) δ 1.36-1.47 (m, 2H), 1.64-1.73 (m, 2H), 1.74-1.84 (m, 2H), 1.86-1.99 (m, 3H), 2.31-2.37 (m, 2H), 2.38-2.51 (m, 3H), 2.85-2.93 (m, 2H), 3.82-3.97 (m, 3H), 4.22-4.31 (m, 1H), 4.59 (d, J=7.3 Hz, 1H), 4.94-5.05 (m, 2H), 6.76 (d, J=8.2 Hz, 1H), 7.12-7.17 (m, 2H), 7.23-7.29 (m, 3H), 7.29-7.32 (m, 1H).

LC-MS (METCR1600): 100% (UV), Rt=3.47 min, m/z (ESI⁺)=427.3 [M+H]⁺

4-{2-[(2R)-1-Benzyl-5-oxopyrrolidin-2-yl]-2-oxoacetamido}-N-cyclopentylpiperidine-1-carboxamide (FP 325)

The title compound was synthesised from 4-[2-(1-benzyl-5-oxopyrrolidin-2-yl)-2-oxoacetamido]piperidin-1-ium chloride (I-460) in a similar manner to general procedure 3c (general scheme 21) as an off-white crystalline solid (64 mg, 97% purity, 43%) after purification by flash column chromatography on normal phase silica (25 g SNAP Ultra cartridge, 0-100% EtOAc in heptane gradient then 0-10% MeOH in EtOAc gradient) followed by preparative LC (acidic pH, standard elution method).

¹H NMR (500 MHz, Chloroform-d) δ 1.29-1.37 (m, 2H), 1.38-1.47 (m, 2H), 1.51-1.74 (m, 4H), 1.87-1.93 (m, 2H), 1.94-2.05 (m, 3H), 2.37-2.51 (m, 3H), 2.83-2.94 (m, 2H), 3.79-3.93 (m, 3H), 3.96 (d, J=14.9 Hz, 1H), 4.09 (h, J=6.9 Hz, 1H), 4.38 (d, J=6.6 Hz, 1H), 4.93-5.04 (m, 2H), 6.75 (d, J=8.1 Hz, 1H), 7.12-7.17 (m, 2H), 7.23-7.33 (m, 3H).

LC-MS (METCR1603): 97% (UV), Rt=3.65 min, m/z (ESI⁺)=441.4 [M+H]⁺

GENERAL SCHEME 22 (Acyclic amides, sulfonamides and ureas)

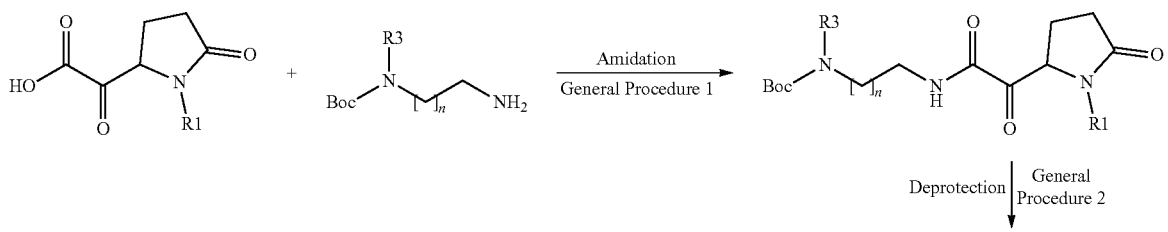

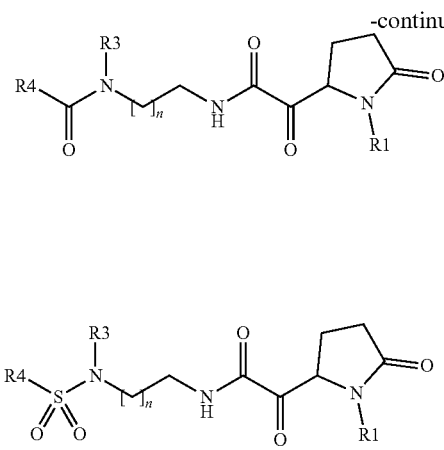

General Procedure 1 (General Scheme 22): Amination

Method A: T3P Coupling

Method as Described in Method A, General Procedure 6 (General Scheme 11a): Coupling Tert-butyl N-2-{2-[(2R)-1-benzyl-5-oxopyrrolidin-2-yl]-2-oxoacetamido}ethyl)carbamate (I-462)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a colourless viscous oil (283 mg, 88% purity by 1H NMR, 67%) after purification by flash column chromatography on normal phase silica (10 g SNAP KP-SIL cartridge, 10-100% EtOAc in heptane gradient).
$^1$H NMR (500 MHz, Chloroform-d) δ 1.47 (s, 9H), 1.93-2.04 (m, 1H), 2.36-2.54 (m, 3H), 3.25-3.53 (m, 4H), 3.94 (d, J=14.9 Hz, 1H), 4.80 (s, 1H), 4.93-5.02 (m, 1H), 5.07 (d, J=14.9 Hz, 1H), 7.11-7.22 (m, 2H), 7.25-7.39 (m, 3H), 7.49 (s, 1H).
LC-MS (METCR0990): 95% (UV), Rt=1.56 min, m/z (ESI$^+$)=390.2 [M+H]$^+$ Tert-butyl N-[3-(4-{3-[2-(1-benzyl-5-oxopyrrolidin-2-yl)-2-oxoacetamido]propoxy}-butoxy)propyl] carbamate (I-463)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine in DMF as solvent to give a colourless viscous oil (210 mg, 97% purity, 45%) after purification by flash column chromatography on normal phase silica (10 g SNAP KP-SIL cartridge, 0-100% EtOAc in heptane gradient).
$^1$H NMR (500 MHz, Chloroform-d) δ 1.43 (s, 9H), 1.63-1.72 (m, 4H), 1.72-1.78 (m, 2H), 1.78-1.84 (m, 2H), 1.93-2.02 (m, 1H), 2.36-2.50 (m, 3H), 3.18-3.26 (m, 2H), 3.37-3.42 (m, 2H), 3.44-3.48 (m, 4H), 3.49 (t, J=6.0 Hz, 2H), 3.55 (t, J=5.5 Hz, 2H), 3.87 (d, J=14.9 Hz, 1H), 4.89-5.00 (m, 2H), 5.07 (d, J=14.9 Hz, 1H), 7.12-7.17 (m, 2H), 7.23-7.32 (m, 3H), 7.58-7.71 (m, 1H).
LC-MS (METCR1602): 97% (UV), Rt=0.63 min, m/z (ESI$^+$)=534.5 [M+H]$^+$ Tert-butyl N-{7-[2-(1-benzyl-5-oxopyrrolidin-2-yl)-2-oxoacetamido]heptyl}carbamate (I-464)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine in DMF as solvent to give a yellow viscous oil (328 mg, 100% purity, 64%) after purification by flash column chromatography on normal phase silica (25 g SNAP KP-SIL cartridge, 0-100% EtOAc in heptane gradient).
$^1$H NMR (500 MHz, Chloroform-d) δ 1.29-1.34 (m, 6H), 1.42-1.48 (m, 11H), 1.50-1.56 (m, 2H), 1.91-2.02 (m, 1H), 2.37-2.51 (m, 3H), 3.06-3.14 (m, 2H), 3.25 (q, J=6.8 Hz, 2H), 3.93 (d, J=14.9 Hz, 1H), 4.50 (s, 1H), 4.94-5.00 (m, 1H), 5.03 (d, J=14.9 Hz, 1H), 6.84 (t, J=5.5 Hz, 1H), 7.12-7.17 (m, 2H), 7.23-7.32 (m, 3H).
LC-MS (METCR1603): 100% (UV), Rt=4.56 min, m/z (ESI$^+$)=460.2 [M+H]$^+$ Tert-butyl N-(3-{4-[3-(2-{1-[(4-chlorophenyl)methyl]-5-oxopyrrolidin-2-yl}-2-oxoacetamido)propoxy] butoxy}propyl)carbamate (I-465)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine in DMF as solvent to give a yellow viscous oil (86 mg, 90% purity, 34%) after purification by flash column chromatography on normal phase silica (10 g SNAP KP-SIL cartridge, 0-100% EtOAc in heptane gradient).
$^1$H NMR (500 MHz, Chloroform-d) δ 1.43 (s, 9H), 1.62-1.71 (m, 4H), 1.72-1.78 (m, 2H), 1.78-1.84 (m, 2H), 1.94-2.00 (m, 1H), 2.37-2.48 (m, 3H), 3.18-3.25 (m, 2H), 3.40 (q, J=5.9 Hz, 2H), 3.44-3.51 (m, 6H), 3.56 (t, J=5.5 Hz, 2H), 3.92 (d, J=15.0 Hz, 1H), 4.89-5.01 (m, 3H), 7.07-7.13 (m, 2H), 7.23-7.30 (m, 2H), 7.66 (s, 1H).
LC-MS (METCR0990): 90% (UV), Rt=1.80 min, m/z (ESI$^+$)=568.2 [M+H]$^+$ Tert-butyl N-(2-{2-[2-(2-{1-[(4-chlorophenyl)methyl]-5-oxopyrrolidin-2-yl}-2-oxoacetamido)ethoxy] ethoxy}ethyl) carbamate (I-466)

The title compound was synthesised from 2-{1-[(4-chlorophenyl)methyl]-5-oxopyrrolidin-2-yl}-2-oxoacetic acid (I-437) in a similar manner to method A, general procedure 6 (general scheme 11a) using the free-base form of the amine in DMF as solvent to give a colourless viscous oil (221 mg, 100% purity, 36%) after purification by preparative LC (acidic pH, early elution method).

$^1$H NMR (500 MHz, Chloroform-d) δ 1.44 (s, 9H), 1.97-2.02 (m, 1H), 2.38-2.48 (m, 3H), 3.29-3.38 (m, 2H), 3.49 (q, J=5.4 Hz, 2H), 3.56 (t, J=5.3 Hz, 2H), 3.60 (t, J=5.1 Hz, 2H), 3.63 (s, 4H), 3.92 (d, J=15.0 Hz, 1H), 4.93-5.01 (m, 3H), 7.11 (d, J=8.3 Hz, 2H), 7.26-7.29 (m, 2H), 7.29-7.43 (m, 1H).

LC-MS (MET-uPLC-AB-102): 100% (UV), Rt=3.20 min, m/z (ESI$^+$)=512.3/514.3 [M+H]$^+$ Tert-butyl N-{6-[2-(1-benzyl-5-oxopyrrolidin-2-yl)-2-oxoacetamido]hexyl}carbamate (I-467)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine in DMF as solvent to give an orange free-flowing oil (10 mg, 100% purity, 22%) after purification by flash column chromatography on normal phase silica (10 g SNAP KP-SIL cartridge, 0-100% EtOAc in heptane gradient) followed by preparative LC (acidic pH, standard elution method).

$^1$H NMR (500 MHz, Chloroform-d) δ 1.30-1.36 (m, 4H), 1.40-1.50 (m, 11H), 1.50-1.58 (m, 2H), 1.91-1.99 (m, 1H), 2.37-2.50 (m, 3H), 3.03-3.16 (m, 2H), 3.26 (q, J=6.8 Hz, 2H), 3.92 (d, J=14.9 Hz, 1H), 4.52 (s, 1H), 4.94-4.99 (m, 1H), 5.03 (d, J=14.9 Hz, 1H), 6.84-6.95 (m, 1H), 7.11-7.17 (m, 2H), 7.23-7.32 (m, 3H).

LC-MS (METCR1603): 100% (UV), Rt=4.35 min, m/z (ESI$^+$)=446.2 [M+H]$^+$

Tert-butyl N-[6-(2-{1-[(4-chlorophenyl)methyl]-5-oxopyrrolidin-2-yl}-2-oxoacetamido)-hexyl]carbamate (I-468)

The title compound was synthesised from 2-(1-benzyl-5-oxopyrrolidin-2-yl)-2-oxoacetic acid (I-432) in a similar manner to method A, general procedure 6 (general scheme 11a) using the free-base form of the amine in DMF as solvent to give a colourless gum (62 mg, 92% purity, 12%) after purification by flash column chromatography on normal phase silica (10 g SNAP KP-SIL cartridge, 0-100% EtOAc in heptane gradient).

$^1$H NMR (500 MHz, Chloroform-d) δ 1.33-1.37 (m, 4H), 1.40-1.51 (m, 11H), 1.52-1.58 (m, 2H), 1.94-2.01 (m, 1H), 2.38-2.49 (m, 3H), 3.07-3.15 (m, 2H), 3.23-3.31 (m, 2H), 3.96 (d, J=15.0 Hz, 1H), 4.52-4.57 (m, 1H), 4.93 (d, J=15.0 Hz, 1H), 4.96-5.01 (m, 1H), 6.88-6.98 (m, 1H), 7.08-7.13 (m, 2H), 7.25-7.28 (m, 2H).

LC-MS (METCR1603): 92% (UV), Rt=4.61 min, m/z (ESI$^+$)=480.2/482.2 [M+H]$^+$

Tert-butyl N-(2-{2-[(2R)-1-benzyl-5-oxopyrrolidin-2-yl]-2-oxoacetamido}ethyl)-N methylcarbamate (I-469)

The title compound was synthesised from 2-[(2R)-1-benzyl-5-oxopyrrolidin-2-yl]-2-oxoacetic acid (I-433) in a similar manner to method A, general procedure 6 (general scheme 11a) using the free-base form of the amine in DMF as solvent to give a yellow viscous oil (129 mg, 85% purity by 1H NMR, 46%) after purification by flash column chromatography on normal phase silica (10 g SNAP KP-SIL cartridge, 10-100% EtOAc in heptane gradient) followed by dissolving the product in EtOAc (5 mL), washing with brine (3×10 mL), drying (Na$_2$SO$_4$), filtration and removal of solvent in vacuo.

$^1$H NMR (500 MHz, Chloroform-d) δ 1.47 (s, 9H), 1.98 (s, 1H), 2.35-2.54 (m, 3H), 2.88 (s, 3H), 3.34-3.51 (m, 4H), 3.80-3.92 (m, 1H), 4.90-5.00 (m, 1H), 5.01-5.13 (m, 1H), 7.10-7.18 (m, 2H), 7.22-7.35 (m, 3H), 7.68 (s, 1H).

LC-MS (METCR0990): 96% (UV), Rt=1.63 min, m/z (ESI$^+$)=404.3 [M+H]$^+$

Method B: HATU Coupling

Method as Described in Method C, General Procedure 6 (General Scheme 11a): Coupling Tert-butyl N-{12-[2-(1-benzyl-5-oxopyrrolidin-2-yl)-2-oxoacetamido]dodecyl}carbamate (I-470)

The title compound was synthesised from 2-(1-benzyl-5-oxopyrrolidin-2-yl)-2-oxoacetic acid (I-432) in a similar manner to method C, general procedure 6 (general scheme 11a) using the free-base form of the amine in DMF as solvent to give a colourless viscous oil (69 mg, 97% purity, 31%) after purification by flash column chromatography on normal phase silica (10 g SNAP KP-SIL cartridge, 0-50% EtOAc in heptane gradient) followed by ion exchange flash chromatography (5 g Isolute SCX-2 cartridge, 20% EtOAc in heptane).

$^1$H NMR (500 MHz, Chloroform-d) δ 1.24-1.32 (m, 16H), 1.42-1.47 (m, 11H), 1.50-1.55 (m, 2H), 1.91-2.02 (m, 1H), 2.37-2.49 (m, 3H), 3.06-3.13 (m, 2H), 3.20-3.32 (m, 2H), 3.93 (d, J=14.9 Hz, 1H), 4.49 (s, 1H), 4.95-5.00 (m, 1H), 5.03 (d, J=14.9 Hz, 1H), 6.81-6.87 (m, 1H), 7.12-7.17 (m, 2H), 7.23-7.32 (m, 3H).

LC-MS (METCR1410): 97% (UV), Rt=1.25-1.45 min (multiple peaks), m/z (ESI$^+$)=530.4 [M+H]$^+$ General Procedure 2 (General Scheme 22): Deprotection Method as Described in Method A, General Procedure 2 (General Scheme 21): Deprotection N-{3-[4-(3-Aminopropoxy)butoxy]propyl}-2-(1-benzyl-5-oxopyrrolidin-2-yl)-2-oxoacetamide hydrochloride (I-471)

The title compound was synthesised from tert-butyl N-[3-[4-[3-[[2-(1-benzyl-5-oxo-pyrrolidin-2-yl)-2-oxo-acetyl]amino]propoxy]butoxy]propyl]carbamate (I-463) in a similar manner to method A, general procedure 2 (general scheme 21) as a yellow gum (182 mg, 86% purity by $^1$H NMR, 87%) after purification by trituration in heptane.

$^1$H NMR (500 MHz, Chloroform-d) δ 1.65-1.69 (m, 4H), 1.79-1.86 (m, 2H), 1.97-2.09 (m, 3H), 2.35-2.48 (m, 3H), 3.21 (t, J=5.8 Hz, 2H), 3.41 (q, J=5.8 Hz, 2H), 3.43-3.51 (m, 4H), 3.57 (t, J=5.5 Hz, 2H), 3.63 (t, J=5.6 Hz, 2H), 3.84 (d, J=14.9 Hz, 1H), 4.97-5.01 (m, 1H), 5.07 (d, J=14.9 Hz, 1H), 7.12-7.18 (m, 2H), 7.23-7.32 (m, 3H), 7.86 (t, J=5.2 Hz, 1H), 8.30 (br.s, 3H).

LC-MS (MET-uPLC-AB-102): 89% (UV), Rt=3.02 min, m/z (ESI$^+$)=434.3 [M+H]$^+$

N-(2-Aminoethyl)-2-[(2R)-1-benzyl-5-oxopyrrolidin-2-yl]-2-oxoacetamide hydrochloride (I-472)

The title compound was synthesised from tert-butyl N-(2-{2-[(2R)-1-benzyl-5-oxopyrrolidin-2-yl]-2- oxoacetamido}ethyl)carbamate (I-462) in a similar manner to method A, general procedure 2 (general scheme 21) as an off-white powder (232 mg, 87% purity, 98%) which was used in the next step without purification.

$^1$H NMR (500 MHz, DMSO-d6) δ 1.96-2.11 (m, 1H), 2.13-2.27 (m, 1H), 2.28-2.42 (m, 2H), 2.93 (q, J=6.0 Hz, 2H), 3.30-3.48 (m, 2H), 3.89 (d, J=15.3 Hz, 1H), 4.84 (d, J=15.3 Hz, 1H), 4.92 (dd, J=2.7, 9.9 Hz, 1H), 7.19-7.24 (m, 2H), 7.24-7.29 (m, 1H), 7.30-7.36 (m, 2H), 7.92 (s, 3H), 8.87 (t, J=6.0 Hz, 1H).

LC-MS (METCR0990): 87% (UV), Rt=1.34 min, m/z (ESI$^+$)=290.3 [M+H]$^+$

N-(12-Aminododecyl)-2-(1-benzyl-5-oxopyrrolidin-2-yl)-2-oxoacetamide hydrochloride (I-473)

The title compound was synthesised from tert-butyl N-{12-[2-(1-benzyl-5-oxopyrrolidin-2-yl)-2-oxoacetamido]dodecyl}carbamate (I-470) in a similar manner to method A, general procedure 2 (general scheme 21) as a colourless gum (24 mg, 93% purity, 38%) after purification by trituration in heptane and preparative LC (acidic method, standard elution method).

$^1$H NMR (500 MHz, DMSO-d6) δ 1.19-1.30 (m, 16H), 1.37-1.47 (m, 2H), 1.47-1.56 (m, 2H), 1.83-1.94 (m, 1H), 2.16-2.27 (m, 1H), 2.28-2.39 (m, 2H), 2.69-2.79 (m, 2H), 3.09 (q, J=6.7 Hz, 2H), 3.87 (d, J=15.2 Hz, 1H), 4.82 (d, J=15.2 Hz, 1H), 4.84-4.89 (m, 1H), 7.14-7.20 (m, 2H), 7.23-7.28 (m, 1H), 7.29-7.35 (m, 2H), 7.78 (br.s, 3H), 8.76 (t, J=6.0 Hz, 1H).

LC-MS (MET-uPLC-AB-101): 93% (UV), Rt=1.90-2.40 min, m/z (ESI$^+$)=430.4 [M+H]$^+$

N-(7-Aminoheptyl)-2-(1-benzyl-5-oxopyrrolidin-2-yl)-2-oxoacetamide hydrochloride (I-474)

The title compound was synthesised from tert-butyl N-{7-[2-(1-benzyl-5-oxopyrrolidin-2-yl)-2-oxoacetamido]heptyl}carbamate (I-464) in a similar manner to method A, general procedure 2 (general scheme 21) as an off-white solid (254 mg, 94% purity, 93%) after purification by trituration in heptane.

$^1$H NMR (500 MHz, Chloroform-d) δ 1.30-1.45 (m, 6H), 1.49-1.59 (m, 2H), 1.73-1.82 (m, 2H), 1.93-2.04 (m, 1H), 2.36-2.49 (m, 3H), 2.93-3.02 (m, 2H), 3.19-3.32 (m, 2H), 3.90 (d, J=14.9 Hz, 1H), 4.93-5.00 (m, 1H), 5.04 (d, J=14.9 Hz, 1H), 7.11 (t, J=6.0 Hz, 1H), 7.12-7.18 (m, 2H), 7.23-7.32 (m, 3H), 8.29 (br. s, 3H).

LC-MS (METCR1603): 94% (UV), Rt=4.32 min, m/z (ESI$^+$)=360.2 [M+H]$^+$

N-{3-[4-(3-Aminopropoxy)butoxy]propyl}-2-{1-[(4-chlorophenyl)methyl]-5-oxopyrrolidin-2-yl}-2-oxoacetamide hydrochloride (I-475)

The title compound was synthesised from tert-butyl N-(3-{4-[3-(2-{1-[(4-chlorophenyl)methyl]-5-oxopyrrolidin-2-yl}-2-oxoacetamido)propoxy]butoxy}propyl)-carbamate (I-465) in a similar manner to method A, general procedure 2 (general scheme 21) as a yellow gum (41 mg, 90% purity by $^1$H NMR, 54%) which was used in the next step without purification.

$^1$H NMR (500 MHz, Chloroform-d) δ 1.58-1.71 (m, 4H), 1.79-1.87 (m, 2H), 1.98-2.08 (m, 3H), 2.33-2.50 (m, 3H), 3.17-3.25 (m, 2H), 3.38-3.51 (m, 6H), 3.57 (t, J=5.4 Hz, 2H), 3.63 (t, J=5.4 Hz, 2H), 3.89 (d, J=15.0 Hz, 1H), 4.94-5.02 (m, 2H), 7.08-7.15 (m, 2H), 7.24-7.29 (m, 2H), 7.87 (t, J=5.1 Hz, 1H), 8.29 (br. s, 3H).

LC-MS (METCR1410): 81% (UV), Rt=0.84-1.00 min, m/z (ESI$^+$)=468.5/470.1 [M+H]$^+$

N-{2-[2-(2-Aminoethoxy)ethoxy]ethyl}-2-{1-[(4-chlorophenyl)methyl]-5-oxopyrrolidin-2-yl}-2-oxoacetamide hydrochloride (I-476)

The title compound was synthesised from tertbutyl N-(2-{2-[2-(2-{1-[(4-chlorophenyl)methyl]-5-oxopyrrolidin-2-yl}-2-oxoacetamido)ethoxy]ethoxy}ethyl) carbamate (I-466) in a similar manner to method A, general procedure 2 (general scheme 21) as a yellow gum (126 mg, 95% purity by 1H NMR, 70%) after purification by trituration in heptane and preparative LC (acidic method, early elution method).

$^1$H NMR (500 MHz, Chloroform-d) δ 2.02-2.06 (m, 1H), 2.34-2.56 (m, 3H), 3.21-3.33 (m, 2H), 3.45-3.54 (m, 2H), 3.60-3.73 (m, 6H), 3.80-3.86 (m, 2H), 3.89 (d, J=15.1 Hz, 1H), 4.93-5.04 (m, 2H), 7.13 (d, J=8.3 Hz, 2H), 7.26-7.31 (m, 2H), 7.97-8.06 (m, 1H), 8.32 (br. s, 3H).

LC-MS (MET-uPLC-AB-102): 97% (UV), Rt=2.60-3.00 min, m/z (ESI$^+$)=412.2/414.2 [M+H]$^+$

N-(6-Azaniumylhexyl)-2-(1-benzyl-5-oxopyrrolidin-2-yl)-2-oxoacetamide chloride (I-477)

The title compound was synthesised from tert-butyl N-{6-[2-(1-benzyl-5-oxopyrrolidin-2-yl)-2-oxoacetamido]hexyl}carbamate (I-467) in a similar manner to method A, general procedure 2 (general scheme 21) as a yellow viscous oil (55 mg, 97% purity by $^1$H NMR, 86%) which was used in the next step without purification.

$^1$H NMR (500 MHz, Chloroform-d) δ 1.31-1.40 (m, 2H), 1.42-1.52 (m, 2H), 1.54-1.63 (m, 2H), 1.75-1.82 (m, 2H), 1.94-2.02 (m, 1H), 2.36-2.49 (m, 3H), 2.97-3.06 (m, 2H), 3.23-3.32 (m, 2H), 3.88 (d, J=14.9 Hz, 1H), 4.94-4.99 (m, 1H), 5.04 (d, J=14.9 Hz, 1H), 7.11-7.18 (m, 2H), 7.27-7.32 (m, 3H), 7.35-7.39 (m, 1H), 8.27 (s, 3H).

LC-MS (METCR1603): 92% (UV), Rt=4.10 min, m/z (ESI$^+$)=346.2 [M+H]$^+$

N-(6-Azaniumylhexyl)-2-{1-[(4-chlorophenyl)methyl]-5-oxopyrrolidin-2-yl}-2-oxoacetamide chloride (I-478)

The title compound was synthesised from tert-butyl N-[6-(2-{1-[(4-chloro-phenyl)methyl]-5-oxopyrrolidin-2-yl}-2-oxoacetamido)hexyl]carbamate (I-468) in a similar manner to method A (general procedure 2, general scheme 21) as an orange solid (53 mg, 90% purity by $^1$H NMR, 98%) which was used in the next step without purification.

$^1$H NMR (500 MHz, Chloroform-d) δ 1.32-1.40 (m, 2H), 1.41-1.52 (m, 2H), 1.53-1.63 (m, 2H), 1.75-1.83 (m, 2H), 1.96-2.02 (m, 1H), 2.37-2.50 (m, 3H), 2.97-3.05 (m, 2H), 3.20-3.35 (m, 2H), 3.92 (d, J=14.9 Hz, 1H), 4.90-5.00 (m, 2H), 7.09-7.14 (m, 2H), 7.24-7.32 (m, 3H), 8.27 (s, 3H).

LC-MS (METCR1410): 100% (UV), Rt=0.80-0.94 min, m/z (ESI$^+$)=380.1/382.1 [M+H]$^+$

2-[(2R)-1-benzyl-5-oxopyrrolidin-2-yl]-N-[2-(methylamino)ethyl]-2-oxoacetamide hydrochloride (I-479)

The title compound was synthesised from tert-butyl N-(2-{2-[(2R)-1-benzyl-5-oxopyrrolidin-2-yl]-2- oxoacetamido}ethylcarbamate (I-469) in a similar manner to method A, general procedure 2 (general scheme 21) as a beige crystalline solid (114 mg, 56% purity, 69%) which was used in the next step without purification.

LC-MS (METCR0990): 56% (UV), Rt=1.47 min, m/z (ESI$^+$)=304.2 [M+H]$^+$

General Procedure 3a (General Scheme 22): Amide Capping

Method as Described in Method A, General Procedure 3a (General Scheme 21): Amide Capping 2-(1-Benzyl-5-oxopyrrolidin-2-yl)-N-(7-acetamido-heptyl)-2-oxoacetamide (FP 326)

The title compound was synthesised from N-(7-amino-heptyl)-2-(1-benzyl-5-oxopyrrolidin-2-yl)-2-oxoacetamide hydrochloride (I-474) in a similar manner to general procedure 3a (general scheme 21) using acetic anhydride to give a yellow viscous oil (89 mg, 100% purity, 46%) after purification by flash column chromatography on normal phase silica (10 g SNAP KP-SIL cartridge, 0-5% MeOH in EtOAc gradient) followed by preparative LC (acidic pH, standard elution method).

$^1$H NMR (500 MHz, Chloroform-d) δ 1.28-1.36 (m, 6H), 1.46-1.56 (m, 4H), 1.93-2.00 (m, 4H), 2.37-2.50 (m, 3H), 3.20-3.30 (m, 4H), 3.92 (d, J=14.9 Hz, 1H), 4.95-5.00 (m, 1H), 5.03 (d, J=14.9 Hz, 1H), 5.46 (s, 1H), 6.83-6.92 (m, 1H), 7.12-7.17 (m, 2H), 7.22-7.33 (m, 3H).

LC-MS (METCR1603): 100% (UV), Rt=3.48 min, m/z (ESI$^+$)=402.3 [M+H]$^+$

2-{1-[(4-Chlorophenyl)methyl]-5-oxopyrrolidin-2-yl}-N-{2-[2-(2-acetamidoethoxy)-ethoxy]ethyl}-2-oxoacetamide (FP 327)

The title compound was synthesised from N-{2-[2-(2-aminoethoxy)ethoxy]-ethyl}-2-{1-[(4-chlorophenyl)methyl]-5-oxopyrrolidin-2-yl}-2-oxoacetamide hydrochloride (I-476) in a similar manner to general procedure 3a (general scheme 21) as a yellow viscous oil (21 mg, 94% purity, 23%) after purification by preparative LC (acidic pH, early elution method).

$^1$H NMR (500 MHz, Chloroform-d) δ 1.96-2.01 (m, 4H), 2.38-2.49 (m, 3H), 3.44-3.52 (m, 4H), 3.55-3.66 (m, 8H), 3.92 (d, J=15.0 Hz, 1H), 4.92-4.99 (m, 2H), 5.86-6.10 (m, 1H), 7.08-7.13 (m, 2H), 7.26-7.29 (m, 2H), 7.31-7.37 (m, 1H).

LC-MS (MET-uPLC-AB-102): 94% (UV), Rt=2.29 min, m/z (ESI$^+$)=454.2/456.2 [M+H]$^+$ 2-(1-Benzyl-5-oxopyrrolidin-2-yl)-N-(6-acetamido-hexyl)-2-oxoacetamide (FP 328)

The title compound was synthesised from N-(6-azanium-ylhexyl)-2-(1-benzyl-5-oxopyrrolidin-2-yl)-2-oxoacetamide chloride (I-477) in a similar manner to general procedure 3a (general scheme 21) using acetic anhydride to give a colourless gum (8 mg, 100% purity, 17%) after purification by preparative LC (acidic pH, standard elution method).

$^1$H NMR (500 MHz, Chloroform-d) δ 1.31-1.38 (m, 4H), 1.46-1.58 (m, 4H), 1.94-2.04 (m, 4H), 2.39-2.48 (m, 3H), 3.20-3.29 (m, 4H), 3.92 (d, J=14.9 Hz, 1H), 4.94-4.99 (m, 1H), 5.03 (d, J=14.9 Hz, 1H), 5.52 (s, 1H), 6.90-6.96 (m, 1H), 7.12-7.17 (m, 2H), 7.23-7.32 (m, 3H).

LC-MS (METCR1603): 100% (UV), Rt=3.29 min, m/z (ESI$^+$)=388.2 [M+H]$^+$

2-{1-[(4-Chlorophenyl)methyl]-5-oxopyrrolidin-2-yl}-N-{3-[4-(3-acetamidopropoxy) butoxy]propyl}-2-oxoacetamide (FP 329)

The title compound was synthesised from N-{3-[4-(3-aminopropoxy)butoxy]-propyl}-2-{1-[(4-chlorophenyl)methyl]-5-oxopyrrolidin-2-yl}-2-oxoacetamide hydrochloride (I-475) in a similar manner to general procedure 3a (general scheme 21) using acetic anhydride to give a colourless viscous oil (6 mg, 100% purity, 16%) after purification by preparative LC (acidic pH, standard elution method) followed by reaction with 17% w/w K$_2$CO$_3$ in EtOH and further purification by preparative LC (acidic pH, standard elution method).

$^1$H NMR (500 MHz, Chloroform-d) δ 1.64-1.73 (m, 4H), 1.75-1.84 (m, 4H), 1.94-2.04 (m, 4H), 2.36-2.47 (m, 3H), 3.35 (q, J=6.4 Hz, 2H), 3.40 (q, J=5.8 Hz, 2H), 3.44-3.49 (m, 4H), 3.52 (t, J=5.9 Hz, 2H), 3.57 (t, J=5.5 Hz, 2H), 3.91 (d, J=15.0 Hz, 1H), 4.91-5.02 (m, 2H), 6.22 (s, 1H), 7.07-7.12 (m, 2H), 7.23-7.29 (m, 2H), 7.69-7.77 (m, 1H).

LC-MS (METCR1603): 100% (UV), Rt=3.63 min, m/z (ESI$^+$)=510.2/512.2 [M+H]$^+$

2-{1-[(4-Chlorophenyl)methyl]-5-oxopyrrolidin-2-yl}-N-(6-acetamidohexyl)-2-oxoacetamide (FP 330)

The title compound was synthesised from N-(6-azanium-ylhexyl)-2-{1-[(4-chlorophenyl)methyl]-5-oxopyrrolidin-2-yl}-2-oxoacetamide chloride (I-478) in a similar manner to general procedure 3a (general scheme 21) using acetic anhydride to give a colourless gum (13 mg, 95% purity by $^1$H NMR, 25%) after purification by preparative LC (acidic pH, standard elution method).

$^1$H NMR (500 MHz, Chloroform-d) δ 1.17-1.44 (m, 4H), 1.47-1.59 (m, 4H), 1.93-2.04 (m, 4H), 2.32-2.57 (m, 3H), 3.13-3.36 (m, 4H), 3.96 (d, J=15.0 Hz, 1H), 4.86-5.04 (m, 2H), 5.57 (s, 1H), 6.90-7.02 (m, 1H), 7.07-7.14 (m, 2H), 7.21-7.33 (m, 2H).

LC-MS (METCR1603): 100% (UV), Rt=3.52 min, m/z (ESI$^+$)=422.1/424.1 [M+H]$^+$

N-(2-{2-[(2R)-1-Benzyl-5-oxopyrrolidin-2-yl]-2-oxoacetamido}ethyl)-2-methyl-propanamide (FP 331)

The title compound was synthesised from N-(2-amino-ethyl)-2-[(2R)-1-benzyl-5-oxopyrrolidin-2-yl]-2-oxoacetamide hydrochloride (I-472) in a similar manner to general procedure 3a (general scheme 21) as a yellow glass (46 mg, 100% purity, 41%) after purification by flash column chromatography on normal phase silica (10 g SNAP KP-SIL cartridge, 50-100% EtOAc in heptane gradient then 0-10% MeOH in EtOAc gradient).

$^1$H NMR (500 MHz, Chloroform-d) δ 1.14 (d, J=6.9 Hz, 6H), 1.92-2.09 (m, 1H), 2.35 (dt, J=6.9 Hz, 13.8 Hz, 1H), 2.39-2.51 (m, 3H), 3.28-3.53 (m, 4H), 3.91 (d, J=14.9 Hz, 1H), 4.88-5.00 (m, 1H), 5.05 (d, J=15.0 Hz, 1H), 5.88-6.02 (m, 1H), 7.08-7.21 (m, 2H), 7.18-7.37 (m, 3H), 7.50-7.69 (m, 1H)

LC-MS (METCR1603): 100% (UV), Rt=3.18 min, m/z (ESI$^+$)=360.3 [M+H]$^+$

2-[(2R)-1-Benzyl-5-oxopyrrolidin-2-yl]-N-[2-(cyclobutylformamido)ethyl]-2-oxoacetamide (FP 332)

The title compound was synthesised from N-(2-amino-ethyl)-2-[(2R)-1-benzyl-5-oxopyrrolidin-2-yl]-2-oxoacetamide hydrochloride (I-472) in a similar manner to general procedure 3a (general scheme 21) as an off-white powder (65 mg, 96% purity by $^1$H NMR, 54%) after purification by flash column chromatography on normal phase silica (10 g SNAP KP-SIL cartridge, 0-15% MeOH in DCM gradient).

$^1$H NMR (500 MHz, Chloroform-d) δ 1.79-1.91 (m, 1H), 1.90-2.04 (m, 2H), 2.07-2.19 (m, 2H), 2.18-2.30 (m, 2H), 2.37-2.52 (m, 3H), 2.98 (pd, J=0.8, 8.5 Hz, 1H), 3.36-3.48 (m, 4H), 3.92 (d, J=15.0 Hz, 1H), 4.90-5.00 (m, 1H), 5.05 (d, J=14.9 Hz, 1H), 5.72-5.89 (m, 1H), 7.12-7.18 (m, 2H), 7.23-7.34 (m, 3H), 7.55-7.66 (m, 1H).

LC-MS (METCR1603): 100% (UV), Rt=3.28 min, m/z (ESI$^+$)=372.2 [M+H]$^+$

N-(2-{2-[(2R)-1-Benzyl-5-oxopyrrolidin-2-yl]-2-oxoacetamido}ethyl)-N,2-dimethyl-propanamide (FP 333)

The title compound was synthesised from 2-[(2R)-1-benzyl-5-oxopyrrolidin-2-yl]-N-[2-(methylamino)ethyl]-2-oxoacetamide hydrochloride (I-479) in a similar manner to general procedure 3a (general scheme 21) as a pale yellow viscous oil (14 mg, 94% purity, 18%) after purification by flash column chromatography on normal phase silica (10 g SNAP KP-SIL cartridge, 10-100% EtOAc in heptane gradient).

$^1$H NMR (500 MHz, Chloroform-d) δ 1.09 (d, J=3.6 Hz, 3H), 1.11 (d, J=3.6 Hz, 3H), 1.93-2.00 (m, 1H), 2.35-2.47 (m, 3H), 2.78 (hept, J=6.6 Hz, 1H), 3.06 (s, 3H), 3.39-3.45 (m, 2H), 3.50-3.57 (m, 1H), 3.57-3.64 (m, 1H), 3.87 (d, J=15.0 Hz, 1H), 4.89-4.94 (m, 1H), 5.08 (d, J=15.0 Hz, 1H), 7.11-7.16 (m, 2H), 7.22-7.32 (m, 3H), 7.66 (br. s, 1H).

LC-MS (METCR1603): 94% (UV), Rt=3.37 min, m/z (ESI$^+$)=374.3 [M+H]$^+$

General Procedure 1 (General Scheme 23): Cyclisation

4,4-Diethyl 6-oxo-5-azaspiro[2.4]heptane-4,4-dicarboxylate (I-480)

To a solution of ethyl 2-cyclopropylideneacetate (587 mg, 4.19 mmol) and 1,3-diethyl 2-acetamidopropanedioate (700 mg, 3.22 mmol) in EtOH (4 mL) was added dropwise NaOEt (21% w/w solution in EtOH, 361 µL, 0.97 mmol) and the mixture stirred at RT for 20 min. The reaction was then heated at 70° C. under microwave irradiation (Biotage Initiator+, high absorbance mode) for 45 min then cooled to RT and acidified to pH~1 using 1N HCl (~3 mL). The solution was further diluted with DCM (10 mL) and the phases separated. The aqueous phase was extracted with DCM (2×10 mL) and the combined organic extracts washed with brine (5 mL), dried over MgSO4, filtered and concentrated in vacuo to afford a yellow oil which was dissolved in 1:2 EtOAc:heptane (3 mL). Upon standing for 18 h, crystals were formed which were filtered off, washed with heptane (2 mL) and dried under vacuum suction for 10 min to afford 610 mg of 4,4-diethyl 6-oxo-5-azaspiro[2.4]heptane-4,4-dicarboxylate as a colourless crystalline solid (100% purity, 74%).

$^1$H NMR (500 MHz, Chloroform-d) δ 0.69-0.75 (m, 2H), 0.94-1.02 (m, 2H), 1.27 (t, J=7.1 Hz, 6H), 2.48 (s, 2H), 4.23 (q, J=7.1 Hz, 4H), 6.50 (s, 1H).

LC-MS (METCR1410): 100% (UV), Rt=0.93 min, m/z (ESI$^+$)=256.1 [M+H]$^+$

2,2-Diethyl 3-methyl-5-oxopyrrolidine-2,2-dicarboxylate (I-481)

The title compound was synthesised in a similar manner to general procedure 1 (general scheme 23) as an off-white

GENERAL SCHEME 23

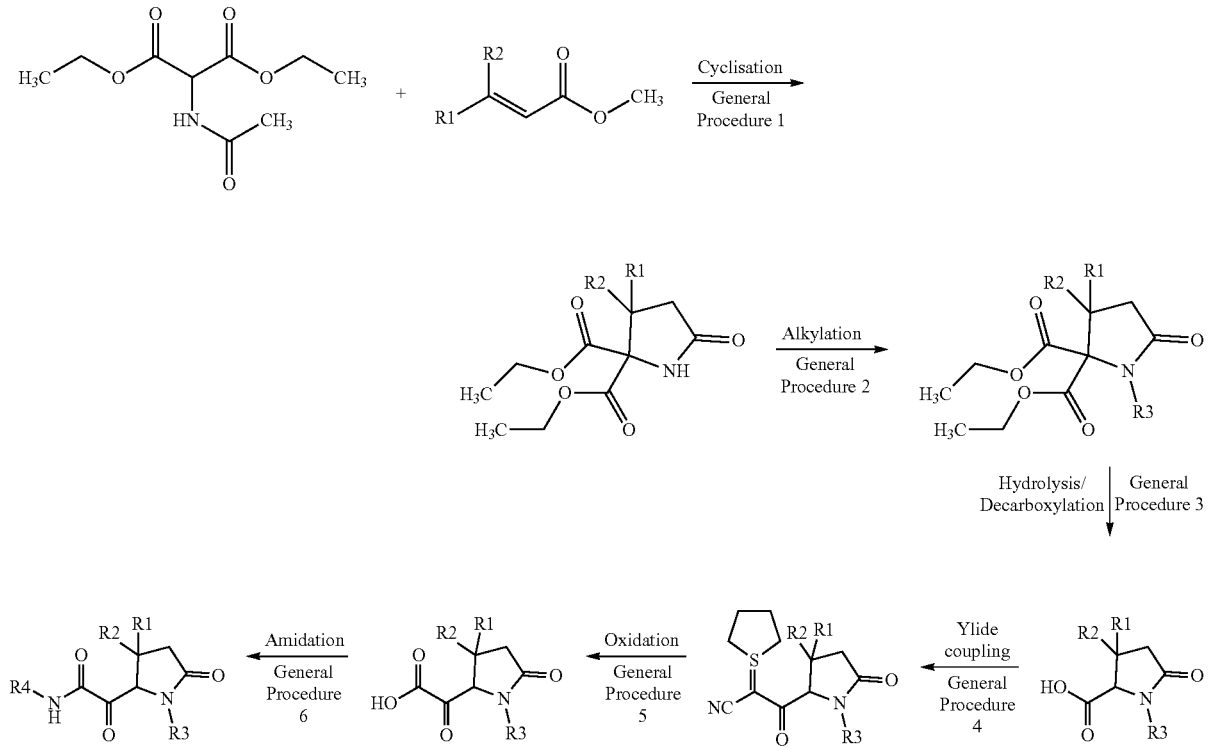

solid (3.24 g, 100% purity by ¹H NMR, 72%) after purification by recrystallisation from heptae/EtOAc.
¹H NMR (500 MHz, Chloroform-d) δ 1.15 (d, J=7.0 Hz, 3H), 1.25-1.33 (m, 6H), 2.14 (dd, J=7.4, 16.7 Hz, 1H), 2.61 (dd, J=8.2, 16.7 Hz, 1H), 3.06-3.17 (m, 1H), 4.20-4.34 (m, 4H), 6.10 (s, 1H).
LC-MS (METCR1410): 88% (UV), Rt=0.90 min, m/z (ESI⁺)=244.2 [M+H]⁺

2,2-Diethyl 3-ethyl-5-oxopyrrolidine-2,2-dicarboxylate (I-482)

The title compound was synthesised in a similar manner to general procedure 1 (general scheme 23) as an off-white powder (5 g, 91% purity, 64%) after purification by recrystallisation from heptane/EtOAc.
¹H NMR (500 MHz, Chloroform-d) δ 0.97 (t, J=7.4 Hz, 3H), 1.13-1.25 (m, 1H), 1.29 (t, J=7.1 Hz, 6H), 1.76-1.86 (m, 1H), 2.19 (dd, J=8.8, 16.8 Hz, 1H), 2.56 (dd, J=8.4, 16.7 Hz, 1H), 2.81-2.91 (m, 1H), 4.18-4.33 (m, 4H), 6.07 (s, 1H).
LC-MS (METCR1410): 91% (UV), Rt=0.98 min, m/z (ESI⁺)=258.1 [M+H]⁺

2,2-Diethyl 5-oxo-3-(propan-2-yl)pyrrolidine-2,2-dicarboxylate (I-483)

The title compound was synthesised in a similar manner to general procedure 1 (general scheme 23) as a yellow solid (1.10 g, 63% purity, 9%) after purification by recrystallisation from heptane/EtOAc.
LC-MS (METCR1410): 63% (UV), Rt=1.02 min, m/z (ESI⁺)=272.1 [M+H]⁺

General Procedure 2 (General Scheme 23): Alkylation 4,4-Diethyl 5-benzyl-6-oxo-5-azaspiro[2.4]heptane-4,4-dicarboxylate (I-484)

To an ice-cooled solution of 4,4-diethyl 5-benzyl-6-oxo-5-azaspiro[2.4]heptane-4,4-dicarboxylate (I-480) (460 mg, 1.80 mmol) in DMF (2 mL) was added NaH (60% dispersion in mineral oil, 76 mg, 1.89 mmol) and the reaction mixture stirred for 15 min. Benzyl bromide (236 μL, 1.98 mmoL) was added and the reaction mixture then allowed to warm to RT for 1 h. The reaction was quenched with saturated NH₄Cl (2 mL) and diluted with DCM (10 mL), the phases were separated and the aqueous phase extracted with DCM (2×10 mL). The combined organic extracts were washed with brine (10 mL), dried over MgSO₄, filtered and concentrated in vacuo. The residue was purified by flash column chromatography on normal phase silica (10 g SNAP KP-SIL cartridge, 0-100% EtOAc in heptane gradient) to afford 190 mg of 4,4-diethyl 5-benzyl-6-oxo-5-azaspiro[2.4]heptane-4,4-dicarboxylate as a colourless oil (96% purity, 29%).
¹H NMR (500 MHz, Chloroform-d) δ 0.73-0.79 (m, 2H), 0.83-0.88 (m, 2H), 1.11 (t, J=7.2 Hz, 6H), 2.65 (s, 2H), 3.83-3.97 (m, 4H), 4.76 (s, 2H), 7.17-7.23 (m, 3H), 7.24-7.28 (m, 2H).
LC-MS (METCR0990): 96% (UV), Rt=1.76 min, m/z (ESI⁺)=346.2 [M+H]⁺

2,2-Diethyl 1-benzyl-3-methyl-5-oxopyrrolidine-2,2-dicarboxylate (I-485)

The title compound was synthesised from 2,2-diethyl 3-methyl-5-oxopyrrolidine-2,2-dicarboxylate (I-481) in a similar manner to general procedure 2 (general scheme 23) as a yellow viscous oil (4.38 g, 95% purity, 94%) which was used in the next step without purification.
¹H NMR (500 MHz, Chloroform-d) δ 1.03 (t, J=7.2 Hz, 3H), 1.13 (d, J=7.0 Hz, 3H), 1.22 (t, J=7.1 Hz, 3H), 2.20 (dd, J=9.7, 16.7 Hz, 1H), 2.72 (dd, J=8.5, 16.7 Hz, 1H), 3.04-3.17 (m, 1H), 3.65 (dq, J=7.2, 10.8 Hz, 1H), 3.94-4.08 (m, 2H), 4.18 (dq, J=7.1, 10.8 Hz, 1H), 4.40 (d, J=15.9 Hz, 1H), 4.99 (d, J=15.9 Hz, 1H), 7.12-7.21 (m, 3H), 7.22-7.27 (m, 2H).
LC-MS (METCR1410): 95% (UV), Rt=1.15 min, m/z (ESI⁺)=334.2 [M+H]⁺

2,2-Diethyl 1-benzyl-5-oxo-3-(propan-2-yl)pyrrolidine-2,2-dicarboxylate (I-486)

The title compound was synthesised from 2,2-diethyl 5-oxo-3-(propan-2-yl)pyrrolidine-2,2-dicarboxylate (I-483) in a similar manner to general procedure 2 (general scheme 23) as a yellow free-flowing oil (675 mg, 95% purity by 1H NMR, 69%) after purification by flash column chromatography on normal phase silica (25 g SNAP KP-SIL cartridge, 0-40% EtOAc in heptane gradient).
¹H NMR (500 MHz, Chloroform-d) δ 0.91 (d, J=6.6 Hz, 3H), 0.96-1.03 (m, 6H), 1.27 (t, J=7.1 Hz, 3H), 1.53-1.61 (m, 1H), 2.22 (dd, J=11.4, 16.6 Hz, 1H), 2.63 (dd, J=8.3, 16.6 Hz, 1H), 2.95 (dt, J=8.6, 11.4 Hz, 1H), 3.55 (dq, J=7.2, 10.8 Hz, 1H), 3.68-3.77 (m, 1H), 4.07 (d, J=16.0 Hz, 1H), 4.17 (dq, J=7.2, 10.8 Hz, 1H), 4.28 (dq, J=7.2, 10.8 Hz, 1H), 5.04 (d, J=16.0 Hz, 1H), 7.12-7.21 (m, 3H), 7.23-7.27 (m, 2H).
LC-MS (METCR1410): 71% (UV), Rt=1.25 min, m/z (ESI⁺)=362.1 [M+H]⁺

2,2-Diethyl 1-benzyl-3-ethyl-5-oxopyrrolidine-2,2-dicarboxylate (I-487)

The title compound was synthesised from 2,2-diethyl 3-ethyl-5-oxopyrrolidine-2,2-dicarboxylate (I-482) in a similar manner to general procedure 2 (general scheme 23) as a colourless free-flowing oil (3.28 g, 74% purity, 79%) which was used in the next step without purification.
¹H NMR (500 MHz, Chloroform-d) δ 0.98 (t, J=7.4 Hz, 3H), 1.02 (t, J=7.2 Hz, 3H), 1.09-1.18 (m, 1H), 1.22 (t, J=7.2 Hz, 3H), 1.69-1.81 (m, 1H), 2.18 (dd, J=10.7, 16.6 Hz, 1H), 2.71 (dd, J=8.5, 16.6 Hz, 1H), 2.89-2.99 (m, 1H), 3.58-3.67 (m, 1H), 3.95 (dq, J=7.1, 10.8 Hz, 1H), 4.04 (dq, J=7.2, 10.8 Hz, 1H), 4.18 (dq, J=7.1, 10.8 Hz, 1H), 4.32 (d, J=15.9 Hz, 1H), 5.00 (d, J=15.9 Hz, 1H), 7.12-7.20 (m, 3H), 7.22-7.28 (m, 2H).
LC-MS (METCR1410): 74% (UV), Rt=1.22 min, m/z (ESI⁺)=348.1 [M+H]⁺

General Procedure 3 (General Scheme 23): Hydrolysis/Decarboxylation

5-Benzyl-6-oxo-5-azaspiro[2.4]heptane-4-carboxylic acid (I-488)

A solution of 4,4-diethyl 5-benzyl-6-oxo-5-azaspiro[2.4]heptane-4,4-dicarboxylate (170 mg, 0.48 mmol) and KOH (81 mg, 1.45 mmol) in 1:1 EtOH:water (4 mL) was heated at 80° C. for 3 h then cooled to RT and concentrated in vacuo. The residue was diluted with water (2 mL), acidified to pH 1 using 6N HCl and the suspension was concentrated in vacuo to half the original volume. The suspension was then heated at 145° C. for 3 h, cooled and concentrated in vacuo. The solid was diluted with MeOH (3 mL) and the insoluble matter was removed via filtration. The filtrate was concentrated in vacuo to afford 100 mg of 5-benzyl-6-oxo-5-azaspiro[2.4]heptane-4-carboxylic acid as a white gum (96% purity, 81%).

$^1$H NMR (500 MHz, Chloroform-d) δ 0.66-0.81 (m, 3H), 0.84-0.96 (m, 1H), 2.24 (d, J=17.0 Hz, 1H), 2.89 (d, J=17.0 Hz, 1H), 3.48 (s, 1H), 3.95 (d, J=15.0 Hz, 1H), 5.15 (d, J=15.0 Hz, 1H), 7.20-7.26 (m, 2H), 7.27-7.36 (m, 3H).

LC-MS (METCR1410): 96% (UV), Rt=0.91 min, m/z (ESI$^+$)=246.0 [M+H]$^+$

1-Benzyl-3-methyl-5-oxopyrrolidine-2-carboxylic acid (I-489)

The title compound was synthesised from 2,2-diethyl 1-benzyl-3-methyl-5-oxopyrrolidine-2,2-dicarboxylate (I-485) in a similar manner to general procedure 3 (general scheme 23) as an off-white powder (528 mg, 100% purity, 61%) after purification by recrystallisation from heptane/EtOAc.

$^1$H NMR (500 MHz, DMSO-d6) δ 0.95-1.06 (m, 3H), 1.92-2.05 (m, 1H), 2.31-2.48 (m, 1H), 2.53-2.68 (m, 1H), 3.41-3.87 (m, 2H), 4.81-4.93 (m, 1H), 7.16-7.22 (m, 2H), 7.25-7.30 (m, 1H), 7.31-7.37 (m, 2H), 12.29-13.76 (m, 1H).

LC-MS (METCR1410): 100% (UV), Rt=0.87 min, m/z (ESI$^+$)=234.1 [M+H]$^+$

1-Benzyl-3-ethyl-5-oxopyrrolidine-2-carboxylic acid (I-490)

The title compound was synthesised from 2,2-diethyl 1-benzyl-3-ethyl-5-oxopyrrolidine-2,2-dicarboxylate (I-487) in a similar manner to general procedure 3 (general scheme 23) as an off-white solid (1.72 g, 97% purity, 96%) after purification by recrystallisation from heptane/EtOAc.

$^1$H NMR (500 MHz, DMSO-d6) δ 0.75-0.91 (m, 3H), 1.15-1.52 (m, 2H), 1.98-2.09 (m, 1H), 2.35-2.46 (m, 1H), 2.52-2.58 (m, 1H), 3.48-3.88 (m, 2H), 4.79-4.93 (m, 1H), 7.16-7.22 (m, 2H), 7.26-7.31 (m, 1H), 7.32-7.37 (m, 2H).

LC-MS (METCR1410): 97% (UV), Rt=0.94 min, m/z (ESI$^+$)=248.1 [M+H]$^+$

1-Benzyl-5-oxo-3-(propan-2-yl)pyrrolidine-2-carboxylic acid (I-491)

The title compound was synthesised from 2,2-diethyl 1-benzyl-5-oxo-3-(propan-2-yl)pyrrolidine-2,2-dicarboxylate (I-486) in a similar manner to general procedure 3 (general scheme 23) as a yellow viscous oil (445 mg, 86% purity, 83%) after purification by recrystallisation from heptane/EtOAc.

$^1$H NMR (500 MHz, DMSO-d6) δ 0.63-0.95 (m, 6H), 1.37-1.66 (m, 1H), 2.08-2.23 (m, 2H), 2.51-2.53 (m, 1H), 3.54-3.88 (m, 2H), 4.76-4.92 (m, 1H), 7.17-7.23 (m, 2H), 7.26-7.31 (m, 1H), 7.31-7.36 (m, 2H).

LC-MS (METCR1410): 86% (UV), Rt=0.96-1.03 min (multiple peaks), m/z (ESI$^+$)=262.1 [M+H]$^+$

General Procedure 4 (General Scheme 23): Ylide Coupling

Method as Described in General Procedure 4 (General Scheme 11a): Ylide Coupling

3-(1-Benzyl-3-methyl-5-oxopyrrolidin-2-yl)-3-oxo-2-(1A'-thiolan-1-ylidene)propanenitrile (I-492)

The title compound was synthesised from 1-benzyl-3-methyl-5-oxopyrrolidine-2-carboxylic acid (I-489) in a similar manner to general procedure 4 (general scheme 11a) as a brown gum (652 mg, 97% purity, 82%) after purification by flash column chromatography on normal phase silica (25 g SNAP Ultra cartridge, 0-100% EtOAc in heptane gradient followed by 0-20% MeOH in EtOAc gradient).

$^1$H NMR (500 MHz, Chloroform-d) δ 0.99-1.18 (m, 3H), 1.96-2.48 (m, 4H), 2.49-2.81 (m, 3H), 3.11-3.39 (m, 4H), 3.98-4.41 (m, 2H), 4.70-4.92 (m, 1H), 7.20-7.27 (m, 3H), 7.27-7.35 (m, 2H).

LC-MS (METCR1410): 97% (UV), Rt=0.89 min, m/z (ESI$^+$)=343.2 [M+H]$^+$

3-[1-Benzyl-5-oxo-3-(propan-2-yl)pyrrolidin-2-yl]-3-oxo-2-(1λ$^4$-thiolan-1-ylidene)-propanenitrile (I-493)

The title compound was synthesised from 1-benzyl-5-oxo-3-(propan-2-yl)pyrrolidine-2-carboxylic acid (I-491) in a similar manner to general procedure 4 (general scheme 11a) as a yellow viscous oil (415 mg, 88% purity by $^1$H NMR, 68%) after purification by flash column chromatography on normal phase silica (10 g SNAP KP-SIL cartridge, 0-100% EtOAc in heptane gradient.

$^1$H NMR (500 MHz, Chloroform-d) δ 0.77-0.86 (m, 6H), 1.68-1.77 (m, 1H), 1.97-2.07 (m, 2H), 2.08-2.15 (m, 1H), 2.20 (dd, J=4.2, 17.1 Hz, 1H), 2.45-2.57 (m, 2H), 2.70 (dd, J=9.5, 17.1 Hz, 1H), 3.01-3.15 (m, 2H), 3.21-3.34 (m, 2H), 4.14-4.19 (m, 2H), 4.66 (d, J=14.8 Hz, 1H), 7.21-7.34 (m, 5H).

LC-MS (METCR1410): 100% (UV), Rt=0.91-1.05 min (multiple peaks), m/z (ESI$^+$)=371.1 [M+H]$^+$

3-(1-Benzyl-3-ethyl-5-oxopyrrolidin-2-yl)-3-oxo-2-(1λ$^4$-thiolan-1-ylidene)propanenitrile (I-494)

The title compound was synthesised from 1-benzyl-3-ethyl-5-oxopyrrolidine-2-carboxylic acid (I-490) in a similar manner to general procedure 4 (general scheme 11a) as a brown gum (2.21 g, 90% purity by 1H NMR, 83%) after purification by flash column chromatography on normal phase silica (50 g SNAP Ultra cartridge, 0-100% EtOAc in heptane gradient followed by 0-20% MeOH in EtOAc gradient).

$^1$H NMR (500 MHz, Chloroform-d) δ 0.84-0.96 (m, 3H), 1.35-1.49 (m, 1H), 1.51-1.63 (m, 1H), 1.98-2.78 (m, 7H), 3.07-3.23 (m, 2H), 3.24-3.38 (m, 2H), 4.02-4.44 (m, 2H), 4.65-4.81 (m, 1H), 7.21-7.27 (m, 3H), 7.27-7.32 (m, 2H)

LC-MS (METCR1410): 99% (UV), Rt=0.92 min, m/z (ESI$^+$)=357.1 [M+H]$^+$

3-{5-Benzyl-6-oxo-5-azaspiro[2.4]heptan-4-yl}-3-oxo-2-(1λ$^4$-thiolan-1-ylidene)propane-nitrile (I-495)

The title compound was synthesised from 5-benzyl-6-oxo-5-azaspiro[2.4]heptane-4-carboxylic acid (I-488) in a similar manner to general procedure 4 (general scheme 11a) as a yellow viscous oil (110 mg, 80% purity by $^1$H NMR, 63%) after purification by flash column chromatography on normal phase silica (10 g SNAP KP-SIL cartridge, 0-100% EtOAc in heptane gradient followed by 0-50% MeOH in EtOAc gradient).

$^1$H NMR (500 MHz, Chloroform-d) δ 0.58-0.68 (m, 2H), 0.71-0.78 (m, 2H), 2.03-2.10 (m, 2H), 2.12 (d, J=16.8 Hz, 1H), 2.46-2.58 (m, 2H), 2.89 (d, J=16.8 Hz, 1H), 3.09-3.17 (m, 2H), 3.29-3.43 (m, 2H), 3.95 (s, 1H), 4.05-4.10 (m, 1H), 4.77 (d, J=14.9 Hz, 1H), 7.22-7.27 (m, 3H), 7.27-7.33 (m, 2H).

LC-MS (METCR1410): 99% (UV), Rt=0.92 min, m/z (ESI$^+$)=355.1 [M+H]$^+$

General Procedure 5 (General Scheme 23): Oxidation

Method As described in general procedure 5 (general scheme 11a): Oxidation 2-(1-Benzyl-3-methyl-5-oxopyrrolidin-2-yl)-2-oxoacetic acid (I-496)

The title compound was synthesised from 3-(1-benzyl-3-methyl-5-oxopyrrolidin-2-yl)-3-oxo-2-(1$\lambda^4$-thiolan-1-ylidene)propanenitrile (I-492) in a similar manner to general procedure 5 (general scheme 11a) as a yellow viscous oil (633 mg, 60% purity estimated by 1H NMR, 79%) after trituration in EtOAc/heptane which was used crude in the next step without further purification.

2-[1-Benzyl-5-oxo-3-(propan-2-yl)pyrrolidin-2-yl]-2-oxoacetic acid (I-497)

The title compound was synthesised from 3-[1-benzyl-5-oxo-3-(propan-2-yl)pyrrolidin-2-yl]-3-oxo-2-(1$\lambda^4$-thiolan-1-ylidene)propanenitrile (I-493) in a similar manner to general procedure 5 (general scheme 11a) as a yellow viscous oil (310 mg, 67% purity estimated by $^1$H NMR, 73%) after trituration in EtOAc/heptane which was used crude in the next step without further purification.

2-(1-Benzyl-3-ethyl-5-oxopyrrolidin-2-yl)-2-oxoacetic acid (I-498)

The title compound was synthesised from 3-(1-benzyl-3-ethyl-5-oxopyrrolidin-2-yl)-3-oxo-2-(1$\lambda^4$-thiolan-1-ylidene)propanenitrile (I-494) in a similar manner to general procedure 5 (general scheme 11a) as a brown viscous oil (1.83 g, 60% purity estimated by $^1$H NMR, 71%) after trituration in EtOAc/heptane which was used crude in the next step without further purification.

2-{5-Benzyl-6-oxo-5-azaspiro[2.4]heptan-4-yl}-2-oxoacetic acid (I-499)

The title compound was synthesised from 3-{5-benzyl-6-oxo-5-azaspiro[2.4]heptan-4-yl}-3-oxo-2-(1$\lambda^4$-thiolan-1-ylidene)propanenitrile (I-495) in a similar manner to general procedure 5 (general scheme 11a) as a yellow viscous oil (85 mg, 65% purity estimated by $^1$H NMR, 81%) after trituration in EtOAc/heptane which was used crude in the next step without further purification.

General Procedure 6 (General Scheme 23): Amidation

Method As described in Method A, general procedure 6 (general scheme 11a): Coupling 2-(1-Benzyl-3-methyl-5-oxopyrrolidin-2-yl)-N-cyclopropylmethyl)-2-oxoacetamide (I-500)

The title compound was synthesised from 2-(1-benzyl-3-methyl-5-oxopyrrolidin-2-yl)-2-oxoacetic acid (I-496) in a similar manner to general procedure 6 (general scheme 11a) using the free-base form of the amine to give a colourless viscous oil (393 mg, 84% purity by $^1$H NMR, 37%) after purification by flash column chromatography on normal phase silica (25 g SNAP Ultra cartridge, 0-80% EtOAc in heptane gradient).

The four diastereoisomers were then separated by chiral preparative HPLC on Gilson LC [column: Chiralpak AS (20 mm×250 mm, 10 μm) at RT; isocratic eluent: 3:2 heptane/EtOH; flow rate: 10 mL/min; detector wavelength: 215/254 nm; dilution solvent: MeOH and acetonitrile; injection volume: 100-700 μL] to afford the following compounds (absolute stereochemistry arbitrarily assigned):

2-[(2S,3S)-1-Benzyl-3-methyl-5-oxopyrrolidin-2-yl]-N-(cyclopropylmethyl)-2-oxoacetamide (FP 334)

The title compound was obtained as a yellow viscous oil (14 mg, 85% purity, 4%)

$^1$H NMR (500 MHz, Chloroform-d) δ 0.20-0.28 (m, 2H), 0.54-0.61 (m, 2H), 0.92-1.00 (m, 1H), 1.23 (d, J=6.9 Hz, 3H), 2.08 (dd, J=1.8, 17.0 Hz, 1H), 2.32-2.42 (m, 1H), 2.56-2.66 (m, 1H), 3.13 (dd, J=5.9, 7.2 Hz, 2H), 3.84 (d, J=14.9 Hz, 1H), 4.57 (d, J=2.0 Hz, 1H), 5.05 (d, J=14.9 Hz, 1H), 6.89-6.98 (m, 1H), 7.14-7.19 (m, 2H), 7.23-7.34 (m, 3H).

LC-MS (MET-uPLC-AB-102): 85% (UV), Rt=2.88 min, m/z (ESI$^+$)=315.2 [M+H]$^+$

LC-MS (CAM-F3): 90% (UV), Rt=7.74 min

2-[(2S,3R)-1-Benzyl-3-methyl-5-oxopyrrolidin-2-yl]-N-(cyclopropylmethyl)-2-oxoacetamide (FP 335)

The title compound was obtained as a yellow solid (23 mg, 93% purity, 6%)

$^1$H NMR (500 MHz, Chloroform-d) δ 0.19-0.26 (m, 2H), 0.52-0.60 (m, 2H), 0.90-1.00 (m, 4H), 2.17 (dd, J=9.1, 16.6 Hz, 1H), 2.58 (dd, J=8.3, 16.6 Hz, 1H), 2.81-2.91 (m, 1H), 3.11 (dd, J=5.9, 7.1 Hz, 2H), 3.99 (d, J=14.7 Hz, 1H), 4.86 (d, J=14.7 Hz, 1H), 5.17 (d, J=8.5 Hz, 1H), 6.78-6.88 (m, 1H), 7.11-7.15 (m, 2H), 7.22-7.31 (m, 3H).

LC-MS (MET-uPLC-AB-102): 93% (UV), Rt=2.94 min, m/z (ESI$^+$)=315.2 [M+H]$^+$

LC-MS (CAM-F3): 90% (UV), Rt=7.50 min

2-[(2R,3R)-1-Benzyl-3-methyl-5-oxopyrrolidin-2-yl]-N-(cyclopropylmethyl)-2-oxoacetamide (FP 336)

The title compound was obtained a brown viscous oil (22 mg, 85% purity, 6%)

$^1$H NMR (500 MHz, Chloroform-d) δ 0.20-0.28 (m, 2H), 0.52-0.60 (m, 2H), 0.92-1.00 (m, 1H), 1.23 (d, J=6.9 Hz, 3H), 2.08 (dd, J=1.9, 17.0 Hz, 1H), 2.32-2.41 (m, 1H), 2.56-2.65 (m, 1H), 3.13 (dd, J=5.9, 7.2 Hz, 2H), 3.84 (d, J=14.9 Hz, 1H), 4.57 (d, J=2.0 Hz, 1H), 5.05 (d, J=14.9 Hz, 1H), 6.90-6.98 (m, 1H), 7.14-7.19 (m, 2H), 7.23-7.33 (m, 3H).

LC-MS (MET-uPLC-AB-102): 85% (UV), Rt=2.86 min, m/z (ESI⁺)=315.2 [M+H]⁺
LC-MS (CAM-F3): 90% (UV), Rt=10.94 min 2-[(2R,3S)-1-Benzyl-3-methyl-5-oxopyrrolidin-2-yl]-N-(cyclopropylmethyl)-2-oxoacetamide (FP 337)

The title compound was obtained as an off-white solid (68 mg, 98% purity, 20%)
¹H NMR (500 MHz, Chloroform-d) δ 0.19-0.26 (m, 2H), 0.51-0.60 (m, 2H), 0.90-1.00 (m, 4H), 2.17 (dd, J=9.1, 16.6 Hz, 1H), 2.58 (dd, J=8.3, 16.6 Hz, 1H), 2.80-2.92 (m, 1H), 3.11 (dd, J=5.9, 7.2 Hz, 2H), 3.99 (d, J=14.7 Hz, 1H), 4.86 (d, J=14.7 Hz, 1H), 5.17 (d, J=8.5 Hz, 1H), 6.79-6.87 (m, 1H), 7.11-7.16 (m, 2H), 7.22-7.31 (m, 3H).
LC-MS (MET-uPLC-AB-102): 98% (UV), Rt=2.94 min, m/z (ESI⁺)=315.2 [M+H]⁺
LC-MS (CAM-F3): 90% (UV), Rt=19.05 min 2-(1-Benzyl-3-methyl-5-oxopyrrolidin-2-yl)-N-cyclopropyl-2-oxoacetamide (I-501)

The title compound was synthesised from 2-(1-benzyl-3-methyl-5-oxopyrrolidin-2-yl)-2-oxoacetic acid (I-496) in a similar manner to general procedure 6 (general scheme 11a) using the free-base form of the amine to give a yellow viscous oil (287 mg, 100% purity, 17%) after purification by flash column chromatography on normal phase silica (50 g SNAP KP-SIL cartridge, 0-100% EtOAc in heptane gradient) then on normal phase silica (25 g SNAP KP-SIL cartridge, 0-80% EtOAc in heptane gradient) followed by preparative LC (acidic pH, standard elution method).
The four diastereoisomers were then separated by chiral SFC on Gilson LC [column: Chiralpak AS (20 mm×250 mm, 10 μm) at RT; isocratic eluent: 3:2 heptane/EtOH; flow rate: 10 mL/min; detector wavelength; 215/254 nm; dilution solvent: EtOH and heptane; injection volume: 100-1000 μL] followed by Waters SFC [column: Chiralpak AS-H (10 mm×250 mm, 5 μm) at 40° C.; isocratic eluent: 75/15 CO₂/EtOH; flow rate: 15 mL/min; detector wavelength; 215/254 nm; dilution solvent: EtOH; injection volume: 250 μL] to afford the following compounds (absolute stereochemistry arbitrarily assigned):

2-[(2S,3R)-1-Benzyl-3-methyl-5-oxopyrrolidin-2-yl]-N-cyclopropyl-2-oxoacetamide (FP 338)

The title compound was obtained as an off-white solid (47 mg, 80% purity by ¹H NMR, 13%)
¹H NMR (500 MHz, Chloroform-d) δ 0.51-0.61 (m, 2H), 0.82-0.88 (m, 2H), 0.94 (d, J=7.1 Hz, 3H), 2.16 (dd, J=9.1, 16.6 Hz, 1H), 2.53-2.61 (m, 1H), 2.69-2.77 (m, 1H), 2.81-2.91 (m, 1H), 4.01 (d, J=14.7 Hz, 1H), 4.81 (d, J=14.7 Hz, 1H), 5.16 (d, J=8.5 Hz, 1H), 6.73 (s, 1H), 7.09-7.14 (m, 2H), 7.23-7.33 (m, 3H).
LC-MS (METCR1603): 90% (UV), Rt=3.63 min, m/z (ESI⁺)=301.2 [M+H]⁺
LC-MS (CAM-F4): 95% (UV), Rt=12.07 min 2-[(2S,3S)-1-Benzyl-3-methyl-5-oxopyrrolidin-2-yl]-N-cyclopropyl-2-oxoacetamide (FP 339)

The title compound was obtained as a colourless gum (14 mg, 100% purity, 5%)
¹H NMR (500 MHz, Chloroform-d) δ 0.53-0.65 (m, 2H), 0.82-0.89 (m, 2H), 1.23 (d, J=6.9 Hz, 3H), 2.07 (dd, J=1.8, 17.0 Hz, 1H), 2.30-2.40 (m, 1H), 2.53-2.64 (m, 1H), 2.70-2.78 (m, 1H), 3.84 (d, J=14.9 Hz, 1H), 4.56 (d, J=1.9 Hz, 1H), 5.02 (d, J=14.9 Hz, 1H), 6.87 (s, 1H), 7.12-7.18 (m, 2H), 7.24-7.33 (m, 3H).
LC-MS (METCR1603): 100% (UV), Rt=3.60 min, m/z (ESI⁺)=301.2 [M+H]⁺
LC-MS (CAM-F4): 95% (UV), Rt=1.64 min 2-[(2R,3R)-1-Benzyl-3-methyl-5-oxopyrrolidin-2-yl]-N-cyclopropyl-2-oxoacetamide (FP 340)

The title compound was obtained as a colourless gum (15 mg, 97% purity, 5%) ¹H NMR (500 MHz, Chloroform-d) δ 0.56-0.63 (m, 2H), 0.82-0.90 (m, 2H), 1.23 (d, J=6.9 Hz, 3H), 2.07 (dd, J=1.6, 17.0 Hz, 1H), 2.30-2.42 (m, 1H), 2.59 (dd, J=8.7, 17.0 Hz, 1H), 2.69-2.80 (m, 1H), 3.83 (d, J=14.9 Hz, 1H), 4.55 (d, J=1.8 Hz, 1H), 5.02 (d, J=14.9 Hz, 1H), 6.88 (s, 1H), 7.12-7.18 (m, 2H), 7.23-7.35 (m, 3H).
LC-MS (METCR1603): 97% (UV), Rt=3.61 min, m/z (ESI⁺)=301.1 [M+H]⁺
LC-MS (CAM-F4): 95% (UV), Rt=24.54 min 2-[(2R,3S)-1-Benzyl-3-methyl-5-oxopyrrolidin-2-yl]-N-cyclopropyl-2-oxoacetamide (FP 341)

The title compound was obtained as an off-white solid (62 mg, 100% purity, 22%)
¹H NMR (500 MHz, Chloroform-d) δ 0.51-0.60 (m, 2H), 0.81-0.89 (m, 2H), 0.94 (d, J=7.1 Hz, 3H), 2.16 (dd, J=9.1, 16.5 Hz, 1H), 2.57 (dd, J=8.3, 16.6 Hz, 1H), 2.68-2.76 (m, 1H), 2.80-2.92 (m, 1H), 4.01 (d, J=14.7 Hz, 1H), 4.81 (d, J=14.7 Hz, 1H), 5.16 (d, J=8.5 Hz, 1H), 6.73 (s, 1H), 7.10-7.15 (m, 2H), 7.22-7.30 (m, 3H).
LC-MS (METCR1603): 100% (UV), Rt=3.65 min, m/z (ESI⁺)=301.2 [M+H]+
LC-MS (CAM-F4): 95% (UV), Rt=38.08 min 2-[(2S,3R)-1-Benzyl-5-oxo-3-(propan-2-yl)pyrrolidin-2-yl]-N-cyclopropyl-2-oxoacetamide and 2-[(2R,3S)-1-benzyl-5-oxo-3-(propan-2-yl)pyrrolidin-2-yl]-N-cyclopropyl-2-oxoacetamide (FP 342)

The compounds were isolated as a racemic mixture of trans enantiomers from 2-[1-benzyl-5-oxo-3-(propan-2-yl)pyrrolidin-2-yl]-2-oxoacetic acid (I-497) in a similar manner to general procedure 6 (general scheme 11a) using the free-base form of the amine to give an off-white solid (37 mg, 92% purity, 15%) after purification by preparative LC (acidic pH, standard elution method).
¹H NMR (500 MHz, Chloroform-d) δ 0.55-0.62 (m, 2H), 0.78 (d, J=6.8 Hz, 3H), 0.83-0.88 (m, 5H), 1.85-1.95 (m, 1H), 2.03-2.10 (m, 1H), 2.25 (dd, J=2.2, 17.4 Hz, 1H), 2.48 (dd, J=9.3, 17.3 Hz, 1H), 2.69-2.78 (m, 1H), 3.91 (d, J=14.6 Hz, 1H), 4.72 (d, J=2.2 Hz, 1H), 4.86 (d, J=14.6 Hz, 1H), 6.81 (s, 1H), 7.13-7.21 (m, 2H), 7.24-7.32 (m, 3H).
LC-MS (METCR1603): 92% (UV), Rt=4.06 min, m/z (ESI⁺)=329.2 [M+H]⁺

2-(1-Benzyl-3-ethyl-5-oxopyrrolidin-2-yl)-N-cyclopropyl-2-oxoacetamide (FP 343)

The title compound was synthesised from 2-(1-benzyl-3-ethyl-5-oxopyrrolidin-2-yl)-2-oxoacetic acid (I-498) in a similar manner to general procedure 6 (general scheme 11a) using the free-base form of the amine in DMF as solvent to give a yellow viscous oil (80 mg, 100% purity, 33%) after purification by preparative LC (acidic pH, standard elution method).

$^1$H NMR (500 MHz, Chloroform-d) δ 0.49-0.63 (m, 2H), 0.83-1.01 (m, 5H), 1.44-1.72 (m, 2H), 2.12-2.77 (m, 4H), 3.82-4.09 (m, 1H), 4.64-5.23 (m, 2H), 6.63-6.89 (m, 1H), 7.12-7.19 (m, 2H), 7.22-7.32 (m, 3H).

LC-MS (METCR1603): 100% (UV), Rt=3.68-4.00 min (2 peaks), m/z (ESI$^+$)=315.2 [M+H]$^+$

2-(1-Benzyl-3-ethyl-5-oxopyrrolidin-2-yl)-N-(oxan-4-yl)-2-oxoacetamide (FP 344)

The title compound was synthesised from 2-(1-benzyl-3-ethyl-5-oxopyrrolidin-2-yl)-2-oxoacetic acid (I-498) in a similar manner to general procedure 6 (general scheme 11a) using the free-base form of the amine in DMF as solvent to give an off-white solid (98 mg, 100% purity, 36%) after purification by preparative LC (acidic pH, standard elution method).

$^1$H NMR (500 MHz, Chloroform-d) δ 0.85-1.02 (m, 3H), 1.44-1.71 (m, 4H), 1.80-1.92 (m, 2H), 2.10-2.68 (m, 3H), 3.42-3.51 (m, 2H), 3.83-4.10 (m, 4H), 4.65-5.23 (m, 2H), 6.54-6.78 (m, 1H), 7.11-7.19 (m, 2H), 7.22-7.34 (m, 3H).

LC-MS (METCR1603): 100% (UV), Rt=3.33-3.90 min (2 peaks), m/z (ESI$^+$)=359.3 [M+H]$^+$

2-{5-Benzyl-6-oxo-5-azaspiro[2.4]heptan-4-yl}-N-cyclopropyl-2-oxoacetamide (FP 345)

The title compound was synthesised from 2-{5-benzyl-6-oxo-5-azaspiro[2.4]heptan-4-yl}-2-oxoacetic acid (I-499) in a similar manner to general procedure 6 (general scheme 11a) using the free-base form of the amine in DMF as solvent to give a colourless viscous oil (20 mg, 99% purity, 31%) after purification by preparative LC (acidic pH, early elution method).

$^1$H NMR (500 MHz, Chloroform-d) δ 0.50-0.61 (m, 3H), 0.68-0.74 (m, 1H), 0.77-0.89 (m, 4H), 2.12 (d, J=16.9 Hz, 1H), 2.66-2.74 (m, 1H), 2.78 (d, J=16.9 Hz, 1H), 4.11 (d, J=14.8 Hz, 1H), 4.60 (s, 1H), 4.77 (d, J=14.8 Hz, 1H), 6.79 (s, 1H), 7.13-7.21 (m, 2H), 7.23-7.33 (m, 3H).

LC-MS (MET-uPLC-AB-102): 99% (UV), Rt=2.70 min, m/z (ESI$^+$)=313.1 [M+H]$^+$

2-{5-Benzyl-6-oxo-5-azaspiro[2.4]heptan-4-yl}-N-[(1R,2S)-2-fluorocyclopropyl]-2-oxoacetamide (FP 346)

The title compound was synthesised from 2-{5-benzyl-6-oxo-5-azaspiro[2.4]heptan-4-yl}-2-oxoacetic acid (I-499) in a similar manner to general procedure 6 (general scheme 11a) using the tosyl salt of the amine in DMF as solvent to give a yellow viscous oil (48 mg, 100% purity, 20%) after purification by preparative LC (acidic pH, standard elution method).

$^1$H NMR (500 MHz, Chloroform-d) δ 0.53-0.63 (m, 1H), 0.67-0.75 (m, 1H), 0.78-0.87 (m, 2H), 0.92-1.03 (m, 1H), 1.14-1.28 (m, 1H), 2.09-2.17 (m, 1H), 2.72-2.85 (m, 2H), 4.06-4.14 (m, 1H), 4.54-4.61 (m, 1H), 4.61-4.77 (m, 1H), 4.78-4.84 (m, 1H), 6.94 (s, 1H), 7.11-7.23 (m, 2H), 7.23-7.34 (m, 3H).

LC-MS (MET-uPLC-AB-102): 100% (UV), Rt=2.57 min, m/z (ESI$^+$)=331.1 [M+H]$^+$

2-{5-Benzyl-6-oxo-5-azaspiro[2.4]heptan-4-yl}-N-methyl-2-oxoacetamide (FP 347)

The title compound was synthesised from 2-{5-benzyl-6-oxo-5-azaspiro-[2.4]heptan-4-yl}-2-oxoacetic acid (I-499) in a similar manner to general procedure 6 (general scheme 11a) using methylamine (2M in THF solution) and DMF as solvent to give a yellow viscous oil (110 mg, 99% purity, 62%) after purification by preparative LC (acidic pH, standard elution method).

$^1$H NMR (500 MHz, Chloroform-d) δ 0.52-0.63 (m, 1H), 0.65-0.74 (m, 1H), 0.77-0.88 (m, 2H), 2.11 (d, J=16.9 Hz, 1H), 2.77 (d, J=16.9 Hz, 1H), 2.81 (d, J=5.2 Hz, 3H), 4.05 (d, J=14.9 Hz, 1H), 4.59 (s, 1H), 4.81 (d, J=14.9 Hz, 1H), 6.74-6.95 (m, 1H), 7.14-7.19 (m, 2H), 7.22-7.33 (m, 3H).

LC-MS (MET-uPLC-AB-102): 99% (UV), Rt=2.29 min, m/z (ESI$^+$)=287.0 [M+H]$^+$

2-{5-Benzyl-6-oxo-5-azaspiro[2.4]heptan-4-yl}-N-ethyl-2-oxoacetamide (FP 348)

The title compound was synthesised from 2-{5-benzyl-6-oxo-5-azaspiro[2.4]heptan-4-yl}-2-oxoacetic acid (I-499) in a similar manner to general procedure 6 (general scheme 11a) using ethylamine (2M in THF solution) and DMF as solvent to give an off-white powder (69 mg, 100% purity, 37%) after purification by preparative LC (acidic pH, standard elution method).

$^1$H NMR (500 MHz, Chloroform-d) δ 0.52-0.61 (m, 1H), 0.66-0.74 (m, 1H), 0.78-0.88 (m, 2H), 1.16 (t, J=7.3 Hz, 3H), 2.11 (d, J=16.9 Hz, 1H), 2.77 (d, J=16.9 Hz, 1H), 3.27 (m, 2H), 4.06 (d, J=14.9 Hz, 1H), 4.61 (s, 1H), 4.81 (d, J=14.9 Hz, 1H), 6.70-6.86 (m, 1H), 7.09-7.21 (m, 2H), 7.22-7.31 (m, 3H).

LC-MS (MET-uPLC-AB-102): 100% (UV), Rt=2.60 min, m/z (ESI$^+$)=301.1 [M+H]$^+$

GENERAL SCHEME 24

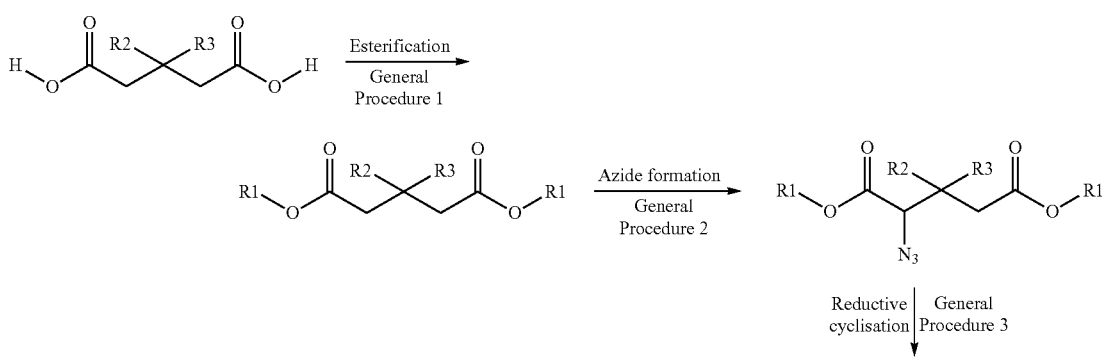

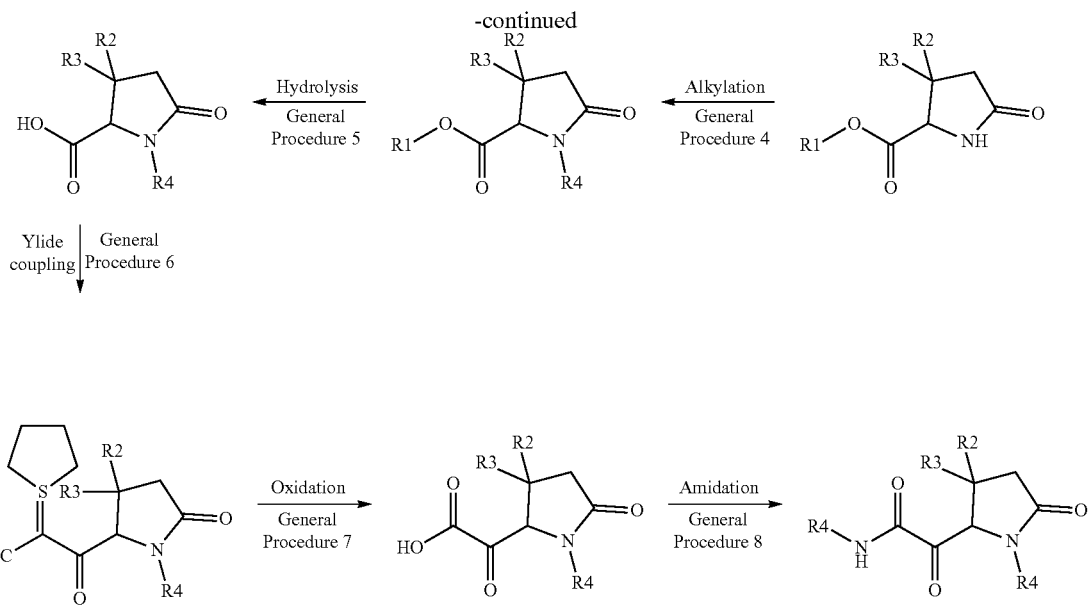

General Procedure 1 (General Scheme 24): Esterification 1,5-Dimethyl 3,3-dimethylpentanedioate (I-502)

To a stirred solution of 3,3-dimethylpentanedioic acid (5.0 g, 31.22 mmol) in MeOH (40 mL) was added conc. $H_2SO_4$ (176 μL, 3.303 mmol). The reaction mixture was heated at 60° C. for 4 h then cooled to RT and concentrated in vacuo. The residue was filtered through a plug of sodium sulfate, the filter cake washed with 20% heptane in EtOAc (~40 mL) and the combined filtrates concentrated in vacuo to afford 5.35 g of 1,5-dimethyl 3,3-dimethylpentanedioate as a pale yellow liquid (100% purity, 91%) which was used without further purification in the next stage.

$^1$H NMR (500 MHz, Chloroform-d) δ 1.13 (s, 6H), 2.44 (s, 4H), 3.67 (s, 6H).

LC-MS (METCR0990): 100% (UV), Rt=1.58 min, m/z (ESI$^+$)=189.2 [M+H]$^+$

General Procedure 2 (General Scheme 24): Azide Formation 1,5-Dimethyl 2-azido-3,3-dimethylpentanedioate (I-503)

To a solution of 1,5-dimethyl 3,3-dimethylpentanedioate (I-502, 2.75 g, 14.61 mmol) in THF (30 mL) at −78° C. under nitrogen was added lithium diisopropylamide (2M in heptane, 8.04 mL, 16.07 mmol) dropwise and the reaction mixture stirred for 1 h. A solution of 2,4,6-tris(propan-2-yl)benzene-1-sulfonyl azide (4.52 g, 13.15 mmol) in THF (50 mL) was added dropwise and the mixture stirred at −78° C. for 2 h. Glacial AcOH (0.84 mL) was added dropwise and the reaction allowed to warm to RT with stirring over 30 min then diluted with water (50 mL). The mixture was extracted with DCM (3×30 mL) and the combined organic extracts washed with brine (50 mL), dried over (MgSO$_4$ and concentrated in vacuo. The residue was purified by flash column chromatography on normal phase silica (50 g SNAP KP-SIL cartridge, 0-30% EtOAc in heptane gradient) to afford 1.55 g of 1,5-dimethyl 2-azido-3,3-dimethylpentanedioate as a yellow viscous oil (60% purity by $^1$H NMR, 28%).

$^1$H NMR (500 MHz, Chloroform-d) δ 1.03 (d, J=2.0 Hz, 6H), 2.29 (d, J=15.1 Hz, 1H), 2.42 (d, J=15.1 Hz, 1H), 3.61 (s, 3H), 3.73 (s, 3H), 4.22 (s, 1H).

LC-MS (METCR1603): 98% (UV), Rt=4.33 min, m/z (ESI$^+$)=230.2 [M+H]$^+$

General Procedure 3 (General Scheme 24): Reductive Cyclisation

Methyl 3,3-dimethyl-5-oxopyrrolidine-2-carboxylate/ethyl 3,3-dimethyl-5-oxopyrrolidine-2-carboxylate (I-504)

A suspension of 1,5-dimethyl 2-azido-3,3-dimethylpentanedioate (I-502, 60% purity by $^1$H NMR, 1.10 g, 2.83 mmol) and 10% palladium on charcoal Pd/C (11% w/w, 121 mg, 1.13 mmol) in EtOH (10 mL) was stirred at RT under 1 atm of hydrogen for 20 h. The reaction mixture was filtered through a plug of Celite washed with EtOAc (20 mL) and MeOH (20 mL). The combined filtrates were concentrated in vacuo and the residue was purified by flash column chromatography on normal phase silica (25 g SNAP KP-SIL cartridge, 0-100% EtOAc in heptane gradient followed by 0-100% MeOH in EtOAc gradient) to afford a mixture of pyrrolidinone and uncyclised glutamic ester. The material was dissolved in EtOH (5 mL) and triethylamine (2 mL), heated at 80° C. for 18 h then concentrated in vacuo to afford the product as a mixture of ethyl and methyl esters in an estimated 1:1 ratio (340 mg, 90% purity by $^1$H NMR, 61%) which were used in the next step without any additional purification.

General Procedure 4 (General Scheme 24): Alkylation

Methyl 1-benzyl-3,3-dimethyl-5-oxopyrrolidine-2-carboxylate (I-505)

To an ice-cooled stirred solution of methyl and ethyl 3,3-dimethyl-5-oxopyrrolidine-2-carboxylate/ethyl 3,3-dimethyl-5-oxopyrrolidine-2-carboxylates (I-504, 340 mg, 90% purity by $^1$H NMR, 199 mol) in anhydrous DMF (3 mL) was added NaH (60% dispersion in mineral oil, 111 mg, 2.78 mmol) and the reaction mixture was stirred for 30 min. Benzyl bromide (236 µL, 0.199 mol) was added dropwise and the reaction mixture allowed to warm to RT with stirring for 1 h, then quenched with water (10 mL). The aqueous layer was extracted with DCM (3×15 mL), the combined organic extracts washed with brine (2×20 mL), dried over MgSO$_4$, filtered and concentrated in vacuo. The residue was purified by flash column chromatography on normal phase silica (25 g SNAP KP-SIL cartridge, 0-100% EtOAc in heptane gradient) to afford 150 mg of a crude mixture of methyl, ethyl and benzyl 1-benzyl-3,3-dimethyl-5-oxopyrrolidine-2-carobxylates which was taken through to the next stage without further purification General Procedure 5 (General Scheme 24): Hydrolysis 1-Benzyl-3,3-dimethyl-5-oxopyrrolidine-2-carboxylic acid (I-506)

A suspension of crude methyl 1-benzyl-3,3-dimethyl-5-oxopyrrolidine-2-carboxylate (I-504, 140 mg, 0.82 mmol) and lithium hydroxide monohydrate (96 mg, 2.29 mmol) in 1:1 MeOH/H$_2$O (3 mL) was stirred at RT for 2 h. The organic solvent was removed in vacuo and the suspension diluted with H$_2$O (5 mL) and acidified to pH~1 using 1N HCl (~3 mL). The precipitate was filtered off and dried under vacuum suction for 20 min to afford 80 mg of 1-benzyl-3,3-dimethyl-5-oxopyrrolidine-2-carboxylic acid as an off-white solid (100% purity, 71%).

$^1$H NMR (500 MHz, Chloroform-d) δ 1.17 (s, 6H), 2.27 (d, J=16.5 Hz, 1H), 2.54 (d, J=16.5 Hz, 1H), 3.58 (s, 1H), 3.88 (d, J=14.8 Hz, 1H), 5.14 (d, J=14.8 Hz, 1H), 7.23-7.27 (m, 2H), 7.29-7.38 (m, 3H).

LC-MS (METCR0990): 100% (UV), Rt=0.97 min, m/z (ESI$^+$)=248.2 [M+H]$^+$

General Procedure 6 (General Scheme 24): Ylide Coupling 3-(1-Benzyl-3,3-dimethyl-5-oxopyrrolidin-2-yl)-2-(1λ$^4$-thiolan-1-ylidene)-3-oxopropanenitrile (I-507)

To a stirred solution of 1-benzyl-3,3-dimethyl-5-oxopyrrolidine-2-carboxylic acid (I-506, 250 mg, 1.01 mmol), HATU (423 mg, 1.11 mmol) and DIPEA (0.53 mL, 3.03 mmol) in DCM (10 mL) was added 1-(cyanomethyl)thiolan-1-ium bromide (320 mg, 1.213 mmol, synthesised by the procedure outlined in WO2014/154829) and the reaction mixture stirred at RT for 1 h. The mixture was quenched with saturated NH$_4$Cl (15 mL) and extracted with DCM (3×10 mL). The combined organic extracts were washed with brine (10 mL), dried over MgSO$_4$, filtered and concentrated in vacuo. The residue was purified by flash column chromatography on normal phase silica (10 g SNAP KP-SIL cartridge, 0-100% EtOAc in heptane gradient then 0-100% MeOH in EtOAc gradient) to afford 260 mg of 3-(1-benzyl-3,3-dimethyl-5-oxopyrrolidin-2-yl)-2-(1λ$^4$-thiolan-1-ylidene)-3-oxopropanenitrile as a viscous yellow oil (100% purity, 72%).

$^1$H NMR (500 MHz, Chloroform-d) δ 1.09 (s, 3H), 1.16 (s, 3H), 2.04-2.16 (m, 3H), 2.53-2.64 (m, 3H), 3.13-3.41 (m, 4H), 3.93-4.09 (m, 2H), 4.77 (d, J=14.6 Hz, 1H), 7.25-7.29 (m, 3H), 7.30-7.36 (m, 2H).

LC-MS (METCR0990): 100% (UV), Rt=1.45 min, m/z (ESI$^+$)=357.2 [M+H]$^+$

General Procedure 7 (General Scheme 24): Oxidation 2-(1-Benzyl-3,3-dimethyl-5-oxopyrrolidin-2-yl)-2-oxoacetic acid (I-508)

To an ice-cooled stirred solution of 3-(1-benzyl-3,3-dimethyl-5-oxopyrrolidin-2-yl)-2-(1λ$^4$-thiolan-1-ylidene)-3-oxopropanenitrile (I-507, 250 mg, 0.701 mmol) in 2:1 THF:H$_2$O (6 mL) was added under nitrogen Oxone (862 mg, 1.403 mmol). The reaction was stirred for 30 min with cooling then allowed to warm to RT and stirred for a further 1 h. The mixture was partitioned between EtOAc (10 mL) and 1N HCl (10 mL) and the phases separated. The aqueous phase was then extracted with EtOAc (2×10 mL) and the combined organic phases dried over MgSO$_4$, filtered and concentrated in vacuo to afford 220 mg of 2-(1-benzyl-3,3-dimethyl-5-oxopyrrolidin-2-yl)-2-oxoacetic acid (65% purity by $^1$H NMR, 74%) which was used crude in the next step without further purification.

$^1$H NMR (500 MHz, Chloroform-d) δ 1.09 (s, 3H), 1.24 (s, 3H), 2.29 (d, J=16.7 Hz, 1H), 2.52 (d, J=16.7 Hz, 1H), 3.94 (d, J=14.6 Hz, 1H), 4.54 (s, 1H), 4.94 (d, J=14.6 Hz, 1H), 5.47 (s, 1H), 7.16-7.20 (m, 2H), 7.31-7.36 (m, 3H).

LC-MS (METCR0990): 94% (UV), Rt=1.03 min, m/z (ESI$^+$)=276.2 [M+H]$^+$

General Procedure 8 (General Scheme 24): Amidation 2-(1-Benzyl-3,3-dimethyl-5-oxopyrrolidin-2-yl)-N-cyclopropyl-2-oxoacetamide (FP 349)

To a stirred solution of 2-(1-benzyl-3,3-dimethyl-5-oxopyrrolidin-2-yl)-2-oxoacetic acid (I-508, 205 mg, 0.48 mmol) and cyclopropylamine (84 µL, 1.21 mmol) in DMF (2 mL) was added DIPEA (253 µL, 1.45 mmol) and T3P (50% solution in DMF, 720 µL, 1.21 mmol) and the reaction mixture stirred at RT for 1 h. The mixture was partitioned between EtOAc (5 mL) and 1N HCl (5 mL). The aqueous phase was extracted with EtOAc (3×10 mL) and the combined organic phases washed with brine (10 mL), dried over MgSO$_4$, filtered and concentrated in vacuo. The residue was purified by flash column chromatography on normal phase silica (10 g SNAP KP-SIL cartridge, 0-100% EtOAc in heptane gradient) to afford 78 mg of 2-(1-benzyl-3,3-dimethyl-5-oxopyrrolidin-2-yl)-N-cyclopropyl-2-oxoacetamide as a yellow solid (95% purity by $^1$H NMR, 49%).

$^1$H NMR (500 MHz, Chloroform-d) δ 0.48-0.64 (m, 2H), 0.81-0.90 (m, 2H), 0.99 (s, 3H), 1.23 (s, 3H), 2.17 (d, J=16.5 Hz, 1H), 2.38 (d, J=16.5 Hz, 1H), 2.68-2.76 (m, 1H), 3.94 (d, J=14.6 Hz, 1H), 4.77 (d, J=14.6 Hz, 1H), 4.81 (s, 1H), 6.75 (s, 1H), 7.08-7.21 (m, 2H), 7.24-7.32 (m, 3H).

LC-MS (MET-uPLC-AB-102): 98% (UV), Rt=2.58 min, m/z (ESI$^+$)=315.2 [M+H]$^+$

TABLE 1

| Intermediates (I-1-I-514) | |
|---|---|
| 3-chlorobenzyl (E)-but-2-enamide | I-1 |
| 3-chlorobenzyl 3-methylbut-2-enamide | I-2 |
| 3-chlorobenzyl (E)-cinnamamide | I-3 |
| cyclopropylmethyl (E)-but-2-enamide | I-4 |
| cyclopropyl (E)-but-2-enamide | I-5 |
| isobutyl (E)-but-2-enamide | I-6 |
| 3-chlorobenzyl acrylamide | I-7 |
| cyclohexylmethyl (E)-but-2-enamide | I-8 |
| 2-(cyclohexyloxy)ethyl (E)-but-2-enamide | I-9 |

TABLE 1-continued
Intermediates (I-1-I-514)
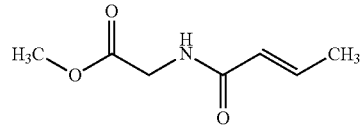 I-10
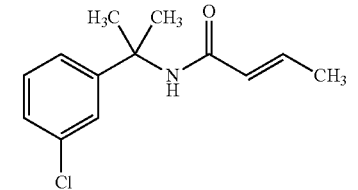 [SMILES: C/C=C/C(=O)NC(C)(C)c1cccc(Cl)c1] I-11
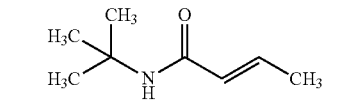 I-12
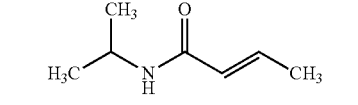 I-13
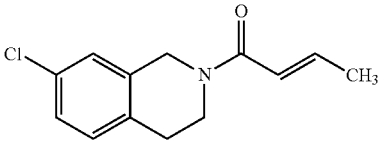 [SMILES: C/C=C/C(=O)N1CCc2ccc(Cl)cc2C1] I-14
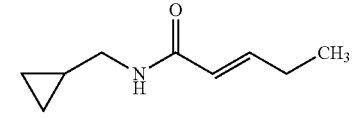 I-15
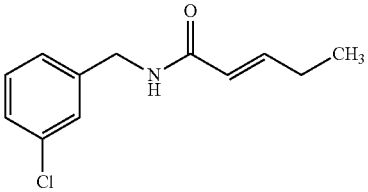 I-16
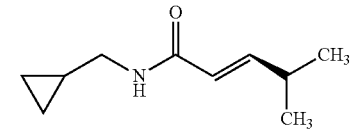 I-17
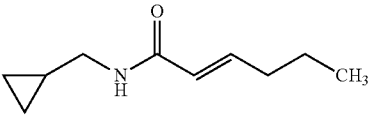 I-18
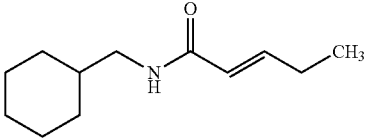 I-19

TABLE 1-continued

Intermediates (I-1-I-514)

| | |
|---|---|
| Structure of N-(3-chlorobenzyl)-4-methylpent-2-enamide | I-20 |
| Structure of N-(cyclopropylmethyl)-5-methylhex-2-enamide | I-21 |
| Structure of N-(3-chlorobenzyl)-5-methylhex-2-enamide | I-22 |
| Ethyl 3-cyclopropylacrylate | I-23a |
| Lithium 3-cyclopropylacrylate | I-23b |
| N-(cyclopropylmethyl)-3-cyclopropylacrylamide | I-23c |
| Diethyl (2-((cyclopropylmethyl)amino)-2-oxoethyl)phosphonate | I-24a |
| N-(cyclopropylmethyl)-5-methoxypent-2-enamide | I-24b |
| N-(cyclopropylmethyl)-3-(tetrahydro-2H-pyran-4-yl)acrylamide | I-25 |
| N-(cyclopropylmethyl)-5-phenylpent-2-enamide | I-26 |

TABLE 1-continued
Intermediates (I-1-I-514)
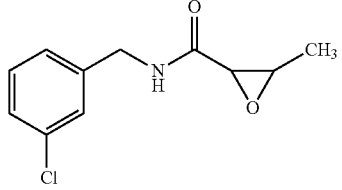 I-27
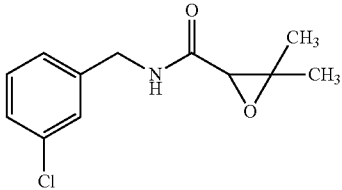 [SMILES: CC1(C)OC1C(=O)NCc1cccc(Cl)c1] I-28
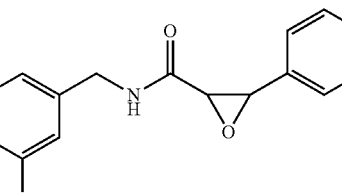 I-29
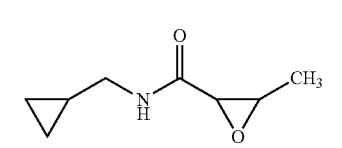 I-30
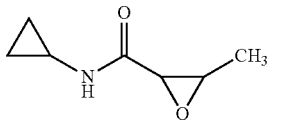 I-31
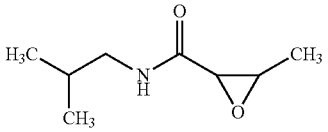 I-32
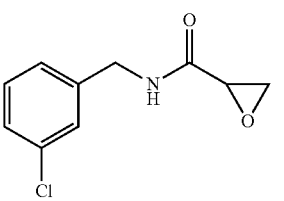 [SMILES: O=C(NCc1cccc(Cl)c1)C1CO1] I-33
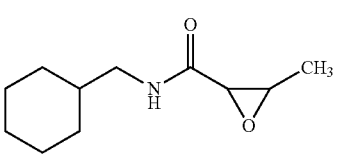 I-34
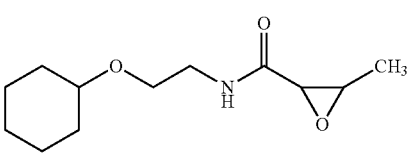 [SMILES: CC1OC1C(=O)NCCOC1CCCCC1] I-35

TABLE 1-continued

Intermediates (I-1-I-514)

| Structure | ID |
|---|---|
| methyl 2-[(3-methyloxiran-2-yl)carbonylamino]acetate | I-36 |
| N-[1-(3-chlorophenyl)-1-methylethyl]-3-methyloxirane-2-carboxamide | I-37 |
| N-tert-butyl-3-methyloxirane-2-carboxamide | I-38 |
| N-isopropyl-3-methyloxirane-2-carboxamide | I-39 |
| (7-chloro-3,4-dihydro-1H-isoquinolin-2-yl)-(3-methyloxiran-2-yl)methanone | I-40 |
| N-(cyclopropylmethyl)-3-ethyloxirane-2-carboxamide | I-41 |
| N-(3-chlorobenzyl)-3-ethyloxirane-2-carboxamide | I-42 |
| N-(cyclopropylmethyl)-3-isopropyloxirane-2-carboxamide | I-43 |
| N-(cyclopropylmethyl)-3-propyloxirane-2-carboxamide | I-44 |
| N-(cyclohexylmethyl)-3-ethyloxirane-2-carboxamide | I-45 |

TABLE 1-continued
Intermediates (I-1-I-514)
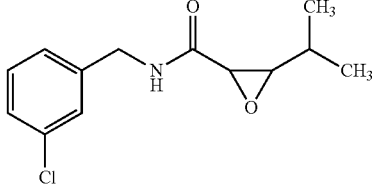 [SMILES: CC(C)C1OC1C(=O)NCc1cccc(Cl)c1]   I-46
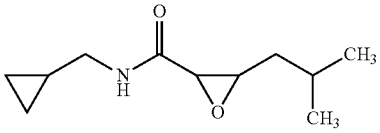   I-47
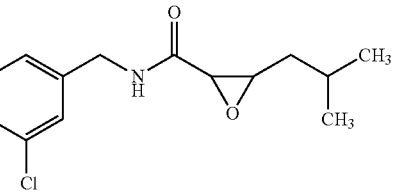   I-48
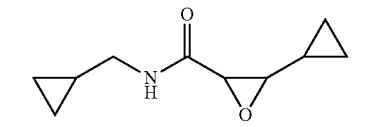 [SMILES: O=C(NCC1CC1)C1OC1C1CC1]   I-49
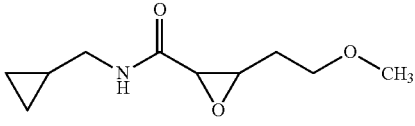   I-50
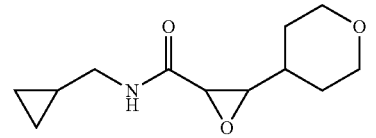 [SMILES: O=C(NCC1CC1)C1OC1C1CCOCC1]   I-51
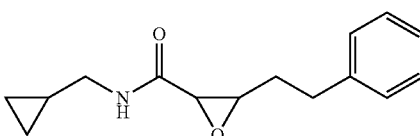   I-52
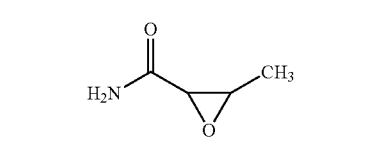   I-53
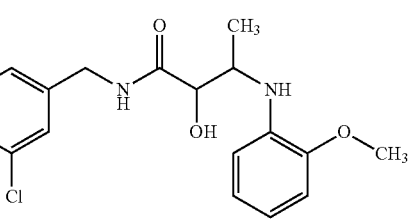   I-54

TABLE 1-continued

Intermediates (I-1-I-514)

| | |
|---|---|
| Structure of I-55: 3-chlorobenzyl amide of 2-hydroxy-3-(cyclohexylamino)butanamide | I-55 |
| Structure of I-56: 3-chlorobenzyl amide of 2-hydroxy-3-((3-methoxyphenyl)amino)butanamide | I-56 |
| Structure of I-57: 3-chlorobenzyl amide of 2-hydroxy-3-((4-methoxyphenyl)amino)butanamide | I-57 |
| Structure of I-58: 3-chlorobenzyl amide of 2-hydroxy-3-(phenylamino)butanamide | I-58 |
| Structure of I-59: 3-chlorobenzyl amide of 2-hydroxy-3-(benzylamino)butanamide | I-59 |
| Structure of I-60: 3-chlorobenzyl amide of 2-hydroxy-3-(isopropylamino)butanamide | I-60 |
| Structure of I-61: 3-chlorobenzyl amide of 2-hydroxy-3-((tetrahydro-2H-pyran-4-yl)amino)butanamide | I-61 |

TABLE 1-continued
Intermediates (I-1-I-514)
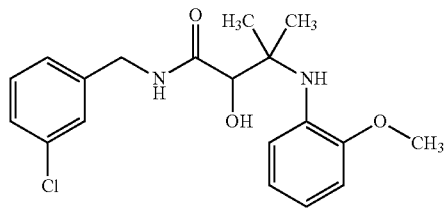 [SMILES: COc1ccccc1NC(C)(C)C(O)C(=O)NCc1cccc(Cl)c1] I-62
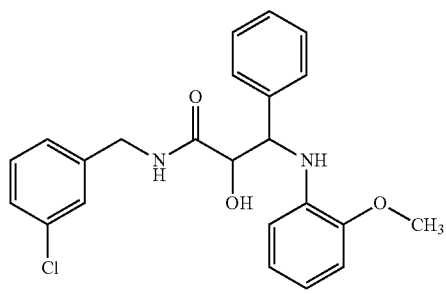 [SMILES: COc1ccccc1NC(c1ccccc1)C(O)C(=O)NCc1cccc(Cl)c1] I-63
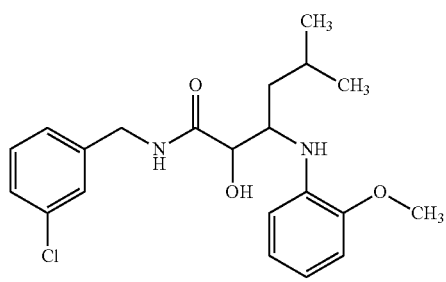 [SMILES: COc1ccccc1NC(CC(C)C)C(O)C(=O)NCc1cccc(Cl)c1] I-64
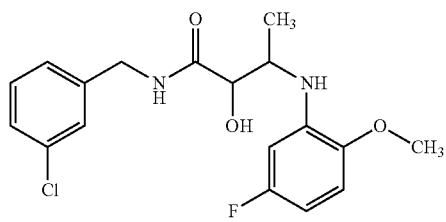 [SMILES: COc1ccc(F)cc1NC(C)C(O)C(=O)NCc1cccc(Cl)c1] I-65
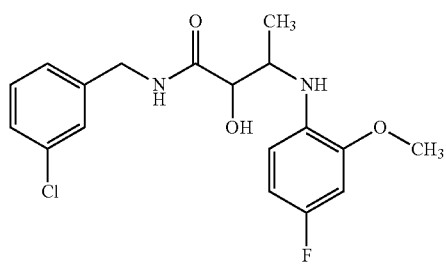 [SMILES: COc1cc(F)ccc1NC(C)C(O)C(=O)NCc1cccc(Cl)c1] I-66
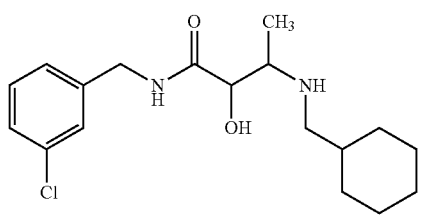 [SMILES: CC(NCC1CCCCC1)C(O)C(=O)NCc1cccc(Cl)c1] I-67

TABLE 1-continued

Intermediates (I-1-I-514)

| | |
|---|---|
| (structure) | I-68 |
| (structure) | I-69 |
| (structure) | I-70 |
| (structure) | I-71 |
| (structure) | I-72 |
| (structure) | I-73 |
| (structure) | I-74 |

TABLE 1-continued
Intermediates (I-1-I-514)
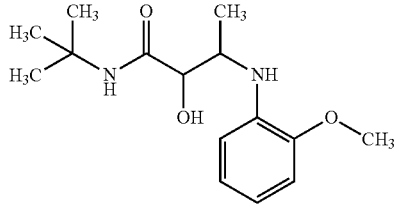 [SMILES: COc1ccccc1NC(C)C(O)C(=O)NC(C)(C)C]
I-75
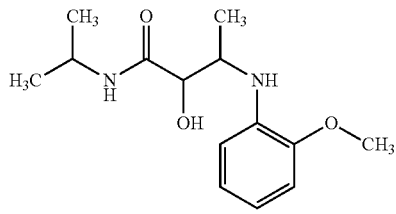 [SMILES: COc1ccccc1NC(C)C(O)C(=O)NC(C)C]
I-76
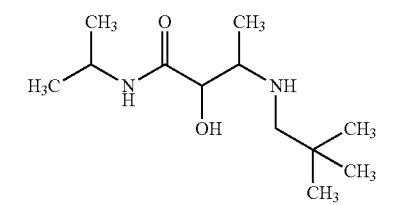 [SMILES: CC(C)NC(=O)C(O)C(C)NCC(C)(C)C]
I-77
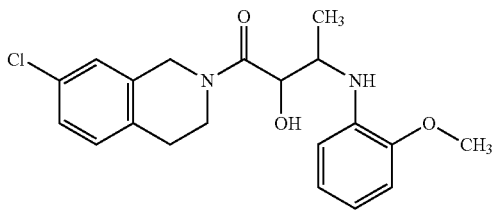 [SMILES: COc1ccccc1NC(C)C(O)C(=O)N1CCc2ccc(Cl)cc2C1]
I-78
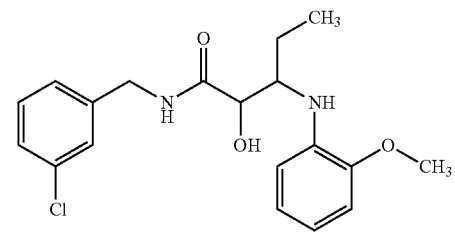 [SMILES: CCC(Nc1ccccc1OC)C(O)C(=O)NCc1cccc(Cl)c1]
I-79
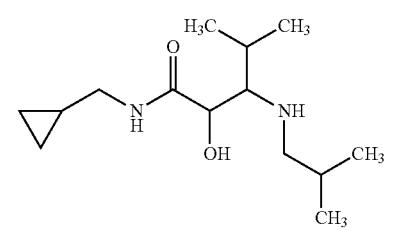 [SMILES: CC(C)CNC(C(C)C)C(O)C(=O)NCC1CC1]
I-80
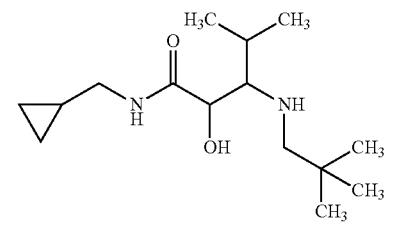 [SMILES: CC(C)C(NCC(C)(C)C)C(O)C(=O)NCC1CC1]
I-81

TABLE 1-continued
Intermediates (I-1-I-514)
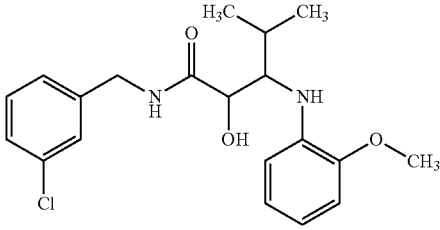 [SMILES: COc1ccccc1NC(C(C)C)C(O)C(=O)NCc1cccc(Cl)c1]  I-82
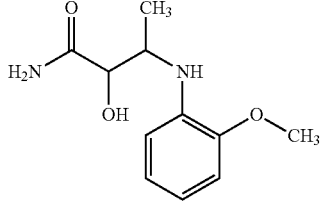 [SMILES: COc1ccccc1NC(C)C(O)C(N)=O]  I-83
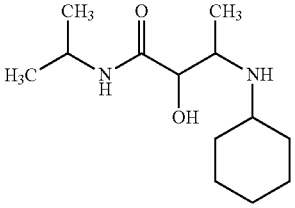 [SMILES: CC(C)NC(=O)C(O)C(C)NC1CCCCC1]  I-84
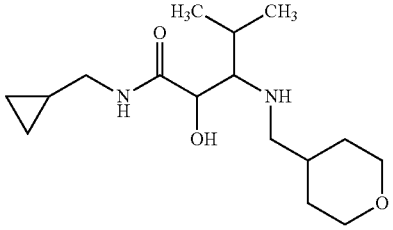 [SMILES: CC(C)C(NCC1CCOCC1)C(O)C(=O)NCC1CC1]  I-85
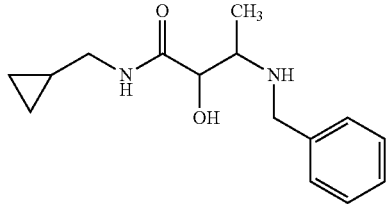 [SMILES: CC(NCc1ccccc1)C(O)C(=O)NCC1CC1]  I-86
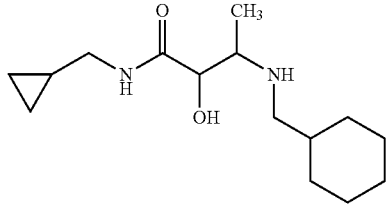 [SMILES: CC(NCC1CCCCC1)C(O)C(=O)NCC1CC1]  I-87
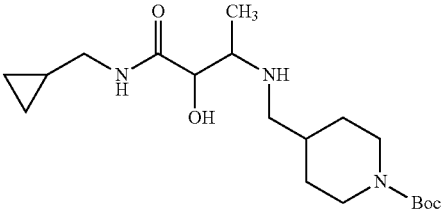 [SMILES: CC(NCC1CCN(C(=O)OC(C)(C)C)CC1)C(O)C(=O)NCC1CC1]  I-88

TABLE 1-continued
Intermediates (I-1-I-514)
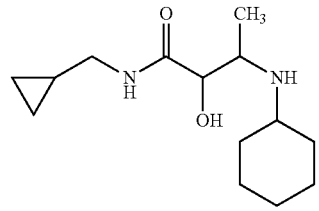 [SMILES: CC(NC1CCCCC1)C(O)C(=O)NCC1CC1] I-89
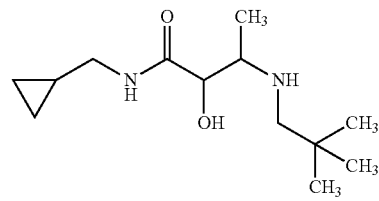 [SMILES: CC(NCC(C)(C)C)C(O)C(=O)NCC1CC1] I-90
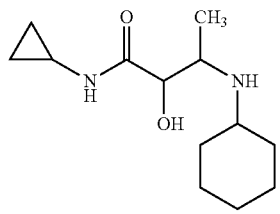 [SMILES: CC(NC1CCCCC1)C(O)C(=O)NC1CC1] I-91
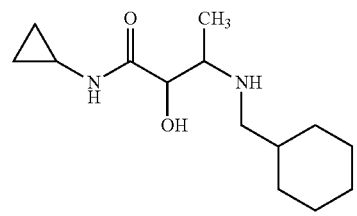 [SMILES: CC(NCC1CCCCC1)C(O)C(=O)NC1CC1] I-92
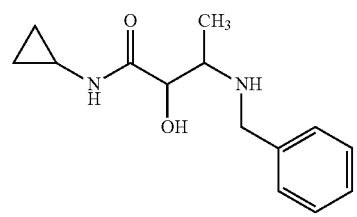 [SMILES: CC(NCc1ccccc1)C(O)C(=O)NC1CC1] I-93
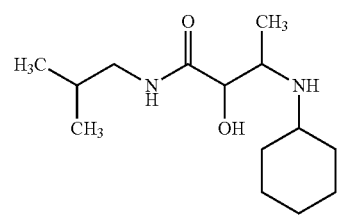 [SMILES: CC(C)CNC(=O)C(O)C(C)NC1CCCCC1] I-94
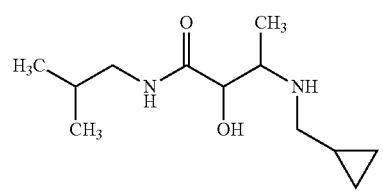 [SMILES: CC(C)CNC(=O)C(O)C(C)NCC1CC1] I-95

TABLE 1-continued
Intermediates (I-1-I-514)
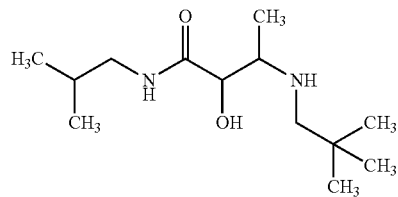 [SMILES: CC(C)CNC(=O)C(O)C(C)NCC(C)(C)C] I-96
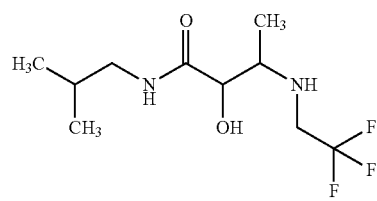 [SMILES: CC(C)CNC(=O)C(O)C(C)NCC(F)(F)F] I-97
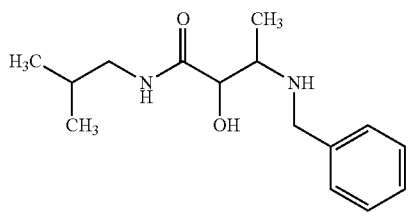 [SMILES: CC(C)CNC(=O)C(O)C(C)NCc1ccccc1] I-98
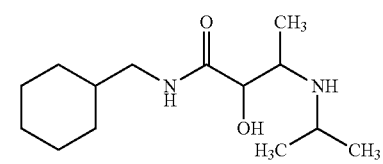 I-99
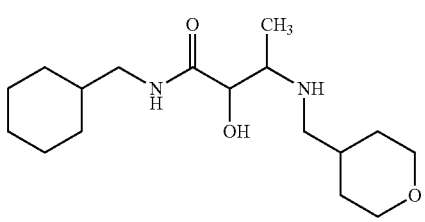 [SMILES: CC(NCC1CCOCC1)C(O)C(=O)NCC1CCCCC1] I-100
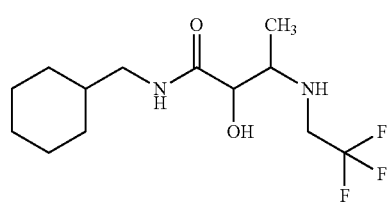 [SMILES: CC(NCC(F)(F)F)C(O)C(=O)NCC1CCCCC1] I-101
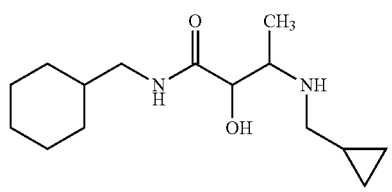 [SMILES: CC(NCC1CC1)C(O)C(=O)NCC1CCCCC1] I-102

TABLE 1-continued
Intermediates (I-1-I-514)
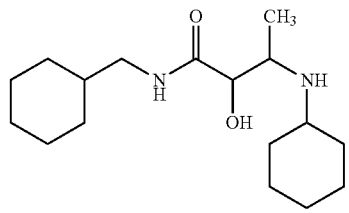 [SMILES: CC(NC1CCCCC1)C(O)C(=O)NCC1CCCCC1]
I-103
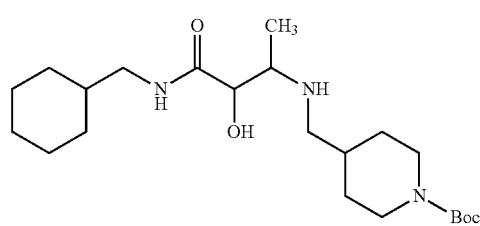 [SMILES: CC(NCC1CCN(C(=O)OC(C)(C)C)CC1)C(O)C(=O)NCC1CCCCC1]
I-104
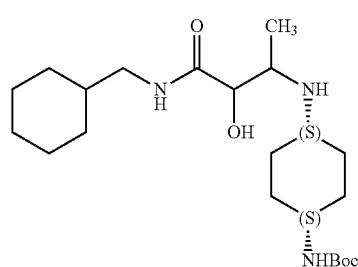
I-105
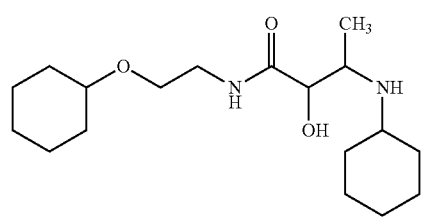 [SMILES: CC(NC1CCCCC1)C(O)C(=O)NCCOC1CCCCC1]
I-106
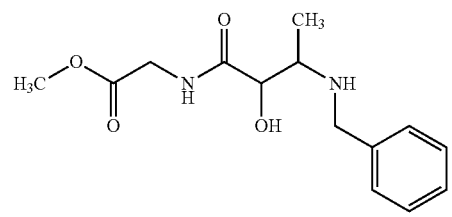 [SMILES: COC(=O)CNC(=O)C(O)C(C)NCc1ccccc1]
I-107
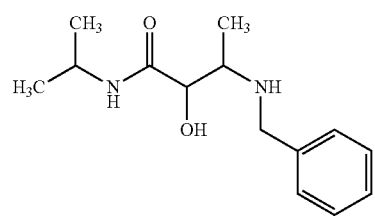 [SMILES: CC(C)NC(=O)C(O)C(C)NCc1ccccc1]
I-108

TABLE 1-continued

Intermediates (I-1-I-514)

| | |
|---|---|
| (structure) | I-109 |
| (structure) | I-110 |
| (structure) | I-111 |
| (structure) | I-112 |
| (structure) | I-113 |
| (structure) | I-114 |

TABLE 1-continued
Intermediates (I-1-I-514)
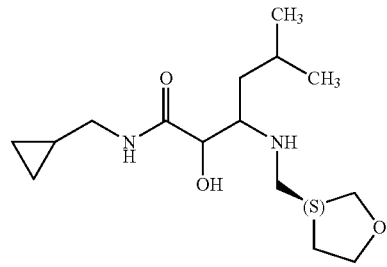
I-115
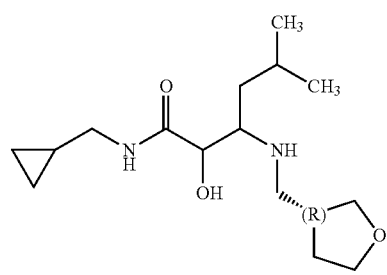
I-116
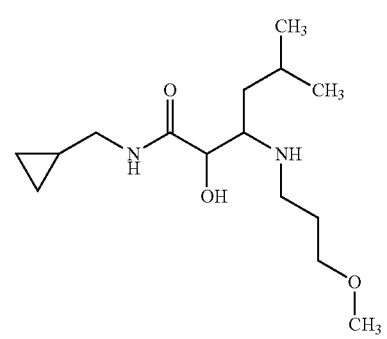 [SMILES: COCCCNC(CC(C)C)C(O)C(=O)NCC1CC1]
I-117
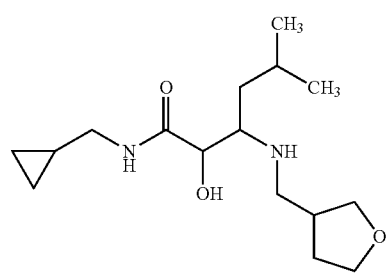 [SMILES: CC(C)CC(NCC1CCOC1)C(O)C(=O)NCC1CC1]
I-118
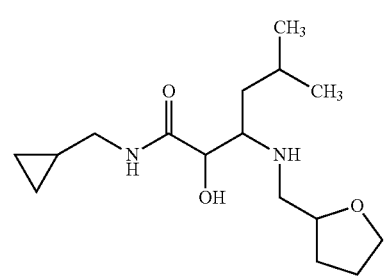 [SMILES: CC(C)CC(NCC1CCCO1)C(O)C(=O)NCC1CC1]
I-119

TABLE 1-continued
Intermediates (I-1-I-514)
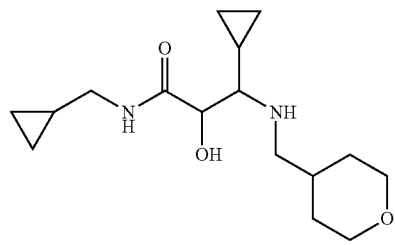 [SMILES: O=C(NCC1CC1)C(O)C(NCC1CCOCC1)C1CC1]
I-120
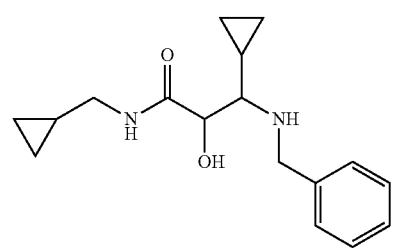 [SMILES: O=C(NCC1CC1)C(O)C(NCc1ccccc1)C1CC1]
I-121
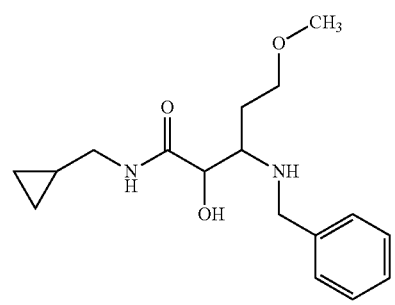 [SMILES: COCCC(NCc1ccccc1)C(O)C(=O)NCC1CC1]
I-122
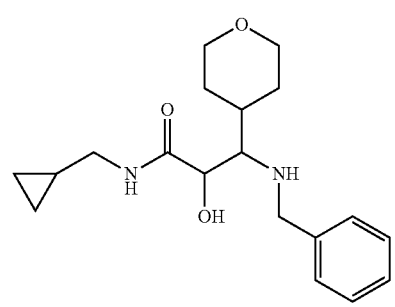 [SMILES: O=C(NCC1CC1)C(O)C(NCc1ccccc1)C1CCOCC1]
I-123
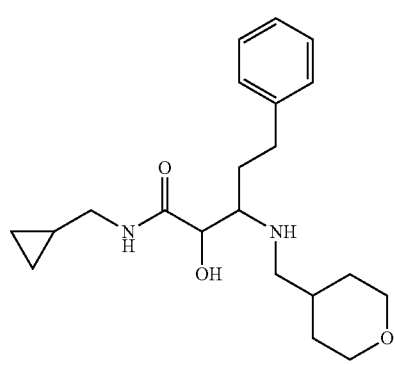 [SMILES: O=C(NCC1CC1)C(O)C(CCc1ccccc1)NCC1CCOCC1]
I-124

TABLE 1-continued
Intermediates (I-1-I-514)
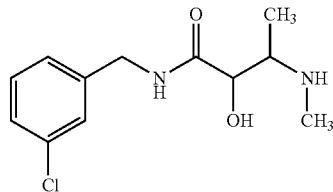 [SMILES: CNC(C)C(O)C(=O)NCc1cccc(Cl)c1] I-125
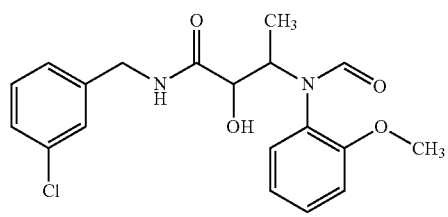 [SMILES: COc1ccccc1N(C=O)C(C)C(O)C(=O)NCc1cccc(Cl)c1] I-126
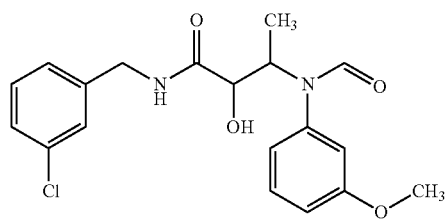 [SMILES: COc1cccc(N(C=O)C(C)C(O)C(=O)NCc2cccc(Cl)c2)c1] I-127
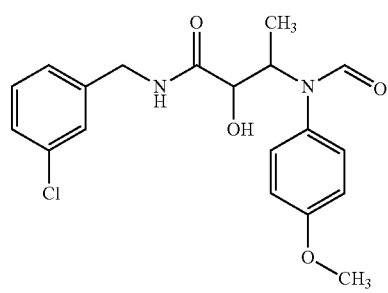 [SMILES: COc1ccc(N(C=O)C(C)C(O)C(=O)NCc2cccc(Cl)c2)cc1] I-128
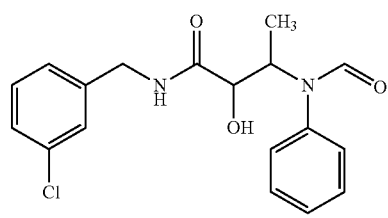 [SMILES: CC(C(O)C(=O)NCc1cccc(Cl)c1)N(C=O)c1ccccc1] I-129
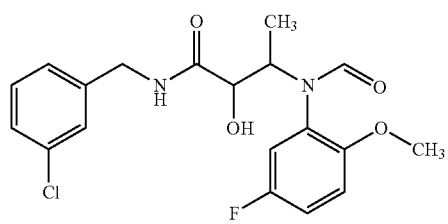 [SMILES: COc1ccc(F)cc1N(C=O)C(C)C(O)C(=O)NCc1cccc(Cl)c1] I-130

TABLE 1-continued

Intermediates (I-1-I-514)

| | |
|---|---|
| (structure) | I-131 |
| (structure) | I-132 |
| (structure) | I-133 |
| (structure) | I-134 |
| (structure) | I-135 |
| (structure) | I-136 |

TABLE 1-continued
Intermediates (I-1-I-514)
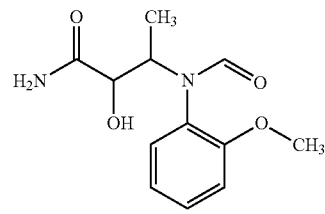 [SMILES: COc1ccccc1N(C=O)C(C)C(O)C(N)=O] I-137
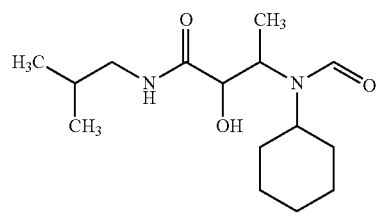 [SMILES: CC(C)CNC(=O)C(O)C(C)N(C=O)C1CCCCC1] I-138
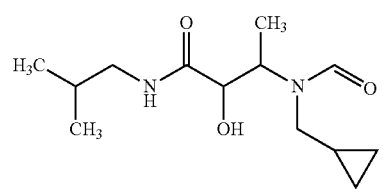 [SMILES: CC(C)CNC(=O)C(O)C(C)N(C=O)CC1CC1] I-139
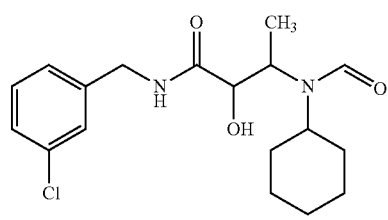 [SMILES: CC(C(O)C(=O)NCc1cccc(Cl)c1)N(C=O)C1CCCCC1] I-140
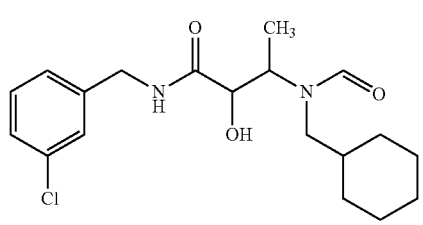 [SMILES: CC(C(O)C(=O)NCc1cccc(Cl)c1)N(C=O)CC1CCCCC1] I-141
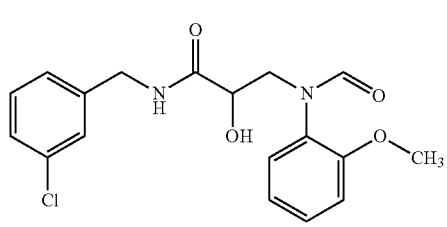 [SMILES: COc1ccccc1N(C=O)CC(O)C(=O)NCc1cccc(Cl)c1] I-142
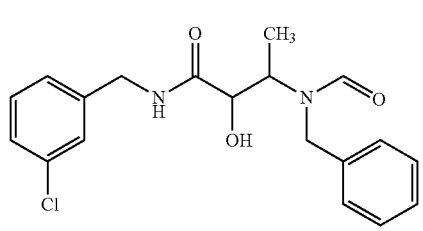 [SMILES: CC(C(O)C(=O)NCc1cccc(Cl)c1)N(C=O)Cc1ccccc1] I-143

TABLE 1-continued
Intermediates (I-1-I-514)
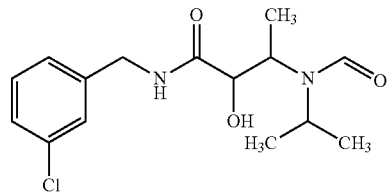 [SMILES: CC(C)N(C=O)C(C)C(O)C(=O)NCc1cccc(Cl)c1]
I-144
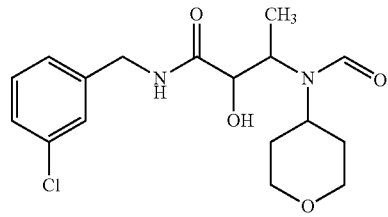 [SMILES: CC(C(O)C(=O)NCc1cccc(Cl)c1)N(C=O)C1CCOCC1]
I-145
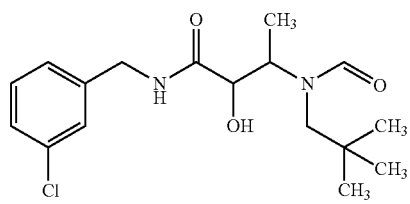
I-146
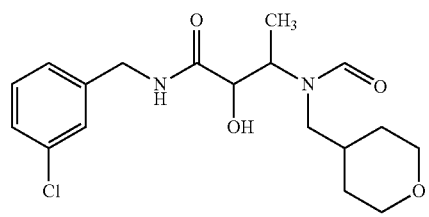 [SMILES: CC(C(O)C(=O)NCc1cccc(Cl)c1)N(C=O)CC1CCOCC1]
I-147
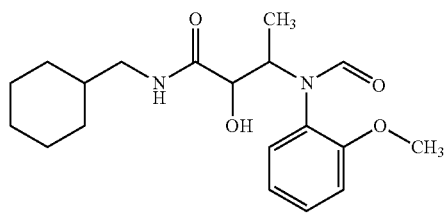 [SMILES: COc1ccccc1N(C=O)C(C)C(O)C(=O)NCC1CCCCC1]
I-148
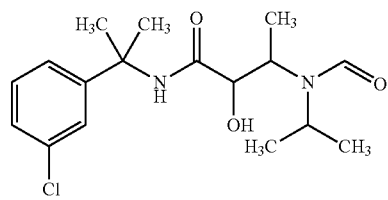 [SMILES: CC(C)N(C=O)C(C)C(O)C(=O)NC(C)(C)c1cccc(Cl)c1]
I-149
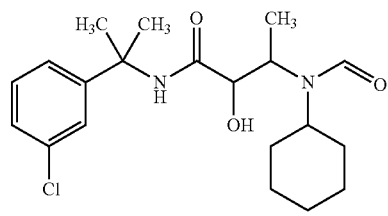 [SMILES: CC(C(O)C(=O)NC(C)(C)c1cccc(Cl)c1)N(C=O)C1CCCCC1]
I-150

TABLE 1-continued

Intermediates (I-1-I-514)

| | |
|---|---|
| (structure) | I-151 |
| (structure) | I-152 |
| (structure) | I-153 |
| (structure) | I-154 |
| (structure) | I-155 |
| (structure) | I-156 |
| (structure) | I-157 |

TABLE 1-continued

Intermediates (I-1-I-514)

| | |
|---|---|
| (structure) | I-158 |
| (structure) | I-159 |
| (structure) | I-160 |
| (structure) | I-161 |
| (structure) | I-162 |
| (structure) | I-163 |
| (structure) | I-164 |

TABLE 1-continued
Intermediates (I-1-I-514)
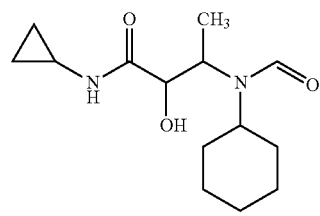 [SMILES: CC(C(O)C(=O)NC1CC1)N(C=O)C1CCCCC1] I-165
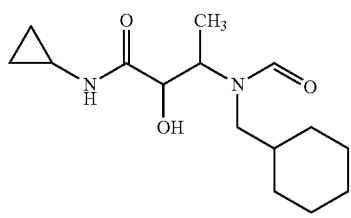 [SMILES: CC(C(O)C(=O)NC1CC1)N(C=O)CC1CCCCC1] I-166
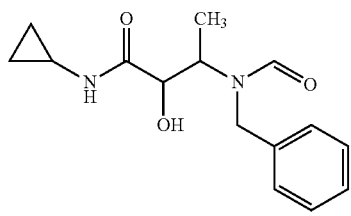 [SMILES: CC(C(O)C(=O)NC1CC1)N(C=O)Cc1ccccc1] I-167
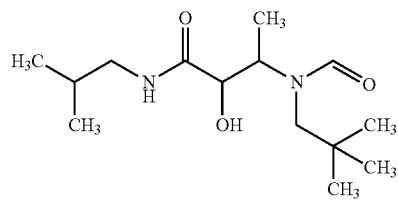 I-168
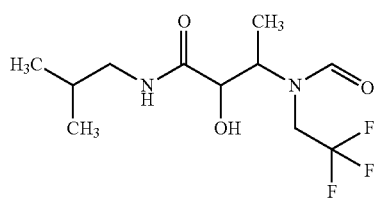 [SMILES: CC(C)CNC(=O)C(O)C(C)N(C=O)CC(F)(F)F] I-169
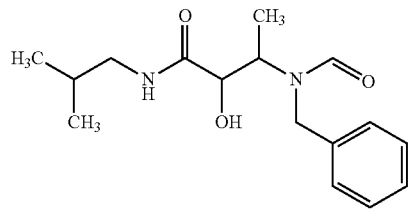 [SMILES: CC(C)CNC(=O)C(O)C(C)N(C=O)Cc1ccccc1] I-170
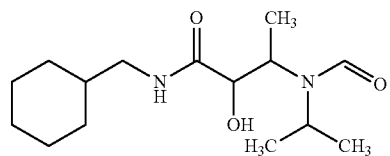 [SMILES: CC(C)N(C=O)C(C)C(O)C(=O)NCC1CCCCC1] I-171

TABLE 1-continued
Intermediates (I-1-I-514)
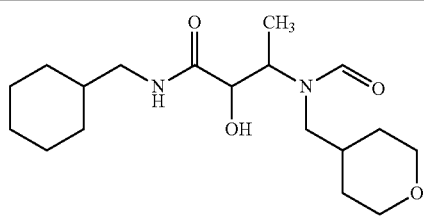 [SMILES: CC(C(O)C(=O)NCC1CCCCC1)N(C=O)CC1CCOCC1] I-172
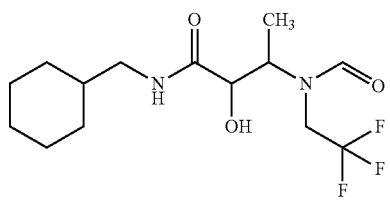 [SMILES: CC(C(O)C(=O)NCC1CCCCC1)N(C=O)CC(F)(F)F] I-173
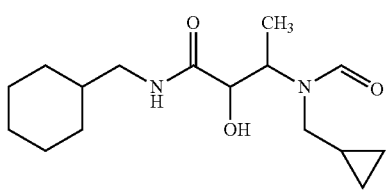 [SMILES: CC(C(O)C(=O)NCC1CCCCC1)N(C=O)CC1CC1] I-174
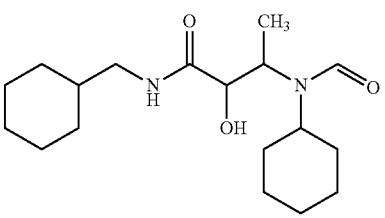 [SMILES: CC(C(O)C(=O)NCC1CCCCC1)N(C=O)C1CCCCC1] I-175
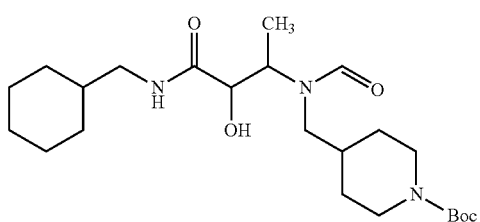 [SMILES: CC(C(O)C(=O)NCC1CCCCC1)N(C=O)CC1CCN(C(=O)OC(C)(C)C)CC1] I-176
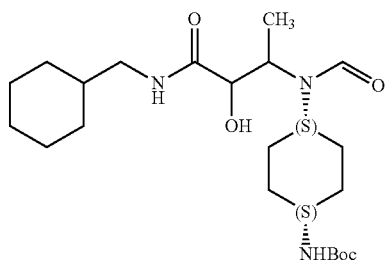 I-177
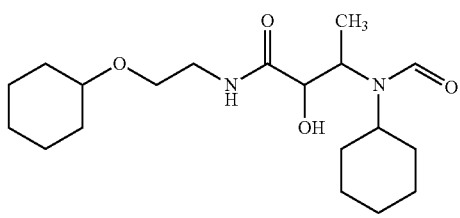 I-178

TABLE 1-continued

Intermediates (I-1-I-514)

| | |
|---|---|
| (structure) | I-179 |
| (structure) | I-180 |
| (structure) | I-181 |
| (structure) | I-182 |
| (structure) | I-183 |
| (structure) | I-184 |

TABLE 1-continued
Intermediates (I-1-I-514)
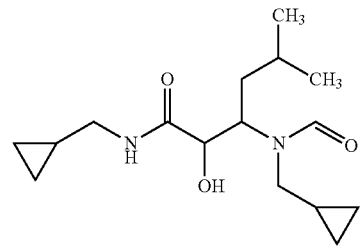 [SMILES: CC(C)CC(C(O)C(=O)NCC1CC1)N(C=O)CC1CC1] I-185
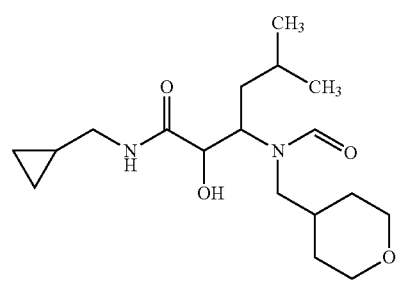 [SMILES: CC(C)CC(C(O)C(=O)NCC1CC1)N(C=O)CC1CCOCC1] I-186
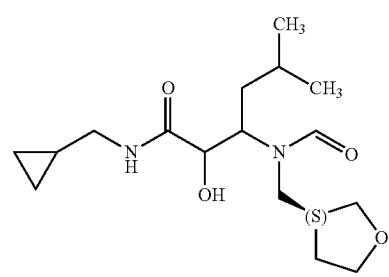 I-187
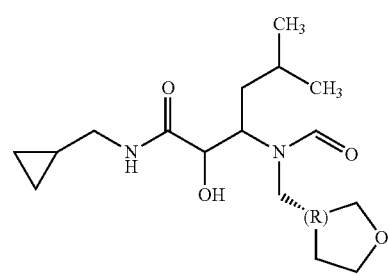 I-188
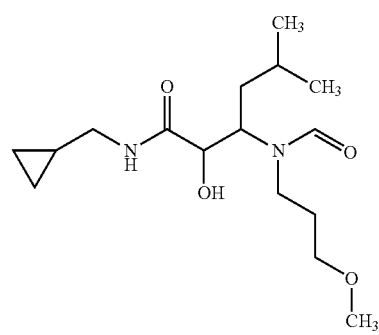 [SMILES: COCCCN(C=O)C(CC(C)C)C(O)C(=O)NCC1CC1] I-189

TABLE 1-continued
Intermediates (I-1-I-514)
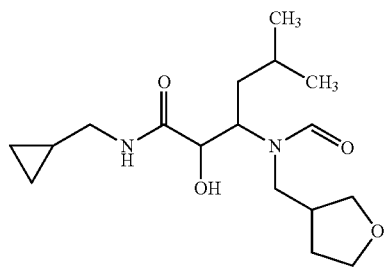 [SMILES: CC(C)CC(C(O)C(=O)NCC1CC1)N(C=O)CC1CCOC1]
I-190
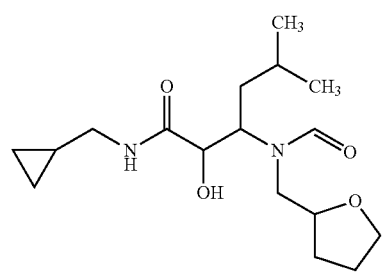 [SMILES: CC(C)CC(C(O)C(=O)NCC1CC1)N(C=O)CC1CCCO1]
I-191
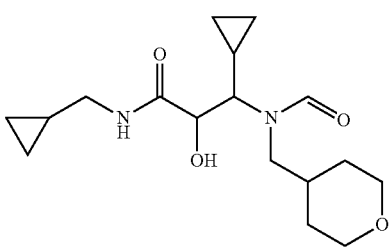 [SMILES: O=CN(CC1CCOCC1)C(C1CC1)C(O)C(=O)NCC1CC1]
I-192
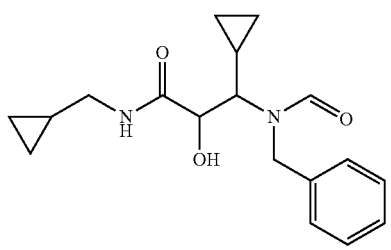 [SMILES: O=CN(Cc1ccccc1)C(C1CC1)C(O)C(=O)NCC1CC1]
I-193
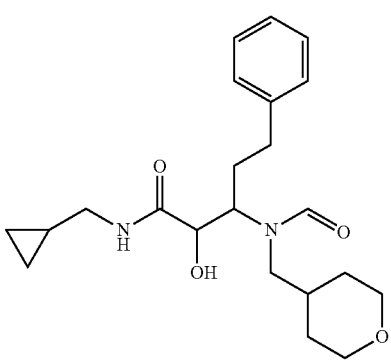 [SMILES: O=CN(CC1CCOCC1)C(CCc1ccccc1)C(O)C(=O)NCC1CC1]
I-194
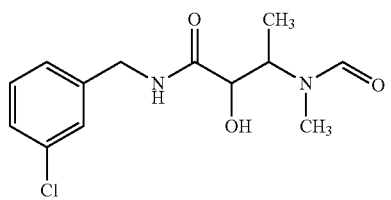 [SMILES: CC(C(O)C(=O)NCc1cccc(Cl)c1)N(C)C=O]
I-195

TABLE 1-continued
Intermediates (I-1-I-514)
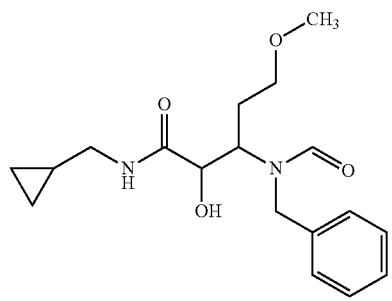 [SMILES: COCCC(C(O)C(=O)NCC1CC1)N(C=O)Cc1ccccc1] I-196
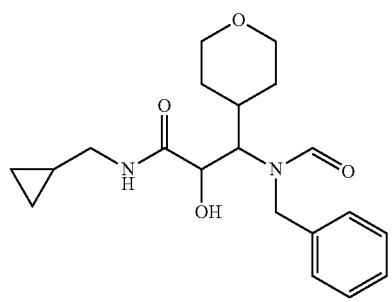 [SMILES: O=CN(Cc1ccccc1)C(C1CCOCC1)C(O)C(=O)NCC1CC1] I-197
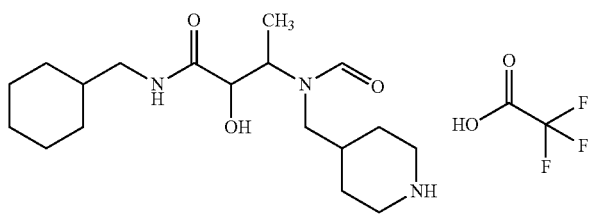 [SMILES: CC(C(O)C(=O)NCC1CCCCC1)N(C=O)CC1CCNCC1 ; O=C(O)C(F)(F)F] I-198
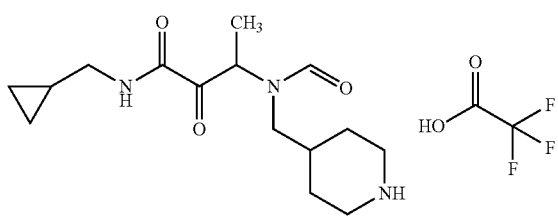 I-199
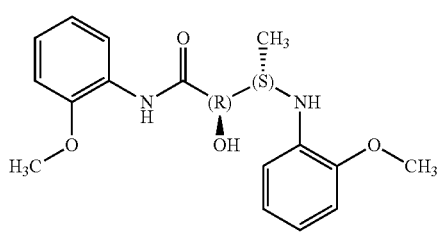 I-200
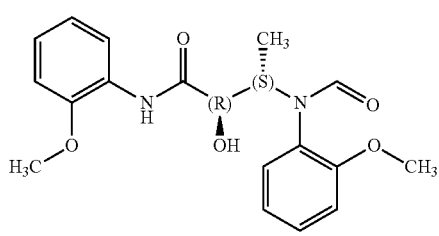 I-201

TABLE 1-continued

Intermediates (I-1-I-514)

| | |
|---|---|
| (structure) | I-202 |
| (structure) | I-203 |
| (structure) | I-204 |
| (structure) | I-205 |
| (structure) | I-206 |
| (structure) | I-207 |
| (structure) | I-208 |

TABLE 1-continued
Intermediates (I-1-I-514)
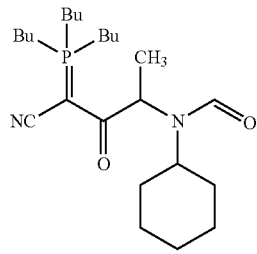
I-209
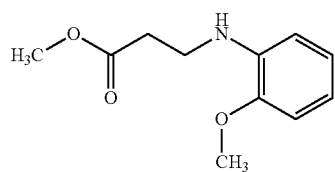
I-210
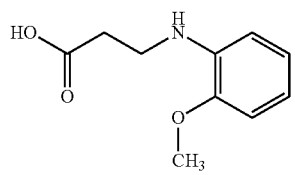
I-211
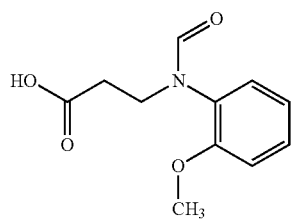 [SMILES: COc1ccccc1N(C=O)CCC(=O)O]
I-212
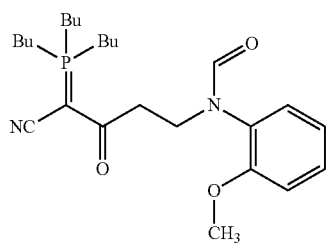
I-213
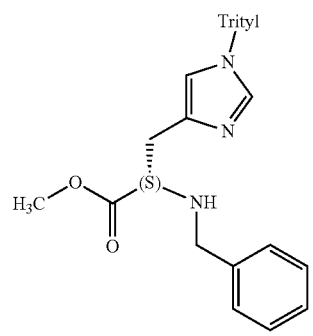
I-214

TABLE 1-continued
Intermediates (I-1-I-514)
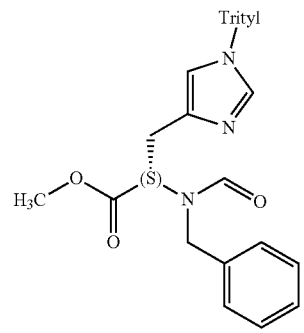
I-215
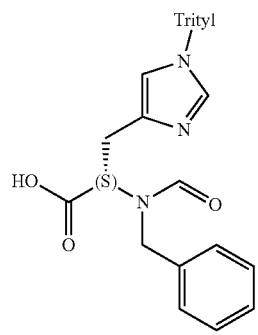
I-216
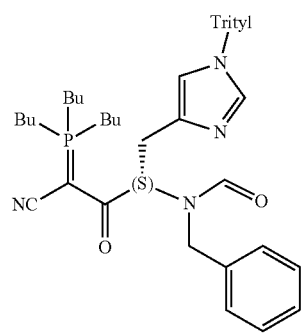
I-217
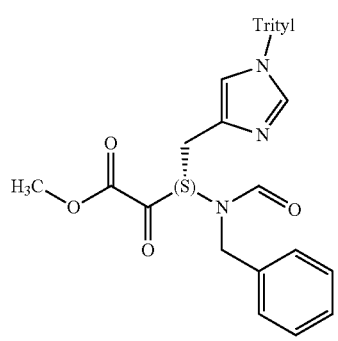
I-218
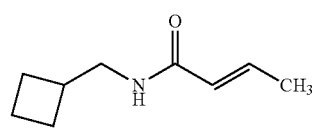
I-219
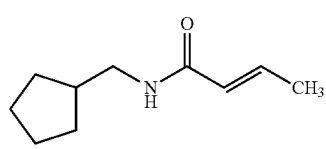
I-220

TABLE 1-continued
Intermediates (I-1-I-514)
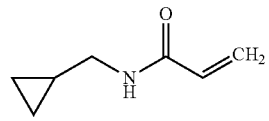 I-221
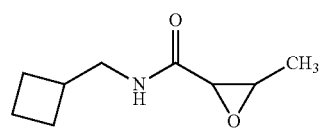 I-222
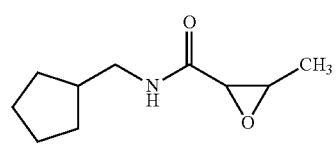 I-223
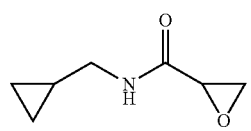 I-224
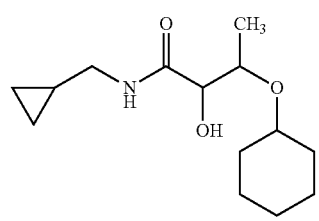 [SMILES: CC(OC1CCCCC1)C(O)C(=O)NCC1CC1] I-225
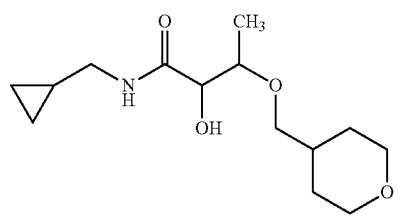 [SMILES: CC(OCC1CCOCC1)C(O)C(=O)NCC1CC1] I-226
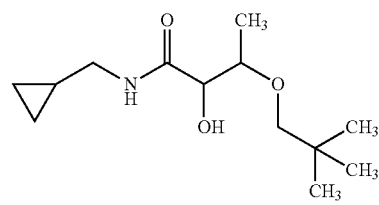 I-227
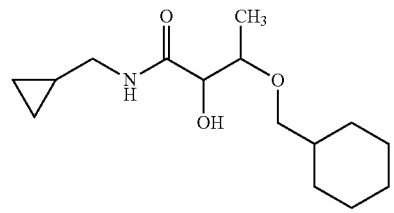 [SMILES: CC(OCC1CCCCC1)C(O)C(=O)NCC1CC1] I-228

TABLE 1-continued
Intermediates (I-1-I-514)
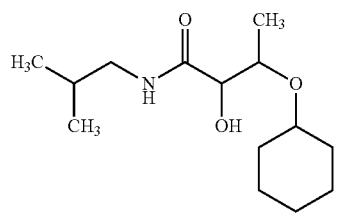 [SMILES: CC(C)CNC(=O)C(O)C(C)OC1CCCCC1]
I-229
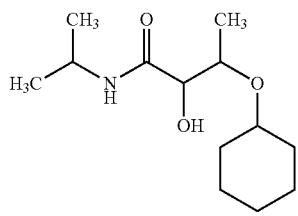 [SMILES: CC(C)NC(=O)C(O)C(C)OC1CCCCC1]
I-230
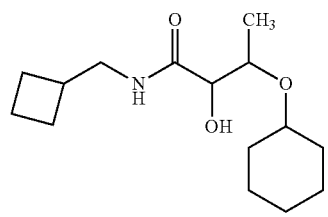 [SMILES: CC(OC1CCCCC1)C(O)C(=O)NCC1CCC1]
I-231
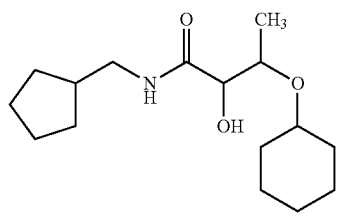 [SMILES: CC(OC1CCCCC1)C(O)C(=O)NCC1CCCC1]
I-232
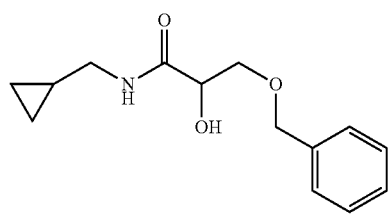 [SMILES: O=C(NCC1CC1)C(O)COCc1ccccc1]
I-233
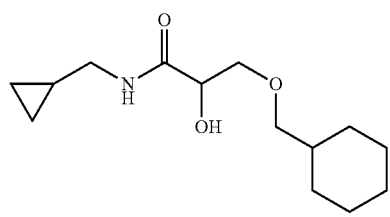 [SMILES: O=C(NCC1CC1)C(O)COCC1CCCCC1]
I-234
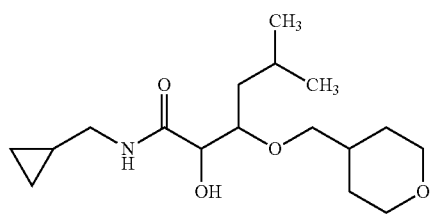 [SMILES: CC(C)CC(OCC1CCOCC1)C(O)C(=O)NCC1CC1]
I-235

TABLE 1-continued
Intermediates (I-1-I-514)
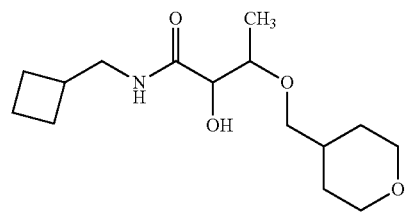 [SMILES: CC(OCC1CCOCC1)C(O)C(=O)NCC1CCC1] I-236
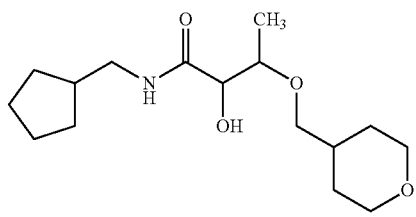 [SMILES: CC(OCC1CCOCC1)C(O)C(=O)NCC1CCCC1] I-237
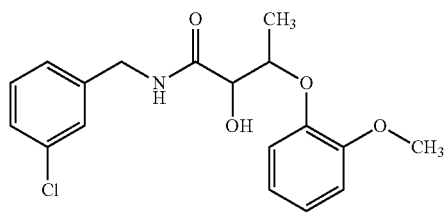 [SMILES: COc1ccccc1OC(C)C(O)C(=O)NCc1cccc(Cl)c1] I-238
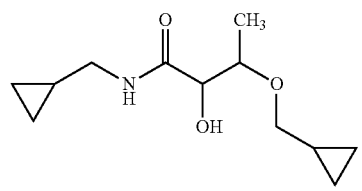 [SMILES: CC(OCC1CC1)C(O)C(=O)NCC1CC1] I-239
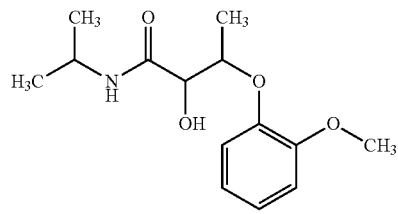 [SMILES: COc1ccccc1OC(C)C(O)C(=O)NC(C)C] I-240
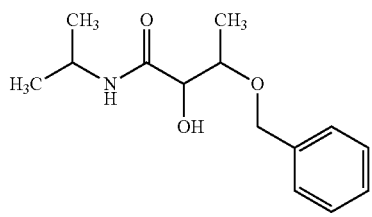 [SMILES: CC(C)NC(=O)C(O)C(C)OCc1ccccc1] I-241
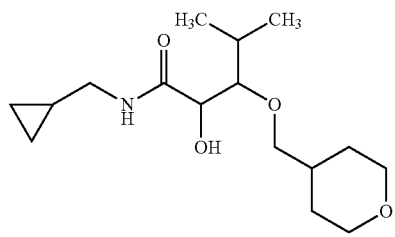 [SMILES: CC(C)C(OCC1CCOCC1)C(O)C(=O)NCC1CC1] I-242

TABLE 1-continued
Intermediates (I-1-I-514)
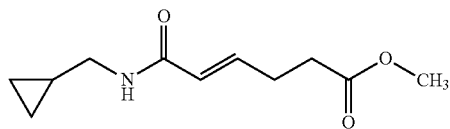 I-243
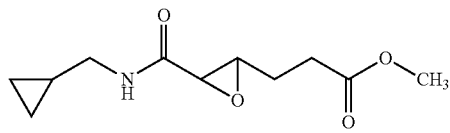 [SMILES: COC(=O)CCC1OC1C(=O)NCC1CC1] I-244
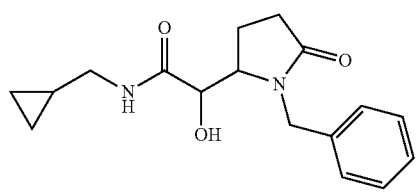 [SMILES: O=C(NCC1CC1)C(O)C1CCC(=O)N1Cc1ccccc1] I-245
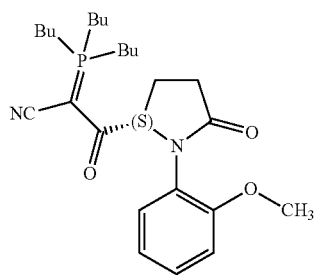 I-246
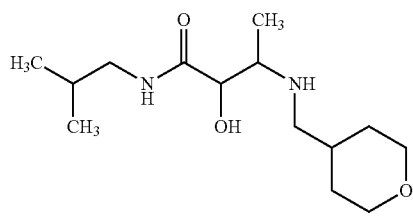 [SMILES: CC(C)CNC(=O)C(O)C(C)NCC1CCOCC1] I-247
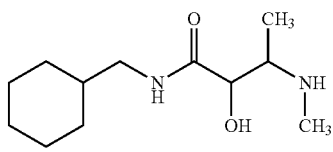 [SMILES: CNC(C)C(O)C(=O)NCC1CCCCC1] I-248
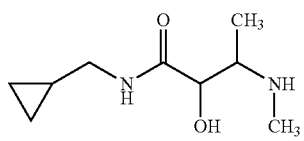 I-249
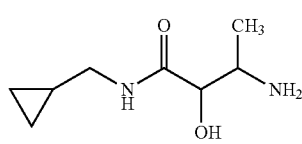 I-250
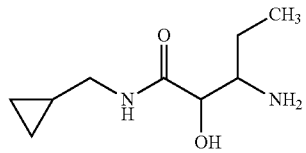 I-251

TABLE 1-continued
Intermediates (I-1-I-514)
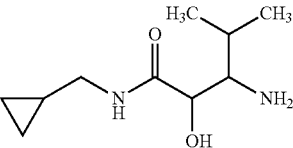 I-252
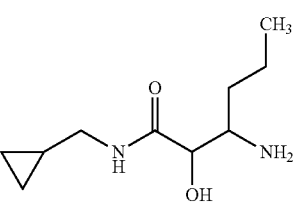 I-253
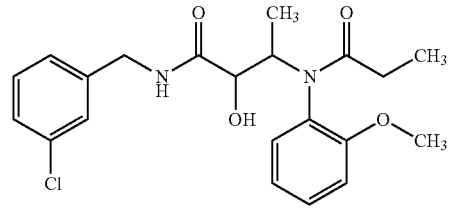 [SMILES: CCC(=O)N(c1ccccc1OC)C(C)C(O)C(=O)NCc1cccc(Cl)c1] I-254
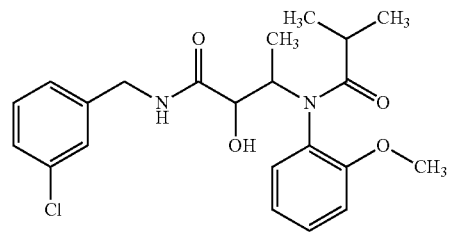 [SMILES: COc1ccccc1N(C(=O)C(C)C)C(C)C(O)C(=O)NCc1cccc(Cl)c1] I-255
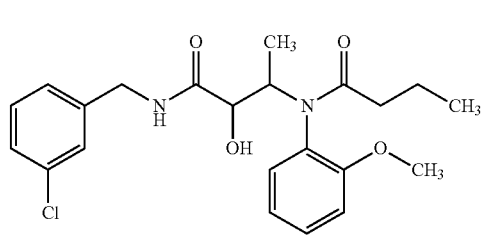 [SMILES: CCCC(=O)N(c1ccccc1OC)C(C)C(O)C(=O)NCc1cccc(Cl)c1] I-256
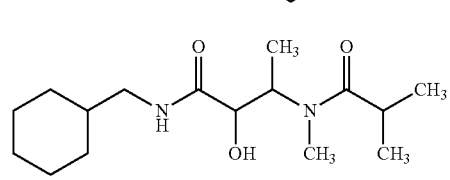 I-257
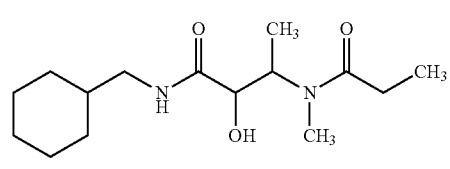 [SMILES: CCC(=O)N(C)C(C)C(O)C(=O)NCC1CCCCC1] I-258
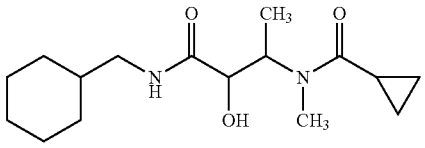 [SMILES: CC(C(O)C(=O)NCC1CCCCC1)N(C)C(=O)C1CC1] I-259

TABLE 1-continued

Intermediates (I-1-I-514)

| Structure | ID |
|---|---|
| Cyclohexylmethyl-NH-C(O)-CH(OH)-CH(CH₃)-N(CH₃)-C(O)-(5-methylisoxazol-3-yl) | I-260 |
| Cyclohexylmethyl-NH-C(O)-CH(OH)-CH(CH₃)-N(CH₃)-C(O)-CH₂-O-CH₃ | I-261 |
| Cyclopropylmethyl-NH-C(O)-CH(OH)-CH(CH₃)-N(CH₃)-C(O)-phenyl | I-262 |
| Cyclopropylmethyl-NH-C(O)-CH(OH)-CH(CH₃)-N(CH₃)-C(O)-cyclohexyl | I-263 |
| Cyclopropylmethyl-NH-C(O)-CH(OH)-CH(CH₃)-N(CH₃)-C(O)-CH(CH₃)₂ | I-264 |
| Isobutyl-NH-C(O)-CH(OH)-CH(CH₃)-N(CH₂-tetrahydropyran-4-yl)-C(O)-O-CH₃ | I-265 |
| Cyclopropylmethyl-NH-C(O)-CH(OH)-CH(CH₃)-NH-C(O)-(4-fluorophenyl) | I-266 |
| Cyclopropylmethyl-NH-C(O)-CH(OH)-CH(n-propyl)-NH-C(O)-phenyl | I-267 |
| Cyclopropylmethyl-NH-C(O)-CH(OH)-CH(ethyl)-NH-C(O)-phenyl | I-268 |

TABLE 1-continued
Intermediates (I-1-I-514)
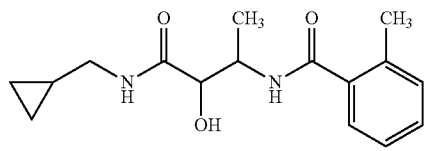 [SMILES: Cc1ccccc1C(=O)NC(C)C(O)C(=O)NCC1CC1] I-269
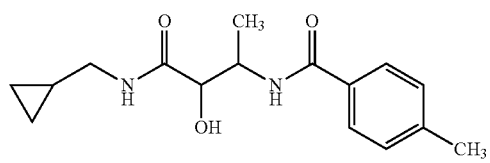 [SMILES: Cc1ccc(C(=O)NC(C)C(O)C(=O)NCC2CC2)cc1] I-270
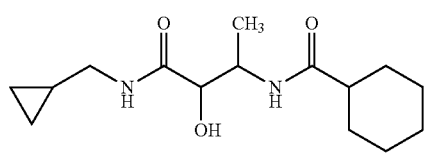 [SMILES: CC(NC(=O)C1CCCCC1)C(O)C(=O)NCC1CC1] I-271
 I-272
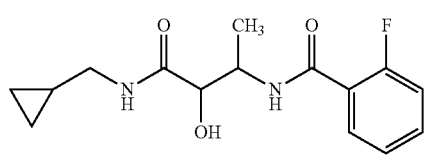 [SMILES: CC(NC(=O)c1ccccc1F)C(O)C(=O)NCC1CC1] I-273
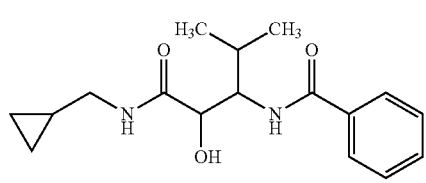 [SMILES: CC(C)C(NC(=O)c1ccccc1)C(O)C(=O)NCC1CC1] I-274
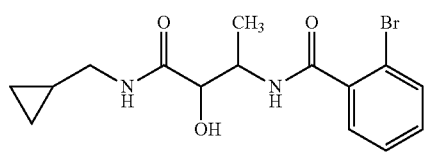 I-275
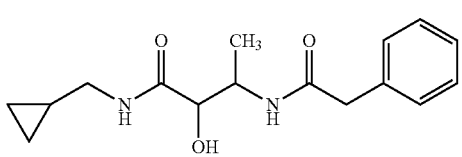 [SMILES: CC(NC(=O)Cc1ccccc1)C(O)C(=O)NCC1CC1] I-276
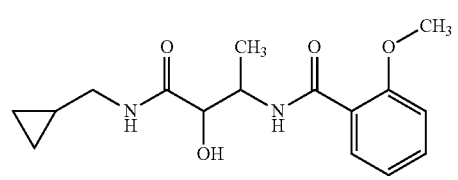 [SMILES: COc1ccccc1C(=O)NC(C)C(O)C(=O)NCC1CC1] I-277

TABLE 1-continued

Intermediates (I-1-I-514)

| Structure | ID |
|---|---|
| (cyclopropylmethyl)NH-C(=O)-CH(OH)-CH(CH₃)-NH-C(=O)-(2-Cl-phenyl) | I-278 |
| (cyclopropylmethyl)NH-C(=O)-CH(OH)-CH(CH₃)-NH-C(=O)-(4-Cl-phenyl) | I-279 |
| (cyclopropylmethyl)NH-C(=O)-CH(OH)-CH(CH₃)-NH-C(=O)-(3-CH₃-phenyl) | I-280 |
| (cyclopropylmethyl)NH-C(=O)-CH(OH)-CH(CH₃)-NH-C(=O)-(3-Cl-phenyl) | I-281 |
| (cyclopropylmethyl)NH-C(=O)-CH(OH)-CH(CH₃)-NH-C(=O)-(4,4-difluorocyclohexyl) | I-282 |
| (cyclopropylmethyl)NH-C(=O)-CH(OH)-CH(CH₃)-NH-C(=O)-(3,3-difluorocyclobutyl) | I-283 |
| (cyclohexylmethyl)NH-C(=O)-CH(OH)-CH(CH₃)-N(cyclohexyl)-C(=O)-CH₂-NH-S(=O)₂-CH₃ | I-284 |
| (3-Cl-benzyl)NH-C(=O)-CH(OH)-CH(CH₃)-N(CH₃)-C(=O)-phenyl | I-285 |
| (3-Cl-benzyl)NH-C(=O)-C(=O)-CH(CH₃)-NH-(2-OCH₃-phenyl) | I-286 |

TABLE 1-continued
Intermediates (I-1-I-514)
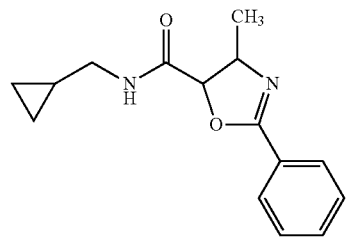 [SMILES: CC1N=C(c2ccccc2)OC1C(=O)NCC1CC1] I-287
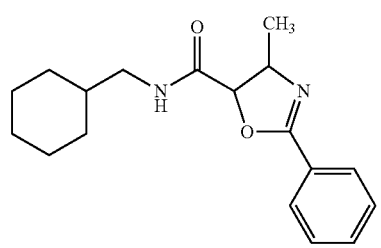 [SMILES: CC1N=C(c2ccccc2)OC1C(=O)NCC1CCCCC1] I-288
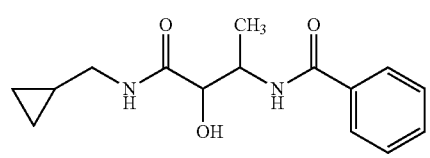 [SMILES: CC(NC(=O)c1ccccc1)C(O)C(=O)NCC1CC1] I-289
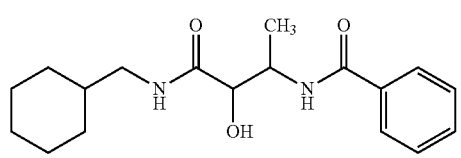 [SMILES: CC(NC(=O)c1ccccc1)C(O)C(=O)NCC1CCCCC1] I-290
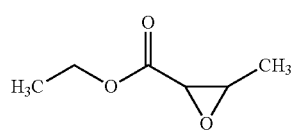 I-291
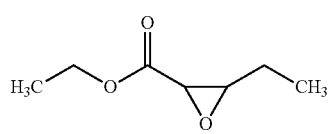 I-292
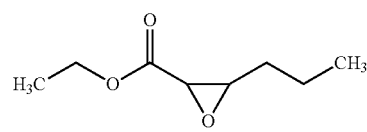 I-293
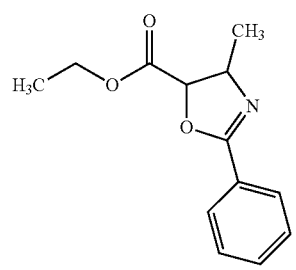 [SMILES: CCOC(=O)C1OC(c2ccccc2)=NC1C] I-294

TABLE 1-continued
Intermediates (I-1-I-514)
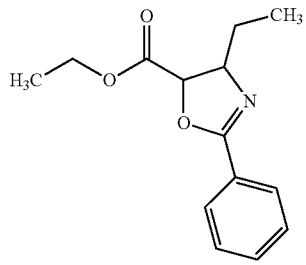 [SMILES: CCOC(=O)C1OC(c2ccccc2)=NC1CC] I-295
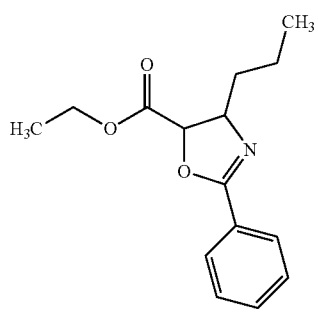 [SMILES: CCCC1N=C(c2ccccc2)OC1C(=O)OCC] I-296
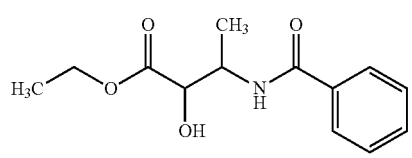 [SMILES: CCOC(=O)C(O)C(C)NC(=O)c1ccccc1] I-297
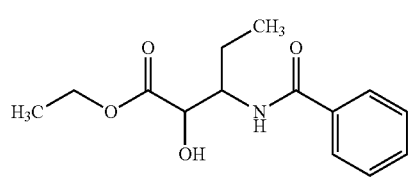 [SMILES: CCOC(=O)C(O)C(CC)NC(=O)c1ccccc1] I-298
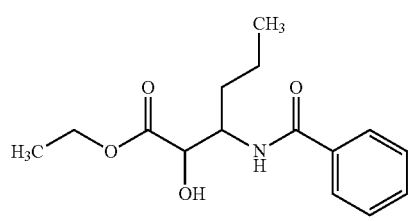 [SMILES: CCCC(NC(=O)c1ccccc1)C(O)C(=O)OCC] I-299
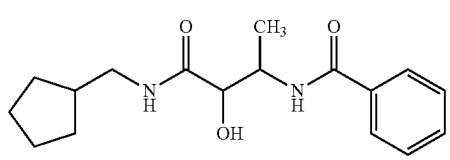 [SMILES: CC(NC(=O)c1ccccc1)C(O)C(=O)NCC1CCCC1] I-300
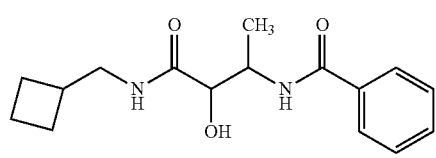 [SMILES: CC(NC(=O)c1ccccc1)C(O)C(=O)NCC1CCC1] I-301
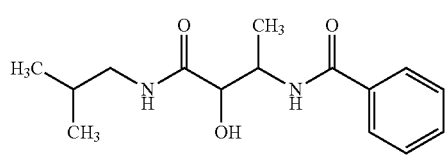 [SMILES: CC(C)CNC(=O)C(O)C(C)NC(=O)c1ccccc1] I-302

TABLE 1-continued
Intermediates (I-1-I-514)
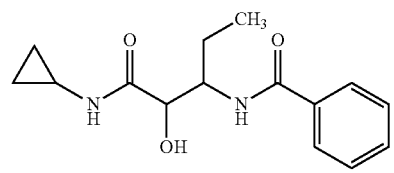 I-303
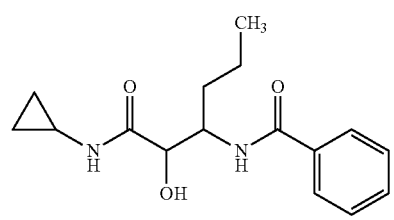 [SMILES: CCCC(NC(=O)c1ccccc1)C(O)C(=O)NC1CC1] I-304
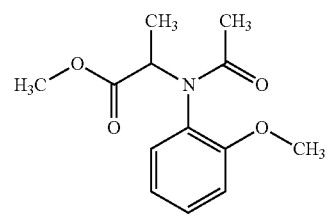 I-305
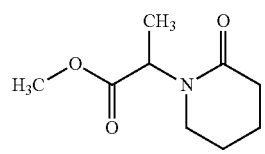 I-306
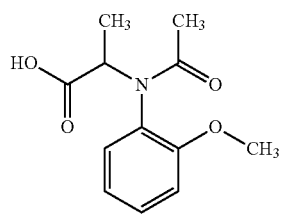 [SMILES: COc1ccccc1N(C(C)=O)C(C)C(=O)O] I-307
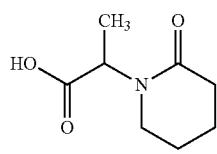 I-308
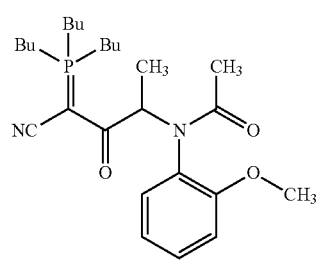 I-309

US 11,091,428 B2
385                                                    386
TABLE 1-continued
Intermediates (I-1-I-514)
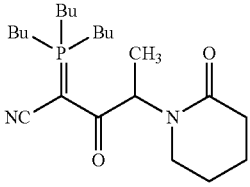 I-310
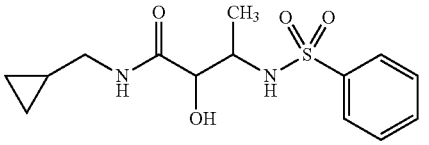 [SMILES: CC(NS(=O)(=O)c1ccccc1)C(O)C(=O)NCC1CC1] I-311
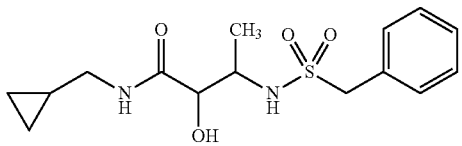 [SMILES: CC(NS(=O)(=O)Cc1ccccc1)C(O)C(=O)NCC1CC1] I-312
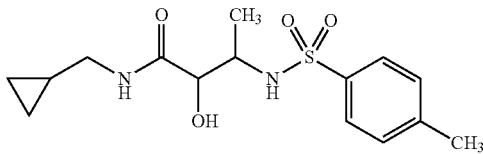 [SMILES: Cc1ccc(S(=O)(=O)NC(C)C(O)C(=O)NCC2CC2)cc1] I-313
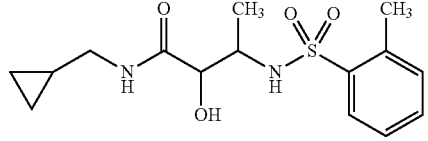 [SMILES: Cc1ccccc1S(=O)(=O)NC(C)C(O)C(=O)NCC1CC1] I-314
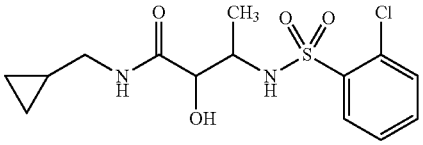 [SMILES: CC(NS(=O)(=O)c1ccccc1Cl)C(O)C(=O)NCC1CC1] I-315
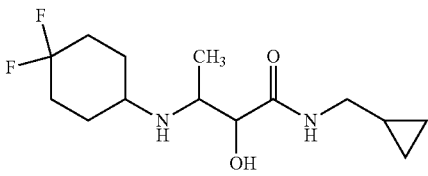 [SMILES: CC(NC1CCC(F)(F)CC1)C(O)C(=O)NCC1CC1] I-316
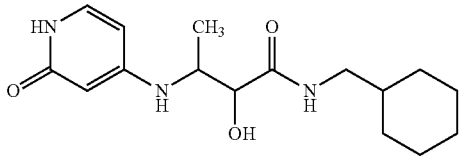 [SMILES: CC(Nc1cc[nH]c(=O)c1)C(O)C(=O)NCC1CCCCC1] I-317
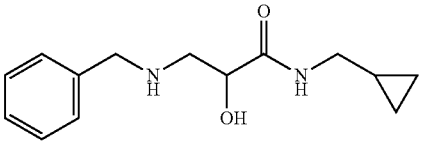 [SMILES: O=C(NCC1CC1)C(O)CNCc1ccccc1] I-318

TABLE 1-continued
Intermediates (I-1-I-514)
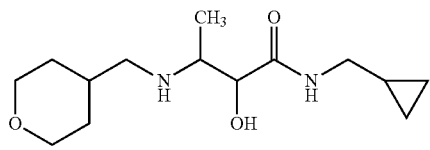 [SMILES: CC(NCC1CCOCC1)C(O)C(=O)NCC1CC1]
I-319
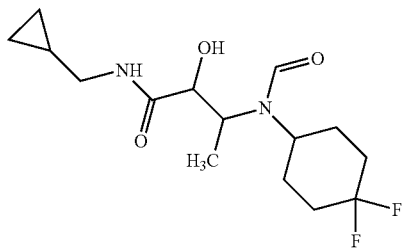 [SMILES: CC(C(O)C(=O)NCC1CC1)N(C=O)C1CCC(F)(F)CC1]
I-320
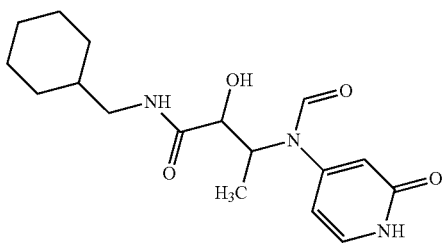 [SMILES: CC(C(O)C(=O)NCC1CCCCC1)N(C=O)c1cc[nH]c(=O)c1]
I-321
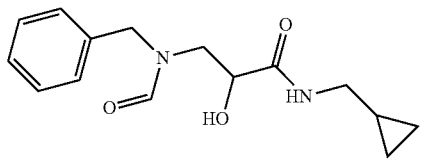 [SMILES: O=CN(Cc1ccccc1)CC(O)C(=O)NCC1CC1]
I-322
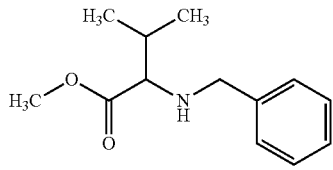 [SMILES: COC(=O)C(NCc1ccccc1)C(C)C]
I-323
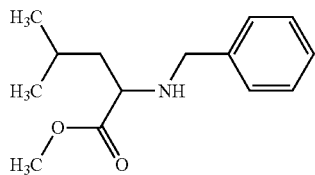 [SMILES: COC(=O)C(CC(C)C)NCc1ccccc1]
I-324
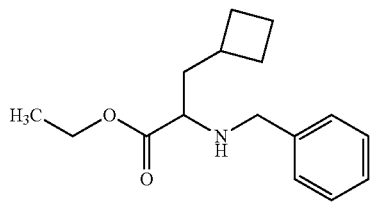 [SMILES: CCOC(=O)C(CC1CCC1)NCc1ccccc1]
I-325
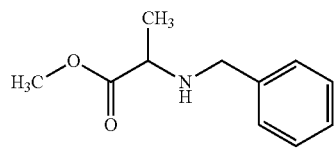
I-326

TABLE 1-continued

Intermediates (I-1-I-514)

| Structure | ID |
|---|---|
| (methyl 2-(N-benzylformamido)propanoate) | I-327 |
| (2-(N-benzylformamido)propanoic acid) | I-328 |
| (2-(benzylamino)-4-methylpentanoic acid) | I-329 |
| (2-(benzylamino)-3-methylbutanoic acid) | I-330 |
| (2-(benzylamino)-3-cyclobutylpropanoic acid) | I-331 |
| (2-(N-benzylformamido)-4-methylpentanoic acid) | I-332 |
| (2-(N-benzylformamido)-3-methylbutanoic acid) | I-333 |

TABLE 1-continued
Intermediates (I-1-I-514)
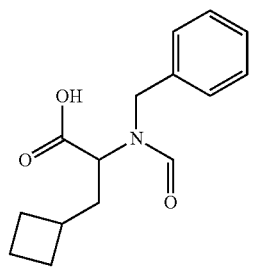 [SMILES: O=CN(Cc1ccccc1)C(CC1CCC1)C(=O)O]
I-334
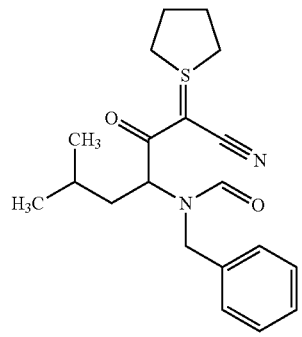 [SMILES: CC(C)CC(C(=O)C(C#N)=S1CCCC1)N(C=O)Cc1ccccc1]
I-335
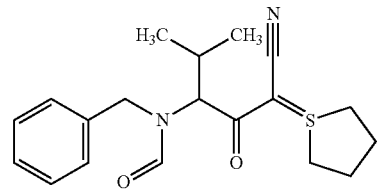 [SMILES: CC(C)C(C(=O)C(C#N)=S1CCCC1)N(C=O)Cc1ccccc1]
I-336
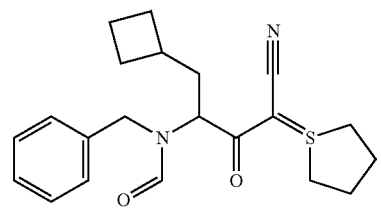 [SMILES: N#CC(C(=O)C(CC1CCC1)N(C=O)Cc1ccccc1)=S1CCCC1]
I-337
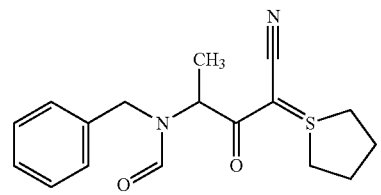 [SMILES: CC(C(=O)C(C#N)=S1CCCC1)N(C=O)Cc1ccccc1]
I-338
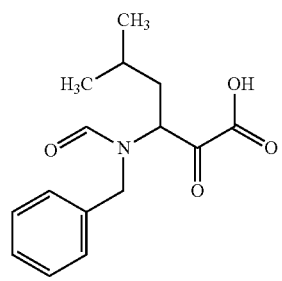 [SMILES: CC(C)CC(C(=O)C(=O)O)N(C=O)Cc1ccccc1]
I-339

TABLE 1-continued
Intermediates (I-1-I-514)
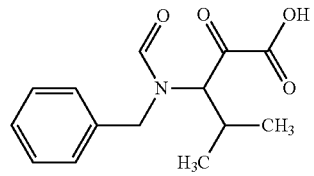 [SMILES: CC(C)C(C(=O)C(=O)O)N(C=O)Cc1ccccc1]
I-340
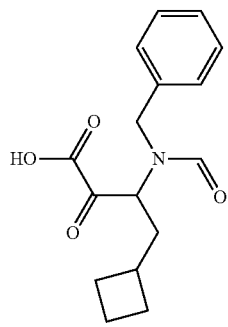 [SMILES: O=CN(Cc1ccccc1)C(CC1CCC1)C(=O)C(=O)O]
I-341
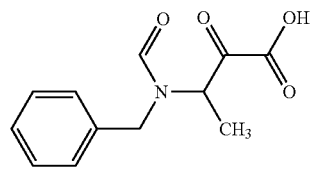 [SMILES: CC(C(=O)C(=O)O)N(C=O)Cc1ccccc1]
I-342
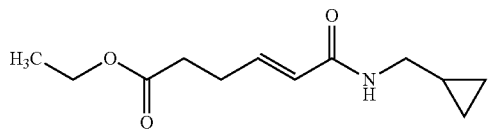 [SMILES: CCOC(=O)CC/C=C/C(=O)NCC1CC1]
I-343
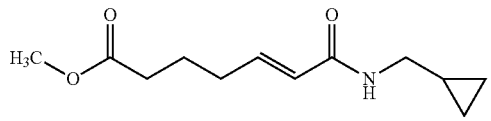 [SMILES: COC(=O)CCC/C=C/C(=O)NCC1CC1]
I-344
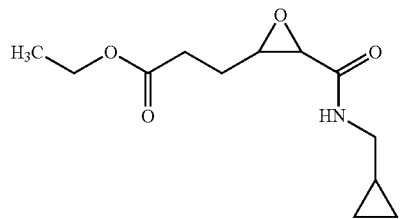 [SMILES: CCOC(=O)CCC1OC1C(=O)NCC1CC1]
I-345
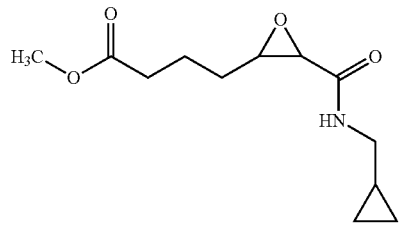 [SMILES: COC(=O)CCCC1OC1C(=O)NCC1CC1]
I-346

TABLE 1-continued
Intermediates (I-1-I-514)
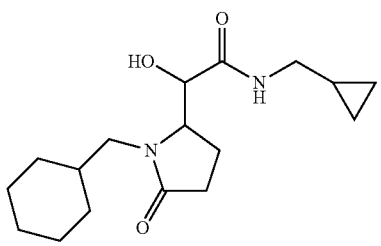 [SMILES: O=C(NCC1CC1)C(O)C1CCC(=O)N1CC1CCCCC1]
I-347
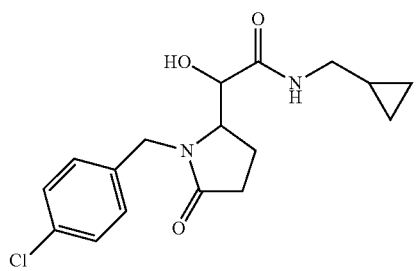 [SMILES: O=C(NCC1CC1)C(O)C1CCC(=O)N1Cc1ccc(Cl)cc1]
I-348
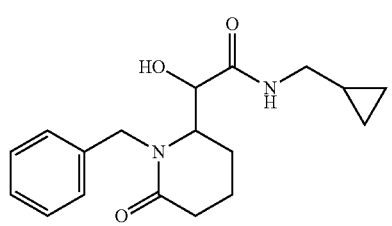 [SMILES: O=C(NCC1CC1)C(O)C1CCCC(=O)N1Cc1ccccc1]
I-349
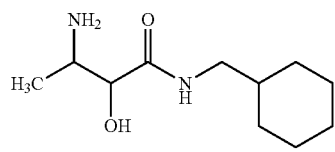
I-350
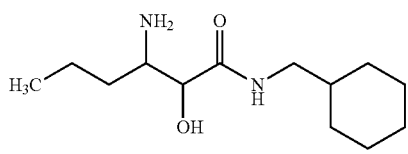 [SMILES: CCCC(N)C(O)C(=O)NCC1CCCCC1]
I-351
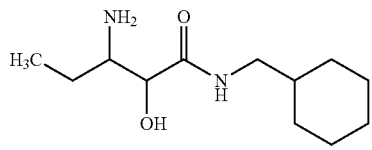 [SMILES: CCC(N)C(O)C(=O)NCC1CCCCC1]
I-352
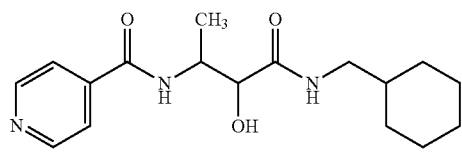 [SMILES: CC(NC(=O)c1ccncc1)C(O)C(=O)NCC1CCCCC1]
I-353
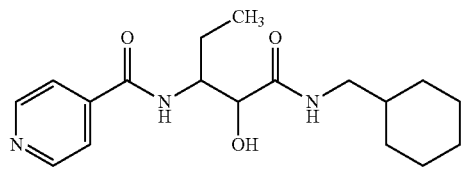 [SMILES: CCC(NC(=O)c1ccncc1)C(O)C(=O)NCC1CCCCC1]
I-354

TABLE 1-continued
Intermediates (I-1-I-514)
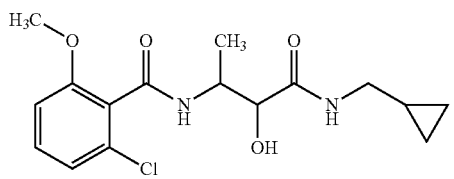 [SMILES: COc1cccc(Cl)c1C(=O)NC(C)C(O)C(=O)NCC1CC1] I-355
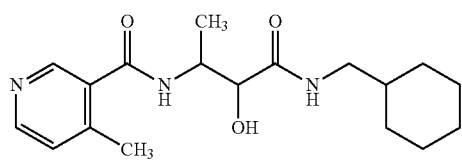 [SMILES: Cc1ccncc1C(=O)NC(C)C(O)C(=O)NCC1CCCCC1] I-356
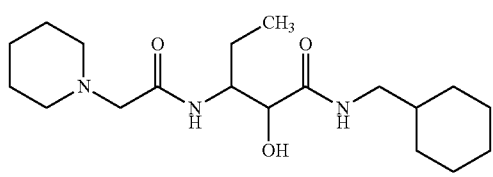 [SMILES: CCC(NC(=O)CN1CCCCC1)C(O)C(=O)NCC1CCCCC1] I-357
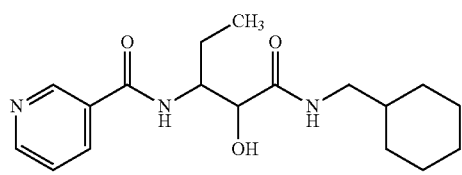 [SMILES: CCC(NC(=O)c1cccnc1)C(O)C(=O)NCC1CCCCC1] I-358
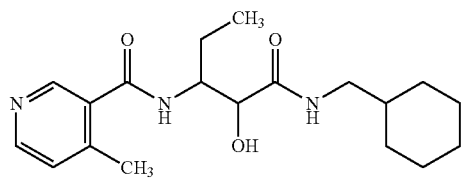 [SMILES: CCC(NC(=O)c1cnccc1C)C(O)C(=O)NCC1CCCCC1] I-359
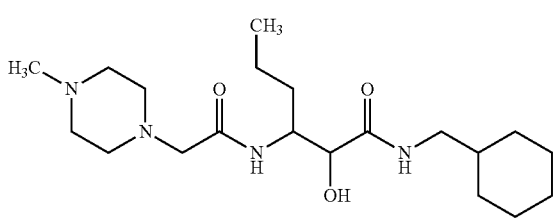 [SMILES: CCCC(NC(=O)CN1CCN(C)CC1)C(O)C(=O)NCC1CCCCC1] I-360
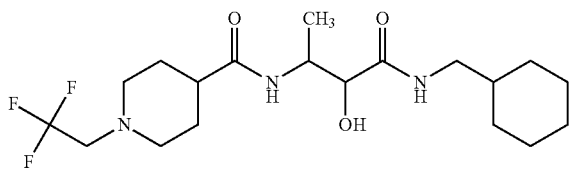 [SMILES: CC(NC(=O)C1CCN(CC(F)(F)F)CC1)C(O)C(=O)NCC1CCCCC1] I-361
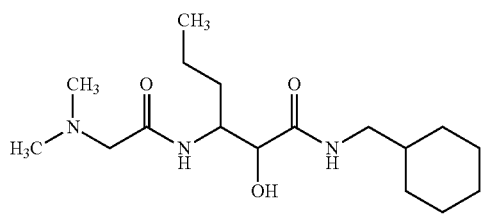 [SMILES: CCCC(NC(=O)CN(C)C)C(O)C(=O)NCC1CCCCC1] I-362

TABLE 1-continued

Intermediates (I-1-I-514)

| | |
|---|---|
| (structure) | I-363 |
| (structure) | I-364 |
| (structure) | I-365 |
| (structure) | I-366 |
| (structure) | I-367 |
| (structure) | I-368 |
| (structure) | I-369 |
| (structure) | I-370 |

TABLE 1-continued
Intermediates (I-1-I-514)
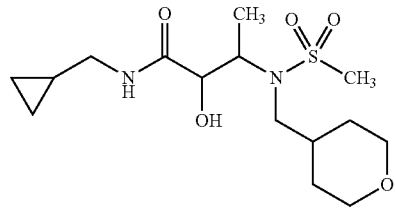 [SMILES: CC(C(O)C(=O)NCC1CC1)N(CC1CCOCC1)S(C)(=O)=O]
I-371
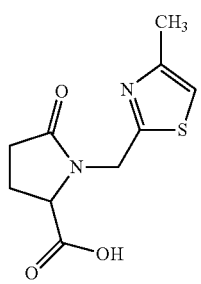 [SMILES: Cc1csc(CN2C(=O)CCC2C(=O)O)n1]
I-372
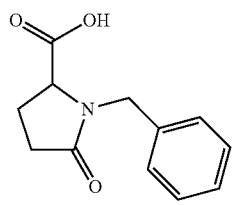
I-373
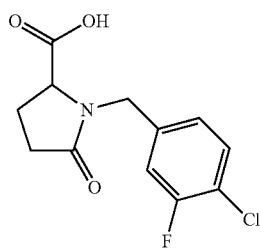 [SMILES: O=C(O)C1CCC(=O)N1Cc1ccc(Cl)c(F)c1]
I-374
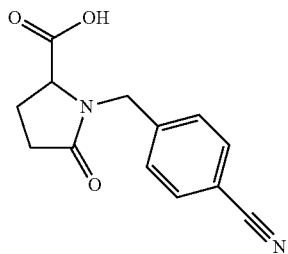 [SMILES: N#Cc1ccc(CN2C(=O)CCC2C(=O)O)cc1]
I-375
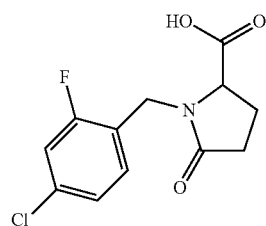 [SMILES: O=C(O)C1CCC(=O)N1Cc1ccc(Cl)cc1F]
I-376

TABLE 1-continued
Intermediates (I-1-I-514)
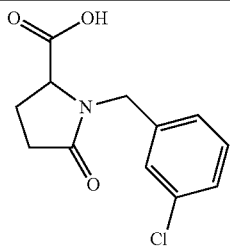  I-377
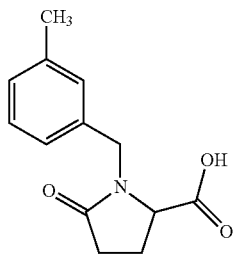 [SMILES: Cc1cccc(CN2C(=O)CCC2C(=O)O)c1]  I-378
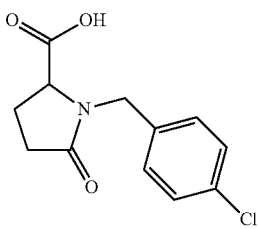 [SMILES: O=C(O)C1CCC(=O)N1Cc1ccc(Cl)cc1]  I-379
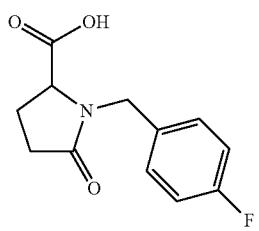 [SMILES: O=C(O)C1CCC(=O)N1Cc1ccc(F)cc1]  I-380
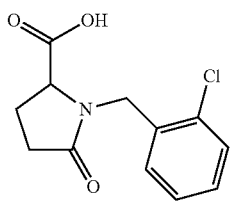 [SMILES: O=C(O)C1CCC(=O)N1Cc1ccccc1Cl]  I-381
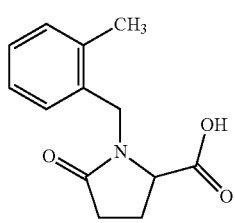 [SMILES: Cc1ccccc1CN1C(=O)CCC1C(=O)O]  I-382
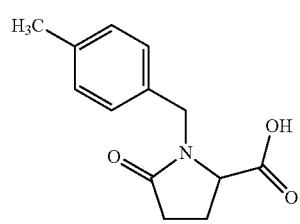 [SMILES: Cc1ccc(CN2C(=O)CCC2C(=O)O)cc1]  I-383

TABLE 1-continued
Intermediates (I-1-I-514)
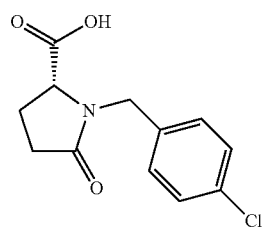 [SMILES: O=C(O)[C@H]1CCC(=O)N1Cc1ccc(Cl)cc1]  I-384
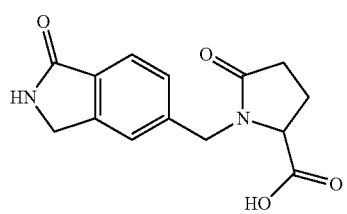 [SMILES: O=C1NCc2cc(CN3C(=O)CCC3C(=O)O)ccc21]  I-385
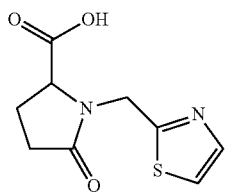 [SMILES: O=C(O)C1CCC(=O)N1Cc1nccs1]  I-386
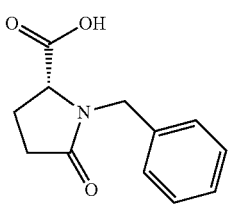 [SMILES: O=C(O)[C@H]1CCC(=O)N1Cc1ccccc1]  I-387
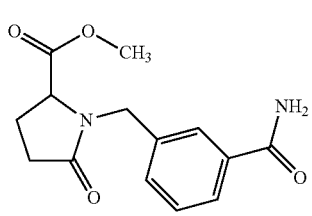 [SMILES: COC(=O)C1CCC(=O)N1Cc1cccc(C(N)=O)c1]  I-388
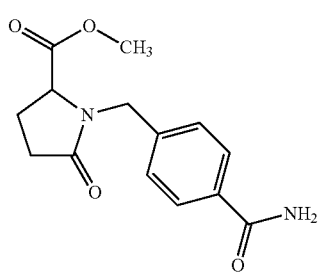 [SMILES: COC(=O)C1CCC(=O)N1Cc1ccc(C(N)=O)cc1]  I-389
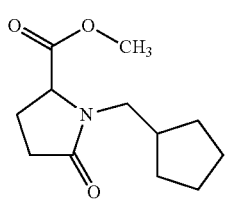 [SMILES: COC(=O)C1CCC(=O)N1CC1CCCC1]  I-390

TABLE 1-continued
Intermediates (I-1-I-514)
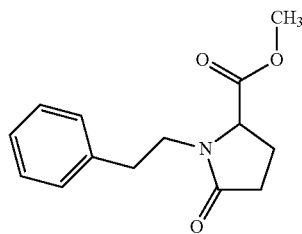 [SMILES: COC(=O)C1CCC(=O)N1CCc1ccccc1]　I-391
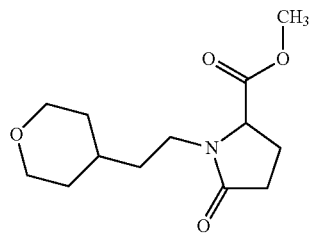 [SMILES: COC(=O)C1CCC(=O)N1CCC1CCOCC1]　I-392
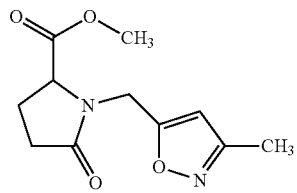 [SMILES: COC(=O)C1CCC(=O)N1Cc1cc(C)no1]　I-393
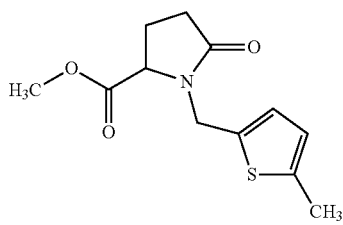　I-394
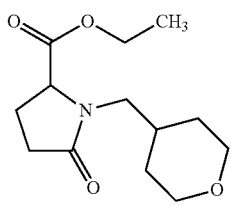 [SMILES: CCOC(=O)C1CCC(=O)N1CC1CCOCC1]　I-395
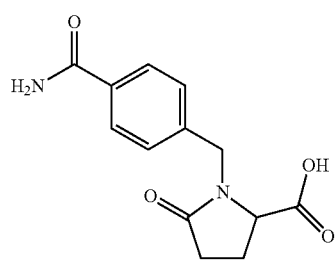 [SMILES: NC(=O)c1ccc(CN2C(=O)CCC2C(=O)O)cc1]　I-396
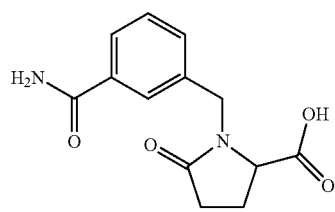 [SMILES: NC(=O)c1cccc(CN2C(=O)CCC2C(=O)O)c1]　I-397

TABLE 1-continued

Intermediates (I-1-I-514)

| Structure | ID |
|---|---|
| (pyrrolidinone with N-CH2CH2-tetrahydropyran-4-yl, carboxylic acid) | I-398 |
| (pyrrolidinone with N-CH2-cyclopentyl, carboxylic acid) | I-399 |
| (pyrrolidinone with N-CH2-(5-methylthiophen-2-yl), carboxylic acid) | I-400 |
| (pyrrolidinone with N-CH2-(3-methylisoxazol-5-yl), carboxylate Li+) | I-401 |
| (pyrrolidinone with N-CH2-tetrahydropyran-4-yl, carboxylate Li+) | I-402 |
| (pyrrolidinone with N-CH2CH2-phenyl, carboxylate Li+) | I-403 |
| (pyrrolidinone with N-CH2-cyclopropyl, carboxylic acid) | I-404 |

TABLE 1-continued
Intermediates (I-1-I-514)
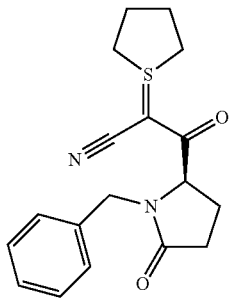 [SMILES: N#CC(C(=O)[C@H]1CCC(=O)N1Cc1ccccc1)=S1CCCC1]
I-405
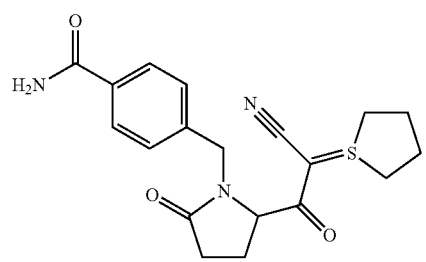 [SMILES: N#CC(C(=O)C1CCC(=O)N1Cc1ccc(C(N)=O)cc1)=S1CCCC1]
I-406
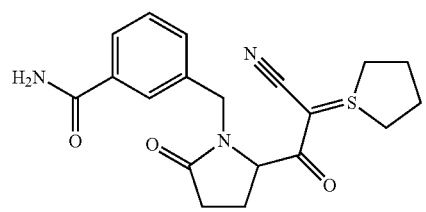 [SMILES: N#CC(C(=O)C1CCC(=O)N1Cc1cccc(C(N)=O)c1)=S1CCCC1]
I-407
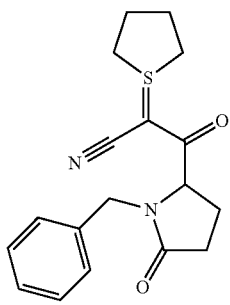 [SMILES: N#CC(C(=O)C1CCC(=O)N1Cc1ccccc1)=S1CCCC1]
I-408
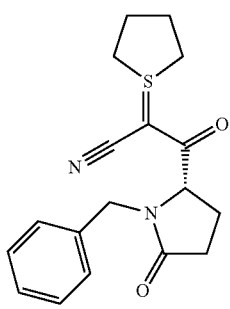 [SMILES: N#CC(C(=O)[C@@H]1CCC(=O)N1Cc1ccccc1)=S1CCCC1]
I-409

TABLE 1-continued
Intermediates (I-1-I-514)
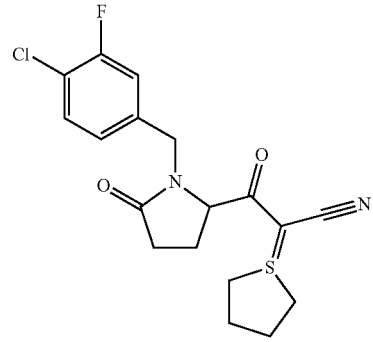 [SMILES: N#CC(C(=O)C1CCC(=O)N1Cc1ccc(Cl)c(F)c1)=S1CCCC1]
I-410
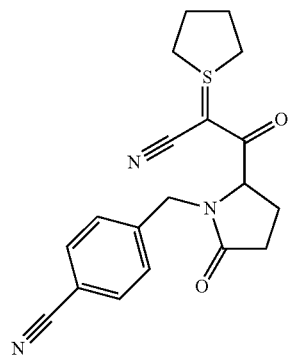 [SMILES: N#CC(C(=O)C1CCC(=O)N1Cc1ccc(C#N)cc1)=S1CCCC1]
I-411
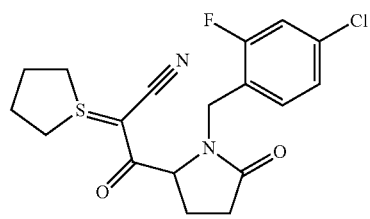 [SMILES: N#CC(C(=O)C1CCC(=O)N1Cc1ccc(Cl)cc1F)=S1CCCC1]
I-412
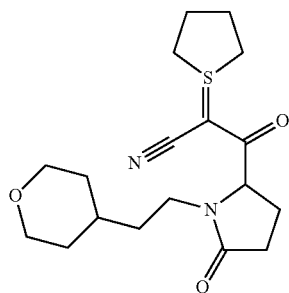 [SMILES: N#CC(C(=O)C1CCC(=O)N1CCC1CCOCC1)=S1CCCC1]
I-413
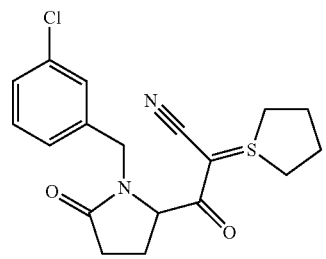
I-414

TABLE 1-continued
Intermediates (I-1-I-514)
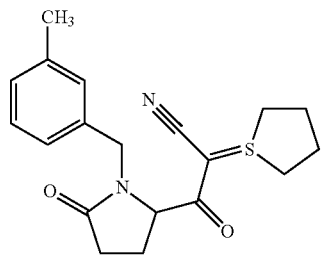 [SMILES: Cc1cccc(CN2C(=O)CCC2C(=O)C(C#N)=S2CCCC2)c1] I-415
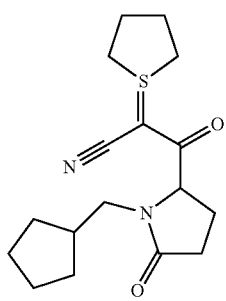 [SMILES: N#CC(C(=O)C1CCC(=O)N1CC1CCCC1)=S1CCCC1] I-416
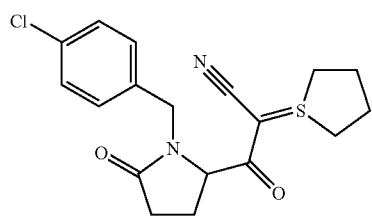 [SMILES: N#CC(C(=O)C1CCC(=O)N1Cc1ccc(Cl)cc1)=S1CCCC1] I-417
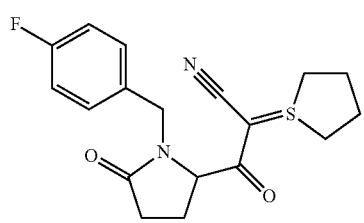 [SMILES: N#CC(C(=O)C1CCC(=O)N1Cc1ccc(F)cc1)=S1CCCC1] I-418
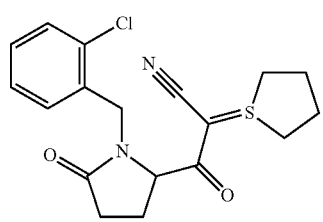 [SMILES: N#CC(C(=O)C1CCC(=O)N1Cc1ccccc1Cl)=S1CCCC1] I-419
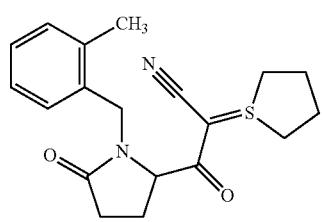 [SMILES: Cc1ccccc1CN1C(=O)CCC1C(=O)C(C#N)=S1CCCC1] I-420

TABLE 1-continued
Intermediates (I-1-I-514)
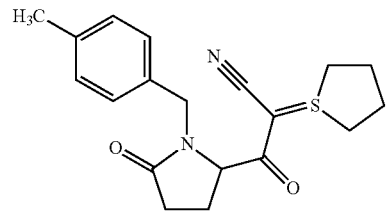 [SMILES: Cc1ccc(CN2C(=O)CCC2C(=O)C(C#N)=S2CCCC2)cc1]
I-421
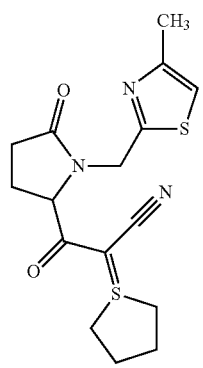 [SMILES: Cc1csc(CN2C(=O)CCC2C(=O)C(C#N)=S2CCCC2)n1]
I-422
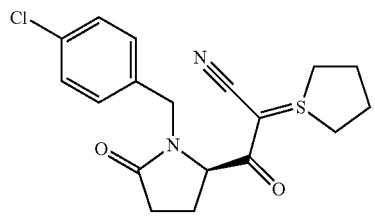 [SMILES: N#CC(C(=O)[C@H]1CCC(=O)N1Cc1ccc(Cl)cc1)=S1CCCC1]
I-423
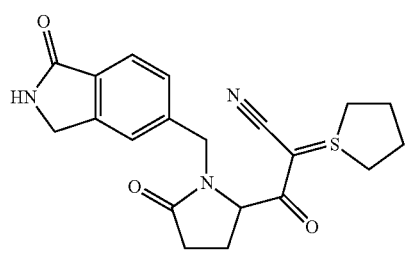 [SMILES: N#CC(C(=O)C1CCC(=O)N1Cc1ccc2c(c1)CNC2=O)=S1CCCC1]
I-424
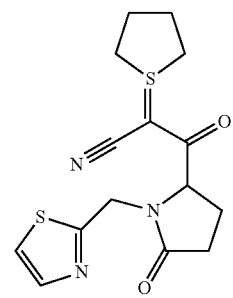 [SMILES: N#CC(C(=O)C1CCC(=O)N1Cc1nccs1)=S1CCCC1]
I-425

TABLE 1-continued
Intermediates (I-1-I-514)
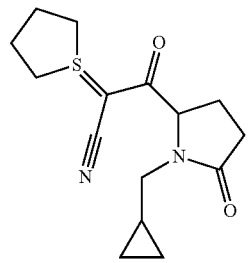 [SMILES: N#CC(C(=O)C1CCC(=O)N1CC1CC1)=S1CCCC1] I-426
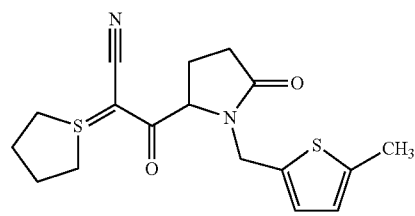 [SMILES: Cc1ccc(CN2C(=O)CCC2C(=O)C(C#N)=S2CCCC2)s1] I-427
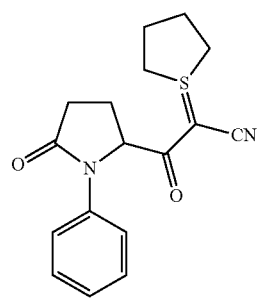 [SMILES: N#CC(C(=O)C1CCC(=O)N1c1ccccc1)=S1CCCC1] I-428
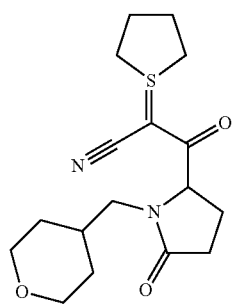 [SMILES: N#CC(C(=O)C1CCC(=O)N1CC1CCOCC1)=S1CCCC1] I-429
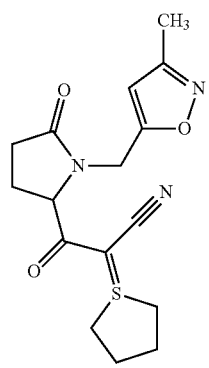 [SMILES: Cc1cc(CN2C(=O)CCC2C(=O)C(C#N)=S2CCCC2)on1] I-430

TABLE 1-continued
Intermediates (I-1-I-514)
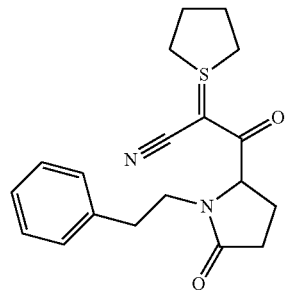 [SMILES: N#CC(C(=O)C1CCC(=O)N1CCc1ccccc1)=S1CCCC1]
I-431
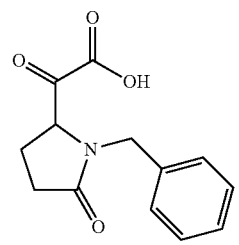 [SMILES: O=C(O)C(=O)C1CCC(=O)N1Cc1ccccc1]
I-432
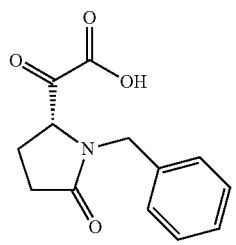
I-433
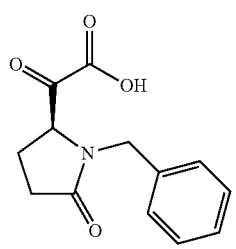 [SMILES: O=C(O)C(=O)[C@@H]1CCC(=O)N1Cc1ccccc1]
I-434
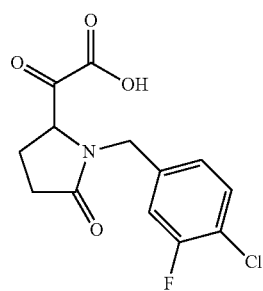 [SMILES: O=C(O)C(=O)C1CCC(=O)N1Cc1ccc(Cl)c(F)c1]
I-435

TABLE 1-continued
Intermediates (I-1-I-514)
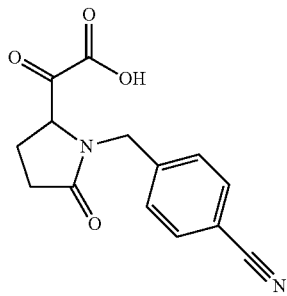 [SMILES: N#Cc1ccc(CN2C(=O)CCC2C(=O)C(=O)O)cc1]
I-436
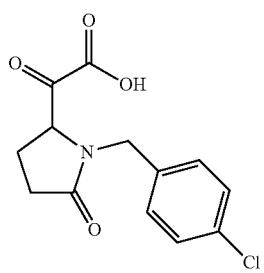 [SMILES: O=C(O)C(=O)C1CCC(=O)N1Cc1ccc(Cl)cc1]
I-437
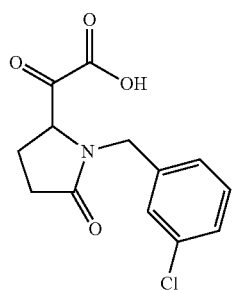 [SMILES: O=C(O)C(=O)C1CCC(=O)N1Cc1cccc(Cl)c1]
I-438
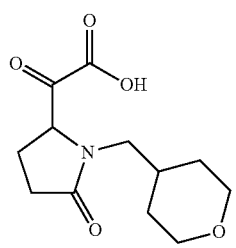 [SMILES: O=C(O)C(=O)C1CCC(=O)N1CC1CCOCC1]
I-439
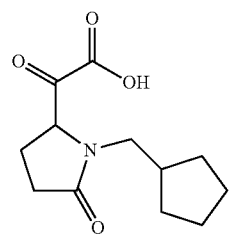 [SMILES: O=C(O)C(=O)C1CCC(=O)N1CC1CCCC1]
I-440

TABLE 1-continued
Intermediates (I-1-I-514)
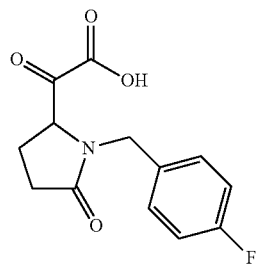 [SMILES: O=C(O)C(=O)C1CCC(=O)N1Cc1ccc(F)cc1]
I-441
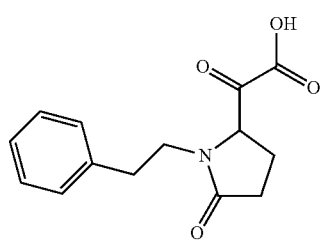 [SMILES: O=C(O)C(=O)C1CCC(=O)N1CCc1ccccc1]
I-442
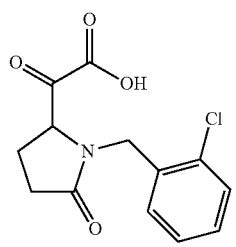 [SMILES: O=C(O)C(=O)C1CCC(=O)N1Cc1ccccc1Cl]
I-443
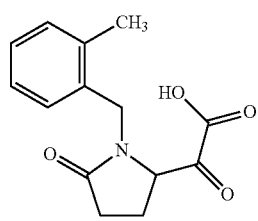 [SMILES: Cc1ccccc1CN1C(=O)CCC1C(=O)C(=O)O]
I-444
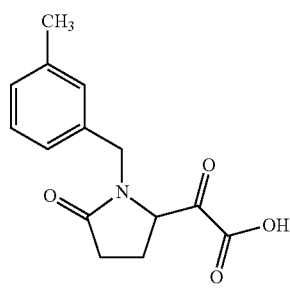 [SMILES: Cc1cccc(CN2C(=O)CCC2C(=O)C(=O)O)c1]
I-445
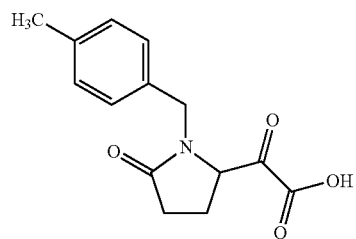 [SMILES: Cc1ccc(CN2C(=O)CCC2C(=O)C(=O)O)cc1]
I-446

TABLE 1-continued
Intermediates (I-1-I-514)
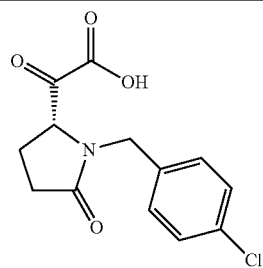
I-447
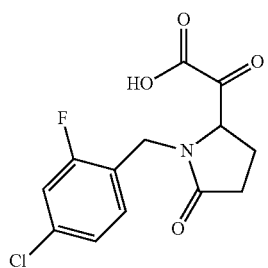 [SMILES: O=C(O)C(=O)C1CCC(=O)N1Cc1ccc(Cl)cc1F]
I-448
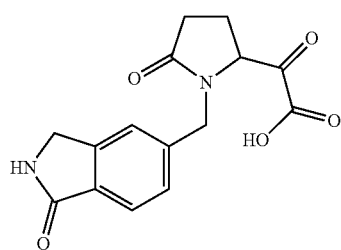 [SMILES: O=C(O)C(=O)C1CCC(=O)N1Cc1ccc2c(c1)CNC2=O]
I-449
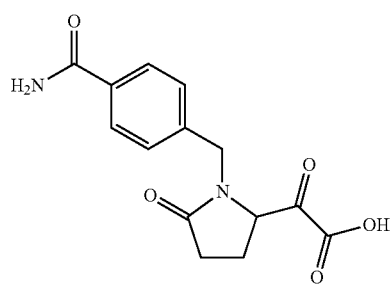 [SMILES: NC(=O)c1ccc(CN2C(=O)CCC2C(=O)C(=O)O)cc1]
I-450
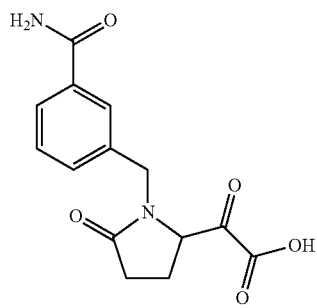 [SMILES: NC(=O)c1cccc(CN2C(=O)CCC2C(=O)C(=O)O)c1]
I-451
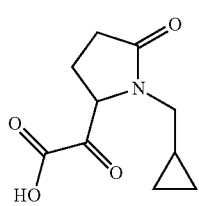 [SMILES: O=C(O)C(=O)C1CCC(=O)N1CC1CC1]
I-452

US 11,091,428 B2
TABLE 1-continued
Intermediates (I-1-I-514)
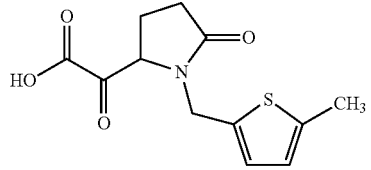 [SMILES: Cc1ccc(CN2C(=O)CCC2C(=O)C(=O)O)s1] I-453
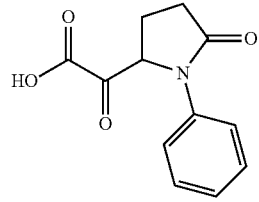 [SMILES: O=C(O)C(=O)C1CCC(=O)N1c1ccccc1] I-454
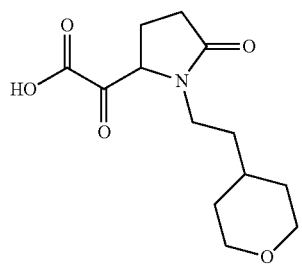 [SMILES: O=C(O)C(=O)C1CCC(=O)N1CCC1CCOCC1] I-455
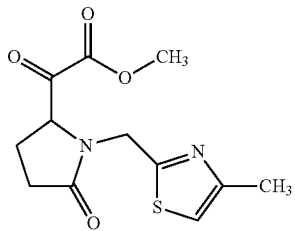 [SMILES: COC(=O)C(=O)C1CCC(=O)N1Cc1nc(C)cs1] I-456
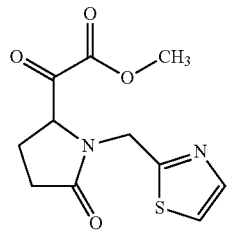 [SMILES: COC(=O)C(=O)C1CCC(=O)N1Cc1nccs1] I-457
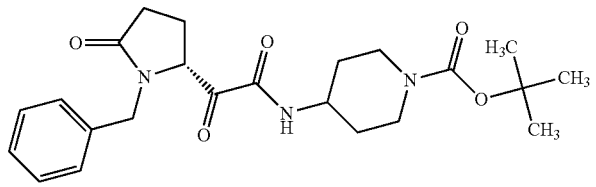 [SMILES: CC(C)(C)OC(=O)N1CCC(NC(=O)C(=O)[C@H]2CCC(=O)N2Cc2ccccc2)CC1] I-458
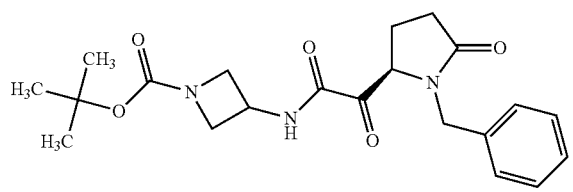 [SMILES: CC(C)(C)OC(=O)N1CC(NC(=O)C(=O)[C@H]2CCC(=O)N2Cc2ccccc2)C1] I-459

TABLE 1-continued

Intermediates (I-1-I-514)

| | |
|---|---|
| (structure) | I-460 |
| (structure) | I-461 |
| (structure) | I-462 |
| (structure) | I-463 |
| (structure) | I-464 |
| (structure) | I-465 |

TABLE 1-continued
Intermediates (I-1-I-514)
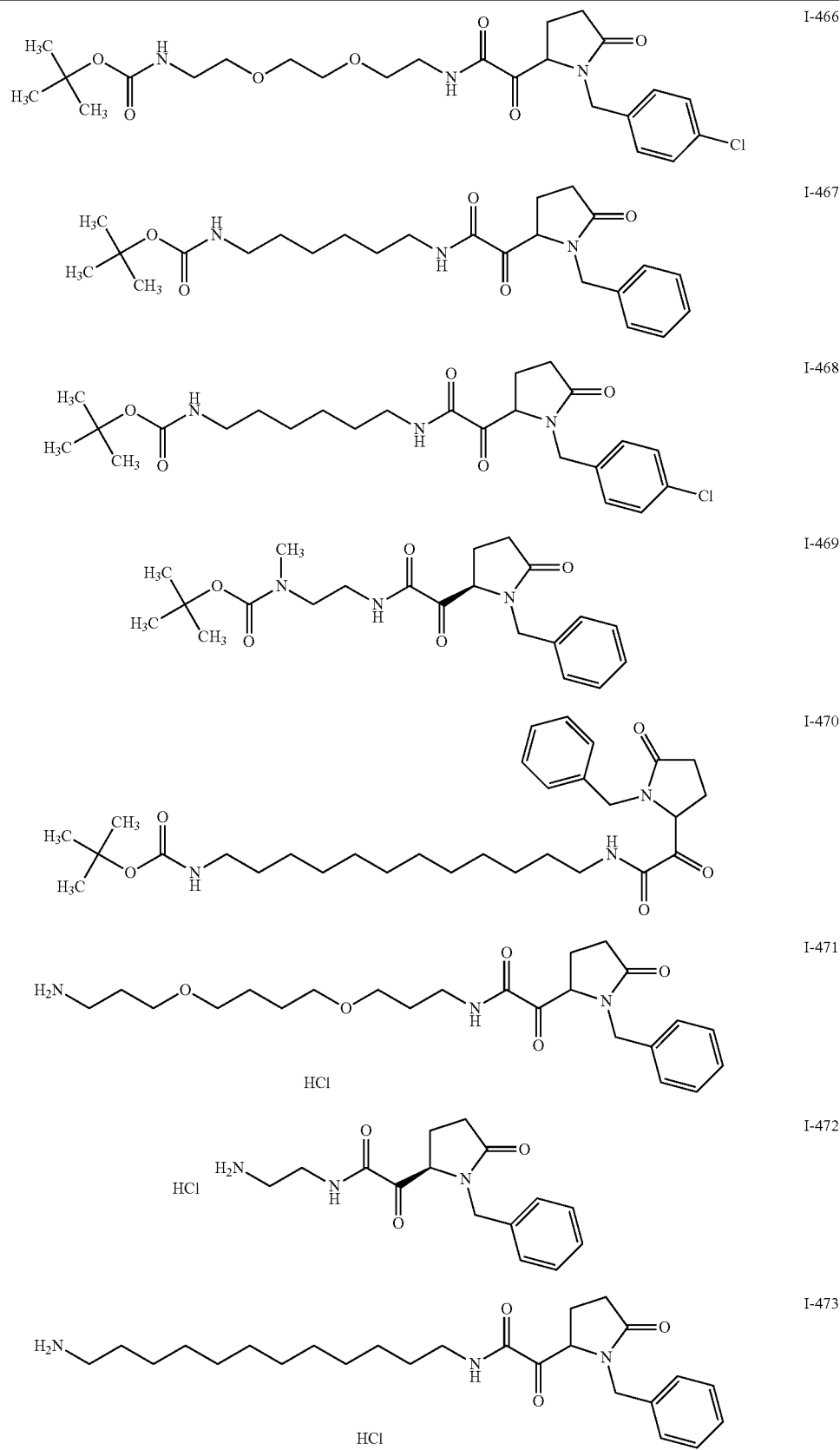

TABLE 1-continued
Intermediates (I-1-I-514)
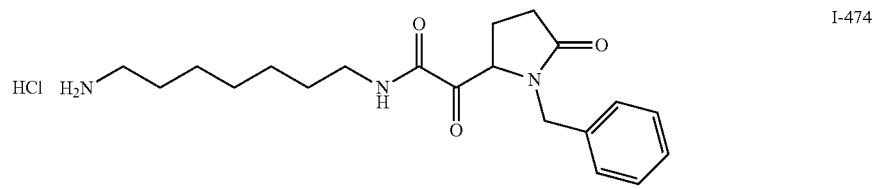 I-474
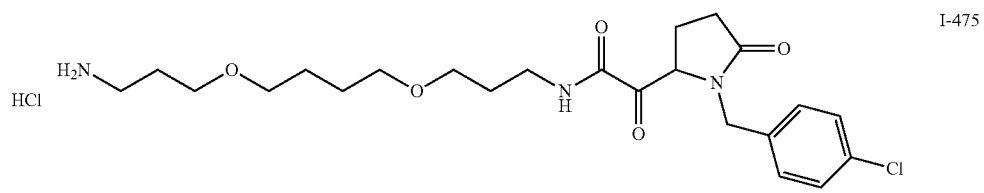 I-475
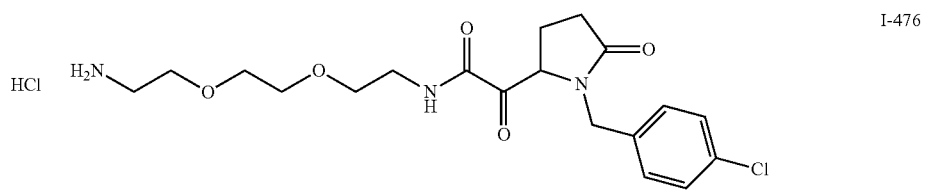 I-476
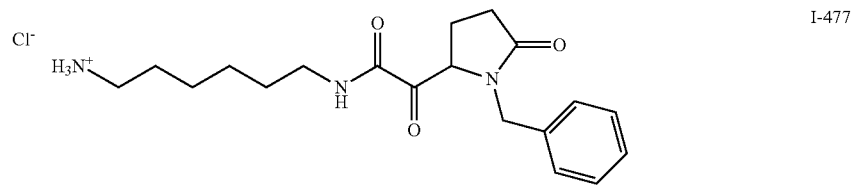 I-477
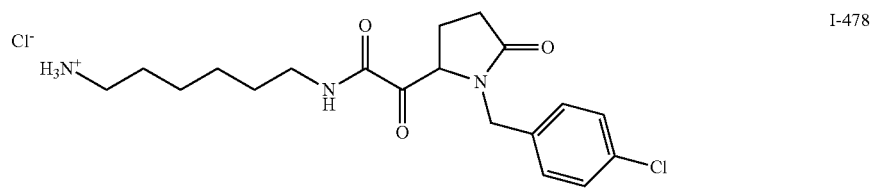 I-478
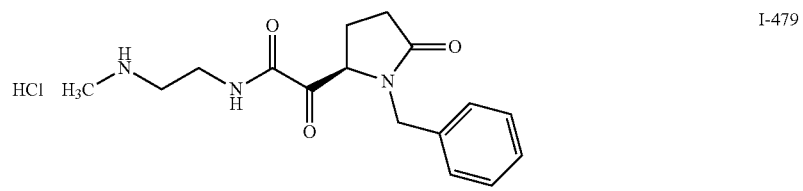 I-479
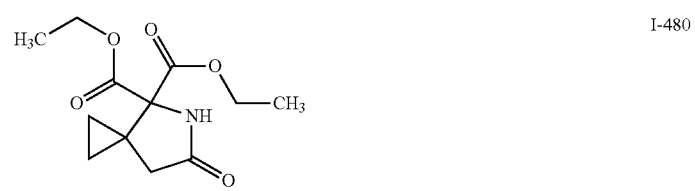 I-480

TABLE 1-continued
Intermediates (I-1-I-514)
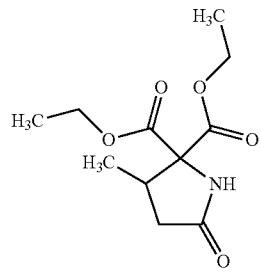 [SMILES: CCOC(=O)C1(C(=O)OCC)NC(=O)CC1C]
I-481
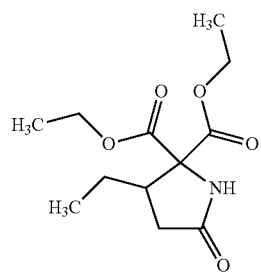 [SMILES: CCOC(=O)C1(C(=O)OCC)NC(=O)CC1CC]
I-482
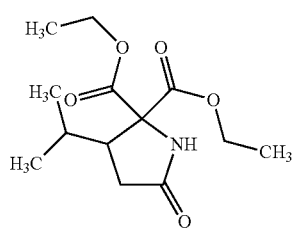 [SMILES: CCOC(=O)C1(C(=O)OCC)NC(=O)CC1C(C)C]
I-483
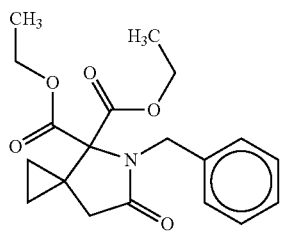
I-484
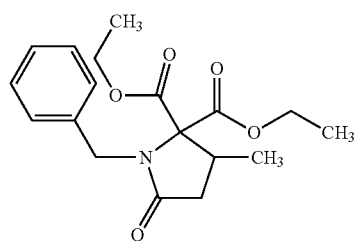 [SMILES: CCOC(=O)C1(C(=O)OCC)C(C)CC(=O)N1Cc1ccccc1]
I-485
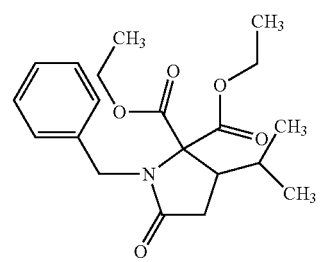 [SMILES: CCOC(=O)C1(C(=O)OCC)C(C(C)C)CC(=O)N1Cc1ccccc1]
I-486

TABLE 1-continued
Intermediates (I-1-I-514)
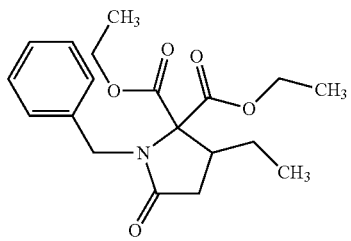 [SMILES: CCOC(=O)C1(C(=O)OCC)C(CC)CC(=O)N1Cc1ccccc1] I-487
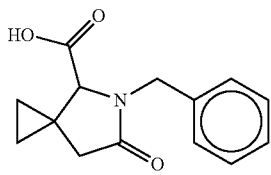 I-488
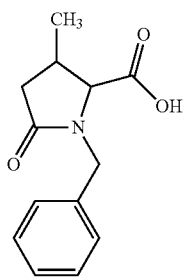 [SMILES: CC1CC(=O)N(Cc2ccccc2)C1C(=O)O] I-489
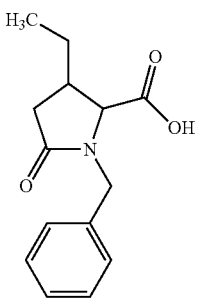 I-490
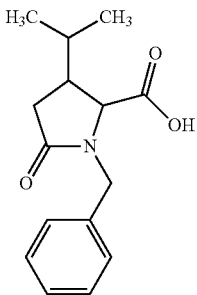 I-491
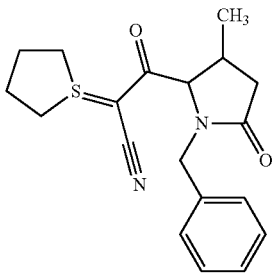 [SMILES: CC1CC(=O)N(Cc2ccccc2)C1C(=O)C(C#N)=S1CCCC1] I-492

TABLE 1-continued
Intermediates (I-1-I-514)
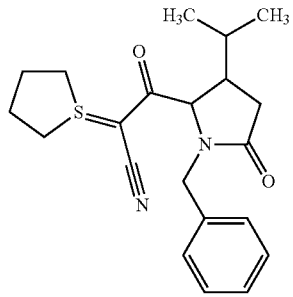 [SMILES: CC(C)C1CC(=O)N(Cc2ccccc2)C1C(=O)C(C#N)=S1CCCC1] I-493
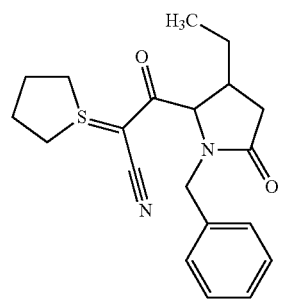 [SMILES: CCC1CC(=O)N(Cc2ccccc2)C1C(=O)C(C#N)=S1CCCC1] I-494
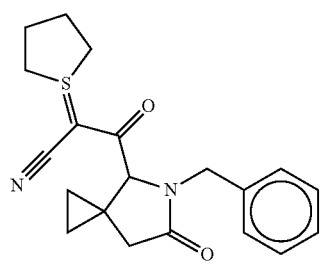 I-495
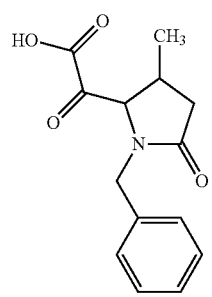 [SMILES: CC1CC(=O)N(Cc2ccccc2)C1C(=O)C(=O)O] I-496
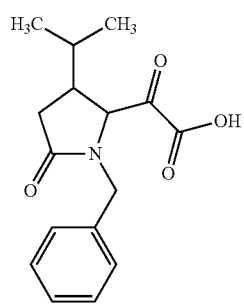 [SMILES: CC(C)C1CC(=O)N(Cc2ccccc2)C1C(=O)C(=O)O] I-497

TABLE 1-continued
Intermediates (I-1-I-514)
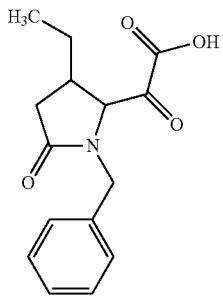 [SMILES: CCC1CC(=O)N(Cc2ccccc2)C1C(=O)C(=O)O]
I-498
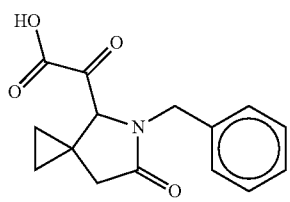
I-499
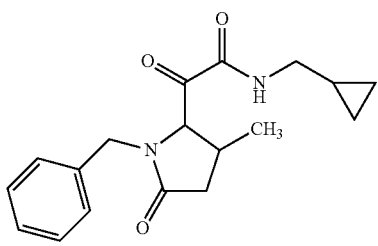 [SMILES: CC1CC(=O)N(Cc2ccccc2)C1C(=O)C(=O)NCC1CC1]
I-500
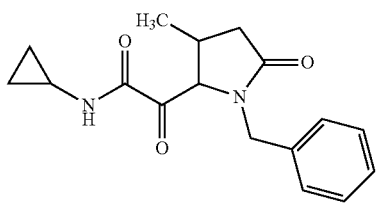 [SMILES: CC1CC(=O)N(Cc2ccccc2)C1C(=O)C(=O)NC1CC1]
I-501
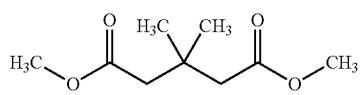
I-502
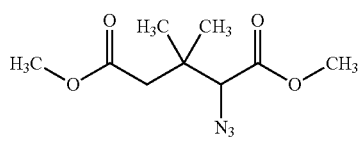
I-503
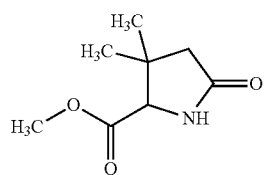
I-504

TABLE 1-continued

Intermediates (I-1-I-514)

I-505

I-506

I-507

I-508

TABLE 2

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

FP 1 (A/I)

FP 2 (A/ND)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

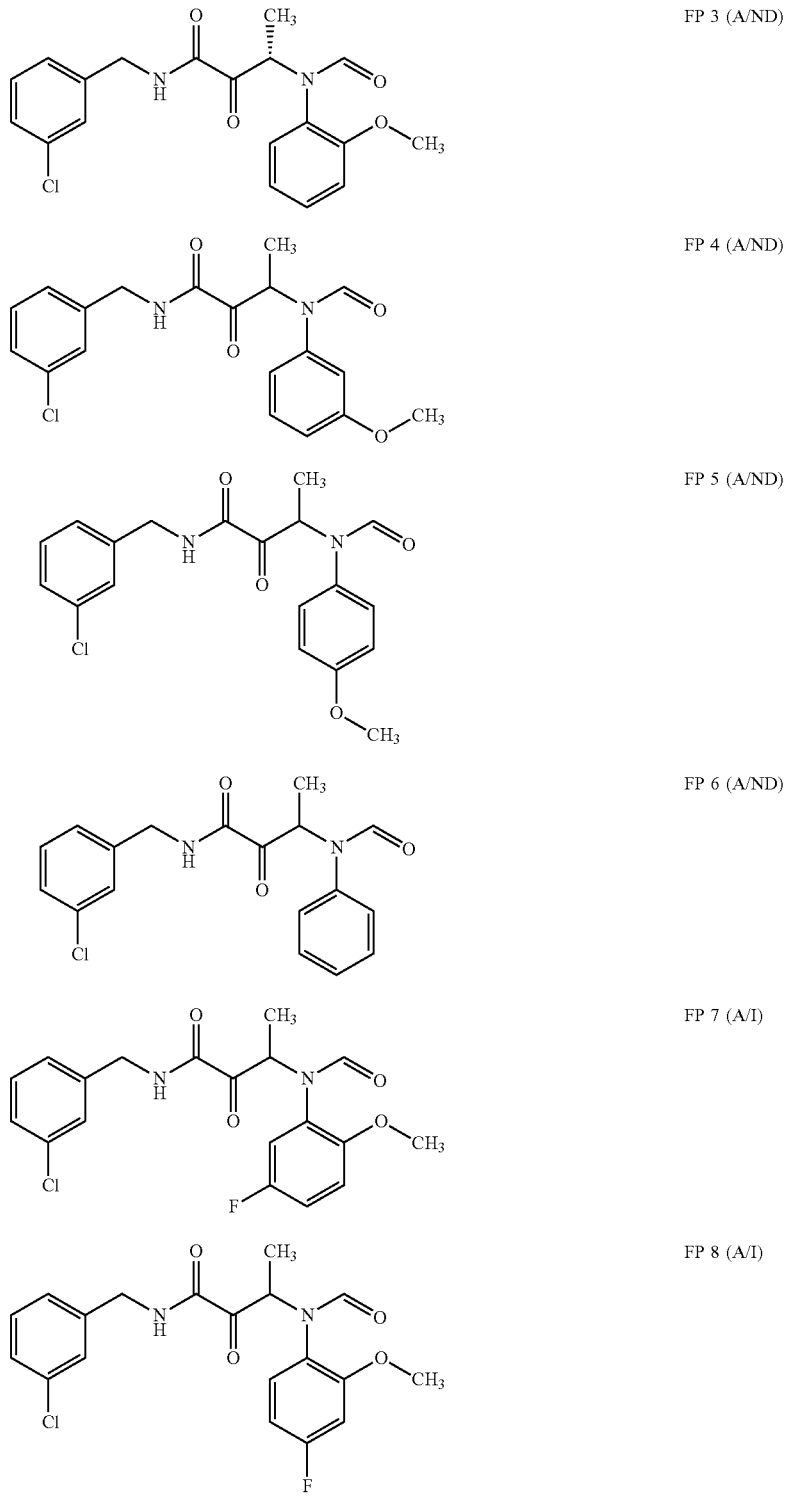

FP 3 (A/ND)

FP 4 (A/ND)

FP 5 (A/ND)

FP 6 (A/ND)

FP 7 (A/I)

FP 8 (A/I)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

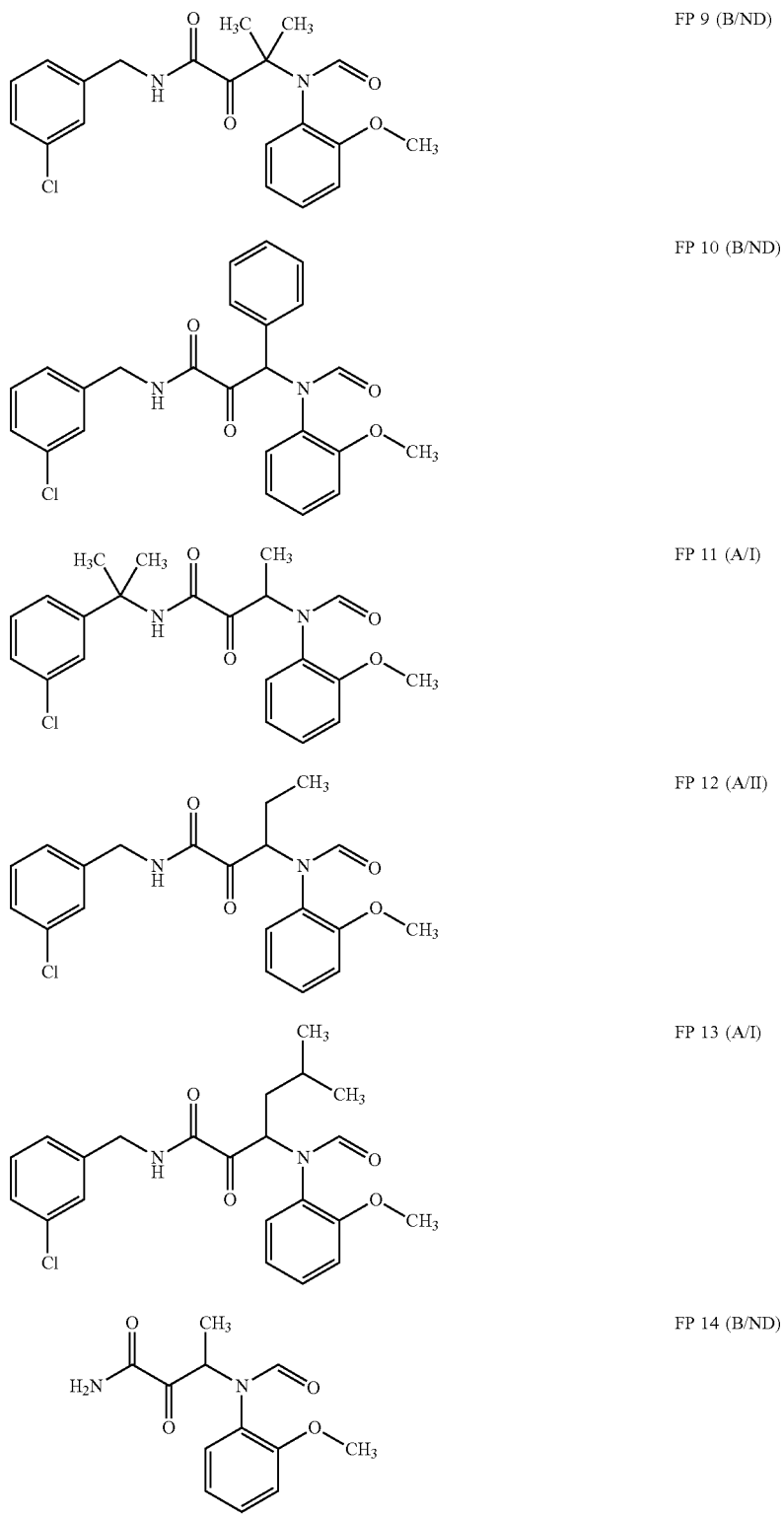

FP 9 (B/ND)

FP 10 (B/ND)

FP 11 (A/I)

FP 12 (A/II)

FP 13 (A/I)

FP 14 (B/ND)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

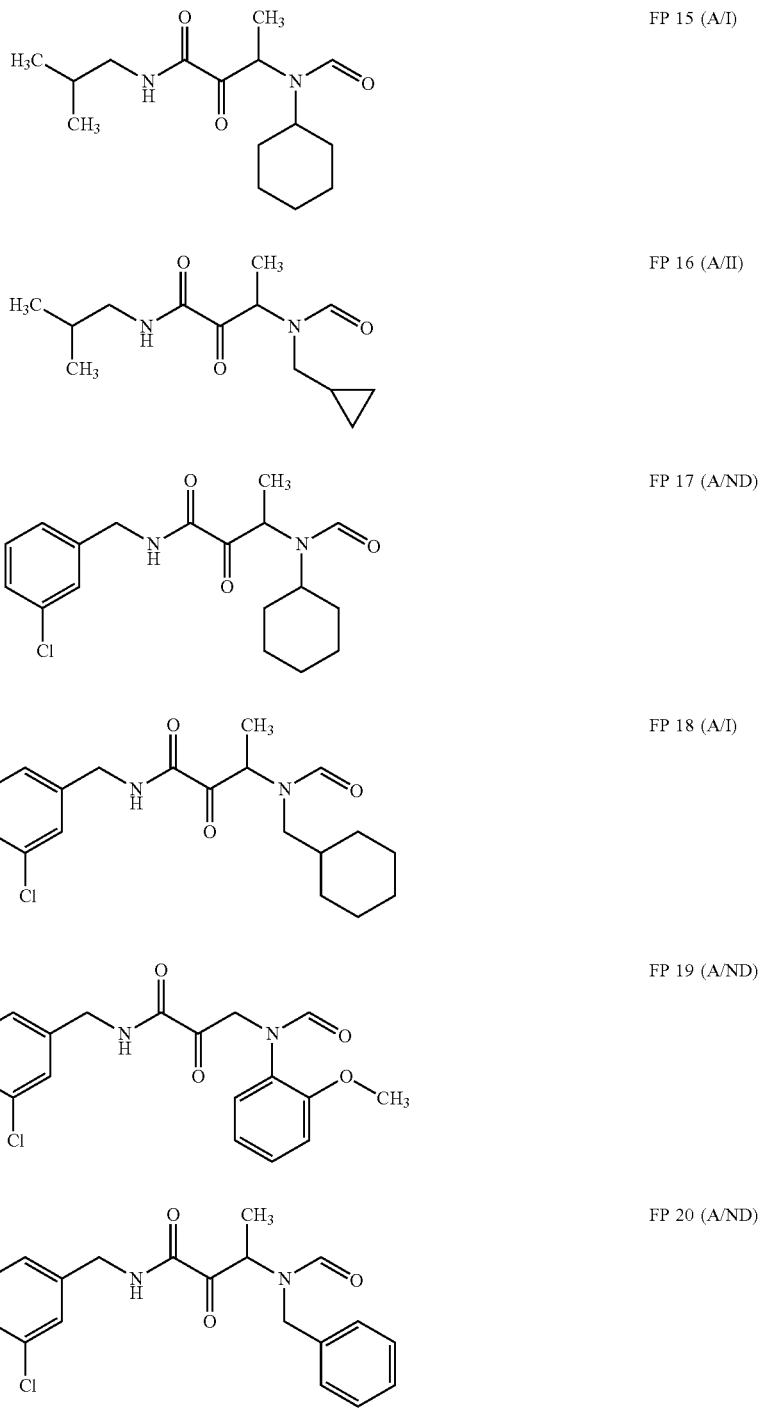

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

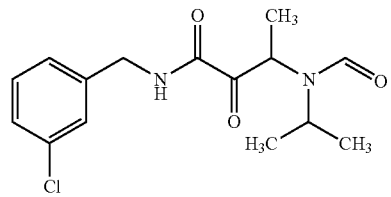 [SMILES: CC(C)N(C=O)C(C)C(=O)C(=O)NCc1cccc(Cl)c1]

FP 21 (A/ND)

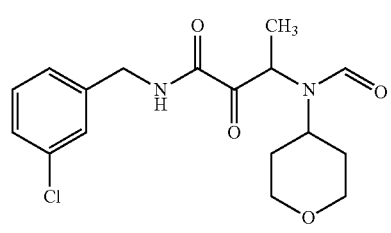 [SMILES: CC(C(=O)C(=O)NCc1cccc(Cl)c1)N(C=O)C1CCOCC1]

FP 22 (A/II)

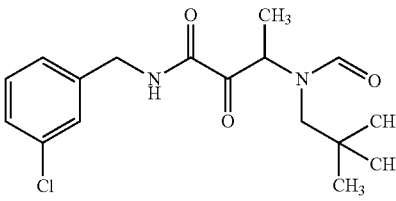

FP 23 (A/I)

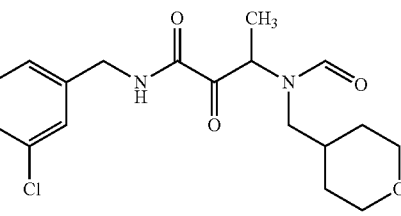

FP 24 (A/II)

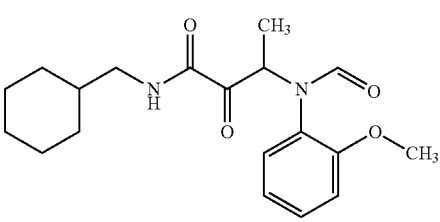 [SMILES: COc1ccccc1N(C=O)C(C)C(=O)C(=O)NCC1CCCCC1]

FP 25 (A/I)

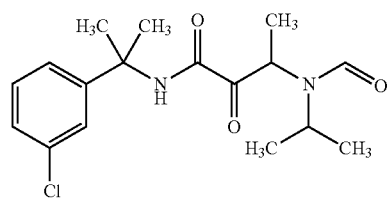 [SMILES: CC(C)N(C=O)C(C)C(=O)C(=O)NC(C)(C)c1cccc(Cl)c1]

FP 26 (B/ND)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

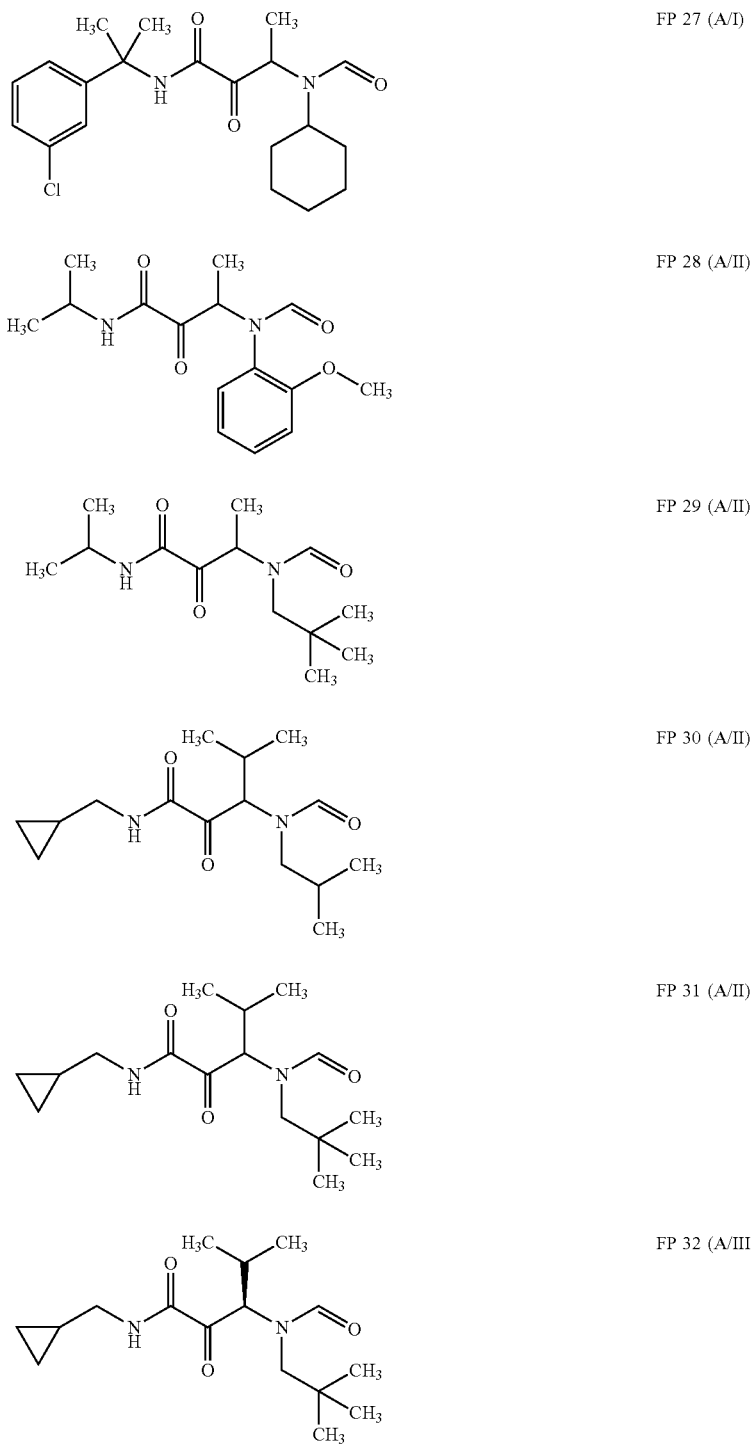

FP 27 (A/I)

FP 28 (A/II)

FP 29 (A/II)

FP 30 (A/II)

FP 31 (A/II)

FP 32 (A/III)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

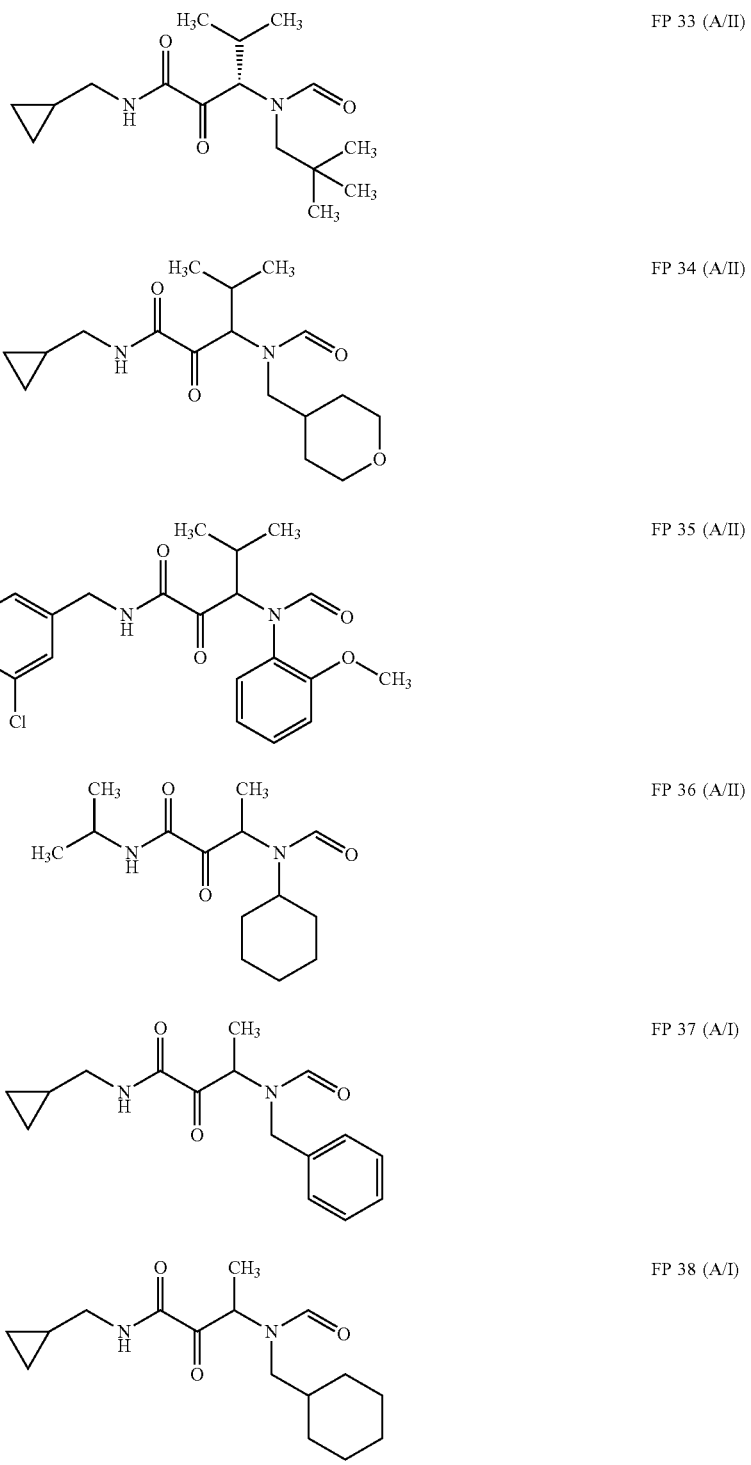

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

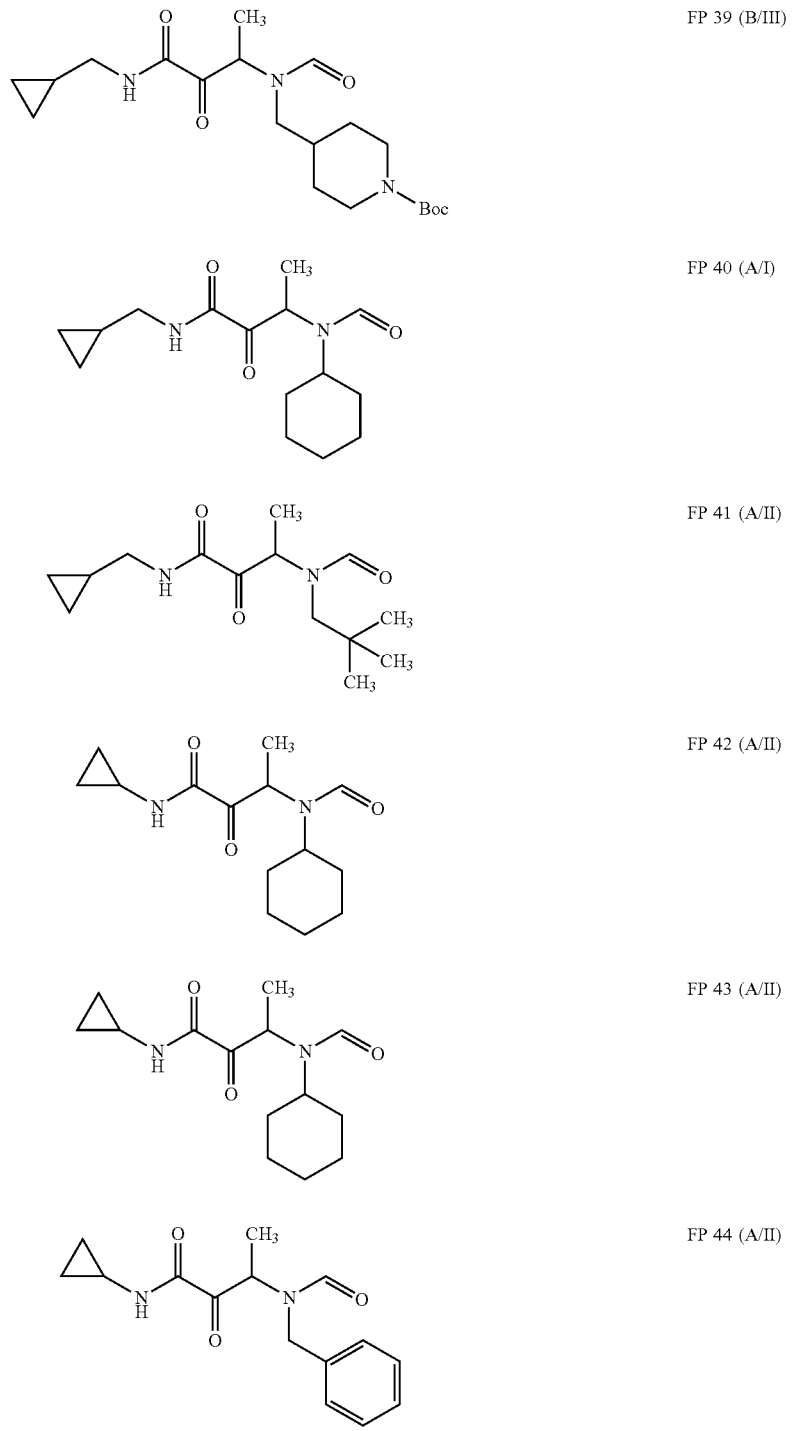

FP 39 (B/III)

FP 40 (A/I)

FP 41 (A/II)

FP 42 (A/II)

FP 43 (A/II)

FP 44 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

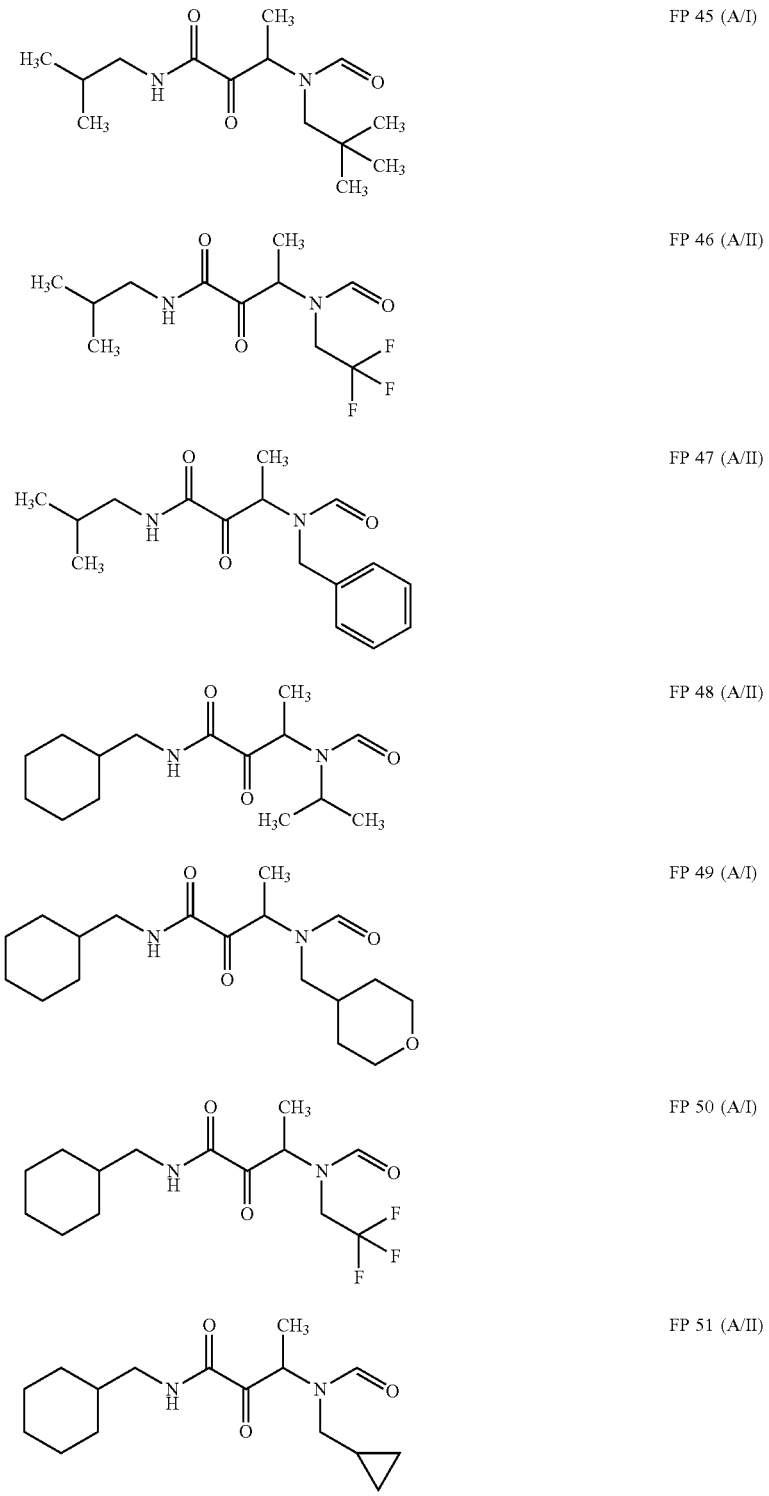

FP 45 (A/I)

FP 46 (A/II)

FP 47 (A/II)

FP 48 (A/II)

FP 49 (A/I)

FP 50 (A/I)

FP 51 (A/II)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

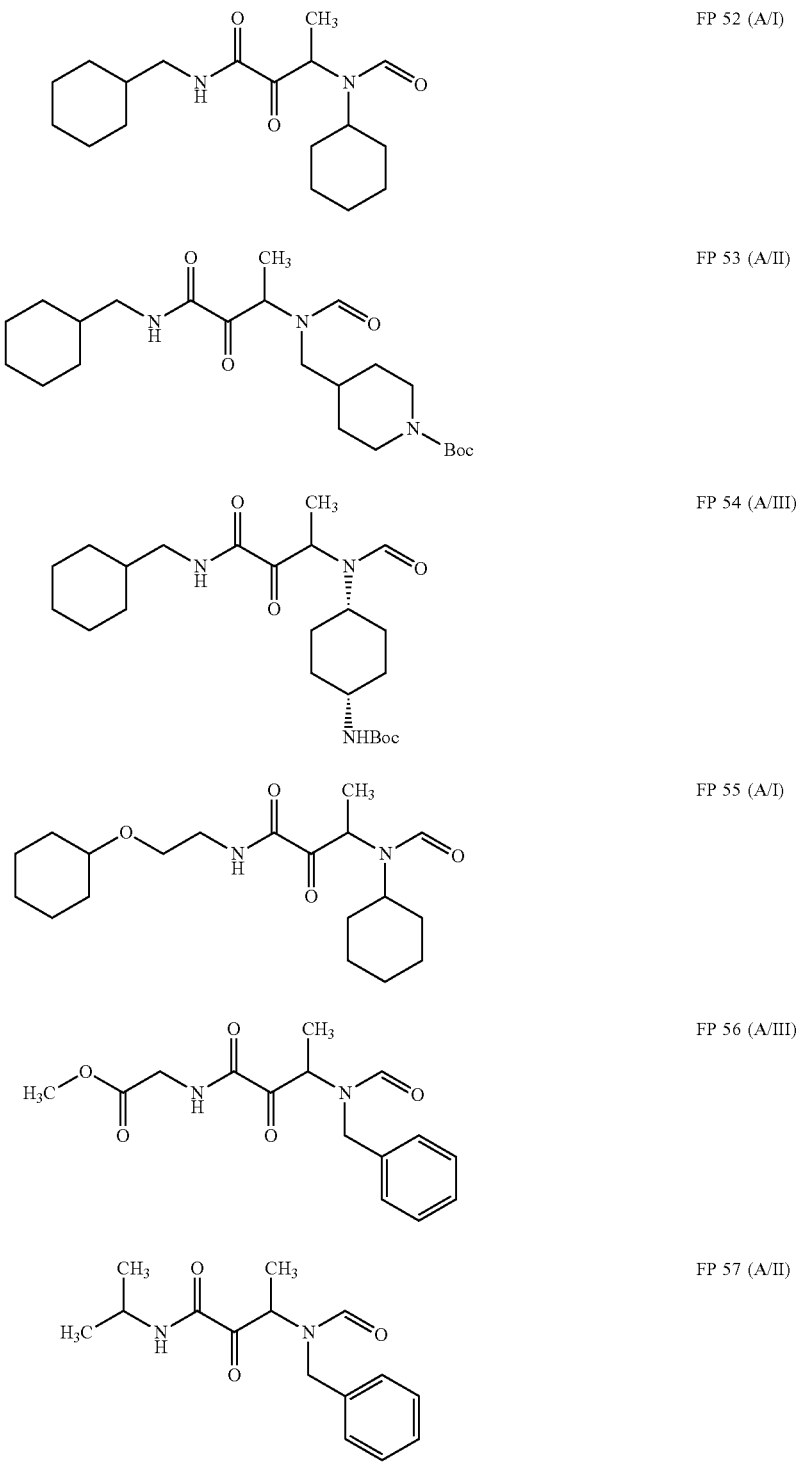

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

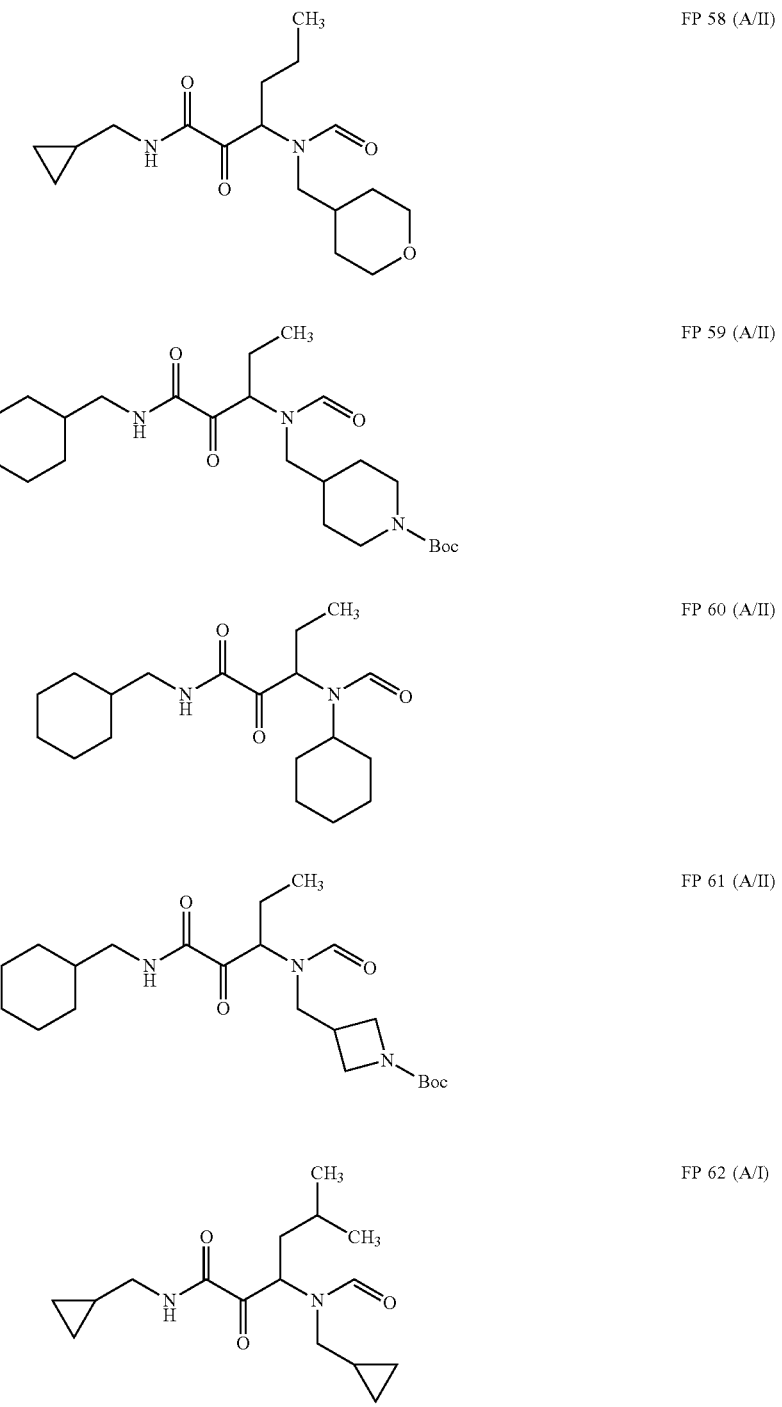

FP 58 (A/II)

FP 59 (A/II)

FP 60 (A/II)

FP 61 (A/II)

FP 62 (A/I)

US 11,091,428 B2

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

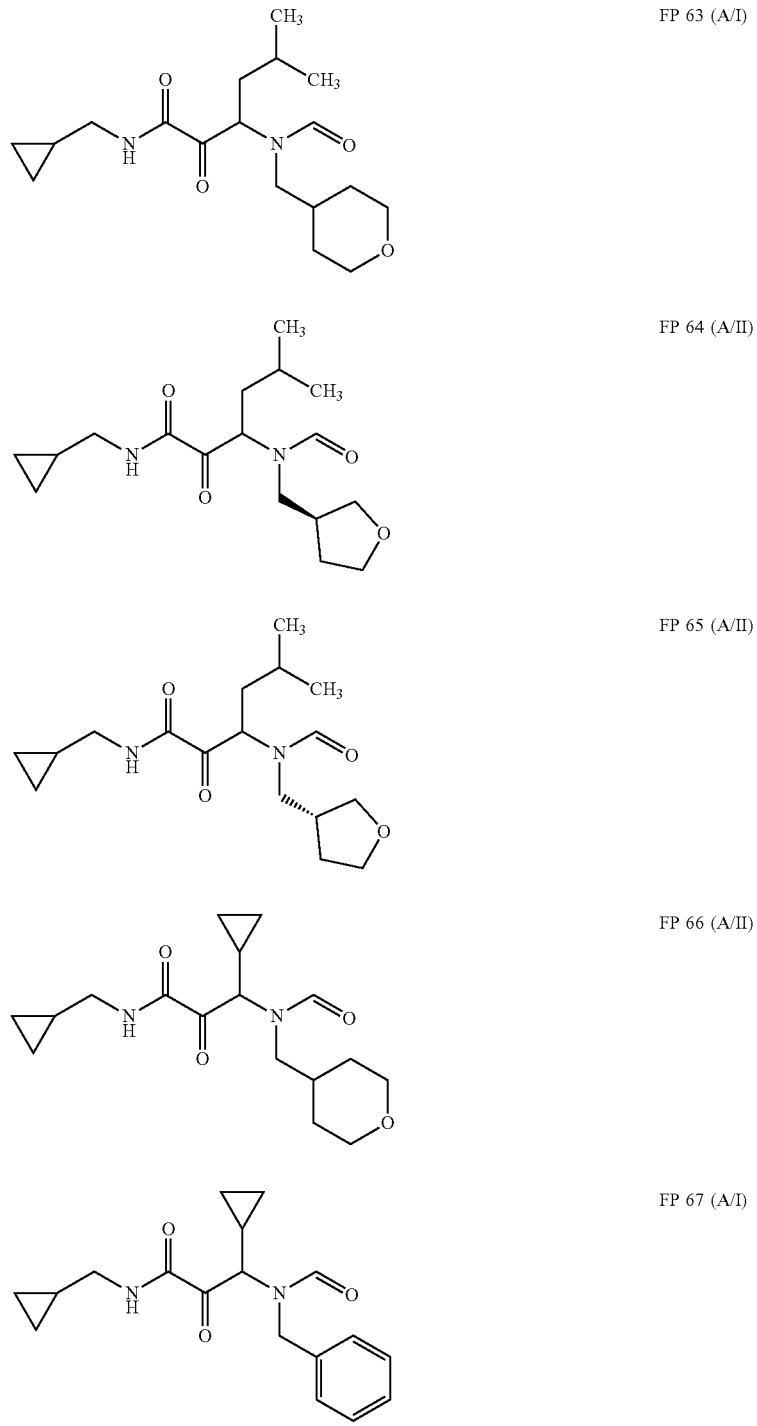

FP 63 (A/I)

FP 64 (A/II)

FP 65 (A/II)

FP 66 (A/II)

FP 67 (A/I)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

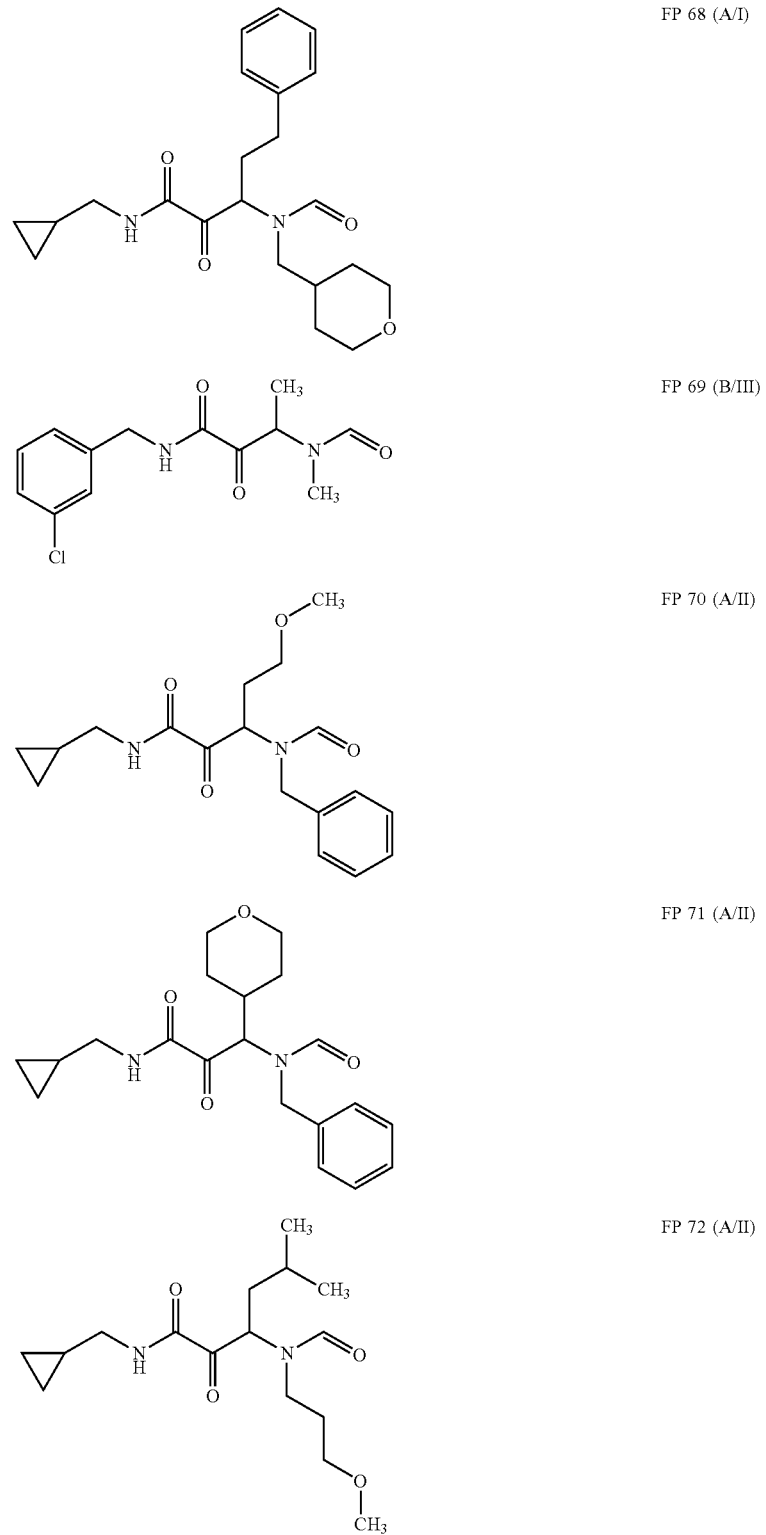

FP 68 (A/I)

FP 69 (B/III)

FP 70 (A/II)

FP 71 (A/II)

FP 72 (A/II)

TABLE 2-continued

Compounds FP 1-FP 191
$IC_{50}$ values of the compounds determined in the enzyme activity assay for PLA2G16 described below and $EC_{50}$ values of the compounds determined in the anti-picornavirus assay described below are given in parentheses. Compounds with $IC_{50}$ values <1 µM (class "A") in the enzymatic activity assay are considered as highly active, compounds with $IC_{50}$ values between 1 and 10 µM (class "B") are considered as medium active and compounds with $IC_{50}$ values greater than 10 µM, but below 50 µM (class "C") are considered as weakly active. Antiviral activity against four different picornaviruses is categorized analogously, where class "I" denotes compounds with $EC_{50}$ <1 µM, class "II" with $EC_{50}$, between 1 µM and 10 µM and class "III" with $EC_{50}$ >10 µM.

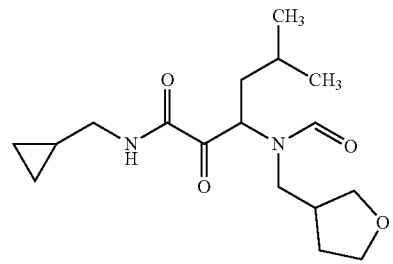 [SMILES: CC(C)CC(C(=O)C(=O)NCC1CC1)N(C=O)CC1CCOC1]

FP 73 (A/II)

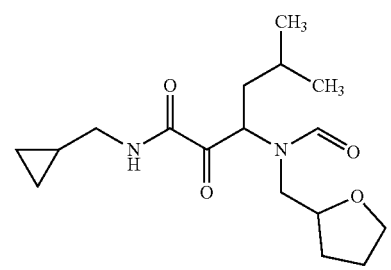 [SMILES: CC(C)CC(C(=O)C(=O)NCC1CC1)N(C=O)CC1CCCO1]

FP 74 (A/II)

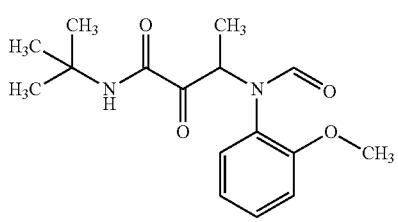 [SMILES: COc1ccccc1N(C=O)C(C)C(=O)C(=O)NC(C)(C)C]

FP 75 (A/II)

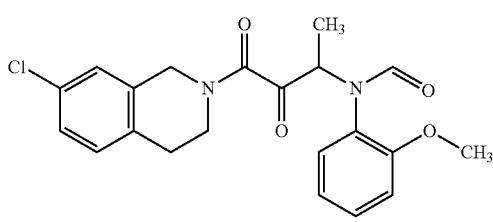 [SMILES: COc1ccccc1N(C=O)C(C)C(=O)C(=O)N1CCc2ccc(Cl)cc2C1]

FP 76 (C/ND)

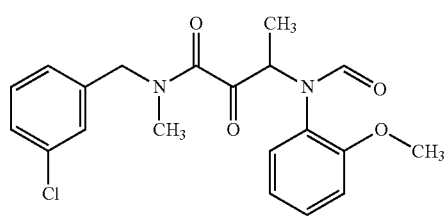 [SMILES: COc1ccccc1N(C=O)C(C)C(=O)C(=O)N(C)Cc1cccc(Cl)c1]

FP 77 (A/ND)

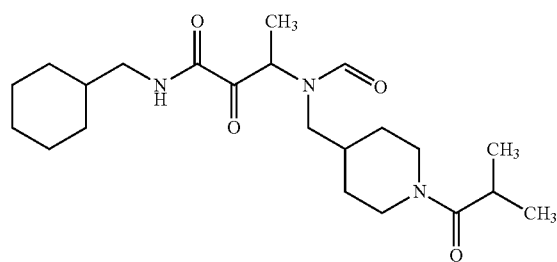 [SMILES: CC(C)C(=O)N1CCC(CN(C=O)C(C)C(=O)C(=O)NCC2CCCCC2)CC1]

FP 78 (B/III)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

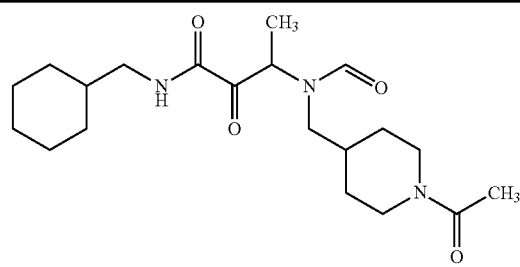

FP 79 (B/III)

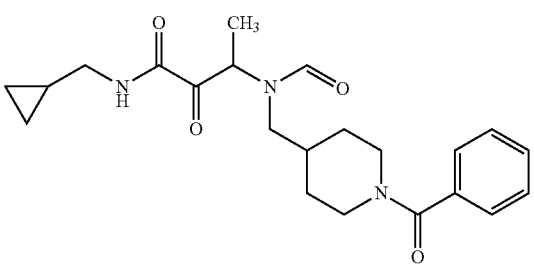 [SMILES: CC(C(=O)C(=O)NCC1CC1)N(C=O)CC1CCN(C(=O)c2ccccc2)CC1]

FP 80 (B/III)

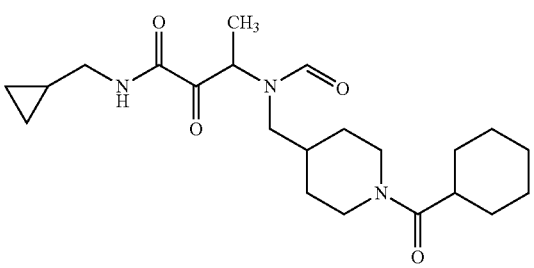 [SMILES: CC(C(=O)C(=O)NCC1CC1)N(C=O)CC1CCN(C(=O)C2CCCCC2)CC1]

FP 81 (B/III)

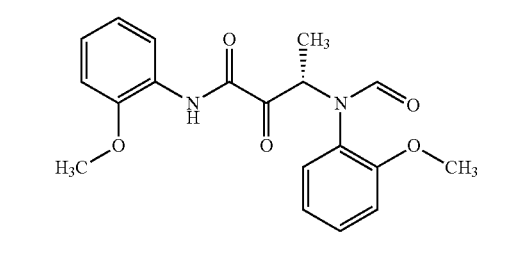 [SMILES: COc1ccccc1NC(=O)C(=O)[C@H](C)N(C=O)c1ccccc1OC]

FP 82 (B/ND)

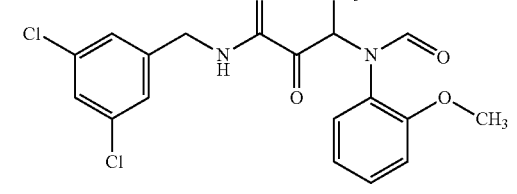

FP 83 (A/ND)

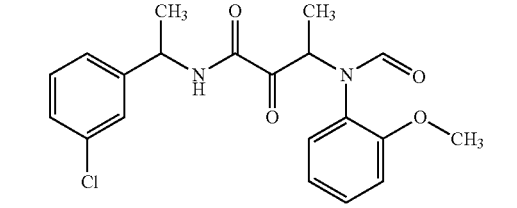 [SMILES: COc1ccccc1N(C=O)C(C)C(=O)C(=O)NC(C)c1cccc(Cl)c1]

FP 84 (A/ND)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

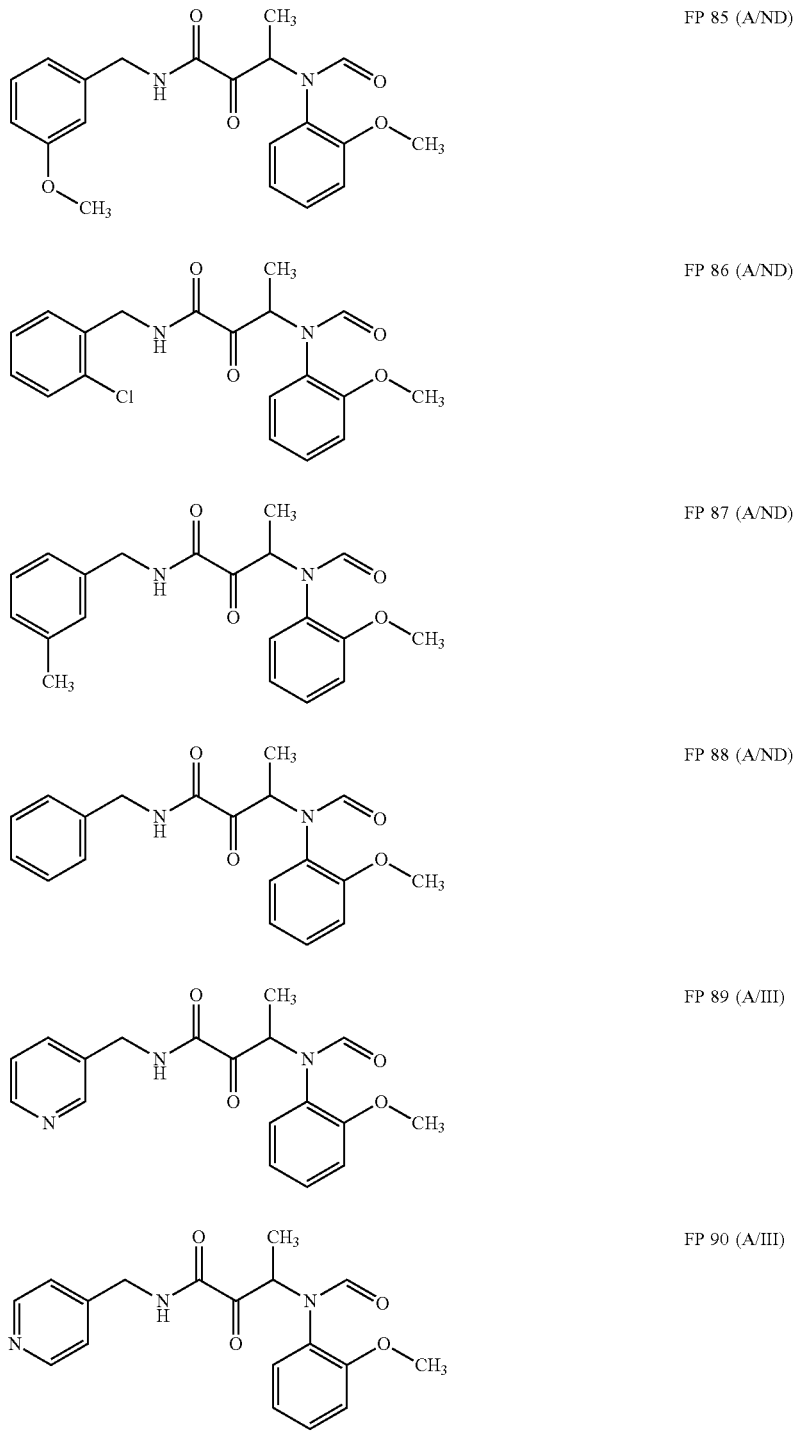

FP 85 (A/ND)

FP 86 (A/ND)

FP 87 (A/ND)

FP 88 (A/ND)

FP 89 (A/III)

FP 90 (A/III)

TABLE 2-continued

Compounds FP 1-FP 191

$IC_{50}$ values of the compounds determined in the enzyme activity assay for PLA2G16 described below and $EC_{50}$ values of the compounds determined in the anti-picornavirus assay described below are given in parentheses. Compounds with $IC_{50}$ values <1 μM (class "A") in the enzymatic activity assay are considered as highly active, compounds with $IC_{50}$ values between 1 and 10 μM (class "B") are considered as medium active and compounds with $IC_{50}$ values greater than 10 μM, but below 50 μM (class "C") are considered as weakly active. Antiviral activity against four different picornaviruses is categorized analogously, where class "I" denotes compounds with $EC_{50}$ <1 μM, class "II" with $EC_{50}$, between 1 μM and 10 μM and class "III" with $EC_{50}$ >10 μM.

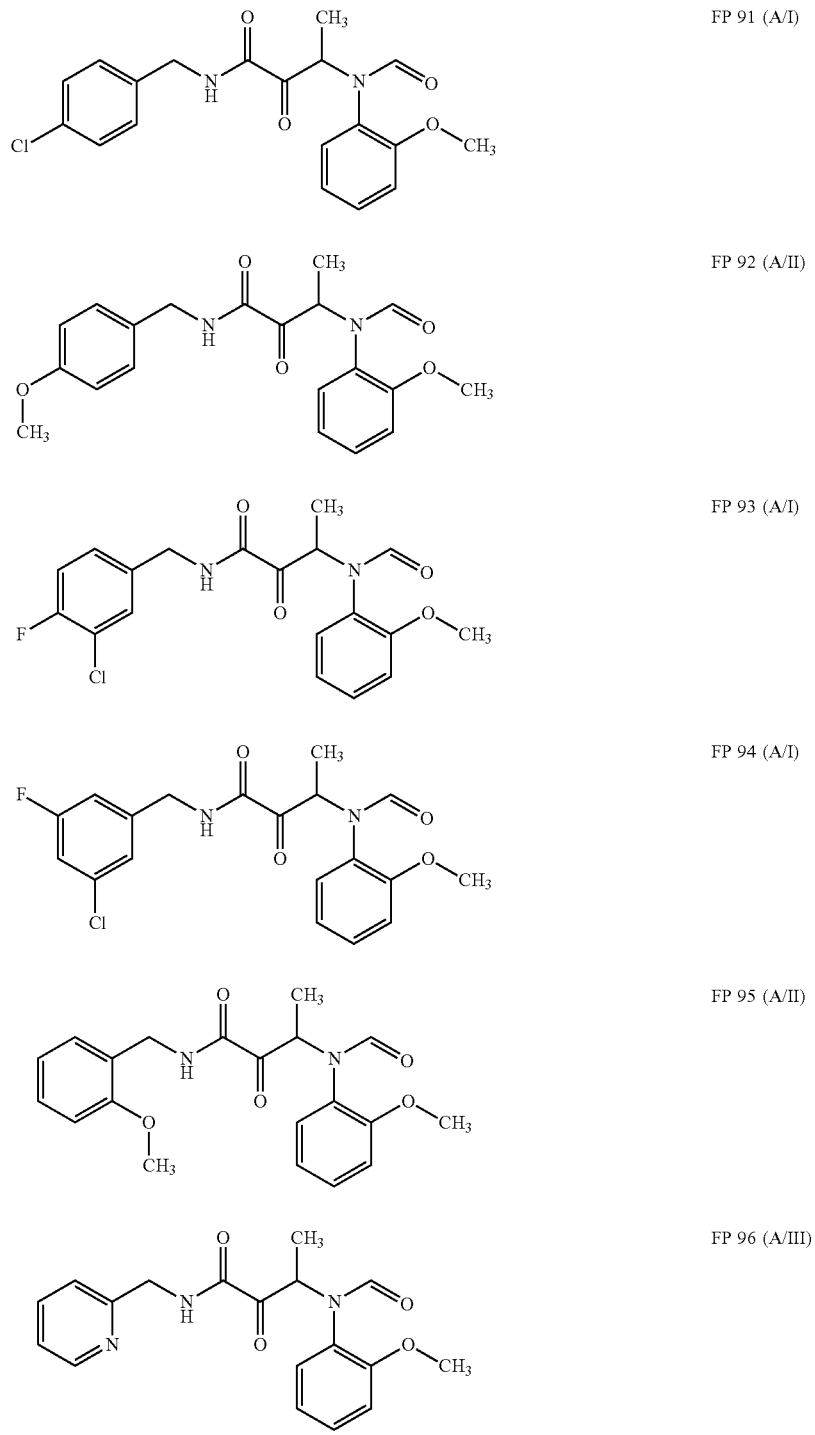

FP 91 (A/I)

FP 92 (A/II)

FP 93 (A/I)

FP 94 (A/I)

FP 95 (A/II)

FP 96 (A/III)

TABLE 2-continued

Compounds FP 1-FP 191

$IC_{50}$ values of the compounds determined in the enzyme activity assay for PLA2G16 described below and $EC_{50}$ values of the compounds determined in the anti-picornavirus assay described below are given in parentheses. Compounds with $IC_{50}$ values <1 µM (class "A") in the enzymatic activity assay are considered as highly active, compounds with $IC_{50}$ values between 1 and 10 µM (class "B") are considered as medium active and compounds with $IC_{50}$ values greater than 10 µM, but below 50 µM (class "C") are considered as weakly active. Antiviral activity against four different picornaviruses is categorized analogously, where class "I" denotes compounds with $EC_{50}$ <1 µM, class "II" with $EC_{50}$, between 1 µM and 10 µM and class "III" with $EC_{50}$ >10 µM.

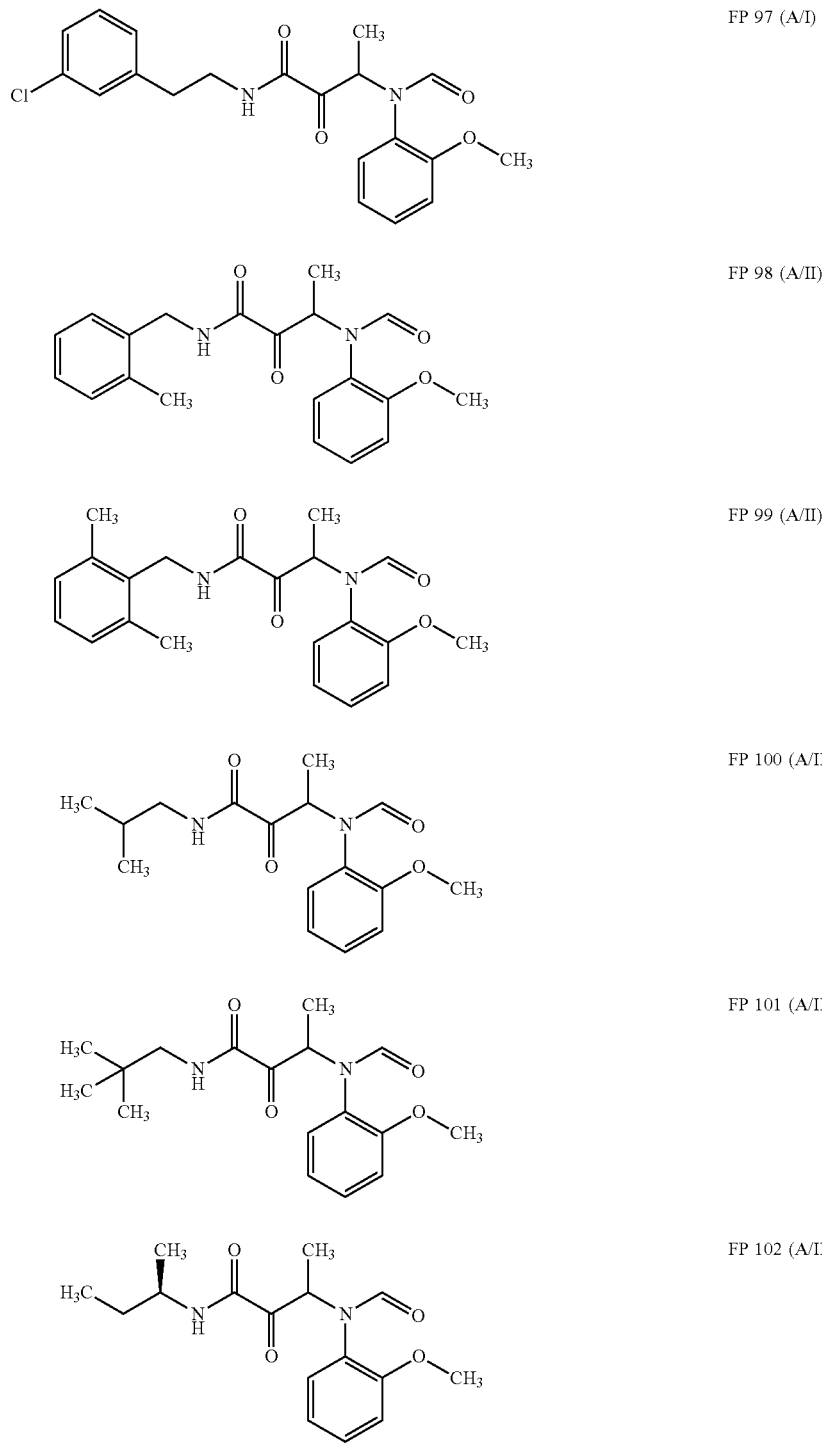

FP 97 (A/I)

FP 98 (A/II)

FP 99 (A/II)

FP 100 (A/II)

FP 101 (A/II)

FP 102 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

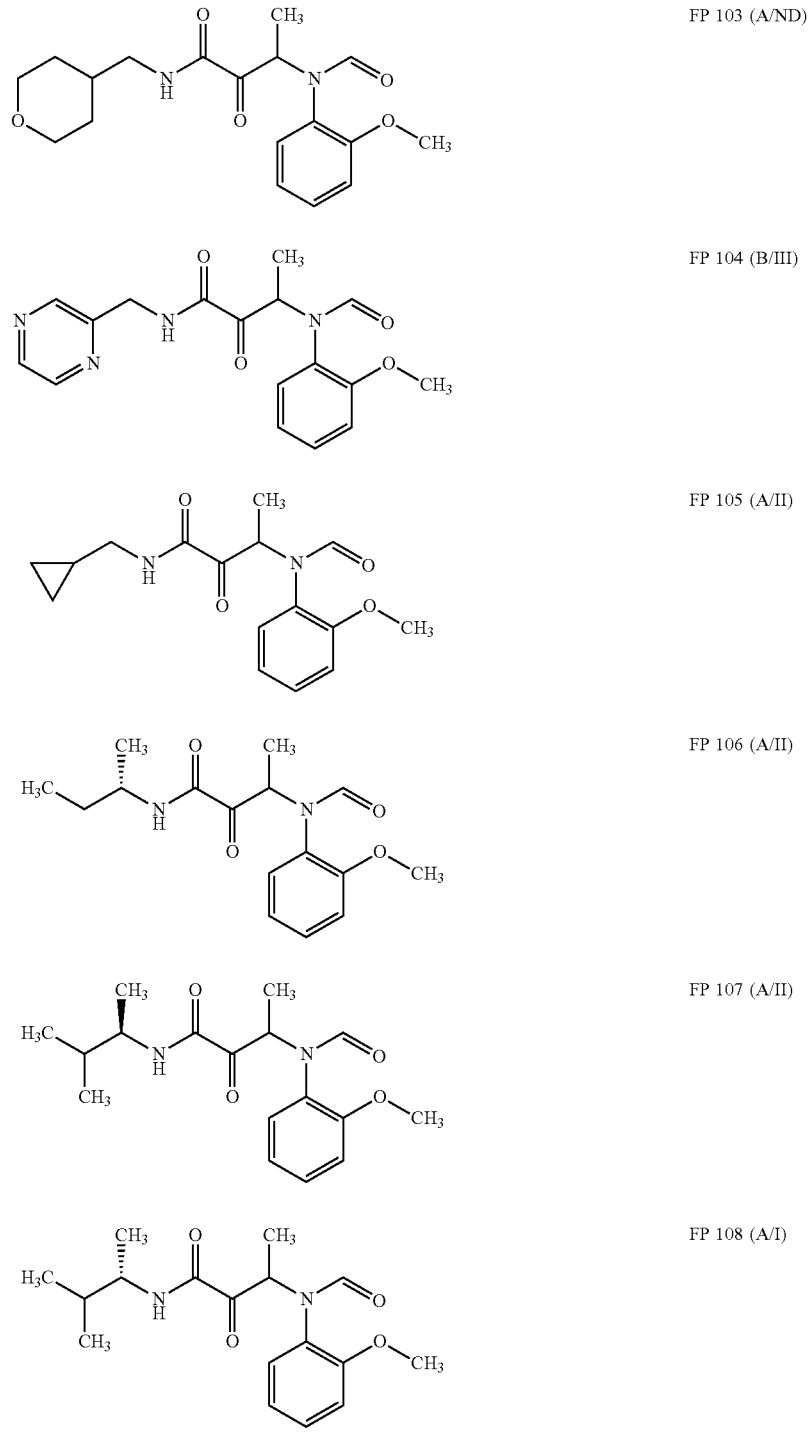

FP 103 (A/ND)

FP 104 (B/III)

FP 105 (A/II)

FP 106 (A/II)

FP 107 (A/II)

FP 108 (A/I)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

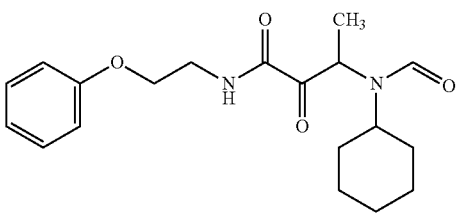 [SMILES: CC(C(=O)C(=O)NCCOc1ccccc1)N(C=O)C1CCCCC1]

FP 109 (A/I)

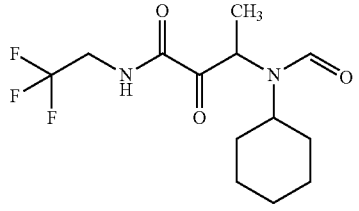 [SMILES: CC(C(=O)C(=O)NCC(F)(F)F)N(C=O)C1CCCCC1]

FP 110 (A/II)

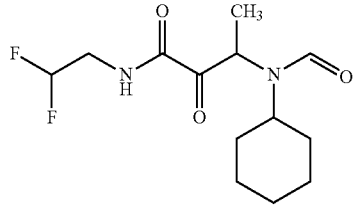 [SMILES: CC(C(=O)C(=O)NCC(F)F)N(C=O)C1CCCCC1]

FP 111 (A/III)

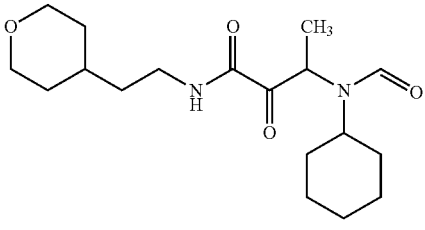 [SMILES: CC(C(=O)C(=O)NCCC1CCOCC1)N(C=O)C1CCCCC1]

FP 112 (A/II)

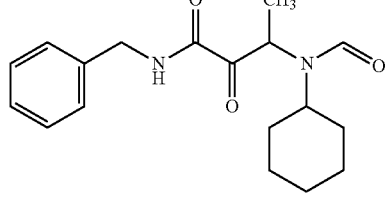

FP 113 (A/ND)

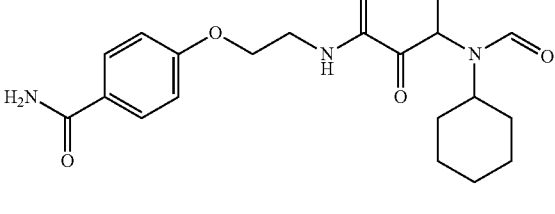

FP 114 (A/III)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

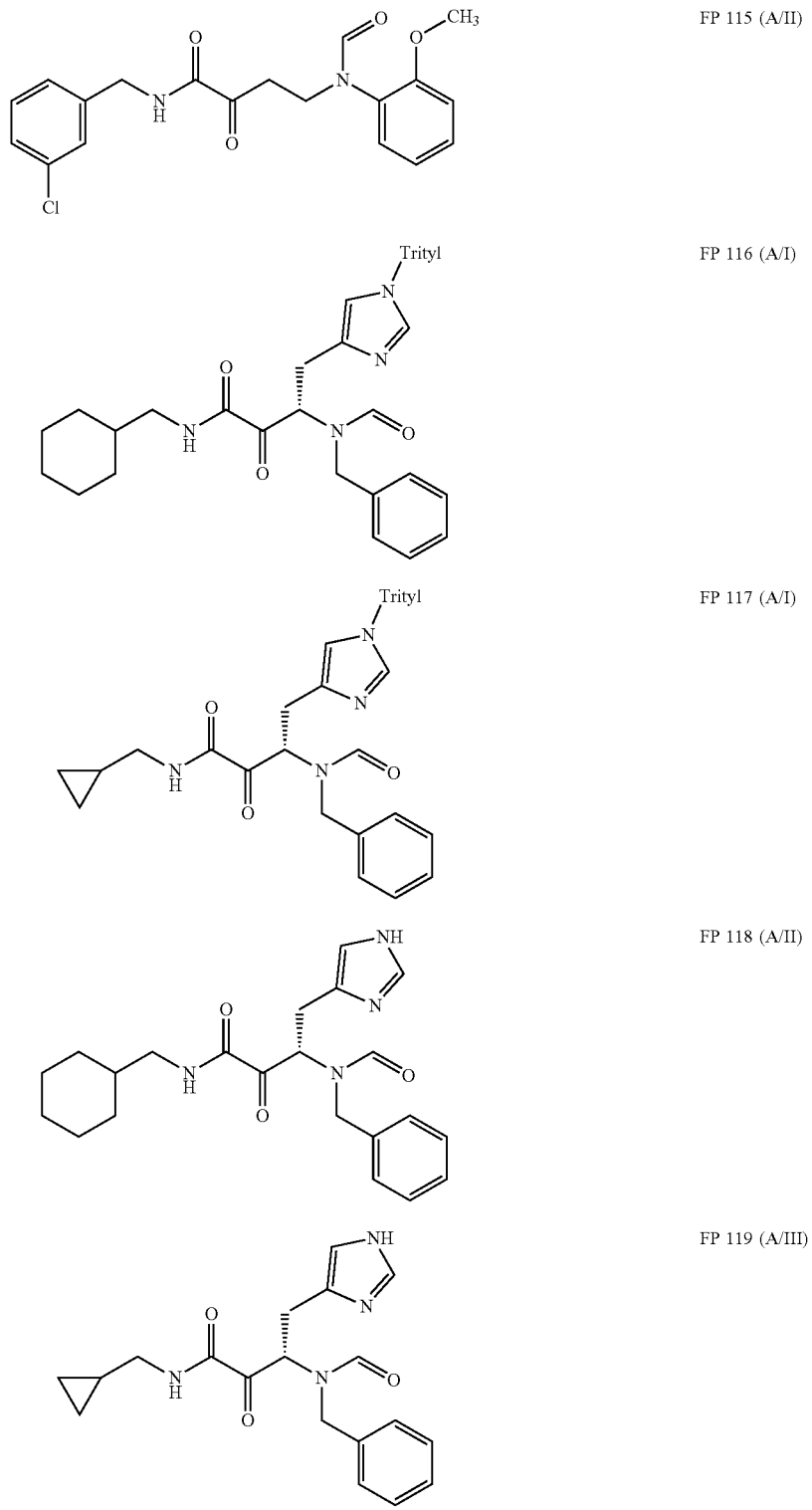

FP 115 (A/II)

FP 116 (A/I)

FP 117 (A/I)

FP 118 (A/II)

FP 119 (A/III)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

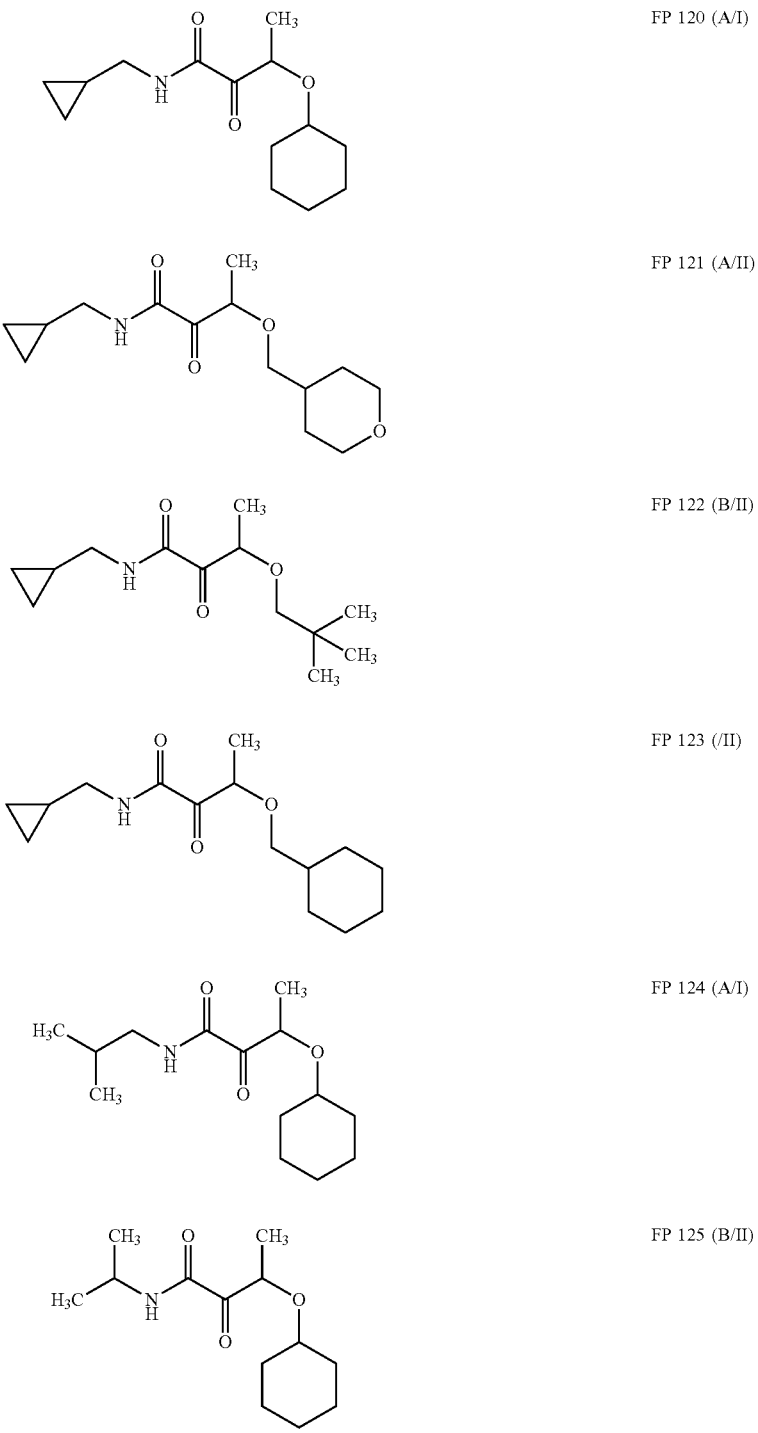

FP 120 (A/I)

FP 121 (A/II)

FP 122 (B/II)

FP 123 (/II)

FP 124 (A/I)

FP 125 (B/II)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

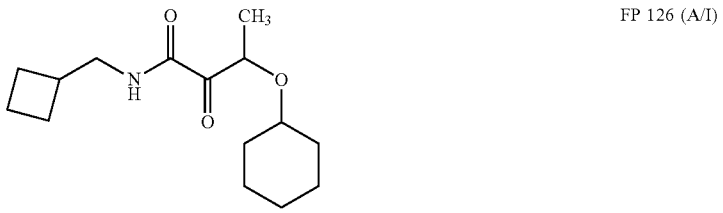

FP 126 (A/I)

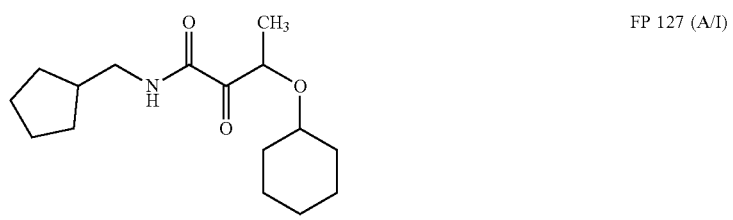

FP 127 (A/I)

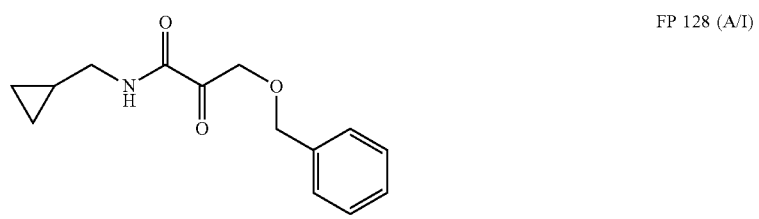

FP 128 (A/I)

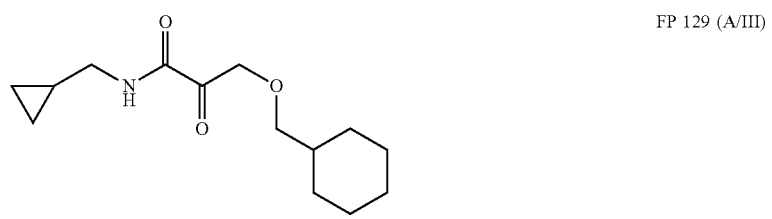

FP 129 (A/III)

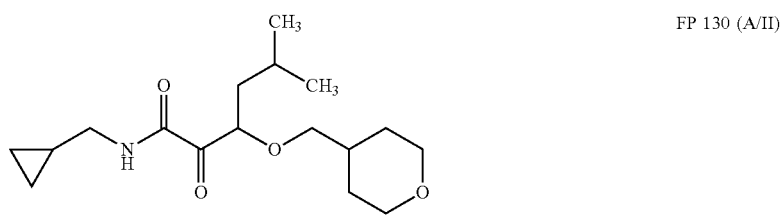

FP 130 (A/II)

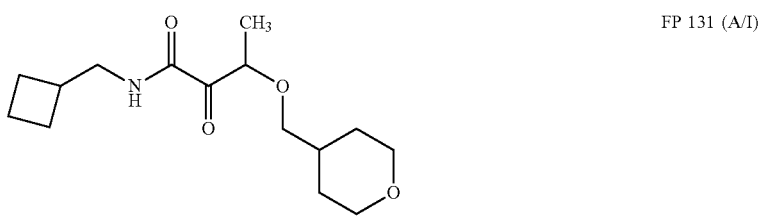

FP 131 (A/I)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

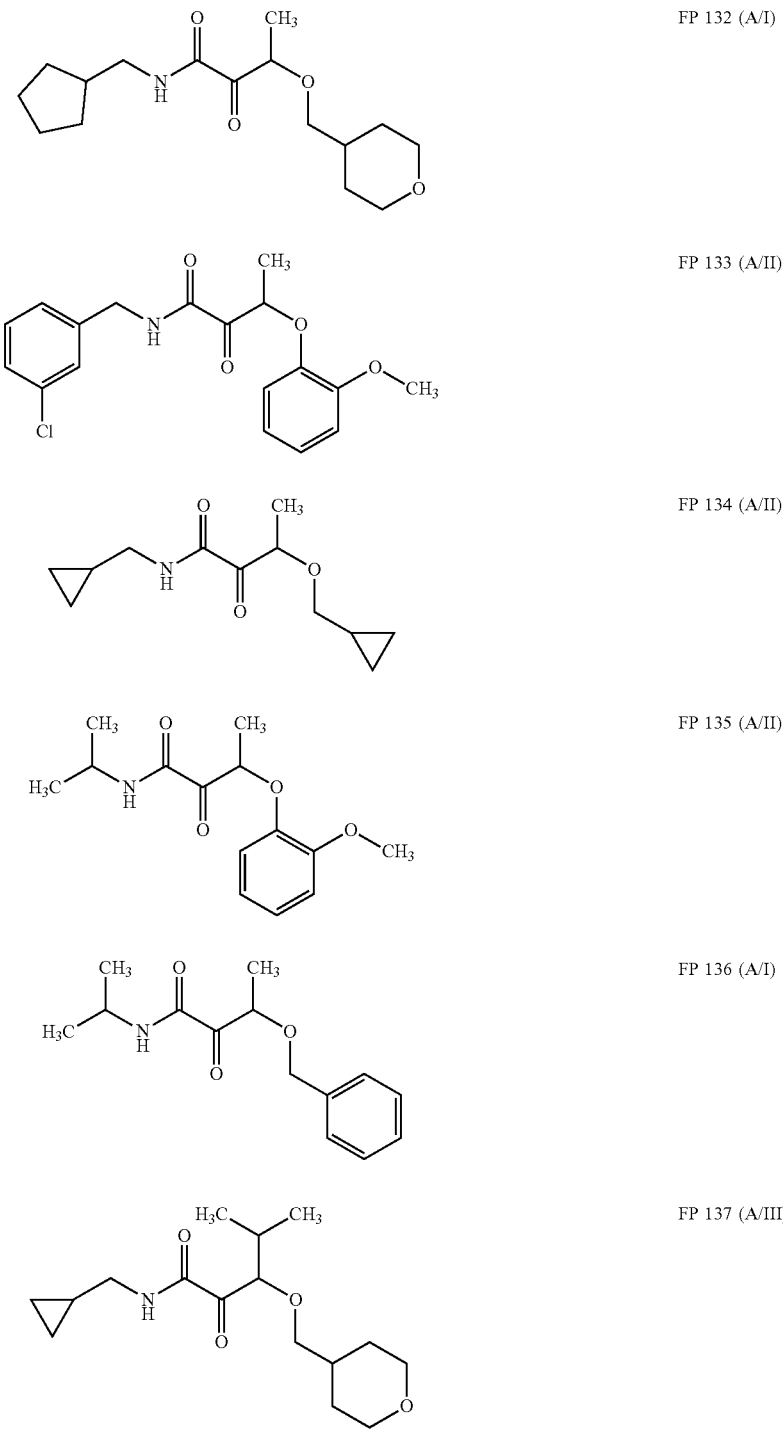

FP 132 (A/I)

FP 133 (A/II)

FP 134 (A/II)

FP 135 (A/II)

FP 136 (A/I)

FP 137 (A/III)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

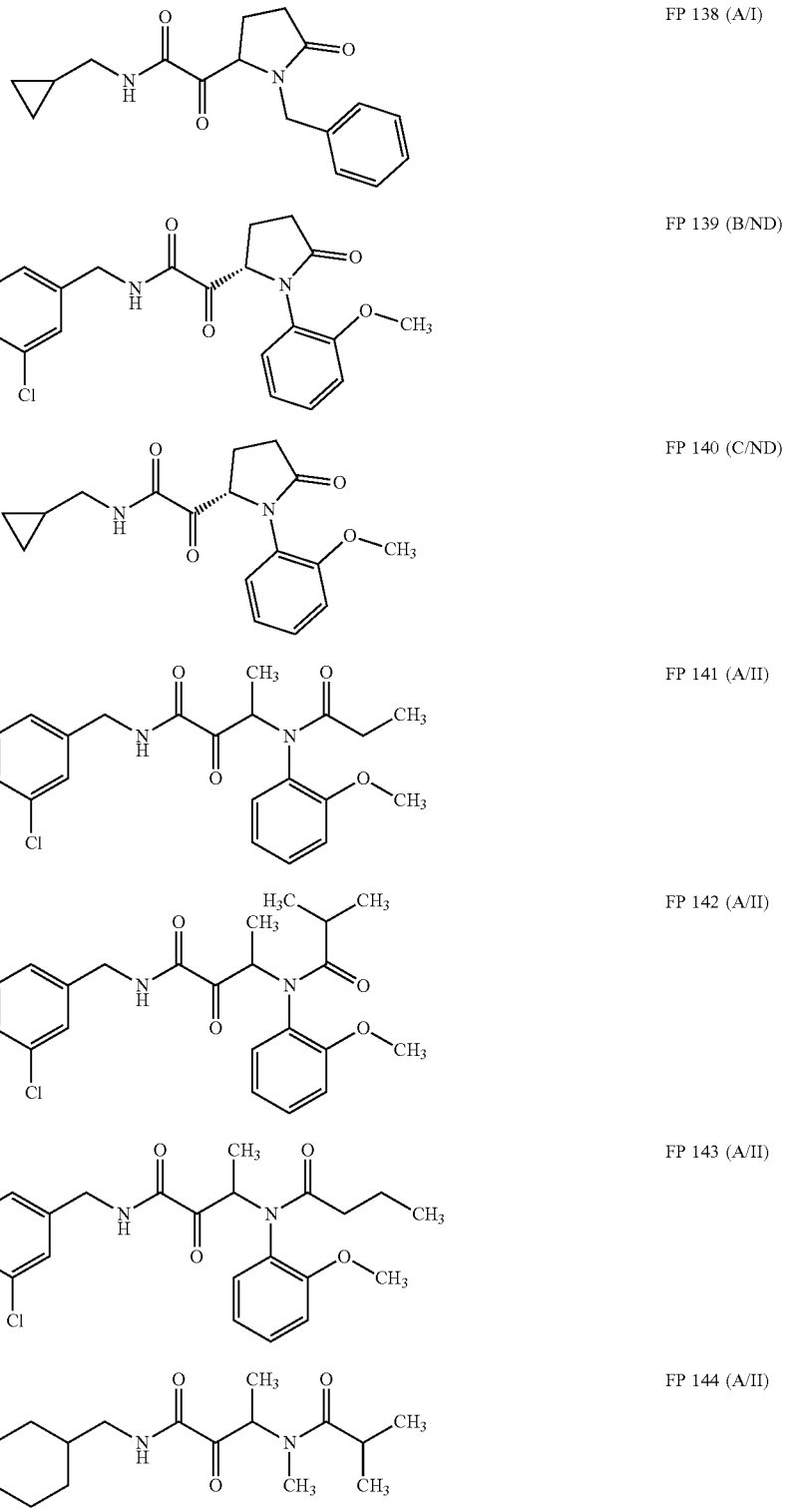

FP 138 (A/I)

FP 139 (B/ND)

FP 140 (C/ND)

FP 141 (A/II)

FP 142 (A/II)

FP 143 (A/II)

FP 144 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

FP 145 (A/II)

FP 146 (A/II)

FP 147 (A/ND)

FP 148 (A/ND)

FP 149 (A/II)

FP 150 (A/II)

FP 151 (B/III)

FP 152 (B/III)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

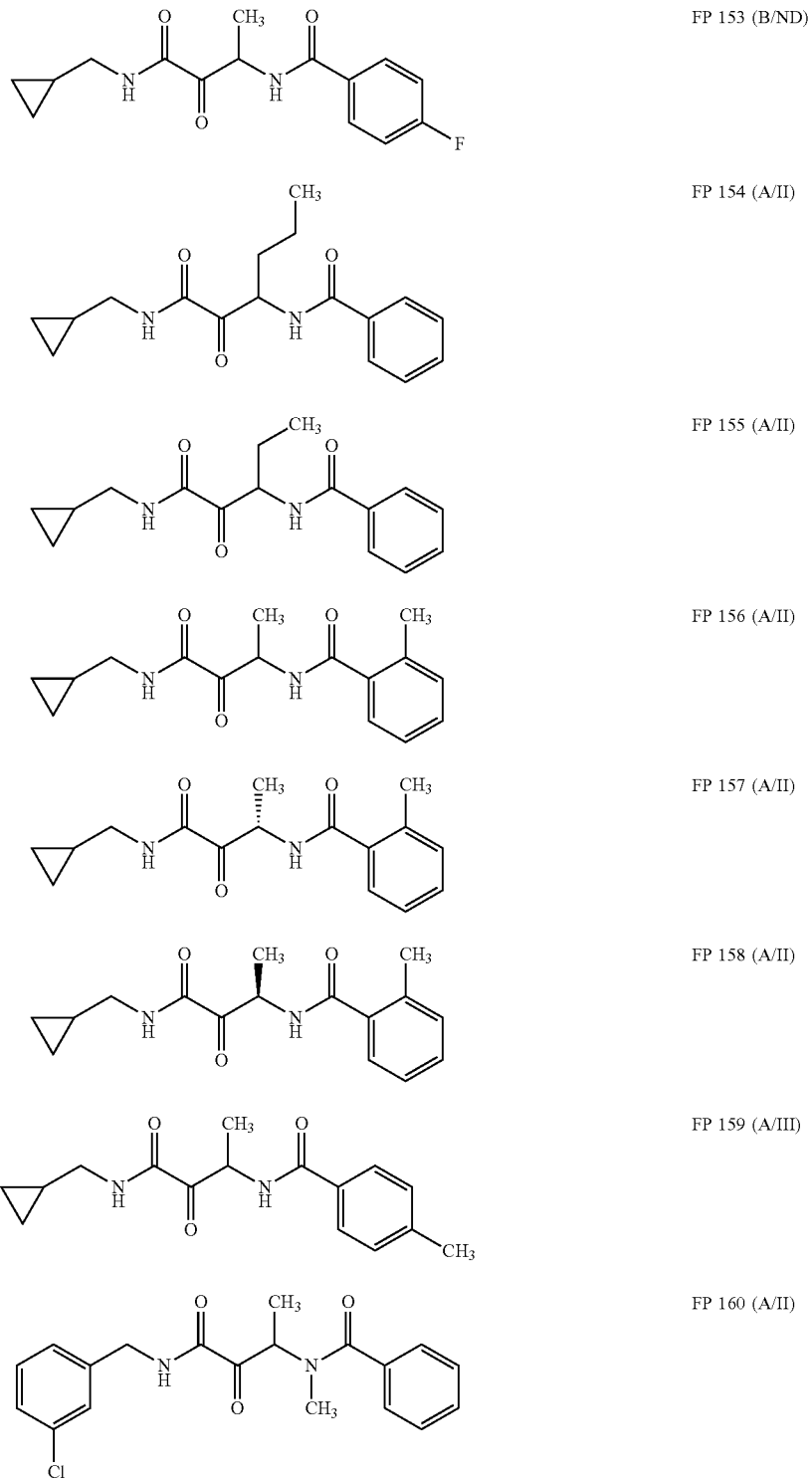

FP 153 (B/ND)

FP 154 (A/II)

FP 155 (A/II)

FP 156 (A/II)

FP 157 (A/II)

FP 158 (A/II)

FP 159 (A/III)

FP 160 (A/II)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

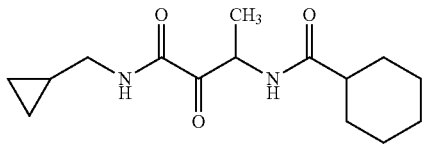 [SMILES: CC(NC(=O)C1CCCCC1)C(=O)C(=O)NCC1CC1]

FP 161 (A/III)

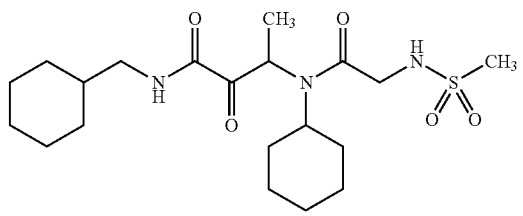 [SMILES: CC(C(=O)C(=O)NCC1CCCCC1)N(C(=O)CNS(C)(=O)=O)C1CCCCC1]

FP 162 (C/III)

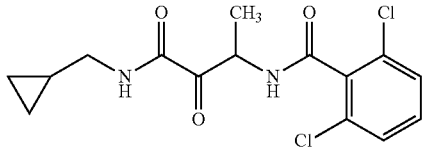 [SMILES: CC(NC(=O)c1c(Cl)cccc1Cl)C(=O)C(=O)NCC1CC1]

FP 163 (A/I)

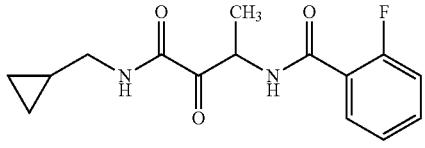 [SMILES: CC(NC(=O)c1ccccc1F)C(=O)C(=O)NCC1CC1]

FP 164 (A/II)

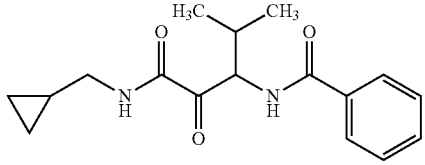 [SMILES: CC(C)C(NC(=O)c1ccccc1)C(=O)C(=O)NCC1CC1]

FP 165 (A/III)

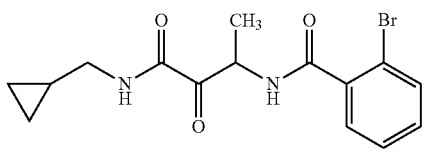 [SMILES: CC(NC(=O)c1ccccc1Br)C(=O)C(=O)NCC1CC1]

FP 166 (A/II)

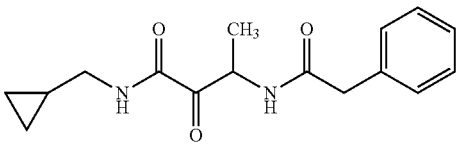 [SMILES: CC(NC(=O)Cc1ccccc1)C(=O)C(=O)NCC1CC1]

FP 167 (A/III)

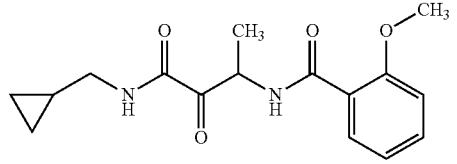 [SMILES: COc1ccccc1C(=O)NC(C)C(=O)C(=O)NCC1CC1]

FP 168 (A/II)

TABLE 2-continued

Compounds FP 1-FP 191

$IC_{50}$ values of the compounds determined in the enzyme activity assay for PLA2G16 described below and $EC_{50}$ values of the compounds determined in the anti-picornavirus assay described below are given in parentheses. Compounds with $IC_{50}$ values <1 µM (class "A") in the enzymatic activity assay are considered as highly active, compounds with $IC_{50}$ values between 1 and 10 µM (class "B") are considered as medium active and compounds with $IC_{50}$ values greater than 10 µM, but below 50 µM (class "C") are considered as weakly active. Antiviral activity against four different picornaviruses is categorized analogously, where class "I" denotes compounds with $EC_{50}$ <1 µM, class "II" with $EC_{50}$, between 1 µM and 10 µM and class "III" with $EC_{50}$ >10 µM.

FP 169 (A/II)

FP 170 (A/II)

FP 171 (B/III)

FP 172 (A/II)

FP 173 (B/III)

FP 174 (B/III)

FP 175 (A/II)

FP 176 (A/I)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

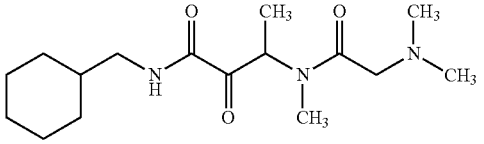 [SMILES: CC(C(=O)C(=O)NCC1CCCCC1)N(C)C(=O)CN(C)C]

FP 177 (B/ND)

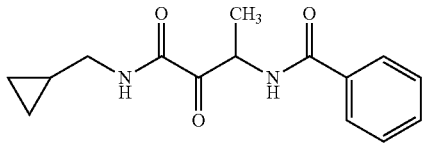 [SMILES: CC(NC(=O)c1ccccc1)C(=O)C(=O)NCC1CC1]

FP 178 (A/II)

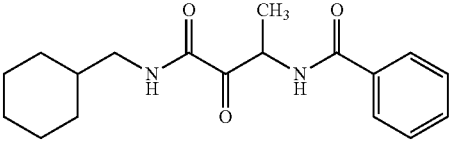 [SMILES: CC(NC(=O)c1ccccc1)C(=O)C(=O)NCC1CCCCC1]

FP 179 (A/I)

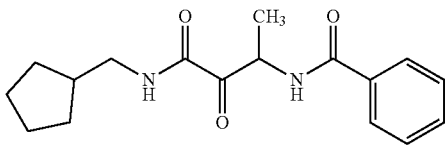 [SMILES: CC(NC(=O)c1ccccc1)C(=O)C(=O)NCC1CCCC1]

FP 180 (A/II)

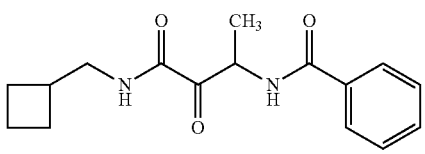 [SMILES: CC(NC(=O)c1ccccc1)C(=O)C(=O)NCC1CCC1]

FP 181 (A/II)

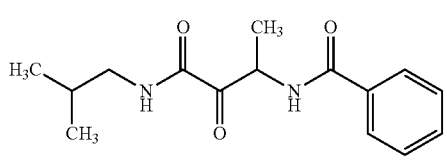 [SMILES: CC(C)CNC(=O)C(=O)C(C)NC(=O)c1ccccc1]

FP 182 (A/III)

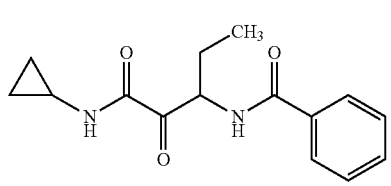 [SMILES: CCC(NC(=O)c1ccccc1)C(=O)C(=O)NC1CC1]

FP 183 (B/III)

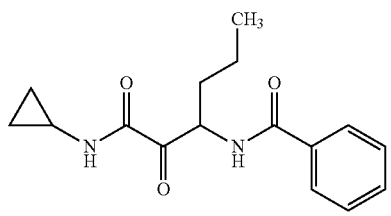 [SMILES: CCCC(NC(=O)c1ccccc1)C(=O)C(=O)NC1CC1]

FP 184 (A/III)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

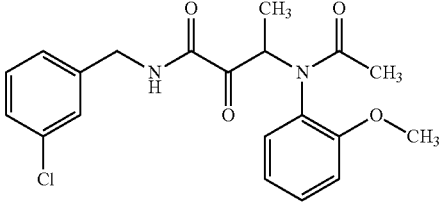 [SMILES: COc1ccccc1N(C(C)=O)C(C)C(=O)C(=O)NCc1cccc(Cl)c1]

FP 185 (A/ND)

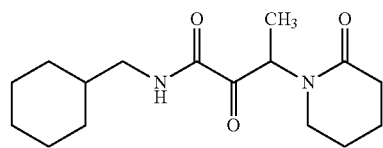 [SMILES: CC(C(=O)C(=O)NCC1CCCCC1)N1CCCCC1=O]

FP 186 (C/ND)

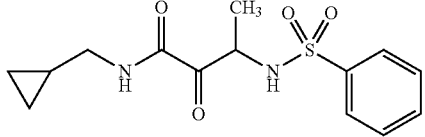 [SMILES: CC(NS(=O)(=O)c1ccccc1)C(=O)C(=O)NCC1CC1]

FP 187 (A/II)

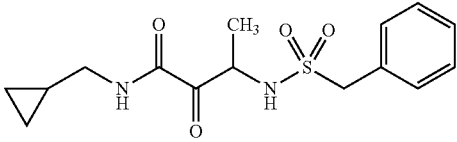 [SMILES: CC(NS(=O)(=O)Cc1ccccc1)C(=O)C(=O)NCC1CC1]

FP 188 (A/III)

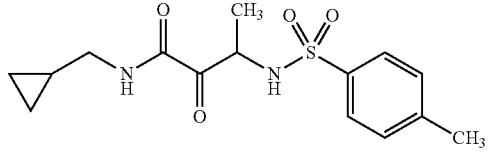 [SMILES: Cc1ccc(S(=O)(=O)NC(C)C(=O)C(=O)NCC2CC2)cc1]

FP 189 (A/II)

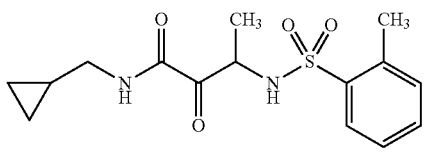 [SMILES: Cc1ccccc1S(=O)(=O)NC(C)C(=O)C(=O)NCC1CC1]

FP 190 (A/II)

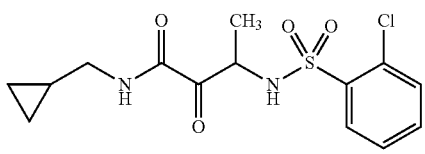 [SMILES: CC(NS(=O)(=O)c1ccccc1Cl)C(=O)C(=O)NCC1CC1]

FP 191 (A/II)

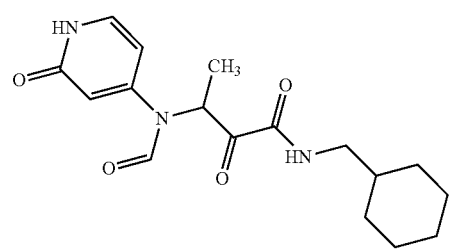 [SMILES: CC(C(=O)C(=O)NCC1CCCCC1)N(C=O)c1cc[nH]c(=O)c1]

FP 192 (A/III)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

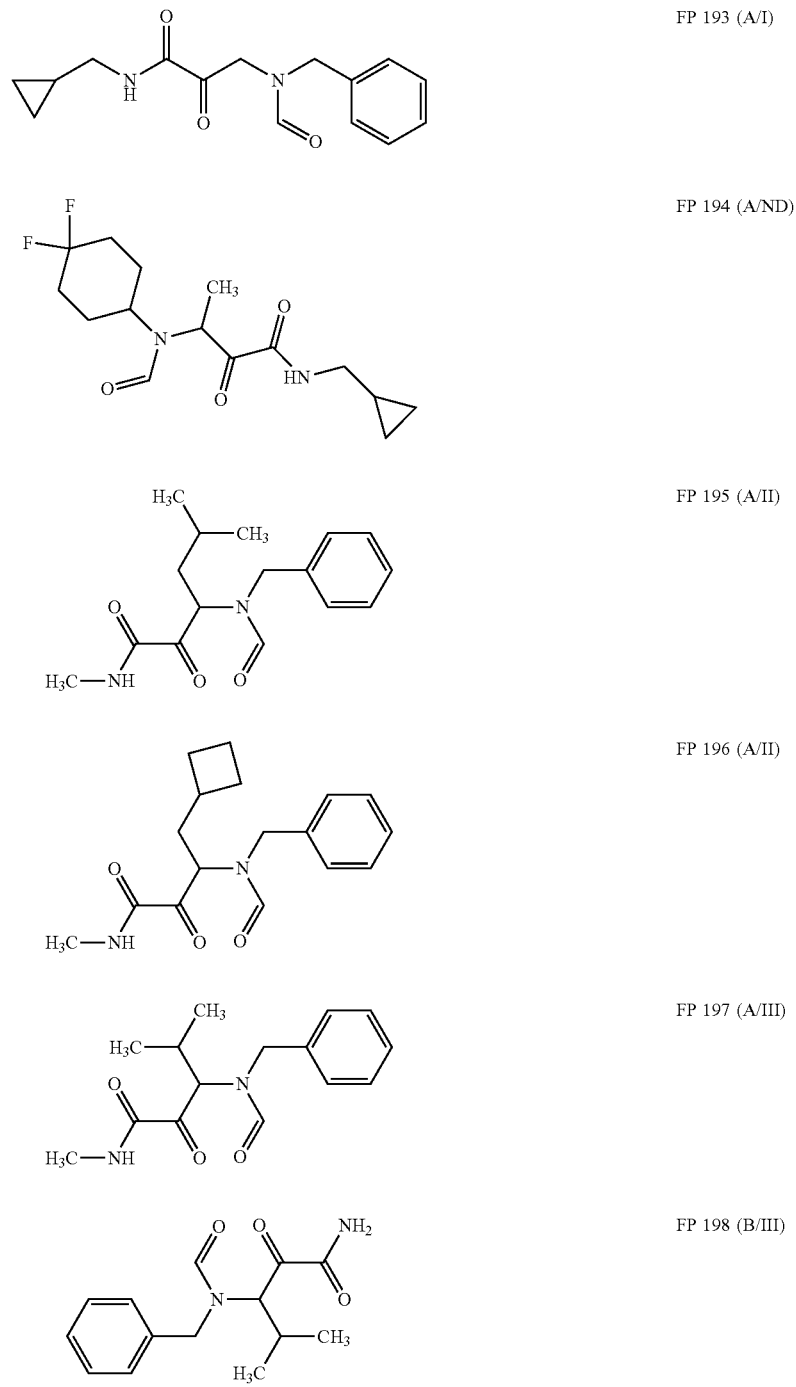

FP 193 (A/I)

FP 194 (A/ND)

FP 195 (A/II)

FP 196 (A/II)

FP 197 (A/III)

FP 198 (B/III)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

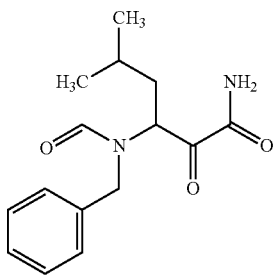 [SMILES: CC(C)CC(C(=O)C(N)=O)N(C=O)Cc1ccccc1]

FP 199 (A/III)

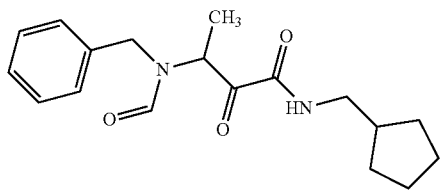 [SMILES: CC(C(=O)C(=O)NCC1CCCC1)N(C=O)Cc1ccccc1]

FP 200 (A/I)

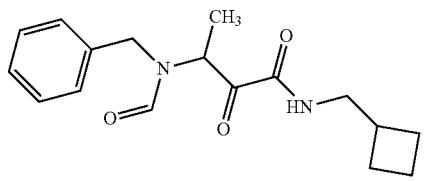 [SMILES: CC(C(=O)C(=O)NCC1CCC1)N(C=O)Cc1ccccc1]

FP 201 (A/I)

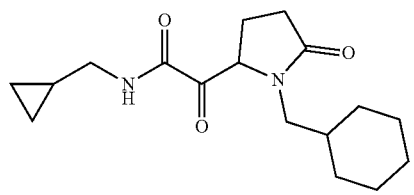 [SMILES: O=C(NCC1CC1)C(=O)C1CCC(=O)N1CC1CCCCC1]

FP 202 (A/I)

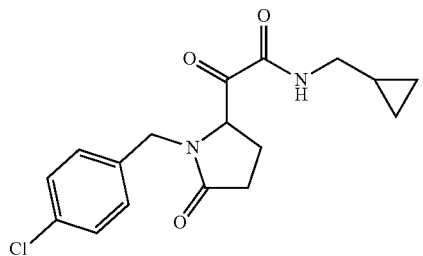 [SMILES: O=C(NCC1CC1)C(=O)C1CCC(=O)N1Cc1ccc(Cl)cc1]

FP 203 (A/I)

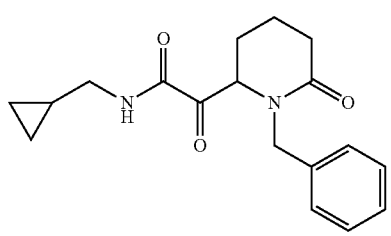 [SMILES: O=C(NCC1CC1)C(=O)C1CCCC(=O)N1Cc1ccccc1]

FP 204 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

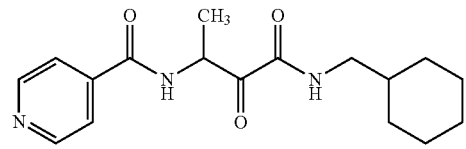 [SMILES: CC(NC(=O)c1ccncc1)C(=O)C(=O)NCC1CCCCC1]
FP 205 (A/II)

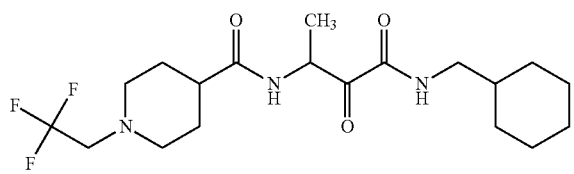 [SMILES: CC(NC(=O)C1CCN(CC(F)(F)F)CC1)C(=O)C(=O)NCC1CCCCC1]
FP 206 (A/II)

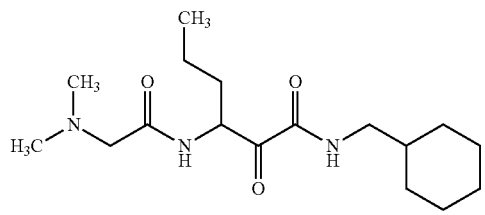 [SMILES: CCCC(NC(=O)CN(C)C)C(=O)C(=O)NCC1CCCCC1]
FP 207 (A/II)

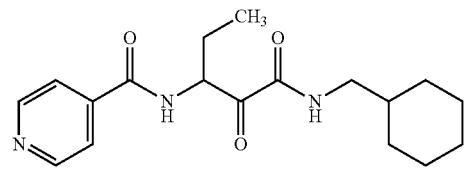 [SMILES: CCC(NC(=O)c1ccncc1)C(=O)C(=O)NCC1CCCCC1]
FP 208 (A/III)

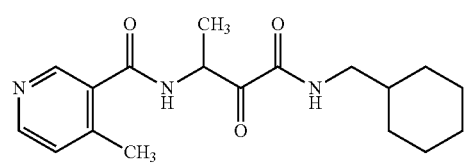
FP 209 (A/II)

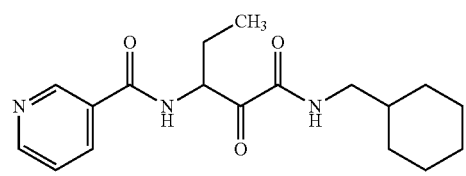 [SMILES: CCC(NC(=O)c1cccnc1)C(=O)C(=O)NCC1CCCCC1]
FP 210 (A/II)

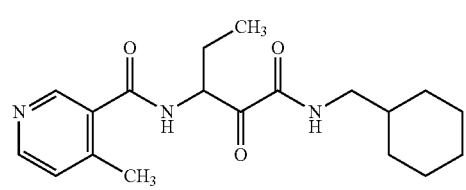 [SMILES: CCC(NC(=O)c1cnccc1C)C(=O)C(=O)NCC1CCCCC1]
FP 211 (A/II)

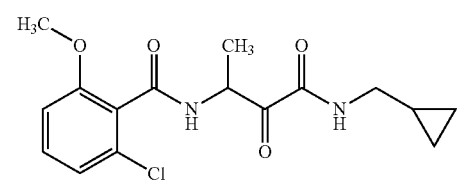 [SMILES: COc1cccc(Cl)c1C(=O)NC(C)C(=O)C(=O)NCC1CC1]
FP 212 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

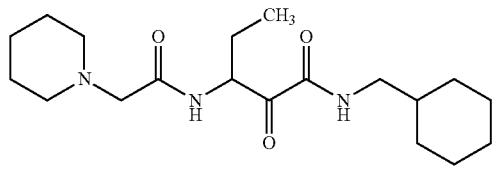 [SMILES: CCC(NC(=O)CN1CCCCC1)C(=O)C(=O)NCC1CCCCC1]

FP 213 (A/II)

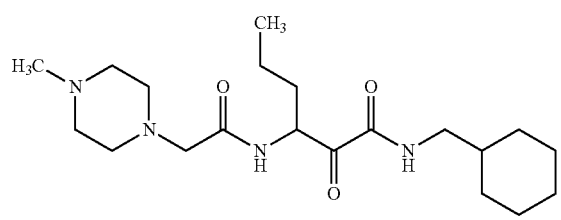 [SMILES: CCCC(NC(=O)CN1CCN(C)CC1)C(=O)C(=O)NCC1CCCCC1]

FP 214 (B/III)

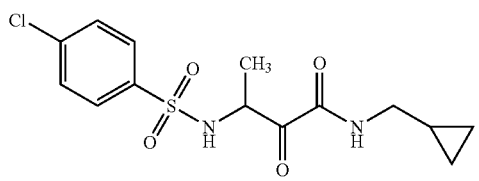 [SMILES: CC(NS(=O)(=O)c1ccc(Cl)cc1)C(=O)C(=O)NCC1CC1]

FP 215 (A/II)

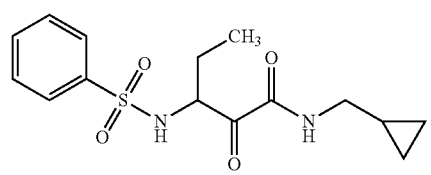 [SMILES: CCC(NS(=O)(=O)c1ccccc1)C(=O)C(=O)NCC1CC1]

FP 216 (A/II)

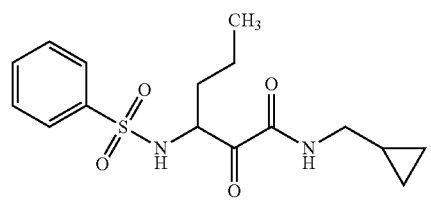 [SMILES: CCCC(NS(=O)(=O)c1ccccc1)C(=O)C(=O)NCC1CC1]

FP 217 (A/II)

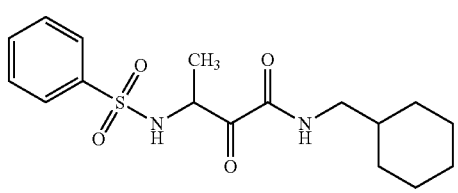 [SMILES: CC(NS(=O)(=O)c1ccccc1)C(=O)C(=O)NCC1CCCCC1]

FP 218 (A/II)

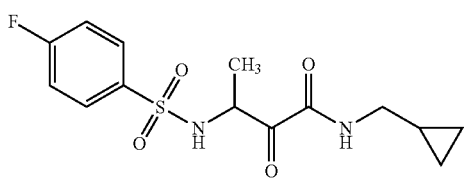 [SMILES: CC(NS(=O)(=O)c1ccc(F)cc1)C(=O)C(=O)NCC1CC1]

FP 219 (A/II)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

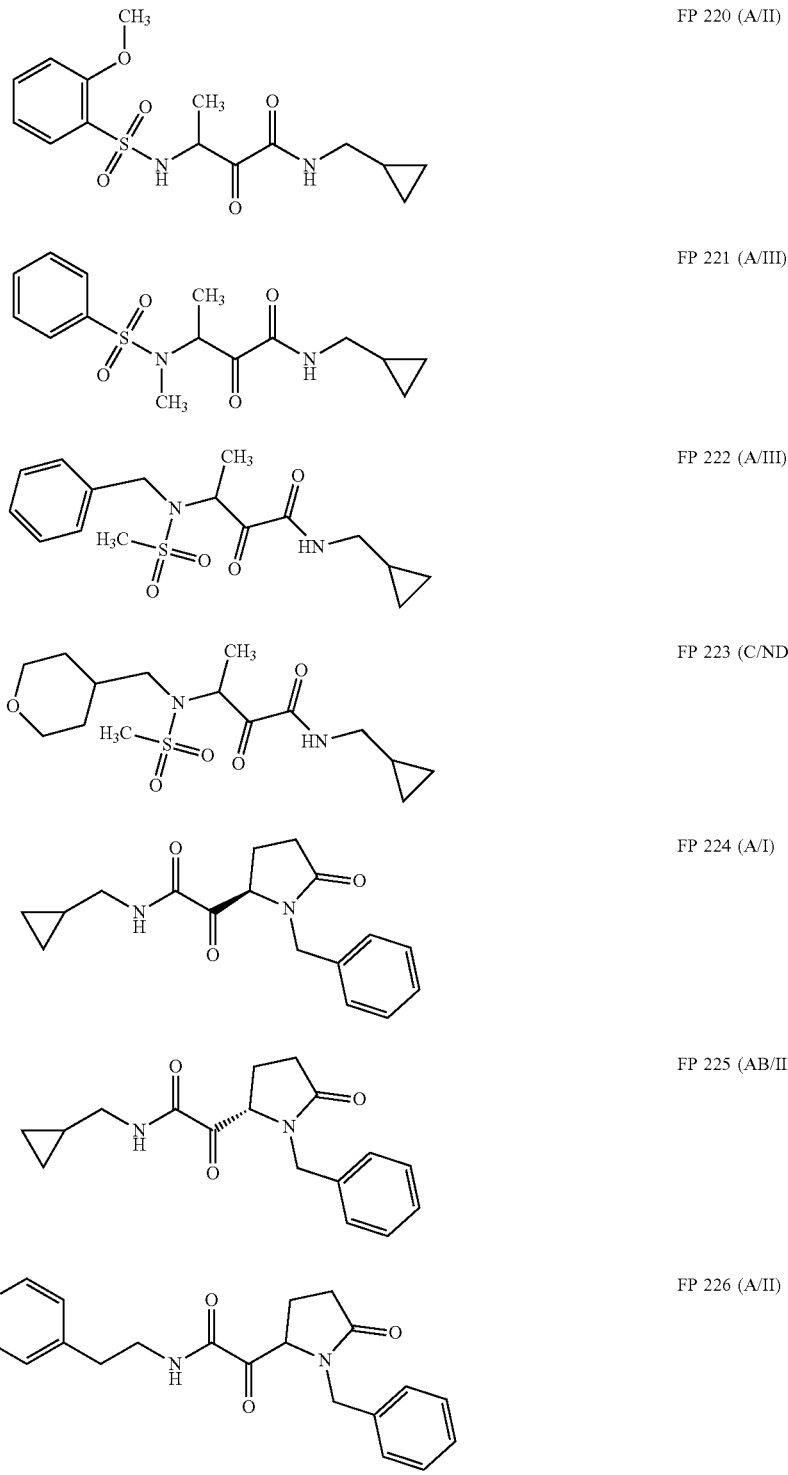

FP 220 (A/II)

FP 221 (A/III)

FP 222 (A/III)

FP 223 (C/ND)

FP 224 (A/I)

FP 225 (AB/III)

FP 226 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

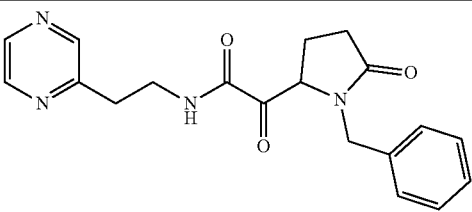

FP 227 (A/II)

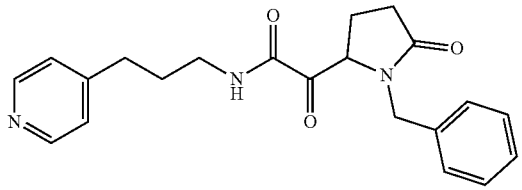 [SMILES: O=C(NCCCc1ccncc1)C(=O)C1CCC(=O)N1Cc1ccccc1]

FP 228 (A/II)

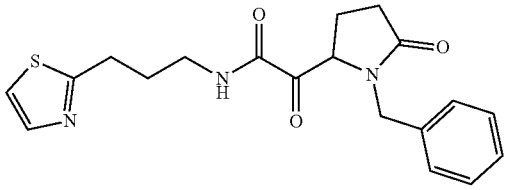 [SMILES: O=C(NCCCc1nccs1)C(=O)C1CCC(=O)N1Cc1ccccc1]

FP 229 (A/I)

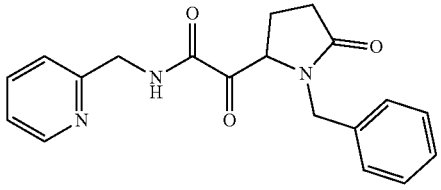 [SMILES: O=C(NCc1ccccn1)C(=O)C1CCC(=O)N1Cc1ccccc1]

FP 230 (A/III)

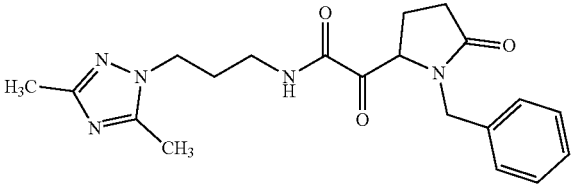 [SMILES: Cc1nc(C)n(CCCNC(=O)C(=O)C2CCC(=O)N2Cc2ccccc2)n1]

FP 231 (A/III)

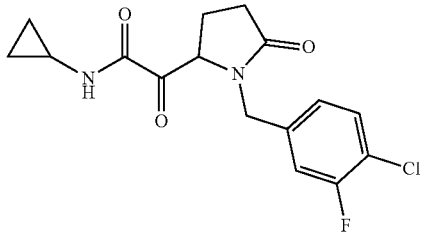 [SMILES: O=C(NC1CC1)C(=O)C1CCC(=O)N1Cc1ccc(Cl)c(F)c1]

FP 232 (A/II)

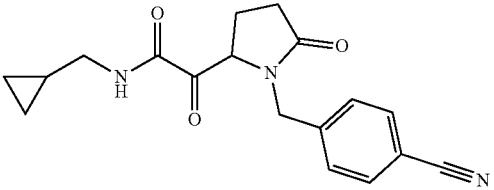 [SMILES: N#Cc1ccc(CN2C(=O)CCC2C(=O)C(=O)NCC2CC2)cc1]

FP 233 (A/II)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

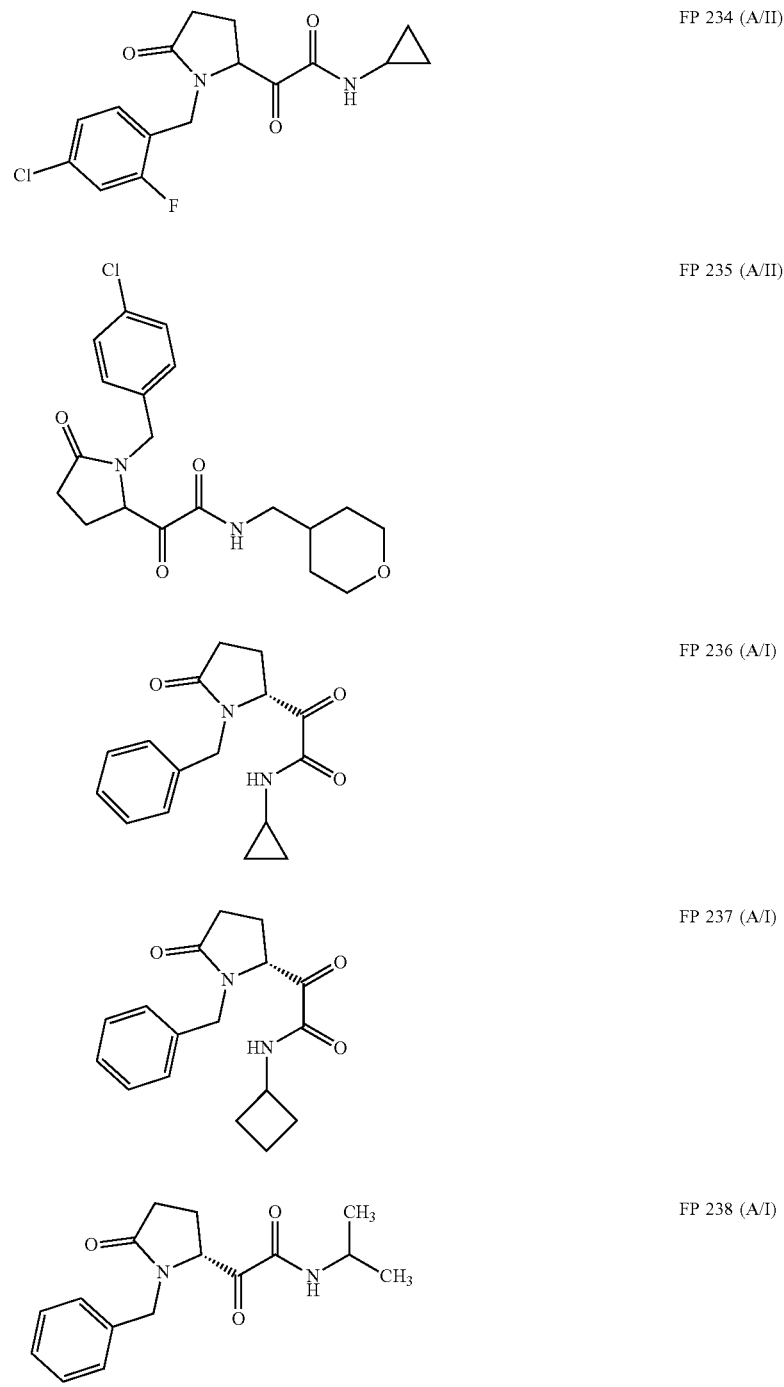

FP 234 (A/II)

FP 235 (A/II)

FP 236 (A/I)

FP 237 (A/I)

FP 238 (A/I)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

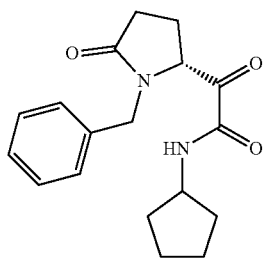 [SMILES: O=C(NC1CCCC1)C(=O)[C@H]1CCC(=O)N1Cc1ccccc1]

FP 239 (A/I)

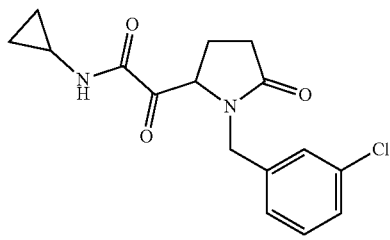 [SMILES: O=C(NC1CC1)C(=O)C1CCC(=O)N1Cc1cccc(Cl)c1]

FP 240 (A/II)

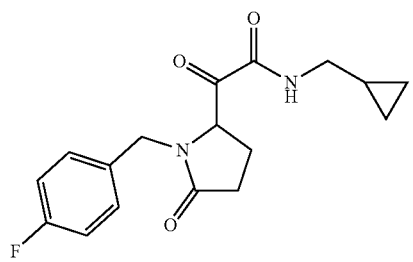 [SMILES: O=C(NCC1CC1)C(=O)C1CCC(=O)N1Cc1ccc(F)cc1]

FP 241 (A/I)

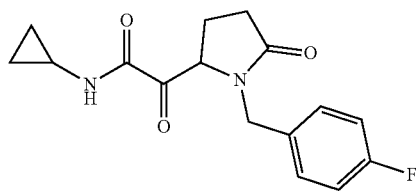 [SMILES: O=C(NC1CC1)C(=O)C1CCC(=O)N1Cc1ccc(F)cc1]

FP 242 (A/II)

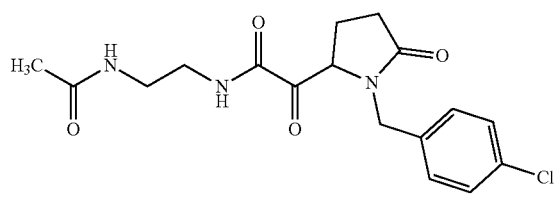 [SMILES: CC(=O)NCCNC(=O)C(=O)C1CCC(=O)N1Cc1ccc(Cl)cc1]

FP 243 (B/III)

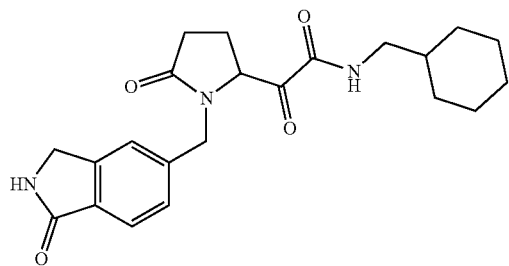 [SMILES: O=C(NCC1CCCCC1)C(=O)C1CCC(=O)N1Cc1ccc2c(c1)CNC2=O]

FP 244 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

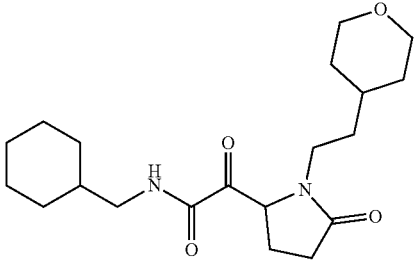 [SMILES: O=C(NCC1CCCCC1)C(=O)C1CCC(=O)N1CCC1CCOCC1]

FP 245 (A/II)

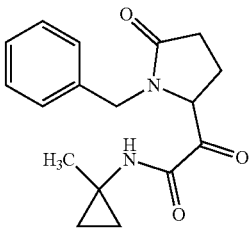 [SMILES: CC1(NC(=O)C(=O)C2CCC(=O)N2Cc2ccccc2)CC1]

FP 246 (A/II)

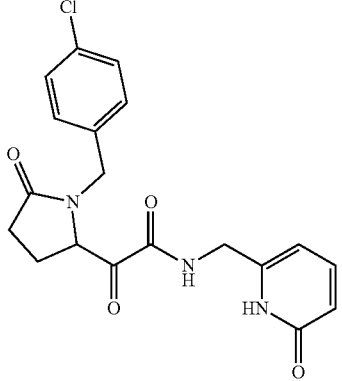 [SMILES: O=C(NCc1cccc(=O)[nH]1)C(=O)C1CCC(=O)N1Cc1ccc(Cl)cc1]

FP 247 (A/II)

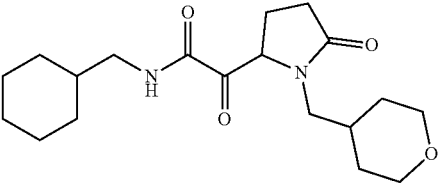 [SMILES: O=C(NCC1CCCCC1)C(=O)C1CCC(=O)N1CC1CCOCC1]

FP 248 (A/I)

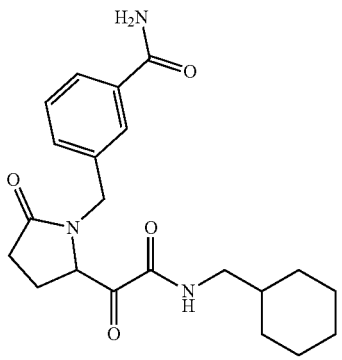 [SMILES: NC(=O)c1cccc(CN2C(=O)CCC2C(=O)C(=O)NCC2CCCCC2)c1]

FP 249 (AI/)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

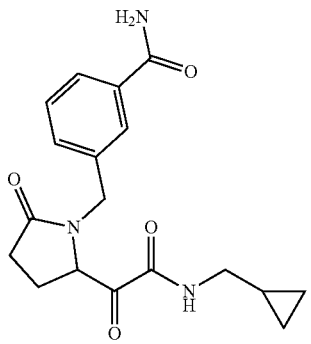 [SMILES: NC(=O)c1cccc(CN2C(=O)CCC2C(=O)C(=O)NCC2CC2)c1]

FP 250 (A/II)

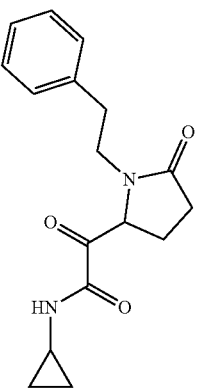 [SMILES: O=C(NC1CC1)C(=O)C1CCC(=O)N1CCc1ccccc1]

FP 251 (A/II)

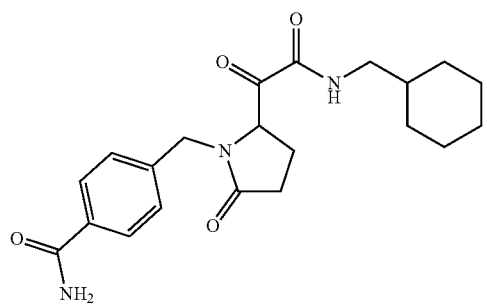 [SMILES: NC(=O)c1ccc(CN2C(=O)CCC2C(=O)C(=O)NCC2CCCCC2)cc1]

FP 252 (A/II)

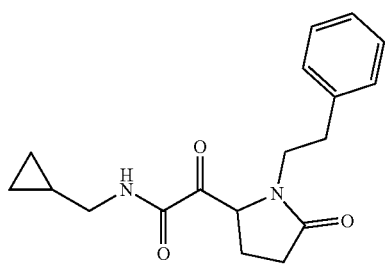 [SMILES: O=C(NCC1CC1)C(=O)C1CCC(=O)N1CCc1ccccc1]

FP 253 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

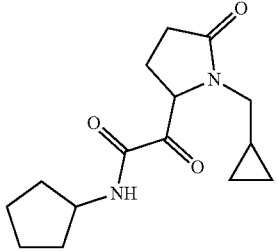 [SMILES: O=C(NC1CCCC1)C(=O)C1CCC(=O)N1CC1CC1]

FP 254 (A/II)

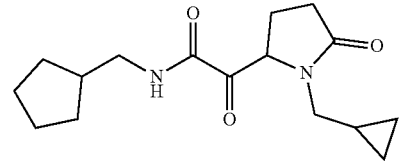 [SMILES: O=C(NCC1CCCC1)C(=O)C1CCC(=O)N1CC1CC1]

FP 255 (A/II)

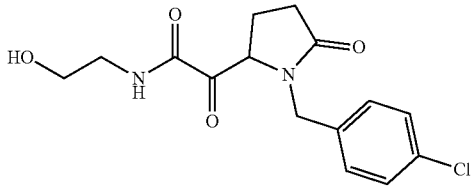 [SMILES: O=C(NCCO)C(=O)C1CCC(=O)N1Cc1ccc(Cl)cc1]

FP 256 (A/II)

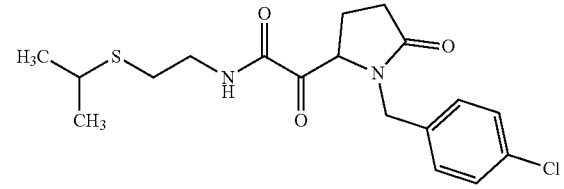 [SMILES: CC(C)SCCNC(=O)C(=O)C1CCC(=O)N1Cc1ccc(Cl)cc1]

FP 257 (A/I)

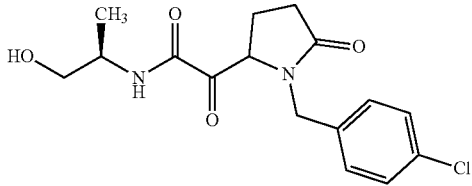 [SMILES: C[C@H](CO)NC(=O)C(=O)C1CCC(=O)N1Cc1ccc(Cl)cc1]

FP 258 (B/II)

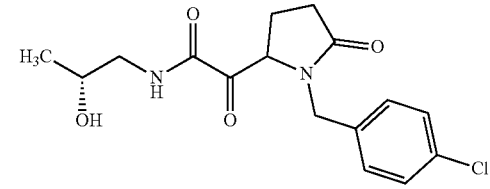 [SMILES: C[C@@H](O)CNC(=O)C(=O)C1CCC(=O)N1Cc1ccc(Cl)cc1]

FP 259 (A/ND)

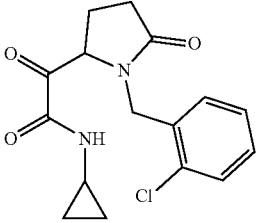 [SMILES: O=C(NC1CC1)C(=O)C1CCC(=O)N1Cc1ccccc1Cl]

FP 260 (A/ND)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

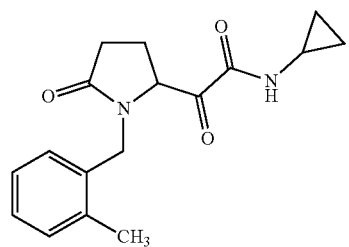 [SMILES: Cc1ccccc1CN1C(=O)CCC1C(=O)C(=O)NC1CC1]

FP 261 (A/II)

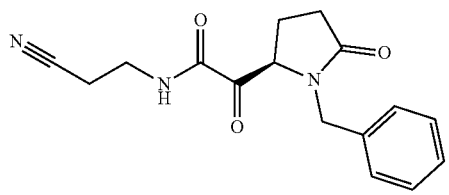 [SMILES: N#CCCNC(=O)C(=O)[C@H]1CCC(=O)N1Cc1ccccc1]

FP 262 (A/II)

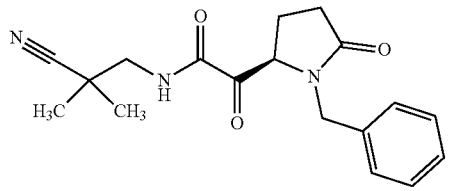 [SMILES: CC(C)(C#N)CNC(=O)C(=O)[C@H]1CCC(=O)N1Cc1ccccc1]

FP 263 (A/II)

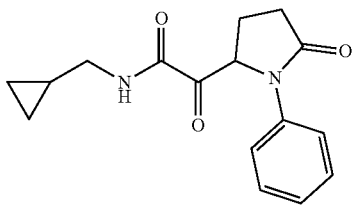 [SMILES: O=C(NCC1CC1)C(=O)C1CCC(=O)N1c1ccccc1]

FP 264 (B/III)

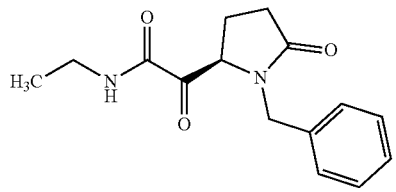 [SMILES: CCNC(=O)C(=O)[C@H]1CCC(=O)N1Cc1ccccc1]

FP 265 (A/I)

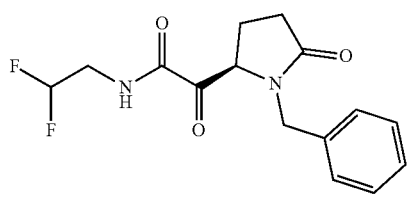 [SMILES: O=C(NCC(F)F)C(=O)[C@H]1CCC(=O)N1Cc1ccccc1]

FP 266 (A/I)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

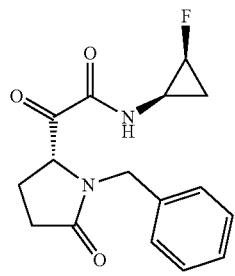 [SMILES: O=C(N[C@@H]1C[C@@H]1F)C(=O)[C@H]1CCC(=O)N1Cc1ccccc1]

FP 267 (A/I)

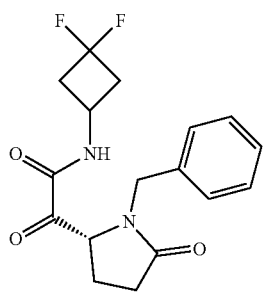 [SMILES: O=C(NC1CC(F)(F)C1)C(=O)[C@H]1CCC(=O)N1Cc1ccccc1]

FP 268 (A/I)

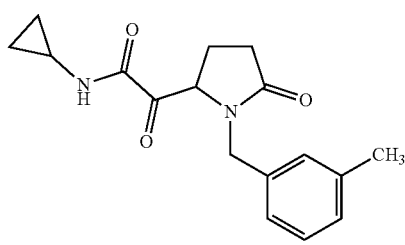 [SMILES: Cc1cccc(CN2C(=O)CCC2C(=O)C(=O)NC2CC2)c1]

FP 269 (A/II)

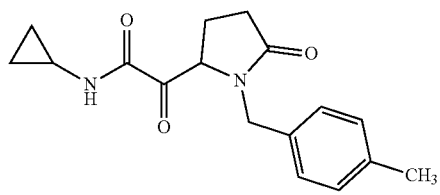 [SMILES: Cc1ccc(CN2C(=O)CCC2C(=O)C(=O)NC2CC2)cc1]

FP 270 (A/I)

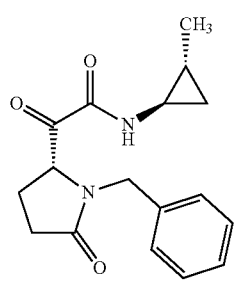 [SMILES: C[C@@H]1C[C@H]1NC(=O)C(=O)[C@H]1CCC(=O)N1Cc1ccccc1]

FP 271 (A/I)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

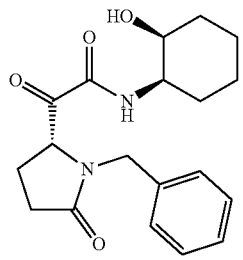 [SMILES: O=C(N[C@@H]1CCCC[C@@H]1O)C(=O)[C@H]1CCC(=O)N1Cc1ccccc1]

FP 272 (B/III)

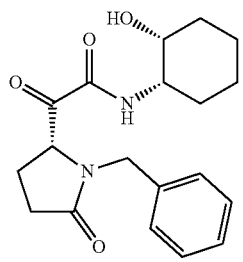 [SMILES: O=C(N[C@H]1CCCC[C@H]1O)C(=O)[C@H]1CCC(=O)N1Cc1ccccc1]

FP 273 (B/II)

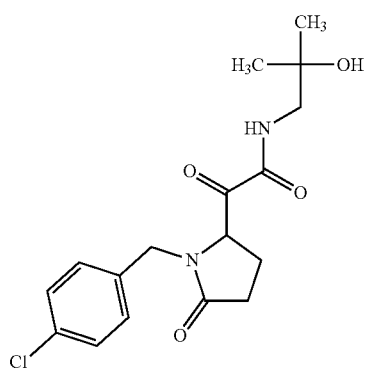 [SMILES: CC(C)(O)CNC(=O)C(=O)C1CCC(=O)N1Cc1ccc(Cl)cc1]

FP 274 (A/II)

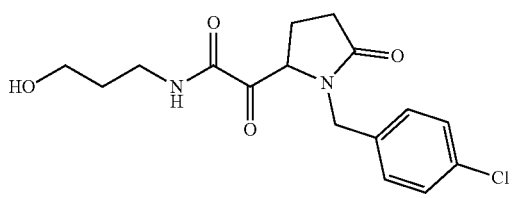 [SMILES: O=C(NCCCO)C(=O)C1CCC(=O)N1Cc1ccc(Cl)cc1]

FP 275 (A/III)

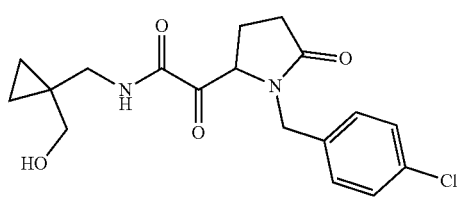 [SMILES: O=C(NCC1(CO)CC1)C(=O)C1CCC(=O)N1Cc1ccc(Cl)cc1]

FP 276 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

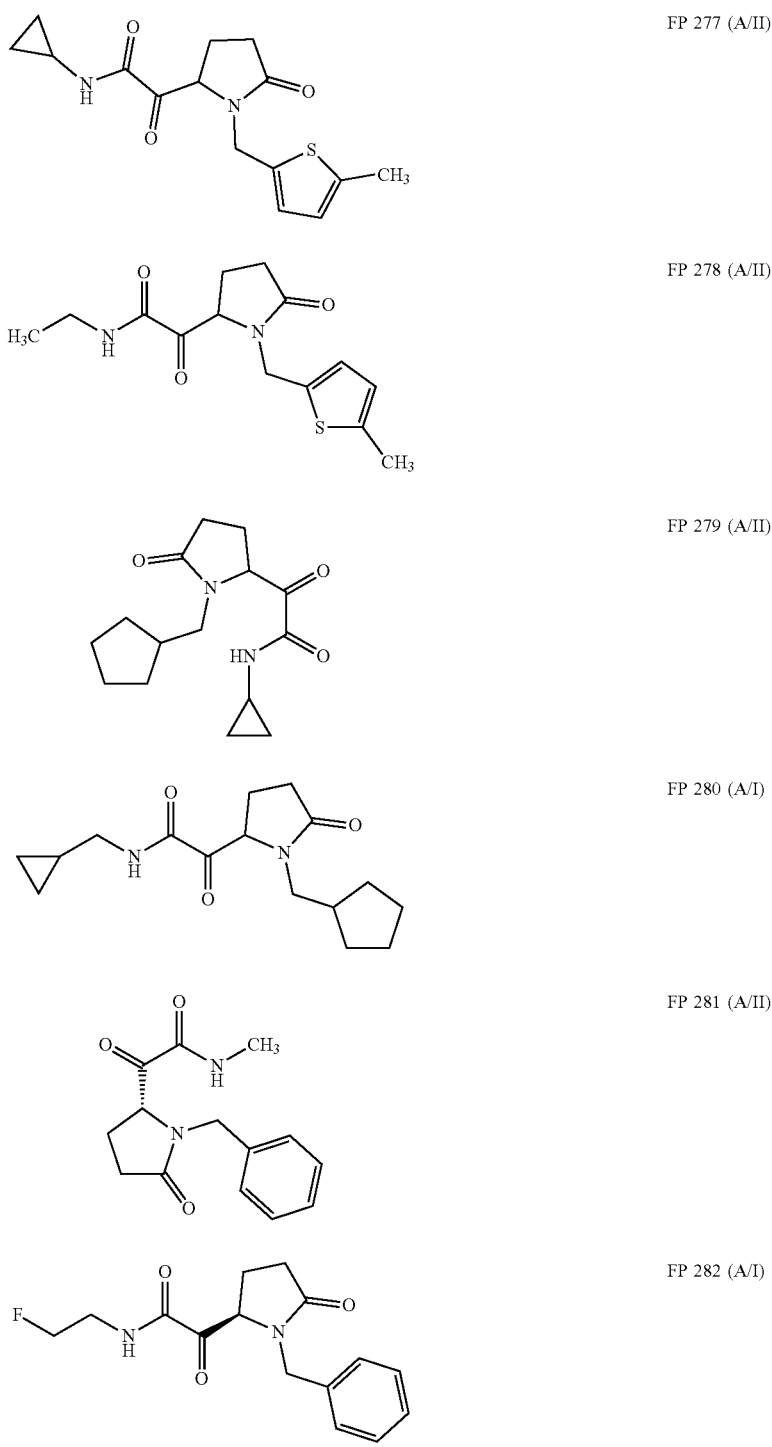

FP 277 (A/II)

FP 278 (A/II)

FP 279 (A/II)

FP 280 (A/I)

FP 281 (A/II)

FP 282 (A/I)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

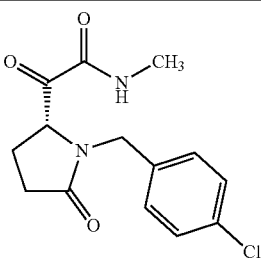

FP 283 (A/II)

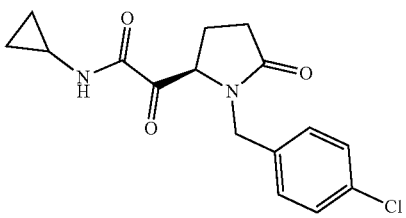 [SMILES: O=C(NC1CC1)C(=O)[C@H]1CCC(=O)N1Cc1ccc(Cl)cc1]

FP 284 (A/I)

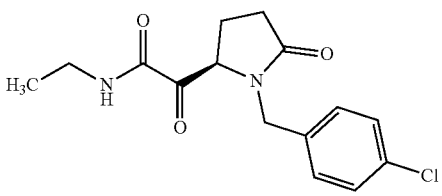 [SMILES: CCNC(=O)C(=O)[C@H]1CCC(=O)N1Cc1ccc(Cl)cc1]

FP 285 (A/I)

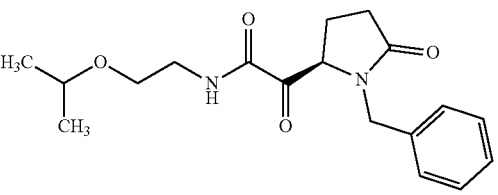 [SMILES: CC(C)OCCNC(=O)C(=O)[C@H]1CCC(=O)N1Cc1ccccc1]

FP 286 (A/II)

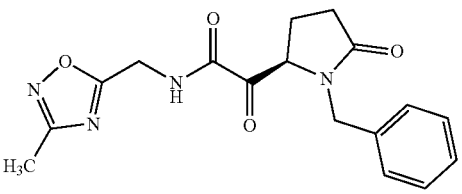 [SMILES: Cc1noc(CNC(=O)C(=O)[C@H]2CCC(=O)N2Cc2ccccc2)n1]

FP 287 (A/II)

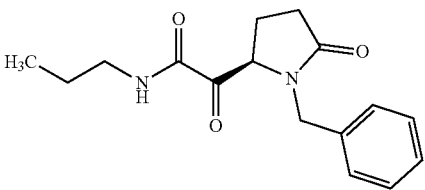 [SMILES: CCCNC(=O)C(=O)[C@H]1CCC(=O)N1Cc1ccccc1]

FP 288 (A/I)

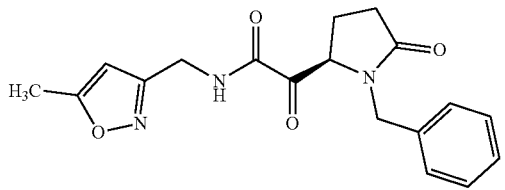 [SMILES: Cc1cc(CNC(=O)C(=O)[C@H]2CCC(=O)N2Cc2ccccc2)no1]

FP 289 (A/I)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

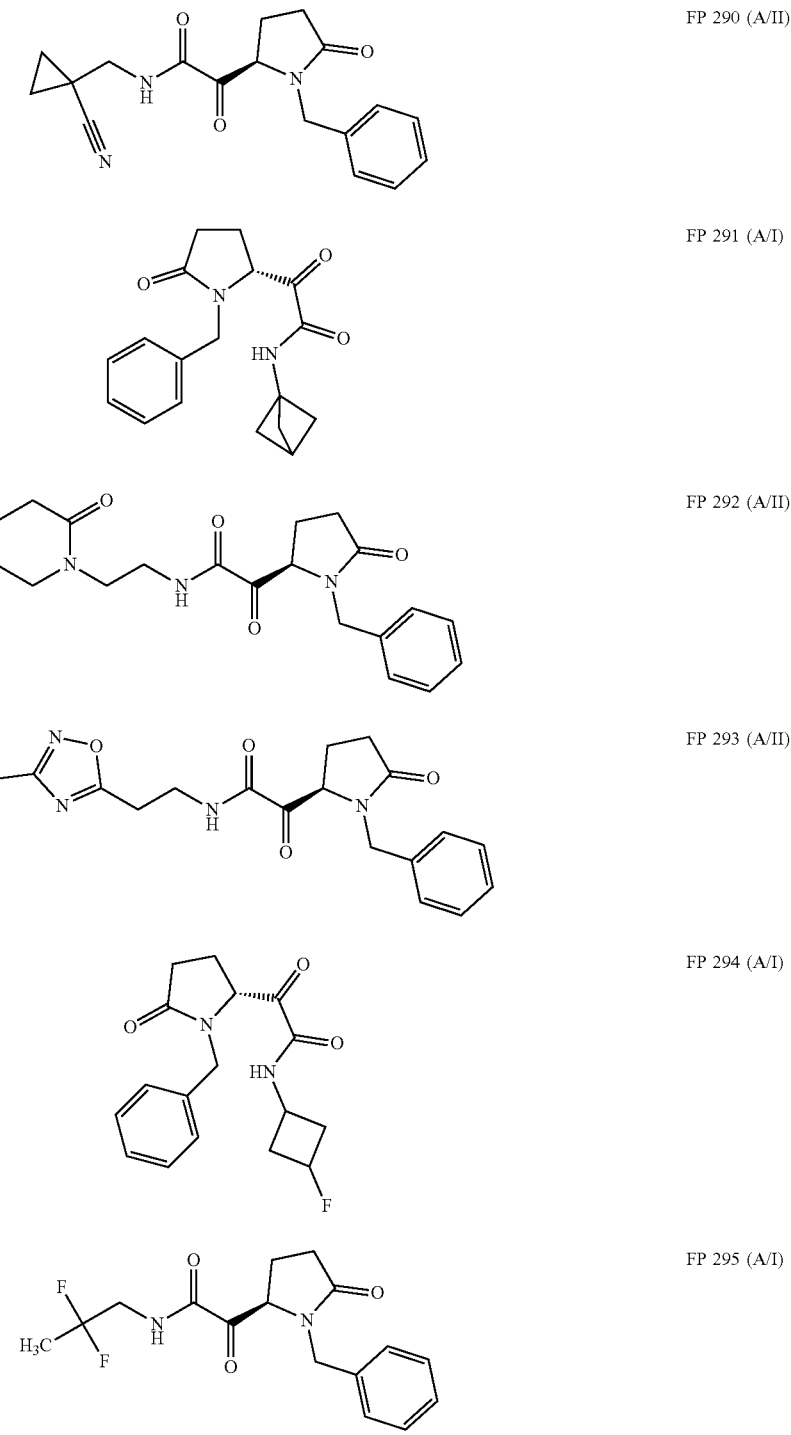

FP 290 (A/II)

FP 291 (A/I)

FP 292 (A/II)

FP 293 (A/II)

FP 294 (A/I)

FP 295 (A/I)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

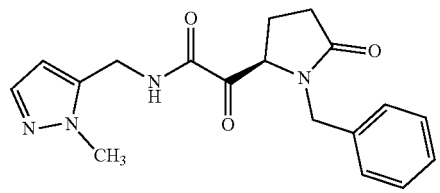 [SMILES: Cn1nccc1CNC(=O)C(=O)[C@H]1CCC(=O)N1Cc1ccccc1]

FP 296 ((A/II)

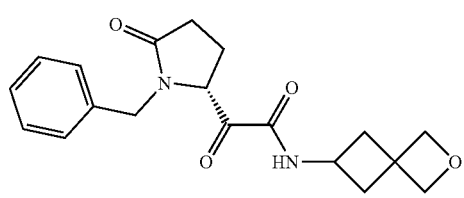 [SMILES: O=C(NC1CC2(COC2)C1)C(=O)[C@H]1CCC(=O)N1Cc1ccccc1]

FP 297 (A/II)

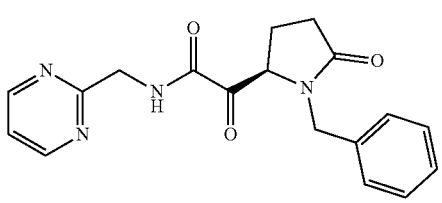 [SMILES: O=C(NCc1ncccn1)C(=O)[C@H]1CCC(=O)N1Cc1ccccc1]

FP 298 (A/II)

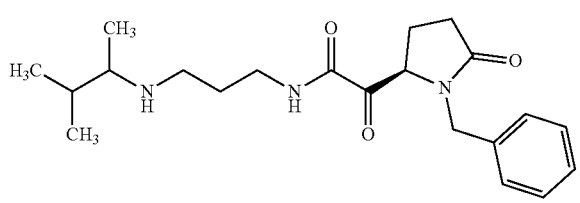 [SMILES: CC(C)C(C)NCCCNC(=O)C(=O)[C@H]1CCC(=O)N1Cc1ccccc1]

FP 299 (A/II)

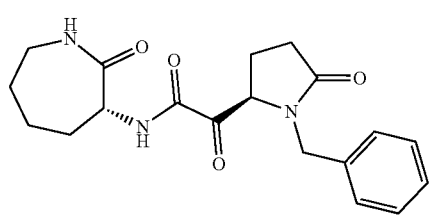 [SMILES: O=C(N[C@@H]1CCCCNC1=O)C(=O)[C@H]1CCC(=O)N1Cc1ccccc1]

FP 300 (A/II)

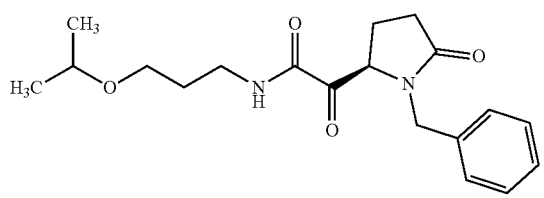 [SMILES: CC(C)OCCCNC(=O)C(=O)[C@H]1CCC(=O)N1Cc1ccccc1]

FP 301 (A/I)

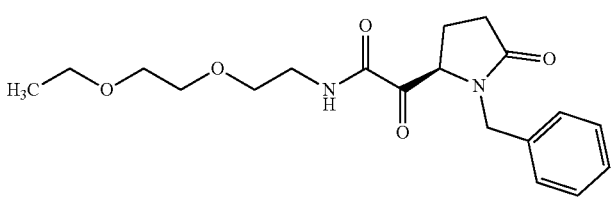 [SMILES: CCOCCOCCNC(=O)C(=O)[C@H]1CCC(=O)N1Cc1ccccc1]

FP 302 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

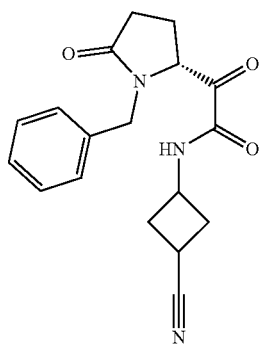 [SMILES: N#CC1CC(NC(=O)C(=O)[C@H]2CCC(=O)N2Cc2ccccc2)C1]

FP 303 (A/II)

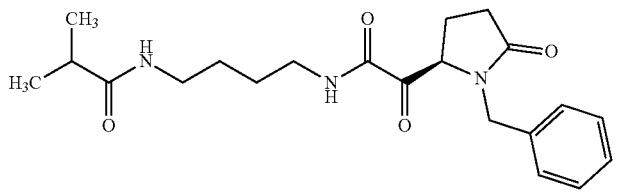 [SMILES: CC(C)C(=O)NCCCCNC(=O)C(=O)[C@H]1CCC(=O)N1Cc1ccccc1]

FP 304 (A/II)

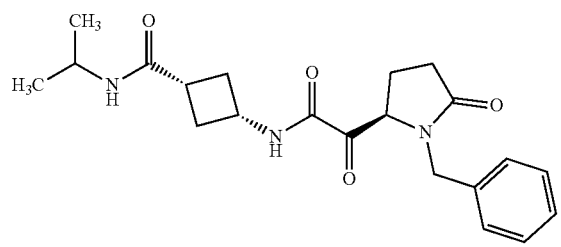 [SMILES: CC(C)NC(=O)[C@H]1C[C@@H](NC(=O)C(=O)[C@H]2CCC(=O)N2Cc2ccccc2)C1]

FP 305 (A/II)

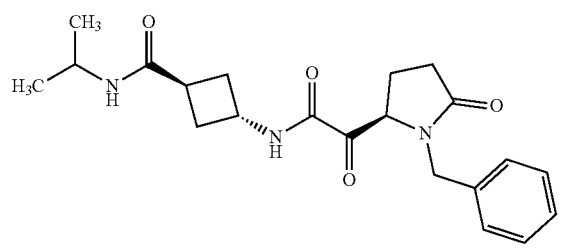 [SMILES: CC(C)NC(=O)[C@H]1C[C@H](NC(=O)C(=O)[C@H]2CCC(=O)N2Cc2ccccc2)C1]

FP 306 (A/II)

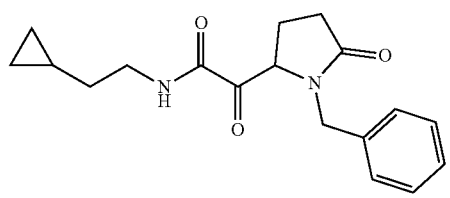 [SMILES: O=C(NCCC1CC1)C(=O)C1CCC(=O)N1Cc1ccccc1]

FP 307 (A/I)

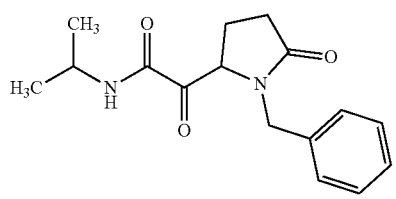 [SMILES: CC(C)NC(=O)C(=O)C1CCC(=O)N1Cc1ccccc1]

FP 308 (A/I)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

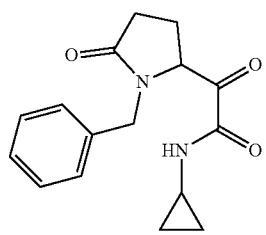 [SMILES: O=C(NC1CC1)C(=O)C1CCC(=O)N1Cc1ccccc1]

FP 309 (A/II)

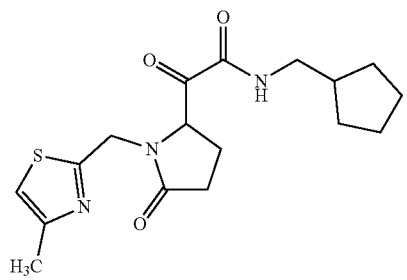 [SMILES: Cc1csc(CN2C(=O)CCC2C(=O)C(=O)NCC2CCCC2)n1]

FP 310 (A/I)

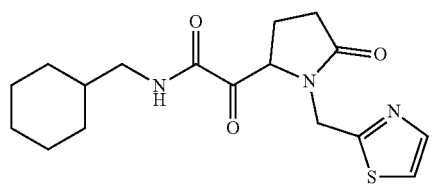 [SMILES: O=C(NCC1CCCCC1)C(=O)C1CCC(=O)N1Cc1nccs1]

FP 311 (A/I)

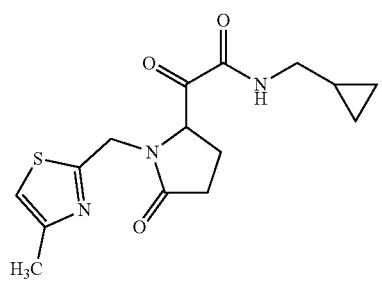 [SMILES: Cc1csc(CN2C(=O)CCC2C(=O)C(=O)NCC2CC2)n1]

FP 312 (A/II)

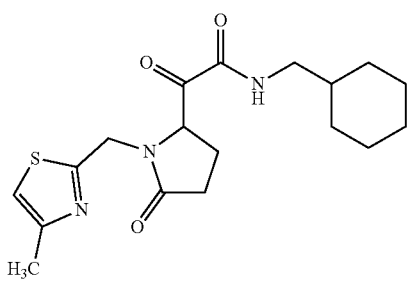 [SMILES: Cc1csc(CN2C(=O)CCC2C(=O)C(=O)NCC2CCCCC2)n1]

FP 313 (A/I)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

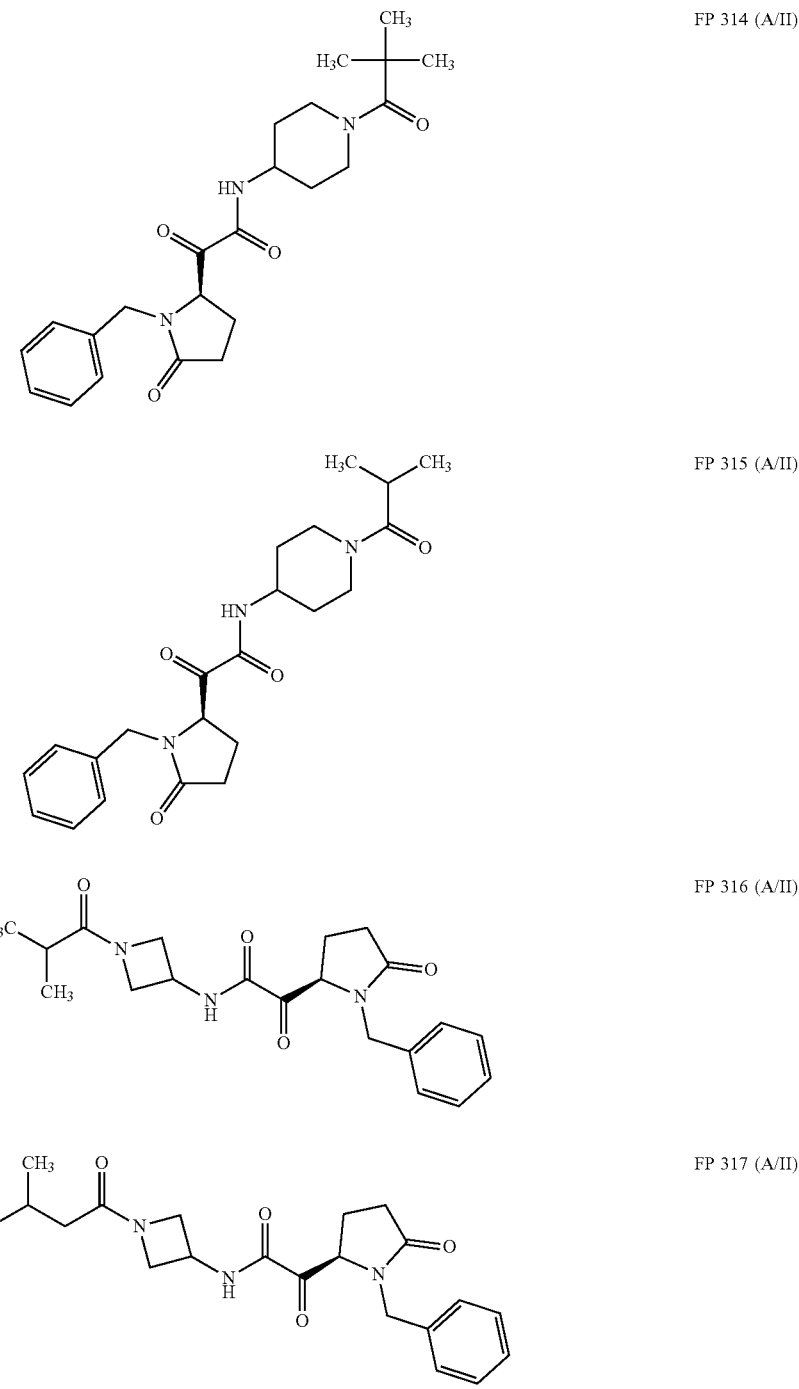

FP 314 (A/II)

FP 315 (A/II)

FP 316 (A/II)

FP 317 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

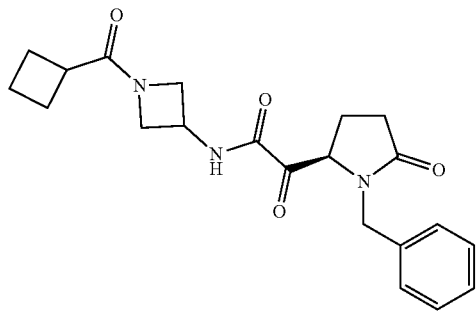 [SMILES: O=C(NC1CN(C(=O)C2CCC2)C1)C(=O)[C@H]1CCC(=O)N1Cc1ccccc1]

FP 318 (A/II)

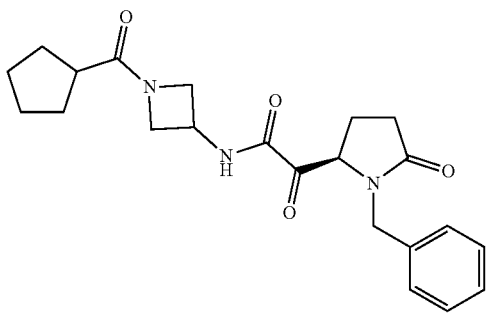 [SMILES: O=C(NC1CN(C(=O)C2CCCC2)C1)C(=O)[C@H]1CCC(=O)N1Cc1ccccc1]

FP 319 (A/II)

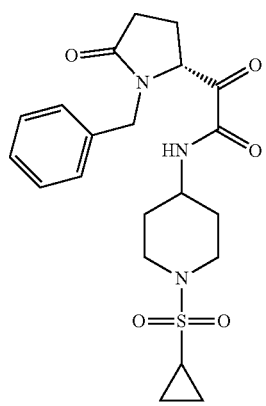 [SMILES: O=C(NC1CCN(S(=O)(=O)C2CC2)CC1)C(=O)[C@H]1CCC(=O)N1Cc1ccccc1]

FP 320 (A/I)

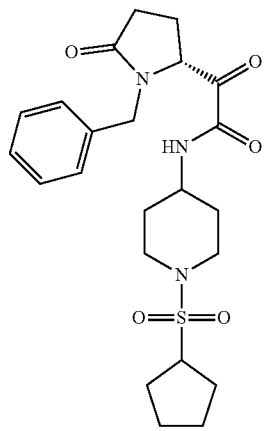 [SMILES: O=C(NC1CCN(S(=O)(=O)C2CCCC2)CC1)C(=O)[C@H]1CCC(=O)N1Cc1ccccc1]

FP 321 (A/I)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

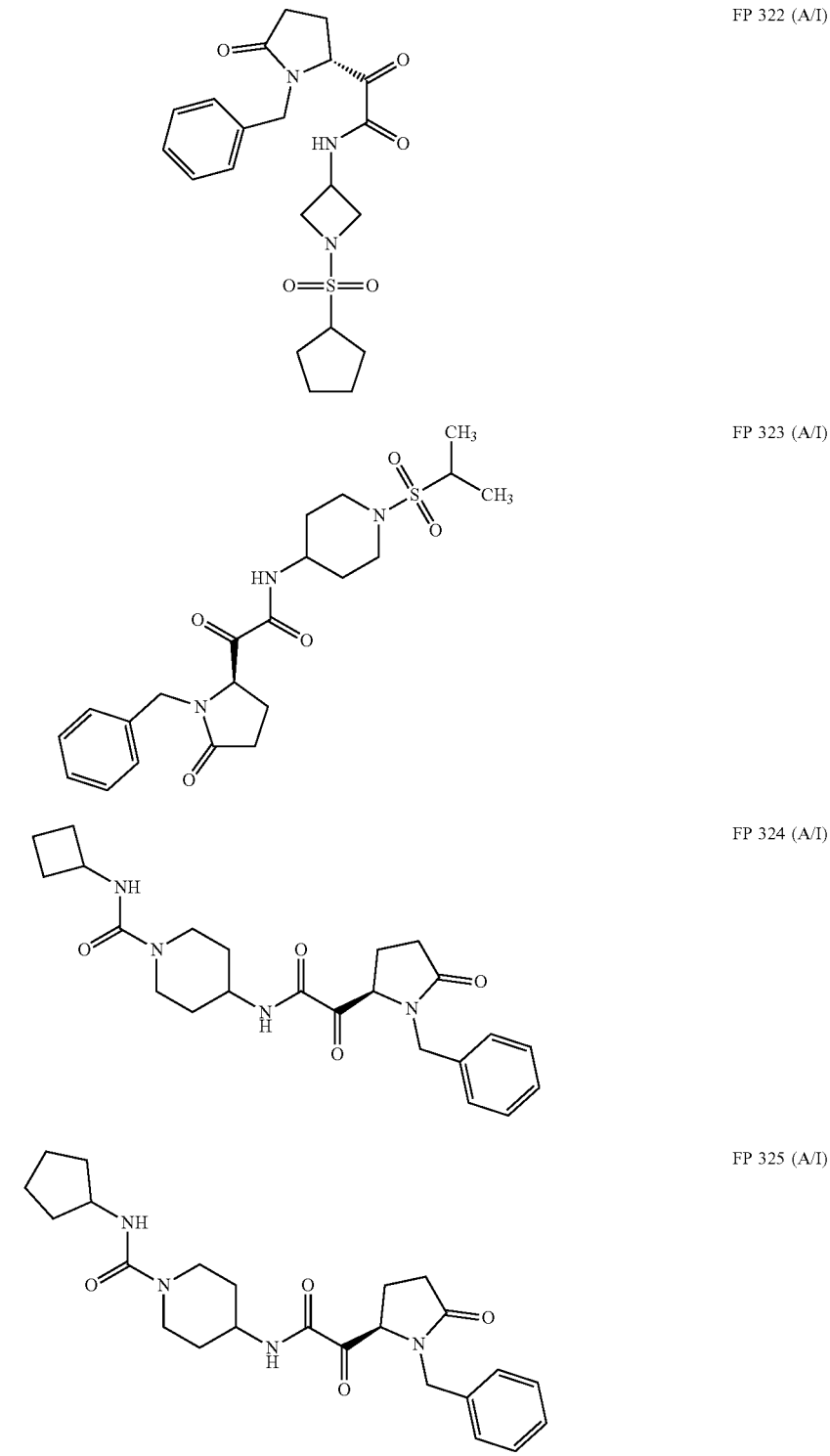

FP 322 (A/I)

FP 323 (A/I)

FP 324 (A/I)

FP 325 (A/I)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 μM (class "A") in the enzymatic activity assay are considered as highly active, compounds with IC$_{50}$ values between 1 and 10 μM (class "B") are considered as medium active and compounds with IC$_{50}$ values greater than 10 μM, but below 50 μM (class "C") are considered as weakly active. Antiviral activity against four different picornaviruses is categorized analogously, where class "I" denotes compounds with EC$_{50}$ <1 μM, class "II" with EC$_{50}$, between 1 μM and 10 μM and class "III" with EC$_{50}$ >10 μM.

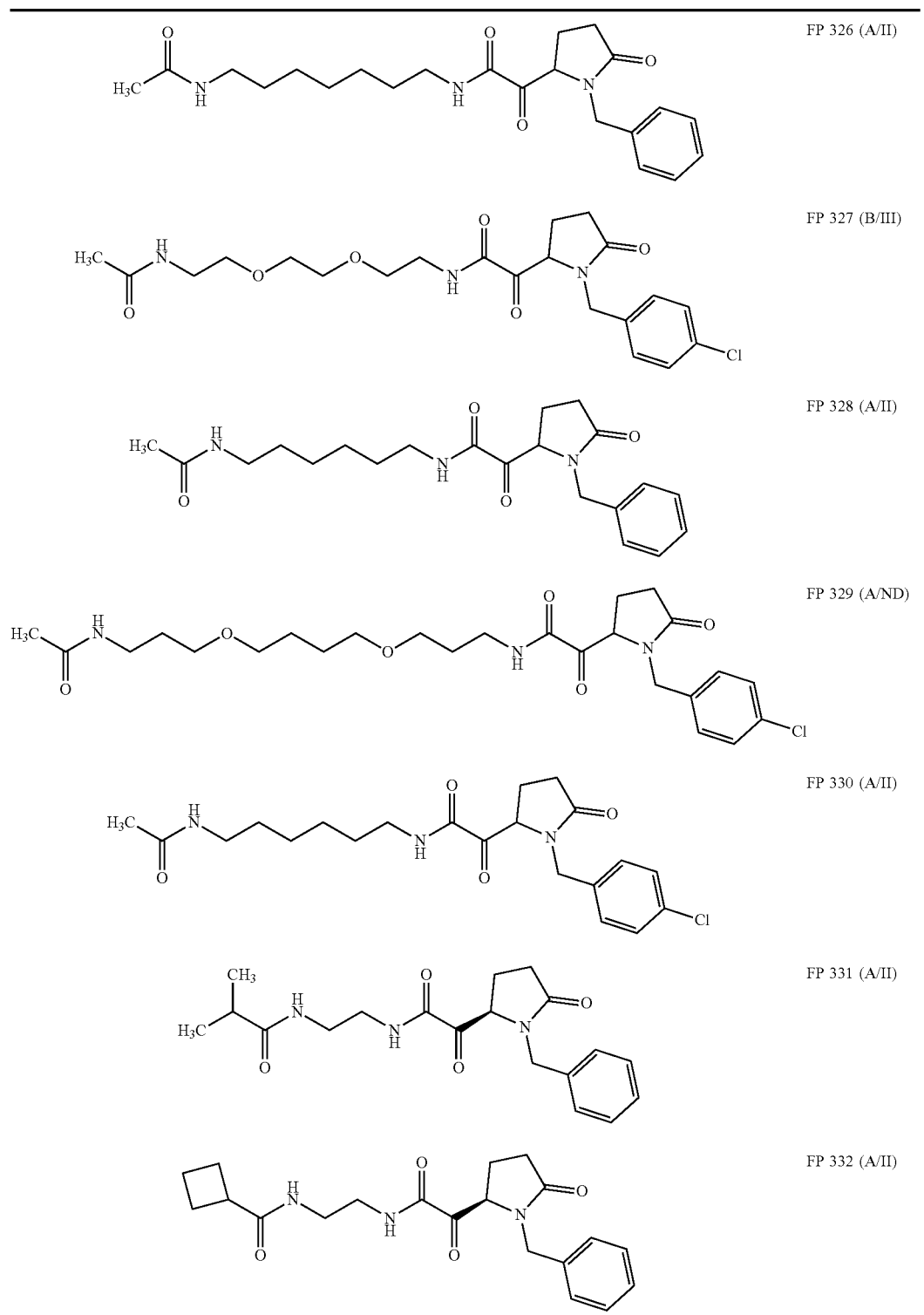

FP 326 (A/II)

FP 327 (B/III)

FP 328 (A/II)

FP 329 (A/ND)

FP 330 (A/II)

FP 331 (A/II)

FP 332 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

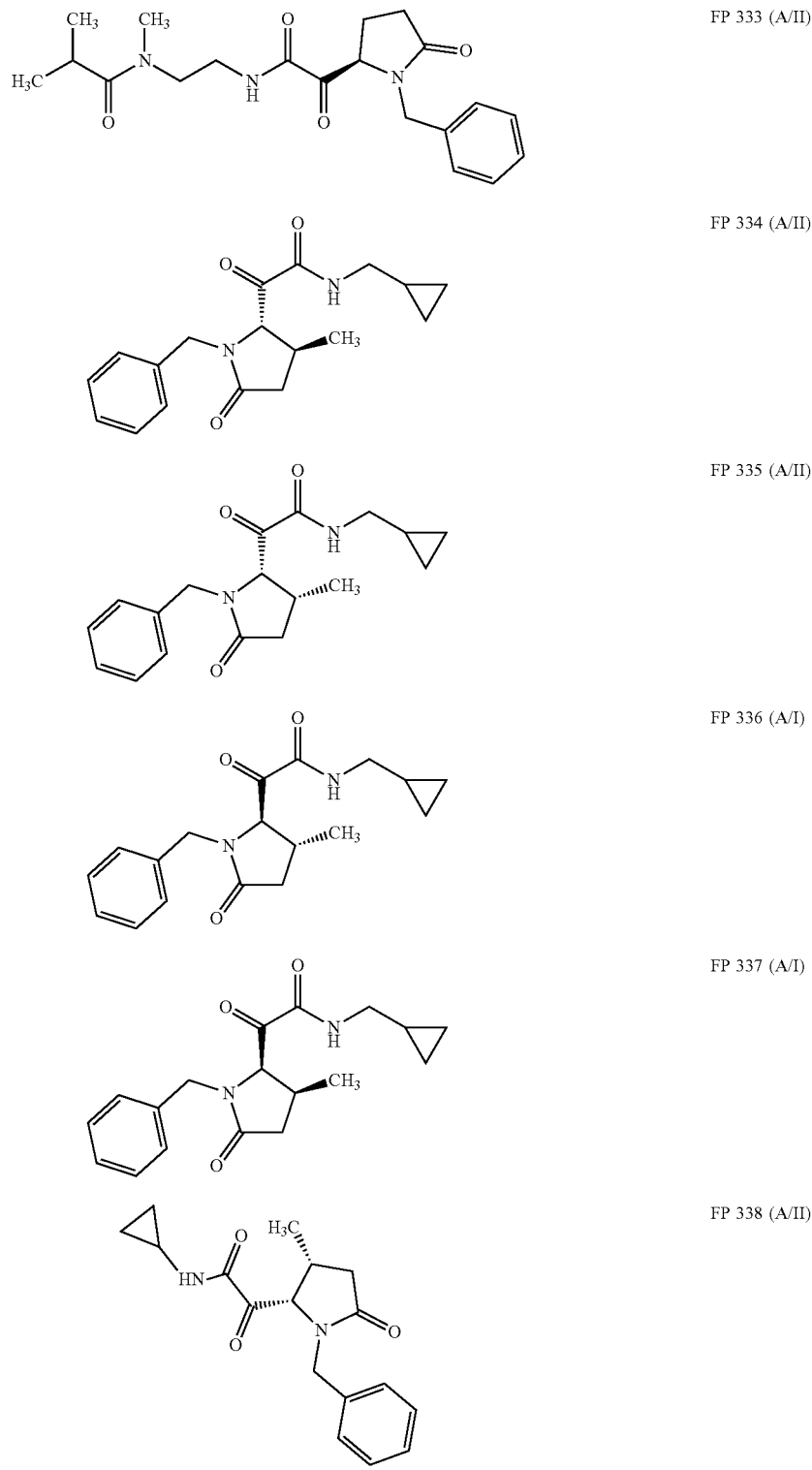

FP 333 (A/II)

FP 334 (A/II)

FP 335 (A/II)

FP 336 (A/I)

FP 337 (A/I)

FP 338 (A/II)

TABLE 2-continued

Compounds FP 1-FP 191
IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

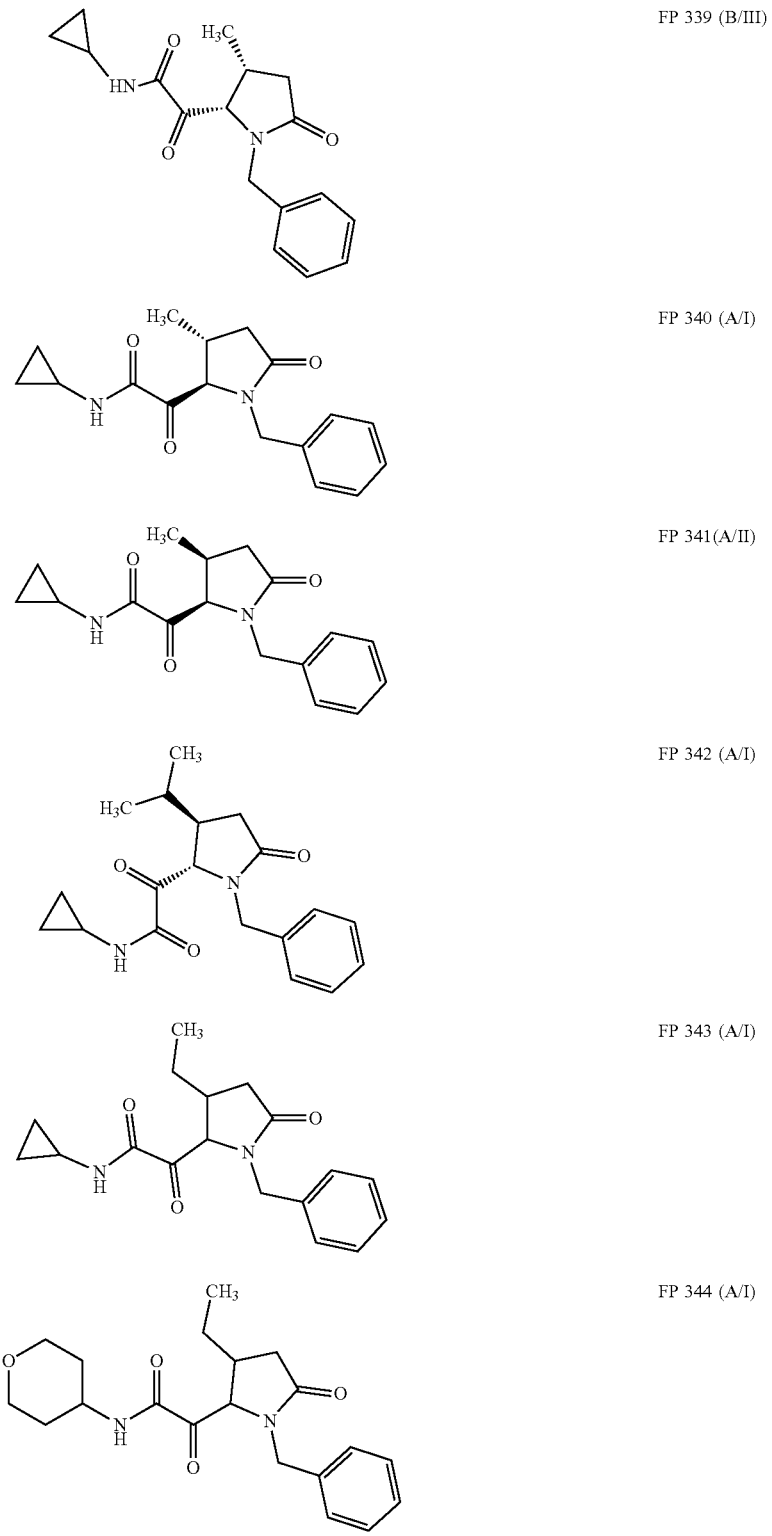

FP 339 (B/III)

FP 340 (A/I)

FP 341 (A/II)

FP 342 (A/I)

FP 343 (A/I)

FP 344 (A/I)

TABLE 2-continued

Compounds FP 1-FP 191

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ <1 µM, class "II" with EC$_{50}$, between 1 µM and 10 µM and class "III" with EC$_{50}$ >10 µM.

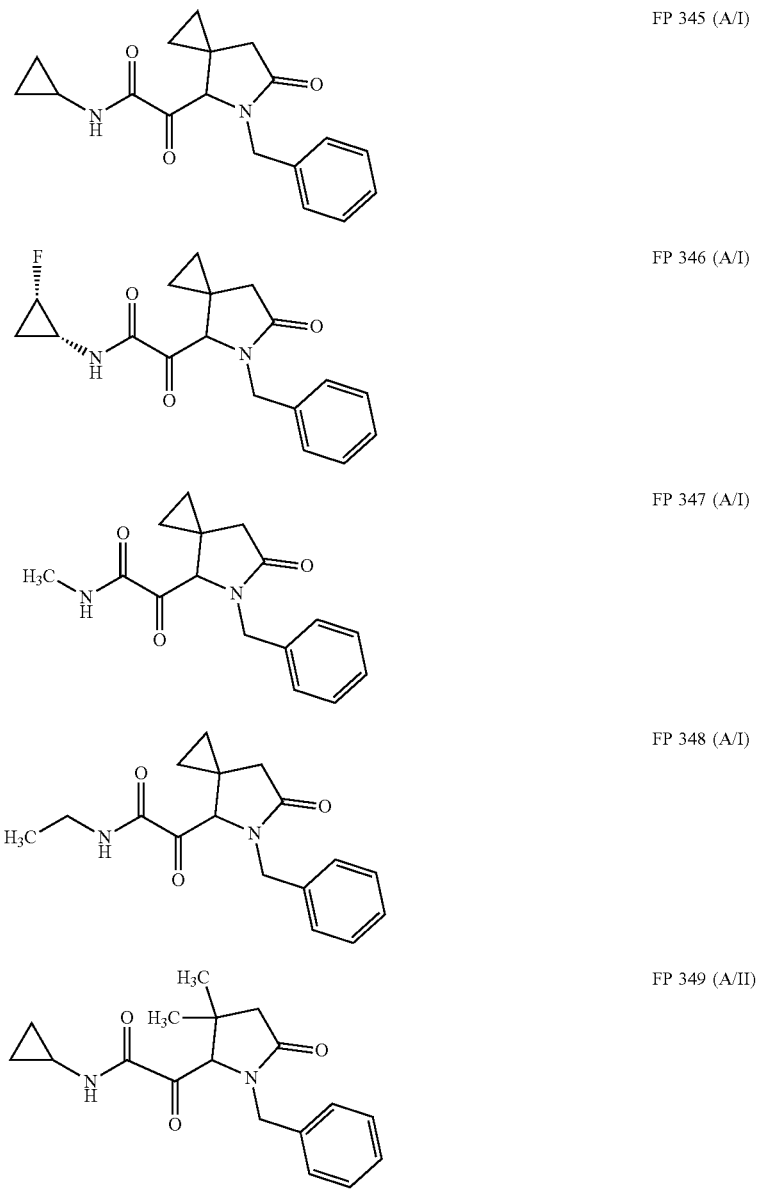

FP 345 (A/I)

FP 346 (A/I)

FP 347 (A/I)

FP 348 (A/I)

FP 349 (A/II)

ND: not determined

Purification and Enzyme Activity Assay for PLA2G16

A cDNA for PLA2G16(NM_007069) was custom-synthesized by Genscript (Piscataway, USA) and inserted into a pET-based bacterial expression vector [Moffatt, B. A. and Studier, F. W. (1986) J. Mol. Biol. 189, 113-130; Rosenberg, A. H., Lade, B. N., Chui, D., Lin, S., Dunn, J. J., and Studier, F. W. (1987) Gene 56, 125-135], enabling the expression of N-terminally Hexa-His-tagged PLA2G16. E. coli BL21 (DE3) (Agilent) were transformed with pET-His-PLA2G16according to the manufacturer's instructions and plated on Carbenicillin-containing agar plates (final concentration: 100 µg/mL). A single clone was in occulated in 100 mL LB medium supplemented with 100 µg/mL Carbenicillin and the in occulated culture was grown at 37° C. overnight in a rotary shaker. On the next day, the bacterial culture was diluted in LB medium supplemented with 100 µg/mL Carbenicillin (30 mL overnight culture in 800 mL total culture volume). Bacteria were grown at 37° C. until the OD$_{600}$

561 reached 0.6. Gene expression was induced by addition of 1 mM isopropyl-β-D-thiogalactopyranosid (IPTG) for 2 h at 18° C. Subsequently, bacteria were harvested by centrifugation (15 min; 10,000×g; 4° C.) and frozen at −80° C. The bacterial pellet was resuspended in Buffer A (50 mM Tris/HCl pH 7.5, 500 mM NaCl, 5% glycerol, 5 mM β-Mercaptoethanol and 1 mM PMSF) and lysed by addition of 1 mg/mL lysozyme (Sigma Aldrich) and 100 µg/mL DNaseI- (Roche). The sample was incubated at 30° C. for 30 min to allow lysis to occur. Then, the lysate was cleared by centrifugation (15,000×g, 15 min, 4° C.) and incubated with 1.5 mL Ni-NTA agarose suspension (Qiagen) for 60 min at 4° C. The Ni-NTA agarose was washed with 10 mL Buffer A. Bound protein was eluted by applying a manual gradient of Buffer A supplemented with increasing concentrations of imidazole (Sigma Aldrich; 25/50/75/100/250 mM). Purified fractions were analyzed by SDS-PAGE followed by Coomassie staining to assess the purity.

Activity of the protein was assessed as follows: Red/Green BODIPY® PC-A2 (Invitrogen, 1 mM in DMSO) was mixed with equal volumes of 1,2-Dioleoyl-sn-glycero-3-phosphocholine (DOPC; Sigma Aldrich, 10 mM in Ethanol) and 1,2-Dioleoyl-sn-glycero-3-phospho-rac-(1-glycerol) (DOPG; Sigma Aldrich, 10 mM in Ethanol) and 0.5 volumes of Cholesterol (CHOL; Sigma Aldrich, 10 mM in Ethanol) and vortexed for 5 s. The mixture (Red/Green BODIPY® PC-A2/DOPC/DOPG/CHOL) was diluted 1:91.4 in activity assay buffer (50 mM Tris/HCl pH 8.5, 100 mM NaCl) using a small-orifice pipette tip under constant vortexing. In the following, this preparation will be referred to as the "substrate solution".

In order to evaluate their inhibitory potential, compounds were dissolved at 10 mM concentration in DMSO and directly spotted into assay plates (Corning, Cat. No. 3576) using acoustic liquid transfer (Labcyte Echo 525). Each compound was spotted at increasing concentrations, ranging from 2 nM to 50 µM (concentration in the final assay volume). 50 µl of PLA2G16 enzyme solution (diluted in activity buffer, supplemented with 5 mM L-Glutathione; Sigma Aldrich) was pre-incubated with compounds for 4 min., followed by addition of 50 µl of substrate solution. Fluorescence was recorded immediately after substrate addition for a total time of 10 min. using a SpectraMax M5 multimode reader (Excitation wavelength: 480 nm, emission wavelength: 530 nm). The relative increase of fluorescence over time is referred to as the enzyme activity. Half-maximal inhibitory concentrations ($IC_{50}$) were derived by non-linear regression analysis using the drc package in R (R Development. Core Team, 2005).

The results of the enzyme activity assay for PLA2G16 are presented in Table 2.

Anti-Picornavirus Assay in Mammalian Cell Culture

The antiviral activity of selected compounds was tested using a cytopathic effect (CPE) reduction assay on HeLa H1 cells (ATCC CRL-1958). Briefly, cells were seeded in 96-well dishes (2×10$^4$ cells/well) in DMEM medium (Life technologies) supplemented with 10% FBS and PenStrep solution (100 U/mL Penicillin and 100 µg/mL streptomycin) and incubated at 37° C., 5% $CO_2$ overnight. The next day, cells were pre-treated with serial dilutions of the compound in DMEM medium supplemented with 2% FBS and Pen-Strep for 2 h at 37° C., 5% $CO_2$. Next, cells were infected with virus (CVB1, HRV-A2, HRV-A23, EV-68) at an multiplicity of infection (MOI) which results in a complete virus-induced CPE within 2 days in control wells (infected and vehicle-treated). After 48 h, supernatants were aspirated and 50 µl/well of CellTiterBlue reagent (Promega) diluted 1:5 in DMEM+2% FBS, was added to the cells. Plates were returned to the incubator and allowed to develop for 1.5 h. After that, plates were equilibrated to RT and subsequently, fluorescence was recorded (Excitation wavelength: 560 nm; emission wavelength: 590 nm) using a SpectraMax M5 multimode plate reader. Viability of cells was calculated according to the formula: $V=(RFU_{Cpd}-RFU_{Veh})/(RFU_M-RFU_{Veh})$, where $RFU_{Cpd}$ refers to infected and compound-treated cells, $RFU_{Veh}$ to infected and vehicle-treated cells and $RFU_M$ to uninfected and vehicle treated cells. Half-maximal effective concentrations ($EC_{50}$) were calculated by non-linear regression analysis using the drc package in R (R Development. Core Team, 2005). $EC_{50}$ categories as presented in Table 2 were calculated by averaging the $EC_{50}$ values from four picornaviruses (CVB1, HRV-A2, HRV-A23, EV68).

The invention claimed is:

1. A compound selected from the group consisting of:

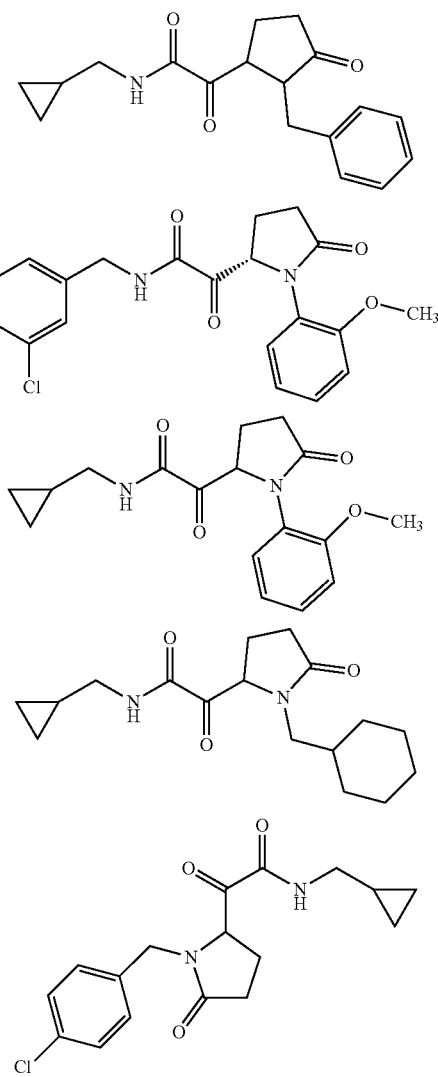

563
-continued
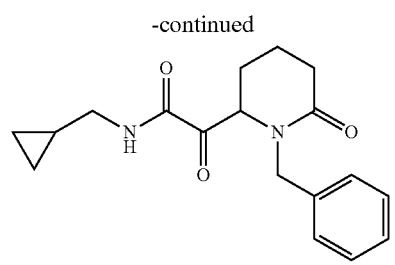
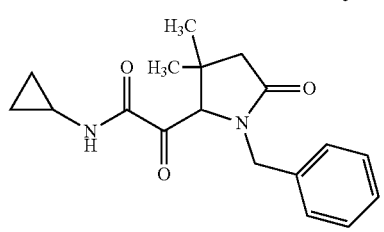
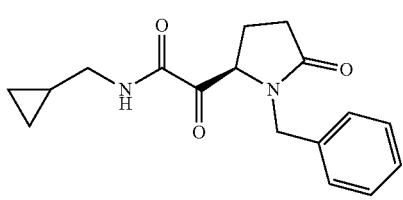
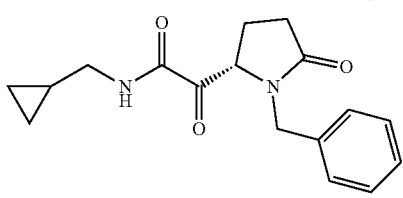
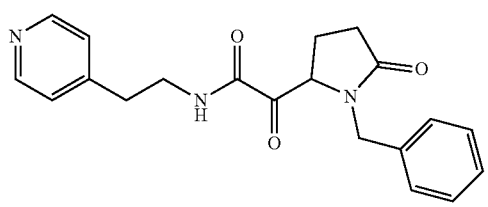
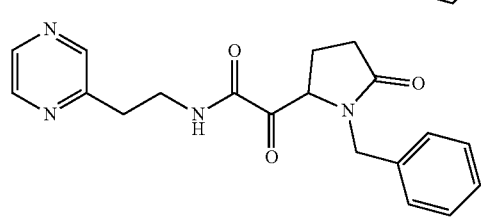
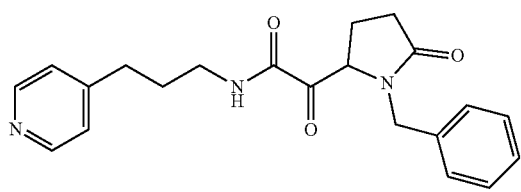
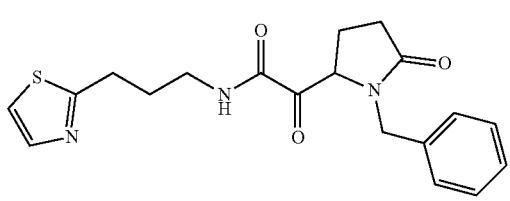
564
-continued
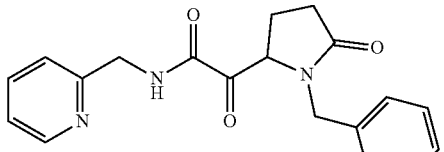
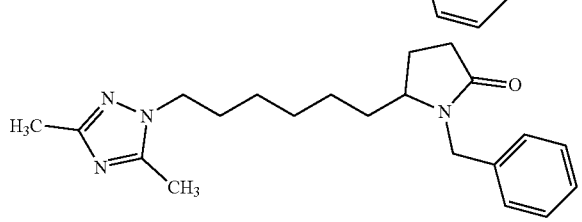
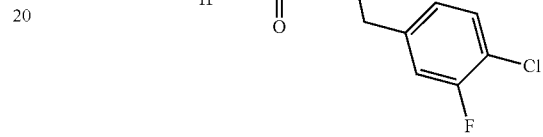
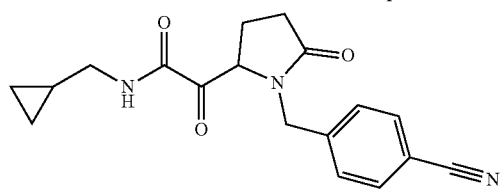
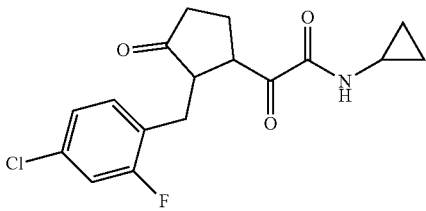
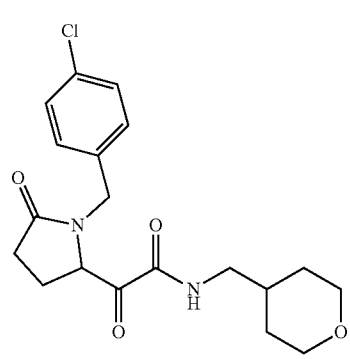
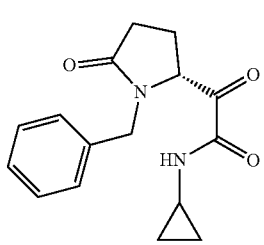

565
-continued
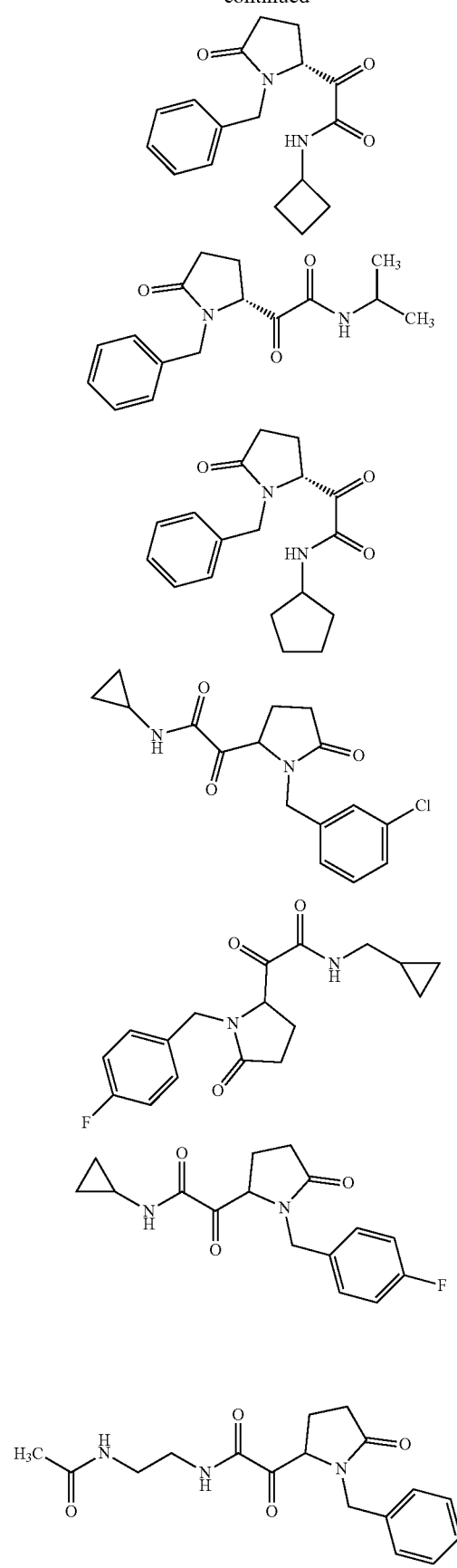
566
-continued
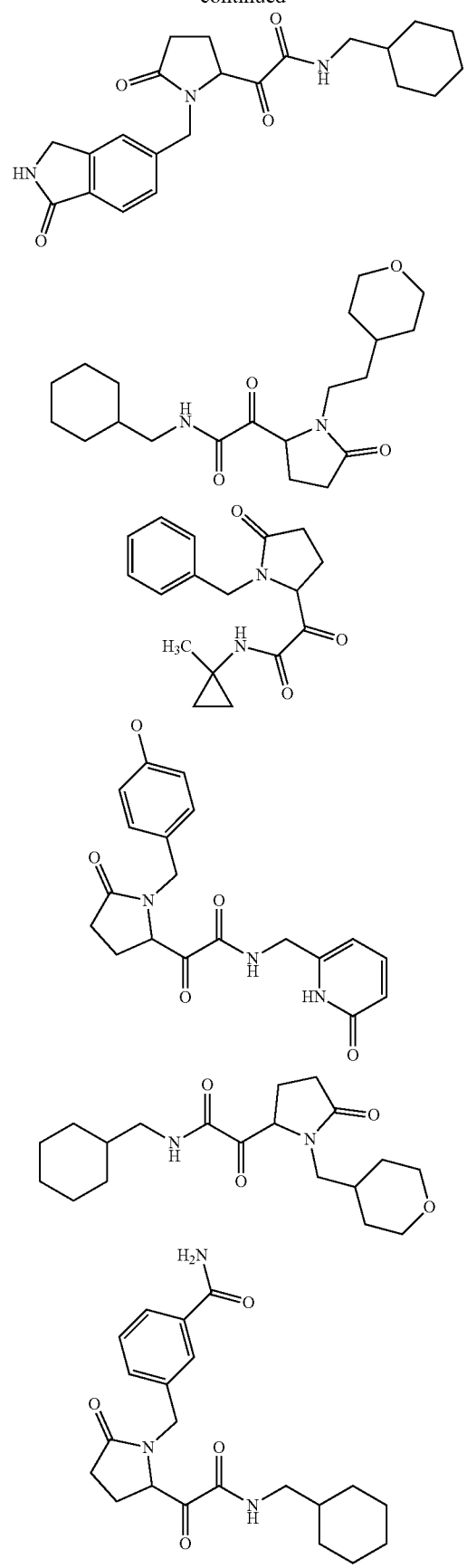

567
-continued
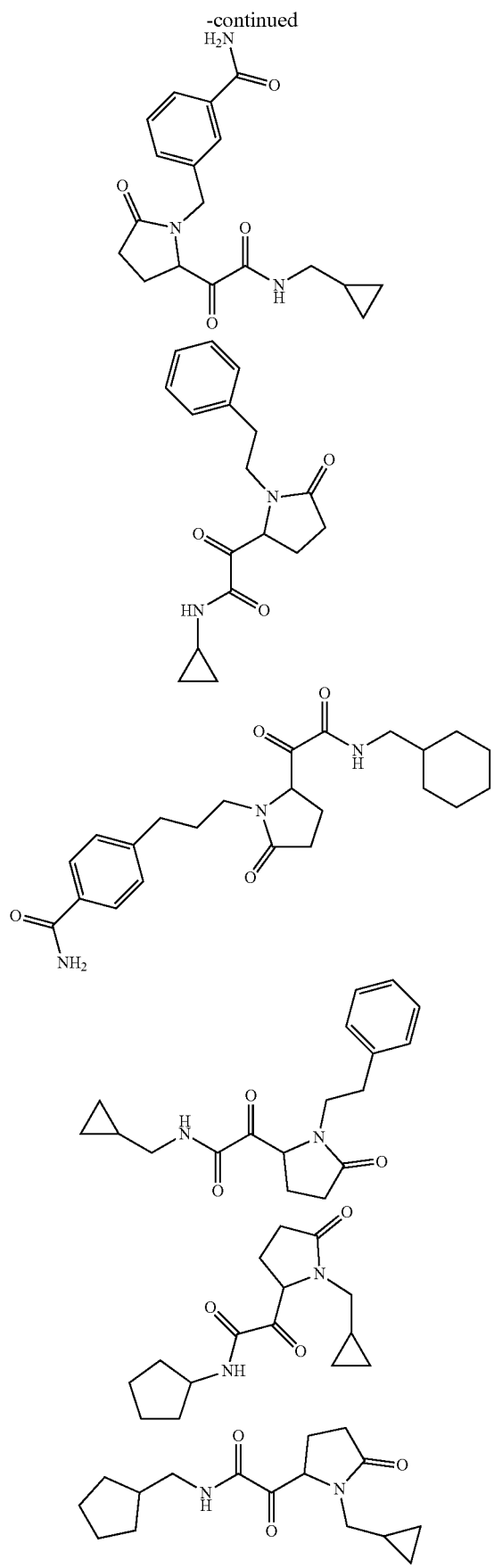
568
-continued
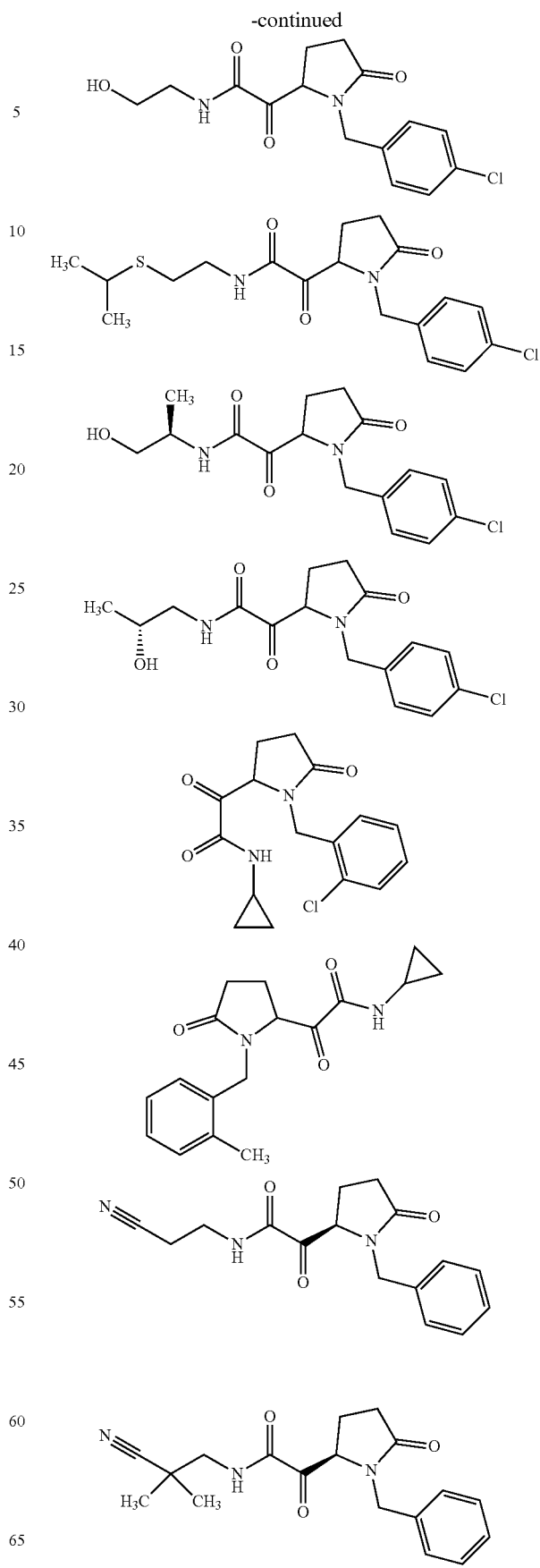

569
-continued
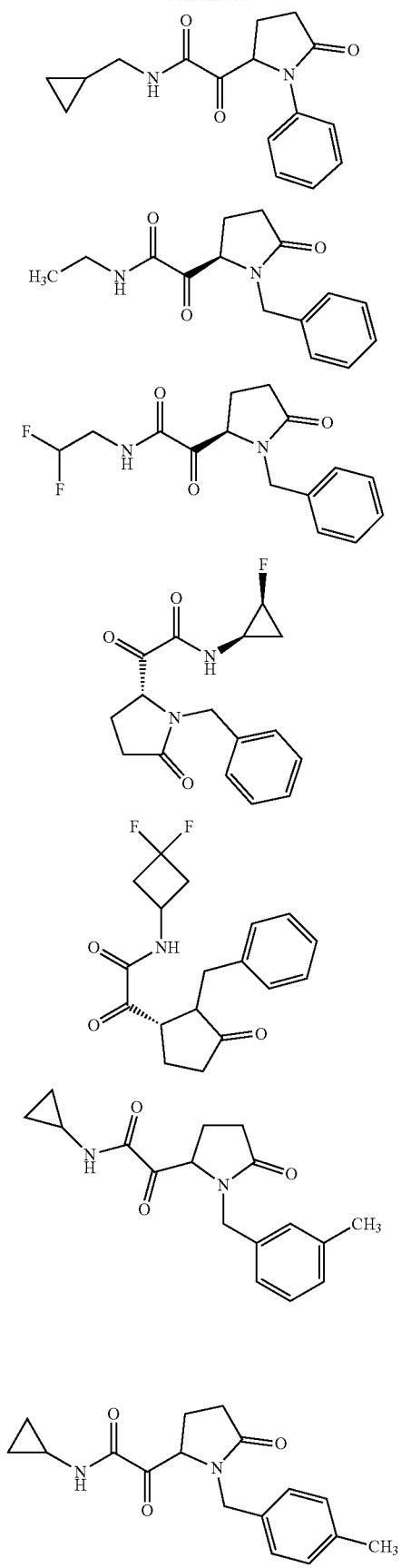
570
-continued
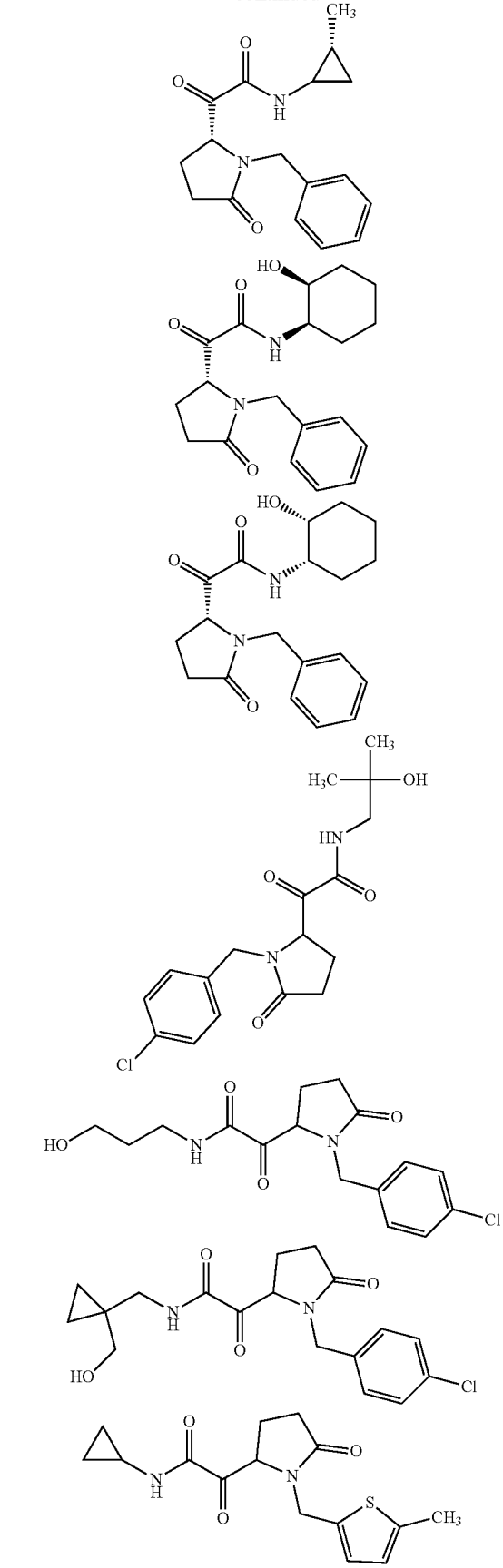

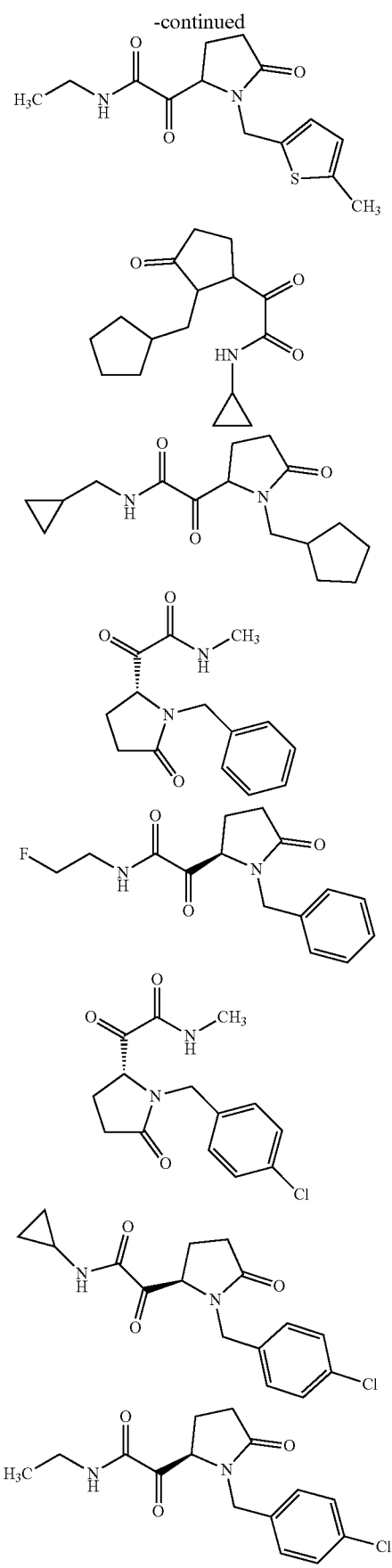

573
-continued
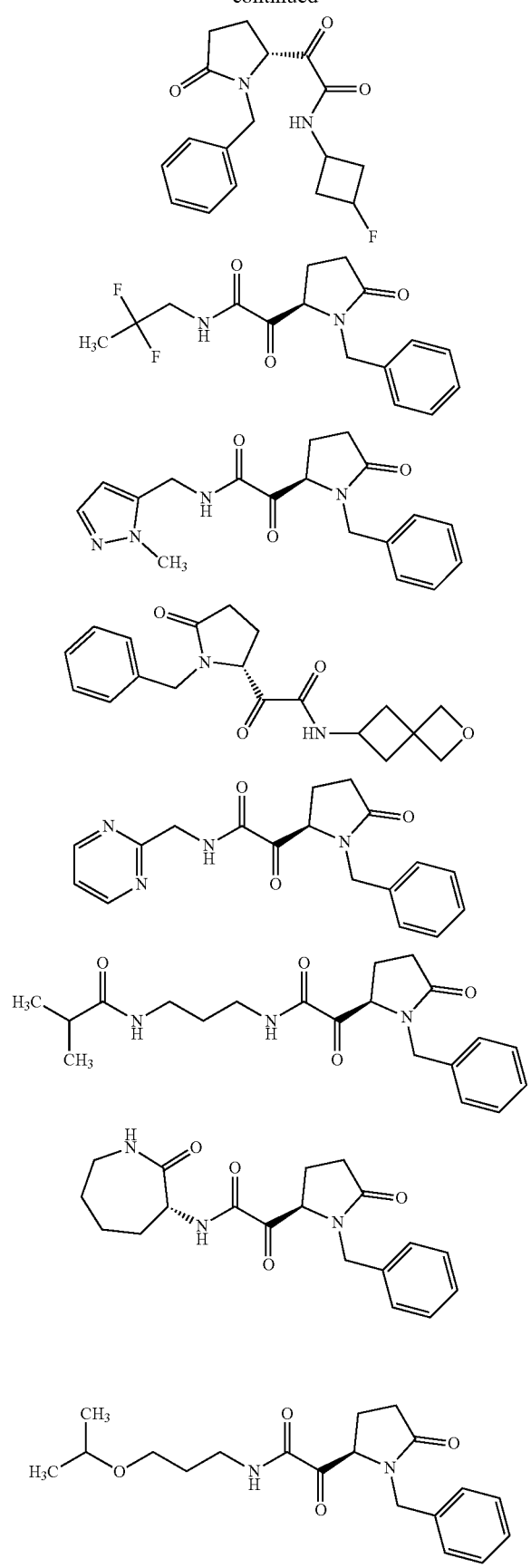
574
-continued
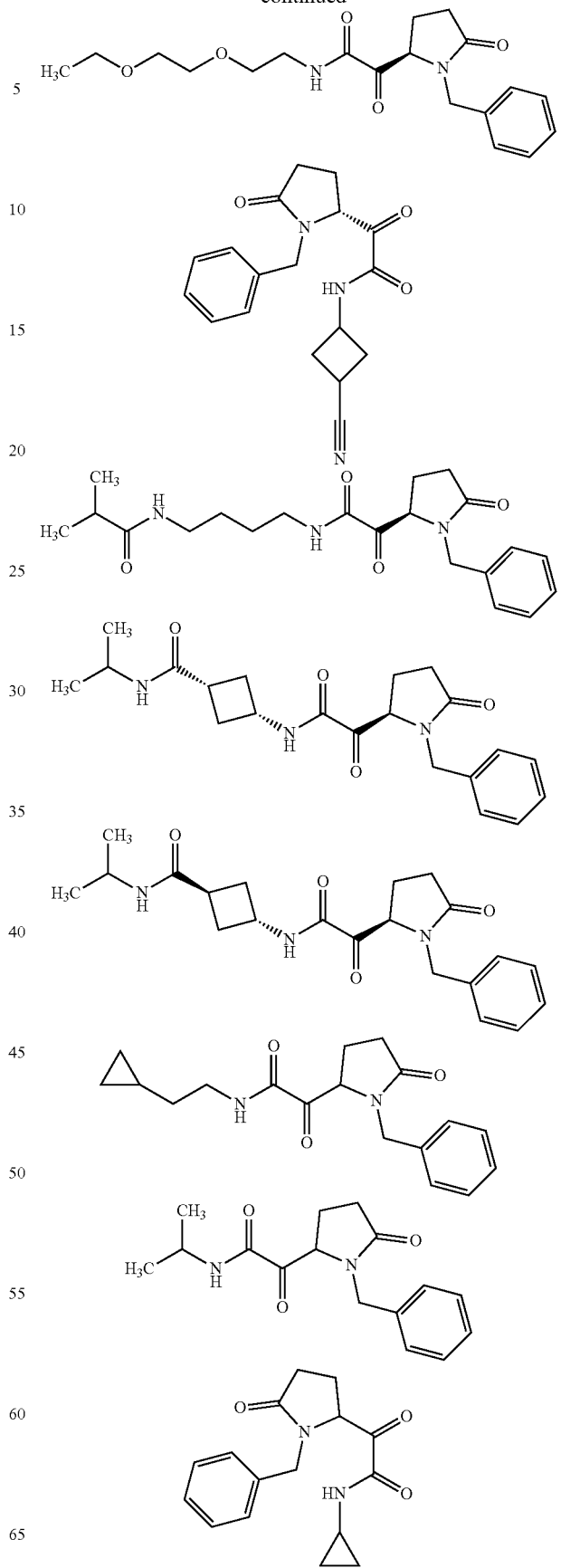

575
-continued
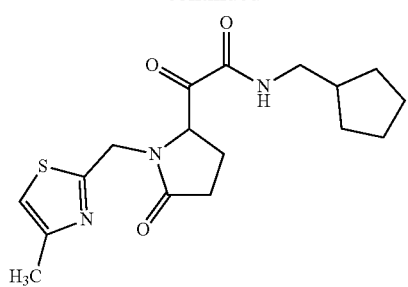
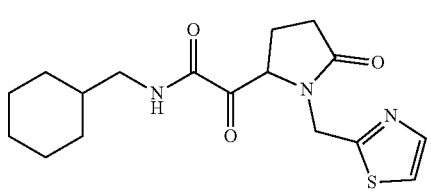
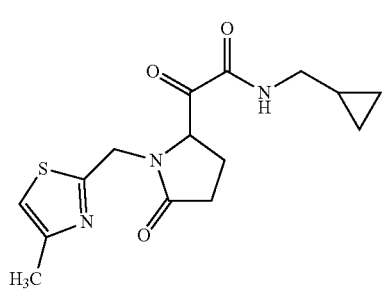
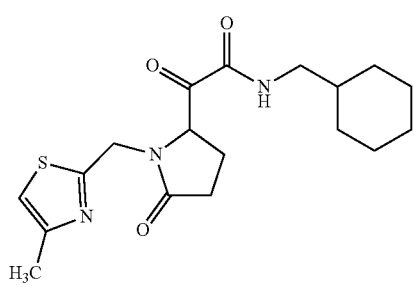
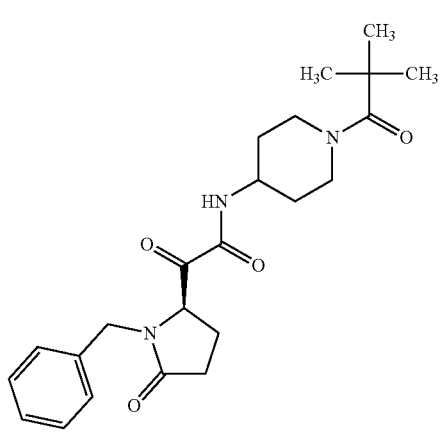
576
-continued
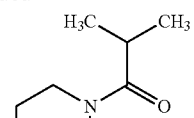
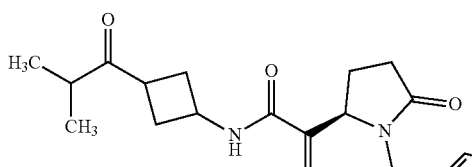
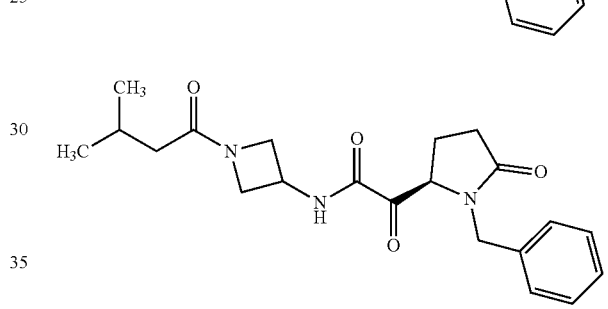
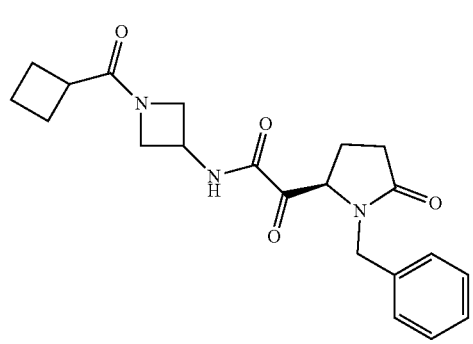
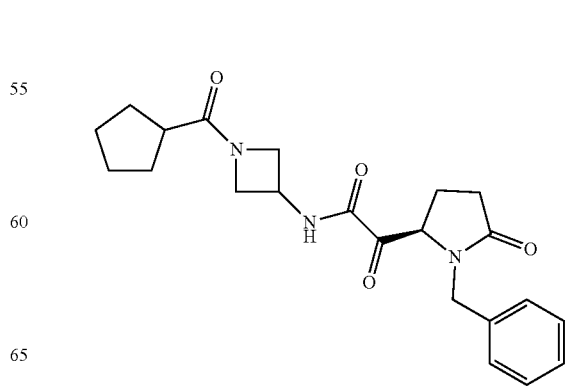

577
-continued
578
-continued
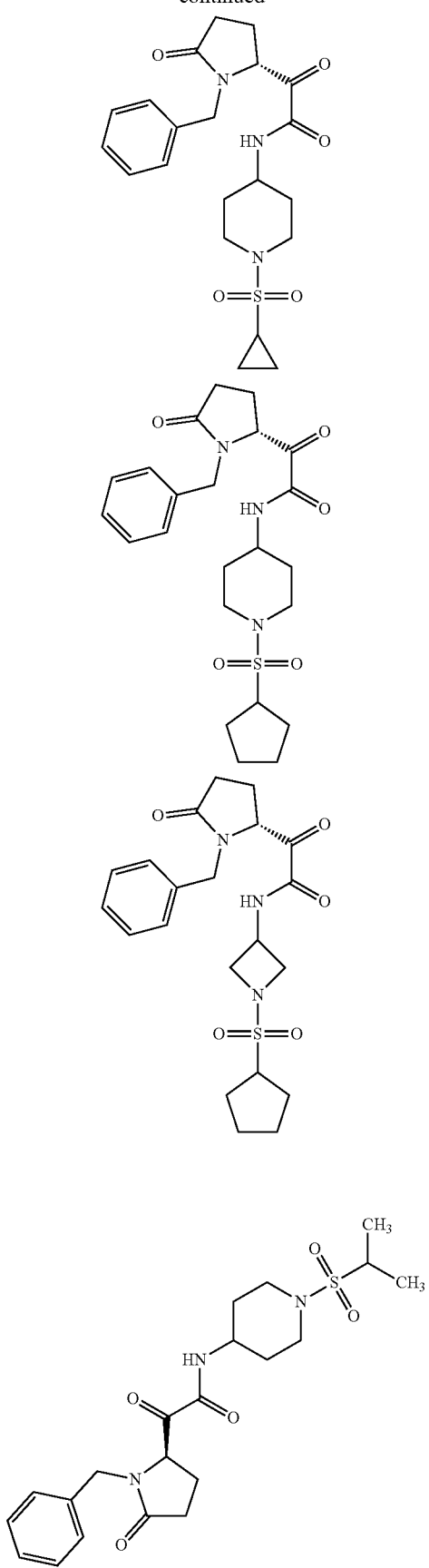
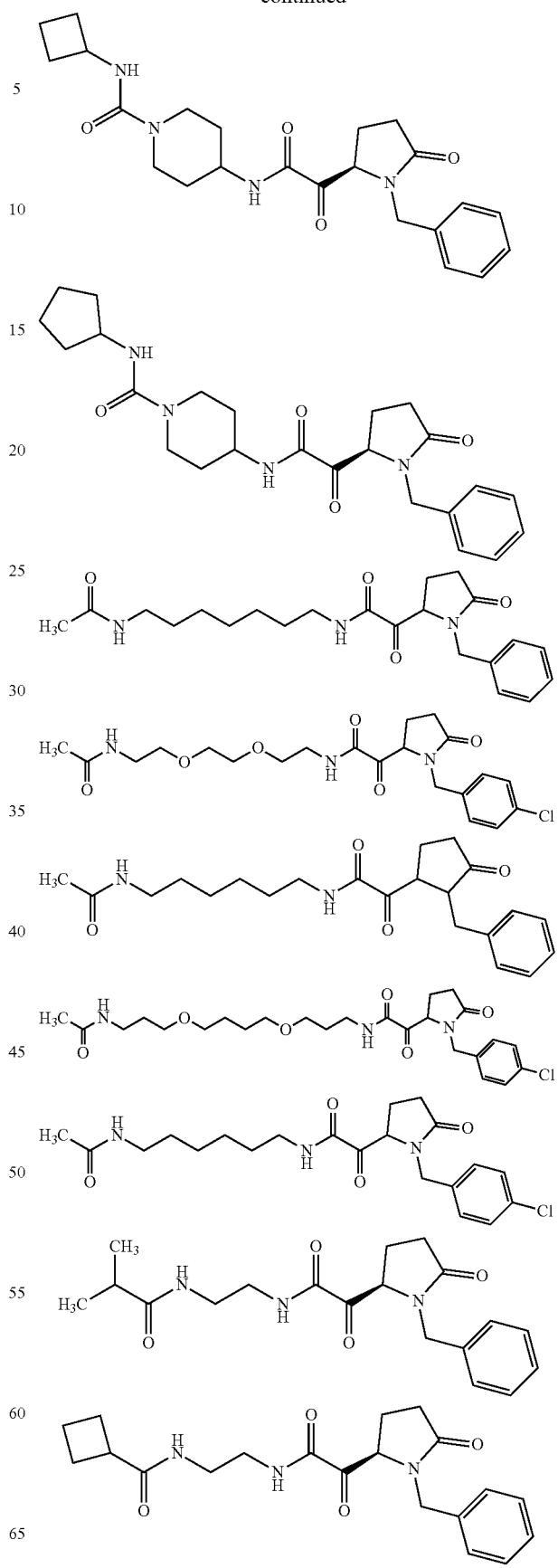

579
-continued
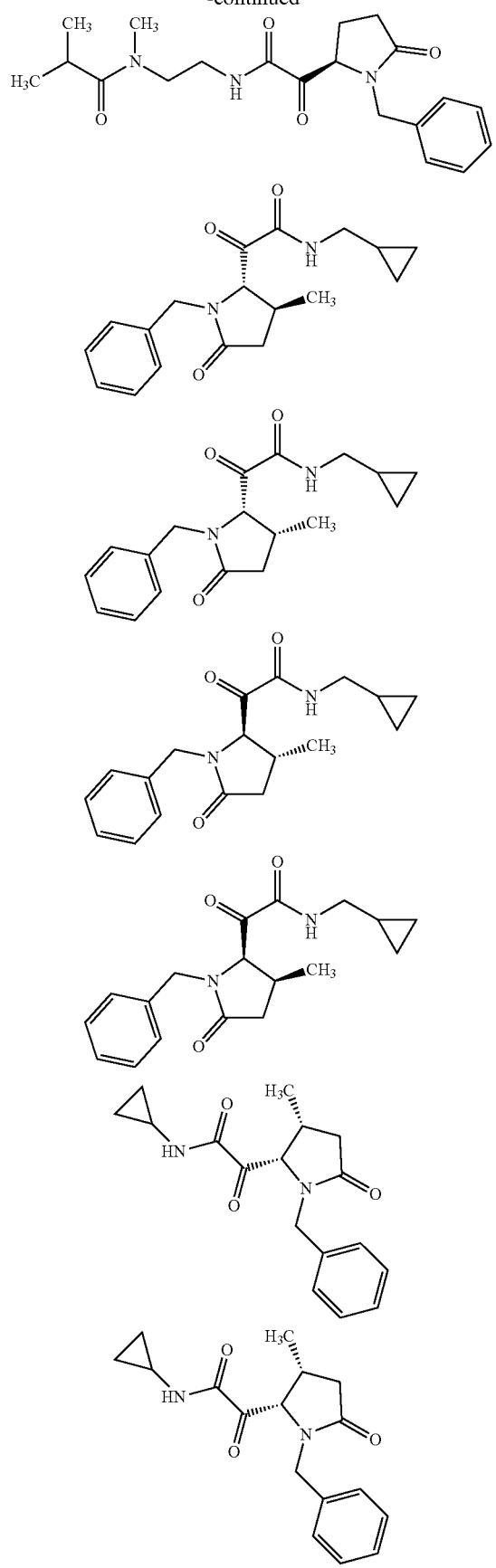
580
-continued
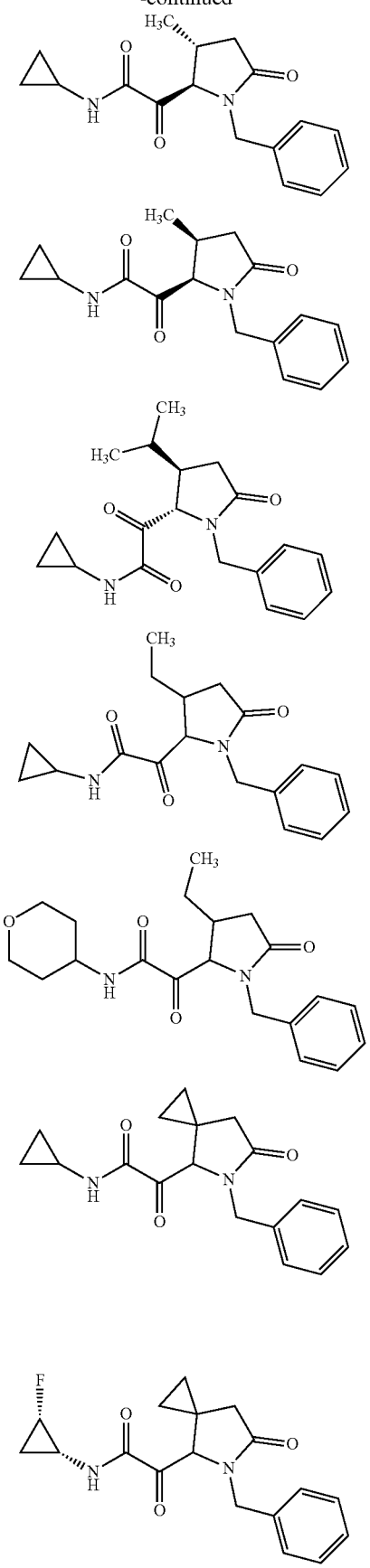

-continued
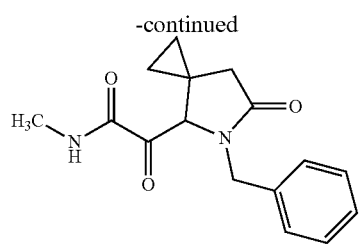
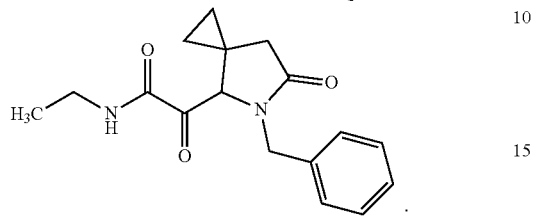
2. A pharmaceutical preparation containing as a pharmacologically active substance one or more compounds according to claim 1 in combination with pharmacologically acceptable excipients and/or carriers.
3. The pharmaceutical preparation of claim 2, comprising at least one further pharmacologically active substance.
* * * * *